US009273028B2

(12) United States Patent
Hopkins et al.

(10) Patent No.: US 9,273,028 B2
(45) Date of Patent: Mar. 1, 2016

(54) HETEROCYCLIC TYROSINE KINASE INHIBITORS

(75) Inventors: Brian T. Hopkins, Newton, MA (US); Daniel Scott, Weston, MA (US); Patrick Conlon, Wakefield, MA (US); Tracy J. Jenkins, Belmont, MA (US); Noel Powell, Westford, MA (US); Bing Guan, Needham, MA (US); Julio H. Cuervo, Arlington, MA (US); Deping Wang, Sharon, MA (US); Art Taveras, Southborough, MA (US)

(73) Assignees: Biogen MA Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/882,449

(22) PCT Filed: Oct. 28, 2011

(86) PCT No.: PCT/US2011/058472
§ 371 (c)(1),
(2), (4) Date: Apr. 29, 2013

(87) PCT Pub. No.: WO2012/058645
PCT Pub. Date: May 3, 2012

(65) Prior Publication Data
US 2013/0345192 A1 Dec. 26, 2013

Related U.S. Application Data

(60) Provisional application No. 61/408,338, filed on Oct. 29, 2010.

(51) Int. Cl.
| *A01N 43/00* | (2006.01) |
| *A61K 31/00* | (2006.01) |
| *C07D 401/12* | (2006.01) |
| *C07D 403/04* | (2006.01) |
| *C07D 413/12* | (2006.01) |
| *C07D 471/04* | (2006.01) |
| *C07D 487/04* | (2006.01) |
| *C07D 519/00* | (2006.01) |
| *C07D 473/34* | (2006.01) |
| *C07D 513/04* | (2006.01) |

(52) U.S. Cl.
CPC ............ *C07D 401/12* (2013.01); *C07D 403/04* (2013.01); *C07D 413/12* (2013.01); *C07D 471/04* (2013.01); *C07D 473/34* (2013.01); *C07D 487/04* (2013.01); *C07D 513/04* (2013.01); *C07D 519/00* (2013.01)

(58) Field of Classification Search
CPC .. C07D 401/12; C07D 403/04; C07D 413/12; C07D 471/04; C07D 473/34; C07D 487/04; C07D 513/04

USPC ............... 514/210.18, 211.15, 217.06, 234.2, 514/234.5, 253.04, 256, 260.1, 262.1, 514/263.22, 264.11, 265.1, 269, 275, 300, 514/318; 540/544, 600; 544/127, 255, 262, 544/277, 279, 280, 298, 324, 329, 362; 546/113, 194

See application file for complete search history.

(56) References Cited

U.S. PATENT DOCUMENTS

| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 7,947,835 | B2 | 5/2011 | Brittelli et al. |
| 8,785,440 | B2 | 7/2014 | Bui et al. |
| 2007/0208056 | A1 | 9/2007 | Carter et al. |
| 2009/0009165 | A1 | 1/2009 | Ichimura et al. |
| 2009/0099165 | A1 | 4/2009 | Hurley et al. |
| 2012/0157442 | A1 | 6/2012 | Bui et al. |

FOREIGN PATENT DOCUMENTS

| WO | WO-96/05309 | A2 | 2/1996 |
| WO | WO-0039124 | A1 | 7/2000 |
| WO | WO-02/068393 | A1 | 9/2002 |
| WO | WO-2005/068468 | A2 | 7/2005 |
| WO | WO-2006044504 | A1 | 4/2006 |
| WO | WO-2006099075 | A2 | 9/2006 |
| WO | WO-2006122014 | A2 | 11/2006 |
| WO | WO-2011/029043 | A1 | 3/2011 |
| WO | WO-2011/029046 | A1 | 3/2011 |
| WO | WO-2013/185082 | A2 | 12/2013 |
| WO | WO-2013/185084 | A1 | 12/2013 |

OTHER PUBLICATIONS

STN Accession No. 2008:743719 CAPLUS, 2008.*
Drug Topics, Oct. 24, 2008.*
U.S. Appl. No. 14/316,710, Bui et al.
Extended European Search Report for European Application EP 11 83 7232 mailed Mar. 5, 2014.
Berge S.M. et al., Pharmaceutical salts, Journal of Pharmaceutical Sciences, 66(1):1-19 (1977).
Carpino, L.A. and El-Faham, A., Tetramethylfluoroformamidinium Hexafluorophosphate: A rapid-acting peptide coupling reagent for solution and solid phase peptide synthesis, Journal of the American Chemical Society, 117:5401 (1995).
Carpino, L.A., 1-Hydroxy-7-azabenzotriazole, An efficient peptide coupling additive, Journal of the American Chemical Society, 115:4397 (1993).
Hu, X et al., Synthesis of trans-(3S)-amino-(4R)-alkyl- and -(4S)-aryl-piperidines via ring-closing metathesis reaction, Organic Letters, 4(25):4499-4502 (2002).
Huang, P et al., First Asymmetric Synthesis of (2R, 3R)-3-Amino-1-benzyl-2-methyl-pyrrolidine via a highly diastereoselective reductive alkylation, Tetrahedron Letters, 38:271 (1997).

(Continued)

*Primary Examiner* — Wu-Cheng Winston Shen
*Assistant Examiner* — Jean Cornet
(74) *Attorney, Agent, or Firm* — Choate, Hall & Stewart, LLP; John P. Rearick

(57) ABSTRACT

The present invention provides compounds useful as inhibitors of Tec family kinases, compositions thereof, and methods of using the same.

8 Claims, No Drawings

(56) References Cited

OTHER PUBLICATIONS

Kitas, E.A. et al., Substituted 2-oxo-azepane derivatives are potent, orally active gamma-secretase inhibitors, Bioorganic and Medicinal Chemistry Letters, 18(1):304-308 (2008).

Li, P. and Xu, JC. The development of highly efficient onium-type peptide coupling reagents based upon rational molecular design, Journal of Peptide Research, 58(2):129-139 (2001).

Mehrotra, M.M. et al., Spirocyclic nonpeptide glycoprotein IIb-IIIa antagonists. Part 3: synthesis and SAR of potent and specific 2,8-diazaspiro[4.5]decanes, Bioorganic and Medicinal Chemistry Letters, 12(7):1103-1107 (2002).

Shafir, A. and Buchwald, S.L., Highly selective room-temperature copper-catalyzed C-N coupling reactions, Journal of the American Chemical Society, 128(27):8742-8743 (2006).

International Search Report for PCT/US2011/058472, 3 pages (mailed Mar. 23, 2012).

Written Opinion for PCT/US2011/058472, 3 pages (mailed Mar. 23, 2012).

* cited by examiner

HETEROCYCLIC TYROSINE KINASE INHIBITORS

CROSS REFERENCE TO RELATED APPLICATIONS

The present application claims priority to PCT application serial number PCT/US11/58472, filed Oct. 28, 2011, which claims priority to U.S. provisional application Ser. No. 61/408,338, filed Oct. 29, 2010, the entire contents of each of which are hereby incorporated herein by reference.

BACKGROUND OF THE INVENTION

The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)). These kinases are primarily expressed in haematopoietic cells, although expression of Bmx and Tec has been detected in endothelial and liver cells. Tec kinases (Itk, Rlk and Tec) are expressed in T cells and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors for Tec kinases such as Btk. The present invention fulfills these and other needs.

SUMMARY OF THE INVENTION

In certain embodiments, the present invention provides a compound of formula I:

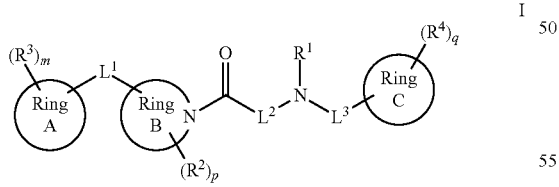

wherein each of $R^1$, $R^2$, $R^3$, $R^4$, $L^1$, $L^2$, $L^3$, Ring A, Ring B, Ring C, m, p, and q is as defined and described herein. Such compounds are inhibitors of the Tec kinase family. Accordingly, provided compounds can be used in a variety of methods including in vitro screening and activity assays as well as in vivo pre-clinical, clinical, and therapeutic settings, as described in detail herein.

In certain embodiments, the present invention provides pharmaceutical formulations comprising provided compounds.

In certain embodiments, the present invention provides a method of decreasing enzymatic activity of a Tec kinase family member. In some embodiments, such methods include contacting a Tec kinase family member with an effective amount of a Tec kinase family member inhibitor.

In certain embodiments, the present invention provides a method of treating a disorder responsive to Tec kinase family inhibition in a subject in need thereof. Such disorders and methods are described in detail herein.

DETAILED DESCRIPTION OF CERTAIN EMBODIMENTS

In certain embodiments, the present invention provides a compound of formula I:

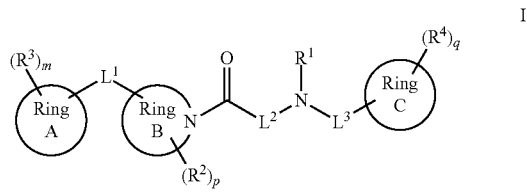

or a pharmaceutically acceptable salt thereof;
wherein:
each of m, p, and q is independently 0-5;
Ring A is a 5-6 membered monocyclic heteroaryl ring having 1-4 heteroatoms independently selected from nitrogen, oxygen or sulfur, or an 8-10 membered bicyclic heteroaryl ring having 1-4 heteroatoms independently selected from nitrogen, oxygen, or sulfur;
Ring B is a 3-8 membered saturated or partially unsaturated monocyclic heterocyclic ring having 0-2 heteroatoms in addition to the depicted ring nitrogen atom independently selected from nitrogen, oxygen, or sulfur, or a 7-10 membered saturated or partially unsaturated bicyclic heterocyclic ring having 0-3 heteroatoms in addition to the depicted ring nitrogen atom independently selected from nitrogen, oxygen, or sulfur;
Ring C is phenyl, an 8-10 membered bicyclic aryl ring, a 3-8 membered saturated or partially unsaturated monocyclic carbocyclic ring, a 7-10 membered saturated or partially unsaturated bicyclic carbocyclic ring, a 5-6 membered heteroaryl ring having 1-4 heteroatoms independently selected from nitrogen, oxygen or sulfur, a 3-8 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-4 heteroatoms independently selected from nitrogen, oxygen, or sulfur, or an 8-10 membered bicyclic heteroaryl ring having 1-4 heteroatoms independently selected from nitrogen, oxygen, or sulfur;
$R^1$ is hydrogen or $C_{1-4}$ aliphatic;
each $R^2$ is independently halogen, —$NO_2$, —CN, —OR, —SR, —N(R)$_2$, —C(O)R, —$CO_2$R, —C(O)C(O)R, —C(O)$CH_2$C(O)R, —S(O)R, —S(O)$_2$R, —C(O)N(R)$_2$, —$SO_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)$SO_2$N(R)$_2$, —N(R)$SO_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered monocyclic or bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur; or:

two $R^2$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur; or:

two $R^2$ groups on non-adjacent carbon atoms are taken together with their intervening atoms to form an optionally substituted bridge of a bridged bicyclic group, wherein the bridge is a $C_{1-3}$ hydrocarbon chain wherein one methylene unit is optionally replaced by —NR—, —O—, —C(O)—, —OC(O)—, —C(O)O—, —S—S—, or —S—; or:

two $R^2$ groups on the same carbon atom are taken together with their intervening atoms to form an oxo group or an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur; or:

two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur;

each $R^3$ and $R^4$ is independently halogen, —$NO_2$, —CN, —OR, —SR, —$N(R)_2$, —C(O)R, —$CO_2R$, —C(O)C(O)R, —C(O)$CH_2$C(O)R, —S(O)R, —$S(O)_2R$, —C(O)N(R)$_2$, —$SO_2N(R)_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

$L^1$ is a covalent bond, —NR$^5$—, —O—, —S—, —S(O)—, —S(O)$_2$—, —C(R$^6$)$_2$—, —C(O)—, —C(=S)—, —C(=NR)—, or —C(=N$_2$)—;

$R^5$ is R, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$;

each $R^6$ is independently R or halogen; and each of $L^2$ and $L^3$ is independently a covalent bond or an optionally substituted, bivalent $C_{1-6}$ saturated or unsaturated, straight or branched, hydrocarbon chain, wherein one or two methylene units of $L^2$ and $L^3$ are optionally and independently replaced by —C(R$^6$)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

provided that when $L^1$ is —O—, Ring B is other than a pyrrolidine ring;

and provided that when $L^1$ is —NH—, $L^2$ is —CH$_2$—, $L^3$ is a bond, $R^1$ is H, Ring B is pyrrolidine, and Ring C is phenyl, Ring A is other than piperazine-substituted quinazolinyl.

DEFINITIONS

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen).

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below.

As used herein, the term "cycloalkylenyl" refers to a bivalent cycloalkyl group of the following structure:

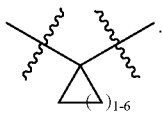

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5,6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1, 4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocycylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-N(R^\circ)_2$; or $-(C_{1-4}$ straight or branched)alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^\bullet_2$, $=NNHC(O)R^\bullet$, $=NNHC(O)OR^\bullet$, $=NNHS(O)_2R^\bullet$, $=NR^\bullet$, $=NOR^\bullet$, $-O(C(R^\bullet_2))_{2-3}O-$, or $-S(C(R^\bullet_2))_{2-3}S-$, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^\bullet_2)_{2-3}O-$, wherein each independent occurrence of $R^\bullet$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^\bullet$ include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, —NHR•, —NR•₂, or —NO₂, wherein each R• is unsubstituted or where preceded by "halo" is substituted only with one or more halogens, and is independently $C_{1-4}$ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), benzyloxymethyl (BOM), p-methoxybenzyloxymethyl (PMBM), t-butoxymethyl, siloxymethyl, 2-methoxyethoxymethyl (MEM), 2,2,2-trichloroethoxymethyl, tetrahydropyranyl (THP), 4-methoxytetrahydropyranyl (MTHP), 1-methyl-1-methoxyethyl, 1-methyl-1-benzyloxyethyl, 2-trimethylsilylethyl, allyl, p-chlorophenyl, p-methoxyphenyl, 2,4-dinitrophenyl, benzyl, p-methoxybenzyl, 3,4-dimethoxybenzyl, p-nitrobenzyl, 2,6-dichlorobenzyl, p-phenylbenzyl, 4-picolyl, diphenylmethyl, p,p'-dinitrobenzhydryl, triphenylmethyl, p-methoxyphenyldiphenylmethyl, 1,1-bis(4-methoxyphenyl)-1'-pyrenylmethyl, trimethylsilyl (TMS), triethylsilyl (TES), triisopropylsilyl (TIPS), dimethylisopropylsilyl (IPDMS), dimethylthexylsilyl, t-butyldimethylsilyl (TBDMS), t-butyldiphenylsilyl (TBDPS), triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, pivaloate, adamantoate, crotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, o-(dibromomethyl)benzoate, 2-(methylthiomethoxy)ethyl, 2-(methylthiomethoxymethyl)benzoate, 2,6-dichloro-4-methylphenoxyacetate, 2,6-dichloro-4-(1,1,3,3-tetramethylbutyl)phenoxyacetate, chlorodiphenylacetate, isobutyrate, monosuccinoate, o-(methoxycarbonyl)benzoate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 3,4-dimethoxybenzylidene acetal, 2-nitrobenzylidene acetal, methoxymethylene acetal, ethoxymethylene acetal, α-methoxybenzylidene ortho ester, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), cyclic carbonates, cyclic boronates, ethyl boronate, and phenyl boronate. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenylyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitobenzyl carbamate, p-chlorobenzyl carbamate, diphenylmethyl carbamate, 2-methylsulfonylethyl carbamate, 2-(p-toluenesulfonyl)ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl) benzyl carbamate, m-nitrophenyl carbamate, 3,5-dimethoxybenzyl carbamate, o-nitrobenzyl carbamate, phenyl(o-nitrophenyl)methyl carbamate, N'-p- toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trifluoroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzylsulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol " ~~~ " except when used as a bond to depict unknown or mixed stereochemistry, denotes the point of attachment of a chemical moiety to the remainder of a molecule or chemical formula.

As described above, in certain embodiments the present invention provides a compound of formula I:

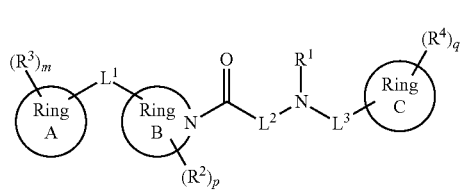

I wherein each of $R^1$, $R^2$, $R^3$, $R^4$, $L^1$, $L^2$, $L^3$, Ring A, Ring B, Ring C, m, p, and q is as defined above and described in classes and subclasses herein.

In some embodiments, Ring A is a 5-6 membered monocyclic heteroaryl ring having 1-4 heteroatoms independently selected from nitrogen, oxygen or sulfur. In some embodiments, Ring A is thienyl, furanyl, pyrrolyl, imidazolyl, pyrazolyl, oxazolyl, isoxazolyl, thiazolyl, isothiazolyl, thiadiazolyl, pyridyl, pyridazinyl, pyrimidinyl, or pyrazinyl.

Exemplary Ring A groups are depicted in Table 1, below.

TABLE 1

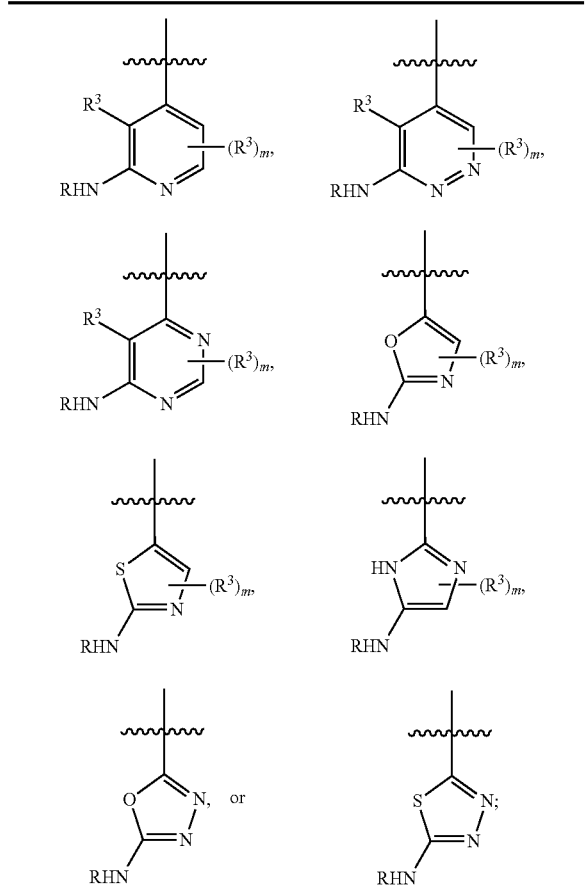

wherein each of R and $R^3$ is as defined above and described in classes and subclasses herein, and each m is independently 0, 1, or 2, as valency permits.

In some embodiments, Ring A is an 8-10 membered bicyclic heteroaryl ring having 1-4 heteroatoms independently selected from nitrogen, oxygen, or sulfur. In some embodiments, Ring A is purinyl.

In some embodiments, Ring A is a group selected from:

-continued

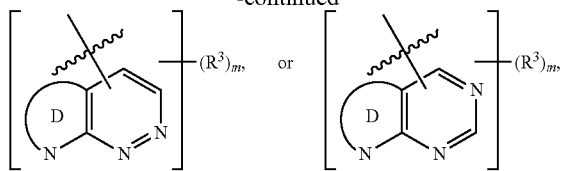

wherein each R³ is independently as defined above and described in classes and subclasses herein, and each Ring D is a 5 membered saturated, partially unsaturated, or heteroaryl fused ring having 1-2 heteroatoms in addition to the nitrogen atom independently selected from nitrogen, oxygen, or sulfur. In some embodiments, each Ring D is independently pyrrolyl, imidazolyl, or pyrazolyl.

In some embodiments, Ring A is selected from the Ring A groups depicted in Table 2, below.

TABLE 2

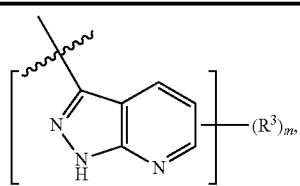

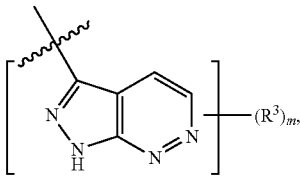

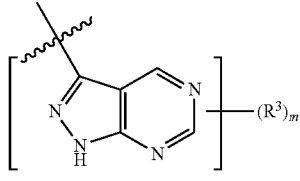

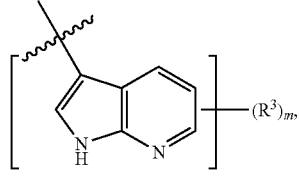

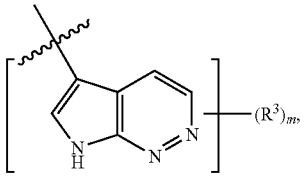

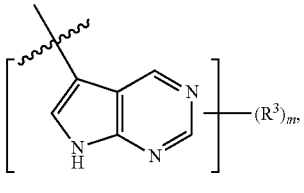

TABLE 2-continued

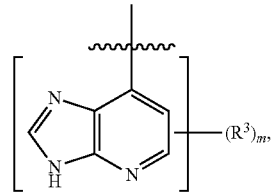

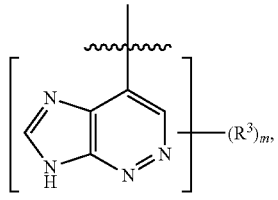

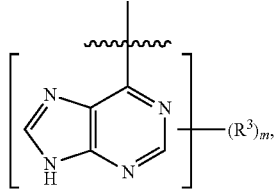

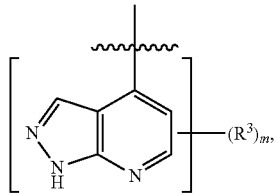

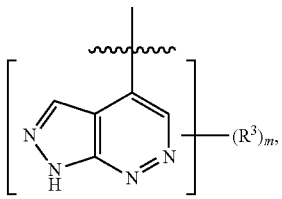

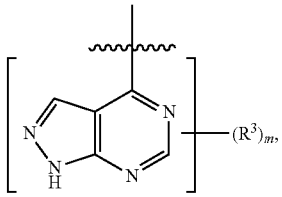

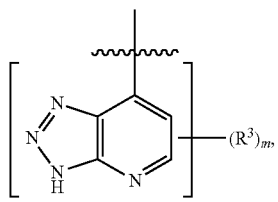

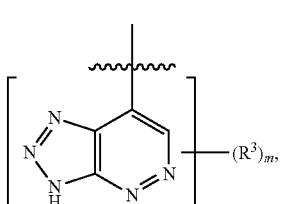

TABLE 2-continued

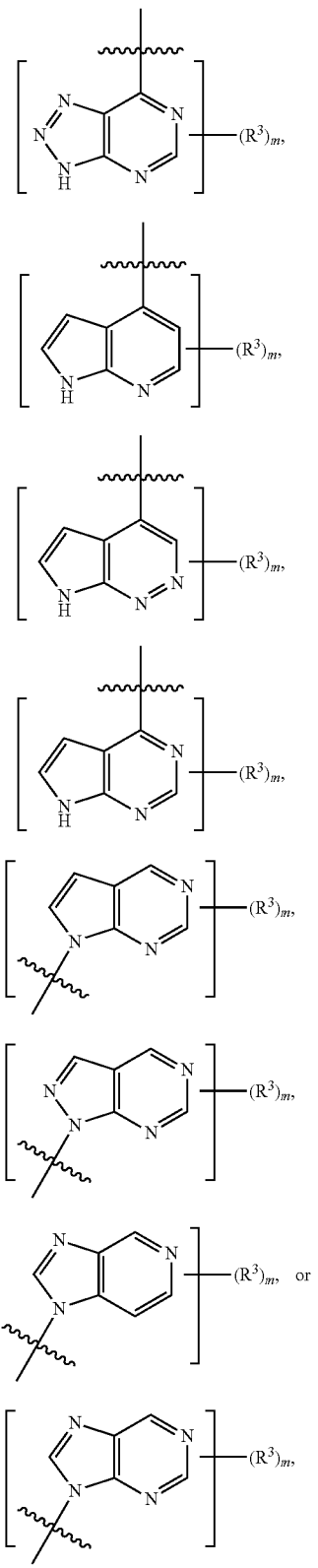

wherein each R³ is independently as defined above and described in classes and subclasses herein, and each m is independently 0, 1, 2, 3, or 4, as valency permits.

In certain embodiments, Ring A is selected from:

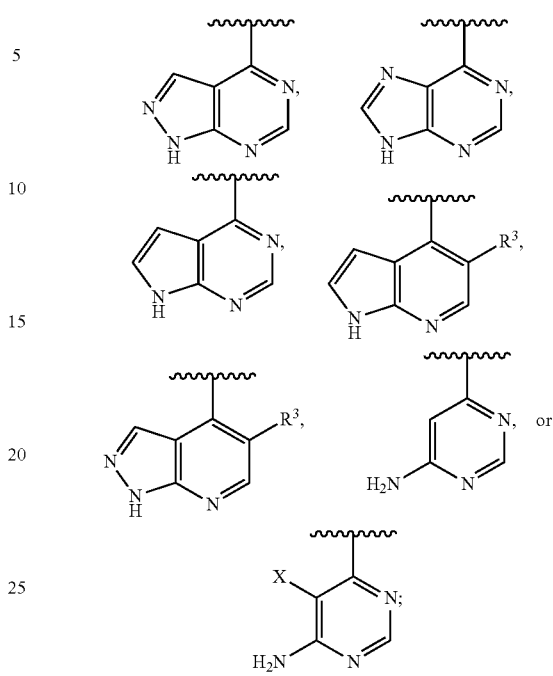

wherein each R³ is independently as defined above and described in classes and subclasses herein, and X is halogen. In certain embodiments, X is fluorine. In certain embodiments, X is chloro. In certain embodiments, X is bromo. In certain embodiments, X is iodo.

In some embodiments, Ring A is other than a benzopyrimidine or quinoline group.

In some embodiments, m is 0. In some embodiments, m is 1. In some embodiments, m is 2. In some embodiments, m is 3. In some embodiments, m is 4. In some embodiments, m is 5. In some embodiments, m is from 1 to 5.

In some embodiments, p is 0. In some embodiments, p is 1. In some embodiments, p is 2. In some embodiments, p is 3. In some embodiments, p is 4. In some embodiments, p is 5. In some embodiments, p is from 1 to 5.

In some embodiments, q is 0. In some embodiments, q is 1. In some embodiments, q is 2. In some embodiments, q is 3. In some embodiments, q is 4. In some embodiments, q is 5. In some embodiments, q is from 1 to 5.

In some embodiments, Ring B is a 3-8 membered saturated or partially unsaturated monocyclic heterocyclic ring having 0-2 heteroatoms in addition to the depicted ring nitrogen atom independently selected from nitrogen, oxygen, or sulfur. In some embodiments, Ring B is a 5-7 membered saturated or partially unsaturated monocyclic heterocyclic ring having 0-2 heteroatoms in addition to the depicted ring nitrogen atom independently selected from nitrogen, oxygen, or sulfur. In some embodiments, Ring B is a 6 membered saturated or partially unsaturated monocyclic heterocyclic ring having 0-1 heteroatoms in addition to the depicted ring nitrogen atom independently selected from nitrogen, oxygen, or sulfur. In certain embodiments, Ring B is piperidinyl. In certain embodiments, Ring B is pyrrolidinyl.

In certain embodiments, Ring B is:

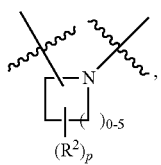

wherein each of R² and p is as defined above and described in classes and subclasses herein.

In certain embodiments, Ring B is:

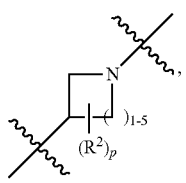

wherein each of R² and p is as defined above and described in classes and subclasses herein.

In certain embodiments, Ring B is selected from:

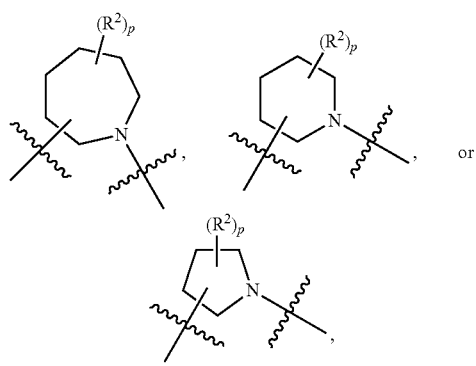

wherein each of R² and p is as defined above and described in classes and subclasses herein.

In certain embodiments, Ring B is selected from:

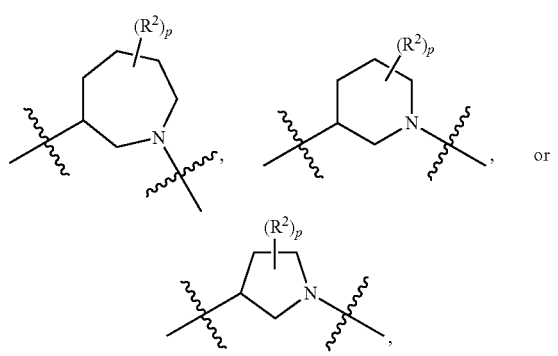

wherein R² is as defined above and described in classes and subclasses herein and p is 0, 1, or 2.

In certain embodiments, Ring B is selected from:

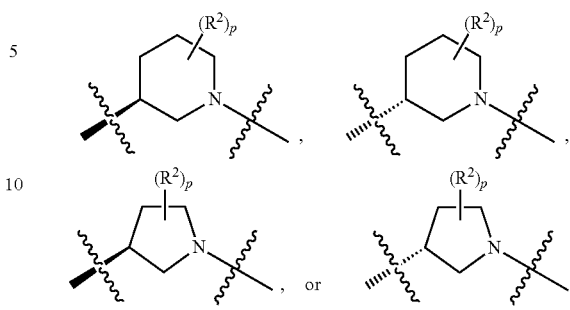

wherein R² is as defined above and described in classes and subclasses herein and p is 0, 1, or 2.

In some embodiments, Ring B is:

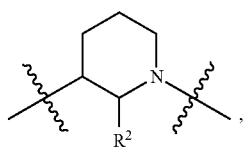

wherein R² is as defined above and described in classes and subclasses herein.

In some embodiments, Ring B is selected from:

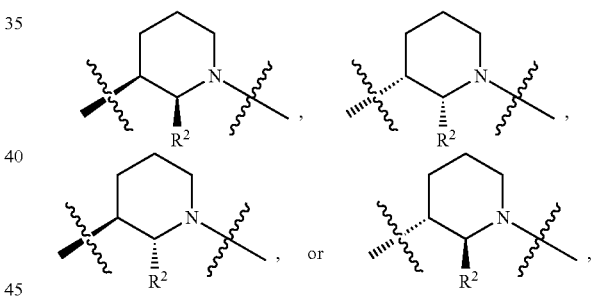

wherein R² is as defined above and described in classes and subclasses herein.

In some embodiments, Ring B is selected from:

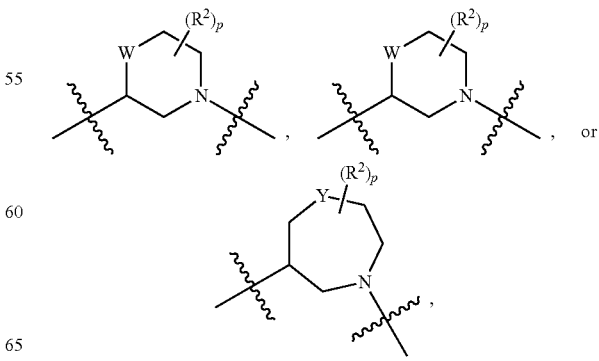

wherein, each of W and Y is independently selected from —CH$_2$—, —S—, —S(O)—, —S(O)$_2$—, —O—, or —NR—;

and each of R, R$^2$ and p is as defined above and described in classes and subclasses herein.

In some embodiments, where L$^1$ is —NR$^5$—, —O—, or —S— for a compound of formula I, W is —CH$_2$—.

In some embodiments, Ring B is:

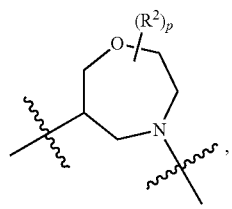

wherein each of R$^2$ and p is as defined above and described in classes and subclasses herein.

In some embodiments, two R$^2$ groups adjacent carbon atoms of Ring B are taken together with their intervening atoms as described above. In some embodiments, Ring B is selected from:

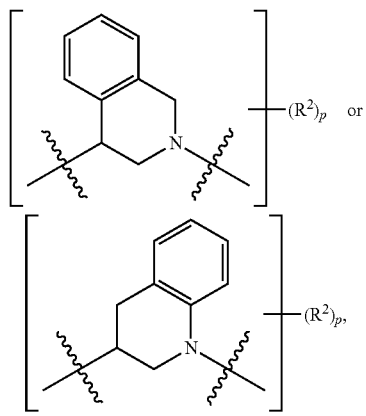

wherein each of R$^2$ and p is as defined above and described in classes and subclasses herein.

In some embodiments, two R$^2$ groups on non-adjacent carbon atoms of Ring B are taken together with their intervening atoms to form an optionally substituted bridge of a bridged bicyclic group as described above. In certain embodiments, Ring B is:

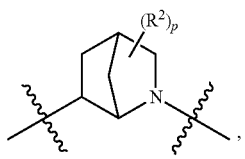

wherein each of R$^2$ and p is as defined above and described in classes and subclasses herein.

In certain embodiments, Ring B is a 7-10 membered saturated or partially unsaturated bicyclic heterocyclic ring having 0-3 heteroatoms in addition to the depicted ring nitrogen atom independently selected from nitrogen, oxygen, or sulfur. In certain embodiments, Ring B is an 8-9 membered saturated or partially unsaturated bicyclic heterocyclic ring having 0-3 heteroatoms in addition to the depicted ring nitrogen atom independently selected from nitrogen, oxygen, or sulfur. In certain embodiments, Ring B is a 9 membered saturated bicyclic heterocyclic ring having 0-1 heteroatoms in addition to the depicted ring nitrogen atom independently selected from nitrogen, oxygen, or sulfur.

In some embodiments, Ring C is phenyl. In some embodiments, Ring C is an 8-10 bicyclic aryl ring. In some embodiments, C is a 10 membered bicyclic aryl ring. In some embodiments, Ring C is a 3-8 membered saturated or partially unsaturated monocylic carbocyclic ring. In some embodiments, Ring C is a 7-10 membered saturated or partially unsaturated bicyclic carbocyclic ring. In some embodiments, Ring C is a 5-6 membered heteroaryl ring having 1-4 heteroatoms independently selected from nitrogen, oxygen or sulfur. In some embodiments, Ring C is a 3-8 membered saturated or partially unsaturated monocyclic heterocyclic ring having 1-2 heteroatoms independently selected from nitrogen, oxygen, or sulfur. In some embodiments, Ring C is a 7-10 membered saturated or partially unsaturated bicyclic heterocyclic ring having 1-4 heteroatoms independently selected from nitrogen, oxygen, or sulfur. In some embodiments, Ring C is an 8-10 membered bicyclic heteroaryl ring having 1-4 heteroatoms independently selected from nitrogen, oxygen, or sulfur.

In certain embodiments, Ring C is phenyl substituted with —(R$^4$)$_q$. In some embodiments, Ring C is selected from:

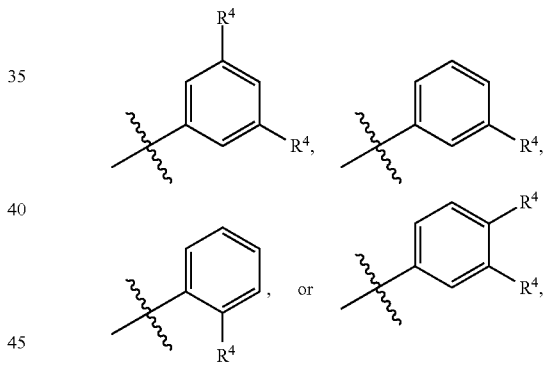

wherein R$^4$ is as defined above and described in classes and subclasses herein.

In some embodiments, Ring C is selected from:

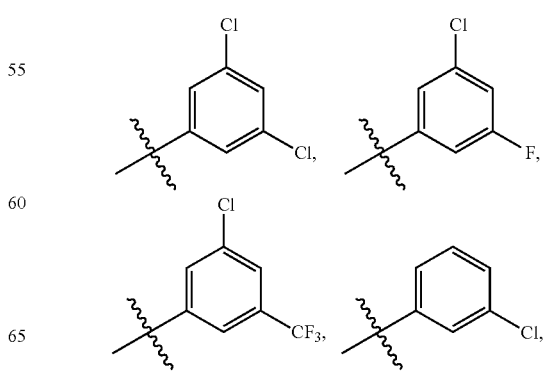

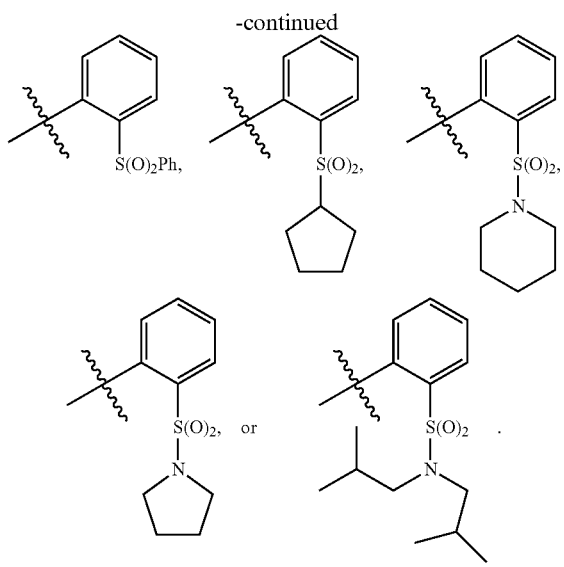

In certain embodiments, $R^1$ is hydrogen. In other embodiments, $R^1$ is $C_{1-4}$ aliphatic. In some embodiments, $R^1$ is methyl. In some embodiments, $R^1$ is formyl. In some embodiments, $R^1$ is taken together with an $R^2$ group to form an optionally substituted 3-7 membered saturated or partially unsaturated monocyclic heterocyclic ring having 1-2 heteroatoms independently selected from nitrogen, oxygen, or sulfur.

In certain embodiments, each $R^2$ is independently halogen, $-NO_2$, $-CN$, $-OR$, $-SR$, $-N(R)_2$, $-C(O)R$, $-CO_2R$, $-C(O)C(O)R$, $-C(O)CH_2C(O)R$, $-S(O)R$, $-S(O)_2R$, $-C(O)N(R)_2$, $-SO_2N(R)_2$, $-OC(O)R$, $-N(R)C(O)R$, $-N(R)N(R)_2$, $-N(R)C(=NR)N(R)_2$, $-C(=NR)N(R)_2$, $-C=NOR$, $-N(R)C(O)N(R)_2$, $-N(R)SO_2N(R)_2$, $-N(R)SO_2R$, $-OC(O)N(R)_2$. In some embodiments, each $R^2$ is independently an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, $R^2$ is halogen. In some embodiments, $R^2$ is optionally substituted $C_{1-12}$ aliphatic. In some embodiments, $R^2$ is $-CF_3$. In some embodiments, $R^2$ is methyl. In some embodiments, $R^2$ is ethyl. In some embodiments, $R^2$ is isopropyl. In some embodiments, $R^2$ is n-butyl. In some embodiments, $R^2$ is a 3-7 membered saturated or partially unsaturated monocyclic carbocyclic ring. In certain embodiments, $R^2$ is cyclopentyl.

In some embodiments, $R^2$ does not comprise a cycloalkylenyl group.

In some embodiments, two $R^2$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, two $R^2$ groups on adjacent carbon atoms are taken together with their intervening atoms to form a 5-7 membered saturated or partially unsaturated monocyclic carbocyclic ring. In some embodiments, two $R^2$ groups on adjacent carbon atoms are taken together with their intervening atoms to form a phenyl ring.

In some embodiments, two $R^2$ groups on non-adjacent carbon atoms are taken together with their intervening atoms to form an optionally substituted bridge of a bridged bicyclic group, wherein the bridge is a $C_{1-3}$ hydrocarbon chain wherein one methylene unit is optionally replaced by $-NR-$, $-O-$, $-C(O)-$, $-OC(O)-$, $-C(O)O-$, $-S-S-$, or $-S-$. In some embodiments, the bridge is a single methylene unit.

In some embodiments, two $R^2$ groups on the same carbon atom are taken together with their intervening atoms to form an oxo group or an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur.

In some embodiments, each $R^3$ is independently halogen, $-NO_2$, $-CN$, $-OR$, $-SR$, $-N(R)_2$, $-C(O)R$, $-CO_2R$, $-C(O)C(O)R$, $-C(O)CH_2C(O)R$, $-S(O)R$, $-S(O)_2R$, $-C(O)N(R)_2$, $-SO_2N(R)_2$, $-OC(O)R$, $-N(R)C(O)R$, $-N(R)N(R)_2$, $-N(R)C(=NR)N(R)_2$, $-C(=NR)N(R)_2$, $-C=NOR$, $-N(R)C(O)N(R)_2$, $-N(R)SO_2N(R)_2$, $-N(R)SO_2R$, or $-OC(O)N(R)_2$. In some embodiments, $R^3$ is an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, $R^3$ is halogen. In certain embodiments, $R^3$ is fluro. In some embodiments, $R^3$ is chloro. In some embodiments, $R^3$ is $-CN$. In some embodiments, $R^3$ is $-N(R)_2$. In some embodiments, $R^3$ is

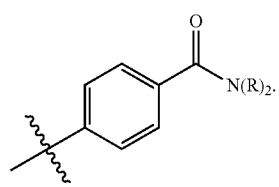

In some embodiments, $R^3$ is $-C(O)NH_2$.

In some embodiments, each $R^4$ is independently halogen, —NO₂, —CN, —OR, —SR, —N(R)₂, —C(O)R, —CO₂R, —C(O)C(O)R, —C(O)CH₂C(O)R, —S(O)R, —S(O)₂R, —C(O)N(R)₂, —SO₂N(R)₂, —OC(O)R, —N(R)C(O)R, —N(R)N(R)₂, —N(R)C(=NR)N(R)₂, —C(=NR)N(R)₂, —C=NOR, —N(R)C(O)N(R)₂, —N(R)SO₂N(R)₂, —N(R)SO₂R, or —OC(O)N(R)₂. In some embodiments, $R^4$ is an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In certain embodiments, $R^4$ is halogen. In certain embodiments, $R^4$ is fluoro. In some embodiments, $R^4$ is chloro. In certain embodiments, each $R^4$ is independently selected from the group consisting of chloro, fluoro, and —CF₃. In some embodiments, $R^4$ is —CF₃. In some embodiments, $R^4$ is —S(O)₂R. In some embodiments, $R^4$ is —SO₂N(R)₂.

In some embodiments, $L^1$ is a covalent bond. In some embodiments, $L^1$ is —NR⁵—. In some embodiments, $L^1$ is —O—. In some embodiments, $L^1$ is —S—. In some embodiments, $L^1$ is —S(O)—. In some embodiments, $L^1$ is —S(O)₂—. In some embodiments, $L^1$ is —C(R⁶)₂—. In some embodiments, $L^1$ is —C(O)—. In some embodiments, $L^1$ is —C(=S)—. In some embodiments, $L^1$ is —C(=NR)—. In some embodiments, $L^1$ is —C(=N₂)—.

In some embodiments, $R^5$ is R. In some embodiments, $R^5$ is R, wherein R is hydrogen or an optionally substituted $C_{1-6}$ aliphatic group. In some embodiments, $R^5$ is hydrogen. In some embodiments, $R^5$ is an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur. In some embodiments, $R^5$ is methyl. In some embodiments, $R^5$ is ethyl. In some embodiments, $R^5$ is propyl. In some embodiments, $R^5$ is —(CH₂)₂OH. In some embodiments, $R^5$ is —CH₂COOH. In some embodiments, $R^5$ is —CH₂C(O)N(CH₃)₂. In some embodiments, $R^5$ is CH(CH₃)₂. In some embodiments, $R^5$ is

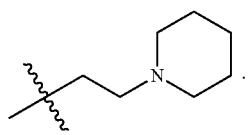 [SMILES: *CCN1CCCCC1]

In some embodiments, $R^5$ is

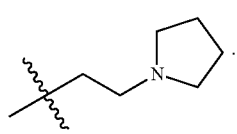 [SMILES: *CCN1CCCC1]

In some embodiments, $R^5$ is

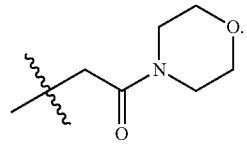 [SMILES: *CC(=O)N1CCOCC1]

In some embodiments, $R^6$ is R. In some embodiments, $R^6$ is hydrogen. In some embodiments, $R^6$ is $C_{1-6}$ aliphatic. In some embodiments, $R^6$ is halogen.

In certain embodiments, $L^2$ is a covalent bond. In some embodiments, $L^2$ is an optionally substituted, bivalent $C_{1-6}$ saturated or unsaturated, straight or branched, hydrocarbon chain, wherein one or two methylene units of $L^2$ are optionally and independently replaced by —C(R⁶)₂—, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—. In some embodiments, $L^2$ is an optionally substituted, bivalent $C_{1-3}$ saturated hydrocarbon chain, wherein one methylene unit of $L^2$ is optionally replaced by —C(R⁶)₂—, —NR—, —O—, —C(O)—, —OC(O)—, —C(O)O—, —S—, —SO—, or —SO₂—. In some embodiments, $L^2$ is a covalent bond or an optionally substituted, bivalent $C_{1-3}$ saturated or unsaturated, straight or branched, hydrocarbon chain. In some embodiments, $L^2$ is —CH₂—. In some embodiments, $L^2$ is —CHR⁶—. In some embodiments, $L^2$ is —CHR—, wherein R is an optionally substituted 3-7 membered saturated or partially unsaturated carbocyclic ring. In some embodiments, $L^2$ is —CHR—, wherein R is cyclopropyl.

In some embodiments, $L^2$ is other than —CHR—, wherein R is t-butyl, cyclohexyl, or isopropyl.

In certain embodiments, $L^3$ is a covalent bond. In some embodiments, $L^3$ is an optionally substituted, bivalent $C_{1-6}$ saturated or unsaturated, straight or branched, hydrocarbon chain, wherein one or two methylene units of $L^3$ are optionally and independently replaced by —C(R⁶)₂—, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—. In some embodiments, $L^3$ is an optionally substituted, bivalent $C_{1-3}$ saturated hydrocarbon chain, wherein one methylene unit of $L^3$ is optionally replaced by —C(R⁶)₂—, —NR—, —O—, —C(O)—, —OC(O)—, —C(O)O—, —S—, —SO—, or —SO₂—. In some embodiments, $L^3$ is a covalent bond or an optionally substituted, bivalent $C_{1-3}$ saturated or unsaturated, straight or branched, hydrocarbon chain. In some embodiments, $L^3$ is —CH₂—. In some embodiments, $L^3$ is —CHR⁶—.

In certain embodiments, when Ring B is a pyrrolidine ring, one or more of the following applies:
 i. $L^1$ is other than —O—;
 ii. $L^2$ is —CH₂—;
 iii. Ring A is other than a quinoxalinyl, quinolinyl, isoquinolinyl, quinazolinyl, indolyl, isoindolyl, benzothiazolyl, benzoxazolyl, benzimidazolyl, or pyridyl ring;
 iv. Ring A is thienyl, furanyl, pyrrolyl, imidazolyl, pyrazolyl, oxazolyl, isoxazolyl, thiazolyl, isothiazolyl, thiadiazolyl, pyridyl, pyridazinyl, pyrimidinyl, or pyrazinyl; or
 v. Ring A is selected from a group depicted in Table 1 or Table 2, above.

In certain embodiments, when a provided compound is of formula A:

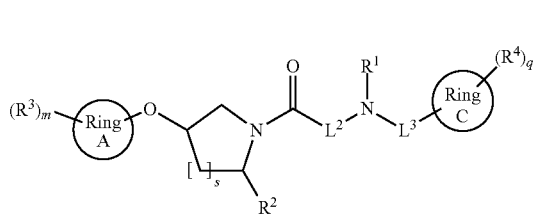

wherein s is 0 to 6, and each of Ring A, Ring C, $R^1$, $R^2$, $R^3$, $R^4$, $L^2$, $L^3$, m, and q is as defined above and defined in classes and subclasses herein;
s is other than 1 or $R^2$ is other than an optionally substituted

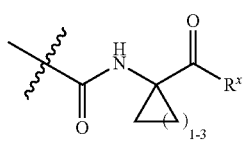

group;
wherein $R^x$ is —OH, —$NHSO_2R$, or —$NH(SO_2)N(R)_2$. In some embodiments, a compound of formula I is other than a compound of formula A wherein s is 1 and $R^2$ is an optionally substituted

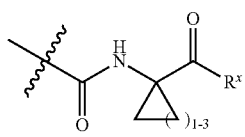

group and $R^x$ is —OH, —$NHSO_2R$, or —$NH(SO_2)N(R)_2$.

In some embodiments, $L^1$ is a covalent bond and Ring B is directly bonded to Ring A. In some embodiments, $L^1$ is a covalent bond and Ring B is a 7-10 membered saturated or partially unsaturated bicyclic heterocyclic ring having 0-3 heteroatoms in addition to the depicted ring nitrogen atom independently selected from nitrogen, oxygen, or sulfur. In some embodiments, the present invention provides a compound of formula II:

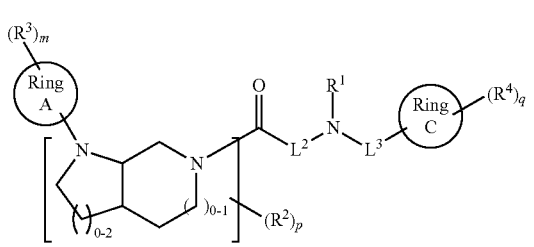

or a pharmaceutically acceptable salt thereof,
wherein each of $R^1$, $R^2$, $R^3$, $R^4$, $L^2$, $L^3$, L Ring A, Ring C, m, p, and q is as defined above and described in classes and subclasses herein.

In some embodiments, the present invention provides a compound of formula II-a:

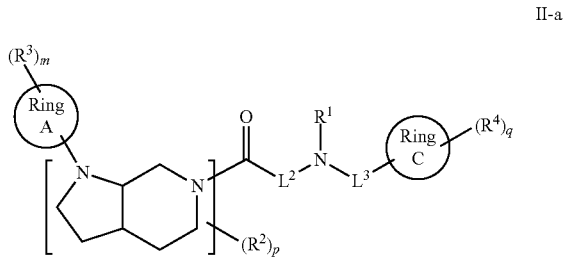

or a pharmaceutically acceptable salt thereof,
wherein each of $R^1$, $R^2$, $R^3$, $R^4$, $L^2$, $L^3$, L Ring A, Ring C, m, p, and q is as defined above and described in classes and subclasses herein.

In some embodiments, the present invention provides a compound of formula II-a-a or II-a-2:

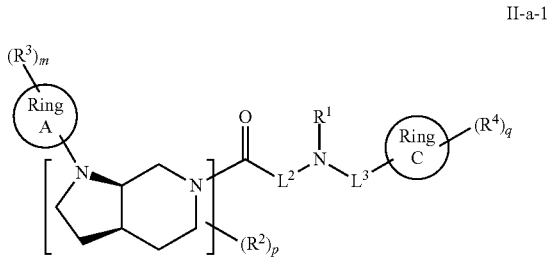

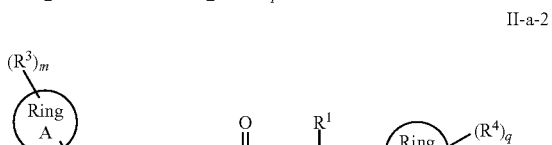

or a pharmaceutically acceptable salt thereof,
wherein each of $R^1$, $R^2$, $R^3$, $R^4$, $L^2$, $L^3$, Ring A, Ring C, m, p, and q is as defined above and described in classes and subclasses herein.

In some embodiments, the present invention provides a compound of formula III:

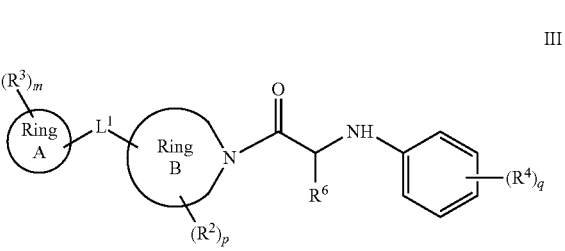

or a pharmaceutically acceptable salt thereof,
wherein each of $R^2$, $R^3$, $R^4$, $L^1$, Ring A, Ring B, m, p, and q is as defined above and described in classes and subclasses herein, and $R^6$ is hydrogen or $C_{1-6}$ aliphatic.

In some embodiments, the present invention provides a compound of formula IV:

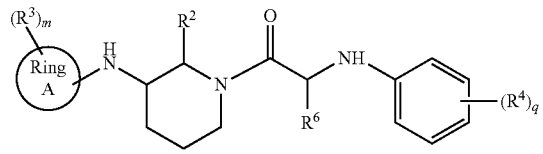

IV or a pharmaceutically acceptable salt thereof,
wherein each of $R^3$, $R^4$, Ring A, m, and q is as defined above and described in classes and subclasses herein, and $R^2$ and $R^6$ are independently hydrogen or $C_{1-6}$ aliphatic.

In some embodiments, the present invention provides a compound of formula V:

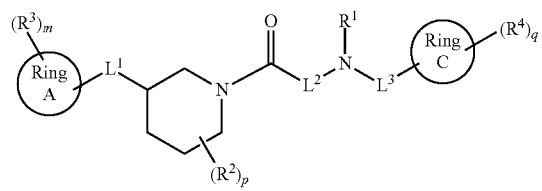

V or a pharmaceutically acceptable salt thereof,
wherein each of Ring A, Ring C, $R^1$, $R^2$, $R^3$, $R^4$, $L^1$, $L^2$, $L^3$, m, p, and q is as defined above and defined in classes and subclasses herein.

In some embodiments, a provided compound is a compound depicted in Table 4, below, or a pharmaceutically acceptable salt thereof.

I. Exemplary Synthesis

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Scheme 1

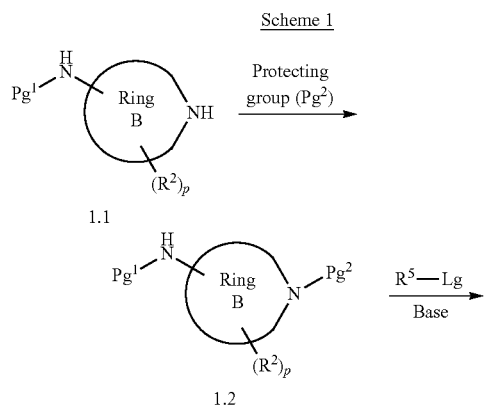

In some embodiments, compounds of formula I are prepared according to Scheme 1, above, using commercially available or synthesized substituted amine protected heterocycles such as 3-(tert-Butoxycarbonylamino)pyrrolidine, 3-(tert-Butoxycarbonylamino)piperidine or 3-(tert-Butoxycarbonylamino)azepane (Huang, P.; Wang, S, Zheng, H, Fei, X. Tetrahedron Lett. 1997, 38, 271. Hu, X. E.; Kim, N. K.; Ledoussal, B. Org. Lett. 2002, 4, 4499. Kitas, E. A.; Galley, G.; Jakob-Roetne, R.; Flohr, A.; Wostl, A.; Mauser, H.; Alker, A. M.; Czech, C.; Ozmen, L.; David-Pierson, P.; Reinhardt, D. Jacobsen, H. Bioorg. Med. Chem. Lett. 2008, 18, 304. Burgey, C. S.; Paone, D. V.; Shaw, A. W.; Nguyen, D. N.; Deng, Z. J.; Williams, T. M.; Vacca, J. P.; Selnick, H. G.; Potteiger, C. M. PCT Int. Appl. (2006), 292 pp. WO 2006044504).

The heterocyclic amine, compound 1.1, is protected using an appropriate protecting group familiar to those skilled in the art to afford compound 1.2. The exo-cyclic amino group is then substituted upon treatment with a base such as sodium hydride or by other bases (e.g., DIEA, $Et_3N$, $K_2CO_3$, etc.) familiar to one skilled in the art and in a solvent such as DMF or other appropriate solvents to yield 1.3.

The protected heterocyclic amine 1.3 is de-protected to afford compound 1.4 which can be reacted with the appropriate electrophile such as a substituted acid chloride, sulfonyl chloride, alkyl halide or carboxylic acid which can be activated using standard peptide coupling reagents such as EDCI/HOBt, PyBOP, HATU or BEM (Carpino, L. A. *J. Am. Chem. Soc.* 1993, 115, 4397. Carpino, L. A.; El-Faham, A. *J. Am. Chem. Soc.* 1995, 117, 5401. Li, P.; Xu, J. C. *J. Pept. Res.* 2001, 58, 129.) in the presence of a base such as DIEA or other bases familiar to one skilled in the art and in an appropriate solvent to yield 1.5.

Alternatively and/or additionally, the cyclic amine 1.4 can be reacted with chloroformate or chlorothioformate or o-, p-nitrophenylchloroformate or phenylchloroformate (or their thiocarbonyl equivalents), or diphenyl cyanocarbonimidate followed by displacement with the appropriate amine can also yield the corresponding urea, thiourea or cyanoguanidine.

The exo-cyclic amine protecting group can be removed upon treatment with suitable conditions as described in Greene and Wuts, Protective Group in Organic Synthesis, 3rd edition, John Wiley & Sons, New York. to afford compound 1.6. Amination of compound 1.6, by treatment with various substituted heteroaromatic such as pyridinyl and pyrimidyl moieties using DIEA or by other bases familiar to one skilled in the art and in a solvent such as DMF or another appropriate solvents, affords 1.7.

Alternatively, the N-amination of 1.6 with various substituted heteroaromatic and aromatic moities can be accomplished utilizing Buchwald coupling (Shafir, A. Buchwald, S. L. *J. Am. Chem. Soc.* 2006, 128, 8742. Mehrotra, M. M. et. al. *Bioorganic & Medicinal Chemistry Letters* 2002, 12, 1103) to afford compound 1.7.

The groups "Lg", "Lg$^1$", and "Lg$^2$" in Schemes 1-3 are each independently suitable leaving groups, i.e., groups that are subject to nucleophilic displacement. A "suitable leaving group" is a chemical group that is readily displaced by a desired incoming chemical moiety such as an amine. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methoxy, methanesulfonyloxy (mesyloxy), tosyloxy, triflyloxy, nitro-phenylsulfonyloxy (nosyloxy), and bromo-phenylsulfonyloxy (brosyloxy).

The groups "Pg$^1$" and "Pg$^2$" in Schemes 1-3 are each independently suitable protecting groups, as defined above and described herein. One of ordinary skill will be familiar with a variety of protecting group and protecting group strategies that many be employed in the Schemes depicted below.

Each of Ring A, Ring B, Ring C, R$^1$, R$^2$, R$^3$, R$^4$, R$^5$, L$^1$, L$^2$, L$^3$, m, p, and q in Schemes 1-3 is as defined above and described in classes and subclasses herein.

In some embodiments, certain compounds of formula I are prepared according to Scheme 2, below, via intermediate 1.4 which can be substituted using the appropriate electrophile such as 2-chloroacetyl chloride in the presence of an organic base such as triethylamine or other suitable bases familiar to those skilled in the art and in a solvent such as dichloromethane or another appropriate solvent to provide compound 2.1. Compound 2.1 can undergo nucleophilic displacement with various nucleophiles such as primary and secondary amines to yield compounds represented by structure 2.2. The exo-cyclic amine protecting group can be removed upon treatment with suitable conditions as described in Greene and Wuts, Protective Group in Organic Synthesis, 3rd edition, John Wiley & Sons, New York to give compound 2.3. The N-amination can also be accomplished utilizing Buchwald coupling (Shafir, A. Buchwald, S. L. *J. Am. Chem. Soc.* 2006, 128, 8742. Mehrotra, M. M. et. al. *Bioorganic & Medicinal Chemistry Letters* 2002, 12, 1103) to afford compound of formula 2.4.

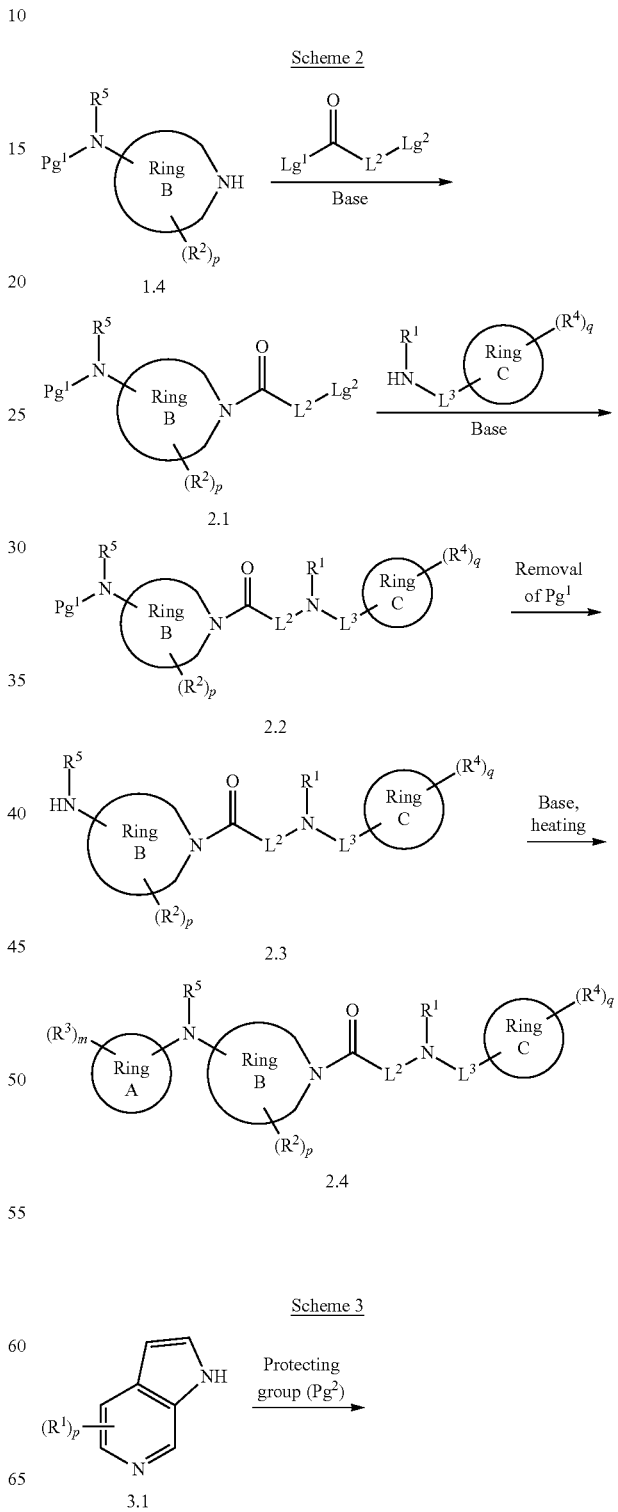

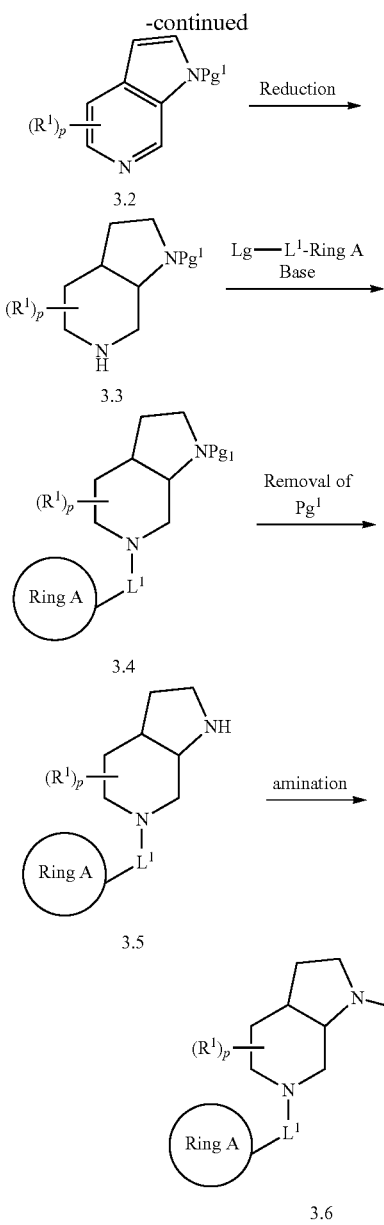

In some embodiments, certain compounds of formula I are prepared according to Scheme 3, above. Heterocyclic amine 3.1 is protected using an appropriate protecting group familiar to those skilled in the art to afford compound. Protected amine 3.2 is reduced using suitable reducing conditions known to the skilled artisan (see March, supra) to afford saturated heterocycle 3.3. The cyclic amine 3.3 can be reacted with the appropriate electrophile such as a substituted acid chloride, sulfonyl chloride, alkyl halide or carboxylic acid which can be activated using standard peptide coupling reagents such as EDCI/HOBt, PyBOP, HATU or BEM (Carpino, L. A. *J. Am. Chem. Soc.* 1993, 115, 4397. Carpino, L. A.; El-Faham, A. *J. Am. Chem. Soc.* 1995, 117, 5401. Li, P.; Xu, J. C. *J. Pept. Res.* 2001, 58, 129.) in the presence of a base such as DIEA or other bases familiar to one skilled in the art and in an appropriate solvent to yield 3.4. Alternatively and/or additionally, the cyclic amine 3.3 can be reacted with chloroformate or chlorothioformate or o-, p-nitrophenylchloroformate or phenylchloroformate (or their thiocarbonyl equivalents), or diphenyl cyanocarbonimidate followed by displacement with the appropriate amine can also yield the corresponding urea, thiourea or cyanoguanidine. Compound 3.4 is then deprotected upon treatment with suitable conditions as described in Greene and Wuts (supra) to yield amine 3.5. Amination of compound 3.5, by treatment with various substituted heteroaromatic such as pyridinyl and pyrimidyl moieties using DIEA or by other bases familiar to one skilled in the art and in a solvent such as DMF or another appropriate solvents, affords 3.6. Alternatively, the N-amination of 3.5 with various substituted heteroaromatic and aromatic moities can be accomplished utilizing Buchwald coupling (Shafir, A. Buchwald, S. L. *J. Am. Chem. Soc.* 2006, 128, 8742. Mehrotra, M. M. et. al. *Bioorganic & Medicinal Chemistry Letters* 2002, 12, 1103) to afford compound 3.6.

In certain embodiments, each of the aforementioned synthetic steps of Schemes 1-3 may be performed sequentially with isolation of each intermediate performed after each step. Alternatively, each of the steps as depicted in Schemes 1-3 above, may be performed in a manner whereby no isolation of each intermediate is performed. Furthermore, it will be readily apparent to the skilled artisan that additional steps may be performed to accomplish particular protection group and/or deprotection strategies.

It will be appreciated by the skilled artisan that certain starting materials depicted in Scheme 1-3 may be readily interchanged with other starting materials or reagents to provide additional compounds of formula I. Such substitutions could be made with routine experimentation. For example, the exocyclic amine group of compound 1.1 could be replaced with an optionally protected —O—, —S—, —S(O)—, —S(O)$_2$—, —C(R$^6$)$_2$—, —C(O)—, —C(=S)—, —C(=NR)—, or —C(=N$_2$)— group, and carrying forth the described synthetic procedure can provide additional compounds of formula I.

Methods of Use

In certain embodiments, compounds of the present invention are for use in medicine. In some embodiments, the present invention provides method of decreasing enzymatic activity of a kinase in the Tec kinase family (e.g., Btk, Tec, Itk, Rlk, Bmx). In some embodiments, such methods include contacting a kinase of the Tec kinase family with an effective amount of a Tec kinase family inhibitor. Therefore, the present invention further provides methods of inhibiting Tec kinase family enzymatic activity by contacting a Tec kinase family member with a Tec kinase family inhibitor of the present invention. As used herein, the term "Tec kinase family member" refers to any non-receptor tyrosine kinase in the Tec kinase family. In some embodiments, Tec kinase family members are Tec, Btk, Itk, Rlk, Txk, Lck, and Bmx.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIPS binding and/or phosphorylation of PLCγ is decreased. In some embodiments, the half maximal inhibitory concentration (IC$_{50}$) of the Btk inhibitor against Btk is less than 1 μM. In some embodiments, the IC$_{50}$ of the Btk inhibitor against Btk is less than 500 nM. In some embodiments, the IC$_{50}$ of the Btk inhibitor against Btk is less than 100 nM. In some embodiments, the IC$_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 µM. In some embodiments, the $IC_{50}$ of the Btk inhibitor against Btk is from 0.1 nM to 1 µM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In some embodiments, the present invention provides methods of decreasing Tec kinase enzymatic activity. In some embodiments, such methods include contacting a Tec with an effective amount of a Tec inhibitor. Therefore, the present invention further provides methods of inhibiting Tec enzymatic activity by contacting a Tec with a Tec inhibitor of the present invention.

Tec enzymatic activity, as used herein, refers to Tec kinase enzymatic activity. In some embodiments, the half maximal inhibitory concentration ($IC_{50}$) of the Tec inhibitor against Tec is less than 1 µM. In some embodiments, the $IC_{50}$ of the Tec inhibitor against Tec is less than 500 nM. In some embodiments, the $IC_{50}$ of the Tec inhibitor against Tec is less than 100 nM. In some embodiments, the $IC_{50}$ of the Tec inhibitor against Tec is less than 10 nM. In some embodiments, the $IC_{50}$ of the Tec inhibitor against Tec is less than 1 nM. In some embodiments, the $IC_{50}$ of the Tec inhibitor against Tec is from 0.1 nM to 10 µM. In some embodiments, the $IC_{50}$ of the Tec inhibitor against Tec is from 0.1 nM to 1 µM. In some embodiments, the $IC_{50}$ of the Tec inhibitor against Tec is from 0.1 nM to 100 nM. In some embodiments, the $IC_{50}$ of the Tec inhibitor against Tec is from 0.1 nM to 10 nM.

In certain embodiments, the present invention provides methods of decreasing Itk kinase enzymatic activity. In some embodiments, such methods include contacting a Itk with an effective amount of a Itk inhibitor. Therefore, the present invention further provides methods of inhibiting Itk enzymatic activity by contacting a Itk with a Itk inhibitor of the present invention.

Itk enzymatic activity, as used herein, refers to Itk kinase enzymatic activity. In some embodiments, the half maximal inhibitory concentration ($IC_{50}$) of the Itk inhibitor against Itk is less than 1 µM. In some embodiments, the $IC_{50}$ of the Itk inhibitor against Itk is less than 500 nM. In some embodiments, the $IC_{50}$ of the Itk inhibitor against Itk is less than 100 nM. In some embodiments, the $IC_{50}$ of the Itk inhibitor against Itk is less than 10 nM. In some embodiments, the $IC_{50}$ of the Itk inhibitor against Itk is less than 1 nM. In some embodiments, the $IC_{50}$ of the Itk inhibitor against Itk is from 0.1 nM to 10 µM. In some embodiments, the $IC_{50}$ of the Itk inhibitor against Itk is from 0.1 nM to 1 µM. In some embodiments, the $IC_{50}$ of the Itk inhibitor against Itk is from 0.1 nM to 100 nM. In some embodiments, the $IC_{50}$ of the Itk inhibitor against Itk is from 0.1 nM to 10 nM.

In certain embodiments, the present invention provides methods of decreasing Rlk kinase enzymatic activity. In some embodiments, such methods include contacting a Rlk with an effective amount of a Rlk inhibitor. Therefore, the present invention further provides methods of inhibiting Rlk enzymatic activity by contacting a Rlk with a Rlk inhibitor of the present invention.

Rlk enzymatic activity, as used herein, refers to Rlk kinase enzymatic activity. In some embodiments, the half maximal inhibitory concentration ($IC_{50}$) of the Rlk inhibitor against Rlk is less than 1 µM. In some embodiments, the $IC_{50}$ of the Rlk inhibitor against Rlk is less than 500 nM. In some embodiments, the $IC_{50}$ of the Rlk inhibitor against Rlk is less than 100 nM. In some embodiments, the $IC_{50}$ of the Rlk inhibitor against Rlk is less than 10 nM. In some embodiments, the $IC_{50}$ of the Rlk inhibitor against Rlk is less than 1 nM. In some embodiments, the $IC_{50}$ of the Rlk inhibitor against Rlk is from 0.1 nM to 10 µM. In some embodiments, the $IC_{50}$ of the Rlk inhibitor against Rlk is from 0.1 nM to 1 In some embodiments, the $IC_{50}$ of the Rlk inhibitor against Rlk is from 0.1 nM to 100 nM. In some embodiments, the $IC_{50}$ of the Rlk inhibitor against Rlk is from 0.1 nM to 10 nM.

In certain embodiments, the present invention provides methods of decreasing Bmx kinase enzymatic activity. In some embodiments, such methods include contacting a Bmx with an effective amount of a Bmx inhibitor. Therefore, the present invention further provides methods of inhibiting Bmx enzymatic activity by contacting a Bmx with a Bmx inhibitor of the present invention.

Bmx enzymatic activity, as used herein, refers to Bmx kinase enzymatic activity. In some embodiments, the half maximal inhibitory concentration ($IC_{50}$) of the Bmx inhibitor against Bmx is less than 1 µM. In some embodiments, the $IC_{50}$ of the Bmx inhibitor against Bmx is less than 500 nM. In some embodiments, the $IC_{50}$ of the Bmx inhibitor against Bmx is less than 100 nM. In some embodiments, the $IC_{50}$ of the Bmx inhibitor against Bmx is less than 10 nM. In some embodiments, the $IC_{50}$ of the Bmx inhibitor against Bmx is less than 1 nM. In some embodiments, the $IC_{50}$ of the Bmx inhibitor against Bmx is from 0.1 nM to 10 µM. In some embodiments, the $IC_{50}$ of the Bmx inhibitor against Bmx is from 0.1 nM to 1 µM. In some embodiments, the $IC_{50}$ of the Bmx inhibitor against Bmx is from 0.1 nM to 100 nM. In some embodiments, the $IC_{50}$ of the Bmx inhibitor against Bmx is from 0.1 nM to 10 nM.

In certain embodiments, the present invention provides methods of decreasing Txk kinase enzymatic activity. In some embodiments, such methods include contacting a Txk with an effective amount of a Txk inhibitor. Therefore, the present invention further provides methods of inhibiting Txk enzymatic activity by contacting a Txk with a Txk inhibitor of the present invention.

Txk enzymatic activity, as used herein, refers to Txk kinase enzymatic activity. In some embodiments, the half maximal inhibitory concentration ($IC_{50}$) of the Txk inhibitor against Txk is less than 1 µM. In some embodiments, the $IC_{50}$ of the Txk inhibitor against Txk is less than 500 nM. In some embodiments, the $IC_{50}$ of the Txk inhibitor against Txk is less than 100 nM. In some embodiments, the $IC_{50}$ of the Txk inhibitor against Txk is less than 10 nM. In some embodiments, the $IC_{50}$ of the Txk inhibitor against Txk is less than 1 nM. In some embodiments, the $IC_{50}$ of the Txk inhibitor against Txk is from 0.1 nM to 10 µM. In some embodiments, the $IC_{50}$ of the Txk inhibitor against Txk is from 0.1 nM to 1 µM. In some embodiments, the $IC_{50}$ of the Txk inhibitor against Txk is from 0.1 nM to 100 nM. In some embodiments, the $IC_{50}$ of the Txk inhibitor against Txk is from 0.1 nM to 10 nM.

In certain embodiments, the present invention provides methods of decreasing Lck kinase enzymatic activity. In some embodiments, such methods include contacting a Lck with an effective amount of a Lck inhibitor. Therefore, the present invention further provides methods of inhibiting Lck enzymatic activity by contacting a Lck with a Lck inhibitor of the present invention.

Lck enzymatic activity, as used herein, refers to Lck kinase enzymatic activity. In some embodiments, the half maximal inhibitory concentration ($IC_{50}$) of the Lck inhibitor against Lck is less than 1 µM. In some embodiments, the $IC_{50}$ of the Lck inhibitor against Lck is less than 500 nM. In some embodiments, the $IC_{50}$ of the Lck inhibitor against Lck is less than 100 nM. In some embodiments, the $IC_{50}$ of the Lck inhibitor against Lck is less than 10 nM. In some embodiments, the $IC_{50}$ of the Lck inhibitor against Lck is less than 1 nM. In some embodiments, the $IC_{50}$ of the Lck inhibitor against Lck is from 0.1 nM to 10 µM. In some embodiments, the $IC_{50}$ of the Lck inhibitor against Lck is from 0.1 nM to 1 µM. In some embodiments, the $IC_{50}$ of the Lck inhibitor against Lck is from 0.1 nM to 100 nM. In some embodiments, the $IC_{50}$ of the Lck inhibitor against Lck is from 0.1 nM to 10 nM.

In some embodiments, inhibitors of such Tec kinases are useful for the treatment of diseases and disorders that may be alleviated by inhibiting (i.e., decreasing) enzymatic activity of one or more Tec kinases. The compounds of the invention are effective inhibitors of Tec family kinases and would thus be useful in treating diseases associated with the activity of one or more of the Tec family kinases. By "diseases" is meant diseases or disease symptoms. Thus, the present invention provides methods of treating autoimmune disorders, inflammatory disorders, and cancers in a subject in need thereof. Such methods include administering to the subject a therapeutically effective amount of an inhibitor of Tec, Btk, Itk, Rlk, Txk, Lck, and/or Bmx kinase.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barré syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

Itk, Rlk, and Tec are expressed in T cells and contribute to multiple aspects of T-cell biology, including T-cell development, T-cell activation, and mature T-cell differentiation. The inhibition of T cell activation is therapeutically useful for selectively suppressing immune function. Thus, the inhibition of Itk is an attractive means for preventing and treating a variety of immune disorders, including inflammatory diseases, autoimmune diseases, organ and bone marrow transplant rejection and other disorders associated with T cell mediated immune response. Therefore, in addition to the disorder, diseases, and conditions mentioned above, compounds of the present invention may be used to prevent or treat contact dermatitis, psoriasis, rheumatoid arthritis, and graft versus host disease (and other forms of organ or bone marrow transplant rejection).

Inhibitors of mast cell activation and degranulation block the release of allergic and pro-inflammatory mediators and cytokines. Thus, inhibitors of Itk have potential utility in treating inflammatory and allergic disorders, including asthma, chronic obstructive pulmonary disease (COPD), adult respiratory distress syndrome (ARDS), bronchitis, conjunctivitis, dermatitis and allergic rhinitis. Other disorders associated with T cell or mast cell mediated immune response will be evident to those of ordinary skill in the art and can also be treated with the compounds and compositions of this invention.

It has been found that in the absence of Itk in mice, increased numbers of memory T cells are generated. Vaccination methods can be improved by increasing the number of memory T cells generated. In some embodiments, the present invention compounds useful in the formulation of vaccines.

Inhibitors of Tec family kinases have potential utility in combination with other therapies for the treatment of immune, inflammatory, proliferative, and allergic disorders. Examples, though not all encompassing, include co-administration with steroids, leukotriene antagonists, anti-histamines, cyclosporin, or rapamycin.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Assays

To develop useful Tec kinase family inhibitors, candidate inhibitors capable of decreasing Tec kinase family enzymatic activity may be identified in vitro. The activity of the inhibitor compounds can be assayed utilizing methods known in the art and/or those methods presented herein.

Compounds that decrease Tec kinase family members' enzymatic activity may be identified and tested using a biologically active Tec kinase family member, either recombinant or naturally occurring. Tec kinases can be found in native cells, isolated in vitro, or co-expressed or expressed in a cell. Measuring the reduction in the Tec kinase family member enzymatic activity in the presence of an inhibitor relative to the activity in the absence of the inhibitor may be performed using a variety of methods known in the art, such as the POLYGAT-LS assays described below in the Examples. Other methods for assaying the activity of Btk and other Tec kinases are known in the art. The selection of appropriate assay methods is well within the capabilities of those of skill in the art.

Once compounds are identified that are capable of reducing Tec kinase family members' enzymatic activity, the compounds may be further tested for their ability to selectively inhibit a Tec kinase family member relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to a Tec kinase family member activity. In addition to cell cultures, animal models may be used to test Tec kinase family member inhibitors for their ability to treat autoimmune disorders, inflammatory disorders, or cancer in an animal model.

Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Example 1

Synthesis of 2-(3-chloro-5-fluorophenylamino)-1-((S)-3-(7H-pyrrolo[2,3-d]pyrimidin-4-ylamino)piperidin-1-yl)ethanone

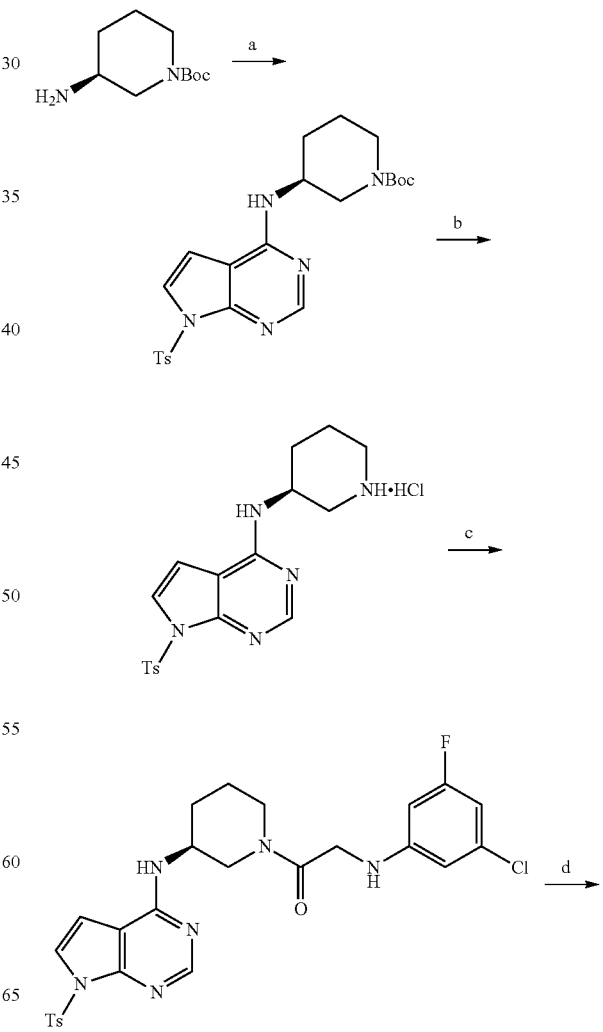

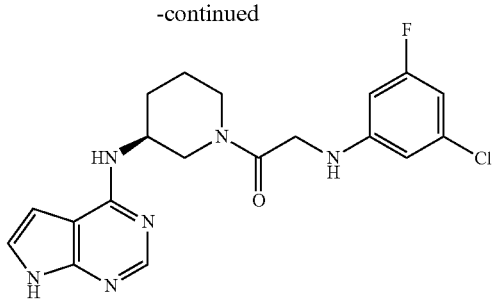

Reagents and conditions: a) 4-Chloro-7-tosyl-7H-pyrrolo[2,3-d]pyrimidine, DIEA, DMF, 90° C., 15 h; b) EtOH:HCl, rt, 30 min.; c) 2-(3-Chloro-5-fluorophenylamino)acetic acid, EDCI, HOBt, DIEA, DMF, rt, 5 h; e) $K_2CO_3$, MeOH:$H_2O$, 50° C., 2 h.

Synthesis of (S)-tert-butyl 3-(7-tosyl-7H-pyrrolo[2,3-d]pyrimidin-4-ylamino)piperidine-1-carboxylate To a solution of (S)-1-benzyl-N-methylpiperidin-3-amine (2.2 g, 11.0 mmol) and 4-chloro-7-tosyl-7H-pyrrolo[2,3-d] pyrimidine (3.4 g, 11.0 mmol) in anhydrous DMF (30 mL), $Et_3N$ (3.8 mL, 27.6 mmol) was added and the reaction mixture was stirred at 90° C. for 4 h. After completion of the reaction (TLC), the reaction mixture was diluted with EtOAc (100 mL) and was washed with water (3×40 mL). The EtOAc layer was then dried over $Na_2SO_4$ and evaporated under vacuo to give a residue that was subjected to purification by column chromatography (silica gel, gradient EtOAc in hexanes) to afford the titled intermediate (3.4 g, 65%). $^1$H NMR (400 MHz, DMSO-$d_6$): δ 8.22 (s, 1H), 7.95 (d, J=8.2 Hz, 2H), 7.57 (d, J=2.5 Hz, 2H), 7.40 (d, J=8.2 Hz, 2H), 6.92 (s, 1H), 3.98-3.90 (m, 2H), 3.70-3.60 (m, 2H), 3.21-2.90 (m, 1H), 2.17 (s, 3H), 1.97-1.78 (m, 2H), 1.71-1.60 (m, 2H), 1.12 (s, 9H). LC-MS: m/z [M+1]=472.

Synthesis of (S)—N-(piperidin-3-yl)-7-tosyl-7H-pyrrolo[2,3-d]pyrimidin-4-amine hydrochloride To a solution of compound (S)-tert-butyl 3-(7-tosyl-7H-pyrrolo[2,3-d]pyrimidin-4-ylamino)piperidine-1-carboxylate (3.4 g, 7.2 mmol) in dioxane (20 mL) at 0° C., a solution of HCl in dioxane (50 mL) was added until the pH was acidic at 0° C. and stirred for 30 min. at the same temperature. The reaction mixture was concentrated in vacuo to give a residue that was triturated with ether to give (S)—N-(piperidin-3-yl)-7-tosyl-7H-pyrrolo[2,3-d]pyrimidin-4-amine hydrochloride (2 g, 74%) as a free flowing solid. $^1$H NMR (400 MHz, DMSO-$d_6$): δ 9.19 (s, 1H), 8.32 (s, 1H), 7.98 (d, J=8.2 Hz, 2H), 7.62 (d, J=2.5 Hz, 1H), 7.42 (d, J=8.2 Hz, 2H), 7.22 (d, J=2.5 Hz, 1H), 5.80 (s, 1H), 4.29-4.25 (m, 2H), 3.38-3.32 (m, 1H), 3.19-3.12 (m, 1H), 3.00-2.97 (m, 1H), 2.35 (s, 3H), 2.01-1.95 (m, 2H), 1.75-1.69 (m, 2H). LC-MS: m/z [M+1]=372.

Synthesis of (2-(3-chloro-5-fluorophenylamino)-1-((S)-3-(7-tosyl-7H-pyrrolo[2,3d]-pyrimidin-4-ylamino)piperidin-1-yl)ethanone To a cooled solution of 2-(2-chlorophenylamino)acetic acid (136 mg, 0.67 mmol) in anhydrous DMF (10 mL) was added HOBt (100 mg, 0.79 mmol) and EDCI (154 mg 0.8 mmol) and the reaction mixture was stirred for 10 min at 0° C. To the reaction mixture was added (S)—N-(piperidin-3-yl)-7-tosyl-7H-pyrrolo[2,3-d]pyrimidin-4-amine hydrochloride (250 mg, 0.67 mmol) and DIEA (104 mg, 0.80 mmol) in succession. The reaction mixture was allowed to warm to rt and was stirred overnight. After completion of the reaction (TLC) the reaction mixture was diluted with EtOAc (50 mL) and was washed with water (3×20 mL). The EtOAc layer was then dried over $Na_2SO_4$ and evaporated in vacuo to give a residue that was purified by column chromatography (silica gel, gradient MeOH in $CH_2Cl_2$) to afford the titled intermediate (250 mg, 61%). LC-MS: m/z [M+1]=558.

Synthesis of 2-(3-chloro-5-fluorophenylamino)-1-((S)-3-(7H-pyrrolo[2,3-d]pyrimidin-4-ylamino)piperidin-1-yl)ethanone To a solution of 2-(3-chloro-5-fluorophenylamino)-1-((S)-3-(7-tosyl-7H-pyrrolo[2,3-d]pyrimidin-4-ylamino)piperidin-1-yl)ethanone (220 mg, 0.39 mmol) in MeOH:$H_2O$ (8:2 mL) was added $K_2CO_3$ (164 mg, 1.18 mmol) and the reaction mixture was heated to 60° C. for 1 h. The reaction mixture was concentrated in vacuo and the residue obtained was diluted with EtOAc. The EtOAc suspension was filtered through celite, the filtrate was then dried over $Na_2SO_4$, and concentrated in vacuo to give a residue that was subjected to purification by column chromatography (silica gel, gradient MeOH in $CH_2Cl_2$) to afford the titled compound (180 mg, 83%). 1H NMR (400 MHz, $CD_3OD$): δ 8.20 and 8.09 (2s, 1H), 7.06 (d, J=3.6 Hz, 1H), 6.61 and 6.58 (2d, J=3.6 Hz, 1H), 6.47 and 6.45 (2s, 1H), 6.35-6.27 (m, 2H), 4.97-4.79 (m, 2H), 4.25-3.95 (m, 3H), 3.11-3.05 (m, 1H), 2.95-2.86 (m, 1H), 2.14-1.85 (m, 2H), 1.80-1.55 (m, 2H). LC-MS: m/z [M+1]=403.

Example 2

Synthesis of 2-(3,5-dichlorophenylamino)-1-((S)-3-(7H-pyrrolo[2,3-d]pyrimidin-4-ylamino)piperidin-1-yl)ethanone

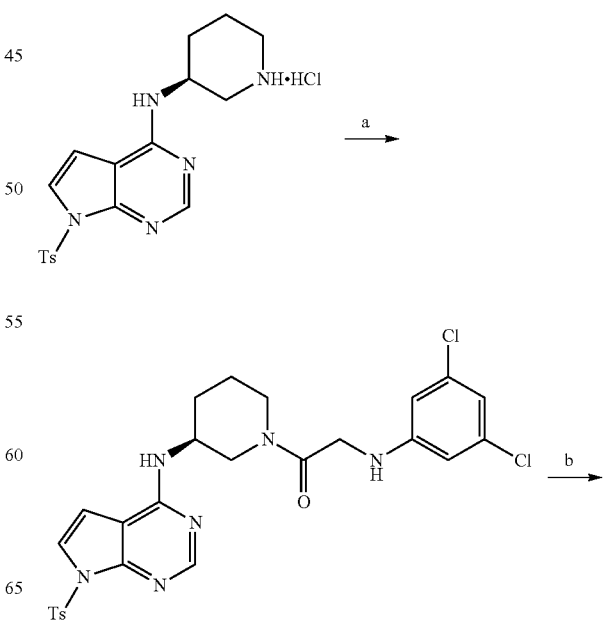

-continued

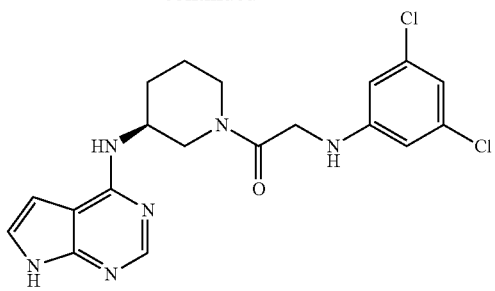

Reagents and conditions: a) 2-(3,5-Dichlorophenylamino)acetic acid, EDCI, HOBt, DIEA, DMF, rt, 5 h; b) K₂CO₃, MeOH:H₂O, 50° C., 2 h.

Synthesis of 2-(3,5-dichlorophenylamino)-1-((S)-3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to give the titled compound (200 mg, 51%). LC-MS: m/z [M+1]=574.

Synthesis of 2-(3,5-dichlorophenylamino)-1-((S)-3-(7H-pyrrolo[2,3-d]pyrimidin-4-ylamino)piperidin-1-yl)ethanone A similar procedure was used as described for the synthesis of 2-(3-chloro-5-fluorophenylamino)-1-((S)-3-(7H-pyrrolo[2,3-d]pyrimidin-4-ylamino)piperidin-1-yl)ethanone to give the titled compound (146 mg, 34%). 1H NMR (400 MHz, DMSO-d₆): δ 11.52 and 11.49 (2s, 1H), 8.16 and 8.08 (2s, 1H), 7.35 and 7.20 (2d, J=6.8 Hz, 1H), 7.08-7.07 (m, 1H), 6.76 (s, 1H), 6.68 (s, 1H), 6.62 (s, 1H), 6.40 and 6.29 (2t, J=2.5 Hz, 1H), 4.17-3.84 (m, 5H), 3.02-2.97 (m, 1H), 2.83 and 2.63 (2t, J=11.6 Hz, 1H), 2.04-1.99 (m, 2H), 1.81-1.79 (m, 1H), 1.67-1.43 (m, 2H). LC-MS: m/z [M+1]=419.

Example 3

Synthesis of (S)-1-(3-(7H-pyrrolo[2,3-d]pyrimidin-4-ylamino)piperidin-1-yl)-2-(2-(piperidin-1-ylsulfonyl)phenylamino)ethanone

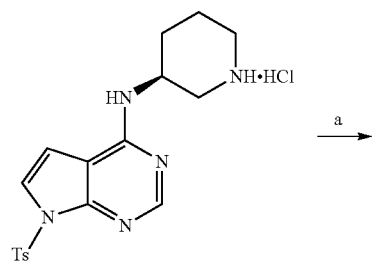

Reagents and conditions: a) 2-(2-(Piperidin-1-ylsulfonyl)phenylamino)acetic acid, EDCI, HOBt, DIEA, DMF, rt, 5 h; b) K₂CO₃, MeOH:H₂O, 50° C., 2 h.

Synthesis of (S)-2-(2-(piperidin-1-ylsulfonyl)phenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (126 mg, 64%) was synthesized. LC-MS: m/z [M+1].

Synthesis of (S)-1-(3-(7H-pyrrolo[2,3-d]pyrimidin-4-ylamino)piperidin-1-yl)-2-(2-(piperidin-1-ylsulfonyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (97 mg, 45%). 1H NMR (400 MHz, CD₃OD): δ 8.22 and 8.12 (2s, 1H), 7.61-7.52 (m, 1H), 7.47-7.32 (m, 1H), 7.09-7.06 (m, 1H), 6.82-6.52 (m, 3H), 4.64-4.59 (m, 1H), 4.31-4.02 (m, 4H), 3.93-3.85 (m, 1H), 3.40-3.25 (m, 2H), 3.20-2.81 (m, 3H), 2.25-1.85 (m, 4H), 1.82-1.48 (m, 6H). LC-MS: m/z [M+1]=498. HPLC (254 nm): 93.68%. HPLC (210 nm): 90.01%.

Example 4

Synthesis of (S)-2-(2-(3-(7H-pyrrolo[2,3-d]pyrimidin-4-ylamino)piperidin-1-yl)-2-oxoethylamino)-N,N-diisobutylbenzenesulfonamide

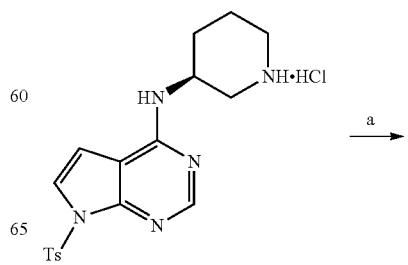

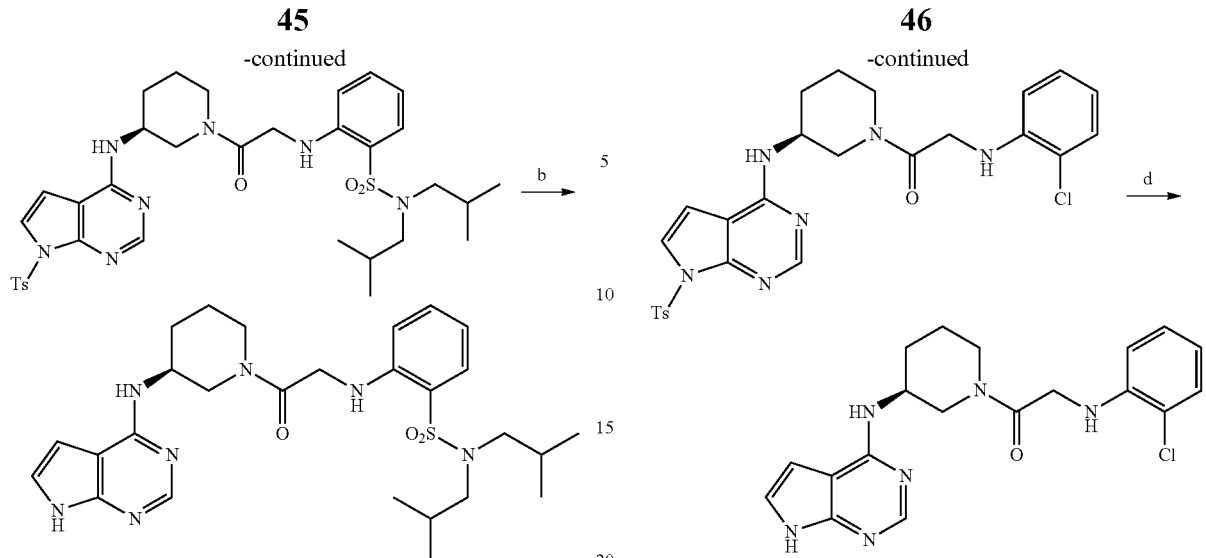

Reagents and conditions: a) 2-(2-(N,N-diisobutylsulfamoyl)phenylamino)acetic acid, EDCI, HOBt, DIEA, DMF, rt, 5 h; b) K₂CO₃, MeOH:H₂O, 50° C., 2 h.

Reagents and conditions: a) 2-(2-Chlorophenylamino)acetic acid, EDCI, HOBt, DIEA, DMF, rt, 5 h; e) K₂CO₃, MeOH:H₂O, 50° C., 2 h.

Synthesis of ((S)—N,N-diisobutyl-2-(2-oxo-2-(3-(7-tosyl-7H-pyrrolo[2,3-d]pyrimidin-4-ylamino)piperidin-1-yl)ethylamino)benzenesulfonamide A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (40 mg, 35%). LC-MS: m/z [M+1]=696.

Synthesis of (S)-2-(2-(3-(7H-pyrrolo[2,3-d]pyrimidin-4-ylamino)piperidin-1-yl)-2-oxoethylamino)-N,N-diisobutylbenzenesulfonamide A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (60 mg, 71%). 1H NMR (400 MHz, CD₃OD): δ 8.19 and 8.11 (2s, 1H), 7.66-7.61 (m, 1H), 7.43-7.33 (m, 1H), 7.07-6.98 (m, 1H), 6.79-6.52 (m, 3H), 4.56-4.54 (m, 1H), 4.26-4.07 (m, 4H), 3.89-3.85 (m, 1H), 3.37-3.13 (m, 1H), 3.00-2.96 (m, 4H), 2.22-2.10 (m, 1H), 2.04-1.89 (m, 4H), 1.69-1.67 (m, 1H), 0.79-0.76 (m, 12H). LC-MS: m/z [M+1]=542.

Example 5

Synthesis of (S)-1-(3-(7H-pyrrolo[2,3-d]pyrimidin-4-ylamino)piperidin-1-yl)-2-(2-chlorophenylamino)ethanone

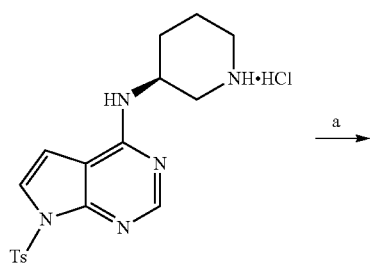

Synthesis of (S)-2-(2-chlorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (270 mg, 93%). LC-MS: m/z [M+1]=539.

Synthesis of (S)-1-(3-(7H-pyrrolo[2,3-d]pyrimidin-4-ylamino)piperidin-1-yl)-2-(2-chlorophenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (60 mg, 28%) was synthesized. ¹H NMR (400 MHz, DMSO-d₆): δ 11.52 (d, J=9.2 Hz, 1H), 8.12 (2s, 1H), 7.36-7.08 (m, 4H), 6.80 (m, 3H), 5.55 (2t, J=2.1 Hz, 1H), 4.13-3.85 (m, 4H), 3.16-2.96 (m, 2H), 2.67 (t, J=12.0 Hz, 1H), 2.04 (m, 1H), 1.84 (m, 1H), 1.62 (m, 1H), 1.51 (m, 1H). LC-MS: m/z [M+1]=385.

Example 6

Synthesis of (S)-1-(3-(7H-pyrrolo[2,3-d]pyrimidin-4-ylamino)piperidin-1-yl)-2-(3-chlorophenylamino)ethanone

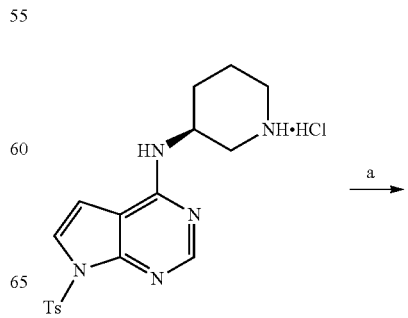

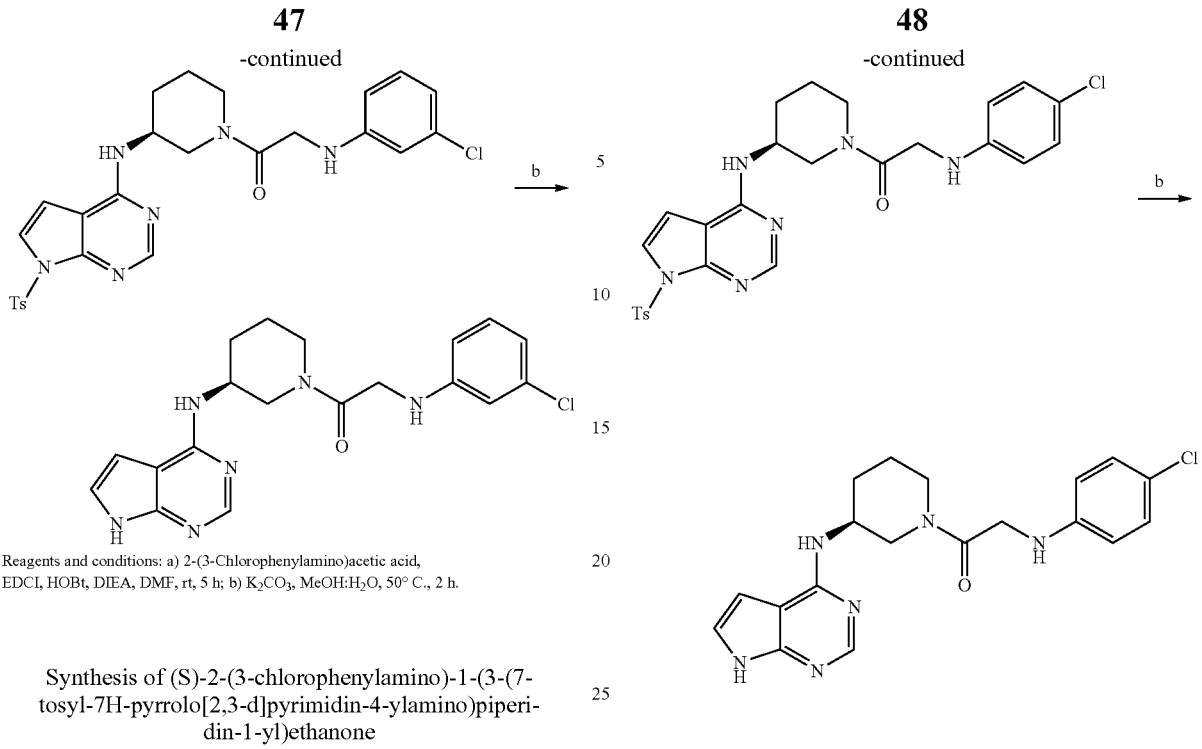

Reagents and conditions: a) 2-(3-Chlorophenylamino)acetic acid,
EDCI, HOBt, DIEA, DMF, rt, 5 h; b) K$_2$CO$_3$, MeOH:H$_2$O, 50° C., 2 h.

Synthesis of (S)-2-(3-chlorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (250 mg, 71%). LC-MS: m/z [M+1]=539.

Synthesis of (S)-1-(3-(7H-pyrrolo[2,3-d]pyrimidin-4-ylamino)piperidin-1-yl)-2-(3-chlorophenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (100 mg, 56%). $^1$H NMR (400 MHz, DMSO-d$_6$): δ 11.51 (d, J=8.9 Hz, 1H), 8.12 (2s, 1H), 7.28 (2d, J=6.0 Hz, 1H), 7.08-7.01 (m, 2H), 6.73-6.55 (m, 4H), 5.98 (2t, J=2.1 Hz, 1H), 4.09-3.84 (m, 4H), 3.03 (m, 1H), 2.87 (t, J=10.8 Hz, 1H), 2.63 (t, J=10.8 Hz, 1H), 2.04 (m, 1H), 1.81 (m, 1H), 1.55 (m, 1H), 1.45 (m, 1H). LC-MS: m/z [M+1]=385.

Example 7

Synthesis of (S)-1-(3-(7H-pyrrolo[2,3-d]pyrimidin-4-ylamino)piperidin-1-yl)-2-(4-chlorophenylamino)ethanone

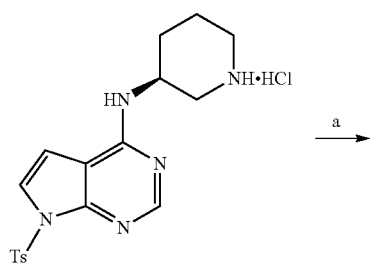

Reagents and conditions: a) 2-(4-chlorophenylamino)acetic acid,
EDCI, HOBt, DIEA, DMF, rt, 5 h; b) K$_2$CO$_3$, MeOH:H$_2$O, 50° C., 2 h.

Synthesis of (S)-2-(4-chlorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (300 mg, 90%). $^1$H NMR (400 MHz, DMSO-d$_6$): δ 8.28 and 8.22 (2s, 1H), 7.96 (d, J=8.0 Hz, 2H), 7.78 and 7.67 (2d, J=6.4 Hz, 1H), 7.57 (dd, J=4.0, 10.0 Hz, 1H), 7.42 (d, J=8.0 Hz, 2H), 7.08 (d, J=8.8 Hz, 1H), 7.05 (d, J=8.8 Hz, 1H), 6.97 and 6.90 (2d, J=3.6 Hz, 1H), 6.66 (d, J=8.8 Hz, 1H), 6.56 (d, J=8.8 Hz, 1H), 5.79-5.77 (m, 1H), 4.06-3.75 (m, 4H), 3.06-3.01 (m, 1H), 2.90-2.63 (m, 2H), 2.35 (s, 3H), 2.00-1.98 (m, 1H), 1.79-1.40 (m, 3H). LC-MS: m/z [M+1]=539.

Synthesis of (S)-1-(3-(7H-pyrrolo[2,3-d]pyrimidin-4-ylamino)piperidin-1-yl)-2-(4-chlorophenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (71 mg, 42%). $^1$H NMR (400 MHz, DMSO-d$_6$): δ 11.51 (d, J=9.0 Hz, 1H), 8.11 (2s, 1H), 7.25 (2d, J=6.5 Hz, 1H), 7.10-7.03 (m, 3H), 6.69-6.56 (m, 3H), 5.86 (2t, J=2.3 Hz, 1H), 4.04-3.76 (m, 4H), 3.17-2.90

(m, 2H), 2.63 (t, 0.1=10.5 Hz, 1H), 2.03 (m, 1H), 1.81 (m, 1H), 1.57 (m, 1H), 1.44 (m, 1H). LC-MS: m/z [M+1]=385.

Example 8

Synthesis of (S)-1-(3-(7H-pyrrolo[2,3-d]pyrimidin-4-ylamino)piperidin-1-yl)-2-(2-(trifluoromethyl)phenylamino)ethanone

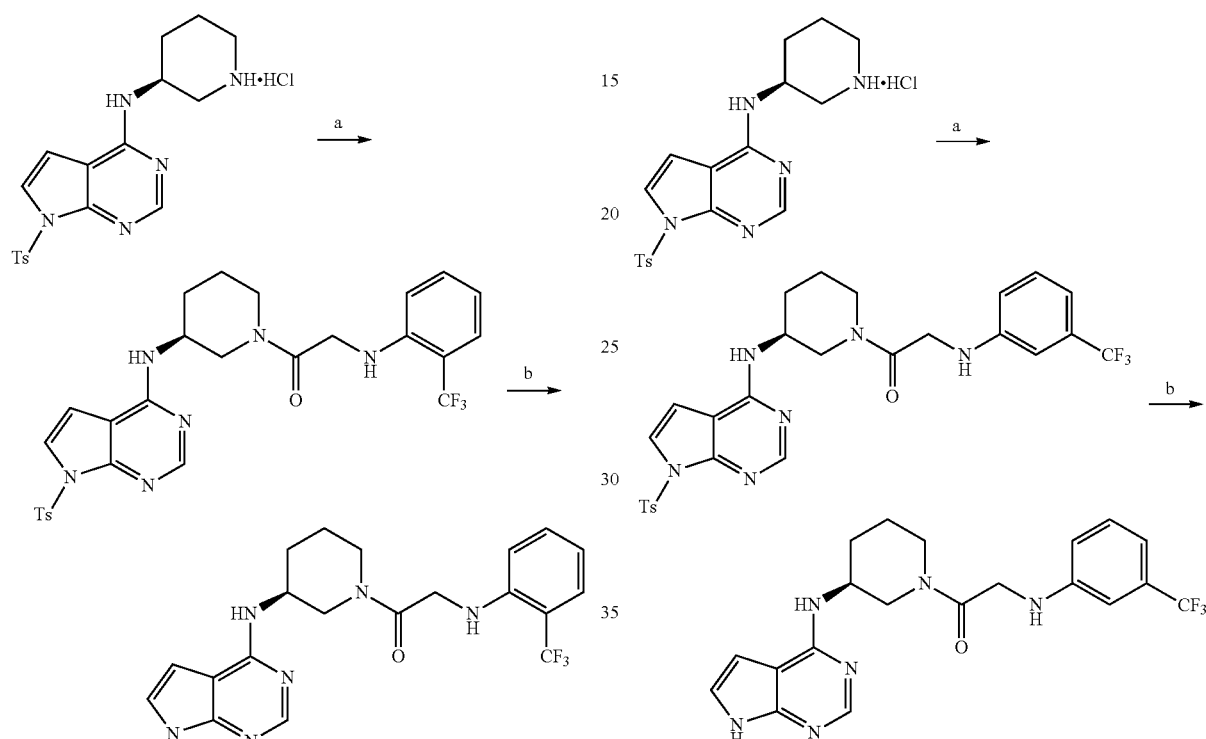

Reagents and conditions: a) 2-(2-(Trifluoromethyl)phenylamino)acetic acid, EDCI, HOBt, DIEA, DMF, rt, 5 h; b) K₂CO₃, MeOH:H₂O, 50° C., 2 h.

Synthesis of (S)-1-(3-(7-tosyl-7H-pyrrolo[2,3-d]pyrimidin-4-ylamino)piperidin-1-yl)-2-(2-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (453 mg, 69%). LC-MS: m/z [M+1]=573.

Synthesis of (S)-1-(3-(7H-pyrrolo[2,3-d]pyrimidin-4-ylamino)piperidin-1-yl)-2-(2-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (120 mg, 36%). ¹H NMR (400 MHz, CDCl₃): δ 10.45 (2s, 1H), 8.42-8.34 (2s, 1H), 7.49-7.43 (m, 1H), 7.37-7.13 (m, 1H), 7.26 (s, 1H), 7.09 (s, 1H), 6.70 (m, 2H), 6.49 (d, J=7.6 Hz, 1H), 6.36 (m, 1H), 5.79 (m, 1H), 4.97 (m, 1H), 4.33-4.14 (m, 3H), 3.79 (m, 1H), 3.47 (m, 1H), 3.21 (m, 1H), 2.18 (m, 1H), 1.89 (m, 1H), 1.75 (m, 1H). LC-MS: m/z [M+1]=419.

Example 9

Synthesis of (S)-1-(3-(7H-pyrrolo[2,3-d]pyrimidin-4-ylamino)piperidin-1-yl)-2-(3-(trifluoromethyl)phenylamino)ethanone

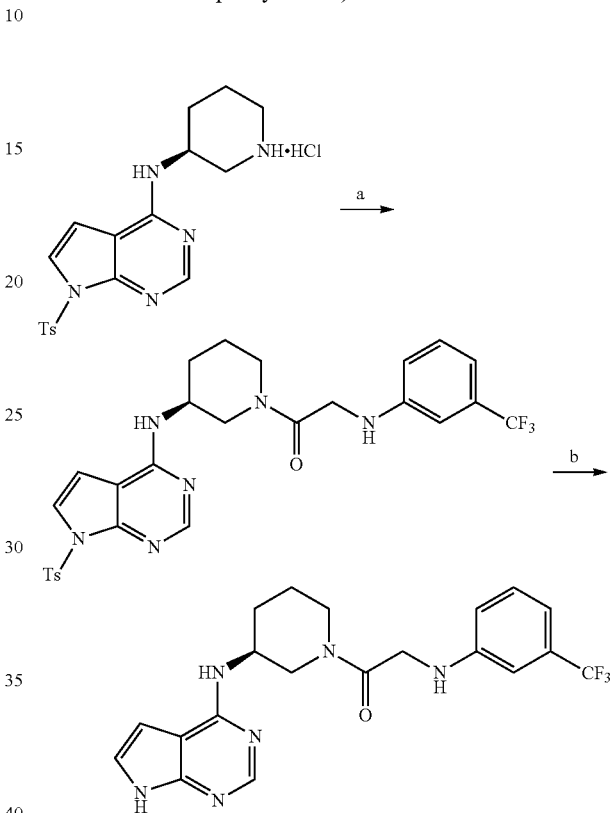

Reagents and conditions: a) 2-(3-(Trifluoromethyl)phenylamino)acetic acid, EDCI, HOBt, DIEA, DMF, rt, 5 h; b) K₂CO₃, MeOH:H₂O, 50° C., 2 h.

Synthesis of (S)-1-(3-(7-tosyl-7H-pyrrolo[2,3-d]pyrimidin-4-ylamino)piperidin-1-yl)-2-(3-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (300 mg, 85%). ¹H NMR (400 MHz, CDCl₃): δ 8.49 and 8.43 (2s, 1H), 8.06 (dd, J=8.4, 14.8 Hz, 2H), 8.01 (s, 2H), 7.46 (dd, J=4.0, 10.8 Hz, 1H), 7.29-7.22 (m, 3H), 6.94 (t, J=6.8 Hz, 1H), 6.78-6.72 (m, 2H), 6.46-6.43 (m, 1H), 5.29-5.15 (m, 1H), 4.30-4.13 (m, 3H), 3.92 (m, 1H), 3.82-3.76 (m, 1H), 3.38-3.36 (m, 1H), 2.37 (s, 3H), 2.17 (m, 1H), 1.84 (m, 1H), 1.71-1.66 (m, 2H). LC-MS: m/z [M+1]=573.

Synthesis of (S)-1-(3-(7H-pyrrolo[2,3-d]pyrimidin-4-ylamino)piperidin-1-yl)-2-(3-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (130 mg, 59%). $^1$H NMR (400 MHz, CD$_3$OD): δ 8.14 (2s, 1H), 7.26-7.20 (m, 1H), 7.06 (m, 1H), 6.89-6.78 (m, 3H), 6.61-6.57 (m, 1H), 4.27-4.06 (m, 4H), 3.91 (d, J=10.5 Hz, 1H), 3.14 (m, 1H), 2.94 (m, 1H), 2.14 (m, 1H), 1.97-1.58 (m, 3H). LC-MS: m/z [M+1]=419.

Example 10

Synthesis of (S)-1-(3-(7H-pyrrolo[2,3-d]pyrimidin-4-ylamino)piperidin-1-yl)-2-(4-(trifluoromethyl)phenylamino)ethanone

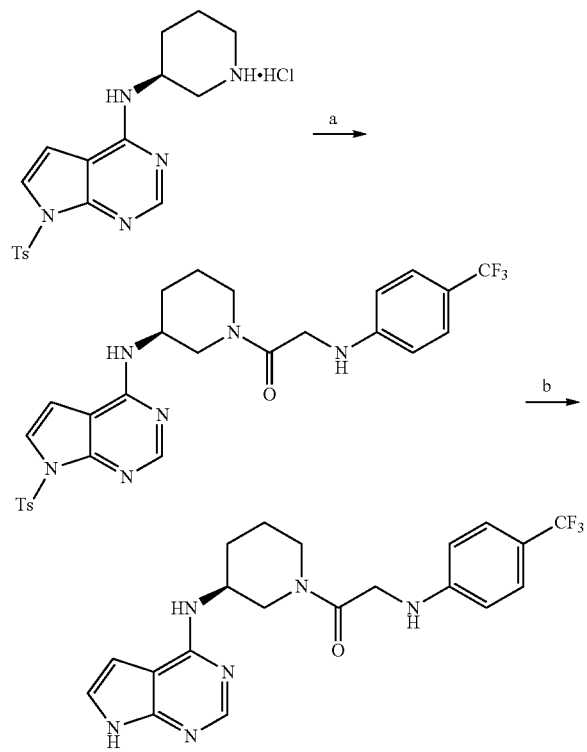

Reagents and conditions: a) 2-(4-(Trifluoromethyl)phenylamino)acetic acid, EDCI, HOBt, DIEA, DMF, rt, 5 h; b) K$_2$CO$_3$, MeOH:H$_2$O, 50° C., 2 h.

Synthesis of (S)-1-(3-(7-tosyl-7H-pyrrolo[2,3-d]pyrimidin-4-ylamino)piperidin-1-yl)-2-(4-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (250 mg, 52%). $^1$H NMR (400 MHz, DMSO-d$_6$): δ 8.28 and 8.22 (2s, 1H), 7.96 (s, 1H), 7.94 (s, 1H), 7.78 and 7.66 (2d, J=6.4 Hz, 1H), 7.56 (dd, J=4.0, 6.8 Hz, 1H), 7.43-7.33 (m, 4H), 6.97-6.90 (m, 1H), 6.77-6.65 (m, 2H), 4.03-3.83 (m, 4H), 3.08-2.87 (m, 2H), 2.72-2.65 (m, 2H), 2.34 (s, 3H), 2.00-1.99 (m, 1H), 1.80-1.56 (m, 3H). LC-MS: m/z [M+1]=573.

Synthesis of (S)-1-(3-(7H-pyrrolo[2,3-d]pyrimidin-4-ylamino)piperidin-1-yl)-2-(4-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (100 mg, 54%). $^1$H NMR (400 MHz, CD$_3$OD): δ 8.14 (2s, 1H), 7.37-7.29 (2d, J=6.6 Hz, 1H), 7.06 (m, 1H), 6.72-6.57 (m, 3H), 6.61-6.57 (m, 1H), 4.24-4.06 (m, 3H), 3.88 (d, J=16.0 Hz, 1H), 3.23 (m, 2H), 3.06 (t, J=10.8 Hz, 1H), 2.14 (m, 1H), 1.90-1.80 (m, 2H), 1.69-1.58 (m, 1H). LC-MS: m/z [M+1]=419.

Example 11

Synthesis of (S)-1-(3-(7H-pyrrolo[2,3-d]pyrimidin-4-ylamino)piperidin-1-yl)-2-(2-fluorophenylamino)ethanone

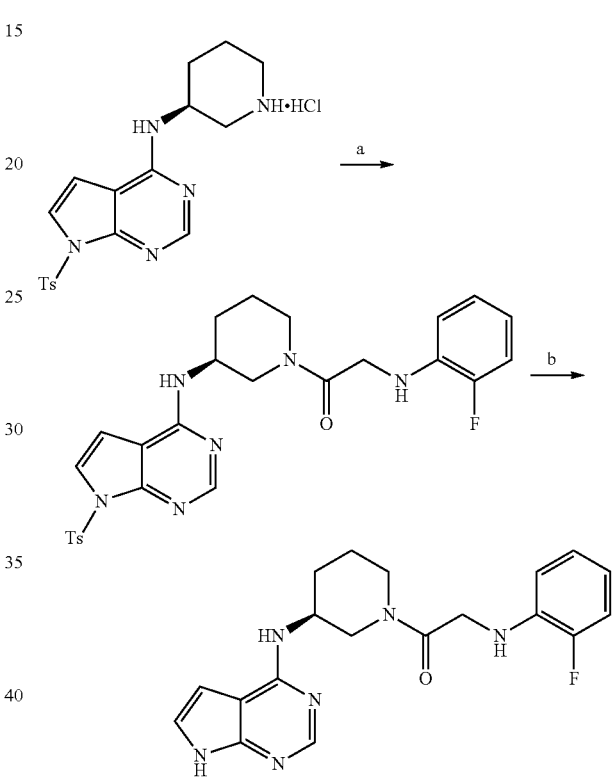

Reagents and conditions: a) 2-(2-(Fluorophenylamino)acetic acid, EDCI, HOBt, DIEA, DMF, 5 h; b) K$_2$CO$_3$, MeOH:H$_2$O, 50° C., 2 h.

Synthesis of (S)-2-(2-fluorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (205 mg, 72%). $^1$H NMR (400 MHz, CDCl$_3$): δ 8.52 and 8.43 (2s, 1H), 8.08-8.02 (m, 2H), 7.50-7.46 (m, 1H), 7.29 (d, J=8.0 Hz, 2H), 6.99-6.94 (m, 2H), 6.64-6.53 (m, 2H), 6.39 (d, J=4.0 Hz, 1H), 5.16-5.10 (m, 1H), 4.87-4.86 (m, 1H), 4.24-3.96 (m, 4H), 3.81 (dd, J=3.6, 16.0 Hz, 1H), 3.53-3.02 (m, 2H), 2.38 (s, 3H), 2.13 (m, 1H), 1.83 (m, 1H), 1.70-1.68 (m, 2H). LC-MS: m/z [M+1]=523.

Synthesis of (S)-1-(3-(7H-pyrrolo[2,3-d]pyrimidin-4-ylamino)piperidin-1-yl)-2-(2-fluorophenylamino)ethanone A similar procedure was used as described for the synthesis of (2-(3-chloro-5-fluorophenylamino)-1-((S)-3-(7-tosyl-7H- pyrrolo[2,3-d]pyrimidin-4-ylamino)piperidin-1-yl)ethanone to yield the titled compound (120 mg, 85%). $^1$H NMR (400 MHz, DMSO-$d_6$): δ 11.51 (d, J=9.0 Hz, 1H), 8.11 (2s, 1H), 7.26 (2d, J=6.8 Hz, 1H), 7.08-6.92 (m, 3H), 6.63-6.56 (m, 3H), 5.32 (m, 1H), 4.09-3.58 (m, 4H), 3.17-2.93 (m, 2H), 2.64 (t, J=10.8 Hz, 1H), 2.12 (m, 1H), 1.81 (m, 1H), 1.59 (m, 1H), 1.41 (m, 1H). LC-MS: m/z [M+1]=369.

Example 12

Synthesis of (S)-1-(3-(7H-pyrrolo[2,3-d]pyrimidin-4-ylamino)piperidin-1-yl)-2-(3-fluorophenylamino)ethanone

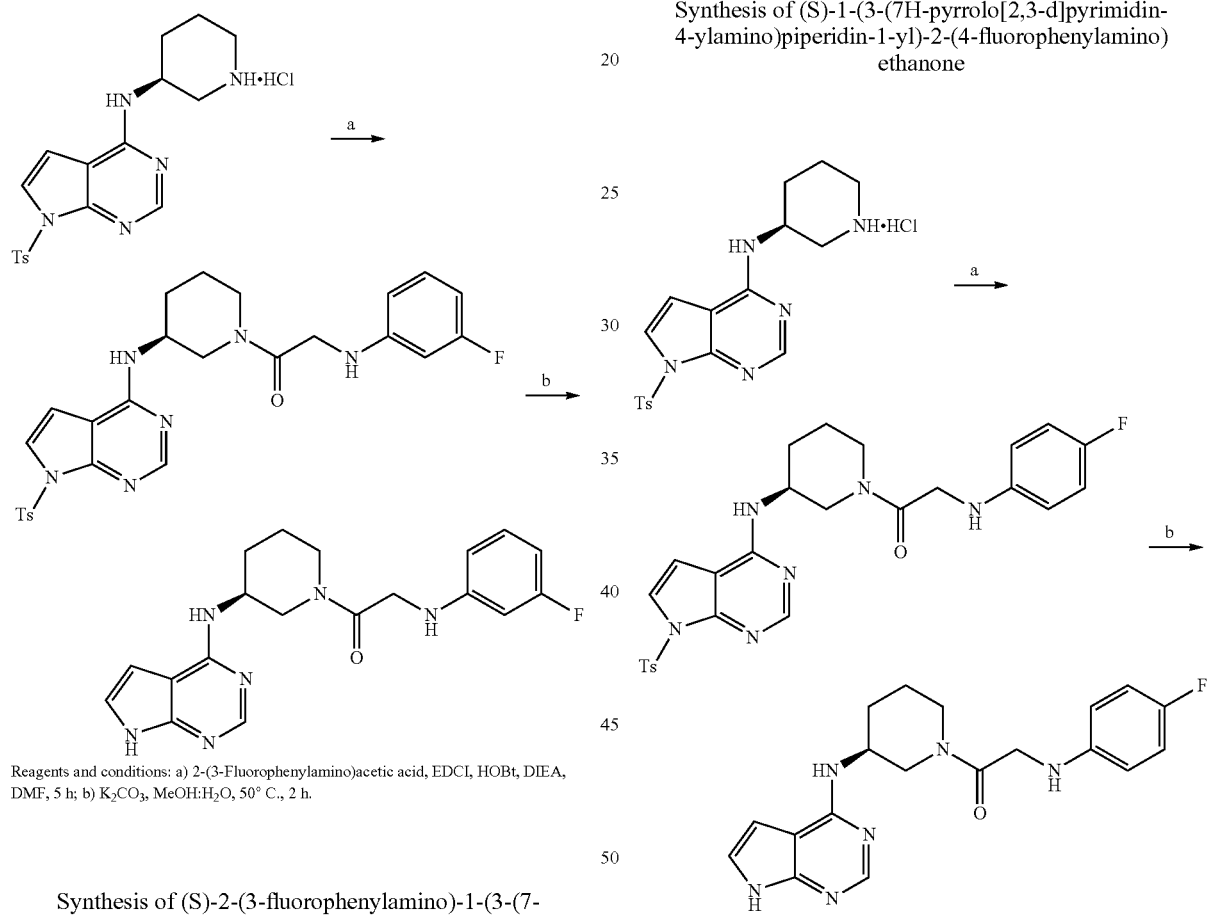

Reagents and conditions: a) 2-(3-Fluorophenylamino)acetic acid, EDCI, HOBt, DIEA, DMF, 5 h; b) K$_2$CO$_3$, MeOH:H$_2$O, 50° C., 2 h.

Synthesis of (S)-2-(3-fluorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (250 mg, 78%). $^1$H NMR (400 MHz, DMSO-$d_6$): δ 8.27 and 8.22 (2s, 1H), 7.96 (d, J=8.4 Hz, 2H), 7.78 and 7.67 (2d, J=6.4 Hz, 1H), 7.57 (dd, J=3.6, 7.6 Hz, 1H), 7.42 (d, J=8.4 Hz, 2H), 7.06-6.99 (m, 1H), 6.96 and 6.91 (2d, J=4.0 Hz, 1H), 6.50-6.29 (m, 2H), 5.95-5.90 (m, 1H), 4.10-3.79 (m, 4H), 3.04-2.98 (m, 2H), 2.88-2.85 (m, 1H), 2.68-2.63 (m, 1H), 2.35 (s, 3H), 2.01-1.99 (m, 1H), 1.79-1.69 (m, 1H), 1.62-1.55 (m, 2H). LC-MS: m/z [M+1]=523.

Synthesis of (S)-1-(3-(7H-pyrrolo[2,3-d]pyrimidin-4-ylamino)piperidin-1-yl)-2-(3-fluorophenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (60 mg, 34%). $^1$H NMR (400 MHz, DMSO-$d_6$): δ 11.51 (d, J=8.9 Hz, 1H), 8.11 (2s, 1H), 7.27 (2d, J=6.9 Hz, 1H), 7.13-7.01 (m, 2H), 6.62-6.30 (m, 3H), 5.98 (2t, J=2.1 Hz, 1H), 4.08-3.81 (m, 3H), 3.08-3.02 (m, 2H), 2.88 (t, J=10.8 Hz, 1H), 2.63 (t, J=10.8 Hz, 1H), 2.04 (m, 2H), 1.81 (m, 1H), 1.58 (m, 1H), 1.45 (m, 1H). LC-MS: m/z [M+1]=369.

Example 13

Synthesis of (S)-1-(3-(7H-pyrrolo[2,3-d]pyrimidin-4-ylamino)piperidin-1-yl)-2-(4-fluorophenylamino)ethanone

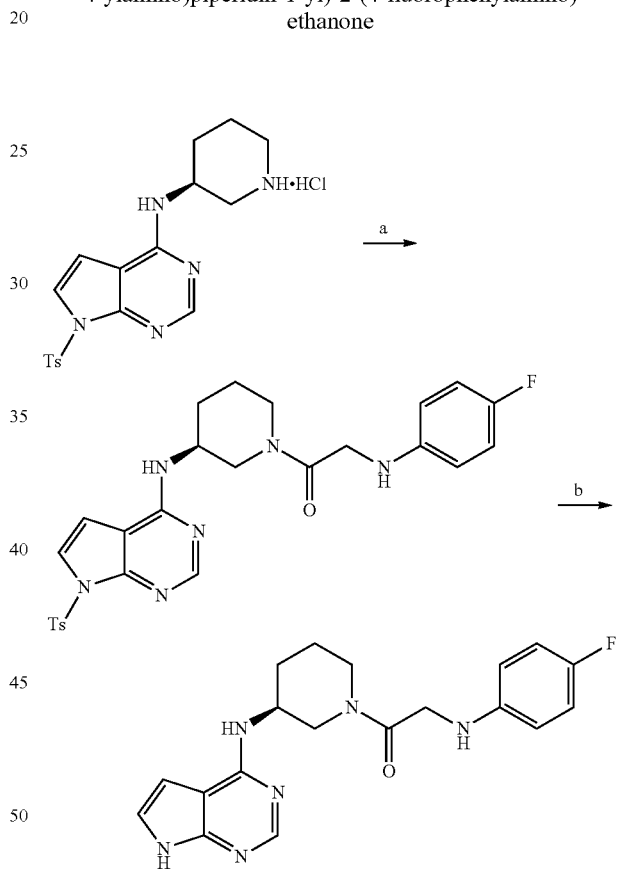

Reagents and conditions: a) 2-(4-Fluorophenylamino)acetic acid, EDCI, HOBt, DIEA, DMF, 5 h; b) K$_2$CO$_3$, MeOH:H$_2$O, 50° C., 2 h.

Synthesis of (S)-2-(4-fluorophenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (212 mg, 75%). $^1$H NMR (400 MHz, CDCl$_3$): δ 8.50 and 8.42 (2s, 1H), 8.08-8.01 (m, 2H), 7.49-7.46 (m, 1H), 7.31-7.26 (m, 3H), 6.90-6.83 (m, 1H), 6.53-6.41 (m, 3H), 5.00 (m, 1H), 4.22-4.06 (m, 3H), 3.91-

3.73 (m, 2H), 3.52-3.3.48 (m, 1H), 3.05-3.01 (m, 1H), 2.38 (s, 3H), 2.10-1.98 (m, 1H), 1.82 (m, 1H), 1.66-1.58 (m, 3H). LC-MS: m/z [M+1]=523.

Synthesis of (S)-1-(3-(7H-pyrrolo[2,3-d]pyrimidin-4-ylamino)piperidin-1-yl)-2-(4-fluorophenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (110 mg, 76%). $^1$H NMR (400 MHz, DMSO-d$_6$): δ 11.52 (d, J=9.0 Hz, 1H), 8.11 (2s, 1H), 7.27 (2d, J=6.5 Hz, 1H), 7.09-7.07 (m, 1H), 6.94-6.85 (m, 2H), 6.68 (m, 1H), 6.56 (m, 2H), 5.58 (2t, J=2.3 Hz, 1H), 4.05-3.76 (m, 3H), 3.38 (m, 1H), 3.13-3.06 (m, 1H), 2.92 (t, J=Hz, 1H), 2.63 (t, J=10.8 Hz, 1H), 2.03 (m, 1H), 1.81 (m, 1H), 1.57 (m, 1H), 1.44 (m, 1H). LC-MS: m/z [M+1]=369.

Example 14

Synthesis of (S)-1-(3-(7H-pyrrolo[2,3-d]pyrimidin-4-ylamino)piperidin-1-yl)-2-(3,5-bis(trifluoromethyl)phenylamino)ethanone

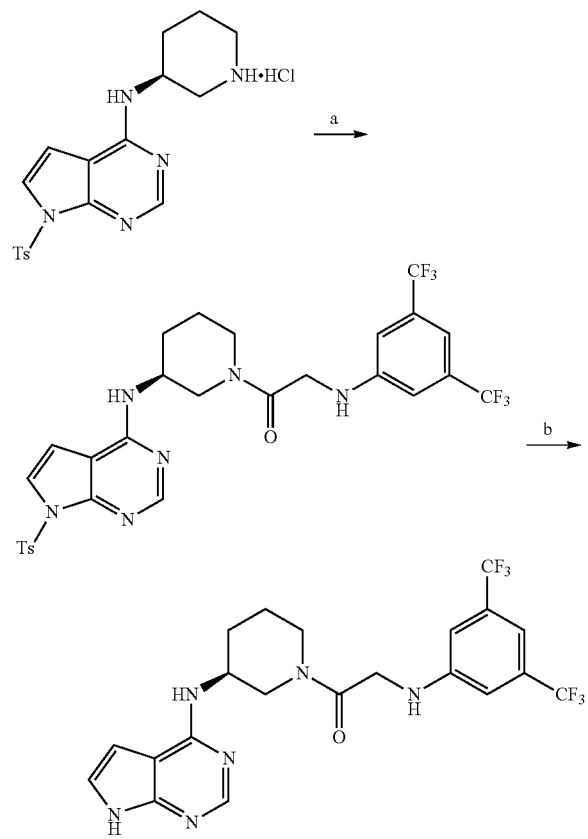

Reagents and conditions: a) 2-(3,5-Bis(trifluoromethyl)phenylamino)acetic acid, EDCI, HOBt, DIEA, DMF, rt, 5 h; b) K$_2$CO$_3$, MeOH:H$_2$O, 50° C., 2 h.

Synthesis of (S)-2-(3,5-bis(trifluoromethyl)phenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (280 mg, 65%). $^1$H NMR (400 MHz, DMSO-d$_6$): δ 8.22 (s, 1H), 7.96 (d, J=8.0 Hz, 2H), 7.82 and 7.68 (2d, J=6.4 Hz, 1H), 7.56 (dd, J=4.0, 6.4 Hz, 1H), 7.41 (t, J=6.4 Hz, 2H), 7.31 (s, 1H), 7.22 (s, 1H), 7.06 (d, J=4.0, 1H), 6.92 (dd, J=3.6, 15.6 Hz, 1H), 6.72-6.67 (m, 1H), 4.43-3.84 (m, 5H), 3.06-2.94 (m, 1H), 2.83-2.65 (m, 1H), 2.50 (s, 3H), 2.00 (m, 1H), 1.80-1.75 (m, 1H), 1.64-1.40 (m, 2H). LC-MS: m/z [M+1]=641.

Synthesis of (S)-1-(3-(7H-pyrrolo[2,3-d]pyrimidin-4-ylamino)piperidin-1-yl)-2-(3,5-bis(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (100 mg, 47%). $^1$H NMR (400 MHz, DMSO-d$_6$): δ 11.51 (d, J=9.0 Hz, 1H), 8.10 (2s, 1H), 7.38-7.21 (m, 3H), 7.07 (m, 2H), 6.79-6.56 (m, 2H), 4.22-3.89 (m, 4H), 3.01 (m, 2H), 2.83 (t, J=10.5 Hz, 1H), 2.64 (t, J=10.5 Hz, 1H), 2.05-1.97 (m, 2H), 1.80 (m, 1H), 1.59 (m, 1H). LC-MS: m/z [M+1]=487.

Example 15

Synthesis of ((S)-1-(3-(7H-pyrrolo[2,3-d]pyrimidin-4-ylamino)piperidin-1-yl)-2-(3-chloro-5-(trifluoromethyl)phenylamino)ethanone

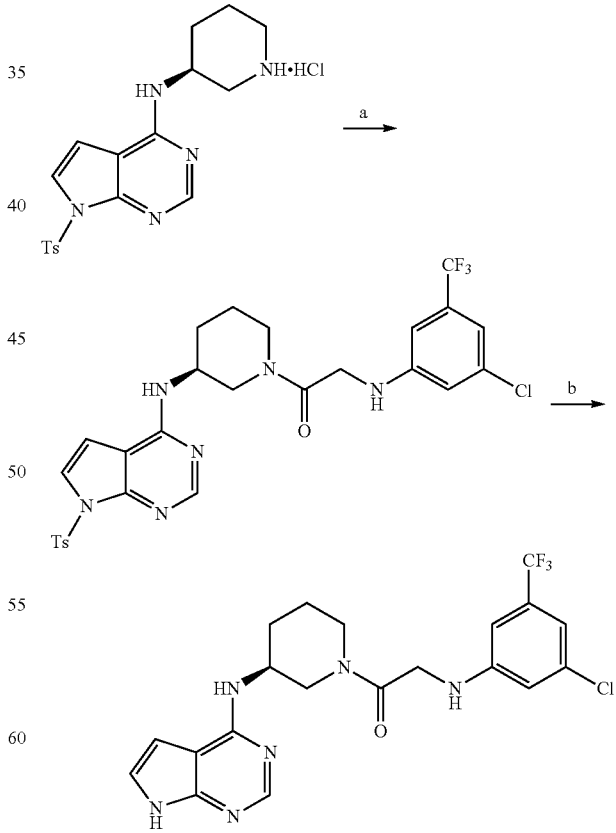

Reagents and conditions: a) 2-(3-Chloro-5-(trifluoromethyl)phenylamino)acetic acid, EDCI, HOBt, DIEA, DMF, rt, 5 h; b) K$_2$CO$_3$, MeOH:H$_2$O, 50° C., 2 h.

Synthesis of (S)-2-(3-chloro-5-(trifluoromethyl)phenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (160 mg, 49%). $^1$H NMR (400 MHz, CDCl$_3$): δ 8.50 and 8.44 (2s, 1H), 8.07 (dd, J=8.4, 16.4 Hz, 2H), 8.01 (s, 1H), 7.49 (dd, J=4.0, 12.8 Hz, 1H), 7.29 (d, J=8.0 Hz, 2H), 6.91 (s, 1H), 6.71 (s, 1H), 6.68 (s, 1H), 6.43 (d, J=4.0 Hz, 1H), 5.40 (m, 1H), 4.33-4.10 (m, 3H), 3.90-3.74 (m, 1H), 3.00 (m, 2H), 2.38 (s, 3H), 1.85 (m, 1H), 1.69-1.61 (m, 3H). LC-MS: m/z [M+1]=607.

Synthesis of (S)-(3-(7H-pyrrolo[2,3-d]pyrimidin-4-ylamino)piperidin-1-yl)-2-(3-chloro-5-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (55 mg, 46%). $^1$H NMR (400 MHz, CD$_3$OD): δ 8.05 (2s, 1H), 6.98-7.95 (m, 1H), 6.77-6.72 (m, 3H), 6.52-6.47 (m, 1H), 4.47-4.23 (m, 1H), 4.23-3.77 (m, 3H), 3.10 (m, 1H), 3.00 (dd, J=9.6, 12.8 Hz, 1H), 2.86 (m, 1H), 2.06 (m, 1H), 1.81-1.48 (m, 3H). LC-MS: m/z [M+1]=453. HPLC (254 nm)=98.61%.

Example 16

Synthesis of (S)-1-(3-(7H-pyrrolo[2,3-d]pyrimidin-4-ylamino)piperidin-1-yl)-2-(3-fluoro-5-(trifluoromethyl)phenylamino)ethanone

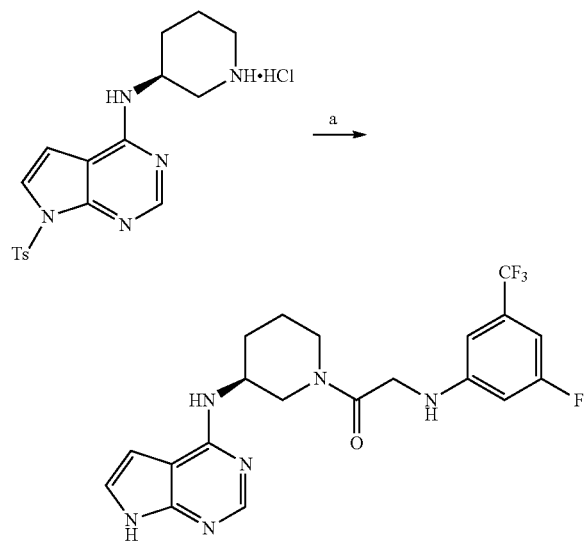

Reagents and conditions: a) i. 2-(3-Fluoro-5-(trifluoromethyl)phenylamino)acetic acid, EDCI, HOBt, DIEA, DMF, rt, 5 h; ii. K$_2$CO$_3$, MeOH:H$_2$O, 50° C., 2 h.

Synthesis of (S)-2-(3-fluoro-5-(trifluoromethyl)phenylamino)-1-(3-(7-tosyl-7H-pyrrolo[2,3-d]pyrimidin-4-ylamino)piperidin-1-yl)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (280 mg, 88%). $^1$H NMR (400 MHz, CDCl$_3$): δ 8.50 and 8.44 (2s, 1H), 8.07 (dd, J=8.4, 16.4 Hz, 2H), 8.01 (s, 1H), 7.49 (dd, J=3.6, 13.6 Hz, 1H), 7.31 (s, 1H), 7.29 (s, 1H), 6.64-6.59 (m, 2H), 6.45-6.41 (m, 2H), 5.43-5.33 (m, 1H), 4.34-4.11 (m, 4H), 3.91-3.75 (m, 2H), 3.50-3.45 (m, 1H), 2.38 (s, 3H), 1.85 (m, 1H), 1.69-1.64 (m, 3H). LC-MS: m/z [M+1]=591.

Synthesis of (S)-1-(3-(7H-pyrrolo[2,3-d]pyrimidin-4-ylamino)piperidin-1-yl)-2-(3-fluoro-5-(trifluoromethyl)phenylamino)ethanone A similar procedure was used as described for the synthesis of (2-(3-chloro-5-fluorophenylamino)-1-((S)-3-(7-tosyl-7H-pyrrolo[2,3-d]pyrimidin-4-ylamino)piperidin-1-yl)ethanone to yield the titled compound (150 mg, 72%). $^1$H NMR (400 MHz, DMSO-d$_6$): δ 11.51 (d, J=9.0 Hz, 1H), 8.10 (2s, 1H), 7.27 (2d, J=6.5 Hz, 1H), 7.07 (m, 1H), 6.92-6.79 (m, 1H), 6.72-6.49 (m, 3H), 4.16-3.85 (m, 4H), 3.24 (m, 1H), 3.03 (m, 1H), 2.85 (t, J=10.8 Hz, 1H), 2.65 (t, 0.1=10.8 Hz, 1H), 2.02 (m, 1H), 1.82 (m, 1H), 1.59 (m, 1H), 1.46 (m, 1H). LC-MS: m/z [M+1]=437. HPLC (254 nm)=98.64%.

Example 17

Synthesis of 2-(3-chloro-5-fluorophenylamino)-1-((R)-3-(7H-pyrrolo[2,3-d]pyrimidin-4-ylamino)piperidin-1-yl)ethanone

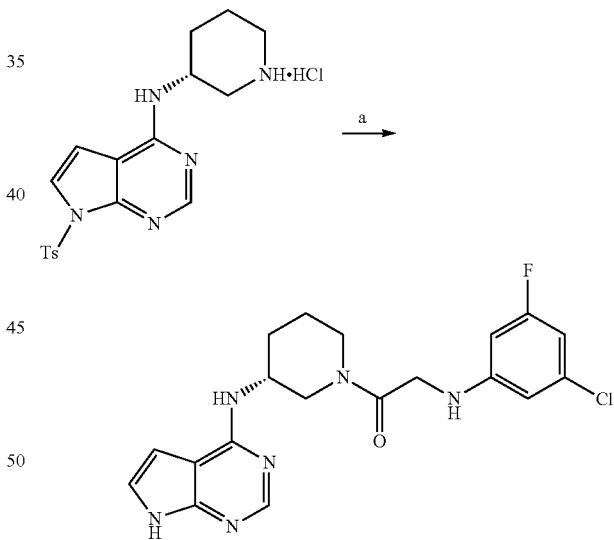

Reagents and conditions: a) i. 2-(3-chloro-5-fluorophenylamino)acetic acid, EDCI, HOBt, DIEA, DMF, rt, 5 h; ii. K$_2$CO$_3$, MeOH:H$_2$O, 50° C., 2 h.

Synthesis of 2-(3-chloro-5-fluorophenylamino)-1-((R)-3-(7H-pyrrolo[2,3-d]pyrimidin-4-ylamino)piperidin-1-yl)ethanone Afford the titled compound (59 mg, 90%) 1H NMR (400 MHz, CD$_3$OD): δ 8.22 and 8.15 (2s, 1H), 7.16-7.13 (m, 1H), 6.63 and 6.59 (2d, J=3.6 Hz, 1H), 6.51 and 6.49 (2s, 1H), 6.39-6.28 (m, 2H), 4.92-4.77 (m, 1H), 4.32-3.83 (m, 4H), 3.39-2.86 (m, 2H), 2.21-2.15 (m, 1H), 1.95-1.61 (m, 3H). LC-MS: m/z [M+1]=403

Example 18

Synthesis of 2-(3,5-dichlorophenylamino)-1-((R)-3-(7H-pyrrolo[2,3-d]pyrimidin-4-ylamino)piperidin-1-yl)ethanone

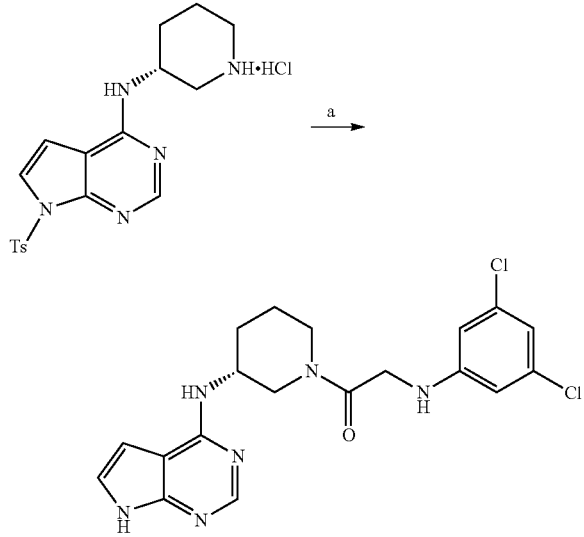

Reagents and conditions: a) i. 2-(3,5-Dichlorophenylamino)acetic acid, EDCI, HOBt, DIEA, DMF, rt, 5 h; ii. K₂CO₃, MeOH:H₂O, 50° C., 2 h.

Synthesis of 2-(3,5-dichlorophenylamino)-1-((R)-3-(7H-pyrrolo[2,3-d]pyrimidin-4-ylamino)piperidin-1-yl)ethanone A similar procedure was used as described for the synthesis of 2-(3-chloro-5-fluorophenylamino)-1-((R)-3-(7H-pyrrolo[2,3-d]pyrimidin-4-ylamino)piperidin-1-yl)ethanone to yield the titled compound (65 mg, 44%). ¹H NMR (400 MHz, CD₃OD): δ 8.21 and 8.17 (2s, 1H), 7.16-7.13 (m, 1H), 6.63-6.59 (m, 4H), 6.39-6.28 (m, 2H), 4.92-4.77 (m, 1H), 4.32-3.83 (m, 4H), 3.39-2.86 (m, 2H), 2.21-2.15 (m, 1H), 1.95-1.61 (m, 3H). LC-MS: m/z [M+1]419.

Example 19

Synthesis of (R)-1-(3-(7H-pyrrolo[2,3-d]pyrimidin-4-ylamino)piperidin-1-yl)-2-(2-(piperidin-1-ylsulfonyl)phenylamino)ethanone

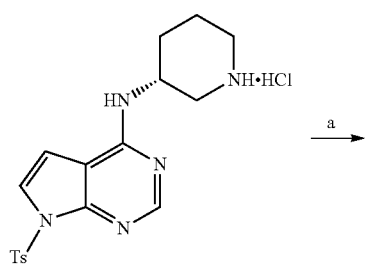

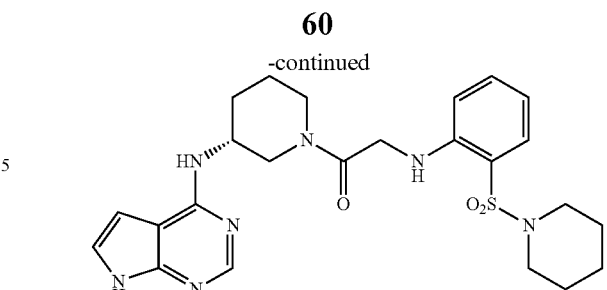

Reagents and conditions: a) i. 2-(2-(Piperidin-1-ylsulfonyl)phenylamibo)acetic acid, EDCI, HOBt, DIEA, DMF, rt, 5 h; ii. K₂CO₃, MeOH:H₂O, 50° C., 2 h.

Synthesis of (R)-1-(3-(7H-pyrrolo[2,3-d]pyrimidin-4-ylamino)piperidin-1-yl)-2-(2-(piperidin-1-ylsulfonyl)phenylamino)ethanone A similar procedure was used as described for the synthesis of 2-(3-chloro-5-fluorophenylamino)-1-((R)-3-(7H-pyrrolo[2,3-d]pyrimidin-4-ylamino)piperidin-1-yl)ethanone to yield the titled compound (65 mg, 78%). ¹H NMR (400 MHz, CD₃OD): δ 8.22 and 8.17 (2s, 1H), 7.61-7.55 (m, 1H), 7.48-7.35 (m, 1H), 7.08-7.00 (m, 1H), 6.81-6.44 (m, 3H), 4.65-4.57 (m, 1H), 4.39-4.09 (m, 3H), 3.87-3.80 (m, 2H), 3.57-2.95 (m, 5H), 2.25-1.82 (m, 4H), 1.75-1.46 (m, 6H). LC-MS: m/z [M+1]=498.

Example 20

Synthesis of (R)-2-(2-(3-(7H-pyrrolo[2,3-d]pyrimidin-4-ylamino)piperidin-1-yl)-2-oxoethylamino)-N,N-diisobutylbenzenesulfonamide

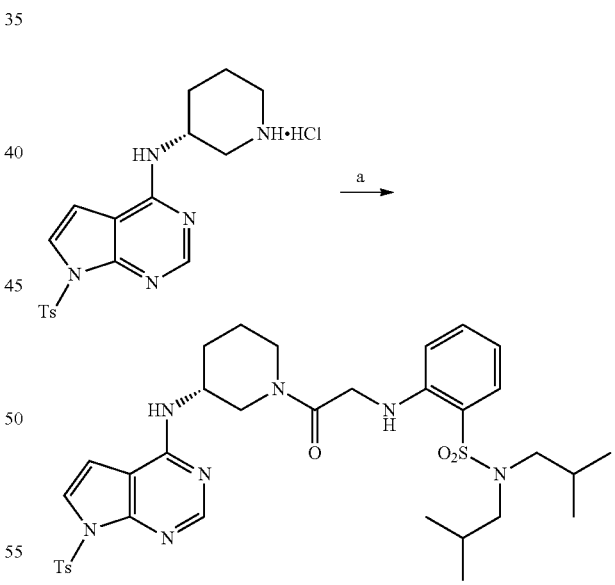

Reagents and conditions: a) i. 2-(2-(N,N-diisobutylsulfamoyl)phenylamino)acetic acid, EDCI, HOBt, DIEA, DMF, rt, 5 h; ii. K₂CO₃, MeOH:H₂O, 50° C., 2 h.

Synthesis of (R)-2-(2-(3-(7H-pyrrolo[2,3-d]pyrimidin-4-ylamino)piperidin-1-yl)-2-oxoethylamino)-N,N-diisobutylbenzenesulfonamide A similar procedure was used as described for the synthesis of 2-(3-chloro-5-fluorophenylamino)-1-((R)-3-(7H-pyrrolo[2,3-d]pyrimidin-4-ylamino)piperidin-1-yl)ethanone to yield the titled compound (46 mg, 60%). ¹H NMR (400 MHz, CD₃OD): δ 8.24 and 8.18 (2s, 1H), 7.63-7.55 (m, 1H), 7.43-7.35 (m, 1H), 7.08-6.95 (m, 1H), 6.80-6.52 (m, 3H), 4.58-4.49 (m, 1H), 4.42-4.19 (m, 3H), 3.87-3.80 (m, 2H), 3.24-3.17 (m, 1H), 3.05-2.95 (m, 4H), 2.19-2.12 (m, 1H), 1.98-1.82 (m, 4H), 1.79-1.65 (m, 1H), 0.85-0.78 (m, 12H). LC-MS: m/z [M+1]=542.

Example 21

Synthesis of (S)-1-(3-(1H-pyrazolo[3,4-d]pyrimidin-4-ylamino)piperidin-1-yl)-2-(3,5-dichlorophenylamino)ethanone

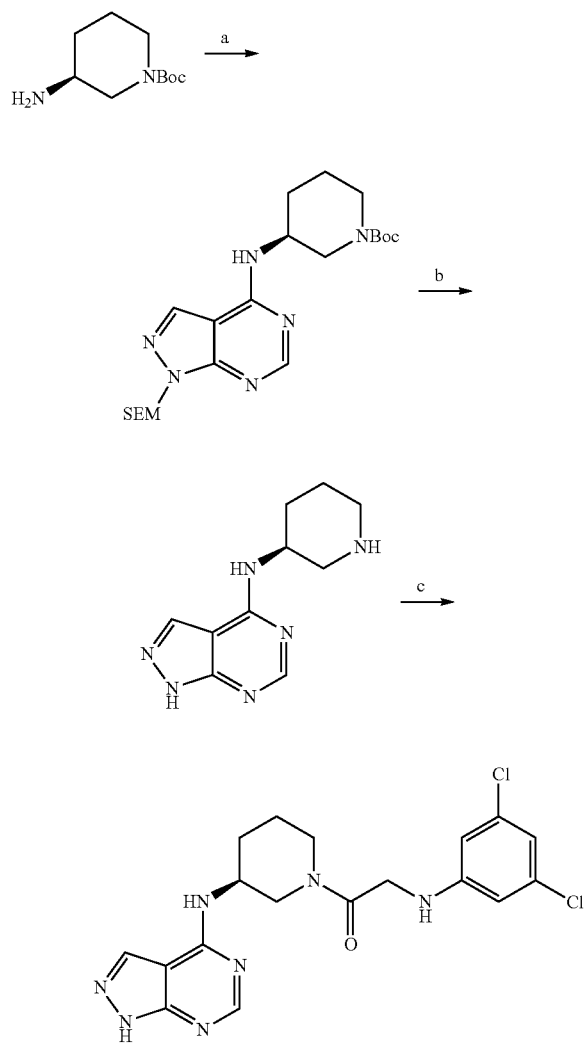

Reagents and conditions: a) 4-Chloro-1-((2-(trimethylsilyl)ethoxy)methyl)-1H-pyrazolo[3,4-d]pyrimidine, DIEA, DMF, 90° C., 15 h; b) (i) EtOH:HCl, rt, 30 min.; (ii) carbonate polyer supported resin, MeOH, rt, 1 h.; c) 2-(3,5-Dichlorophenylamino)acetic acid, EDCI, HOBt, DIEA, DMF, rt, 5 h.

Synthesis of (S)-tert-butyl 3-(1-((2-(trimethylsilyl)ethoxy)methyl)-1H-pyrazolo[3,4-d]pyrimidin-4-ylamino)piperidine-1-carboxylate To a solution of (S)-1-benzyl-N-methylpiperidin-3-amine (4.3 g, 21.46 mmol) and 4-chloro-1-((2-(trimethylsilyl)ethoxy)methyl)-1H-pyrazolo[3,4-d]pyrimidine (6.11 g, 21.5 mmol) in anhydrous DMF (40 mL), Et₃N (4.4 mL, 32.2 mmol) was added and the reaction mixture was stirred at 90° C. for 4 h. After completion of the reaction as indicated by TLC, the reaction mixture was diluted with EtOAc (100 mL) and was washed with water (3×40 mL). The EtOAc layer was then dried over Na₂SO₄ and evaporated in vacuo to give a residue that was subjected to purification by column chromatography (silica gel, gradient EtOAc in hexanes) to afford the titled intermediate (5.9 g, 61%). ¹H NMR (400 MHz, DMSO-d₆): δ 8.30 (s, 1H), 8.24 (s, 1H), 8.09 (s, 1H), 5.59 (s, 2H), 4.09 (m, 2H), 3.72 (m, 1H), 3.53 (t, J=8.0 Hz, 2H), 3.38 (m, 1H), 3.17 (m, 1H), 1.98 (m, 1H), 1.81 (m, 1H), 1.60 (m, 1H), 1.38 (m, 1H), 1.21 (s, 9H), 0.81 (t, J=8.4 Hz, 2H), −0.09 (s, 9H). LC-MS: m/z [M+1]=449.

Synthesis of (S)—N-(piperidin-3-yl)-1H-pyrazolo[3,4-d]pyrimidin-4-amine

To a solution of compound (S)-tert-butyl 3-(1-((2-(trimethylsilyl)ethoxy)methyl)-1H-pyrazolo[3,4-d]pyrimidin-4-ylamino)piperidine-1-carboxylate (1 g, 2.22 mmol) in dioxane (10 mL) at 0° C., was added a solution of HCl in dioxane (10 mL) until the pH was acidic at 0° C. and stirred for 30 min at the same temperature. The reaction mixture was concentrated in vacuo to give a residue that was triturated with ether to give (S)—N-(piperidin-3-yl)-1H-pyrazolo[3,4-d]pyrimidin-4-amine hydrochloride as a free flowing solid. Then the compound was dissolved in MeOH, and to the reaction mixture resin was added until the mixture turns basic (Checked by pH paper). The reaction mixture was filtered and the filtrate was concentrated in vacuo to yield the titled intermediate (350 mg, 72%). ¹H NMR (400 MHz, DMSO-d₆): δ 13.1 (bs, 1H), 8.28 (s, 1H), 8.23 (s, 1H), 4.46 (bs, 2H), 3.36-3.34 (m, 2H), 3.16-3.08 (m, 1H), 2.99-2.86 (m, 2H), 2.50 (bs, 1H), 1.97-1.81 (m, 2H), 1.68-1.58 (m, 2H). LC-MS: m/z [M+1]=219.

Synthesis of ((S)-1-(3-(1H-pyrazolo[3,4-d]pyrimidin-4-ylamino)piperidin-1-yl)-2-(3,5-dichlorophenylamino)ethanone To a cooled solution of 2-(3,5-dichlorophenylamino)acetic acid (102 mg, 0.45 mmol) at 0° C. in anhydrous DMF (5 mL), HOBt (135 mg, 0.68 mmol) was added and the reaction mixture was stirred for 10 min before EDCI (132 mg 0.68 mmol), (S)—N-(piperidin-3-yl)-1H-pyrazolo[3,4-d]pyrimidin-4-amine (100 mg, 0.45 mmol) and DIEA (117 mg, 0.90 mmol) were added in succession. The reaction mixture was allowed to warm to rt and stirred overnight. After completion of the reaction as indicated by TLC, the reaction mixture was diluted with EtOAc (50 mL) and was washed with water (3×20 mL). The EtOAc layer was then dried over Na₂SO₄ and evaporated in vacuo to give a residue that was purified by column chromatography (silica gel, gradient MeOH in CH₂Cl₂) to afford the titled intermediate (62 mg, 32%). ¹H NMR (400 MHz, CDCl₃): δ 11.42 (bs, 1H), 8.58 and 8.49 (2s, 1H), 7.98 (s, 1H), 6.71 and 6.68 (2s, 2H), 6.41 and 6.39 (2s, 2H), 5.29-5.18 (m, 1H), 4.40-4.09 (m, 2H), 3.94-3.42 (m, 3H), 3.18-3.03 (m, 1H), 2.27-2.20 (m, 1H), 1.97-1.56 (m, 4H). LC-MS: m/z [M+1]=420.

Example 22

Synthesis of (S)-2-(2-(3-(1H-pyrazolo[3,4-d]pyrimidin-4-ylamino)piperidin-1-yl)-2-oxoethylamino)-N,N-diisobutylbenzenesulfonamide

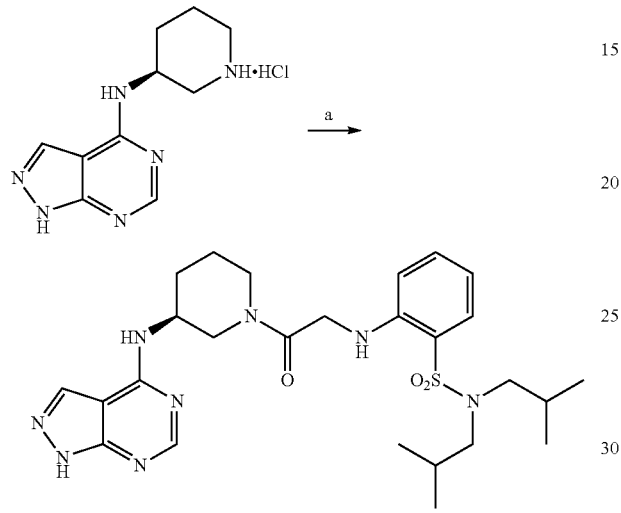

Reagents and conditions: a) 2-(2-(N,N-Diisobutylsulfamoyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (38 mg, 22%). ¹H NMR (400 MHz, CD₃OD): δ 8.27 and 8.20 (2s, 2H), 7.61 (d, J=7.6 Hz, 1H), 7.31 (t, J=7.6 Hz, 1H), 6.72 (t, J=7.6 Hz, 1H), 6.57 (d, J=7.6 Hz, 1H), 4.39-4.37 (m, 1H), 4.30-4.25 (m, 1H), 4.05-3.98 (m, 1H), 3.87-3.76 (m, 2H), 3.70-3.60 (m, 2H), 2.98 (d, J=7.6 Hz, 4H), 2.12-1.96 (m, 1H), 1.94-1.82 (m, 3H), 1.76-1.66 (m, 2H), 0.89-0.79 (m, 12H). LC-MS: m/z [M+1]=543.

Example 23

Synthesis of (S)-1-(3-(1H-pyrazolo[3,4-d]pyrimidin-4-ylamino)piperidin-1-yl)-2-(2-chlorophenylamino)ethanone

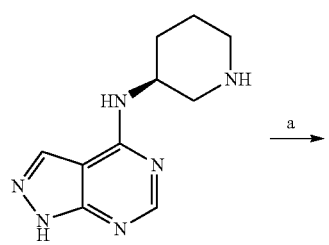

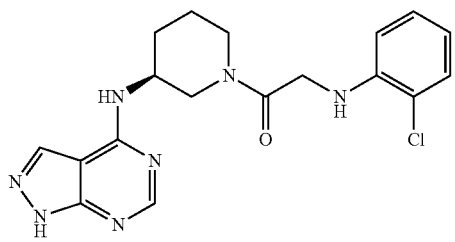

Reagents and conditions: a) 2-(2-Chlorophenylamino)acetic acid, EDCI, HOBt, DIEA, DMF, rt, 5 h.

Synthesis of (S)-1-(3-(1H-pyrazolo[3,4-d]pyrimidin-4-ylamino)piperidin-1-yl)-2-(2-chlorophenylamino)ethanone A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (60 mg, 29%). LC-MS: m/z [M+1]=386.

Example 24

Synthesis of (S)-1-(3-(1H-pyrazolo[3,4-d]pyrimidin-4-ylamino)piperidin-1-yl)-2-(3-chlorophenylamino)ethanone

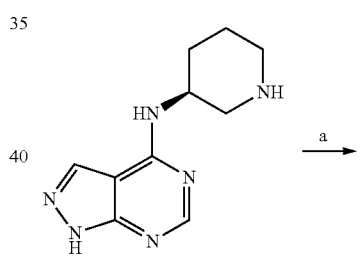

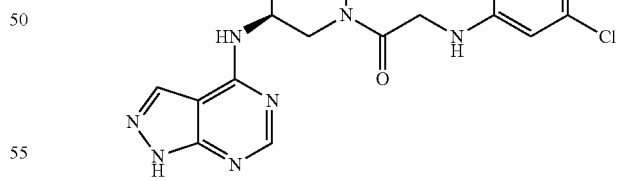

Reagents and conditions: a) 2-(3-Chlorophenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (70 mg, 19%). ¹H NMR (400 MHz, CD₃OD): δ 8.28 (2s, 1H), 8.12 (brs, 1H), 7.03 (2t, J=8.5 Hz, 1H), 6.65-6.50 (m, 3H), 4.20 (m, 3H), 4.01 (d, J=3.2 Hz, 1H), 3.17 (m, 1H), 3.00 (m, 1H), 3.23 (m, 1H), 2.17 (m, 1H), 1.97-1.57 (m, 3H). LC-MS: m/z [M+1]=386.

Example 25

Synthesis of (S)-1-(3-(1H-pyrazolo[3,4-d]pyrimidin-4-ylamino)piperidin-1-yl)-2-(4-chlorophenylamino)ethanone

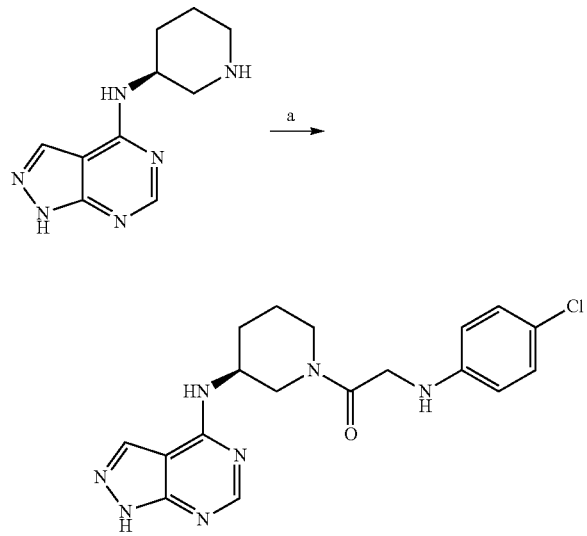

Reagents and conditions: a) 2-(4-chlorophenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (100 mg, 28%). $^1$H NMR (400 MHz, DMSO-d$_6$): δ 13.42 (2s, 1H), 8.27-8.01 (m, 2H), 7.09 (d, J=8.8 Hz, 1H), 7.04 (d, J=8.8 Hz, 1H), 6.68 (d, J=6.5 Hz, 1H), 6.56 (d, J=6.5 Hz, 1H), 5.86-5.79 (m, 1H), 4.11-3.79 (m, 4H), 3.17 (m, 1H), 3.15 (m, 1H), 2.72 (m, 1H), 2.05 (m, 1H), 1.82 (m, 1H), 1.59 (m, 1H), 1.45 (m, 1H). LC-MS: m/z [M+1]=386.

Example 26

Synthesis of (S)-1-(3-(1H-pyrazolo[3,4-d]pyrimidin-4-ylamino)piperidin-1-yl)-2-(2-(trifluoromethyl)phenylamino)ethanone

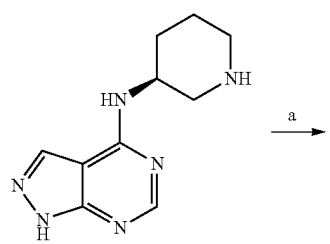

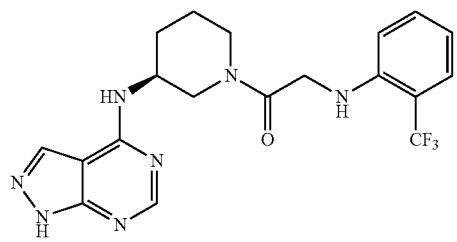

Reagents and conditions: a) 2-(2-(Trifluoromethyl)phenylamino)acetic acid, EDCI, HOBt, DIEA, DMF, rt, 5 h.

Experimental procedure: Following a similar procedure as for ((S)-1-(3-(1H-pyrazolo[3,4-d]pyrimidin-4-ylamino)piperidin-1-yl)-2-(3,5-dichlorophenylamino)ethanone, the titled compound (62 mg, 16%) was synthesized. $^1$H NMR (400 MHz, DMSO-d$_6$): δ 13.43 (s, 1H), 8.27-7.94 (m, 3H), 7.44 (m, 2H), 6.89-6.68 (m, 2H), 5.76 (m, 1H), 4.49 (m, 1H), 4.15-3.83 (m, 4H), 3.20-3.08 (m, 2H), 2.06 (m, 1H), 1.83 (m, 1H), 1.62-1.54 (m, 2H). LC-MS: m/z [M+1]=420.

Example 27

Synthesis of (S)-1-(3-(1H-pyrazolo[3,4-d]pyrimidin-4-ylamino)piperidin-1-yl)-2-(3-(trifluoromethyl)phenylamino)ethanone

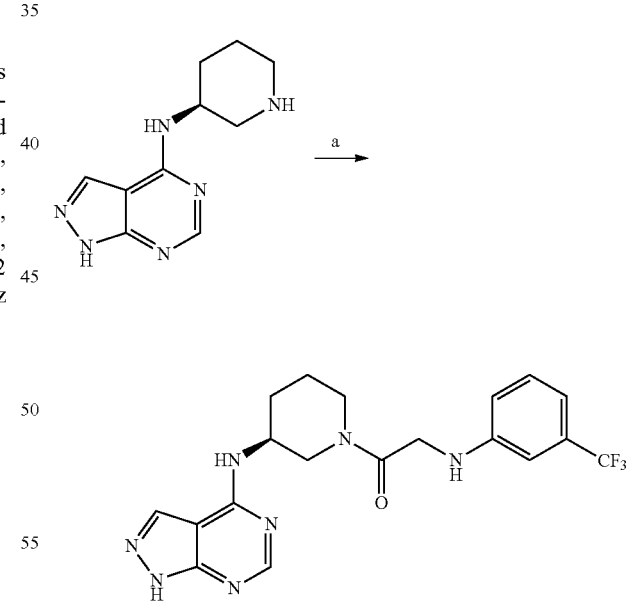

Reagents and conditions: a) 2-(3-(Trifluoromethyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (125 mg, 43%). $^1$H NMR (400 MHz, DMSO-d$_6$): δ 13.42 (2s, 1H), 8.25-8.01 (m, 3H), 7.25 (m, 1H), 6.98-6.82 (m, 3H), 6.14 (2t, J=2.1 Hz, 1H), 4.08-3.85

(m, 4H), 3.38 (m, 1H), 3.12 (m, 1H), 2.96 (m, 1H), 2.71 (m, 1H), 2.06 (m, 1H), 1.83 (m, 1H), 1.61 (m, 1H), 1.47 (m, 1H). LC-MS: m/z [M+1]=420.

Example 28

Synthesis of (S)-1-(3-(1H-pyrazolo[3,4-d]pyrimidin-4-ylamino)piperidin-1-yl)-2-(4-(trifluoromethyl)phenylamino)ethanone

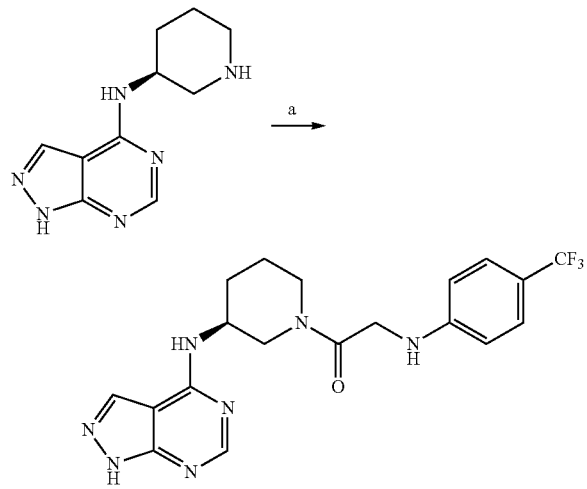

Reagents and conditions: a) 2-(4-(trifluoromethyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (85 mg, 22%). $^1$H NMR (400 MHz, CD3OD): δ 8.33 and 8.23 (2s, 1H), 8.15 (s, 1H), 7.34 (dd, J=8.0, 18.8 Hz, 2H), 6.71 and 6.64 (2d, J=8.0 Hz, 2H), 4.23-4.07 (m, 4H), 3.94-3.84 (m, 1H), 3.24 (m, 1H), 3.07-2.95 (m, 1H), 2.16-2.14 (m, 1H), 2.03-1.83 (m, 2H), 1.71-1.58 (m, 1H). LC-MS: m/z [M+1]=420.

Example 29

Synthesis of (S)-1-(3-(7H-pyrrolo[2,3-d]pyrimidin-4-ylamino)piperidin-1-yl)-2-(2-fluorophenylamino)ethanone

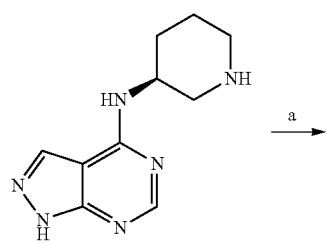

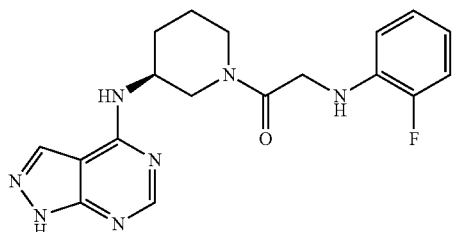

Reagents and conditions: a) 2-(2-Fluorophenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (84 mg, 24%). $^1$H NMR (400 MHz, DMSO-d$_6$): δ 13.41 (d, J=10.4 Hz, 1H), 8.27-7.95 (m, 3H), 7.01-6.57 (m, 3H), 5.32 (m, 1H), 4.49-4.46 (m, 1H), 4.13-3.84 (m, 4H), 3.22-3.06 (m, 3H), 2.06-1.83 (m, 2H), 1.69-1.49 (m, 2H). LC-MS: m/z [M+1]=370.

Example 30

Synthesis of (S)-1-(3-(1H-pyrazolo[3,4-d]pyrimidin-4-ylamino)piperidin-1-yl)-2-(3-fluorophenylamino)ethanone

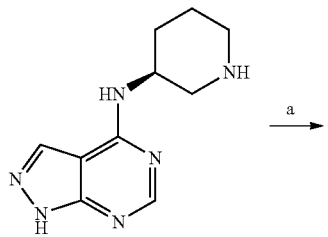

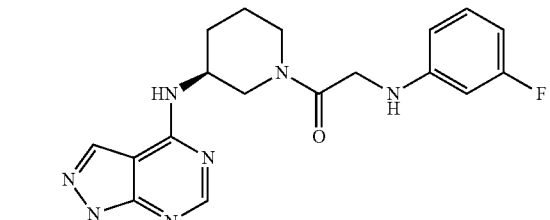

Reagents and conditions: a) 2-(3-(Fluorophenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (60 mg, 14%). $^1$H NMR (400 MHz, CD$_3$OD): δ 8.54-8.52 (m, 1H), 7.08-7.06 (m, 1H), 6.46-6.33

(m, 4H), 4.47-4.38 (m, 1H), 4.19-3.85 (m, 4H), 3.16-2.93 (m, 2H), 2.20 (m, 1H), 1.94-1.74 (m, 3H). LC-MS: m/z [M+1]=370.

Example 31

Synthesis of (S)-1-(3-(1H-pyrazolo[3,4-d]pyrimidin-4-ylamino)piperidin-1-yl)-2-(4-fluorophenylamino)ethanone

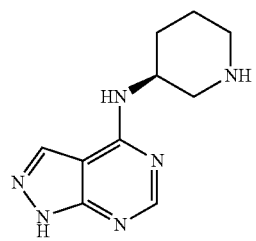

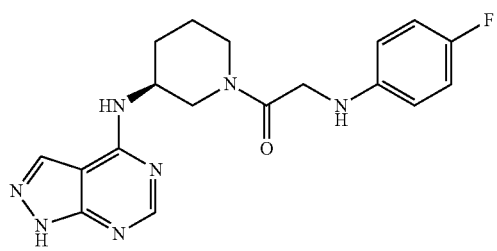

Reagents and conditions: a) 2-(4-Fluorophenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (65 mg, 19%). $^1$H NMR (400 MHz, CD$_3$OD): δ 8.28 (2s, 1H), 8.12 (d, J=8.8 Hz, 1H), 6.88-6.78 (m, 2H), 6.65-6.54 (m, 2H), 4.18-3.81 (m, 4H), 3.24 (m, 2H), 3.10-2.94 (m, 2H), 1.92-1.77 (m, 2H), 1.72-1.57 (m, 2H). LC-MS: m/z [M+1]=370.

Example 32

Synthesis of (S)-1-(3-(1H-pyrazolo[3,4-d]pyrimidin-4-ylamino)piperidin-1-yl)-2-(3,5-bis(trifluoromethyl)phenylamino)ethanone

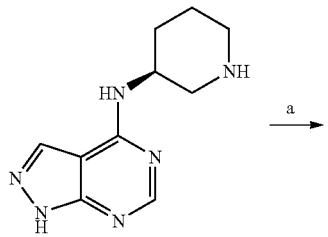

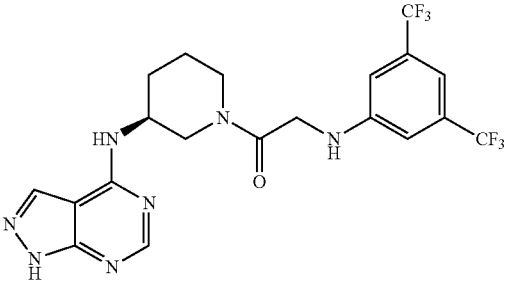

Reagents and conditions: a) 2-(3,5-Bis(trifluoromethyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (180 mg, 40%). $^1$H NMR (400 MHz, DMSO-d$_6$): δ 13.42 (2s, 1H), 8.22-8.02 (m, 3H), 7.30 (s, 1H), 7.24 (s, 1H), 7.07 (s, 1H), 6.71 (m, 1H), 4.14-3.87 (m, 4H), 3.09 (m, 2H), 2.91 (t, J=13.2 Hz, 1H), 2.72 (t, J=13.2 Hz, 1H), 2.06 (m, 1H), 1.83 (m, 1H), 1.62 (m, 1H), 1.47 (m, 1H). LC-MS: m/z [M+1]=488.

Example 33

Synthesis of (S)-1-(3-(1H-pyrazolo[3,4-d]pyrimidin-4-ylamino)piperidin-1-yl)-2-(3-chloro-5-(trifluoromethyl)phenylamino)ethanone

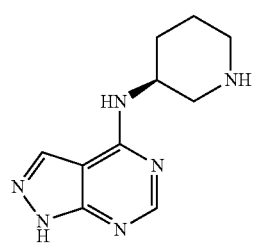

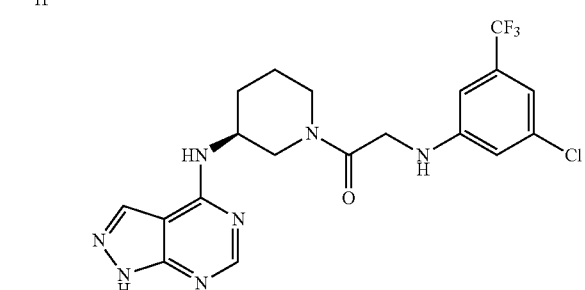

Reagents and conditions: a) 2-(3-Chloro-5-(trifluoromethyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (40 mg, 9%). $^1$H NMR (400 MHz, CD$_3$OD): NMR (400 MHz, DMSO-d$_6$): δ 13.41 (2s, 1H), 8.31-8.02 (m, 3H), 7.03 (s, 1H), 6.95 (s, 1H), 6.83 (s, 1H), 6.52 (2t, J=2.1 Hz, 1H), 4.11-3.824 (m, 4H), 3.08 (m, 2H), 2.92 (t, J=13.2 Hz, 1H), 2.75 (t, J=Hz, 1H), 2.06 (m, 1H), 1.69 (m, 1H), 1.62 (m, 1H), 1.51 (m, 1H). LC-MS: m/z [M+1]=454.

Example 34

Synthesis of (S)-1-(3-(1H-pyrazolo[3,4-d]pyrimidin-4-ylamino)piperidin-1-yl)-2-(3-fluoro-5-(trifluoromethyl)phenylamino)ethanone

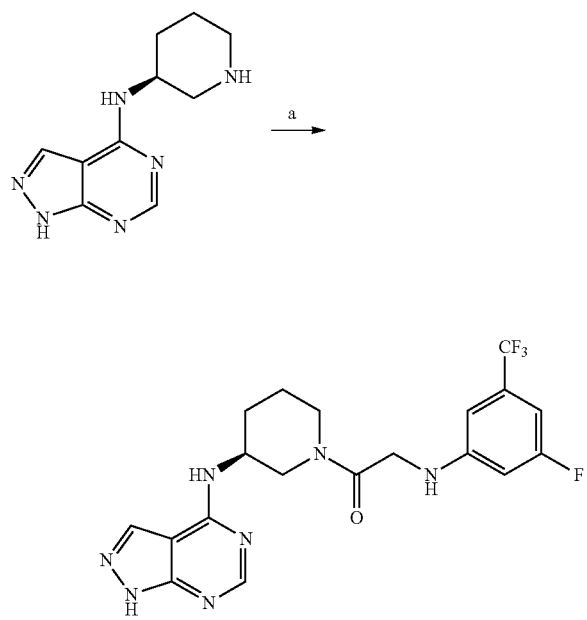

Reagents and conditions: a) 2-(3-Fluoro-5-(trifluoromethyl)phenylamino)acetic acid, EDCI, HOBt, DIEA, DMF, rt, 5 h.

A similar procedure was used as described for the synthesis of ((S)-1-(3-(1H-pyrazolo[3,4-d]pyrimidin-4-ylamino)piperidin-1-yl)-2-(3,5-dichlorophenylamino)ethanone to yield the titled compound (100 mg, 25%). $^1$H NMR (400 MHz, DMSO-$d_6$): δ 13.41 (2s, 1H), 8.31-8.01 (m, 3H), 6.88 (2s, 1H), 6.74 (2d, J=8.5 Hz, 1H), 6.64 (d, J=6.5 Hz, 1H), 6.52 (2t, J=3.0 Hz, 1H), 4.10-3.83 (m, 4H), 3.10 (m, 2H), 2.93 (t, J=12.5 Hz, 1H), 2.72 (t, J=12.5 Hz, 1H), 2.06 (m, 1H), 1.83 (m, 1H), 1.62 (m, 1H), 1.48 (m, 1H). LC-MS: m/z [M+1]=438. HPLC (254 nm)=94.85%.

Example 35

Synthesis of (S)-2-(3,5-dichlorophenylamino)-1-(3-(methyl(1H-pyrazolo[3,4-d]pyrimidin-4-yl)amino)piperidin-1-yl)ethanone

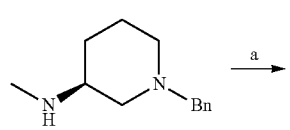

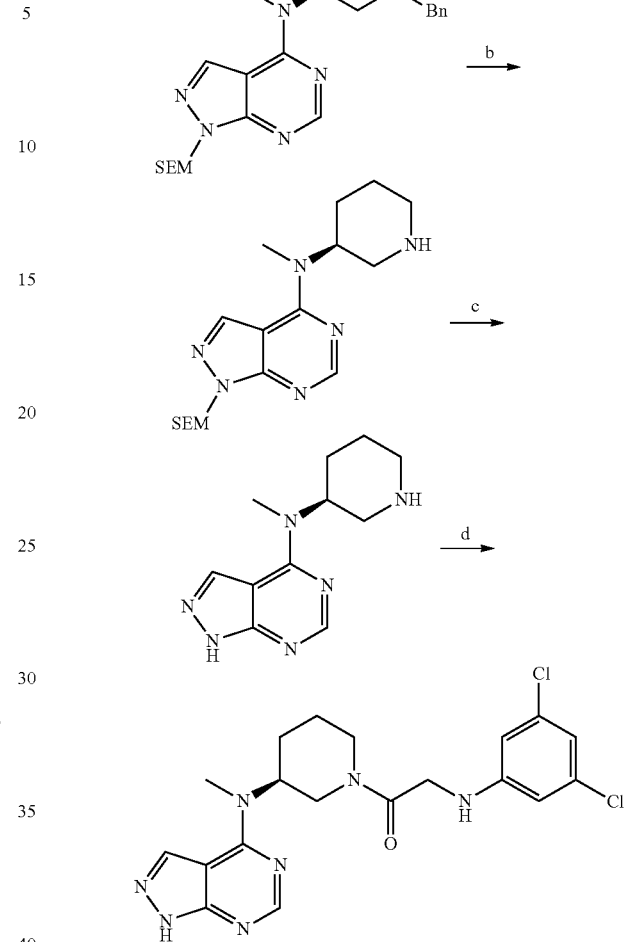

Reagents and conditions: a) 4-Chloro-1-((2-(trimethylsily)ethoxy)methyl)-1H-pyrazolo[3,4-d]pyrimidine, DIEA, DMF, 90° C.; b) Pd/C, HCOONH$_4$, MeOH, reflux; c) EtOH•HCl, 80° C.; d) 2-(3,5-dichlorophenylamino)acetic acid, EDCI, HOBt, DIEA, DMF, rt, 15 h.

Synthesis of (S)—N-(1-benzylpiperidin-3-yl)-N-methyl-1-((2-(trimethylsilyl)ethoxy)methyl)-1H-pyrazolo[3,4-d]pyrimidin-4-amine To a solution of (S)-1-benzyl-N-methylpiperidin-3-amine (500 mg, 2.4 mmol) and 4-chloro-1-((2-(trimethylsilyl)ethoxy)methyl)-1H-pyrazolo[3,4-d]pyrimidine (697 mg, 2.4 mmol) in DMF (10 mL), DIEA (1.26 g, 9.7 mmol) was added and the reaction mixture was stirred at 60° C. overnight. After reaction was completed as indicated by TLC, the reaction mixture was diluted with EtOAc (40 mL) and was washed with water (3×20 mL). The EtOAc layer was then dried over Na$_2$SO$_4$ and evaporated in vacuo to give a residue that was purified by column chromatography (silica gel, gradient EtOAc in hexanes) to afford the titled intermediate (550 mg, 49%). $^1$H NMR (400 MHz, CD$_3$OD): δ 8.26 (s, 1H), 8.15 (bs, 1H), 7.32 (m, 3H), 7.22 (m, 2H), 5.67 (s, 2H), 3.61 (t, J=9.2 Hz, 2H), 3.57 (m, 2H), 3.31 (s, 3H), 2.95 (m, 2H), 2.24 (m, 1H), 2.03 (m, 2H), 1.80 (m, 4H), 0.86 (m, 2H), 0.07 (s, 9H). LC-MS: m/z [M+1]=453.

Synthesis of (S)—N-methyl-N-(piperidin-3-yl)-1-((2-(trimethylsilyl)ethoxy)methyl)-1H-pyrazolo[3,4-d]pyrimidin-4-amine To a solution of (S)—N-(1-benzylpiperidin-3-yl)-N-methyl-1-((2-(trimethylsilyl)ethoxy)methyl)-1H-pyrazolo[3,4-d]pyrimidin-4-amine (540 mg, 1.19 mmol) in McOH under nitrogen, 10% Pd/C (540 mg) was added. To this suspension, ammonium formate (752 mg, 11.9 mmol) was added and the reaction mixture was refluxed under nitrogen for 4 h. After completion of the reaction as indicated by TLC, the reaction mixture was cooled to rt and filtered over celite. The filtrate was concentrated in vacuo to give a residue that was purified by column chromatography (silica gel, gradient EtOAc in hexanes) to afford the titled intermediate (325 mg, 80%). $^1$H NMR (400 MHz, CD$_3$OD): δ 8.34 (s, 1H), 8.29 (s, 1H), 5.70 (s, 2H), 3.63 (t, J=8.4 Hz, 2H), 3.39 (s, 3H), 3.22 (m, 2H), 3.03 (m, 1H), 2.11 (m, 1H), 2.00 (m, 1H), 1.32 (m, 4H), 0.87 (t, J=8.4 Hz, 2H), 0.00 (9H). LC-MS: m/z [M+1]=363.

Synthesis of (S)—N-methyl-N-(piperidin-3-yl)-1H-pyrazolo[3,4-d]pyrimidin-4-amine To a solution of (S)—N-methyl-N-(piperidin-3-yl)-1-((2-(trimethylsilyl)ethoxy)methyl)-1H-pyrazolo[3,4-d]pyrimidin-4-amine (310 mg, 0.85 mmol) in EtOH (7.5 mL), conc. HCl (2.5 mL) was added and the reaction mixture was heated at 60° C. for 5 h. The reaction mixture was concentrated in vacuo and the residue was dissolved in MeOH (5 mL) and a polymer support carbonate resin was added until the mixture turned basic (Checked by litmus paper). The reaction mixture was filtered and the filtrate was concentrated in vacuo to yield the titled intermediate (189 mg, 95%), which was used further without further purification. LC-MS: m/z [M+1]=233.

Synthesis of (S)-2-(3,5-dichlorophenylamino)-1-(3-(methyl(1H-pyrazolo[3,4d]-pyrimidin-4-yl)amino)piperidin-1-yl)ethanone To a cooled solution of 2-(3,5-dichlorophenylamino)acetic acid (170 mg, 0.77 mmol) at 0° C. in DMF (5 mL), HOBt (156 mg, 1.16 mmol) was added and the reaction mixture was stirred for 10 min before EDCI (222 mg, 1.16 mmol), (S)—N-methyl-N-(piperidin-3-yl)-1H-pyrazolo[3,4-d]pyrimidin-4-amine (180 mg, 0.77 mmol) and DIEA (150 mg, 1.16 mmol) were added in succession. The reaction mixture was allowed to warm to rt and was stirred overnight. After completion of the reaction as indicated by TLC, the reaction mixture was diluted with EtOAc (50 mL) and was washed with water (3×20 mL). The EtOAc layer was then dried over Na$_2$SO$_4$ and evaporated in vacuo to give a residue that purified by column chromatography (silica gel, gradient MeOH in DCM) to afford the titled intermediate (50 mg, 14.8%). $^1$H NMR (400 MHz, CD$_3$OD): δ 8.79 (s, 1H), 8.50 and 8.49 (2s, 1H), 6.61 (s, 2H), 6.59 (s, 1H), 5.21-5.18 (m, 1H), 4.61-4.55 (m, 1H), 4.14-3.84 (m, 3H), 3.54 (s, 3H), 3.38-3.13 (m, 1H), 3.02-2.68 (m, 1H), 2.14-1.93 (m, 3H), 1.76-1.65 (m, 1H). LC-MS: m/z [M+1]=434.

Example 36

Synthesis of (S)-2-(3-chloro-5-(trifluoromethyl)phenylamino)-1-(3-(methyl(1H-pyrazolo[3,4-d]pyrimidin-4-yl)amino)piperidin-1-yl)ethanone

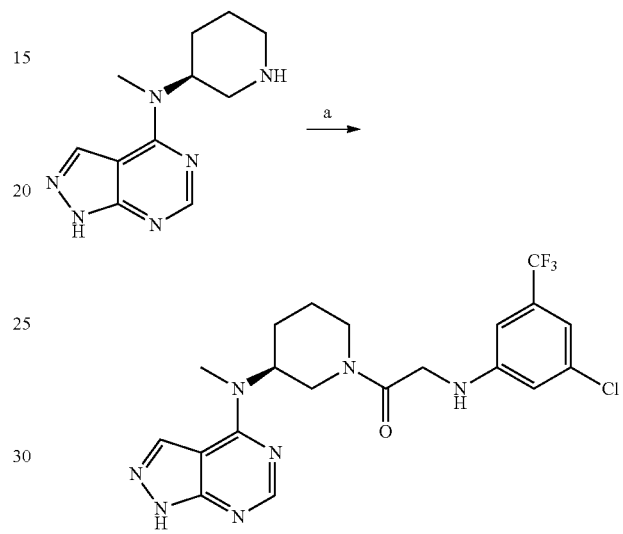

Reagents and conditions: a) 2-(3-Chloro-5-(trifluoromethyl)phenylamino)acetic acid, EDCI, HOBt, DIEA, DMF, rt, 15 h.

A similar procedure was used as described for the synthesis of (S)-2-(3,5-dichlorophenylamino)-1-(3-(methyl(1H-pyrazolo[3,4-d]pyrimidin-4-yl)amino)piperidin-1-yl)ethanone to yield the titled compound (12 mg, 3%). $^1$H NMR (400 MHz, CD$_3$OD): δ 8.74 (s, 1H), 8.46 (s, 1H), 6.88 (s, 1H), 6.85 (s, 2H), 5.20-5.18 (m, 1H), 4.63-4.59 (m, 1H), 4.20-3.90 (m, 3H), 3.53 (s, 3H), 3.30-3.13 (m, 1H), 3.04-2.68 (m, 1H), 2.11-1.93 (m, 3H), 1.74-1.62 (m, 1H). LC-MS: m/z [M+1]=468.

Example 37

Synthesis of (S)-2-(3,5-bis(trifluoromethyl)phenylamino)-1-(3-(methyl(1H-pyrazolo[3,4-d]pyrimidin-4-yl)amino)piperidin-1-yl)ethanone

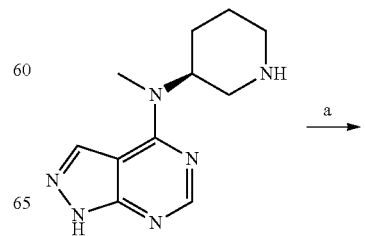

-continued

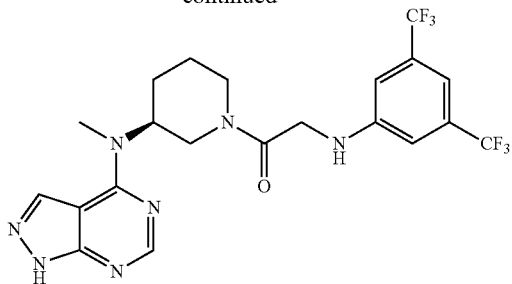

Reagents and conditions: a) 2-(3,5-Bis(trifluoromethyl)phenylamino)acetic acid, EDCI, HOBt, DIEA, DMF, rt, 15 h.

A similar procedure was used as described for the synthesis of (S)-2-(3,5-dichlorophenylamino)-1-(3-(methyl(1H-pyrazolo[3,4-d]pyrimidin-4-yl)amino)piperidin-1-yl)ethanone to yield the titled compound (30 mg, 96%). $^1$H NMR (400 MHz, CD$_3$OD): δ 8.80 (s, 1H), 8.47 (s, 1H), 7.14 (s, 1H), 7.12 (s, 1H), 7.09 (s, 1H), 5.20-5.18 (m, 1H), 4.63-4.56 (m, 1H), 4.23-4.04 (m, 3H), 3.56 and 3.53 (s, 3H), 3.30-3.13 (m, 1H), 3.14-2.78 (m, 1H), 2.11-1.93 (m, 3H), 1.79-1.59 (m, 1H). LC-MS: m/z [M+1]=468.

Example 38

Synthesis of (S)-2-(3-chloro-5-fluorophenylamino)-1-(3-(methyl(1H-pyrazolo[3,4-d]pyrimidin-4-yl)amino)piperidin-1-yl)ethanone

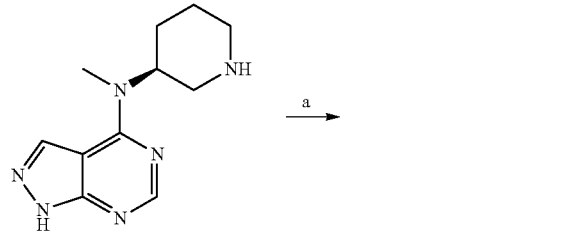

Reagents and conditions: a) 2-(3-Chloro-5-fluorophenylamino)acetic acid, EDCI, HOBt, DIEA, DMF, rt, 15 h.

A similar procedure was used as described for the synthesis of (S)-2-(3,5-dichlorophenylamino)-1-(3-(methyl(1H-pyrazolo[3,4-d]pyrimidin-4-yl)amino)piperidin-1-yl)ethanone to yield the titled compound (55 mg, 17%). $^1$H NMR (400 MHz, CD$_3$OD): δ 8.77 (s, 1H), 8.49 and 8.48 (s, 1H), 6.50-6.33 (m, 3H), 5.23-5.18 (m, 1H), 4.60-4.55 (m, 1H), 4.14-3.93 (m, 3H), 3.54 (s, 3H), 3.30-3.13 (m, 1H), 3.04-2.68 (m, 1H), 2.14-1.93 (m, 3H), 1.74-1.65 (m, 1H). LC-MS: m/z [M+1]=418.

Example 39

Synthesis of (R)-1-(3-(1H-pyrazolo[3,4-d]pyrimidin-4-ylamino)piperidin-1-yl)-2-(3-chloro-5-fluorophenylamino)ethanone

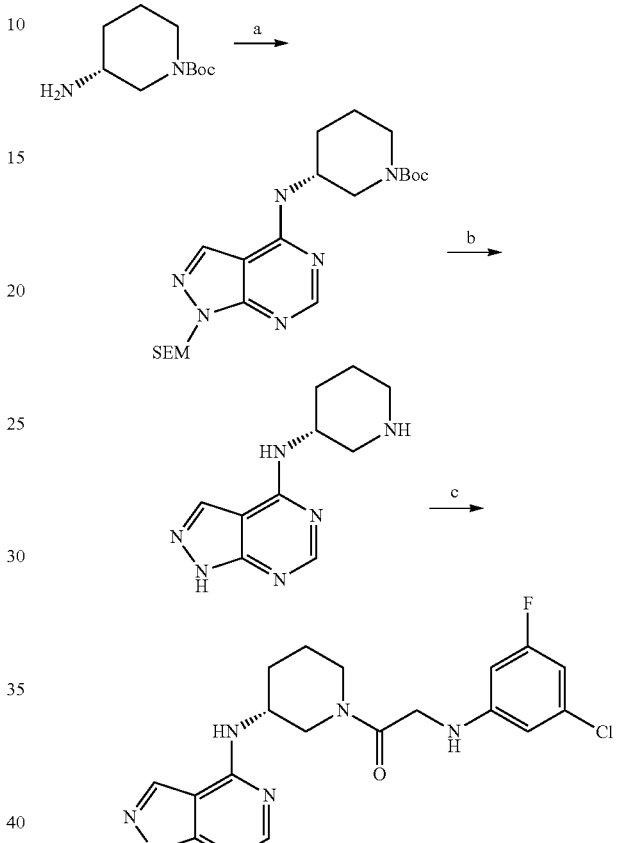

Reagents and conditions: a) 4-Chloro-1-((2-(trimethylsilyl)ethoxy)methyl)-1H-pyrazolo[3,4-d]pyrimidine, DIEA, DMF, 90° C., 15 h; b) (i) EtOH:HCl, rt, 30 min.; (ii) Carbonate polymer support resin, MeOH, rt, 1 h.; c) 2-(3-Chloro-5-fluorophenylamino)acetic acid, EDCI, HOBt, DIEA, DMF, rt. 5 h.

Synthesis of (R)-tert-butyl 3-(1-((2-(trimethylsilyl)ethoxy)methyl)-1H-pyrazolo[3,4-d]pyrimidin-4-ylamino)piperidine-1-carboxylate To a solution of (R)-1-benzyl-N-methylpiperidin-3-amine (4.3 g, 21.46 mmol) and 4-chloro-1-((2-(trimethylsilyl)ethoxy)methyl)-1H-pyrazolo[3,4-d]pyrimidine (6.11 g, 21.5 mmol) in anhydrous DMF (40 mL), Et$_3$N (4.4 mL, 32.2 mmol) was added and the reaction mixture was stirred at 90° C. for 4 h. After completion of the reaction as indicated by TLC, the reaction mixture was diluted with EtOAc (100 mL) and was washed with water (3×40 mL). The EtOAc layer was then dried over Na$_2$SO$_4$ and evaporated in vacuo to give a residue that was subjected to purification by column chromatography (silica gel, gradient EtOAc in hexanes) to afford the titled compound (5.9 g, 61%). $^1$H NMR (400 MHz, DMSO-d$_6$): δ 8.30 (s, 1H), 8.24 (s, 1H), 8.09 (s, 1H), 5.59 (s, 2H), 4.09 (m, 2H), 3.72 (m, 1H), 3.53 (t, J=8.0 Hz, 2H), 3.38 (m, 1H), 3.17 (m, 1H), 1.98 (m, 1H), 1.81 (m, 1H), 1.60 (m, 1H), 1.38 (m, 1H), 1.21 (s, 9H), 0.81 (t, J=8.4 Hz, 2H), −0.09 (s, 9H). LC-MS: m/z [M+1]=449.

Synthesis of (R)—N-(piperidin-3-yl)-1H-pyrazolo[3,4-d]pyrimidin-4-amine

To a solution of compound (R)-tert-butyl 3-(1-((2-(trimethylsilyl)ethoxy)methyl)-1H-pyrazolo[3,4-d]pyrimidin-4-ylamino)piperidine-1-carboxylate (1 g, 2.22 mmol) in dioxane (10 mL) at 0° C., a solution of HCl in dioxane (10 mL) was added until the pH was acidic at 0° C. and stirred for 30 min, at the same temperature. The reaction mixture was concentrated to give a residue that was triturated with ether to give (R)—N-(piperidin-3-yl)-1H-pyrazolo[3,4-d]pyrimidin-4-amine hydrochloride as a free flowing solid. Then the compound was dissolved in MeOH, and to the reaction mixture was added a carbonate polymer support resin until the mixture turns basic (Checked by pH paper). The reaction mixture was filtered and the filtrate was concentrated in vacuo to yield the titled compound (350 mg, 72%). $^1$H NMR (400 MHz, DMSO-$d_6$): δ 13.1 (bs, 1H), 8.28 (s, 1H), 8.23 (s, 1H), 4.46 (bs, 2H), 3.36-3.34 (m, 2H), 3.16-3.08 (m, 1H), 2.99-2.86 (m, 2H), 2.50 (bs, 1H), 1.97-1.81 (m, 2H), 1.68-1.58 (m, 2H). LC-MS: m/z [M+1]=219.

Synthesis of (R)-1-(3-(1H-pyrazolo[3,4-d]pyrimidin-4-ylamino)piperidin-1-yl)-2-(3-chloro-5-fluorophenylamino)ethanone To a cooled solution of 2-(3-chloro-5-fluorophenylamino) acetic acid (70 mg, 0.34 mmol) at 0° C. in DMF (5 mL), HOBt (69 mg, 0.51 mmol) was added and the reaction mixture was stirred for 10 min. before EDCI (101 mg 0.51 mmol), (R)—N-(piperidin-3-yl)-1H-pyrazolo[3,4-d]pyrimidin-4-amine (75 mg, 0.34 mmol) and DIEA (104 mg, 0.80 mmol) were added in succession. The reaction mixture was allowed to warm to rt and was stirred overnight. After completion of the reaction as indicated by TLC the reaction mixture was diluted with EtOAc (50 mL) and was washed with water (3×20 mL). The EtOAc layer was then dried over $Na_2SO_4$ and evaporated in vacuo to give a residue that was purified by column chromatography (silica gel, gradient MeOH in $CH_2Cl_2$) to afford the titled compound (14 mg, 10%). 1H NMR (400 MHz, $CD_3OD$): δ 8.52-8.43 (m, 1H), 6.45-6.08 (m, 4H), 4.49-3.82 (m, 5H), 3.31-2.95 (m, 2H), 1.96-1.63 (m, 4H). LC-MS: m/z [M+1]=404.

Example 40

Synthesis of (R)-1-(3-(1H-pyrazolo[3,4-d]pyrimidin-4-ylamino)piperidin-1-yl)-2-(3,5-dichlorophenylamino)ethanone

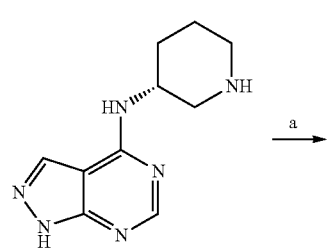

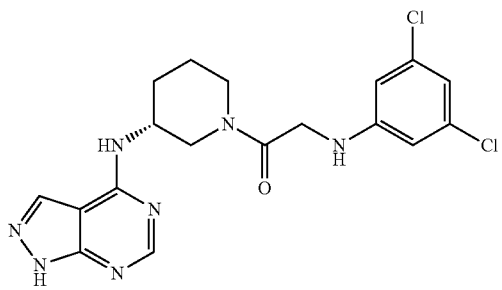

Reagents and conditions: a) 2-(3,5-Dichlorophenylamino)acetic acid, EDCI, HOBt, DIEA, DMF, rt, 5 h.

A similar procedure was used as described for the synthesis of (R)-1-(3-(1H-pyrazolo[3,4-d]pyrimidin-4-ylamino)piperidin-1-yl)-2-(3-chloro-5-fluorophenylamino)ethanone to yield the titled compound (80 mg, 83%). $^1$H NMR (400 MHz, $CD_3OD$): δ 8.34 and 8.22 (2s, 1H), 8.12 and 8.09 (2s, 1H), 6.60-6.55 (m, 3H), 4.56-3.81 (m, 5H), 3.20-2.93 (m, 2H), 2.21-2.01 (m, 2H), 1.92-1.62 (m, 2H). LC-MS: m/z [M+1]=420.

Example 41

Synthesis of (R)-2-(3,5-dichlorophenylamino)-1-(3-(methyl(7H-pyrrolo[2,3-d]pyrimidin-4-yl)amino)piperidin-1-yl)ethanone

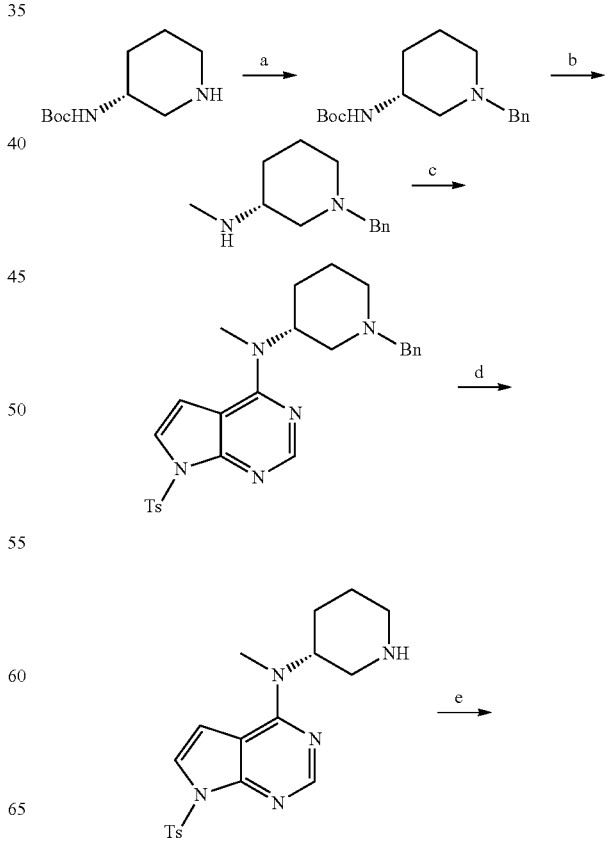

-continued

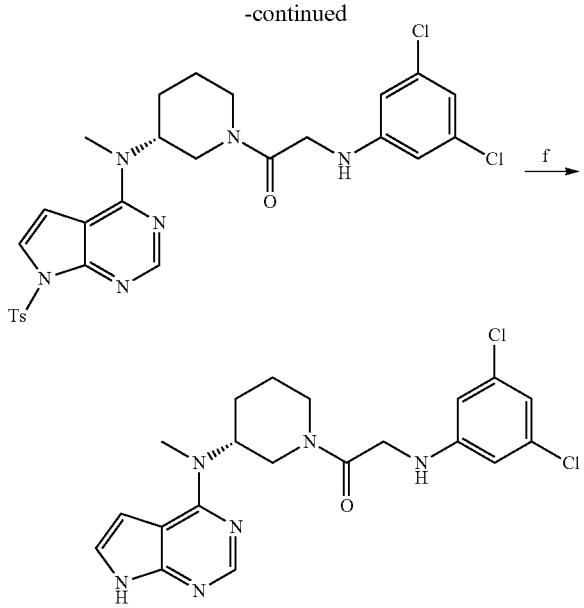

Reagents and conditions: a) PhCHO, NaBH₃CN, CH₂Cl₂, rt; b) LiAlH₄, THF, reflux; c) 4-chloro-7-tosyl-7H-pyrrolo[2,3-d]pyrimidine, DIEA, DMF, 90° C.; d) Pd/C, HCOONH₄, MeOH, reflux; e) 2-(3,5-dichlorophenylamino)acetic acid, EDCI, HOBt, DIEA, DMF; f) K₂CO₃, MeOH:H₂O, 50° C.

Synthesis of (R)-tert-butyl 1-benzylpiperidin-3-ylcarbamate

To a solution of (R)-tert-butyl piperidin-3-ylcarbamate (500 mg, 2.4 mmol) in MeOH (15 mL), AcOH (0.75 mL, 12.4 mmol) and NaCNBH₃ (310 mg, 4.8 mmol) were added sequentially. To this stirred solution was added benzaldehyde (0.25 mL, 2.4 mmol) drop-wise. The reaction mixture was stirred at rt for 60 h before saturated K₂CO₃(aq) solution was added to neutralize it. The reaction mixture was concentrated in vacuo to give a residue which was dissolved in water and extracted with EtOAc (30 mL×3). The combined EtOAc layer was dried over Na₂SO₄ and concentrated in vacuo to afford the titled intermediate (725 mg, 48%) that was used in the next step without further purification. LC-MS: m/z [M+1]=291.

Synthesis of (R)-1-benzyl-N-methylpiperidin-3-amine

To a stirred solution of (R)-tert-butyl 1-benzylpiperidin-3-ylcarbamate (300 mg, 1.03 mmol) in THF (5 mL) at −30° C., LiAlH₄ (0.77 mL of 2 M solution in THF, 1.5 mmol) was added dropwise under inert atmosphere. After addition the reaction mixture was warmed to rt and then heated to reflux for 2 h. After completion of the reaction, a 20% aq. solution of NaOH solution (5 mL) was added dropwise to the reaction mixture. The reaction mixture was diluted with EtOAc (50 mL) and the suspension was filtered over a short pad of celite. The filtrate was dried over Na₂SO₄ and concentrated in vacuo to give the titled intermediate (200 mg, 94%). The compound was used in the further steps without purification. LC-MS: m/z [M+1]=205.

Synthesis of (R)—N-(1-benzylpiperidin-3-yl)-N-methyl-7-tosyl-7H-pyrrolo[2,3-d]pyrimidin-4-amine To a solution of (R)-1-benzyl-N-methylpiperidin-3-amine (800 mg, 3.9 mmol) and 4-chloro-7-tosyl-7H-pyrrolo[2,3-d]pyrimidine (1.2 g, 3.9 mmol) in DMF (10 mL), DIEA (2.02 mL, 15.6 mmol) was added and the reaction mixture was stirred at 60° C. overnight. After completion of the reaction (monitored by TLC), the reaction mixture was diluted with EtOAc (100 mL) and was washed with water (3×40 mL). The EtOAc layer was then dried over Na₂SO₄ and evaporated in vacuo to give a residue that was purified by column chromatography (silica gel, gradient EtOAc in hexanes) to afford the titled intermediate (750 mg, 40%). ¹H-NMR (400 MHz, CDCl₃): δ 8.37 (s, 1H), 8.02 (d, J=8.4 Hz, 2H), 7.38 (d, 0.1=4.0 Hz, 1H), 7.28 (m, 7H), 6.53 (d, J=3.6 Hz, 1H), 3.59 (d, J=13.2 Hz, 1H), 3.46 (d, J=13.2 Hz, 1H), 3.13 (s, 3H), 2.89 (m, 2H), 2.37 (s, 3H), 2.09 (t, J=10.8 Hz, 1H), 1.96 (dt, J=1.2, 10.8 Hz, 1H), 1.83 (m, 2H), 1.65 (m, 3H). LC-MS: m/z [M+1]=476.

Synthesis of (R)—N-methyl-N-(piperidin-3-yl)-7-tosyl-7H-pyrrolo[2,3-d]pyrimidin-4-amine To a solution of (R)—N-(1-benzylpiperidin-3-yl)-N-methyl-7-tosyl-7H-pyrrolo[2,3-d]pyrimidin-4-amine (750 mg, 1.5 mmol) in MeOH under nitrogen, 10% Pd/C (750 mg) was added. To this suspension, ammonium formate (995 mg, 15 mmol) was added and the reaction mixture was refluxed under nitrogen for 2 h. After completion of the reaction (TLC), the reaction mixture was cooled to rt and filtered over celite. The filtrate was concentrated in vacuo to give a residue, that was purified by column chromatography (silica gel, gradient EtOAc in hexanes) to afford the titled intermediate (395 mg, 65%). ¹H NMR (400 MHz, DMSO-d₆): δ 8.27 (s, 1H), 7.97 (d, J=7.6 Hz, 2H), 7.65 (d, J=2.8 Hz, 1H), 7.43 (d, J=8.0 Hz, 2H), 7.01 (d, J=3.2 Hz, 1H), 5.03 (bs, 1H), 3.10-2.95 (m, 3H), 2.82-2.76 (m, 2H), 2.50 (s, 3H), 2.36 (s, 3H), 1.89-1.75 (m, 4H). LC-MS: m/z [M+1]=386.

Synthesis of (R)-2-(3,5-dichlorophenylamino)-1-(3-(methyl(7-tosyl-7H-pyrrolo[2,34]pyrimidin-4-yl)amino)piperidin-1-yl)ethanone To a cooled solution of 2-(3,5-dichlorophenylamino)acetic acid (85 mg, 0.3 mmol) in DMF (5 mL) was added HOBt (78 mg, 0.5 mmol) EDCI (112 mg 0.5 mmol), at 0° C. and the reaction mixture was stirred for 10 min, before (R)—N-methyl-N-(piperidin-3-yl)-7-tosyl-7H-pyrrolo[2,3-d]pyrimidin-4-amine (150 mg, 0.3 mmol) and DIEA (0.13 mL, 0.7 mmol) were added in succession. The reaction mixture was allowed to warm to rt and was stirred overnight. After completion of the reaction (TLC), the reaction mixture was diluted with EtOAc (50 mL) and was washed with water (3×20 mL). The EtOAc layer was then dried over Na₂SO₄ and evaporated in vacuo to give a residue that purified by column chromatography (silica gel, gradient MeOH in DCM) to afford the titled intermediate (228 mg, 67%). LC-MS: m/z [M+1]=587.

Synthesis of (R)-2-(3,5-dichlorophenylamino)-1-(3-(methyl(7H-pyrrolo[2,3-d]pyrimidin-4-yl)amino)piperidin-1-yl)ethanone To a solution of (R)-2-(3,5-dichlorophenylamino)-1-(3-(methyl(7-tosyl-7H-pyrrolo[2,3-d]pyrimidin-4-yl)amino)piperidin-1-yl)ethanone (150 mg, 0.25 mmol) in MeOH:H₂O (4:1 mL) was added K₂CO₃ (141 mg, 1.0 mmol) and the reaction mixture was heated to 60° C. for 1 h. The reaction mixture was concentrated in vacuo and the residue obtained was diluted in EtOAc (50 mL). The EtOAc suspension was filtered through celite and the filtrate was then dried over Na₂SO₄, and concentrated in vacuo to give a residue that was subjected to purification by column chromatography (silica gel, gradient MeOH in DCM) to afford the titled intermediate (110 mg, 50%). $^1$H NMR (400 MHz, DMSO-$d_6$): δ 11.65 (d, J=11.2 Hz, 1H), 8.10 (d, J=6.4 Hz, 1H), 7.14 (d, J=13.6 Hz, 1H), 6.75 (s, 1H), 6.69 (s, 1H), 6.62 (s, 1H), 6.55 (s, 1H), 6.35 (m, 1H), 4.69 (m, 1H), 4.41 (m, 1H), 3.99 (m, 2H), 3.00 (m, 1H), 2.88 (m, 1H), 2.60 (m, 1H), 2.49 (s, 3H), 1.94-1.80 (m, 2H), 1.65 (m, 1H), 1.49 (m, 1H). LC-MS: m/z [M+1]=455.

Example 42

Synthesis of (R)-2-(3,5-dichlorophenylamino)-1-(3-(methyl(1H-pyrazolo[3,4-d]pyrimidin-4-yl)amino)piperidin-1-yl)ethanone

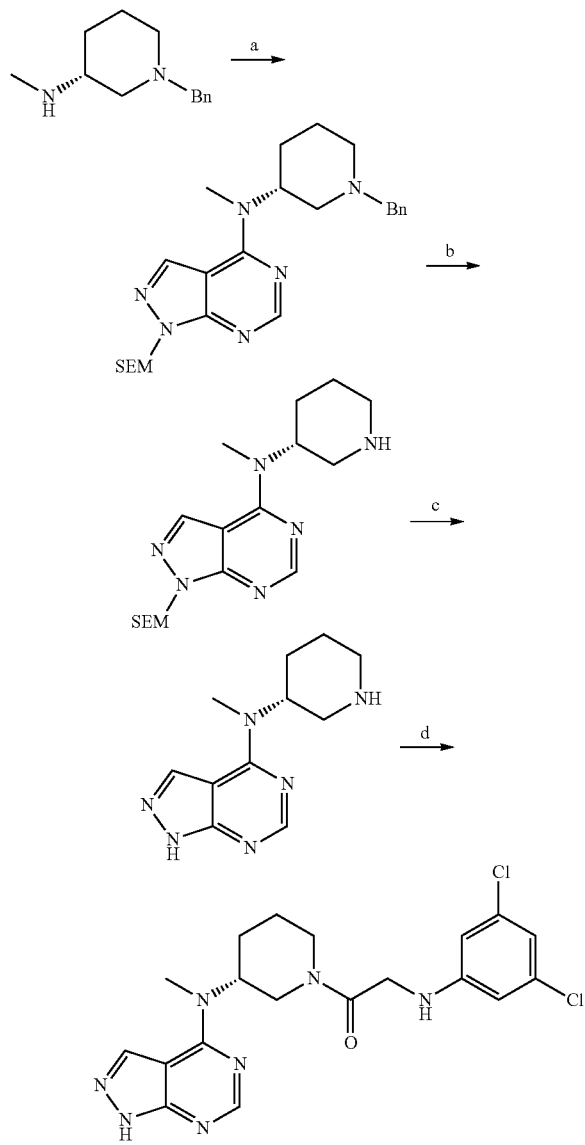

Reagents and conditions: a) 4-chloro-1-((2-(trimethylsily)ethoxy)methyl)-1H-pyrazolo[3,4-d]pyrimidine, DIEA, DMF, 90° C.; b) Pd/C, HCOONH$_4$, MeOH, reflux; c) EtOH•HCl, 80° C.; d) 2-(3,5-dichlorophenylamino)acetic acid, EDCI, HOBt, DIEA, DMF.

Synthesis of (R)—N-(1-benzylpiperidin-3-yl)-N-methyl-1-((2-(trimethylsilyl)ethoxy)methyl)-1H-pyrazolo[3,4-d]pyrimidin-4-amine To a solution of (R)-1-benzyl-N-methylpiperidin-3-amine (500 mg, 2.4 mmol) and 4-chloro-1-((2-(trimethylsilyl)ethoxy)methyl)-1H-pyrazolo[3,4-d]pyrimidine (697 mg, 2.4 mmol) in DMF (10 mL) was added DIEA (1.26 g, 9.7 mmol) and the reaction mixture was stirred at 60° C. overnight. The reaction mixture was diluted with EtOAc (40 mL) and was washed with water (3×20 mL). The EtOAc layer was dried over Na$_2$SO$_4$ and evaporated in vacuo to give a residue that was purified by column chromatography (silica gel, gradient EtOAc in hexanes) to afford the titled intermediate (550 mg, 49%). $^1$H NMR (400 MHz, CDCl$_3$): δ 8.37 (s, 1H), 7.98 (s, 1H), 7.34-7.20 (m, 5H), 5.71 (s, 2H), 3.62 (t, J=8.0 Hz, 2H), 3.55 (m, 2H), 3.24 (s, 3H), 2.91 (m, 2H), 2.17 (m, 1H), 1.99 (m, 2H), 1.79 (m, 2H), 1.41 (m, 1H), 1.27 (m, 1H), 0.92 (t, J=8.0 Hz, 2H), −0.054 (s, 9H). LC-MS: m/z [M+1]=453.

Synthesis of (R)—N-methyl-N-(piperidin-3-yl)-1-((2-(trimethylsilyl)ethoxy)methyl)-1H-pyrazolo[3,4-d]pyrimidin-4-amine To a solution of (R)—N-(1-benzylpiperidin-3-yl)-N-methyl-1-((2-(trimethylsilyl)ethoxy)methyl)-1H-pyrazolo[3,4d]-yl)pyrimidin-4-amine (540 mg, 1.19 mmol) in MeOH under nitrogen was added 10% Pd/C (540 mg). To this suspension was added ammonium formate (752 mg, 11.9 mmol) and the reaction mixture was refluxed under nitrogen for 4 h. The reaction mixture was cooled to rt and filtered over celite. The filtrate was concentrated in vacuo to give a residue, that was purified by column chromatography (silica gel, gradient EtOAc in hexanes) to afford the titled intermediate (325 mg, 80%). $^1$H NMR (400 MHz, CD$_3$OD): δ 8.31 (s, 1H), 8.25 (s, 1H), 5.69 (s, 2H), 3.63 (t, J=8.4 Hz, 2H), 3.35 (s, 3H), 3.22 (m, 2H), 3.05 (t, J=12.0 Hz, 1H), 2.81 (t, J=7.8 Hz, 1H), 2.04-1.96 (m, 3H), 1.84 (m, 1H), 1.33 (m, 2H), 0.87 (t, J=8.4 Hz, 2H), −0.07 (s, 9H). LC-MS: m/z [M+1]=363.

Synthesis of (R)—N-methyl-N-(piperidin-3-yl)-1H-pyrazolo[3,4-d]pyrimidin-4-amine To a solution of (R)—N-methyl-N-(piperidin-3-yl)-1-((2-(trimethylsilyl)ethoxy)methyl)-1H-pyrazolo[3,4-d]pyrimidin-4-amine (310 mg, 0.85 mmol) in EtOH (7.5 mL) was added conc. HCl (2.5 mL) and the reaction mixture was heated at 60° C. for 5 h. The reaction mixture was concentrated in vacuo and the residue was dissolved in MeOH (5 mL) and treated with a polymer supported carbonate resin. The reaction mixture was filtered and the filtrate was concentrated in vivo to yield the titled intermediate (189 mg, 95%), which was used further without further purification. $^1$H NMR (400 MHz, CD$_3$OD): δ 8.23 (s, 1H), 8.21 (s, 1H), 3.31 (s, 3H), 3.30 (m, 1H), 3.09 (m, 2H), 2.89 (t, J=11.2 Hz, 1H), 2.63 (dt, J=2.8, 12.8 Hz, 1H), 1.93 (m, 2H), 1.76 (m, 2H), 1.75 (m, 1H), 1.35 (m, 1H). LC-MS: m/z [M+1]=233.

Synthesis of (R)-2-(3,5-dichlorophenylamino)-1-(3-(methyl(1H-pyrazolo[3,4-d]pyrimidin-4-yl)amino)piperidin-1-yl)ethanone To a solution of 2-(3,5-dichlorophenylamino)acetic acid (170 mg, 0.77 mmol) in DMF (5 mL) was added HOBt (156 mg, 1.16 mmol) at 0° C. and the reaction mixture was stirred for 10 min, followed by the addition of EDCI (222 mg, 1.16 mmol), (R)—N-methyl-N-(piperidin-3-yl)-1H-pyrazolo[3, 4-d]pyrimidin-4-amine (180 mg, 0.77 mmol) and DIEA (150 mg, 1.16 mmol). The reaction mixture was allowed to warm to rt and was stirred overnight, diluted with EtOAc (50 mL) and washed with water (3×20 mL). The EtOAc layer was dried over Na$_2$SO$_4$ and evaporated in vacuo to give a residue that purified by column chromatography (silica gel, gradient MeOH in DCM) to afford the titled intermediate (50 mg, 14.8%). $^1$H NMR (400 MHz, DMSO-d$_6$): δ 13.50 (d, J=10.8 Hz, 1H), 8.22 (s, 1H), 8.17 (m, 1H), 6.77 (s, 1H), 6.70 (s, 1H), 6.62 (s, 1H), 6.32 (m, 1H), 4.40 (d, J=12.4 Hz, 1H), 4.00 (m, 3H), 3.28 (s, 3H), 3.02 (t, J=7.8 Hz, 1H), 2.80 (m, 1H), 2.62 (t, J=7.8 Hz, 1H), 2.00 (m, 2H), 1.82 (m, 2H). LC-MS: m/z [M+1]=434.

Example 43

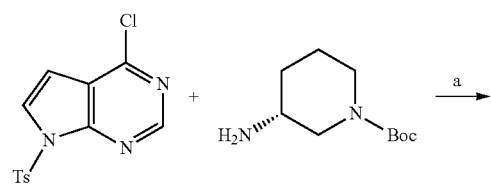

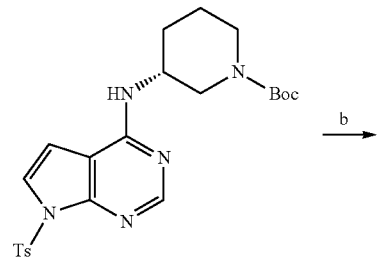

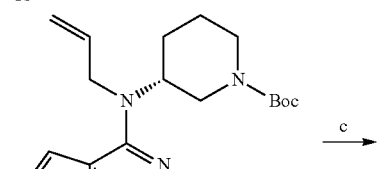

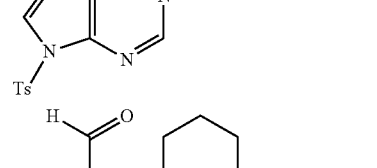

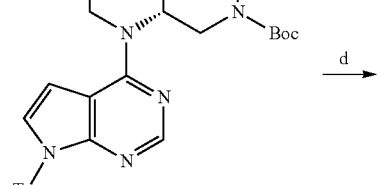

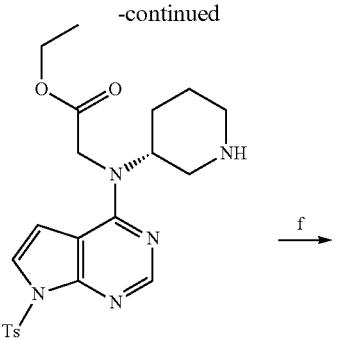

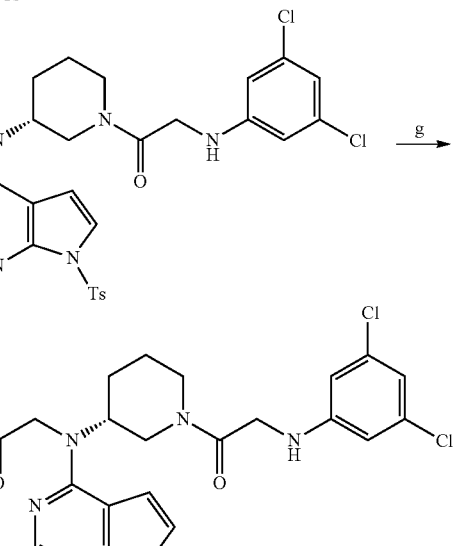

Reagents and conditions: (a) DIEA, DMF, 80° C., 4 h. (b) sodium hydride, C$_3$H$_5$Br, DMF. (c) i. OsO$_4$, THF/water. ii. NaIO$_4$, DCM. (d) NaO$_2$Cl, NaH$_2$PO$_4$, 30% H$_2$O$_2$, CH$_3$CN. (e) i. SOCl$_2$, EtOH, reflux. (f) C$_8$H$_7$O$_2$NCl$_2$, EDCl, HOBt, DIEA, DMF. (g) LiOH, MeOH, 0° C. to rt.

Synthesis of (R)-tert-butyl 3-(7-tosyl-7H-pyrrolo[2,3-d]pyrimidin-4-ylamino) piperidine-1-carboxylate To a solution of 4-chloro-7-tosyl-7H-pyrrolo[2,3-d]pyrimidine (15.35 g, 50 mmol) and (R)-tert-butyl 3-aminopiperidine-1-carboxylate (10 g, 50 mmol) in anhydrous DMF (20 ml) at rt was added diisopropylethylamine (13.3 mL, 75 mmol). The reaction mixture was stirred at rt for 15 h before it was poured on ice and extracted with EtOAc. The EtOAc layer was separated and was washed with water, brine and dried over Na$_2$SO$_4$ and concentrated in vacuo to give the crude product that was purified by column chromatography (silica gel, gradient, EtOAc in hexanes) to give titled compound (20 g, 86%). LCMS [M+1]: 472.

Synthesis of (R)-tert-butyl 3-(allyl(7-tosyl-7H-pyrrolo[2,3-d]pyrimidin-4-yl)amino)piperidine-1-carboxylate To a solution of (R)-tert-butyl 3-(7-tosyl-7H-pyrrolo[2,3-d]pyrimidin-4-ylamino)piperidine-1-carboxylate (1.0 g, 2.1 mmol) in DMF (5 mL), NaH (60% suspension in mineral oil, 100 mg, 2.5 mmol) was added at 0° C. and the reaction mixture was stirred for 1 h. To the reaction mixture was added allyl bromide (308 mg, 2.12 mmol) and the reaction mixture was stirred for 6 h. The solution was diluted with ice-cooled water and stirred for 15 min, the solution was then extracted with EtOAc, dried over $Na_2SO_4$ and concentrated in vacuo to give the crude product that was purified by column chromatography (silica gel, gradient, EtOAc in hexanes) to give (0.9 g, 83%) of the titled compound. $^1H$ NMR (400 MHz, $CDCl_3$): δ 8.42 (s, 1H), 8.06 (d, J=8.0 Hz, 2H), 7.43 (d, J=3.2 Hz, 1H), 7.31 (d, J=8.0 Hz, 2H), 6.57 (d, J=3.2 Hz, 1H), 5.98-5.90 (m, 1H), 5.26-5.19 (m, 2H), 4.62-4.51 (m, 1H), 4.29-4.09 (m, 4H), 2.85 (t, J=11.6 Hz, 1H), 2.68-2.60 (m, 1H), 2.41 (s, 3H), 1.97-1.93 (m, 1H), 1.83-1.72 (m, 2H), 1.65-1.58 (m, 1H), 1.42 (s, 9H). LCMS [M+1]: 512.

Synthesis of (R)-tert-butyl 3-((2,3-dihydroxypropyl) (7-tosyl-7H-pyrrolo[2,3-d]pyrimidin-4-yl)amino) piperidine-1-carboxylate To a solution of (R)-tert-butyl 3-(allyl(7-tosyl-7H-pyrrolo [2,3-d]pyrimidin-4-yl)amino)piperidine-1-carboxylate (1.33 g, 2.60 mmol) in THF (10 mL) and water (10 mL) was added $OsO_4$ (33 mg, 0.13 mmol) and the suspension was stirred for 30 min at rt. $NaIO_4$ (700 mg, 3.12 mmol) was added and the reaction mixture was stirred overnight at rt. The suspension was partitioned between EtOAc and water and the organic phase was separated, washed with water, brine, and concentrated in vacuo to yield the crude product, which was purified by column chromatography (silica gel, gradient MeOH in $CHCl_3$) to afford (1.0 g, 70%) the titled compound. $^1H$ NMR (400 MHz, $CDCl_3$): δ 8.39 (s, 1H), 8.04 (d, J=8.4 Hz, 2H), 7.58 (d, J=3.2 Hz, 1H), 7.31 (d, J=8.0 Hz, 2H), 6.59 (d, J=3.2 Hz, 1H), 4.40-4.01 (m, 4H), 3.82-3.56 (m, 6H), 2.96-2.83 (m, 1H), 2.74-2.62 (m, 1H), 2.42 (s, 3H), 2.10-1.98 (m, 1H), 1.92-1.76 (m, 2H), 1.65-1.49 (m, 1H), 1.42 (s, 9H). LCMS [M+1]: 545.

Synthesis of (R)-tert-butyl 3-((2-oxoethyl) (7-tosyl-7H-pyrrolo[2,3-d]pyrimidin-4-yl)amino) piperidine-1-carboxylate To a solution of (R)-tert-butyl 3-((2,3-dihydroxypropyl)(7-tosyl-7H-pyrrolo[2,3-d]pyrimidin-4-yl)amino)piperidine-1-carboxylate (0.5 g, 0.92 mmol) in $CH_2Cl_2$ (10 mL) was added $NaIO_4$ (392 mg, 1.83 mmol, supported on silica) at 0° C. followed by stirring for 30 min. The reaction mixture was filtered through a Celite pad and the filtrate was in vacuo to give a residue, that was purified by column chromatography (silica gel, gradient MeOH in $CHCl_3$) to afford the titled compound (200 mg, 42%). LCMS [M+1]: 514.

Synthesis of (R)-2-((1-(tert-butoxycarbonyl) piperidin-3-yl) (7-tosyl-7H-pyrrolo[2,3-d]pyrimidin-4-yl) amino)acetic acid To a solution of (R)-tert-butyl 3-((2-oxoethyl)(7-tosyl-7H-pyrrolo[2,3-d]pyrimidin-4-yl)amino)piperidine-1-carboxylate (0.5 g, 0.97 mmol) in $CH_3CN$ (2 mL) at rt, was added an aq. solution of $NaH_2PO_4$ (3 mL, 0.21 g, 1.75 mmol), aq. $NaO_2Cl$ (2 mL, 0.16 g, 1.75 mmol) and 30% $H_2O_2$ (0.17 ml, 1.5 mmol) at 0° C. The reaction mixture was warmed to rt and stirred for overnight. The organic phase was concentrated in vacuo to afford a residue that was dissolved in EtOAc, filtered and dried over $Na_2SO_4$, concentrated in vacuo and purified by column chromatography (Silica gel, gradient MeOH: $CH_2Cl_2$) to afford the titled compound (0.105 g, 20.38%). LCMS [M+1]: 530.

Synthesis of (R)-ethyl 2-(piperidin-3-yl(7-tosyl-7H-pyrrolo[2,3-d]pyrimidin-4-yl)amino)acetate (R)-2-((1-(tert-butoxycarbonyl) piperidin-3-yl) (7-tosyl-7H-pyrrolo[2,3-d]pyrimidin-4-yl)amino) acetic acid (0.2 g, 0.38 mmol) was dissolved in EtOH (5 mL) and treated with a solution of thionyl chloride (0.08 g, 0.68 mmol). After the reaction had gone to completion; the organic solvent was removed in vacuo and the residue (0.180 g, crude yield 85%) was used as such for next step. LCMS [M+1]: 458.

Synthesis of (R)-ethyl 2-((1-(2-(3,5-dichlorophenylamino)acetyl)piperidin-3-yl)(7-tosyl-7H-pyrrolo[2, 3-d]pyrimidin-4-yl)amino)acetate To a solution of (R)-ethyl 2-(piperidin-3-yl(7-tosyl-7H-pyrrolo[2,3-d]pyrimidin-4-yl)amino)acetate (0.2 g, 0.44 mmol) in DMF (2 mL) was added EDCI (0.13 g, 0.66 mmol), HOBt (89 mg, 0.7 mmol), 2-(3,5-dichlorophenylamino)acetic acid (0.1 g, 0.5 mmol) and DIEA (0.12 mL, 0.66 mmol) at 0° C. The solution was stirred at rt overnight, diluted with EtOAc and washed with water, brine, dried over $Na_2SO_4$ and concentrated in vacuo to give a residue which was purified by column chromatography (silica gel gradient methanol in chloroform) to afford (0.09 g, 31%) the titled compound. LCMS [M+1]: 659.

Synthesis of (R)-2-((1-(2-(3,5-dichlorophenylamino) acetyl)piperidin-3-yl)(7H-pyrrolo[2,3-d]pyrimidin-4-yl)amino)acetic acid To a solution of (R)-ethyl 2-((1-((2-(3,5-dichlorophenylamino)acetyl)piperidin-3-yl)(7-tosyl-7H-pyrrolo[2,3-d]pyrimidin-4-yl)amino)acetate (0.2 g, 0.30 mmol) in MeOH (5 mL), $H_2O$ (3 mL) was added LiOH (0.03 g, 0.61 mmol) and the reaction mixture was stirred for 2 h at rt. The reaction mixture was then evaporated in vacuo to give a solid that was triturated with ether to give the lithium salt of the acid as a free flowing solid, which was purified by preparative HPLC to afford (20 mg, 13%) the titled compound. $^1H$ NMR (400 MHz, $CD_3OD$): δ 8.52 (s, 2H), 8.20 (s, 1H), 7.05 (s, 1H), 6.65 (s, 1H), 6.62 (s, 1H), 6.59 (s, 1H), 4.59-3.82 (m, 7H), 3.20 (t, J=11.6 Hz, 1H), 2.65 (t, J=11.6 Hz, 1H), 2.19-2.11 (m, 1H), 1.95-1.82 (m, 2H), 1.63-1.58 (m, 1H). LCMS [M+1]: 477.

Example 44

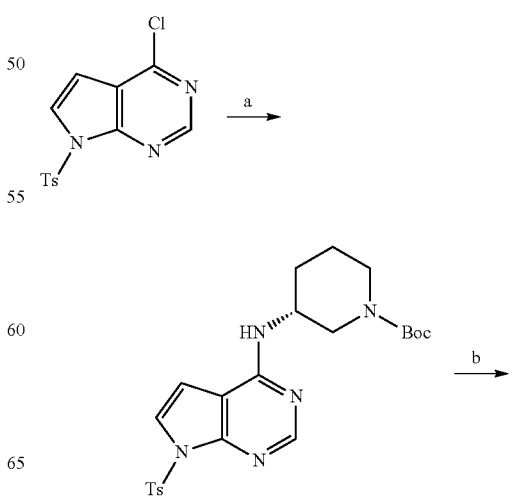

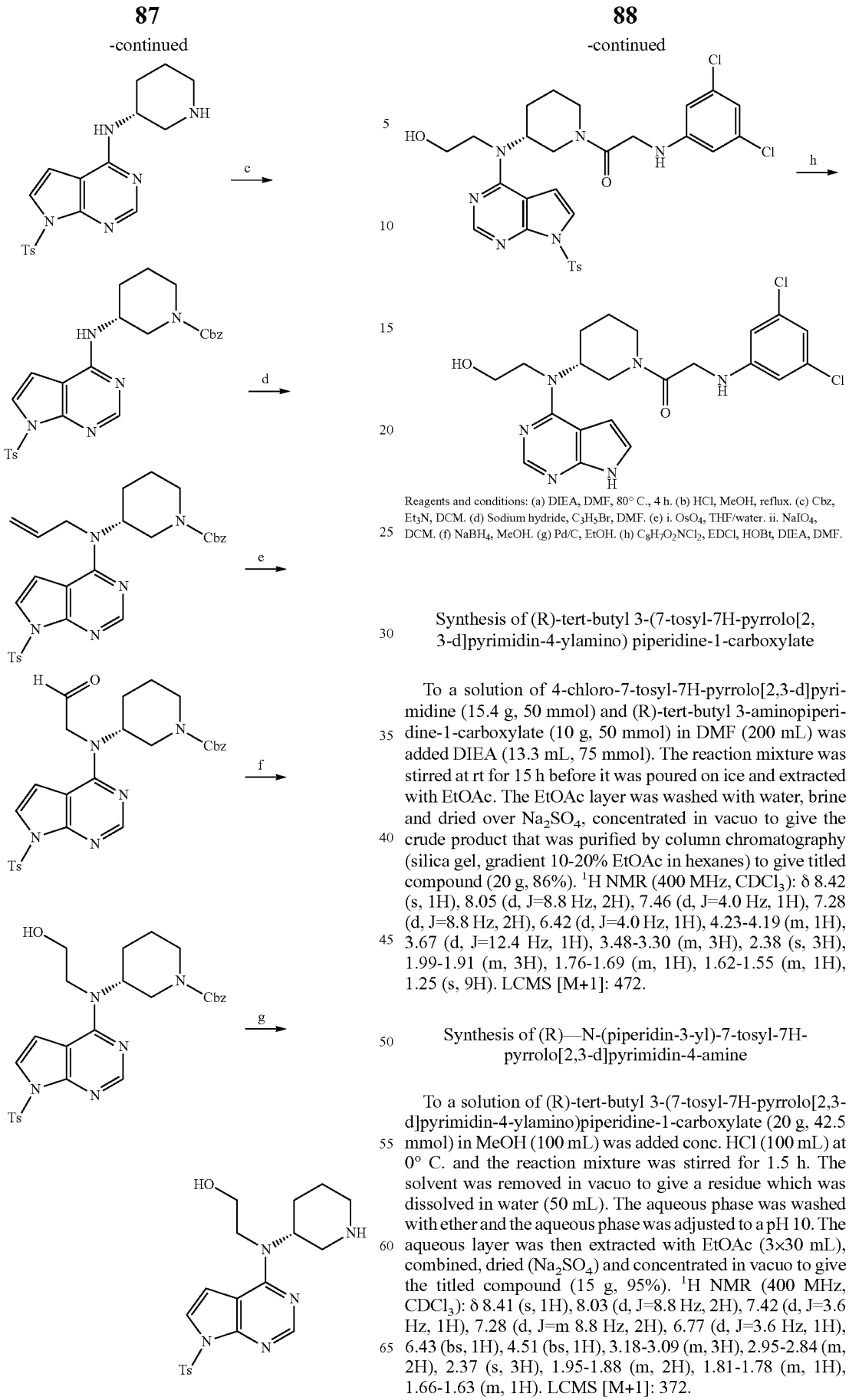

Reagents and conditions: (a) DIEA, DMF, 80° C., 4 h. (b) HCl, MeOH, reflux. (c) Cbz, Et₃N, DCM. (d) Sodium hydride, C₃H₅Br, DMF. (e) i. OsO₄, THF/water. ii. NaIO₄, DCM. (f) NaBH₄, MeOH. (g) Pd/C, EtOH. (h) C₈H₇O₂NCl₂, EDCl, HOBt, DIEA, DMF.

Synthesis of (R)-tert-butyl 3-(7-tosyl-7H-pyrrolo[2,3-d]pyrimidin-4-ylamino) piperidine-1-carboxylate To a solution of 4-chloro-7-tosyl-7H-pyrrolo[2,3-d]pyrimidine (15.4 g, 50 mmol) and (R)-tert-butyl 3-aminopiperidine-1-carboxylate (10 g, 50 mmol) in DMF (200 mL) was added DIEA (13.3 mL, 75 mmol). The reaction mixture was stirred at rt for 15 h before it was poured on ice and extracted with EtOAc. The EtOAc layer was washed with water, brine and dried over Na₂SO₄, concentrated in vacuo to give the crude product that was purified by column chromatography (silica gel, gradient 10-20% EtOAc in hexanes) to give titled compound (20 g, 86%). ¹H NMR (400 MHz, CDCl₃): δ 8.42 (s, 1H), 8.05 (d, J=8.8 Hz, 2H), 7.46 (d, J=4.0 Hz, 1H), 7.28 (d, J=8.8 Hz, 2H), 6.42 (d, J=4.0 Hz, 1H), 4.23-4.19 (m, 1H), 3.67 (d, J=12.4 Hz, 1H), 3.48-3.30 (m, 3H), 2.38 (s, 3H), 1.99-1.91 (m, 3H), 1.76-1.69 (m, 1H), 1.62-1.55 (m, 1H), 1.25 (s, 9H). LCMS [M+1]: 472.

Synthesis of (R)—N-(piperidin-3-yl)-7-tosyl-7H-pyrrolo[2,3-d]pyrimidin-4-amine

To a solution of (R)-tert-butyl 3-(7-tosyl-7H-pyrrolo[2,3-d]pyrimidin-4-ylamino)piperidine-1-carboxylate (20 g, 42.5 mmol) in MeOH (100 mL) was added conc. HCl (100 mL) at 0° C. and the reaction mixture was stirred for 1.5 h. The solvent was removed in vacuo to give a residue which was dissolved in water (50 mL). The aqueous phase was washed with ether and the aqueous phase was adjusted to a pH 10. The aqueous layer was then extracted with EtOAc (3×30 mL), combined, dried (Na₂SO₄) and concentrated in vacuo to give the titled compound (15 g, 95%). ¹H NMR (400 MHz, CDCl₃): δ 8.41 (s, 1H), 8.03 (d, J=8.8 Hz, 2H), 7.42 (d, J=3.6 Hz, 1H), 7.28 (d, J=m 8.8 Hz, 2H), 6.77 (d, J=3.6 Hz, 1H), 6.43 (bs, 1H), 4.51 (bs, 1H), 3.18-3.09 (m, 3H), 2.95-2.84 (m, 2H), 2.37 (s, 3H), 1.95-1.88 (m, 2H), 1.81-1.78 (m, 1H), 1.66-1.63 (m, 1H). LCMS [M+1]: 372.

Synthesis of (R)-benzyl 3-(7-tosyl-7H-pyrrolo[2,3-d]pyrimidin-4-ylamino) piperidine-1-carboxylate To a solution of (R)—N-(piperidin-3-yl)-7-tosyl-7H-pyrrolo[2,3-d]pyrimidin-4-amine (15 g, 40.4 mmol) in CH$_2$Cl$_2$ (180 mL) as added Et$_3$N (11.3 mL, 80.9 mmol) and Cbz-Cl (6.3 mL, 44.5 mmol) dropwise at 0° C. The reaction mixture was allowed to warm to rt and stirred for 3 h, diluted with CH$_2$Cl$_2$ (100 mL) and organic layer was washed with water (50 mL×3), dried over Na$_2$SO$_4$ and concentrated in vacuo to give crude product to give the titled compound (19 g, 92%). $^1$H NMR (400 MHz, CDCl$_3$): δ 8.40 (s, 1H), 8.03 (d, J=8.0 Hz, 2H), 7.47-7.26 (m, 8H), 6.53 (s, 1H), 5.10-5.09 (m, 2H), 4.24-4.19 (m, 1H), 4.01-3.96 (m, 1H), 3.68-3.61 (m, 3H), 3.30-3.28 (m, 1H), 2.37 (s, 3H), 1.97-1.91 (m, 3H), 1.75-1.70 (m, 1H), 1.63-1.56 (m, 1H). LCMS [M+1]: 506.

Synthesis of (R)-benzyl 3-(allyl(7-tosyl-7H-pyrrolo[2,3-d]pyrimidin-4-yl)amino) piperidine-1-carboxylate To a suspension of (R)-benzyl 3-(7-tosyl-7H-pyrrolo[2,3-d]pyrimidin-4-ylamino) piperidine-1-carboxylate (19 g, 37.6 mmol) and NaH (60% suspension in mineral oil, 1.1 g, 45.1 mmol) in DMF (150 mL) was added allyl bromide (6.8 g, 56.4 mmol) at 0° C. The solution was stirred for 4 h, diluted with EtOAc (200 mL) and washed with water (3×50 mL), dried over Na$_2$SO$_4$ and concentrated in vacuo to give the crude product that was purified by column chromatography (silica gel, gradient 15-25% EtOAc in hexanes) to give of the titled compound (14.7 g, 71%). $^1$H NMR (400 MHz, CDCl$_3$): δ 8.39 (s, 1H), 8.05 (d, J=8.4 Hz, 2H), 7.34-7.26 (m, 8H), 6.49 (s, 1H), 5.97-5.90 (m, 1H), 5.22-5.07 (m, 4H), 4.69-4.61 (m, 1H), 4.35-4.21 (m, 4H), 2.88 (t, J=12.0 Hz, 1H), 2.72-2.65 (m, 1H), 2.38 (s, 3H), 1.98-1.95 (m, 1H), 1.81-1.72 (m, 3H). LCMS [M+1]: 546.

Synthesis of 3(R)-benzyl 3-((2,3-dihydroxypropyl)(7-tosyl-7H-pyrrolo[2,3-d]pyrimidin-4-yl)amino) piperidine-1-carboxylate To a solution of (R)-benzyl 3-(allyl(7-tosyl-7H-pyrrolo[2,3-d]pyrimidin-4-yl)amino) piperidine-1-carboxylate (14.7 g, 27.0 mmol) in THF: water (1:1, 160 mL), was added OsO$_4$ (340 mg, 1.34 mmol) at 0° C. and the reaction mixture was stirred for 30 min. NaIO$_4$ (8.6 g, 40.5 mmol) was added at 0° C. and the reaction mixture stirred for overnight at rt. The reaction mixture was diluted with EtOAc (200 mL) and washed with water. The organic layer was washed with brine, and concentrated in vacuo to yield the crude product, which was purified by column chromatography (silica gel, 0-2% MeOH in CH$_2$Cl$_2$) to afford the titled compound (9.5 g, 60%). LCMS [M+1]: 580.

Synthesis of (R)-benzyl 3-((2-oxoethyl) (7-tosyl-7H-pyrrolo[2,3-d]pyrimidin-4-yl)amino) piperidine-1-carboxylate To a solution of (R)-benzyl 3-((2,3-dihydroxypropyl)(7-tosyl-7H-pyrrolo[2,3-d]pyrimidin-4-yl)amino) piperidine-1-carboxylate (9.5 g, 16.40 mmol) in CH$_2$Cl$_2$ (100 mL) was added NaIO$_4$ (5.3 g, 24.6 mmol, supported on silica) at 0° C. The reaction mixture was stirred for 30 min at rt and filtered through celite pad, the filtrate was concentrated in vacuo to crude the titled compound, which was used directly for next step (6 g, 67%). LCMS [M+1]: 548.

Synthesis of (R)-benzyl 3-((2-hydroxyethyl)(7-tosyl-7H-pyrrolo[2,3-d]pyrimidin-4-yl)amino)piperidine-1-carboxylate To a solution of (R)-benzyl 3-((2-oxoethyl) (7-tosyl-7H-pyrrolo[2,3-d]pyrimidin-4-yl)amino) piperidine-1-carboxylate (6.0 g, 11.0 mmol) in MeOH (50 mL) was added NaBH$_4$ (622 mg, 16.5 mmol) at 0° C. under an atmosphere of nitrogen. The reaction mixture was stirred at rt for 2 h, diluted with ice cool water (10 mL) and stirred for 15 min. The solvent was reduced in vacuo and the residue was dissolved in EtOAc, the organic layer was washed with water, dried over Na$_2$SO$_4$ and concentrated in vacuo to give crude compound which was purified by column chromatography (silica gel, 0-4% MeOH in CH$_2$Cl$_2$) to afford the titled compound (1.3 g, 21%). LCMS [M+1]: 550, [M+23]: 572.

Synthesis of (R)-2-(piperidin-3-yl(7-tosyl-7H-pyrrolo[2,3-d]pyrimidin-4-yl)amino)ethanol To a stirred solution of (R)-benzyl 3-((2-hydroxyethyl)(7-tosyl-7H-pyrrolo[2,3-d]pyrimidin-4-yl)amino)piperidine-1-carboxylate (1.3 g, 2.4 mmol) in EtOH (10 mL) was added 10% Pd/C (0.8 g) under an atmosphere of N$_2$ and the reaction was placed under an atmosphere of hydrogenated (1 atm.) for 2 h. The mixture was filtered through a celite pad and the filtrate was concentrated in vacuo to afford a residue which was used without further purification (0.9 g, 91%). LCMS [M+1]: 416.

Synthesis of (R)-2-(3,5-dichlorophenylamino)-1-(3-((2-hydroxyethyl)(7-tosyl-7H-pyrrolo[2,3-d]pyrimidin-4-yl)amino)piperidin-1-yl)ethanone To a solution of (R)-2-(piperidin-3-yl(7-tosyl-7H-pyrrolo[2,3-d]pyrimidin-4-yl)amino)ethanol (0.9 mg, 2.2 mmol) in DMF (10 mL) was added EDCI (494 mg, 2.6 mmol), HOBt (351 mg, 2.6 mmol), 2-(3,5-dichlorophenylamino)acetic acid (475 mg, 2.16 mmol) and DIEA (0.574 ml, 3.24 mmol) at 0° C. The solution was stirred at rt over night, diluted with EtOAc (25 mL) and washed with water. The aqueous layer was extracted with EtOAc, dried (Na$_2$SO$_4$) and concentrated in vacuo to give a residue which was purified by column chromatography (silica gel, gradient 0-2% methanol in chloroform) to afford the titled compound (0.4 g, 30%). LCMS [M+1]: 617.

Synthesis of (R)-2-(3,5-dichlorophenylamino)-1-(3-((2-hydroxyethyl)(7H-pyrrolo[2,3-d]pyrimidin-4-yl)amino)piperidin-1-yl)ethanone A solution of (R)-2-(3,5-dichlorophenylamino)-1-(3-((2-hydroxyethyl)(7-tosyl-7H-pyrrolo[2,3-d]pyrimidin-4-yl)amino)piperidin-1-yl)ethanone (400 mg, 0.649 mmol) and K$_2$CO$_3$ (341 mg, 2.46 mmol) in MeOH (16 mL) was heated at 70° C. for 2 h. The solvent was concentrated in vacuo to give a solid, which was purified by column chromatography (silica gel, gradient 0-4% methanol in chloroform) to afford the titled compound (0.14 g, 46%). $^1$H NMR (400 MHz, DMSO-d$_6$): 11.73 and 11.68 (2s, 1H), 8.12 (d, J=6.4 Hz, 1H), 7.35 (s, 1H), 7.20 and 7.15 (2s, 1H), 6.76 (s, 1H), 6.69 and 6.56 (2s, 1H), 6.62 and 6.49 (2s, 1H), 6.37-6.34 (m, 1H), 5.10-5.00 (m, 1H), 4.69-4.60 (m, 1H), 4.49-4.39 (m, 1H), 4.14-3.88 (m, 3H), 3.79-3.59 (m, 3H), 3.18 and 2.99 (2t, J=12.4 Hz, 1H), 2.84 and 2.70 (2t, J=12.4 Hz, 1H), 2.61-2.57 (m, 1H), 2.02-1.81 (m, 3H), 1.65-1.49 (m, 1H). LCMS [M+1]: 463.

Example 45

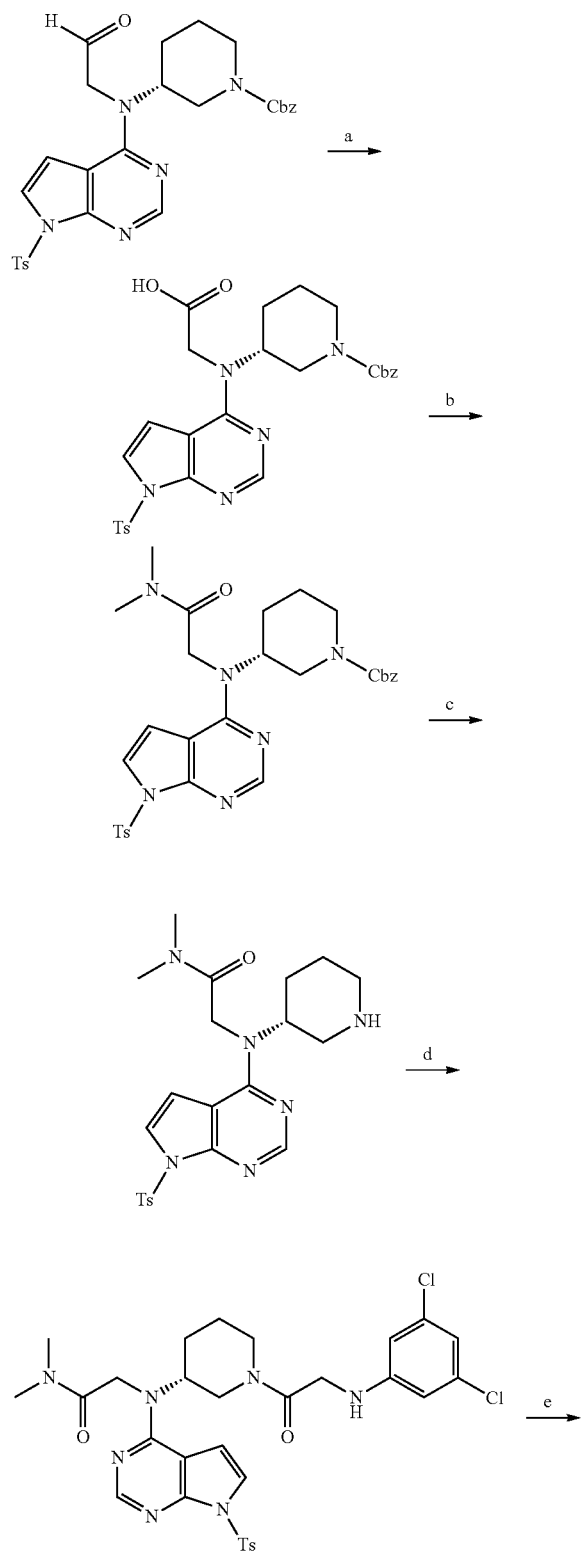

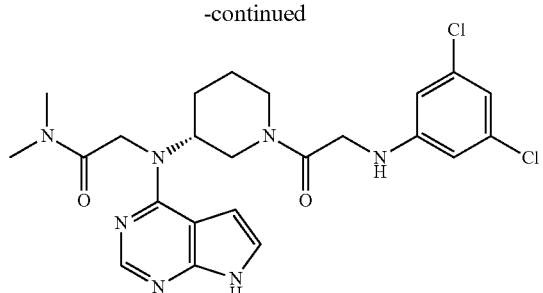

Reagents and conditions: (a) NaClO$_2$, NaHPO$_4$, H$_2$O$_2$, CH$_3$CN. (b) NHMe$_2$, EDCl, HOBt, DIEA, DCM, rt. (c) 10% Pd/C, H$_2$, EtOH. (d) C$_8$H$_7$O$_2$NCl$_2$, EDCl, HOBt, DIEA, CH$_2$Cl$_2$, rt. (e) K$_2$CO$_3$, MeOH/water, 80° C.

Synthesis of (R)-2-((1-(benzyloxycarbonyl) piperidin-3-yl) (7-tosyl-7H-pyrrolo[2,3-d]pyrimidin-4-yl) amino) acetic acid To a solution of (R)-benzyl 3-((2-oxoethyl) (7-tosyl-7H-pyrrolo[2,3-d]pyrimidin-4-yl)amino) piperidine-1-carboxylate (1.4 g, 2.6 mmol) in CH$_3$CN (8 mL), was added NaH$_2$PO$_4$ (520 mg, 3.83 mmol), NaClO$_2$ (347 mg, 3.83 mmol) in 7 mL of water and 30% H$_2$O$_2$ (0.13 mL, 3.83 mmol) at 0° C. The reaction mixture was warmed to rt and stirred for overnight. The solvent was reduced in vacuo and the residue was dissolved in EtOAc, filtered, dried over Na$_2$SO$_4$ and concentrated in vacuo and purified by column chromatography (Silica gel, 0-2% gradient MeOH: CH$_2$Cl$_2$) to afford the titled compound (500 mg, 34%). LCMS [M+1]: 564.

Synthesis of (R)-benzyl 3-((2-(dimethylamino)-2-oxoethyl) (7-tosyl-7H-pyrrolo[2,3-d]pyrimidin-4-yl) amino) piperidine-1-carboxylate To a solution of (R)-2-((1-(benzyloxycarbonyl) piperidin-3-yl) (7-tosyl-7H-pyrrolo[2,3-d]pyrimidin-4-yl)amino) acetic acid (250 mg, 0.44 mmol) in CH$_2$Cl$_2$ (10 mL) was added EDCI (101 mg, 0.53 mmol), HOBt (71 mg, 0.53 mmol), NHMe$_2$ (20 mg, 0.44 mmol) and DIEA (0.090 ml, 3.24 mmol) at 0° C. The solution was stirred at rt overnight and the reaction mixture was diluted with EtOAc (25 mL) and washed with water. The aqueous layer was re-extracted with EtOAc, dried (Na$_2$SO$_4$) and concentrated in vacuo to give a residue which was purified by column chromatography (silica gel, gradient 0-2% methanol in chloroform) to afford the titled compound (150 mg, 57%). LCMS [M+1]: 691.

Synthesis of (R)—N, N-dimethyl-2-(piperidin-3-yl (7-tosyl-7H-pyrrolo[2,3-d]pyrimidin-4-yl)amino) acetamide To a solution of (R)-benzyl 3-((2-(dimethylamino)-2-oxoethyl) (7-tosyl-7H-pyrrolo[2,3-d]pyrimidin-4-yl)amino) piperidine-1-carboxylate (140 mg, 0.23 mmol) in EtOH (10 mL) was added 10% Pd/C (80 mg) and the reaction mixture was hydrogenated under 1 atm pressure for 2 h. The suspension was filtered through a celite pad and the filtrate was concentrated in vacuo to obtain a residue that was used for next step without further purification (100 mg, 92%). LCMS [M+1]: 457.

Synthesis of (R)-2-((1-(2-(3,5-dichlorophenylamino) acetyl) piperidin-3-yl) (7-tosyl-7H-pyrrolo[2,3-d] pyrimidin-4-yl)amino)-N, N-dimethylacetamide To a solution of (R)—N, N-dimethyl-2-(piperidin-3-yl(7-tosyl-7H-pyrrolo[2,3-d]pyrimidin-4-yl)amino) acetamide (100 mg, 0.24 mmol) in DMF (7 mL) was added EDCI (54 mg, 0.3 mmol), HOBt (39 mg, 0.3 mmol), 2-(3,5-dichlorophenylamino)acetic acid (53 mg, 0.24 mmol) and DIEA (0.50 mL, 0.36 mmol) at 0° C. The solution was stirred at rt overnight and the reaction mixture was diluted with water (50 mL). The organic layer was dried (Na₂SO₄) and concentrated in vacuo to give a residue which was purified by column chromatography (silica gel, gradient 0-2% methanol in chloroform) to afford the titled compound (50 mg, 31%). LCMS [M+1]: 675.

Synthesis of (R)-2-((1-(2-(3,5-dichlorophenylamino) acetyl)piperidin-3-yl)(7H-pyrrolo[2,3-d]pyrimidin-4-yl)amino)-N,N-dimethylacetamide A solution of (R)-2-((1-(2-(3,5-dichlorophenylamino) acetyl) piperidin-3-yl) (7-tosyl-7H-pyrrolo[2,3-d]pyrimidin-4-yl)amino)-N, N-dimethylacetamide (45 mg, 0.068 mmol) and K₂CO₃ (37 mg, 0.27 mmol) in MeOH (5 mL) was heated at 70° C. for 2 h. The solvent was then evaporated in vacuo to give a solid, which was purified by column chromatography (silica gel, gradient 0-3% methanol in chloroform) to afford the titled compound (14 mg, 41%). ¹H NMR (400 MHz, CDCl₃): δ 10.19 (s, 1H), 8.32 and 8.23 (2s, 1H), 7.04 (s, 1H), 6.66 (s, 1H), 6.48 (s, 1H), 6.18 (s, 1H), 5.21 (s, 1H), 4.65-4.64 (m, 2H), 4.41-4.20 (m, 3H), 3.80-3.76 (m, 1H), 3.20 (s, 3H), 3.05 (s, 3H), 3.02-2.88 (m, 2H), 2.60 (t, J=11.6 Hz, 1H), 2.36 (t, J=11.6 Hz, 1H), 1.99-1.67 (m, 4H). LCMS [M+1]: 504, [M+23]: 526.

Example 46

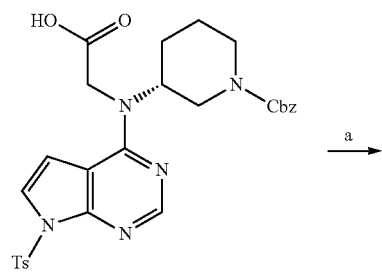

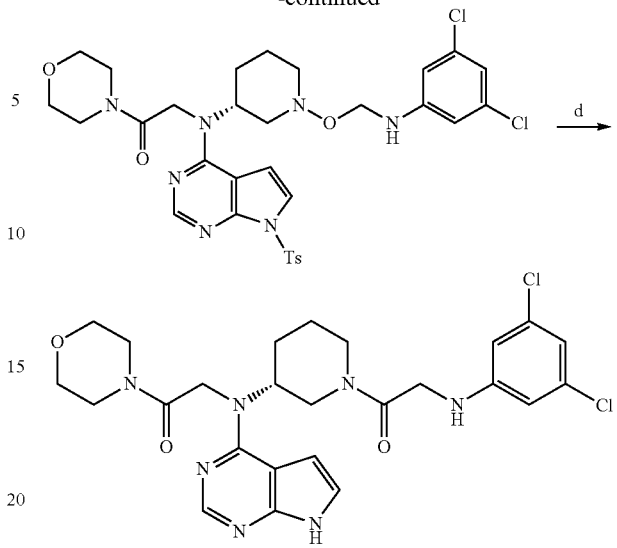

Reagents and conditions: (a) Morpholine, EDCl, HOBt, DIEA, CH₂Cl₂, rt. (b) 10% Pd/C, H₂, EtOH. (c) C₈H₇O₂NCl₂, EDCl, HOBt, DIEA, CH₂Cl₂, rt. (d) K₂CO₃, MeOH/water, 80° C.

Synthesis of (R)-2-(3,5-dichlorophenylamino)-1-(3-((2-morpholino-2-oxoethyl)(7H-pyrrolo[2,3-d]pyrimidin-4-yl)amino)piperidin-1-yl)ethanone A similar procedure was used as described for the synthesis of (R)-2-((1-(2-(3,5-dichlorophenylamino)acetyl)piperidin-3-yl)(7H-pyrrolo[2,3-d]pyrimidin-4-yl)amino)-N,N-dimethylacetamide to afford the titled compound (14 mg, 36%). ¹H NMR (400 MHz, CDCl₃): δ 10.11 (s, 1H), 8.36 (s, 1H), 7.11-6.98 (m, 2H), 6.82 (s, 1H), 6.66 (s, 1H), 6.46 (s, 1H), 5.19-5.11 (m, 1H), 5.01-4.94 (m, 1H), 4.69-4.61 (m, 2H), 4.40-4.11 (m, 4H), 3.81-3.61 (m, 5H), 3.25-3.20 (m, 1H), 3.15-3.10 (m, 1H), 2.36-2.17 (m, 1H), 2.00-1.65 (m, 4H). LCMS [M+1]: 546, [M+23]: 567.

Example 47

Synthesis of (S)-2-(3,5-dichlorophenylamino)-1-(3-(ethyl(7H-pyrrolo[2,3-d]pyrimidin-4-yl)amino)piperidin-1-yl)ethanone

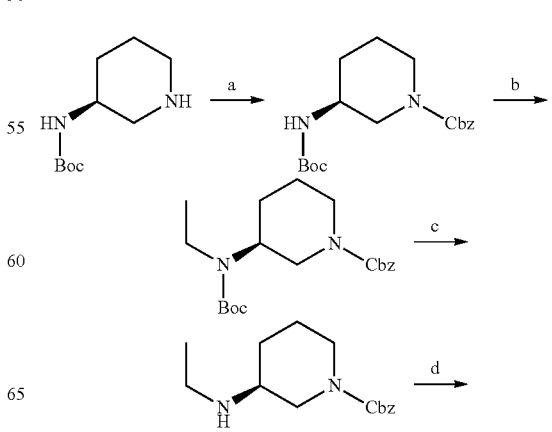

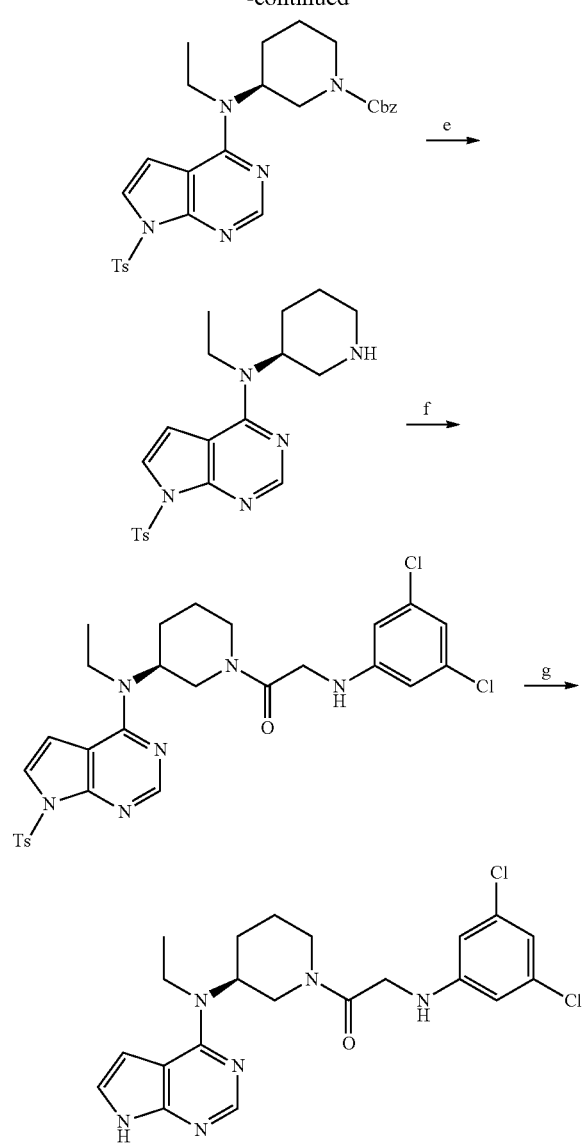

Reagents and conditions: a) Et₃N, CH₂Cl₂, Cbz—Cl, 0° C., 4 h; b) NaH, DMF, EtBr, rt, 4 h; c) Dioxane•HCl, rt, 1 h; d) 4-chloro-7-tosyl-7H-pyrrolo[2,3-d]pyrimidine, DIEA, DMF, 100° C., 4 h; e) 10% Pd/C, H₂, rt, 1 h; f) 2-(3,5-dichlorophenylamino)acetic acid, EDCl, HOBt, DIEA, DMF, rt, 15 h; g) K₂CO₃, aq. MeOH, 60° C., 1 h.

Synthesis of (S)-benzyl 3-(tert-butoxycarbonylamino)piperidine-1-carboxylate

To a solution of (S)-tert-butyl piperidin-3-ylcarbamate (5 g, 24.9 mmol) and Et₃N (3.8 mL, 27.4 mmol) in CH₂Cl₂ (75 mL) was added Cbz-Cl (3.92 mL, 27.4 mmol) at 0° C., after the addition was complete the reaction was warmed to rt and stirred for 4 h. The reaction was diluted with ice cooled water (30 mL) and the CH₂Cl₂ layer was separated and dried over Na₂SO₄ and concentrated in vacuo to give (7.5 g, 89%) of the tilted compound. ¹H NMR (400 MHz, CDCl₃): δ 7.40-7.24 (m, 5H), 5.18 (s, 2H), 4.58 (bs, 1H), 3.80-3.62 (m, 2H), 3.55-3.41 (m, 1H), 3.37-3.21 (m, 2H), 1.82-1.78 (m, 1H), 1.75-1.69 (m, 1H), 1.61-1.53 (m, 2H), 1.42 (s, 9H). ES-MS: m/z [M+1]=335.

Synthesis of (S)-benzyl 3-(tert-butoxycarbonyl(ethyl)amino)piperidine-1-carboxylate To a solution of (S)-benzyl 3-(tert-butoxycarbonylamino)piperidine-1-carboxylate (500 mg, 1.49 mmol) in DMF (5 mL) was added NaH (60% suspension in mineral oil, 120 mg, 1.64 mmol) and the reaction mixture was stirred for 1 h. To the reaction mixture was added ethyl bromide (0.12 mL, 1.64 mmol) and the reaction mixture was stirred for 4 h. The reaction mixture was diluted with ice-cooled water and the solution was extracted with EtOAc, the EtOAc layer was dried over Na₂SO₄ and concentrated in vacuo to give the crude product that was purified by column chromatography (silica gel, gradient, EtOAc in hexanes) to give (300 mg, 55%) of the titled compound. ¹H NMR (400 MHz, CDCl₃): δ 7.36-7.30 (m, 5H), 5.18-5.12 (m, 2H), 4.18-4.13 (m, 2H), 3.68-3.62 (m, 1H), 3.22-3.17 (m, 2H), 3.01-2.85 (m, 1H), 2.68-2.59 (m, 1H), 1.89-1.81 (m, 1H), 1.78-1.73 (m, 2H), 1.55 (s, 9H), 1.54-1.48 (m, 1H), 1.08 (t, J=6.4 Hz, 3H). ES-MS: m/z [M+1]=363.

Synthesis of (S)-benzyl 3-(ethylamino)piperidine-1-carboxylate

A solution of (S)-benzyl 3-(tert-butoxycarbonylamino)piperidine-1-carboxylate (300 mg, 0.82 mmol) in 1,4-dioxane (2.5 mL) was treated with dioxane. HCl (5 mL) and the solution was stirred at rt 1 h. The solvent was reduced in vacuo to afford a residue which was then dissolved in water (5 mL). The aqueous solution was treated with solid Na₂CO₃ and the aqueous solution was extracted with EtOAc (3×15 mL). The combined organic layer was dried over Na₂SO₄, concentrated in vacuo to yield titled intermediate (217 mg, 92%), which was used in the next step without further purification. ¹H NMR (400 MHz, CDCl₃): δ 7.36-7.26 (m, 5H), 5.13 (s, 2H), 4.20-3.82 (m, 2H), 2.94-2.60 (m, 5H), 1.94-1.92 (m, 1H), 1.69-1.68 (m, 1H), 1.47-1.28 (m, 3H), 1.09 (t, J=6.8 Hz, 3H). ES-MS: m/z [M+1]=263.

Synthesis of (S)-benzyl 3-(ethyl(7-tosyl-7H-pyrrolo[2,3-d]pyrimidin-4-yl)amino)piperidine-1-carboxylate To a solution of (S)-benzyl 3-(ethylamino)piperidine-1-carboxylate (200 mg, 0.76 mmol), 4-chloro-7-tosyl-7H-pyrrolo[2,3-d]pyrimidine (234 mg, 0.76 mmol) and DIEA (0.27 mL, 1.52 mmol) in DMF (3 mL) was heated to 100° C. for 4 h. The reaction was cooled to rt, diluted with ice cooled water (10 mL) and extracted with EtOAc (3×25 mL). The combined EtOAc layer was dried over Na₂SO₄ and concentrated in vacuo to give the crude product that was purified by column chromatography (silica gel, gradient 0-10% EtOAc hexane) to afford the titled intermediate (300 mg, 73%). ¹H NMR (400 MHz, DMSO-d₆): δ 8.22 (d, J=5.6 Hz, 1H), 7.98 (d, J=8.0 Hz, 2H), 7.95 (s, 1H), 7.58-7.57 (m, 1H), 7.43 (d, J=8.0 Hz, 2H), 7.39-7.29 (m, 5H), 5.12 and 5.09 (2s, 2H), 4.69-4.63 (m, 1H), 4.05-3.98 (m, 3H), 3.65-3.63 (m, 2H), 3.01-2.77 (m, 1H), 2.36 (s, 3H), 1.89-1.75 (m, 3H), 1.51-1.39 (m, 1H), 1.17 (t, J=6.8 Hz, 3H). LC-MS: m/z [M+1]=534.

Synthesis of (S)—N-ethyl-N-(piperidin-3-yl)-7-tosyl-7H-pyrrolo[2,3-d]pyrimidin-4-amine A mixture of (S)-benzyl 3-(ethyl(7-tosyl-7H-pyrrolo[2,3-d]pyrimidin-4-yl)amino)piperidine-1-carboxylate (130 mg, 0.243 mmol), 10% Pd/C (130 mg) in ethanol (4 mL) was placed under an atmosphere of hydrogen (1 atm) for 1 h. The reaction mixture was filtered through a celite pad and the filtrate was concentrated in vacuo to yield the title intermediate (60 mg, 61%). LC-MS: m/z [M+1]=400.

Synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone To a solution of (S)—N-ethyl-N-(piperidin-3-yl)-7-tosyl-7H-pyrrolo[2,3-d]pyrimidin-4-amine (60 mg, 0.15 mmol), in DMF (5 mL), was added EDCI (34 mg, 0.18 mmol), HOBt (24 mg, 0.18 mmol), 2-(3,5-dichlorophenylamino)acetic acid (33 mg, 0.15 mmol) and DIEA (0.06 mL, 0.36 mmol) at 0° C. The reaction mixture was stirred overnight at rt. After completion of the reaction, the reaction mixture was diluted with EtOAc (25 mL) and the organic phase was washed with water (10 mL). The organic layer was dried over Na$_2$SO$_4$ and concentrated in vacuo to give the crude compound that was purified by column chromatography (silica gel, gradient MeOH in CH$_2$Cl$_2$) to afford the titled compound (75 mg, 82%). LC-MS: m/z [M+1]=601.

Synthesis of (S)-2-(3,5-dichlorophenylamino)-1-(3-(ethyl(7H-pyrrolo[2,3-d]pyrimidin-4-yl)amino)piperidin-1-yl)ethanone To a solution of (S)-2-(3,5-dichlorophenylamino)-1-(3-(ethyl(7-tosyl-7H-pyrrolo[2,3-d]pyrimidin-4-yl)amino)piperidin-1-yl) ethanone (70 mg, 0.11 mmol) in MeOH:H$_2$O (4:1, 10 mL), K$_2$CO$_3$ (48 mg, 0.35 mmol) was added and the reaction mixture was heated at 60° C. for 1 h, the reaction was monitored by TLC. After completion of reaction, the reaction mixture was concentrated under vacuo to give a residue. The residue triturated with 10% MeOH in EtOAc (15 mL), the suspension was filtrated, the filtrate was evaporated under vacuo to give the crude compound that was subjected to column chromatography (silica gel, gradient MeOH in CH$_2$Cl$_2$) to afford (25 mg, 45%) of the titled compound. $^1$H NMR (400 MHz, DMSO-d$_6$): δ 11.79 and 11.6 (2s, 1H), 8.106 (d, J=6.8 Hz, 1H), 7.18 and 7.13 (2s, 1H), 6.76 (s, 1H), 6.69 (s, 1H), 6.62 (s, 1H), 6.49 and 6.43 (2s, 1H), 6.37 and 6.33 (2t, J=2.3 Hz, 1H), 4.74-4.69 (m, 1H), 4.46-4.39 (m, 1H), 4.13-3.88 (m, 4H), 3.76-3.70 (m, 2H), 3.20-3.16 (m, 1H), 3.00 (t, J=12.0 Hz, 1H), 2.86 (t, J=12.0 Hz, 1H), 2.62 (t, J=13.6 Hz, 1H), 1.98-1.81 (m, 3H), 1.65-1.49 (m, 1H), 1.19 (t, J=6.8 Hz, 3H). LC-MS: m/z [M+1]=447. HPLC (254 nm): 97.68%. HPLC (210 nm): 98.20%.

Example 48

Synthesis of (S)-2-(3,5-dichlorophenylamino)-1-(3-(propyl(7H-pyrrolo[2,3-d]pyrimidin-4-yl)amino)piperidin-1-yl)ethanone

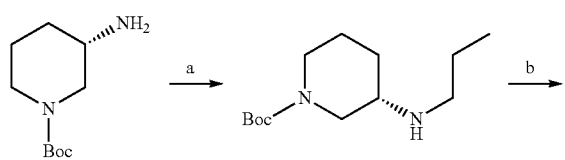

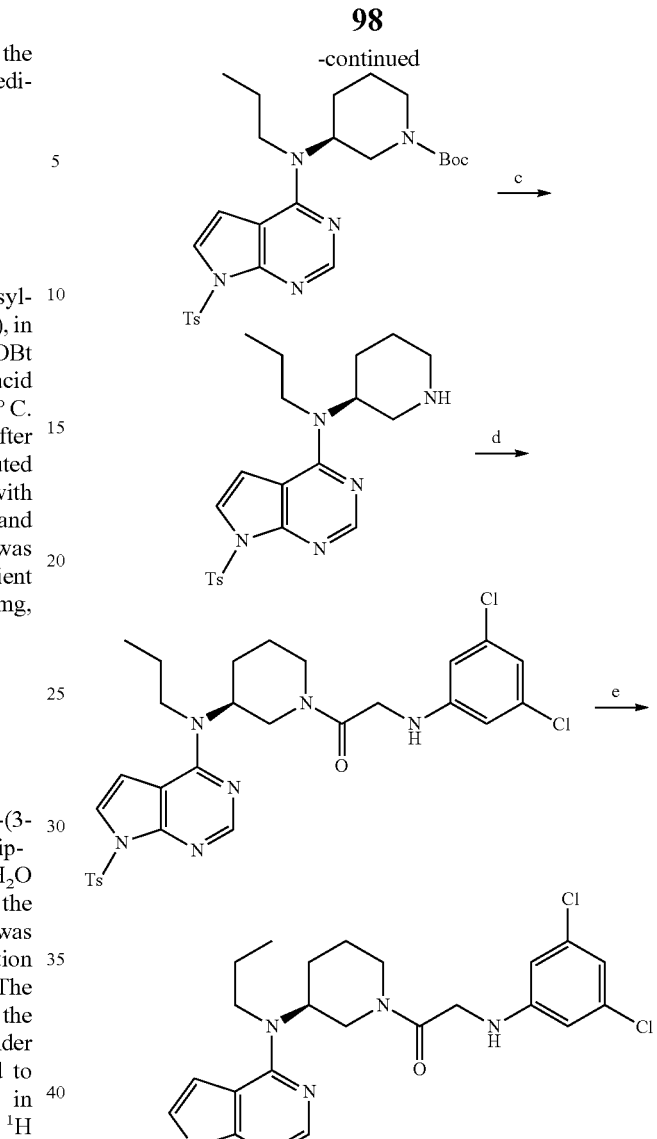

Reagents and conditions: a) DIEA, DMF, 1-bromopropane, 100° C., overnight; b) 4-chloro-7-tosyl-7H-pyrrolo[2,3-d]pyrimidine, DIEA, DMF, 100° C., 4 h; c) Dioxane•HCl, rt, 1 h; d) 2-(3,5-dichlorophenylamino)acetic acid, EDCl, HOBt, DIEA, DMF, rt, 15 h; e) K$_2$CO$_3$, aq. MeOH, 60° C., 1 h.

Synthesis of (S)-tert-butyl 3-(propylamino)piperidine-1-carboxylate

A solution of (S)-tert-butyl 3-aminopiperidine-1-carboxylate (500 mg, 2.49 mmol) and 1-bromopropane (335 mg, 2.74 mmol) and DIEA (0.11 mL, 6.24 mmol) in DMF (4 mL) was heated at 100° C. for overnight. After reaction was shown to be complete as indicated by TLC, the mixture was diluted with EtOAc (30 mL) and washed with water (2×15 mL). The organic layer was separated, dried over Na$_2$SO$_4$, concentrated in vacuo to afford a residue which was purified by column chromatography (silica gel, gradient MeOH in CH$_2$Cl$_2$) to yield the titled intermediate (605 mg, 57%). $^1$H NMR (400 MHz, DMSO-d$_6$): δ 3.89-3.64 (m, 3H), 2.80-2.66 (m, 2H), 2.50-2.35 (m, 3H), 1.89-1.83 (m, 2H), 1.61-1.58 (m, 2H), 1.38 (s, 9H), 1.35-1.29 9m, 2H), 0.82 (t, J=7.2 Hz, 3H). ES-MS: m/z [M+1]=243.

Synthesis of (S)-tert-butyl 3-(propyl(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled intermediate (300 mg, 42%). $^1$H NMR (400 MHz, DMSO-d$_6$): δ 8.37 (1H), 8.06 (2H), 7.45 (1H), 7.27 (2H), 6.50 (1H), 4.49 (1H), 1.14 (1H), 3.67 (2H), 3.44 (1H), 2.83 (1H), 2.61 (1H), 2.39 (3H), 1.93 (1H), 1.78 (1H), 1.55 (2H), 1.44 (2H), 1.24 (9H), 0.95 (3H). LC-MS: m/z [M+1]=514.

Synthesis of (S)—N-(piperidin-3-yl)-N-propyl-7-tosyl-7H-pyrrolo[2,3-d]pyrimidin-4-amine A solution of (S)-tert-butyl 3-(propyl(7-tosyl-7H-pyrrolo[2,3-d]pyrimidin-4-yl)amino)piperidine-1-carboxylate (300 mg, 0.58 mmol) in 1,4-dioxane (5 mL) was treated with 4 N HCl in 1,4-dioxane (10 mL) at rt for 1 h. The solvent was removed in vacuo and the residue was suspended in water (10 mL). The aqueous layer was adjusted to a pH 9 with solid NaHCO$_3$ and the solution was extracted with EtOAc (3×25 mL). The combined organic layer was dried over Na$_2$SO$_4$, concentrated in vacuo to yield titled intermediate (241 mg, 83%), which was used in the next step without further purification. $^1$H NMR (400 MHz, DMSO-d$_6$): δ 8.23 (1s, 1H), 7.98 (d, J=8.0 Hz, 2H), 7.69 and 7.65 (2d, 0.1=4.0 Hz, 1H), 7.43 (d, J=8.0 Hz, 2H), 6.81 (d, J=4.0 Hz, 1H), 3.69-3.64 (m, 3H), 3.51-3.47 (m, 2H), 3.25-3.18 (m, 2H), 52.85-2.83 (m, 1H), 2.35 (s, 3H), 1.94-1.89 (m, 2H), 1.79-1.76 (m, 1H), 1.55-1.53 (m, 1H), 1.16 and 0.93 (t, J=7.2 Hz, 3H). LC-MS: m/z [M+1]=414.

Synthesis of (S)-2-(3,5-dichlorophenylamino)-1-(3-(propyl(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to afford the titled compound (297 mg, 50%). $^1$H NMR (400 MHz, DMSO-d$_6$): δ 8.31 and 8.22 (2s, 1H), 8.05-7.94 (m, 3H), 7.67-7.42 (m, 2H), 6.74 (s, 1H), 6.65 (s, 1H), 6.64 (s, 1H), 6.62 (s, 1H), 3.98-3.93 (m, 3H), 3.52-3.51 (m, 2H), 3.42-2.99 (m, 2H), 2.72-2.55 (m, 3H), 2.35 (s, 3H), 1.98-1.78 (m, 3H), 1.59-1.1.53 (m, 3H), 0.96 and 0.93 (2t, J=6.2 Hz, 3H). LC-MS: m/z [M+1]=615.

Synthesis of (S)-2-(3,5-dichlorophenylamino)-1-(3-(propyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (50 mg, 44%). $^1$H NMR (400 MHz, DMSO-d$_6$): δ 11.79 and 11.72 (2s, 1H), 8.11 (d, J=6.4 Hz, 1H), 7.19 and 7.14 (2t, J=1.2 Hz, 1H), 6.76 (s, 1H), 6.69 (s, 1H), 6.37-6.33 (m, 2H), 4.71-7.62 (m, 1H), 4.47-4.38 (m, 1H), 4.09 (dt, J=1.2, 16.8 Hz, 1H), 4.00-3.87 (m, 2H), 3.61-3.53 (m, 2H), 3.18 and 3.04 (2t, J=12.0 Hz, 1H), 2.87 and 2.63 (2t, J=12.0 Hz, 1H), 2.03-1.81 (m, 3H), 1.79-1.54 (m, 3H), 0.97 and 0.95 (2t, J=6.4 Hz, 3H). LC-MS: m/z [M+1]=461.

Example 49

Synthesis of (S)-2-(3,5-dichlorophenylamino)-1-(3-(phenethyl(7H-pyrrolo[2,3-d]pyrimidin-4-yl)amino)piperidin-1-yl)ethanone

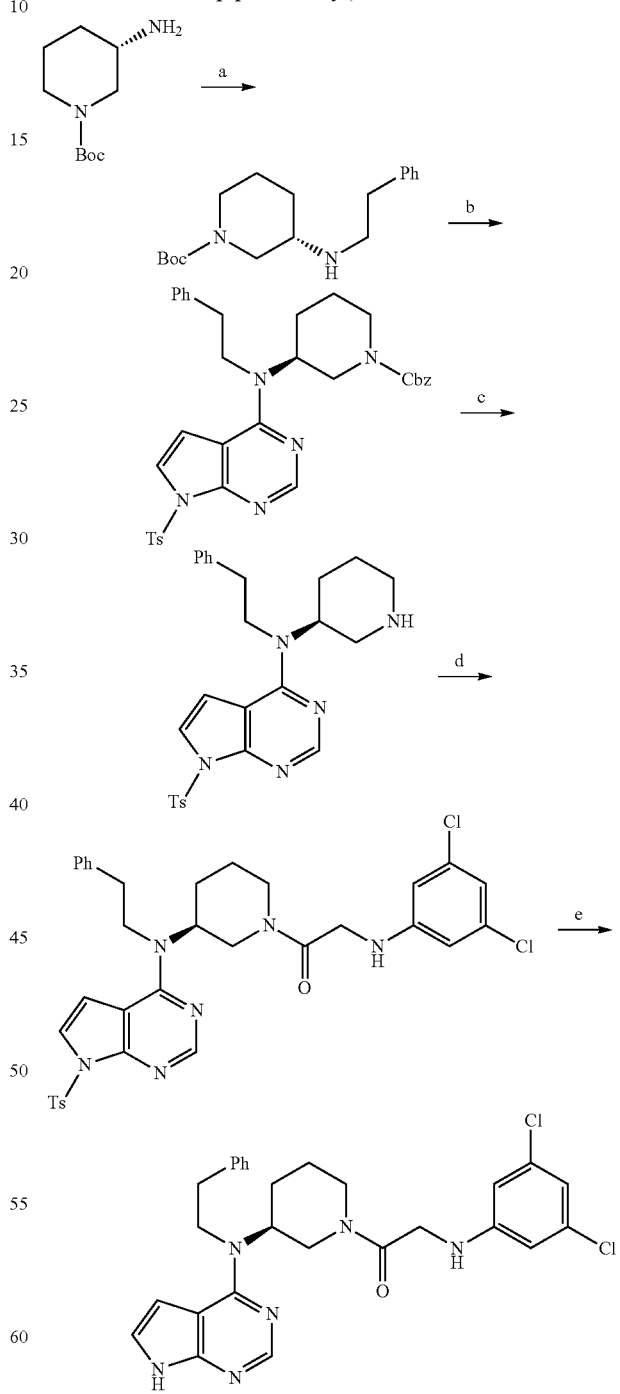

Reagents and conditions: a) DIEA, DMF, 1-bromopropane(2-bromoethyl)benzene, 100° C., overnight; b) 4-chloro-7-tosyl-7H-pyrrolo[2,3-d]pyrimidine, DIEA, DMF, 100° C., 4 h; c) dioxane•HCl, rt, 1 h; d) 2-(3,5-dichlorophenylamino)acetic acid, EDCl, HOBt, DIEA, DMF, rt, 15 h; e) K$_2$CO$_3$, aq. MeOH, 60° C., 1 h.

Synthesis of (S)-tert-butyl 3-(phenethylamino)piperidine-1-carboxylate

A similar procedure was used as described for the synthesis of (S)-tert-butyl 3-(propylamino)piperidine-1-carboxylate to give the titled compound (600 mg, 78%). $^1$H NMR (400 MHz, DMSO-d$_6$): δ 7.28-7.23 (m, 2H), 7.21-7.15 (m, 3H), 3.81-3.59 (m, 2H), 2.88-2.62 (m, 6H), 2.48-2.42 (m, 2H), 1.89-1.80 (m, 1H), 1.60-1.53 (m, 2H), 1.37 (s, 9H), 1.29-1.21 (m, 1H). ES-MS: m/z [M+1]=305.

Synthesis of (S)-tert-butyl 3-(phenethyl(7-tosyl-7H-pyrrolo[2,3-d]pyrimidin-4-yl)amino) piperidine-1-carboxylate Following a similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound (200 mg, 17%). $^1$H NMR (400 MHz, DMSO-d$_6$): δ 8.33 (s, 1H), 7.99 (d, J=7.4 Hz, 2H), 7.69 (s, 1H), 7.44 (d, J=8.4 Hz, 2H), 7.34-7.21 (m, 5H), 6.69 (s, 1H), 3.89-3.77 (m, 5H), 2.97-2.84 (m, 4H), 2.36 (s, 3H), 1.98-1.81 (m, 2H), 1.75-1.72 (m, 1H), 1.48-1.39 (m, 1H), 1.37 (s, 9H). LC-MS: m/z [M+1]=576.

Synthesis of (S)—N-phenethyl-N-(piperidin-3-yl)-7-tosyl-7H-pyrrolo[2,3-d]pyrimidin-4-amine A similar procedure was used as described for the synthesis of (S)—N-(piperidin-3-yl)-N-propyl-7-tosyl-7H-pyrrolo[2,3-d]pyrimidin-4-amine to give the titled compound (150 mg, 90%). $^1$H NMR (400 MHz, DMSO-d$_6$): δ 9.44 (s, 1H), 8.35 (s, 1H), 8.00 (d, J=8.4 Hz, 2H), 7.71 (d, J=4.4 Hz, 1H), 7.44 (d, J=8.4 Hz, 2H), 7.35-7.23 (m, 5H), 6.96 (s, 1H), 4.93 (s, 1H), 3.79 (t, J=8.0 Hz, 2H), 3.24-3.18 (m, 3H), 2.89-2.79 (m, 3H), 2.36 (s, 3H), 2.03-1.98 (m, 1H), 1.88-1.81 (m, 3H). LC-MS: m/z [M+1]=476.

Synthesis of (S)-2-(3,5-dichlorophenylamino)-1-(3-(phenethyl(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to give the titled compound (170 mg, 59%). $^1$H NMR (400 MHz, DMSO-d$_6$): δ 8.31 (d, J=8.4 Hz, 1H), 8.01-7.98 (m, 2H), 7.70 and 7.63 (2d, J=3.2 Hz, 1H), 7.45-7.25 (m, 7H), 6.75-6.62 (m, 4H), 6.32 (bs, 1H), 4.51-4.38 (m, 2H), 4.03-3.82 (m, 5H), 3.03-2.88 (m, 3H), 2.67-2.61 (m, 1H), 2.36 (s, 3H), 1.98-1.79 (3H), 1.59-1.49 (m, 1H). LC-MS: m/z [M+1]=677.

Synthesis of (S)-2-(3,5-dichlorophenylamino)-1-(3-(phenethyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (130 mg, 98%). $^1$H NMR (400 MHz, DMSO-d$_6$): δ 11.70 (s, 1H), 8.18 (s, 1H), 7.37 (d, J=4.0 Hz, 2H), 7.28-7.16 (m, 3H), 6.76 (s, 1H), 6.68 (s, 1H), 6.62 (s, 1H), 6.47 and 6.42 (2s, 1H), 6.40-6.32 (m, 1H), 4.69-4.59 (m, 1H), 4.44 (dd, J=12.0, 16.0 Hz, 1H), 4.11-3.84 (m, 5H), 3.40-3.22 (m, 1H), 3.07-2.86 (m, 3H), 2.66 (t, J=11.2 Hz, 1H), 2.11-1.82 (m, 3H), 1.66-1.48 (m, 1H). LC-MS: m/z [M+1]=523.

Example 50

Synthesis of 2-(3,5-dichlorophenylamino)-1-(3-(ethyl(7H-pyrrolo[2,3-d]pyrimidin-4-yl)amino)piperidin-1-yl)ethanone

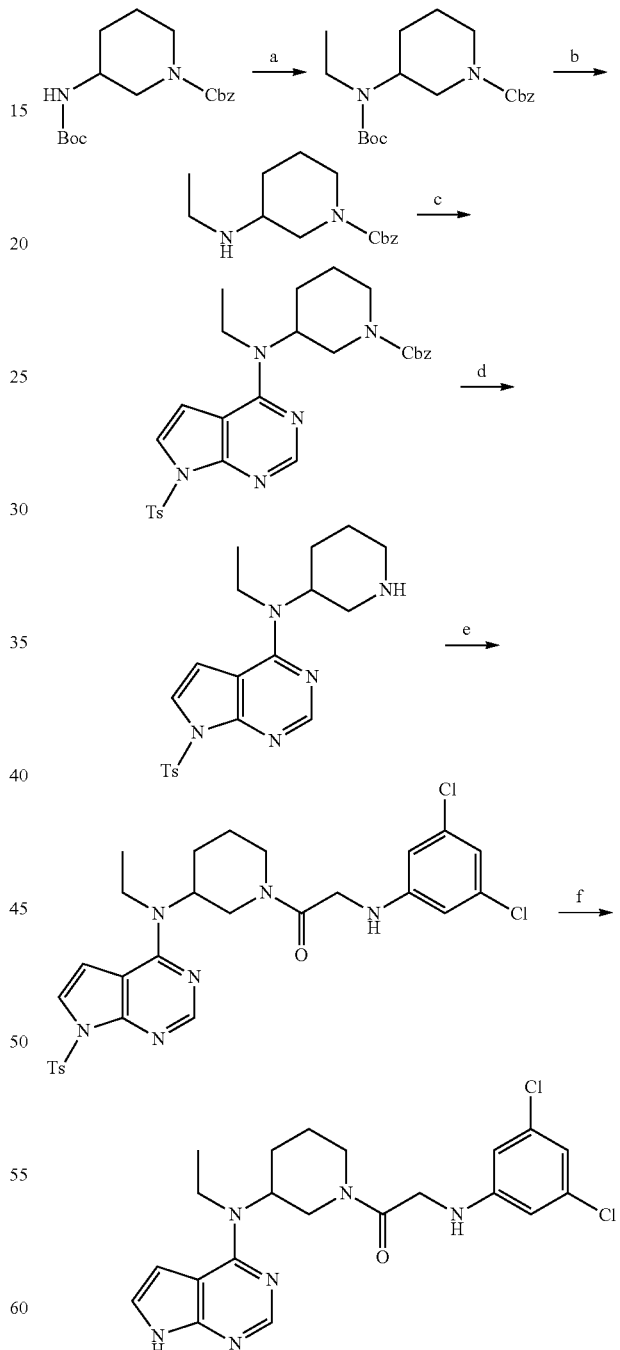

Reagents and conditions: a) NaH, DMF, EtBr, rt 4 h; b) Dioxane•HCl, rt, 1 h; c) 4-chloro-7-tosyl-7H-pyrrolo[2,3-d]pyrimidine, DIEA, DMF 100° C., 4 h; d) 10% Pd/C, H$_2$, rt, overnight; e) 2-(3,5-dichlorophenylamino)acetic acid, EDCl, HOBt, DIEA, DMF, rt, 15 h; f) K$_2$CO$_3$, aq. MeOH, 60° C., 1 h.

Synthesis of benzyl 3-(tert-butoxycarbonyl(ethyl) amino)piperidine-1-carboxylate A similar procedure was used as described for the synthesis of (S)-benzyl 3-(tert-butoxycarbonyl(ethyl)amino)piperidine-1-carboxylate to afford the titled compound (500 mg, 92%). $^1$H NMR (400 MHz, CDCl$_3$): δ 7.36-7.30 (m, 5H), 5.07 (s, 2H), 3.99-3.89 (m, 2H), 3.68-3.62 (m, 1H), 3.19-3.05 (m, 2H), 3.01-2.85 (m, 1H), 2.68-2.59 (m, 1H), 1.71-1.69 (m, 3H), 1.55 (s, 9H), 1.54-1.48 (m, 1H), 1.01 (t, J=6.4 Hz, 3H). ES-MS: m/z [M+1]=363.

Synthesis of benzyl 3-(ethylamino)piperidine-1-carboxylate

A similar procedure was used as described for the synthesis of (S)-benzyl 3-(ethylamino)piperidine-1-carboxylate, the titled compound (350 mg, 80%). $^1$H NMR (400 MHz, CDCl$_3$): δ 7.38-7.29 (m, 5H), 5.05 (s, 2H), 3.86-3.64 (m, 2H), 2.94-2.87 (m, 2H), 2.74-2.67 (m, 1H), 2.52-2.49 (m, 1H), 2.44-2.39 (m, 1H), 1.89-1.82 (m, 1H), 1.65-1.62 (m, 1H), 1.36-1.23 (m, 3H), 0.96 (t, J=6.8 Hz, 3H). ES-MS: m/z [M+1]=263.

Synthesis of benzyl 3-(ethyl(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylatem to afford the titled compound (200 mg, 28%). $^1$H NMR (400 MHz, DMSO-d$_6$): 8.22 (d, J=5.6 Hz, 1H), 7.98 (d, J=8.0 Hz, 2H), 7.95 (s, 1H), 7.58-7.57 (m, 1H), 7.43 (d, J=8.0 Hz, 2H), 7.39-7.29 (m, 5H), 6.73-6.71 (m, 1H), 5.12 and 5.09 (2s, 1H), 5.08-5.05 (m, 1H), 4.65-4.62 (m, 1H), 4.05-3.98 (m, 2H), 3.65-3.63 (m, 1H), 3.01-2.85 (m, 1H), 2.79-2.50 (m, 1H), 2.35 (s, 3H), 1.89-1.75 (m, 3H), 1.51-1.39 (m, 1H), 1.17 (t, J=6.8 Hz, 3H). LC-MS: m/z [M+1]=534.

Synthesis of N-ethyl-N-(piperidin-3-yl)-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3-d]pyrimidin-4-amine to afford the titled compound (120 mg, 80%). $^1$H NMR (400 MHz, DMSO-d$_6$): δ 8.25 and 8.23 (2s, 1H), 7.98 (d, J=8.0 Hz, 2H), 7.66 and 7.65 (2d, J=4.0 Hz, 1H), 7.43 (d, J=8.0 Hz, 2H), 6.82 and 6.72 (2d, J=3.6 Hz, 1H), 4.85-4.65 (m, 2H), 3.65-3.62 (m, 2H), 3.05-3.02 (m, 1H), 2.89-2.82 (m, 2H), 2.70-2.53 (m, 1H), 2.35 (s, 3H), 2.09-1.75 (m, 3H), 1.63-1.60 (m, 1H), 0.97 and 0.85 (2t, J=6.0 Hz, 3H). LC-MS: m/z [M+1]=400.

Synthesis of 2-(3,5-dichlorophenylamino)-1-(3-(ethyl(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to afford the titled compound (80 mg, 44%) was synthesized. $^1$H NMR (400 MHz, DMSO-d$_6$): δ 8.23 (s, 1H), 8.01-7.95 (m, 2H), 7.66-7.58 (m, 1H), 7.43 (d, J=6.8 Hz, 2H), 6.96-6.80 (m, 1H), 6.75 (s, 1H), 6.66 (s, 1H), 6.62 (s, 1H), 6.39-6.28 (m, 1H), 4.64-4.36 (m, 1H), 3.98-3.68 (m, 3H), 3.25-3.21 (m, 1H), 2.99-2.85 (m, 2H), 2.67-2.59 (m, 1H), 2.35 (s, 3H), 1.97-1.79 (m, 3H), 1.63-1.37 (m, 1H), 1.19 (t, J=6.85 Hz, 3H). LC-MS: m/z [M+1]=601.

Synthesis of 2-(3,5-dichlorophenylamino)-1-(3-(ethyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (30 mg, 50%). $^1$H NMR (400 MHz, DMSO-d$_6$): δ 11.69 and 11.63 (2s, 1H), 8.10 (d, J=6.8 Hz, 1H), 7.18 and 7.13 (2s, 1H), 6.76 (s, 1H), 6.69 (s, 1H), 6.62 (s, 1H), 6.49 and 6.43 (2s, 1H), 6.37 and 6.33 (2t, J=2.3 Hz, 1H), 4.74-4.69 (m, 1H), 4.46-4.39 (m, 1H), 4.13-3.88 (m, 4H), 3.76-3.70 (m, 2H), 3.20-3.16 (m, 1H), 3.00 (t, J=12.0 Hz, 1H), 2.86 (t, J=12.0 Hz, 1H), 2.62 (t, J=13.6 Hz, 1H), 1.98-1.81 (m, 3H), 1.65-1.49 (m, 1H), 1.19 (t, J=6.8 Hz, 3H). LC-MS: m/z [M+1]=447.

Example 51

Synthesis of 2-(3,5-dichlorophenylamino)-1-(3-(propyl(7H-pyrrolo[2,3-d]pyrimidin-4-yl)amino)piperidin-1-yl)ethanone

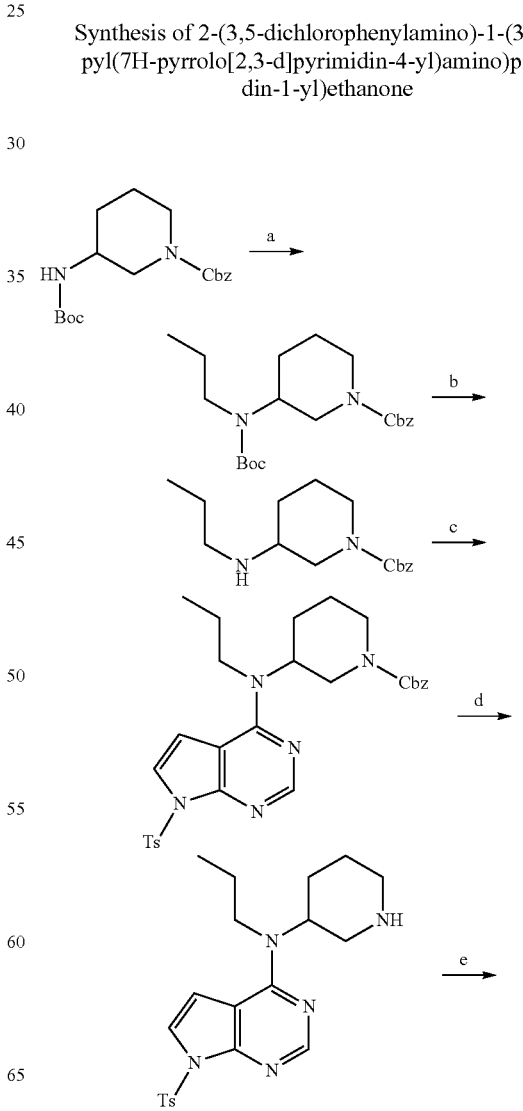

-continued

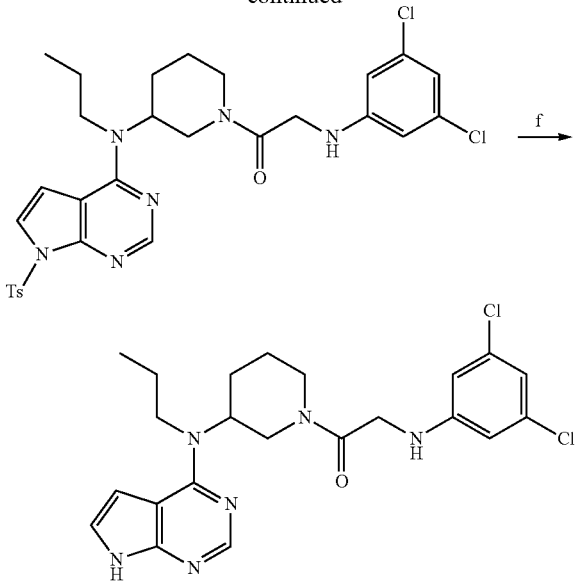

Reagents and conditions: a) NaH, DMF, EtBr, rt 4 h; b) Dioxane•HCl, rt, 1 h; c) 4-chloro-7-tosyl-7H-pyrrolo[2,3-d]pyrimidine, DIEA, DMF, 100° C., 4 h; d) 10% Pd/C, H₂, rt, overnight; e) 2-(3,5-dichlorophenylamino)acetic acid, EDCI, HOBt, DIEA, DMF, rt, 15 h; f) K₂CO₃, aq. MeOH, 60° C., 1 h.

Synthesis of benzyl 3-(tert-butoxycarbonyl(propyl) amino)piperidine-1-carboxylate A similar procedure was used as described for the synthesis of (S)-benzyl 3-(tert-butoxycarbonyl(ethyl)amino)piperidine-1-carboxylate, the titled intermediate (870 mg, 96%) was synthesized. ¹H NMR (400 MHz, DMSO-d₆): δ 7.51-7.36 (m, 5H), 5.06 (s, 2H), 3.95-3.87 (m, 2H), 3.36-3.30 (m, 2H), 3.03-2.66 (m, 3H), 1.72-1.64 (m, 3H), 1.49-1.39 (m, 3H), 1.38 (s, 9H), 0.80 (t, J=6.8 Hz, 3H). ES-MS: m/z [M+1]=377.

Synthesis of benzyl 3-(propylamino)piperidine-1-carboxylate

A similar procedure was used as described for the synthesis of (S)-benzyl 3-(ethylamino)piperidine-1-carboxylate, the titled intermediate (500 mg, 75%) was synthesized. ¹H NMR (400 MHz, DMSO-d₆): δ 7.45-7.25 (m, 5H), 5.06 (s, 2H), 3.90-3.64 (m, 2H), 2.90 (t, J=10.8 Hz, 1H), 2.75-2.40 (m, 4H), 1.90-1.62 (m, 3H), 1.49-1.23 (m, 4H), 0.83 (t, J=6.8 Hz, 3H). ES-MS: m/z [M+1]=277.

Synthesis of benzyl 3-(propyl(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound (200 mg, 20%). ¹H NMR (400 MHz, DMSO-d₆): δ 8.22 (d, J=5.6 Hz, 1H), 7.98 (d, J=7.6 Hz, 2H), 7.69-7.57 (m, 1H), 7.44 (d, J=7.6 Hz, 2H), 7.42-7.32 (m, 5H), 6.61 (s, 1H), 5.12-5.07 (m, 2H), 4.03-3.98 (m, 3H), 3.53-3.48 (m, 2H), 3.02-2.66 (m, 2H), 2.36 (s, 3H), 1.90-1.75 (m, 3H), 1.55-1.34 (m, 3H), 0.91 (t, J=7.2 Hz, 3H). LC-MS: m/z [M+1]=548.

Synthesis of N-(piperidin-3-yl)-N-propyl-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3-d]pyrimidin-4-amine to afford the titled compound (110 mg, 73%). ¹H NMR (400 MHz, DMSO-d₆): δ 8.21 (2s, 1H), 7.98 (d, J=8.4 Hz, 2H), 7.69 and 7.56 (2d, J=3.6 Hz, 1H), 7.44 (d, J=8.4 Hz, 2H), 6.73 and 6.59 (2s, 1H), 3.50-3.42 (m, 2H), 3.32-3.25 (m, 2H), 3.16-3.05 (m, 3H), 2.77 (t, J=4.4 Hz, 1H), 2.36 (s, 3H), 1.90-1.69 (m, 3H), 1.60-1.51 (m, 2H), 1.33-1.18 (m, 1H), 0.93 (t, J=6.8 Hz, 3H). LC-MS: m/z [M+1]=414.

Synthesis of 2-(3,5-dichlorophenylamino)-1-(3-(propyl(7-tosyl-7H-pyrrolo[2,3-d]pyrimidin-4-yl)amino) piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to afford the titled intermediate (80 mg, 50%). ¹H NMR (400 MHz, DMSO-d₆): δ 8.22 (s, 1H), 7.99 and 7.96 (2d, J=7.6 Hz, 2H), 7.67-7.58 (m, 1H), 7.44-7.37 (m, 2H), 6.76-6.53 (m, 4H), 6.32 (s, 1H), 4.62-4.37 (m, 1H), 3.98-3.58 (m, 2H), 3.53-3.51 (m, 2H), 3.25-3.00 (m, 2H), 2.89-2.60 (m, 2H), 2.36 (s, 3H), 1.99-1.79 (m, 2H), 1.81-1.62 (m, 1H), 1.47-1.339 (m, 1H), 0.97-0.86 (2t, J=6.8 Hz, 3H). LC-MS: m/z [M+1]=615.

Synthesis of 2-(3,5-dichlorophenylamino)-1-(3-(propyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (45 mg, 75%). ¹H NMR (400 MHz, DMSO-d₆): δ 11.69 (1s, 1H), 8.10 (d, J=6.0 Hz, 1H), 7.19 and 7.14 (2s, 1H), 6.76 (s, 1H), 6.69 (s, 1H), 6.62 (s, 1H), 6.37-6.35 (m, 2H), 4.70-4.66 (m, 1H), 4.47-4.39 (m, 1H), 4.14-3.87 (m, 3H), 3.59-3.55 (m, 2H), 3.18 and 3.01 (2t, J=11.6 Hz, 1H), 2.87 and 2.62 (2t, J=11.6 Hz, 1H), 2.08-1.81 (m, 3H), 1.71-1.62 (m, 2H), 1.52-1.47 (m, 1H), 0.99 and 0.95 (2t, J=6.8 Hz, 3H). LC-MS: m/z [M+1]=461.

Example 52

Synthesis of 2-(3,5-dichlorophenylamino)-1-(3-(isopropyl(7H-pyrrolo[2,3-d]pyrimidin-4-yl)amino)piperidin-1-yl)ethanone

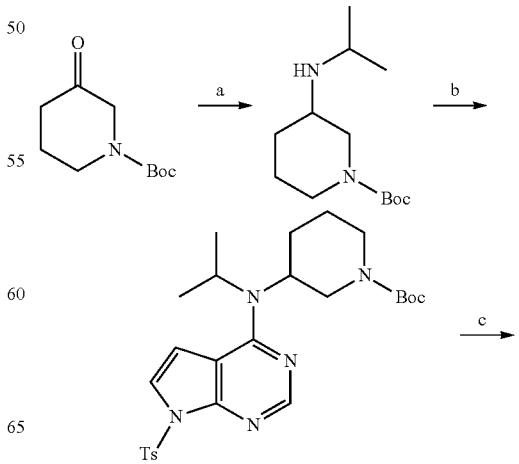

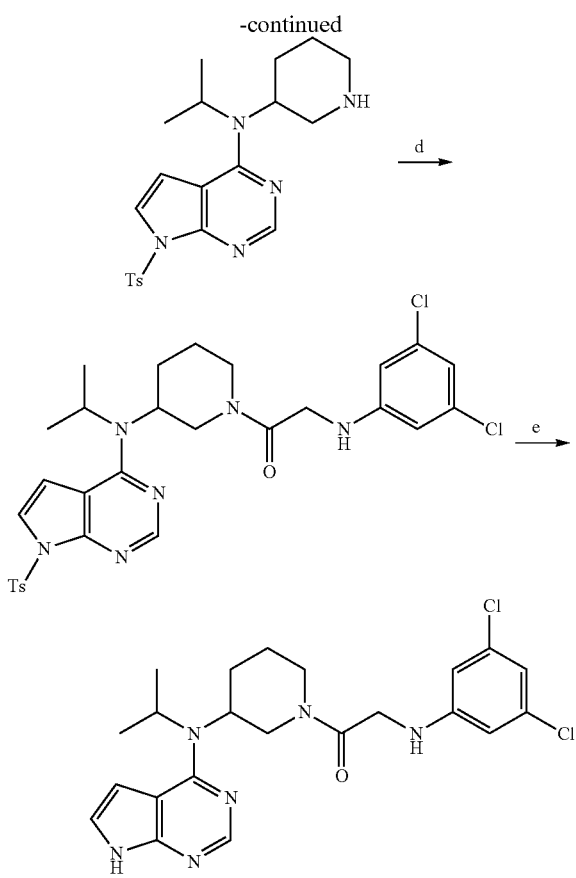

Reagents and conditions: a) NaBH₄, MeOH, rt, overnight; b) 4-chloro-7-tosyl-7H-pyrrolo[2,3-d]pyrimidine, n-BuLi, THF, rt, 4 h; c) Dioxane•HCl, rt, 1 h; d) 2-(3,5-dichlorophenylamino)acetic acid, EDCI, HOBt, DIEA, DMF, rt, 15 h; e) K₂CO₃, aq. MeOH, 60° C., 1 h.

Synthesis is tert-butyl 3-(isopropylamino)piperidine-1-carboxylate

A solution of tert-butyl 3-oxopiperidine-1-carboxylate (2 g, 10.03 mmol) and 2-aminopropane (710 mg, 12.04 mmol) in MeOH (40 mL) was stirred at rt for 1 h. To the solution was added NaBH₄ (758 mg, 20.06 mmol) at 0° C. and the reaction mixture was stirred at rt for 12 h. The reaction mixture was diluted with ice-cooled water and the solvent was reduced to afford a residue which was dissolved in CH₂Cl₂ and washed with water. The organic layer was dried over Na₂SO₄, concentrated in vacuo and purified by column chromatography (silica gel, gradient MeOH in CH₂Cl₂) to afford the titled compound (2 g, 82%). $^1$H NMR (400 MHz, CDCl₃): δ 4.01-3.90 (m, 1H), 3.78 (dt, J=3.6, 9.2 Hz, 1H), 3.48 (s, 1H), 2.96 (heptate, 0.1=6.4 Hz, 1H), 2.92-2.79 (m, 1H), 2.69-2.55 (m, 1H), 1.90-1.87 (m, 1H), 1.68-1.61 (m, 1H), 1.46 (s, 9H), 1.29-1.18 (m, 2H), 1.05 (d, J=6.0 Hz, 6H). ES-MS: m/z [M+1]=243.

Synthesis of tert-butyl 3-(isopropyl(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound. LC-MS: m/z [M-99]=414.

Synthesis of N-isopropyl-N-(piperidin-3-yl)-7-tosyl-7H-pyrrolo[2,3-d]pyrimidin-4-amine A similar procedure was used as described for the synthesis of (S)—N-(piperidin-3-yl)-N-propyl-7-tosyl-7H-pyrrolo[2,3-d]pyrimidin-4-amine to afford the titled compound (150 mg, 10%). $^1$H NMR (400 MHz, CDCl₃): δ 8.39 (s, 1H), 8.04 (d, J=8.4 Hz, 2H), 7.49 (d, J=6.1 Hz, 1H), 7.28 (d, J=8.4 Hz, 2H), 6.6.3 (d, J=6. Hz, 1H), 4.62 (d, J=6.1 Hz, 1H), 4.38 (d, J=6.3 Hz, 1H), 3.19 (t, J=4.8 Hz, 1H), 3.09-2.99 (m, 2H), 2.83-2.79. LC-MS: m/z [M+1]=414.

Synthesis of 2-(3,5-dichlorophenylamino)-1-(3-(isopropyl(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to afford the titled intermediate (70 mg, 31%). $^1$H NMR (400 MHz, DMSO-d₆): δ 8.25 and 8.23 (2s, 1H), 7.98 (d, J=8.4 Hz, 2H), 7.62 (d, J=4.0 Hz, 1H), 7.42 (d, J=8.4 Hz, 2H), 6.94 and 6.89 (2d, J=4.4 Hz, 1H), 6.73 (s, 1H), 6.69 (s, 1H), 6.59 (s, 1H), 6.31-6.21 (m, 1H), 4.49-4.36 (m, 2H), 4.08-4.00 (m, 1H), 3.90-3.68 (m, 3H), 3.27-3.12 (m, 1H), 2.85-2.65 (m, 1H), 2.34 (s, 3H), 1.82-1.75 (m, 1H), 1.61-1.52 (m, 1H), 1.36-1.28 (m, 2H), 1.18 and 1.07 (2d, J=6.4 Hz, 6H). LC-MS: m/z [M+1]=614.

Synthesis of 2-(3,5-dichlorophenylamino)-1-(3-(isopropyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (45 mg, 75%). $^1$H NMR (400 MHz, DMSO-d₆): δ 11.72 (s, 1H), 8.18 and 8.11 (2s, 1H), 7.22 (s, 1H), 6.79 (s, 2H), 6.68-6.57 (m, 2H), 6.34 (s, 1H), 4.71-4.58 (m, 2H), 4.19-4.13 (m, 1H), 3.98-3.82 (m, 2H), 3.77-3.70 (m, 1H), 3.35-3.19 (m, 1H), 2.99 and 2.75 (2t, J=11.7 Hz, 1H), 1.89-1.75 (m, 2H), 1.65-1.48 (m, 2H), 1.19 and 1.05 (2d, J=6.4 Hz, 6H). LC-MS: m/z [M+1]=461.

Example 53

Synthesis of 2-(3,5-dichlorophenylamino)-1-(3-((2-morpholinoethyl)(7H-pyrrolo[2,3-d]pyrimidin-4-yl)amino)piperidin-1-yl)ethanone

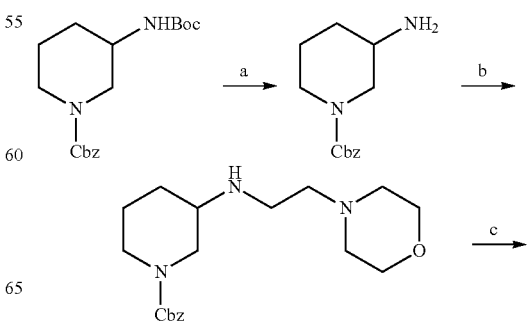

-continued

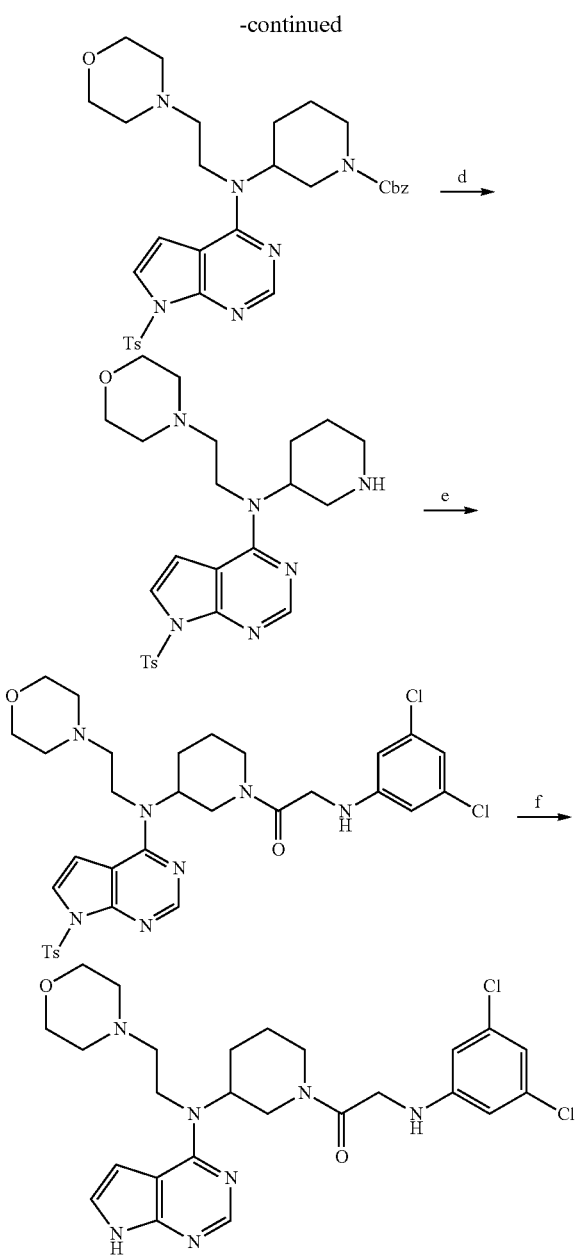

Reagents and conditions: a) Dioxane•HCl, rt, 1 h; b) NaH, DMF, 2-morpholinoethyl methanesulfonate, rt 4 h; c) 4-chloro-7-tosyl-7H-pyrrolo[2,3-d]pyrimidine, DIEA, DMF, 100° C., 4 h; d) 10% Pd/C, H₂, rt, overnight; e) 2-(3,5-dichlorophenylamino)-acetic acid, EDCI, HOBt, DIEA, DMF, rt, 15 h; f) K₂CO₃, aq. MeOH, 60° C., 1 h.

Synthesis of benzyl 3-aminopiperidine-1-carboxylate

Benzyl 3-(tert-butoxycarbonylamino)piperidine-1-carboxylate (1 g, 2.99 mmol) was treated with Dioxane.HCl (30 mL) at 0° C. The reaction mixture was stirred at rt for 1 h. After completion of the reaction mixture, the solvent was removed under vacuo and the residue was dissolved in H₂O (10 mL). The aqueous layer was treated with solid Na₂CO₃ until effervescence ceases and the solution was extracted with EtOAc (3×25 mL). The combined organic layer was dried over Na₂SO₄, concentrated to yield titled intermediate (700 mg, 92%), which was used in the next step without further purification. ¹H NMR (400 MHz, DMSO-d₆): δ 7.41-7.25 (m, 5H), 5.08 (s, 2H), 3.95-3.78 (m, 2H), 3.22 (bs, 2H), 2.82-2.75 (m, 1H), 2.61-2.45 (m, 2H), 1.82-1.78 (m, 1H), 1.69-1.59 (m, 1H), 1.40-1.33 (m, 1H), 1.22-1.10 (m, 1H). ES-MS: m/z [M+1]=235.

Synthesis of benzyl 3-(2-morpholinoethylamino)piperidine-1-carboxylate

A similar procedure was used as described for the synthesis of (S)-tert-butyl 3-(propylamino)piperidine-1-carboxylate to afford the titled compound (110 mg, 56%). ES-MS: m/z [M+1]=348.

Synthesis of benzyl 3-((2-morpholinoethyl)(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound. LC-MS: m/z [M+1]=619.

Synthesis of N-(2-morpholinoethyl)-N-(piperidin-3-yl)-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3-d]pyrimidin-4-amine to afford the titled compound (110 mg, 73%). LC-MS: m/z [M+1]=485.

2-(3,5-Dichlorophenylamino)-1-(3-((2-morpholinoethyl)(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone, the titled intermediate (70 mg, 31%). LC-MS: m/z [M+1]=686.

2-(3,5-Dichlorophenylamino)-1-(3-((2-morpholinoethyl)(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (45 mg, 75%). ¹H NMR (400 MHz, CD3OD): δ 8.03 (s, 1H), 7.05 and 6.99 (2d, J=3.6 Hz, 1H), 6.65 (d, J=3.6 Hz, 1H), 6.52 (s, 1H), 6.50 (s, 2H), 5.71-5.69 (m, 1H), 5.05-4.47 (m, 4H), 4.25-3.65 (m, 5H), 3.38-3.05 (m, 4H), 2.69-2.42 (m, 3H), 1.99-1.93 (m, 3H), 1.75-1.58 (m, 4H). LC-MS: m/z [M+1]=532.

Example 54

Synthesis of 2-(3,5-dichlorophenylamino)-1-(3-((2-(piperidin-1-yl)ethyl)(7H-pyrrolo[2,3-d]pyrimidin-4-yl)amino)piperidin-1-yl)ethanone

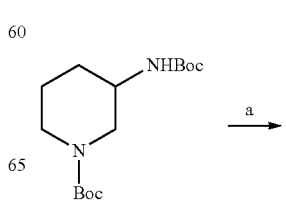

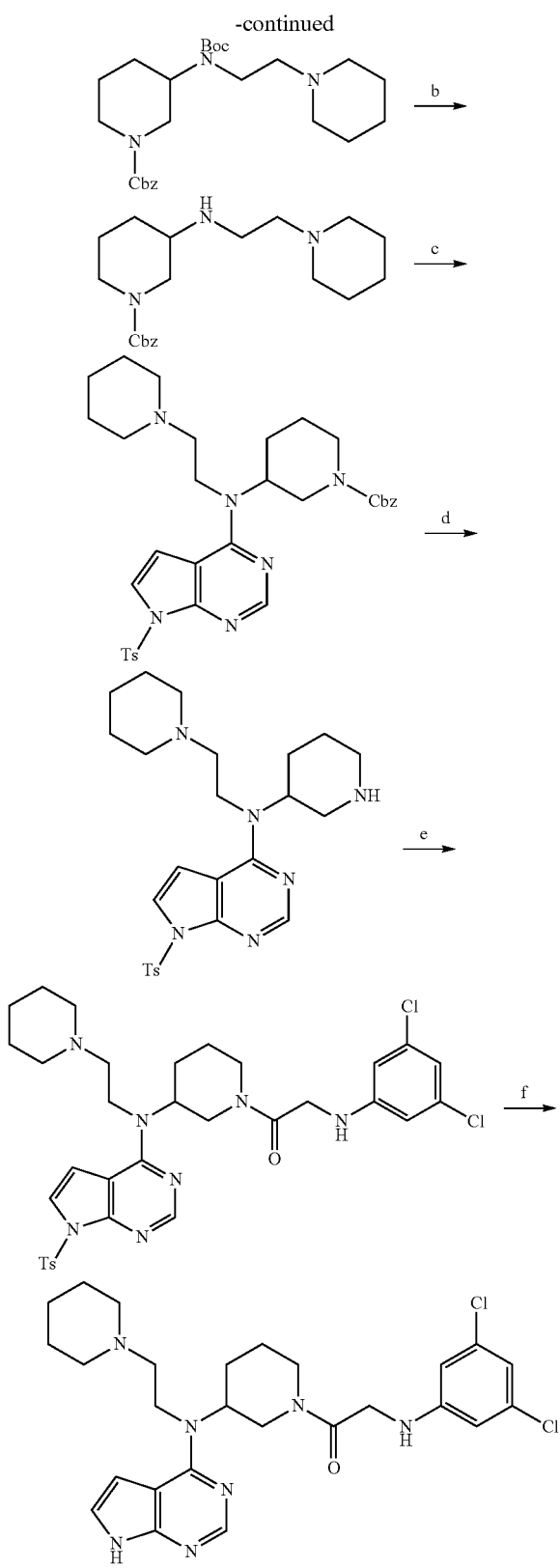

Reagents and conditions: a) NaH, DMF, 2-(piperidin-1-yl)ethyl methanesulfonate, rt 4 h; b) dioxane•HCl, rt, 1 h; c) 10% Pd/C, H₂, rt; d) 4-chloro-7-tosyl-7H-pyrrolo[2,3-d]pyrimidine, DIEA, DMF, 100° C., 4 h; d) 10% Pd/C, H₂, rt, overnight; e) 2-(3,5-dichlorophenylamino))acetic acid, EDCl, HOBt, DIEA, DMF, rt, 15 h; f) K₂CO₃, aq. MeOH, 60° C., 1 h.

Synthesis of benzyl 3-(tert-butoxycarbonyl(2-(piperidin-1-yl)ethyl)amino)piperidine-1-carboxylate A similar procedure was used as described for the synthesis of (S)-benzyl 3-(tert-butoxycarbonyl(ethyl)amino)piperidine-1-carboxylate to afford the titled compound (450 mg, 67%). $^1$H NMR (400 MHz, CDCl$_3$): δ 7.34-7.26 (m, 5H), 5.29 (s, 1H), 5.11 (s, 2H), 4.20-7.09 (m, 2H), 3.61-3.47 (m, 3H), 3.41-3.24 (m, 3H), 2.95-2.88 (m, 2H), 2.60-2.59 (m, 2H), 1.84-1.79 (m, 2H), 1.76-1.73 (m, 2H), 1.55-1.44 (m, 6H), 1.25 (s, 9H). ES-MS: m/z [M+1]=446.

Synthesis of benzyl 3-(2-(piperidin-1-yl)ethylamino)piperidine-1-carboxylate

A similar procedure was used as described for the synthesis of (S)-benzyl 3-(ethylamino)piperidine-1-carboxylate to afford the titled i compound (300 mg, 86%). $^1$H NMR (400 MHz, CDCl$_3$): δ 7.36-7.28 (m, 5H), 5.12 (s, 2H), 4.14-4.05 (m, 1H), 3.94-3.90 (dt, J=2.4, 13.6 Hz, 1H), 2.90 (dt, J=2.8, 14.0 Hz, 1H), 2.72-2.69 (m, 3H), 2.61-2.51 (m, 1H), 2.41-2.34 (m, 6H), 1.96-1.93 (m, 1H), 1.61-1.41 (m, 3H), 1.56-1.52 (m, 5H), 1.43-1.41 (m, 2H). ES-MS: m/z [M+1]=346.

Synthesis of benzyl 3-((2-(piperidin-1-yl)ethyl)(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound (400 mg, 74%). $^1$H NMR (400 MHz, DMSO-d$_6$): 8.23 (s, 1H), 7.98 (d, J=8.4 Hz, 2H), 7.72-7.61 (m, 1H), 7.43 (d, J=8.4 Hz, 2H), 7.35-7.32 (m, 5H), 6.97-6.85 (m, 1H), 5.12-4.96 (m, 2H), 4.55-4.46 (m, 1H), 4.11-4.07 (m, 5H), 4.00-3.97 (m, 3H), 3.68-3.66 (m, 2H), 3.03-2.98 (m, 1H), 2.78-2.69 (m, 1H), 2.35 (s, 3H), 1.87-1.75 (m, 3H), 1.53-1.42 (m, 4H), 1.40-1.33 (m, 3H). LC-MS: m/z [M+1]=617.

Synthesis of N-(2-(piperidin-1-yl)ethyl)-N-(piperidin-3-yl)-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3-d]pyrimidin-4-amine the titled compound (300 mg, 96%). $^1$H NMR (400 MHz, CDCl$_3$): δ 8.35 (s, 1H), 8.02 (d, J=8.4 Hz, 2H), 7.56 (d, J=3.6 Hz, 1H), 7.28 (d, J=8.4 Hz, 2H), 7.22 (d, J=4.0 Hz, 1H), 4.80 (bs, 1H), 4.21-4.11 (m, 2H), 3.71-3.61 (m, 2H), 3.42-3.00 (m, 7H), 2.37 (s, 3H), 2.15-2.09 (m, 2H), 2.00-1.91 (m, 5H), 1.72-1.59 (m, 2H), 1.44-1.33 (m, 3H). LC-MS: m/z [M+1]=483.

Synthesis of 2-(3,5-dichlorophenylamino)-1-(3-((2-(piperidin-1-yl)ethyl)(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3 pyrimidin-d]-yl)amino)piperidin-1-yl)ethanone afford the titled compound (390 mg, 91%). $^1$H NMR (400 MHz, CDCl$_3$): δ 8.38 (s, 1H), 8.12 and 8.06 (2d, J=8.0 Hz, 2H), 7.53 and 7.49 (2d, J=4.0 Hz, 1H), 7.30 and 7.26 (2d, J=8.0 Hz, 2H), 6.85 (d, J=3.6 Hz, 1H), 6.69 (s, 1H), 6.47 (s, 1H), 6.45 (s, 1H), 5.20-5.17 (m, 1H), 4.73-4.65 (m, 1H), 3.85-3.68 (m, 7H), 3.03-2.97 (m, 1H), 2.60-2.47 (m, 6H), 2.39 (s, 3H), 2.01-1.90 (m, 4H), 1.42-1.25 (m, 6H). LC-MS: m/z [M+1]=684.

Synthesis of 2-(3,5-dichlorophenylamino)-1-(3-((2-(piperidin-1-yl)ethyl)(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (200 mg, 69%). ¹H NMR (400 MHz, DMSO-d₆): δ 11.65 (s, 1H), 8.11 (d, J=6.8 Hz, 1H), 7.20 and 7.14 (2s, 1H), 6.75 (s, 1H), 6.68 (s, 1H), 6.62 (s, 1H), 6.61 and 6.53 (2s, 1H), 6.37 and 6.33 (2t, J=2.4 Hz, 1H), 4.69-4.57 (m, 1H), 4.47 and 4.39 (2d, J=10.4 Hz, 1H), 4.14-3.74 (m, 5H), 3.22 and 3.02 (2t, J=11.6 Hz, 1H), 2.86 and 2.62 (2t, J=11.6 Hz, 1H), 2.59-2.42 (m, 4H), 2.02-1.84 (m, 4H), 1.65-1.54 (m, 5H), 1.49-4.38 (m, 3H). LC-MS: m/z [M+1]=530.

Example 55

Synthesis of 2-(3,5-dichlorophenylamino)-1-(3-(phenethyl(7H-pyrrolo[2,3-d]pyrimidin-4-yl)amino)piperidin-1-yl)ethanone

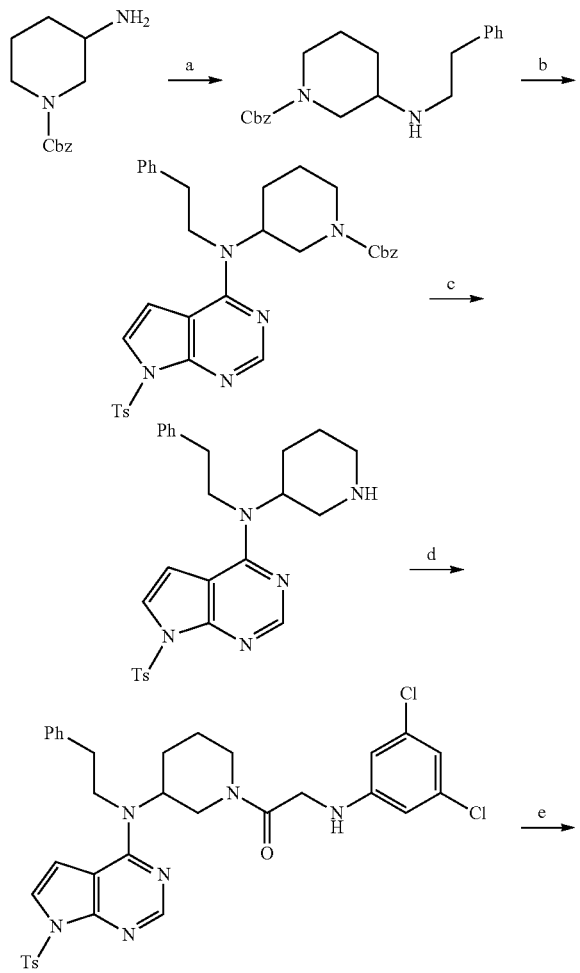

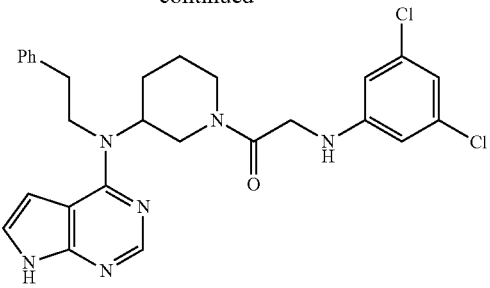

Reagents and conditions: a) DIEA, DMF, (2-bromoethyl)benzene, 100° C., overnight; b) 4-chloro-7-tosyl-7H-pyrrolo[2,3-d]pyrimidine, DIEA, DMF, 100° C., 4 h; c) EtOH•HCl, rt, 1 h; d) 2-(3,5-dichlorophenylamino)acetic acid, EDCl, HOBt, DIEA, DMF, rt, 15 h; e) K₂CO₃, aq. MeOH, 60° C., 1 h. LC-MS: m/z [M + 1] =.

Synthesis of benzyl 3-(phenethylamino)piperidine-1-carboxylate

A similar procedure was used as described for the synthesis of benzyl 3-(2-morpholinoethylamino)piperidine-1-carboxylate, the titled intermediate (350 mg, 80%) was synthesized. ¹H NMR (400 MHz, CDCl₃): δ 7.34-7.18 (m, 10H), 5.29 (s, 1H), 5.12 (s, 2H), 4.21-3.86 (m, 2H), 2.95-2.88 (m, 3H), 2.81-2.72 (m, 3H), 2.63-2.56 (m, 1H), 1.90-1.88 (m, 1H), 1.71-1.66 9m, 1H), 1.48-1.28 (m, 2H). ES-MS: m/z [M+1]=339.

Synthesis of benzyl 3-(phenethyl(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate to afford the titled compound (160 mg, 22%). ¹H NMR (400 MHz, CDCl₃): δ 8.44 and 8.39 (2s, 1H), 8.07 (d, J=8.0 Hz, 2H), 7.34-7.24 (m, 13H), 6.66-6.51 (m, 1H), 5.20-5.12 (m, 2H), 4.48-4.21 (m, 2H), 3.79-3.71 (m, 1H), 2.97-2.85 (m, 3H), 2.39 (s, 3H), 2.04-1.82 (m, 3H), 1.79-1.45 (m, 4H). LC-MS: m/z [M+1]=610.

Synthesis of N-phenethyl-N-(piperidin-3-yl)-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3-d]pyrimidin-4-amine, the titled intermediate (100 mg, 80%) was synthesized. ¹H NMR (400 MHz, CDCl₃): δ 8.42 (s, 1H), 8.07 (d, J=8.4 Hz, 2H), 7.52 (d, J=4.0 Hz, 1H), 7.33-7.28 (m, 8H), 6.70 (d, J=3.4 Hz, 1H), 4.59-4.52 (m, 1H), 3.79-3.72 (m, 1H), 3.26-3.24 (m, 1H), 3.13-3.07 (m, 3H), 2.96 (t, J=8 Hz, 1H), 2.39 (s, 3H), 2.07-2.03 (m, 2H), 1.94-1.89 (m, 4H). LC-MS: m/z [M+1]=476.

Synthesis of 2-(3,5-dichlorophenylamino)-1-(3-(phenethyl(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone to afford the titled intermediate (85 mg, 59%). LC-MS: m/z [M+1]=677.

115

Synthesis of 2-(3,5-dichlorophenylamino)-1-(3-(phenethyl(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone to afford the titled compound (17 mg, 26%). $^1$H NMR (400 MHz, DMSO-d6): δ 11.68 (s, 1H), 8.19 (s, 1H), 7.41-7.16 (m, 6H), 6.79 (s, 1H), 6.69 (s, 1H), 6.64 (s, 1H), 6.45-6.32 (m, 2H), 4.89-4.41 (m, 2H), 4.09-3.82 (m, 5H), 3.12-2.89 (m, 3H), 2.79-2.52 (m, 1H), 1.89-1.75 (m, 2H), 1.79-1.54 (m, 2H). LC-MS: m/z [M+1]=523.

Example 56

Synthesis of 2-(3,5-dichlorophenylamino)-1-(3-((2-(pyrrolidin-1-yl)ethyl)(7H-pyrrolo[2,3-d]pyrimidin-4-yl)amino)piperidin-1-yl)ethanone

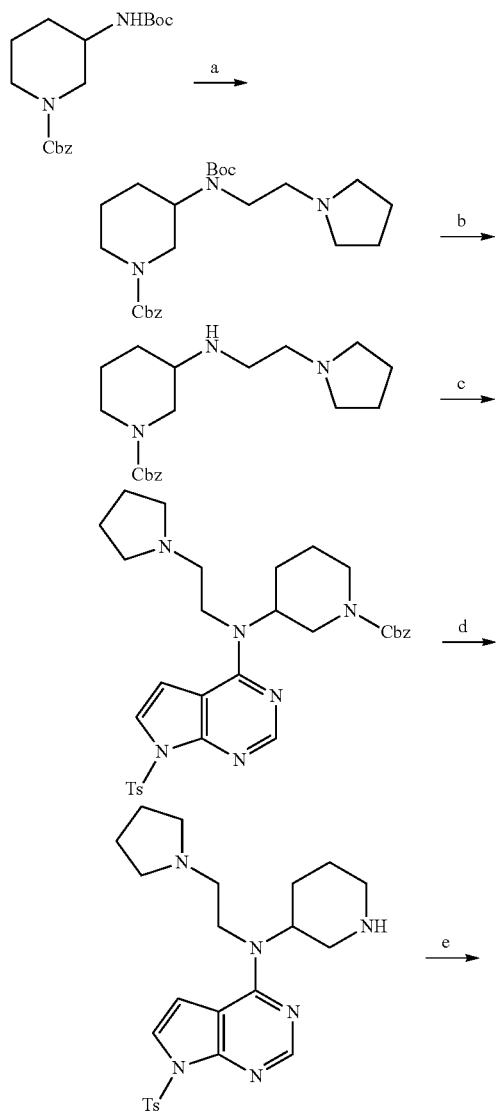

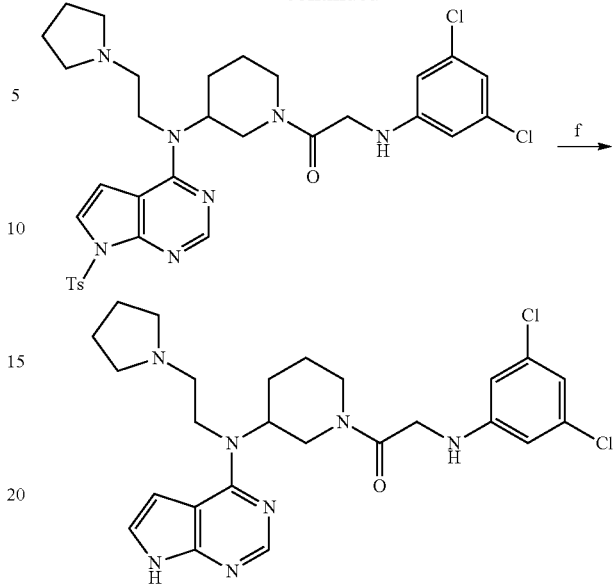

Reagents and conditions: a) NaH, DMF, 2-(pyrrolidin-1-yl)ethyl methanesulfonate, rt 4 h; b) dioxane•HCl, rt, 1 h; c) 10% Pd/C, H$_2$, rt; d) 4-chloro-7-tosyl-7H-pyrrolo[2,3-d]pyrimidine, DIEA, DMF, 100° C., 4 h; d) 10% Pd/C, H$_2$, rt, overnight; e) 2-(3,5-dichlorophenylamino)acetic acid, EDCI, HOBt, DIEA, DMF, rt, 15 h; f) K$_2$CO$_3$, aq. MeOH, 60° C., 1 h.

Synthesis of benzyl 3-(tert-butoxycarbonyl(2-(pyrrolidin-1-yl) ethyl)amino)piperidine-1-carboxylate A similar procedure was used as described for the synthesis of (S)-benzyl 3-(tert-butoxycarbonyl(ethyl)amino)piperidine-1-carboxylate, the titled intermediate (350 mg, 54%) was synthesized. $^1$H NMR (400 MHz, CDCl$_3$): δ 7.36-7.31 (m, 5H), 5.11 (s, 2H), 4.21-4.09 (m, 2H), 3.73-3.44 (m, 3H), 3.41-3.31 (m, 3H), 2.86-2.79 (m, 2H), 2.72-2.59 (m, 3H), 1.81-1.73 (m, 4H), 1.45-1.33 (m, 4H), 1.25 (s, 9H). ES-MS: m/z [M+1]=432.

Synthesis of benzyl 3-(2-(pyrrolidin-1-yl)ethylamino)piperidine-1-carboxylate

A similar procedure was used as described for the synthesis of (S)-benzyl 3-(ethylamino)piperidine-1-carboxylate to afford the titled compound (215 mg, 76%). δ 7.36-7.31 (m, 5H), 5.05 (s, 2H), 3.86-3.81 (m, 2H), 3.72-3.61 (m, 2H), 3.06-2.91 (m, 3H), 2.80-2.60 (m, 1H), 2.60-2.38 (m, 5H), 1.98-1.82 (m, 4H), 1.72-1.53 (m, 5H). ES-MS: m/z [M+1]=332.

Synthesis of benzyl 3-((2-(pyrrolidin-1-yl)ethyl)(7-tosyl-7H-pyrrolo[2,3-d]pyrimidin-4-yl)amino)piperidine-1-carboxylate A similar procedure was used as described for the synthesis of (S)-benzyl 3-(ethyl(7-tosyl-7H-pyrrolo[2,3-d]pyrimidin-4-yl)amino)piperidine-1-carboxylate afford the titled compound (150 mg, 39%). LC-MS: m/z [M+1]=603.

Synthesis of N-(piperidin-3-yl)-N-(2-(pyrrolidin-1-yl)ethyl)-7-tosyl-7H-pyrrolo[2,3-d]pyrimidin-4-amine A similar procedure was used as described for the synthesis of (S)—N-ethyl-N-(piperidin-3-yl)-7-tosyl-7H-pyrrolo[2,3- d]pyrimidin-4-amine afford the titled compound (98 mg, 84%). LC-MS: m/z [M+1]=469.

Synthesis of 2-(3,5-dichlorophenylamino)-1-(3-((2-(pyrrolidin-1-yl)ethyl)(7-tosyl-7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7-tosyl-7H-pyrrolo[2,3-d]pyrimidin-4-yl)amino)piperidin-1-yl)ethanone afford the titled compound (63 mg, 45%). LC-MS: m/z [M+1]=670.

Synthesis of 2-(3,5-dichlorophenylamino)-1-(3-((2-(pyrrolidin-1-yl)ethyl)(7H-pyrrolo[2,3-d]pyrimidin-4-yl)amino)piperidin-1-yl)ethanone A similar procedure was used as described for the synthesis of (S)-2-(3,5-dichlorophenylamino)-1-(3-(ethyl(7H-pyrrolo[2,3-d]pyrimidin-4-yl)amino)piperidin-1-yl)ethanone afford the titled compound (26 mg, 56%). $^1$H NMR (400 MHz, DMSO-d6): δ 11.64 (s, 1H), 8.11 (s, 1H), 7.33-7.15 (m, 1H), 6.76 (s, 1H), 6.68 (s, 1H), 6.62 (s, 1H), 6.54 (s, 1H), 6.33 (d, J=4.0 Hz, 1H), 4.64-4.42 (m, 3H), 4.09-3.78 (m, 4H), 3.81-3.42 (m, 3H), 3.38-3.15 (m, 2H), 3.02-2.81 (m, 3H), 2.12-1.78 (m, 4H), 1.72-1.49 (m, 4H). LC-MS: m/z [M+1]=516.

Example 57

Synthesis of (S)-1-(3-(7H-pyrrolo[2,3-d]pyrimidin-4-yloxy)piperidin-1-yl)-2-(3-chloro-5-fluorophenylamino)ethanone

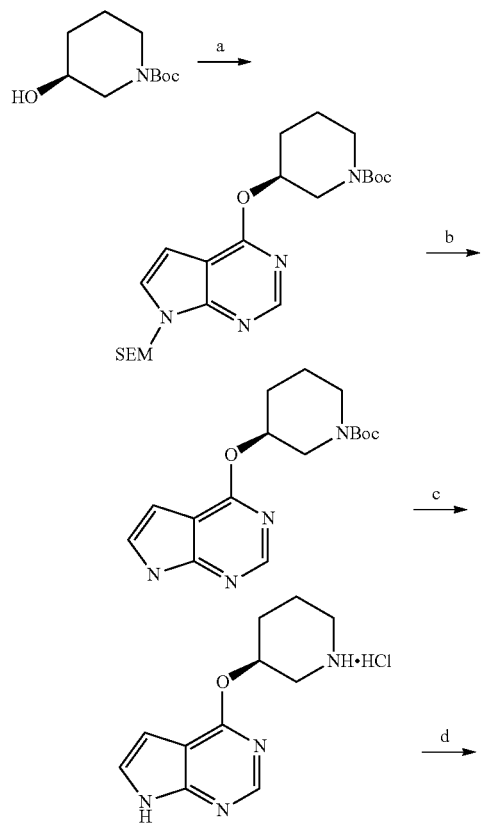

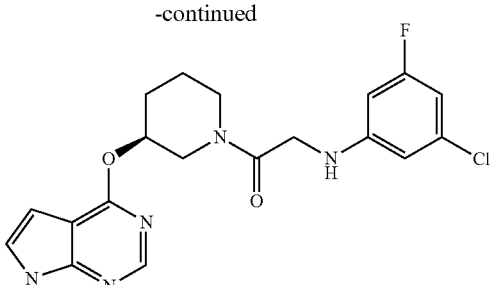

Reagents and conditions: a) NaH, DMSO, 4-chloro-7-((2-(trimethylsilyl)ethoxy)methyl)-7H-pyrrolo[2,3-d]pyrimidine; b) TBAF, THF, reflux, 5 h; c) HCl in 1,4-dioxane, rt, 30 min; d) EDCl, HOBt, 2-(3-chloro-5-fluorophenylamino)acetic acid, DMF, rt, 24 h.

Synthesis of (S)-tert-butyl 3-(7-((2-(trimethylsilyl)ethoxy)methyl)-7H-pyrrolo[2,3-d]pyrimidin-4-yloxy)piperidine-1-carboxylate To a solution of (S)-tert-butyl 3-hydroxypiperidine-1-carboxylate (0.4 g, 2.0 mmol) in DMSO (5 mL) under nitrogen, was added NaH (60% suspension in mineral oil, 79 mg, 2.0 mmol). After the reaction was stirred for 1.5 h at rt, a solution of 4-chloro-7-((2-(trimethylsilyl)ethoxy)methyl)-7H-pyrrolo[2,3-d]pyrimidine (564 mg, 2.0 mmol) in DMSO (5 mL) was added dropwise at rt and the mixture was heated at 50° C. for 2 h. The reaction mixture was cooled to rt, diluted with water (10 mL) and extracted with EtOAc (4×60 mL). The combined organic layer was washed with water (50 mL), dried over Na$_2$SO$_4$ and concentrated in vacuo to give the crude compound which was purified by column chromatography (silica gel, gradient EtOAc in Hexanes) to give (750 mg, 85%) of the titled intermediate.

Synthesis of (S)-tert-butyl 3-(7H-pyrrolo[2,3-d]pyrimidin-4-yloxy)piperidine-1-carboxylate To a solution of (S)-tert-butyl-3-(7-((2-(trimethylsilyl)ethoxy)methyl)-7H-pyrrolo[2,3-d]pyrimidin-4-yloxy)piperidine-1-carboxylate (0.1 g, 0.22 mmol) in THF (5 mL) was added TBAF (291 mg, 1.1 mmol) and the reaction mixture was refluxed for 5 h. The reaction mixture was cooled and was concentrated in vacuo to give a residue which was partitioned between EtOAc (25 mL) and water (25 mL). The EtOAc layer was separated and the water layer was extracted with EtOAc (3×25 mL). The combined organic layer was dried over Na$_2$SO$_4$ and evaporated in vacuo to give the crude compound which was purified by column chromatography (silica gel, gradient EtOAc in hexanes) to give (65 mg, 74%) the titled compound.

Synthesis of (S)-4-(piperidin-3-yloxy)-7H-pyrrolo[2,3-d]pyrimidine hydrochloride To a solution of (S)-tert-butyl 3-(7H-pyrrolo[2,3-d]pyrimidin-4-yloxy)piperidine-1-carboxylate (60 mg, 0.18 mmol) in 1,4-dioxane (2 mL) was added 4 N HCl in 1,4-dioxane (2 mL) and the reaction mixture was stirred for 30 min. After completion of the reaction as indicated by TLC, the reaction mixture was concentrated in vacuo to give a residue which was triturated with ether to give (31 mg, 74%) the titled compound.

Synthesis of (S)-1-(3-(7H-pyrrolo[2,3-d]pyrimidin-4-yloxy)piperidin-1-yl)-2-(3-chloro-5-fluorophenylamino)ethanone To a cooled solution of 2-(3-chloro-5-fluorophenylamino) acetic acid (139 mg, 0.68 mmol) at 0° C. in DMF (5 mL) was added HOBt (136 mg, 0.10 mmol), EDCI (197 mg, 0.10 mmol), (S)-4-(piperidin-3-yloxy)-7H-pyrrolo[2,3-d]pyrimidine hydrochloride (150 mg, 0.7 mmol) and Et₃N (0.2 mL, 1.37 mmol) at 0° C. The reaction mixture was allowed to warm to rt and was stirred overnight. The reaction mixture was diluted with EtOAc (50 mL) and washed with water (3×20 mL). The combined EtOAc layer was dried over Na₂SO₄ and concentrated in vacuo to give a residue that was purified by column chromatography (silica gel, gradient MeOH in CH₂Cl₂) to afford (45 mg, 17%) the titled compound. ¹H NMR (400 MHz, DMSO-d₆): δ 12.08 and 12.05 (2s, 1H), 8.41 and 8.39 (2s, 1H), 7.35 (s, 1H), 6.62-6.25 (m, 4H), 5.39-5.24 (m, 1H), 4.05-3.62 (m, 5H), 3.55-3.42 (m, 2H), 1.89-1.45 (m, 4H). LC-MS: m/z [M+1]=404.

Example 58

Synthesis of (S)-1-(3-(1H-pyrazolo[3,4-d]pyrimidin-4-yloxy)piperidin-1-yl)-2-(3-chloro-5-fluorophenylamino)ethanone

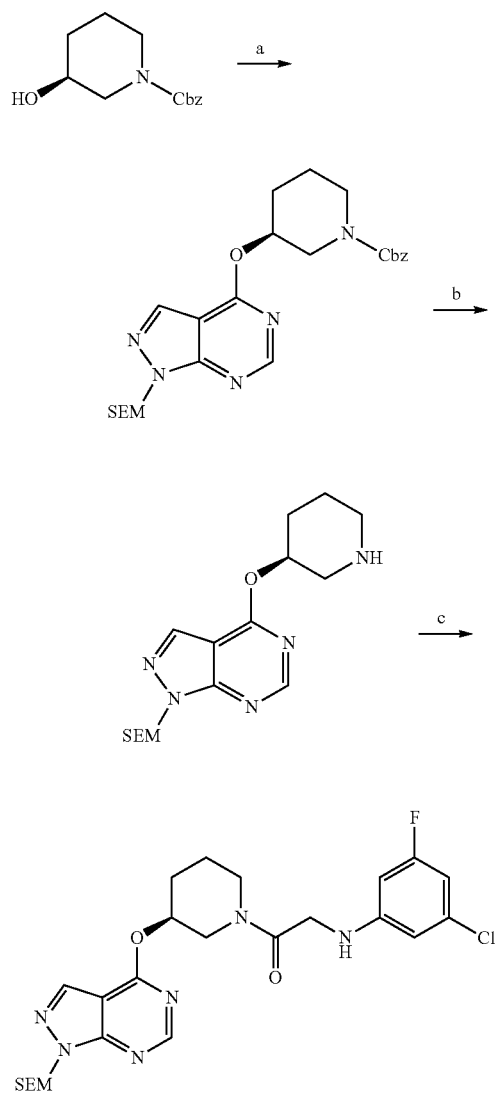

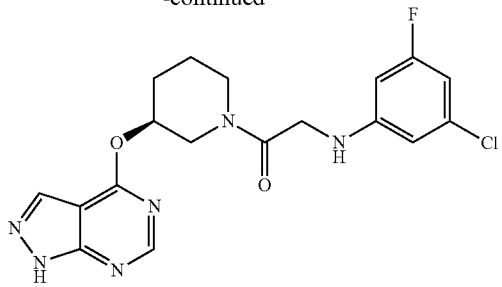

Reagents and conditions: a) NaH, DMSO, 4-chloro-1-((2-(trimethylsilyl)ethoxy)methyl)-1H-pyrazolo[3,4-d]pyrimidine; b) TBAF, THF, reflux, 5 h; c) 4N HCl in dioxane, rt, 30 min; d) EDCI, HOBt, 2-(3-chloro-5-fluorophenylamino)acetic acid, DMF, rt, 24 h.

Synthesis of (S)-benzyl 3-(1-((2-(trimethylsilyl)ethoxy)methyl)-1H-pyrazolo[3,4-d]pyrimidin-4-yloxy)piperidine-1-carboxylate Following a similar procedure as (S)-tert-butyl 3-(7-((2-(trimethylsilyl)ethoxy)methyl)-7H-pyrrolo[2,3-d]pyrimidin-4-yloxy)piperidine-1-carboxylate the tilted compound (200 mg, 90%) was synthesized. ¹H NMR (400 MHz, CDCl₃): δ 8.58-8.51 (m, 1H), 8.01 (s, 1 h), 7.36-7.09 (m, 5H), 5.92-5.77 (m, 3H), 5.51-4.91 (m, 3H), 3.95-3.41 (m, 5H), 2.15-1.85 (m, 3H), 1.75-1.62 (m, 1H), 0.95 (t, J=6.4 Hz, 2H), −0.05 (s, 9H). LC-MS: m/z [M+1]=484.

Synthesis of (S)-4-(piperidin-3-yloxy)-1-((2-(trimethylsilyl)ethoxy)methyl)-1H-pyrazolo[3,4-d]pyrimidine To a solution of (S)-benzyl 3-(1-((2-(trimethylsilyl)ethoxy)methyl)-1H-pyrazolo[3,4-d]pyrimidin-4-yloxy)piperidine-1-carboxylate (200 mg, 0.41 mmol) in EtOH (10 mL) was added 10% Pd/C (40 mg) and the solution was placed under an atmsphere of hydrogen (1 psi). The reaction mixture was purged with nitrogen and filtered through a Celite pad, and the filtrate was evaporated in vacuo to give (115 mg, 79%) the titled compound which was used without further purification. ¹H NMR (400 MHz, DMSO-d₆): δ 8.63 and 8.60 (2s, 1H), 8.31-8.21 (2s, 1H), 5.72 and 5.70 (2s, 2H), 5.38-5.22 (m, 1H), 3.63-3.59 (m, 2H), 3.21-3.07 (m, 1H), 2.81-2.63 (m, 2H), 2.23-2.01 (m, 2H), 1.79-1.61 (m, 2H), 1.58-1.45 (m, 2H), 0.85 (t, J=6.4 Hz, 2H), −0.91 (s, 9H). LC-MS: m/z [M+1]=350.

Synthesis of (S)-2-(3-chloro-5-fluorophenylamino)-1-(3-(1-((2-(trimethylsilyl)ethoxy)methyl)-1H-pyrazolo[3,4-d]pyrimidin-4-yloxy)piperidin-1-yl)ethanone Following a similar the procedure used for the synthesis of (S)-1-(3-(7H-pyrrolo[2,3-d]pyrimidin-4-yloxy)piperidin-1-yl)-2-(3-chloro-5-fluorophenylamino)ethanone the titled compound (150 mg, 85%) was synthesis. LC-MS: m/z [M+1]=535.

Synthesis of (S)-1-(3-(1H-pyrazolo[3,4-d]pyrimidin-4-yloxy)piperidin-1-yl)-2-(3-chloro-5-fluorophenylamino)ethanone Following the procedure for synthesis of (S)-tert-butyl 3-(7H-pyrrolo[2,3-d]pyrimidin-4-yloxy)piperidine-1-carboxylate the titled compound (40 mg, 35 mg) was synthesized. $^1$H NMR (400 MHz, CD$_3$OD): δ 8.54 and 8.50 (2s, 1H), 8.05 and 7.99 (2s, 1H), 6.46-6.13 (m, 3H), 5.50 (bs, 1H), 4.25-3.63 (m, 6H), 3.56-3.42 (m, 1H), 2.16-1.62 (m, 4H). LC-MS: m/z [M+1]=405.

Example 59

Synthesis of (R)-1-(3-(7H-pyrrolo[2,3-d]pyrimidin-4-yloxy)piperidin-1-yl)-2-(3-chloro-5-fluorophenylamino)ethanone

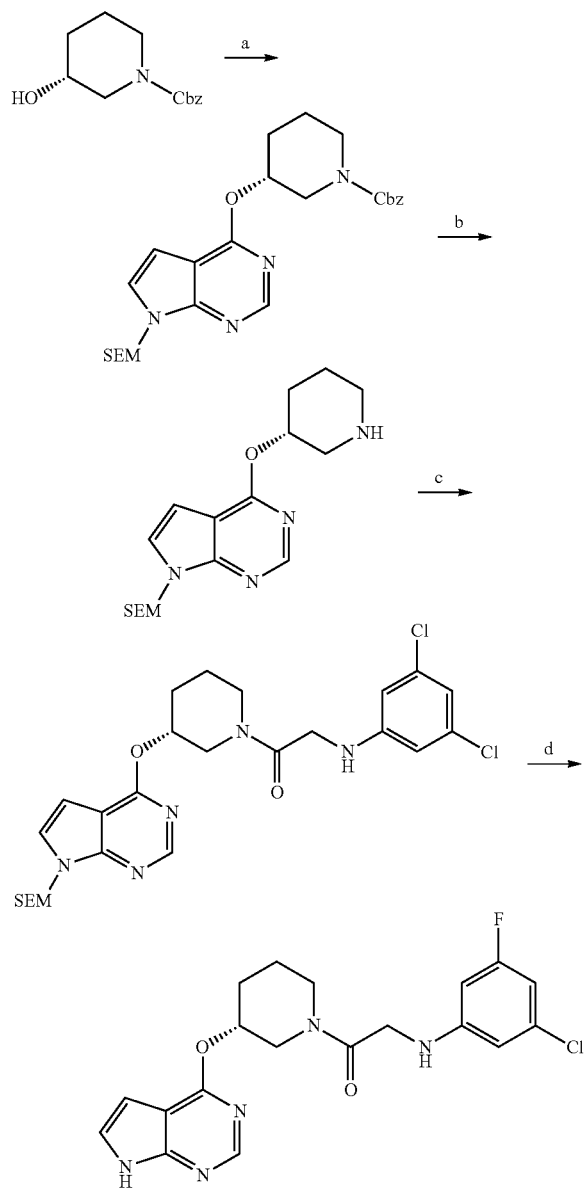

Reagents and conditions: a) NaH, DMSO, 4-chloro-7-((2-(trimethylsilyl)ethoxy)methyl)-7H-pyrrolo[2,3-d]pyrimidine; b) 10% Pd/C, H$_2$; c) EDCI, HOBt, 2-(3,5-dichlorophenylamino)acetic acid, DMF, rt, 24 h d) TBAF, THF, reflux, 5 h.

Synthesis of (R)-1-(3-(7H-pyrrolo[2,3-d]pyrimidin-4-yloxy)piperidin-1-yl)-2-(3-chloro-5-fluorophenylamino)ethanone Following the procedure for synthesis of (S)-tert-butyl 3-(7H-pyrrolo[2,3-c]pyrimidin-4-yloxy)piperidine-1-carboxylate the titled compound (40 mg, 35 mg) was synthesized. $^1$H NMR (400 MHz, DMSO-d$_6$): δ 12.03 and 11.99 (2s, 1H), 8.36 and 8.33 (2s, 1H), 7.32-7.31 (m, 1H), 6.72 (s, 1H), 6.61 and 6.58 (2s, 2H), 6.37-6.27 (m, 2H), 5.32-5.24 (m, 1H), 4.04-3.83 (m, 2H), 3.79-3.64 (m, 3H), 3.52-3.47 (m, 2H), 2.07-1.86 (m, 2H), 1.72-1.51 (m, 2H). LC-MS: m/z [M+1]=420.

Example 60

Synthesis of 1-((S)-3-(2-aminopyrimidin-4-ylamino)piperidin-1-yl)-2-(3,5-dichlorophenylamino)ethanone

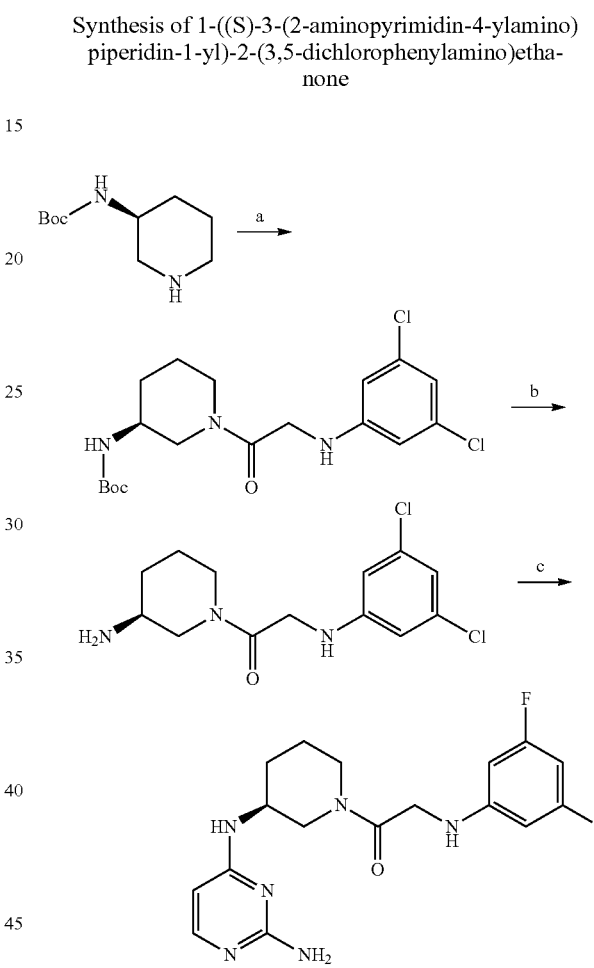

Reagents and conditions: a) 2-(3,5-dicholorphenylamino)acetic acid, EDCI, HOBt, DIEA, DMF, rt, 15 h; b) 4N HCl in 1,4-dioxane, rt, 1 h; c) 4-chloropyrimidin-2-amine, DIEA, n-BuOH, 100° C., 2 days.

Synthesis of tert-butyl(S)-1-(2-(3,5-dichlorophenylamino)acetyl)piperidin-3-ylcarbamate To a solution of tert-butyl(S)-piperidin-3-ylcarbamate (500 mg, 2.5 mmol), in DMF (5 mL) was added EDCI (573 mg, 3.0 mmol), HOBt (405 mg, 3.0 mmol), 2-(3,5-dichlorophenylamino)acetic acid (550 mg, 2.5 mmol) and DIEA (0.5 mL, 3.0 mmol) at 0° C. The reaction mixture was stirred at rt overnight, the reaction mixture was diluted with EtOAc and washed with water. The water layer was extracted with the EtOAc and the combined organic layer was dried over Na$_2$SO$_4$ and evaporated in vacuo to give the crude compound that was purified by column chromatography (silica gel, gradient MeOH in CH$_2$Cl$_2$) to afford (900 mg, 98%) of the titled intermediate. LCMS: m/z: [M+1]=402.

Synthesis of 2-(3,5-dichlorophenylamino)-1-((S)-3-aminopiperidin-1-yl)ethanone To a solution of tert-butyl(S)-1-(2-(3,5-dichlorophenylamino)acetyl)piperidin-3-ylcarbamate (0.9 mg, 2.2 mmol) in 1,4-dioxane (5 mL) was added 4 N HCl in dioxane (10 mL) and the reaction mixture was stirred for 1 h. The reaction mixture was concentrated in vacuo and the resultant residue was dissolved in water and aqueous phase was adjusted to a pH 9 with sat. NaHCO$_3$ and extracted with EtOAc (3×50 mL). The combined organic layer was dried over Na$_2$SO$_4$ and evaporated in vacuo to afford the titled intermediate (540 mg, 79%), which was used in the next step without purification. LCMS: m/z: [M+1]=302.

Synthesis of 1-((S)-3-(2-aminopyrimidin-4-ylamino)piperidin-1-yl)-2-(3,5-dichlorophenylamino)ethanone A stirred solution of 2-(3,5-dichlorophenylamino)-1-((S)-3-aminopiperidin-1-yl)ethanone (150 mg, 0.49 mmol) 4-chloropyrimidin-2-amine (60 mg, 0.53 mmol), DIEA (0.15 mL, 1.57 mmol) in n-BuOH (2 mL) was heated to 100° C. for 2 days. The solvent was concentrated in vacuo to give the crude compound which was purified by reverse phase column chromatography (C-18, 500 mm×30 mm×10µ (gradient ACN: H$_2$O: TFA) to give the titled intermediate (20 mg, 10%). $^1$H NMR (400 MHz, DMSO): δ 11.89 (bs, 2H), 7.65 (s, 1H), 6.75-6.60 (m, 3H), 6.11-6.06 (d, 1H), 4.00-3.89 (m, 4H), 3.72-3.62 (m, 2H), 3.07 (bs, 1H), 2.77-2.07 (m, 2H), 1.60-1.32 (m, 2H), 1.30-1.11 (m, 2H). LCMS: m/z: [M+1]=395 & [M+23]=417.

Example 61

Synthesis of (S)-4-amino-6-(1-(2-(3,5-dichlorophenylamino)acetyl)piperidin-3-ylamino)pyrimidine-5-carbonitrile

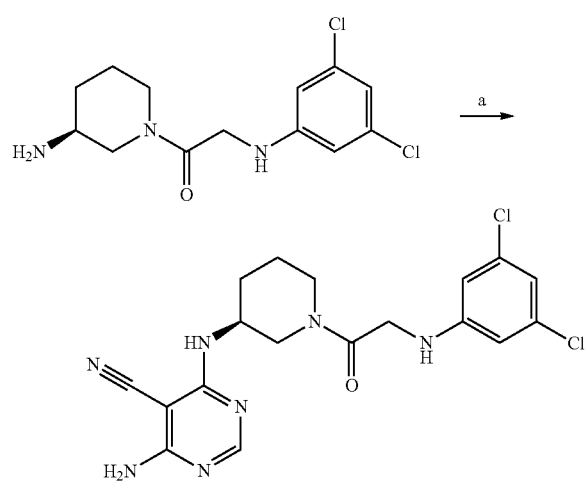

Reagents and conditions: a) 4-amino-6-chloropyrimidine-5-carbonitrile, Et$_3$N, n-BuOH, 100° C., 2 days.

(S)-4-amino-6-(1-(2-(3,5-dichlorophenylamino)acetyl)piperidin-3-ylamino)pyrimidine-5-carbonitrile A similar procedure was used as described for the synthesis of 1-((S)-3-(2-aminopyrimidin-4-ylamino) piperidin-1-yl)-2-(3,5-dichlorophenylamino)ethanone to afford the title compound (30 mg, 18%). $^1$H NMR (400 MHz, CD$_3$OD): δ 8.21 & 8.20 (s, 1H), 6.53-6.68 (m, 3H), 4.46-4.36 (m, 1H), 4.20-3.84 (m, 3H), 3.17-2.86 (m, 1H), 2.91-2.71 (m, 1H), 2.05-2.00 (m, 1H), 1.65-1.55 (m, 3H), 1.39-1.20 (m, 1H). LC-MS: m/z [M+1]=420, [M+23]=442.

Example 62

Synthesis of 4-((S)-1-(2-(3,5-dichlorophenylamino)acetyl)piperidin-3-ylamino)-5,6-dihydropyrido[2,3-d]pyrimidin-7(8H)-one

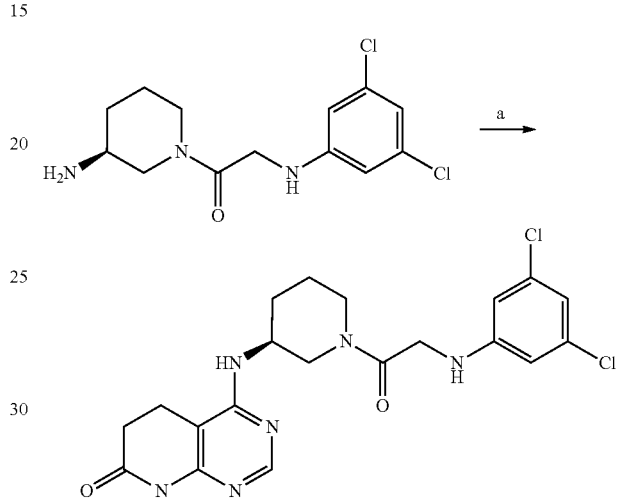

Reagents and conditions: a) 4-chloro-5,6-dihydropyrido[2,3-d]pyrimidin-7(8H)-one, Et$_3$N, n-BuOH, 100° C., 2 days.

Synthesis of 4-((S)-1-(2-(3,5-dichlorophenylamino)acetyl)piperidin-3-ylamino)-5,6-dihydropyrido[2,3-d]pyrimidin-7(8H)-one A similar procedure was used as described for the synthesis of 1-((S)-3-(2-aminopyrimidin-4-ylamino) piperidin-1-yl)-2-(3,5-dichlorophenylamino)ethanone to afford the titled compound (18 mg, 10%). $^1$H NMR (400 MHz, CD$_3$OD): δ 8.26 (s, 1H), 6.61 (s, 1H), 6.45 (s, 2H), 4.00-3.90 (m, 1H), 3.74-3.73 (d, 2H), 3.69-3.47 (m, 2H), 2.82-2.78 (m, 2H), 2.58-2.54 (m, 2H), 1.89-1.86 (m, 1H), 1.76-1.65 (m, 3H), 1.36-1.25 (m, 2H). LC-MS: m/z [M+1]=449.

Example 63

Synthesis of (S)—N-(6-(1-(2-(3,5-dichlorophenylamino)acetyl)piperidin-3-ylamino)pyrimidin-4-yl)acetamide

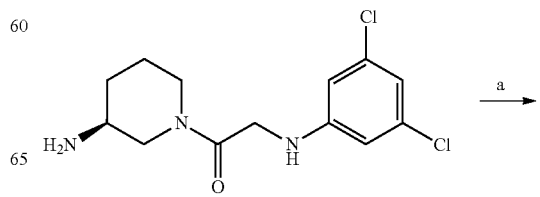

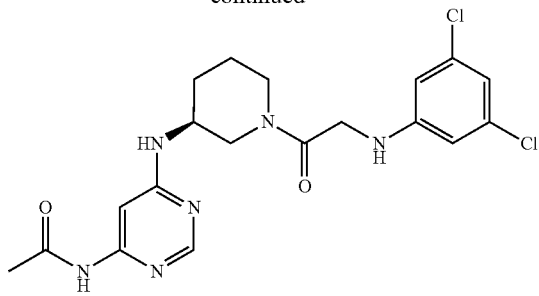

Reagents and conditions: a) N-(6-chloropyrimidin-4-yl)acetamide, DIEA, DMF, 100° C., 2 days.

Synthesis of (S)—N-(6-(1-(2-(3,5-dichlorophenylamino)acetyl)piperidin-3-ylamino)pyrimidin-4-yl)acetamide A similar procedure was used as described for the synthesis of 1-((S)-3-(2-aminopyrimidin-4-ylamino) piperidin-1-yl)-2-(3,5-dichlorophenylamino)ethanone to afford the titled compound (10 mg, 4.6%). $^1$H NMR (400 MHz, CD$_3$OD): δ 8.39 and 8.36 (s, 1H), 7.88 (s, 1H), 6.58-6.57 (d, 2H), 6.52 (s, 1H), 4.00-3.85 (m, 4H), 2.19 (s, 3H), 2.12-2.01 (m, 2H), 1.71-1.60 (m, 2H), 1.5-1.24 (m, 3H). LC-MS: m/z [M+1]=437 & [M+23]: 459. HPLC (254 nm): 95.02%. HPLC (210 nm): 92.32%.

Example 64

Synthesis of (S)-1-(3-(9H-purin-6-ylamino)piperidin-1-yl)-2-(3,5-dichlorophenylamino)ethanone

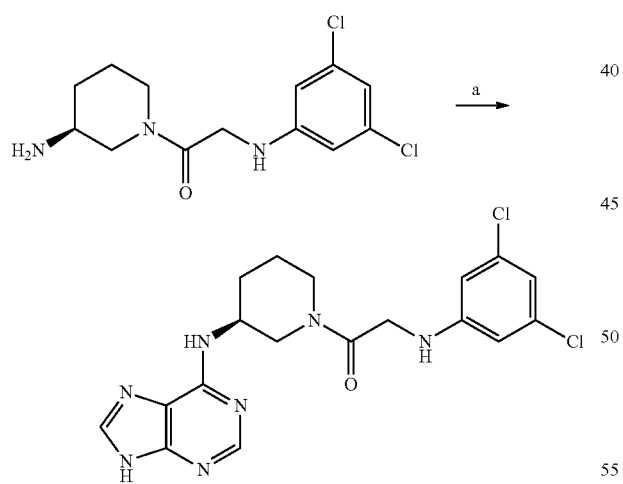

Reagents and conditions: a) 6-chloro-9H-purine, DIEA, DMF, 100° C., 12 h.

Synthesis of (S)-1-(3-(9H-purin-6-ylamino)piperidin-1-yl)-2-(3,5-dichlorophenylamino)ethanone A similar procedure was used as described for the synthesis of 1-((S)-3-(2-aminopyrimidin-4-ylamino) piperidin-1-yl)-2-(3,5-dichlorophenylamino)ethanone to afford the crude material that was purified by column chromatography (silica gel, gradient MeOH in CH$_2$Cl$_2$) afford the title compound (18 mg, 13%). $^1$H NMR (400 MHz, DMSO): δ 8.64 (bs, 1H), 8.47 (s, 1H), 8.40 (s, 1H), 6.75 (s, 1H), 6.66 (s, 1H), 6.61 (s, 1H), 4.20 (bs, 2H), 4.03-3.88 (m, 3H), 3.76-3.73 (m, 1H), 2.13-2.06 (m, 2H), 1.95-1.86 (m, 1H), 1.79-1.77 (m, 2H), 1.62-1.60 (m, 1H), 1.47-1.41 (m, 1H). LC-MS: m/z [M+1]=420.

Example 65

Synthesis of 2-(3,5-dichlorophenylamino)-1-((S)-3-(6-aminopyrimidin-4-ylamino)piperidin-1-yl)ethanone

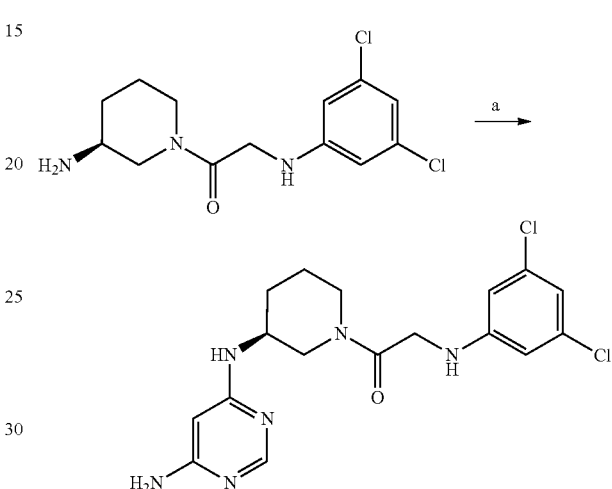

Reagents and conditions: a) 6-chloropyrimidin-4-amine, Et$_3$N, n-BuOH, 100° C., 2 days Synthesis of 2-(3,5-dichlorophenylamino)-1-((S)-3-(6-aminopyrimidin-4-ylamino)piperidin-1-yl)ethanone A similar procedure was used as described for the synthesis of 1-((S)-3-(2-aminopyrimidin-4-ylamino) piperidin-1-yl)-2-(3,5-dichlorophenylamino)ethanone to obtained the crude compound was purified by Prep-TLC (10% MeOH in CHCl$_3$) to afford (8 mg, 3%) of the title compound. $^1$H NMR (400 MHz, CD$_3$OD): δ 7.93 (s, 1H), 6.64-6.63 (m, J=1.6 Hz, 1H), 6.47-6.47 (d, J=1.6 Hz, 2H), 5.71 (s, 1H), 3.87-3.67 (m, 4H), 1.91-1.89 (m, 1H), 1.73-1.53 (m, 3H), 1.37-1.16 (m, 3H). LC-MS: m/z [M+1]=395 & [M+23]=417.

Example 66

Synthesis of 1-{(S)-3-[(2-Amino-pyrimidin-4-yl)-methyl-amino]-piperidin-1-yl}-2-(3,5-dichloro-phenylamino)-ethanone

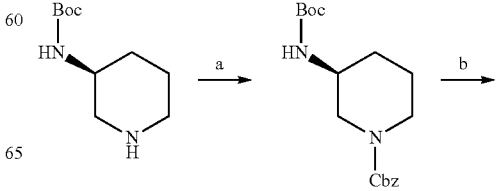

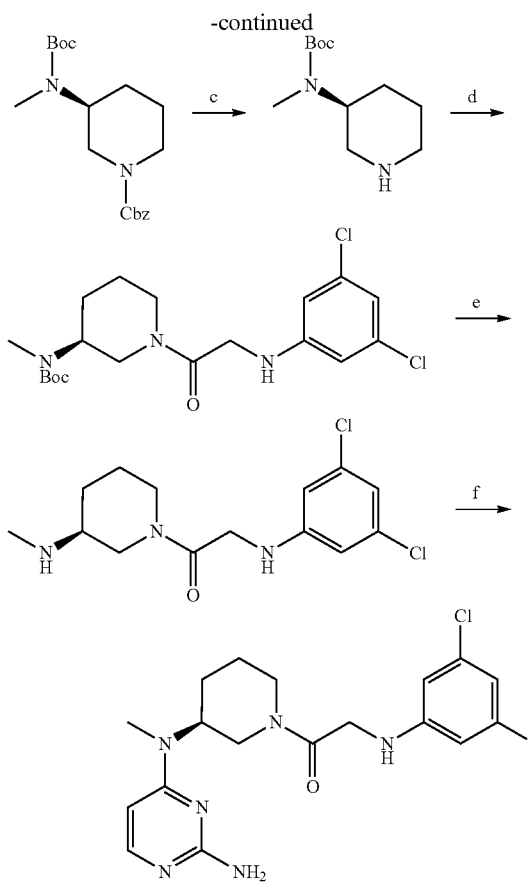

Reagents and conditions: a) Cbz—Cl, Et₃N, CH₂Cl₂, rt, 3 h; b) MeI, NaH, DMF, 4 h, rt; c) 10% Pd/C, H₂, MeOH, 2 h; d) EDCI, HOBt, rt, DMF; e) Dioxane, HCl; f) 4-chloropyrimidin-2-amine, DIEA, DMF, 100° C., 2 days.

Synthesis of (S)-benzyl 3-(tert-butoxycarbony-lamino)piperidine-1-carboxylate

To a solution of tert-butyl(S)-piperidin-3-ylcarbamate (1.0 g, 5.0 mmol) and Et₃N (0.76 mL) in CH₂Cl₂ was added Cbz-Cl (50% solution in toluene, 5.49 mmol, 0.78 mL) at 0° C. The reaction mixture was then warmed to rt and stirred for 3 h, diluted with CH₂Cl₂ (50 mL) and washed with water (3×5 mL). The organic layer was then dried over Na₂SO₄ and concentrated in vacuo to give (1.5 g, 89%) of the titled compound which was used without further purification. $^1$H NMR (400 MHz, CDCl₃): δ 7.35-7.38 (m, 5H), 5.13-5.12 (d, 2H), 4.61 (bs, 1H), 3.73-3.67 (m, 2H), 3.51-3.46 (m, 2H), 3.26-2.23 (m, 2H), 1.86-1.80 (m, 2H), 1.66-1.50 (m, 1H), 1.42 (s, 9H). LC-MS: m/z [M−100]=235 & [M+23]=357.

Synthesis of (S)-benzyl 3-(tert-butoxycarbonyl(me-thyl)amino)piperidine-1-carboxylate To a solution of tert-butyl(S)-benzyl 3-(tert-butoxycarbonylamino)piperidine-1-carboxylate (1.5 g, 4.5 mmol) in DMF (10 mL) was added NaH (60% suspension in paraffin oil, 215 mg, 5.38 mmol) at 0° C. and the reaction mixture was stirred for 2 h followed by the addition of MeI (0.3 mL, 4.9 mmol). The reaction was stirred for 4 h at rt, diluted with ice-water and the solution was extracted with EtOAc (3×25 mL). The combined EtOAc layer was dried over Na₂SO₄ and concentrated in vacuo to give the titled intermediate (1.3 g, 83%), which was used next without further purification. $^1$H NMR (400 MHz, CDCl₃): δ 7.36-7.30 (m, 5H), 5.13-5.12 (d, 2H), 2.77 (s, 3H), 2.65-2.60 (m, 2H), 2.04 (s, 2H), 1.85-1.80 (m, 2H), 1.63-1.62 (m, 2H), 1.43 (s, 9H), 0.90-0.85 (m, 1H). LC-MS: m/z [M+23]=371.

Synthesis of tert-butyl methyl(S)-piperidin-3-ylcarbamate

To a solution of (S)-benzyl 3-(tert-butoxycarbonyl(methyl)amino)piperidine-1-carboxylate (1.3 g, 3.7 mmol) in MeOH was added 10% Pd/C (500 mg) and the suspension was placed under an atmosphere of hydrogen for 2 h. The reaction was filtered under nitrogen, and the filtrated was concentrated in vacuo to afford a residue which was purified (silica gel, gradient MeOH in CH₂Cl₂) to give the titled intermediate (700 mg, 87%). $^1$H NMR (400 MHz, CDCl₃): δ 4.98 (bs, 1H), 3.02-2.98 (m, 2H), 2.75 (s, 3H), 2.68-2.60 (m, 1H), 2.48-2.42 (m, 1H), 1.83-1.75 (m, 3H), 1.61-1.55 (m, 2H), 0.90 (s, 9H). LC-MS: m/z [M+1]=215.

Synthesis of tert-butyl(S)-1-(2-(3,5-dichlorophenylamino)acetyl)piperidin-3-ylmethylcarbamate To a solution of tert-butyl methyl (S)-piperidin-3-ylcarbamate (0.7 g, 3.2 mmol) in DMF (5 mL) was added EDCI (745 mg, 3.9 mmol), HOBt (529 mg, 3.9 mmol), 2-(3,5-dichlorophenylamino)acetic acid (704 mg, 3.2 mmol) and DIEA (0.69 mL, 3.9 mmol) at 0° C. The reaction mixture was stirred at rt overnight and then diluted with EtOAc and water (1:1, 20 mL). The aqueous layer was re-extracted with the EtOAc, dried over Na₂SO₄ and concentrated in vacuo to give the crude compound that purified by column chromatography (silica gel, gradient MeOH in CH₂Cl₂) to afford (1.0 g, 73%) of the titled intermediate. $^1$H NMR (400 MHz, CDCl₃): δ 6.67 (s, 1H), 6.49-6.46 (d, 2H), 5.18 (bs, 1H), 3.81-3.80 (d, 2H), 3.70-3.57 (m, 2H), 3.04-2.98 (m, 1H), 2.83 and 2.81 (m, 3H), 2.54-2.48 (m, 1H), 1.92-1.71 (m, 3H), 1.70-1.69 (m, 2H), 1.50 (s, 9H). LC-MS: m/z [M+23]=437.

Synthesis of 2-(3,5-dichlorophenylamino)-1-((S)-3-(methylamino) piperidin-1-yl) ethanone To a solution of (tert-butyl (S)-1-(2-(3,5-dichlorophenylamino) acetyl) piperidin-3-ylmethylcarbamate (1.0 g, 2.4 mmol) in 1,4-dioxane (5 mL) was added 4 N HCl in dioxane (20 mL) and the reaction mixture was stirred for 1 h. The reaction mixture was concentrated in vacuo and the resultant residue was triturated with ether and filtered. The solid was dried under vacuo to afford the titled intermediate (730 mg, 98%), which was used in the next step without purification. $^1$H NMR (400 MHz, DMSO): δ 6.72-6.71 (d, 2H), 6.60 (s, 1H), 4.09-4.04 (m, 1H), 3.90-3.92 (d, 3H), 3.68-3.62 (m, 1H), 3.10-2.90 (m, 2H), 2.71-2.66 (m, 1H), 2.40-2.35 (m, 1H), 2.25 (s, 3H), 1.98 (s, 1H), 1.88-1.80 (m, 2H), 1.41-1.31 (m, 1H). LC-MS: m/z [M+1]=316.

Synthesis of 1-{(S)-3-[(2-amino-pyrimidin-4-yl)-methyl-amino]-piperidin-1-yl}-2-(3,5-dichloro-phenylamino)-ethanone A stirred solution of 2-(3,5-dichlorophenylamino)-1-((S)-3-(methylamino)piperidin-1-yl)ethanone (0.3 mg, 1.0 mmol), 4-chloropyrimidin-2-amine (60 mg, 0.5 mmol), DIEA (0.17 mL, 1.9 mmol) in DMF (2 mL) was heated to 100° C. for 2 days. The reaction mixture was diluted with EtOAc and washed with water. The organic layer was dried over Na$_2$SO$_4$ and evaporated in vacuo to give the crude compound which was purified (silica gel, gradient MeOH in CH$_2$Cl$_2$) to give the (20 mg, 5.2%). $^1$H NMR (400 MHz, CD$_3$OD): δ 7.77-7.73 (m, 1H), 6.64-6.56 (m, 3H), 6.10-6.00 (m, 1H), 4.58-4.45 (m, 2H), 4.10-3.84 (m, 3H), 2.96 (s, 3H), 2.58-2.81 (m, 1H), 2.03-1.90 (m, 4H), 1.60-1.48 (m, 1H). LC-MS: m/z [M+1]=409 & [M+23]=431.

Example 67

Synthesis of 4-(N—((S)-1-(2-(3,5-dichlorophenylamino) acetyl) piperidin-3-yl)-N-methylamino)-6-aminopyrimidine-5-carboxamide

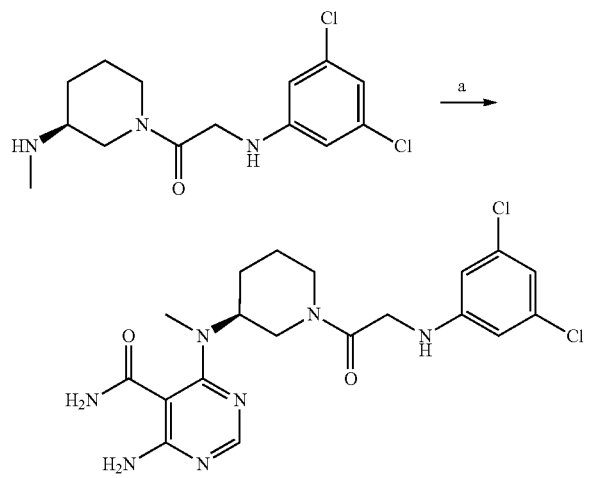

Reagents and conditions: a) 4-amino-6-chloropyrimidine-5-carboxamide, DIEA, DMF, 110° C., 2 days.

Synthesis of 4-(N—((S)-1-(2-(3,5-dichlorophenylamino) acetyl) piperidin-3-yl)-N-methylamino)-6-aminopyrimidine-5-carboxamide A similar procedure was used as described for the synthesis of 1-{(S)-3-[(2-amino-pyrimidin-4-yl)-methyl-amino]-piperidin-1-yl}-2-(3,5-dichloro-phenylamino)-ethanone to obtained crude compound which was purified by Prep-TLC (10% MeOH in CHCl$_3$) to afford (8 mg, 2%) of the title compound. $^1$H NMR (400 MHz, CD$_3$OD): δ 8.02 (s, 1H), 6.62-6.60 (m, 3H), 4.58-4.49 (m, 2H), 4.35-4.25 (m, 1H), 4.11-3.97 (m, 2H), 3.49-3.48 (d, 1H), 2.99 (s, 3H), 2.66-2.60 (m, 1H), 2.03-1.93 (m, 1H), 1.93-1.84 (m, 1H), 1.37-1.17 (m, 2H). LC-MS: m/z [M+23]=474.

Example 68

Synthesis of 4-(N—((S)-1-(2-(3,5-dichlorophenylamino)acetyl)piperidin-3-yl)-N-methylamino)-6-aminopyrimidine-5-carbonitrile

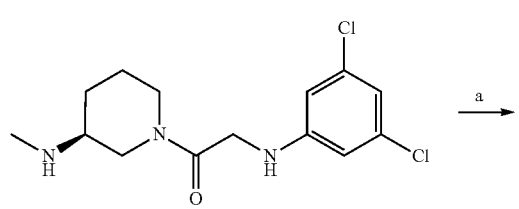

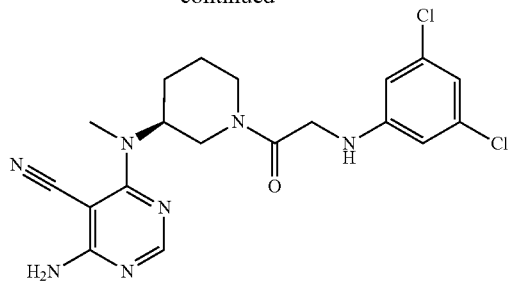

Reagents and conditions: a) 4-amino-6-chloropyrimidine-5-carbonitrile, DIEA, DMF, 100° C., 2 days.

Synthesis of 4-(N—((S)-1-(2-(3,5-dichlorophenylamino)acetyl)piperidin-3-yl)-N-methylamino)-6-aminopyrimidine-5-carbonitrile A similar procedure was used as described for the synthesis of 1-{(S)-3-[(2-amino-pyrimidin-4-yl)-methyl-amino]-piperidin-1-yl}-2-(3,5-dichloro-phenylamino)-ethanone to obtained crude compound which was purified by Prep-TLC (10% MeOH in CHCl$_3$) to afford (6 mg, 4%) of the title compound. $^1$H NMR (400 MHz, CD$_3$OD): δ 8.06 & 8.00 (s, 1H), 7.01-6.59 (m, 3H), 4.60-4.56 (m, 2H), 4.25-4.21 (d, 1H), 4.00-3.94 (m, 2H), 3.51-3.46 (m, 1H), 3.27 (s, 3H), 2.66-2.60 (m, 1H), 2.01-1.85 (m, 4H). LC-MS: m/z [M+1]=434 and [M+23]=456.

Example 69

Synthesis of 2-(3,5-dichloro-phenylamino)-1-{(S)-3-[methyl-(9H-purin-6-yl)-amino]-piperidin-1-yl}-ethanone

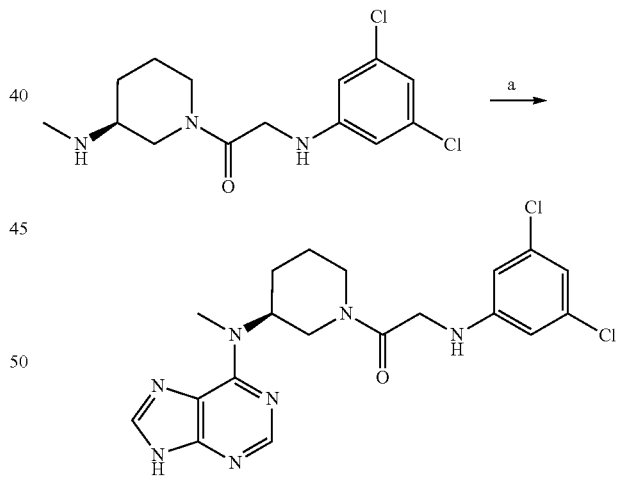

Reagents and conditions: a) 6-Chloro-9H-purine, DIEA, DMF, 90° C., 48 h.

Synthesis of 2-(3,5-dichloro-phenylamino)-1-{(S)-3-[methyl-(9H-purin-6-yl)-amino]-piperidin-1-yl}-ethanone A similar procedure was used as described for the synthesis of 1-{(S)-3-[(2-amino-pyrimidin-4-yl)-methyl-amino]-piperidin-1-yl}-2-(3,5-dichloro-phenylamino)-ethanone to obtained crude compound which was purified (silica gel, gradient MeOH in CH$_2$Cl$_2$) to give the (28 mg, 10%). $^1$H NMR (400 MHz, CD$_3$OD): δ 8.25 (s, 1H), 7.93 (s, 1H), 6.60-6.57 (m, 3H), 4.62-4.55 (d, 1H), 4.50-4.41 (d, 1H), 4.19-3.90 (m, 3H), 3.46 (s, 3H), 2.69-2.63 (m, 1H), 2.13-2.01 (m, 2H), 2.01-1.89 (m, 2H), 1.80-1.17 (m, 1H). LC-MS: m/z [M+1]=434 & [M+23]=456. HPLC (254 nm): 91.94%. HPLC (210 nm): 91.62%.

Example 70

Synthesis of 1-{(S)-3-[(6-Amino-pyrimidin-4-yl)-methyl-amino]-piperidin-1-yl}-2-(3,5-dichloro-phenylamino)-ethanone

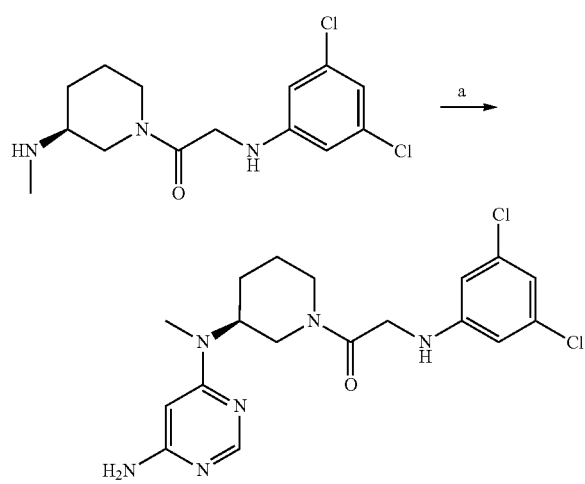

Reagents and conditions: a) 6-chloropyrimidin-4-amine, DIEA, DMF, 150° C., microwave, 150 watt, 1 h

Synthesis of 1-{(S)-3-[(6-amino-pyrimidin-4-yl)-methyl-amino]-piperidin-1-yl}-2-(3,5-dichloro-phenylamino)-ethanone A similar procedure was used as described for the synthesis of 1-{(S)-3-[(2-amino-pyrimidin-4-yl)-methyl-amino]-piperidin-1-yl}-2-(3,5-dichloro-phenylamino)-ethanone to obtained crude compound which was purified by reverse phase column chromatography (C-18, 500 mm×30 mm×10 gradient ACN: H₂O: TFA) to give the (25 mg, 19%). ¹H NMR (400 MHz, CD₃OD): δ 8.07 & 8.04 (s, 1H), 6.50 (s, 1H) & 6.49 (s, 2H), 5.78 and 5.77 (s, 1H), 4.25-4.19 (m, 2H), 3.91-3.90 (m, 2H), 3.08-3.05 (m, 2H), 2.94 (s, 3H), 2.87-2.84 (m, 1H), 1.92-1.80 (m, 4H). LC-MS: m/z [M+1]=409 & [M+23]=431.

Example 71

Synthesis of (S)-4-((1-(2-(3,5-dichlorophenylamino)acetyl)piperidin-3-yl)(methyl)amino)-5,6-dihydropyrido[2,3-d]pyrimidin-7(8H)-one

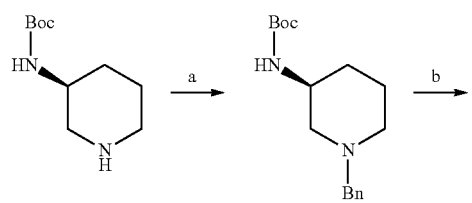

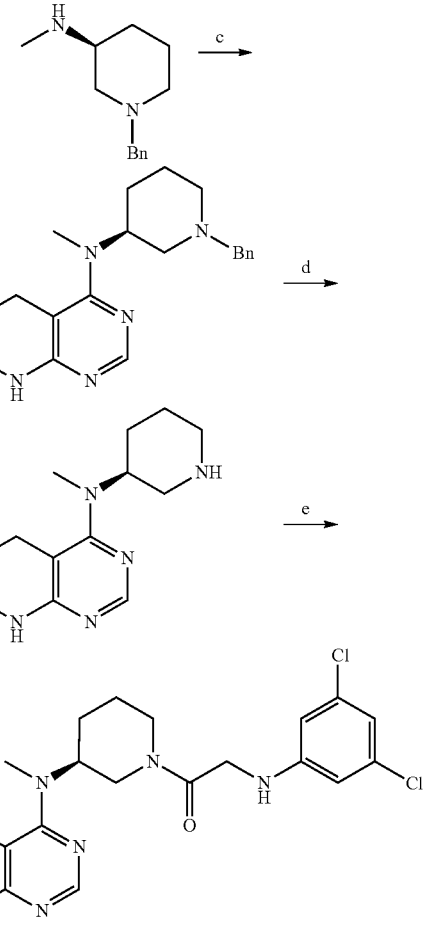

Reagents and conditions: a) PhCHO, Na(OAc)₃BH, CH₂Cl₂, 4 A mol. sieves, rt, 15 h; b) LAH, THF, reflux, 2 h; c) 4-chloro-5,6-dihydropyrido[2,3-d]pyrimidin-7(8H)-one, DMF, DIEA, 100° C., d) 10% Pd/C, HCOONH₄, MeOH, reflux, e) 2-(3,5-dichloro-phenylamino)acetic acid, EDCI, HOBt, DMF, rt.

Synthesis of (S)-tert-butyl 1-benzylpiperidin-3-ylcarbamate

To a solution of (S)-tert-butyl piperidin-3-ylcarbamate (2.0 g, 10.0 mmol) and benzaldehyde (1.3 g, 12.0 mmol) in CH₂Cl₂ under nitrogen was added NaBH(OAc)₃ (4.2 g, 20.0 mmol) and the reaction was stirred for overnight. The mixture was diluted with CH₂Cl₂ (50 mL) and ice cooled water (20 mL). The CH₂Cl₂ layer was separated and the aqueous layer was extracted with CH₂Cl₂ (3×20 mL). The combined CH₂Cl₂ layer was dried over Na₂SO₄ and evaporated in vacuo to give the crude product which was purified by column chromatography (silica gel, gradient EtOAc in hexanes) to afford (1.0 g, 34%) of the titled intermediate. LC-MS: m/z [M+1]=291.

Synthesis of (S)-1-benzyl-N-methylpiperidin-3-amine

To a stirred solution of LAH (12.9 g, 12.9 mmol) in THF (50 mL) under nitrogen was added a solution of tert-butyl (S)-tert-butyl 1-benzylpiperidin-3-ylcarbamate (2.5 g, 8.60 mmol) in THF (15 mL) dropwise at 0° C. After addition was complete the reaction mixture was heated to reflux for 2 h. The reaction mixture was cooled to 0° C. and was quenched with aq. NaOH solution. Then the reaction mixture was filtered through celite, filtrate was concentrated in vacuo to afford the title compound, which was used directly for next step. (1.5 g, 86%). ¹H NMR (400 MHz, DMSO): δ 7.30-7.22 (m, 5H), 3.43 (s, 2H), 2.79-2.77 (m, 1H), 2.60-2.54 (m, 1H), 2.40-2.35 (m, 1H), 2.21 (s, 3H), 1.93-1.88 (m, 2H), 1.78-1.55 (m, 3H), 1.42-1.35 (m, 1H), 0.98-0.94 (m, 1H). LC-MS: m/z [M+1]=205.

Synthesis of (S)-4-((1-benzylpiperidin-3-yl)(methyl) amino)-5,6-dihydropyrido[2,3-d]pyrimidin-7(8H)-one A solution of (S)-1-benzyl-N-methylpiperidin-3-amine (0.2 g, 1.0 mmol), 4-chloro-5,6-dihydropyrido[2,3-d]pyrimidin-7(8H)-one (90 mg, 0.5 mmol) and DIEA (253 mg, 2.0 mmol) was heated in a sealed tube at 100° C. overnight. The reaction mixture was cooled to rt and poured into ice water. The reaction mixture was extracted with EtOAc (3×15 mL) and the combined EtOAc layer was dried over Na₂SO₄, evaporated in vacuo to give the crude product which was purified by column chromatography (silica gel, gradient EtOAc in hexanes) to afford (100 mg, 29%) of the titled intermediate. ¹H NMR (400 MHz, CD₃OD): δ 7.97 (s, 1H), 7.33-7.26 (m, 5H), 4.60-4.57 (m, 1H), 4.01-3.99 (m, 2H), 3.53 (s, 2H), 2.92 (s, 3H), 2.58-2.53 (m, 3H), 2.25-2.21 (m, 1H), 2.07-2.01 (m, 2H), 1.76-1.69 (m, 2H), 1.43-1.33 (m, 3H). LC-MS: m/z [M+1]=451 & [M+23]: 473.

Synthesis of (S)-4-(methyl(piperidin-3-yl)amino)-5,6-dihydropyrido[2,3-d]pyrimidin-7(8H)-one To a solution of (S)-4((1-benzylpiperidin-3-yl)(methyl) amino)-5,6-dihydropyrido[2,3-d]pyrimidin-7(8H)-one (100 mg, 0.3 mmol) in MeOH (3 mL) was added 10% Pd/C (100 mg) and ammonium formate (179 mg, 2.8 mmol) and the reaction mixture was heated for overnight. The reaction mixture was filtered and concentrated in vacuo to afford (72 mg, 96%) of the titled intermediate which was used without purification. LC-MS: m/z [M+1]=262.

Synthesis of (S)-4-((1-(2-(3,5-dichlorophenylamino) acetyl)piperidin-3-yl)(methyl)amino)-5,6-dihydropyrido[2,3-d]pyrimidin-7(8H)-one To a solution of (S)-4-(methyl(piperidin-3-yl)amino)-5,6-dihydropyrido[2,3-d]pyrimidin-7(8H)-one (150 mg, 0.6 mmol) in DMF (5 mL) was added EDCI (164 mg, 0.85 mmol), HOBt (114 mg, 0.85 mmol), 2-(3,5-dichlorophenylamino)acetic acid (126 mg, 0.57 mmol) and DIEA (147 mg, 1.14 mmol) at 0° C. The reaction mixture was stirred at rt overnight, diluted with EtOAc and washed with water. The aqueous layer was extracted with the EtOAc, the combined organic layer was dried over Na₂SO₄ and evaporated in vacuo to give the crude compound that was purified by column chromatography (silica gel, gradient MeOH in CH₂Cl₂) to afford (25 g, 9%) of the titled compound. ¹H NMR (400 MHz, CD₃OD): δ 8.29 (s, 1H), 6.61-6.60 (d, 1H), 6.59-6.58 (m, 2H), 4.28-4.01 (m, 1H), 3.99-3.95 (m, 2H), 3.68-3.66 (t, J=4.4 Hz, 1H), 3.57-3.54 (t, J=4.4 Hz, 1H), 3.34 (s, 3H), 3.08-2.97 (m, 3H), 2.60-2.53 (m, 2H), 2.03-2.00 (m, 2H), 1.43-1.26 (m, 3H). LC-MS: m/z [M+1]=463.

Example 72

Synthesis of (S)—N-(6-((1-(2-(3,5-dichlorophenylamino) acetyl) piperidin-3-yl)(methyl)amino)pyrimidin-4-yl) acetamide

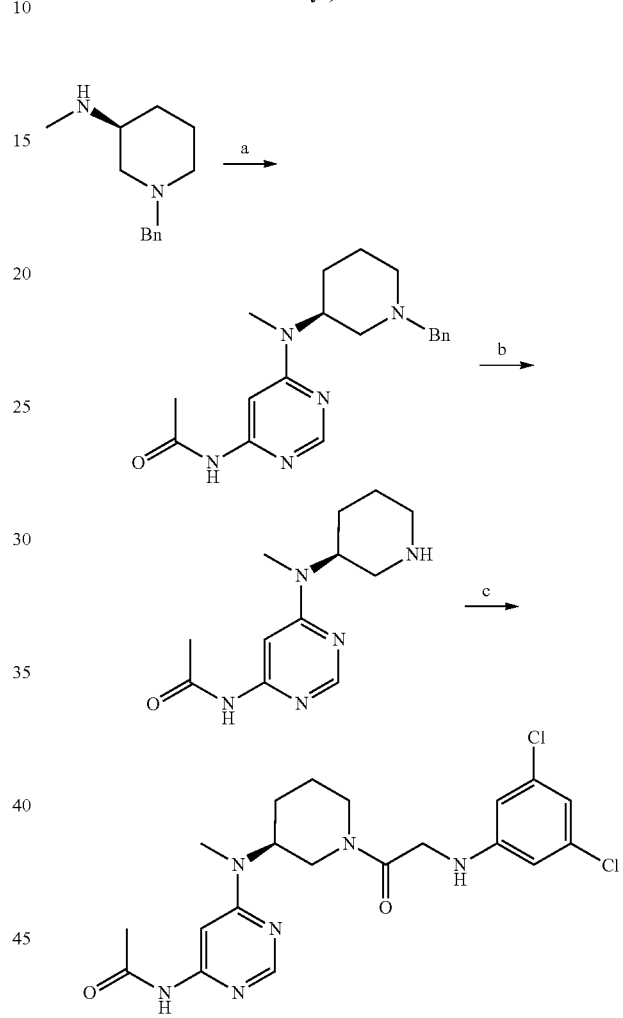

Reagents and conditions: a) N-(6-chloropyrimidin-4-yl)acetamide, DMF, DIEA, 100° C., b) 10% Pd/C, Ammonium formate, MeOH, reflux; c) 2-(3,5-dichlorophenylamino)acetic acid, EDCI, HOBt, DMF, rt.

Synthesis of (S)—N-(6-((1-(2-(3,5-dichlorophenylamino) acetyl) piperidin-3-yl)(methyl)amino)pyrimidin-4-yl) acetamide A similar procedure was used as described for the synthesis of (S)-4-((1-(2-(3,5-dichlorophenylamino)acetyl)piperidin-3-yl)(methyl)amino)-5,6-dihydropyrido[2,3-d]pyrimidin-7 (8H)-one to obtain crude material that was purified by column chromatography (silica gel, gradient MeOH in CH₂Cl₂) to afford (100 mg, 36%) of the titled compound. ¹H NMR (400 MHz, DMSO): δ 10.72 and 10.68 (s, 1H), 8.31 (s, 1H), 7.09 (s, 1H), 6.74 (s, 1H), 6.70 (s, 1H), 6.61 (s, 1H), 4.36 (bs, 1H), 3.98-3.84 (m, 5H), 3.20-3.17 (m, 1H), 2.95 and 2.92 (s, 3H), 2.10 and 2.08 (s, 3H), 1.91-1.75 (m, 3H), 1.55-1.40 (m, 2H). LC-MS: m/z [M+1]=451. & [M+23]=473.

Example 73

Synthesis of N-(6-{1-[2-(3,5-Dichloro-phenylamino)-acetyl]-piperidin-3-ylamino}-pyrimidin-4-yl)-acetamide

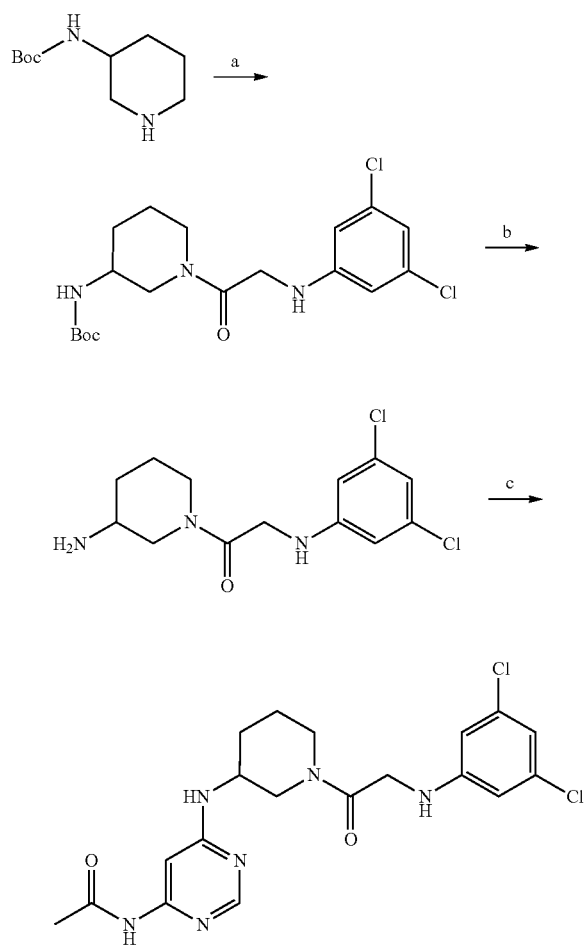

Reagents and conditions: a) 2-(3,5-dichlorophenylamino)acetic acid, EDCI, HOBt, DIEA, DMF, rt, 15 h; b) 4N HCl in 1,4-dioxane, rt, 1 h; c) N-(6-chloropyrimidin-4-yl)acetamide, Et₃N, n-BuOH, 150° C., overnight.

Synthesis of N-(6-{1-[2-(3,5-dichloro-phenylamino)-acetyl]-piperidin-3-ylamino}-pyrimidin-4-yl)-acetamide A similar procedure was used as described for the synthesis of 1-((S)-3-(2-aminopyrimidin-4-ylamino) piperidin-1-yl)-2-(3,5-dichlorophenylamino) ethanone to obtain crude material that was purified by reverse phase column chromatography (C-18, 500 mm×30 mm×10μ, gradient ACN: H₂O: TFA) to give the title compound (35 mg, 12%). ¹H NMR (400 MHz, DMSO): δ 10.73 (bs, 1H), 8.32 (s, 1H), 8.29 (s, 1H), 8.00 (s, 1H), 6.73 (s, 1H), 6.64-6.59 (d, 2H), 3.98-3.81 (m, 3H), 3.66-3.53 (m, 2H), 3.08-2.92 (m, 3H), 2.07 (s, 3H), 1.92-1.74 (m, 2H), 1.55-1.41 (m, 2H), 1.21-1.14 (m, 1H). LC-MS: m/z [M+1]=437 & [M+Na]=459.

Example 74

Synthesis of 4-(1-(2-(3,5-dichlorophenylamino) acetyl)piperidin-3-ylamino)-5,6-dihydropyrido[2,3-d]pyrimidin-7(8H)-one

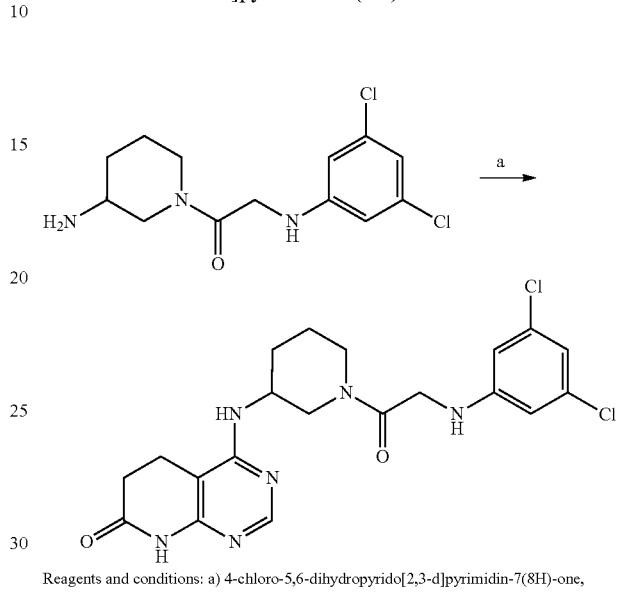

Reagents and conditions: a) 4-chloro-5,6-dihydropyrido[2,3-d]pyrimidin-7(8H)-one, Et₃ n-BuOH, 150° C., overnight.

Synthesis of 4-(1-(2-(3,5-dichlorophenylamino) acetyl)piperidin-3-ylamino)-5,6-dihydropyrido[2,3-d]pyrimidin-7(8H)-one A similar procedure was used as described for the synthesis of 1-((S)-3-(2-aminopyrimidin-4-ylamino) piperidin-1-yl)-2-(3,5-dichlorophenylamino) ethanone to obtain crude material that was purified by reverse phase column chromatography (C-18, 500 mm×30 mm×10μ (gradient ACN: H2O: TFA) to give the (39 mg, 15%). ¹H NMR (400 MHz, DMSO): δ 10.50 (s, 1H), 8.31 (s, 1H), 8.26 (s, 1H), 8.05-8.03 (d, 1H), 6.63-6.58 (m, 1H), 6.53-6.52 (d, 2H), 3.59-3.70 (m, 2H), 2.92-2.83 (m, 2H), 2.72-2.69 (m, 2H), 2.47-2.43 (m, 2H), 1.80-1.61 (m, 2H), 1.54-1.50 (m, 2H), 1.31-1.11 (m, 4H). LC-MS: m/z [M+1]=449.

Example 75

Synthesis of 4-(1-(2-(3,5-dichlorophenylamino) acetyl) piperidin-3-ylamino)-6-aminopyrimidine-5-carboxamide

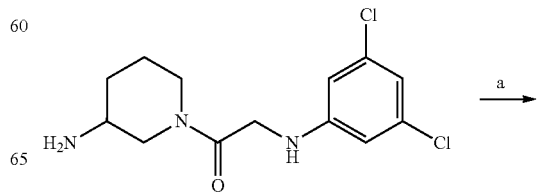

Synthesis of 4-(1-(2-(3,5-dichlorophenylamino)acetyl) piperidin-3-ylamino)-6-aminopyrimidine-5-carboxamide

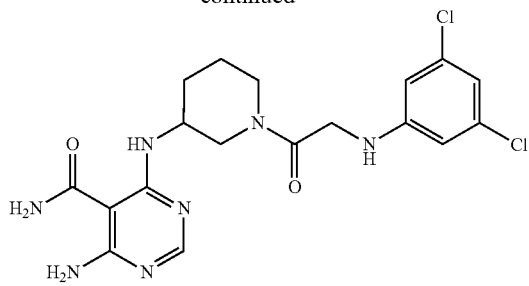

Reagents and conditions: a) 4-amino-6-chloropyrimidine-5-carboxamide, Et₃N, n-BuOH, 150° C., overnight.

A similar procedure was used as described for the synthesis of 1-((S)-3-(2-aminopyrimidin-4-ylamino) piperidin-1-yl)-2-(3,5-dichlorophenylamino) ethanone to obtain crude material that was purified by reverse phase column chromatography (C-18, 500 mm×30 mm×10µ (gradient ACN: H2O: TFA) to give (6 mg, 4%) the titled compound. ¹H NMR (400 MHz, DMSO): δ 8.18 and 8.16 (s, 1H), 7.70 and 6.68 (bs, 2H), 7.36 (bs, 2H), 6.74-6.62 (m, 3H), 3.95-3.91 (m, 3H), 3.20-2.99 (m, 2H), 1.90-2.00 (m, 2H), 1.40-1.64 (m, 3H), 1.23-1.15 (m, 3H). LC-MS: m/z [M+1]=438 & [M+23]=460.

Synthesis of 2-(3,5-dichlorophenylamino)-1-(3-(6-(methylamino)pyrimidin-4-ylamino) piperidin-1-yl) ethanone

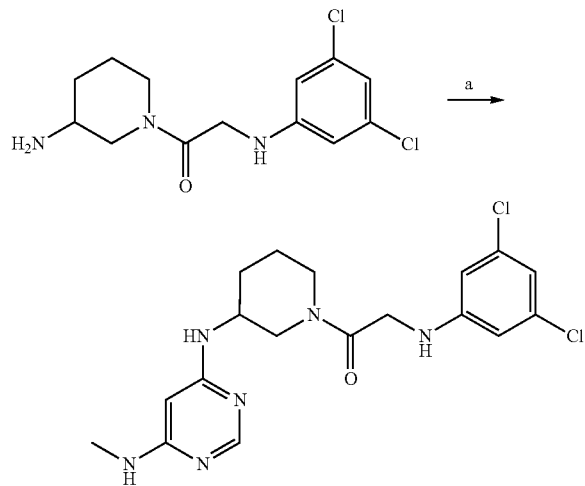

Reagents and conditions: a) chloro-N-methylpyrimidin-4-amine, Et₃N, n-BuOH, 150° C., overnight.

A similar procedure was used as described for the synthesis of 1-((S)-3-(2-aminopyrimidin-4-ylamino) piperidin-1-yl)-2-(3,5-dichlorophenylamino) ethanone to obtain crude material that was purified by reverse phase column chromatography (C-18, 500 mm×30 mm×10µ. (gradient ACN: H2O: TFA) to give the titled compound (160 mg, 28%). ¹H NMR (400 MHz, DMSO): δ 7.93 (s, 1H), 6.64-6.63 (m, J=1.6 Hz, 1H), 6.47-6.47 (d, J=1.6 Hz, 2H), 5.71 (s, 1H), 3.87-3.67 (m, 4H), 1.91-1.89 (m, 1H), 1.73-1.53 (m, 3H), 1.37-1.16 (m, 3H). LC-MS: m/z [M+1]=409.

Example 76

Synthesis of 2-(3,5-dichlorophenylamino)-1-(3-(6-amino-5-fluoropyrimidin-4-ylamino)piperidin-1-yl) ethanone

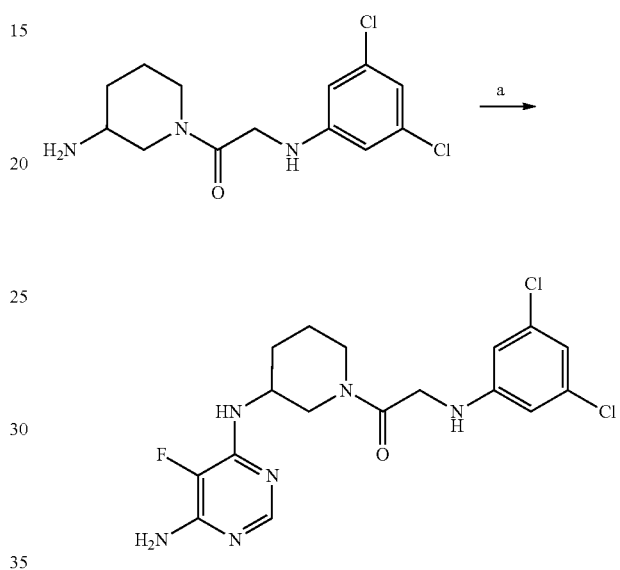

Reagents and conditions: a) chloro-5-fluoropyrimidin-4-amine, Et₃N, n-BuOH, 150° C., overnight.

A similar procedure was used as described for the synthesis of 14(S)-3-(2-aminopyrimidin-4-ylamino) piperidin-1-yl)-2-(3,5-dichlorophenylamino) ethanone to obtain crude material that was purified by reverse phase purified by reverse phase column chromatography (C-18, 500 mm×30 mm×10µ (gradient ACN: H₂O: TFA) to yield the titled compound (50 mg, 36%). ¹H NMR (400 MHz, DMSO): δ 7.96 (s, 1H), 7.42 (s, 1H), 7.10 (bs, 2H), 6.73-6.18 (m, 3H), 4.34-4.31 (m, 1H), 4.00-3.89 (m, 3H), 3.10-2.95 (m, 2H), 2.69-2.67 (m, 2H), 1.92-1.90 (m, 1H), 1.63-1.55 (m, 2H), 1.22-1.15 (m, 1H). LC-MS: m/z [M+1]=413.

Example 77

Synthesis of 1-(3-(1H-pyrazolo[3,4-d]pyrimidin-4-ylamino) azepan-1-yl)-2-(3, 5-dichlorophenylamino) ethanone

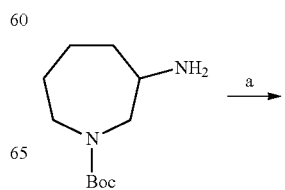

139

-continued

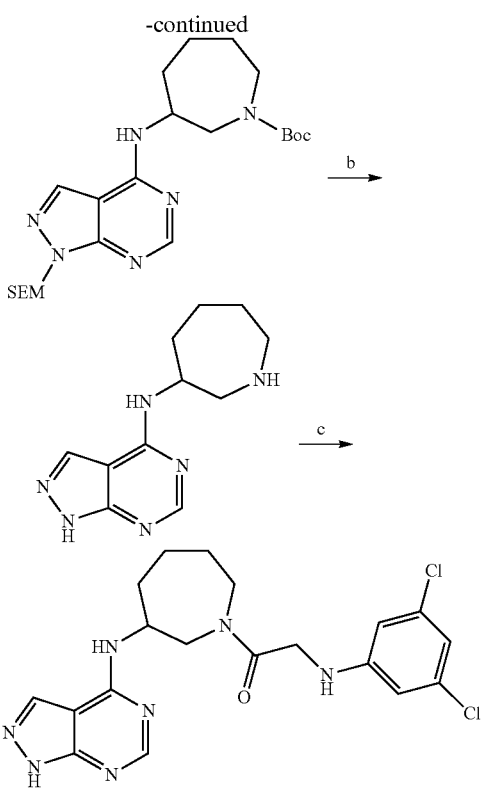

Reagents and condition: a) 4-chloro-1-((2-(trimethlsilyl)ethoxy)methyl)-1H-pyrazolo[3,4-d]pyrimidine, DIEA, DMF, 100° C., 4 h; b) EtOH•HCl, 60° C., 4 h, then MeOH, resin, 2 h; c) 2-(3,5-dichlorophenylamino)acetic acid, EDCI, HOBt, DIEA, DMF, rt, 15 h.

Synthesis of tert-butyl 3-(1-((2-(trimethylsilyl)ethoxy)methyl)-1H-pyrazolo[3, 4-d]pyrimidin-4-ylamino) azepane-1-carboxylate A solution of tert-butyl 3-aminoazepane-1-carboxylate (2.0 g, 9.3 mmol), 4-chloro-1-((2-(trimethylsilyl)ethoxy)methyl)-1H-pyrazolo[3, 4-d]pyrimidine (2.9 g, 10.3 mmol) and DIEA (2.4 mL, 14.0 mmol) in DMF (20 mL) was heated to 100° C. for 4 h. The reaction was cooled to rt and ice cooled water (100 mL) was added. The reaction mixture was extracted with EtOAc (3×50 mL). The combined EtOAc layer was dried over $Na_2SO_4$ and evaporated in vacua to give the crude product that was purified by column chromatography (silica gel, gradient 0-10% EtOAc hexane) to afford the titled intermediate (3.7 g, 85.8%). LCMS: m/z [M+1]=463.

Synthesis of N-(azepan-3-yl)-1H-pyrazolo[3,4-d]pyrimidin-4-amine

Tert-butyl 3-(1-((2-(trimethylsilyl)ethoxy)methyl)-1H-pyrazolo[3,4-d]pyrimidin-4-ylamino)azepane-1-carboxylate (0.5 g, 1.1 mmol) was dissolved conc HCl:EtOH (1:3, 10 mL) and the solution was heated to 60° C. for 4 h. The reaction mixture was concentrated in vacuo and the residue obtained was dissolved in MeOH and treated with solid supported carbonate resin to neutralize the solution. The reaction mixture stirred for 2 h and filtered off slurry, washed solid with MeOH (2×20 mL). The filtrate was concentrated in vacua to afford the titled intermediate (200 mg, 80%), which was used in the next step without further purification. LCMS: m/z [M+1]=233.

140

Synthesis of 1-(3-(1H-pyrazolo[3,4-d]pyrimidin-4-ylamino) azepan-1-yl)-2-(3, 5-dichlorophenylamino) ethanone To a solution of N-(azepan-3-yl)-1H-pyrazolo[3,4-d]pyrimidin-4-amine (200 mg, 0.862 mmol) in DMF (4 mL) was added EDCI (196 mg, 1.03 mmol), HOBt (139 mg, 1.03 mmol), 2-(3,5-dichlorophenylamino)acetic acid (189 mg, 0.862 mmol) and DIEA (0.22 mL, 1.29 mmol) at 0° C. The reaction mixture was stirred overnight at rt, diluted with EtOAc (100 mL) and washed with water (50 mL). The organic layer was dried over $Na_2SO_4$ and evaporated in vacuo to give the crude compound that purified by column chromatography (silica gel, gradient MeOH in $CH_2Cl_2$) to afford the titled compound (150 mg, 40%). $^1$H NMR (DMSO-$d_6$, 400 MHz): δ 13.49-13.36 (m, 1H), 8.27-7.96 (m, 2H), 6.74 (s, 1H), 6.67 (s, 1H), 6.62 (s, 1H), 6.34 (s, 1H), 4.50-4.30 (m, 1H), 4.08-3.8 (m, 5H), 3.36 (m, 2H), 1.8-2.2 (m, 2H), 1.8-1.35 (m, 2H), 1.3-1.1 (m, 2H), LCMS: m/z [M+1]=434 & [M+23]=456.

Example 78

Synthesis of 1-(3-(1H-pyrazolo[3,4-d]pyrimidin-4-yl-N-methylamino)azepan-1-yl)-2-(3,5-dichlorophenylamino)ethanone

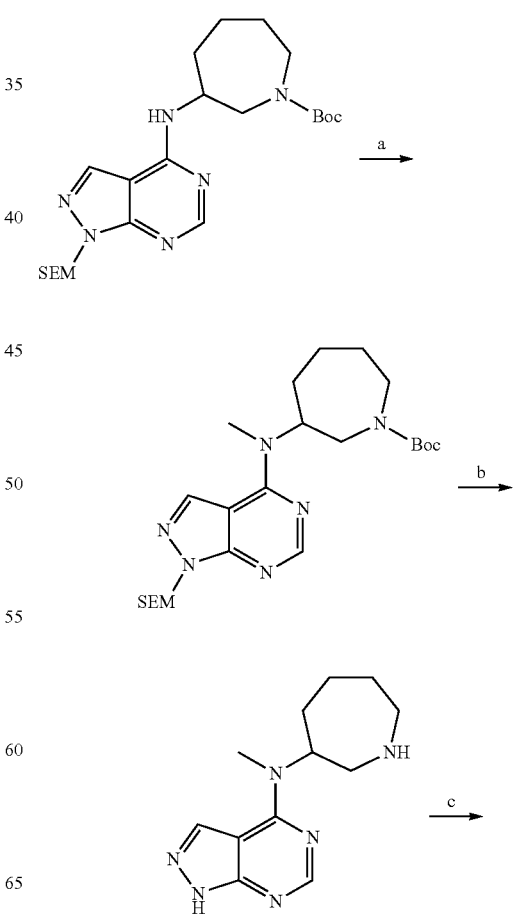

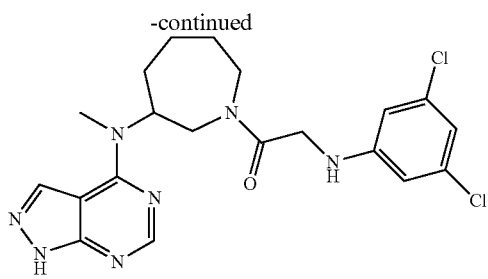

Reagents and conditions: a) NaH, DMF, MeI, rt, 1 h; b) EtOH·HCl, 60° C., 4 h, then MeOH, resin, 2 h; c) 2-(3,5-dichlorophenylamino)acetic acid, EDCI, HOBt, DIEA, DMF, rt, 15 h.

Synthesis of tert-butyl 3-(N-(1-((2-(trimethylsilyl)ethoxy)methyl)-1H-pyrazolo[3,4-d]pyrimidin-4-yl)-N-methylamine)azepane-1-carboxylate To a solution of tert-butyl 3-(1-((2-(trimethylsilyl)ethoxy)methyl)-1H-pyrazolo[3,4-d]pyrimidin-4-ylamino) azepane-1-carboxylate (500 mg, 1.0 mmol) in DMF (10 mL) was added NaH (38 mg, 1.6 mmol) at 0° C. The reaction mixture was stirred for 30 min, followed by the addition of MeI (0.1 mL, 1.6 mmol). The reaction mixture was stirred at rt for 50 min and diluted with ice-cooled water (50 mL). The reaction mixture was extracted with EtOAc (3×50 mL). The combined EtOAc layer was dried over Na$_2$SO$_4$ and evaporated in vacuo to give the crude product that was purified by column chromatography (silica gel, gradient EtOAc in CHCl$_3$) to afford the titled intermediate (465 mg, 90%). LC-MS: m/z [M+1]=477.

Synthesis of N-(azepan-3-yl)-N-methyl-1H-pyrazolo[3,4-d]pyrimidin-4-amine

Tert-butyl 3-(N-(1-((2-(trimethylsilyl)ethoxy)methyl)-1H-pyrazolo[3,4-d]pyrimidin-4-yl)-N-methylamino)azepane-1-carboxylate (730 mg, 1.53 mmol), was dissolved in conc. HCl: ethanol (6 mL: 15 mL) and the solution was heated at 90° C. overnight. The reaction mixture was concentrated in vacuo and the residue was taken in MeOH (2×20 mL) concentrated in vacuo to afford (350 mg, 92%) the titled intermediate, which was used in the next step without purification. LC-MS: m/z [M+1]=247.

Synthesis of 1-(3-(1H-pyrazolo[3,4-d]pyrimidin-4-yl-N-methylamino) azepan-1-yl)-2-(3,5-dichlorophenylamino)ethanone To a solution of N-(azepan-3-yl)-N-methyl-1H-pyrazolo[3,4-d]pyrimidin-4-amine (350 mg, 1.4 mmol) in DMF (7 mL) was added EDCI (409 mg, 2.1 mmol), HOBt (287 mg, 2.1 mmol), 2-(3,5-dichlorophenylamino)acetic acid (312 mg, 1.4 mmol) and DIEA (0.5 mL, 2.8 mmol) at 0° C. The reaction mixture was stirred at rt overnight and diluted with water and ethyl acetate (3:1, 400 mL). The organic layer was dried over Na$_2$SO$_4$ and evaporated in vacuo to give the crude compound that purified by column chromatography (silica gel, gradient MeOH in CH$_2$Cl$_2$) to afford (325 mg 51%) the titled compound. $^1$H NMR (DMSO-d$_6$, 400 MHz): δ 13.50 and 13.44 (2s, 1H), 8.25-8.19 (m, 2H), 6.74 (s, 1H), 6.68 (s, 1H), 6.62 (s, 1H), 6.36 (bs, 1H), 4.21-3.71 (m, 5H), 3.42-3.01 (m, 2H), 3.31 (s, 3H), 1.93-1.65 (m, 6H). LC-MS: m/z [M+1]=448.

Example 79

Synthesis of 2-(3,5-dichlorophenylamino)-1-(3-(7H-pyrrolo[2,3-d]pyrimidin-4-ylamino) azepan-1-yl) ethanone

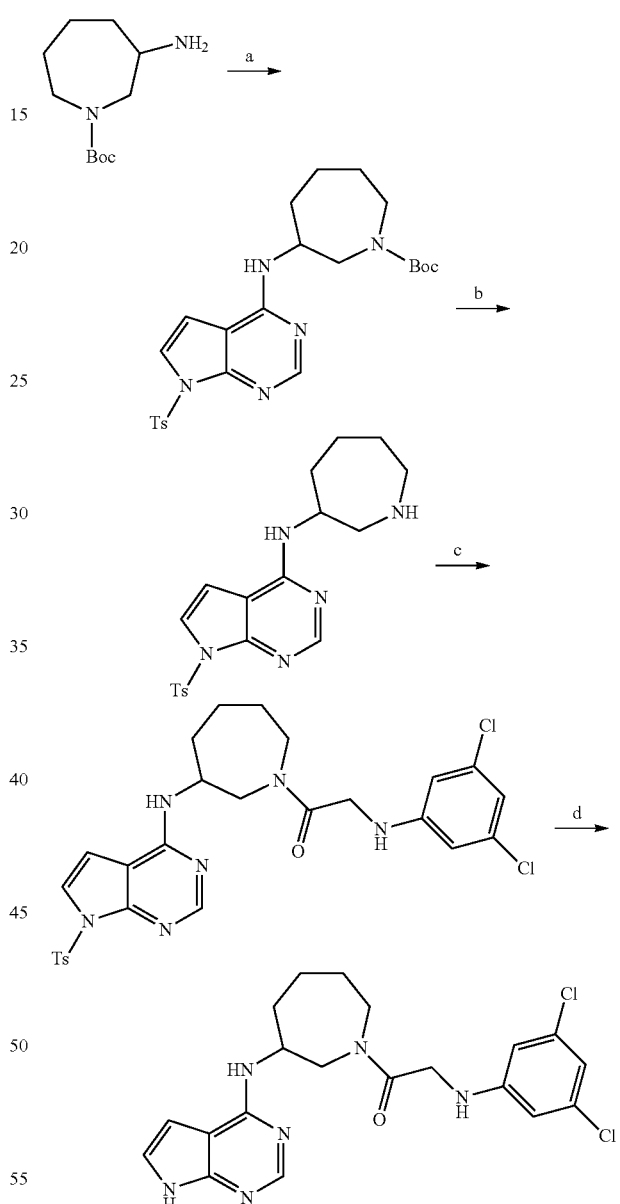

Reagents and condition: a) 4-chloro-7-tosyl-7H-pyrrolo[2,3-d]pyrimidine, DIEA, DMF 100° C., 4 h; b) 4N HCl in 1,4-dioxane, rt, 2 h; c) 2-(3,5-dichlorophenylamino) acetic acid, EDCI, HOBt, DIEA, DMF, rt, 15 h; d) K$_2$CO$_3$, MeOH:H$_2$O, 60° C., 1 h.

Synthesis of tert-butyl 3-(7-tosyl-7H-pyrrolo[2,3-d]pyrimidin-4-ylamino)azepane-1-carboxylate To a solution of tert-butyl 3-aminoazepane-1-carboxylate (1 g, 4.7 mmol), 4-chloro-7-tosyl-7H-pyrrolo[2,3-d]pyrimidine (3.1 g, 5.1 mmol) in DMF (10 mL) was added DIEA (1.2 mL, 7.0 mmol) and the reaction mixture was heated to 90° C. for 3 h. The reaction was cooled to rt and diluted with ice cooled water (50 mL). The mixture was extracted with EtOAc (3×100 mL), the EtOAc layers were combined, dried over Na$_2$SO$_4$ and evaporated in vacuo to give the crude product that was purified by column chromatography (silica gel, gradient 0-20% EtOAc hexane) to afford the titled intermediate (1.4 g, 89%). LC-MS: m/z [M+1]=486.

Synthesis of N-(azepan-3-yl)-7-tosyl-7H-pyrrolo[2,3-d]pyrimidin-4-amine

To a solution of test-butyl 3-(7-tosyl-7H-pyrrolo[2,3-d]pyrimidin-4-ylamino)azepane-1-carboxylate (1.4 g, 2.9 mmol) in 1,4-dioxane (15 mL) was added 6 N HCl (2 mL) and the reaction mixture was stirred for 2 h. The reaction mixture was concentrated in vacuo and the resultant residue was dissolved in EtOAc, washed with 10% NaHCO$_3$. The EtOAc layer was separated, dried over Na$_2$SO$_4$ and concentrated in vacuo to afford the titled intermediate (910 mg, 88%), which was used in the next step without purification. LC-MS: m/z [M+1]=386.

Synthesis of 2-(3,5-dichlorophenylamino)-1-(3-(7-tosyl-7H-pyrrolo[2,3-d]pyrimidin-4-ylamino)azepan-1-yl)ethanone To a solution of N-(azepan-3-yl)-7-tosyl-7H-pyrrolo[2,3-d]pyrimidin-4-amine (0.6 g, 1.6 mmol), in DMF (10 mL) was added EDCI (335 mg, 1.9 mmol), HOBt (250 mg, 1.9 mmol), 2-(3,5-dichlorophenylamino)acetic acid (342 mg, 1.6 mmol) and DIEA (301 mg, 2.3 mmol) at 0° C. The reaction mixture was stirred at rt overnight, diluted with EtOAc (100 mL) and washed with water (50 mL). The organic layer was dried over Na$_2$SO$_4$ and evaporated in vacuo to give the crude compound that purified by column chromatography (silica gel, gradient MeOH in CH$_2$Cl$_2$) to afford the titled compound (800 mg, 87%). LC-MS: m/z [M+1]=587.

Synthesis of 2-(3,5-dichlorophenylamino)-1-(3-(7H-pyrrolo[2,3-d]pyrimidin-4-ylamino)azepan-1-yl)ethanone To a solution of 2-(3,5-dichlorophenylamino)-1-(3-(7-tosyl-7H-pyrrolo[2,3-d]pyrimidin-4-ylamino)azepan-1-yl)ethanone (800 mg, 1.36 mmol) in MeOH:H$_2$O (4:1, 5 mL) was added K$_2$CO$_3$ (656 mg, 4.77 mmol) and the reaction mixture was heated at 80° C. for 4 h. The reaction mixture was concentrated in vacuo to give a residue which was triturated with 10% MeOH in EtOAc (20 mL), filtrated, the filtrate was evaporated in vacuo to give the crude compound that was subjected to column chromatography (silica gel, gradient MeOH in CH$_2$Cl$_2$) to afford (393 mg, 66%) the titled compound. $^1$H NMR (DMSO-d6, 400 MHz): 11.53 and 11.47 (2s, 1H), 8.15 and 8.07 (2s, 1H), 7.30 and 7.17 (2d, J=4 Hz, 1H), 7.07 (2t, d=2.4 Hz, 1H), 6.74 (s, 1H), 6.68 (m, 1H), 6.62 (s, 1H), 6.38-6.33 (m, 1H), 4.54-4.46 (m, 1H), 4.36-4.27 (m, 1H), 4.12-3.96 (m, 2H), 3.94-3.86 (m, 1H), 3.52-3.42 (m, 1H), 3.24-3.12 (m, 1H), 2.02-1.78 (m, 3H), 1.74-1.52 (m, 3H). LC-MS: m/z [M+1]=433.

Example 80

Synthesis of 2-(3,5-dichloro-phenylamino)-1-{3-[methyl-(7H-pyrrolo[2,3-d]pyrimidin-4-yl)-amino]-azepan-1-yl}-ethanone

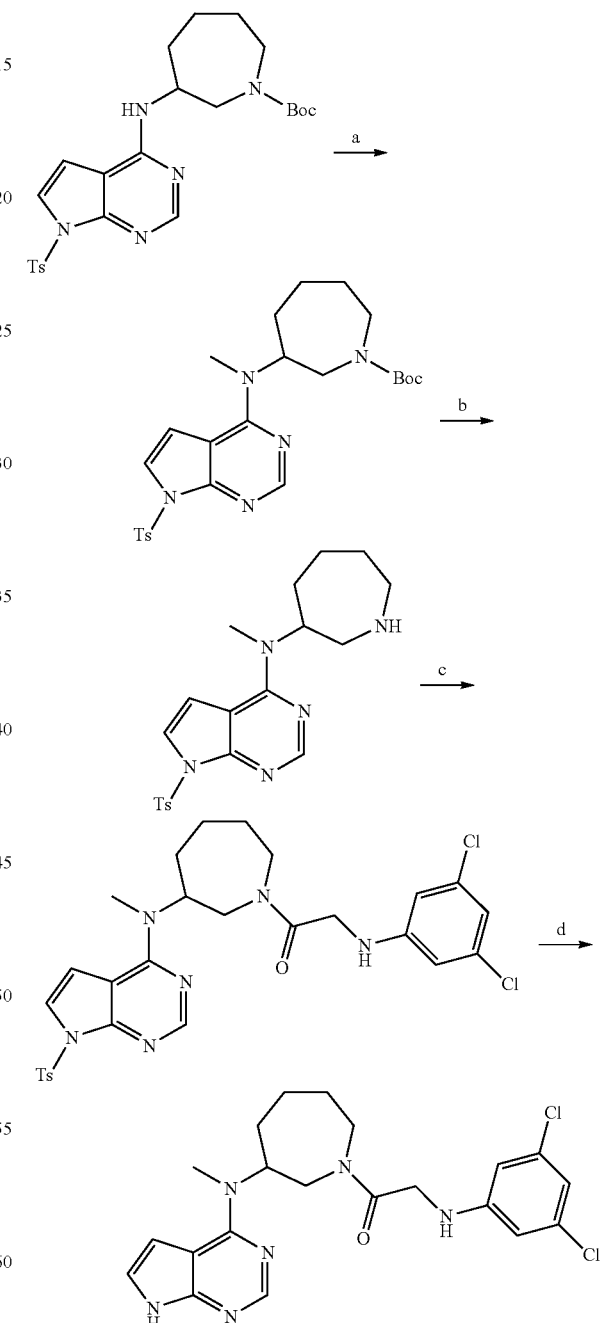

Reagents and condition: a) NaH, MeI, DMF, rt, 1 h; b) 1,4-Dioxane•HCl, rt, 2 h; c) 2-(3,5-dichlorophenylamino)acetic acid, EDCI, HOBt, DIEA, DMF, rt, 15 h; d) K$_2$CO$_3$, MeOH:H$_2$O, 60° C., 1 h.

Synthesis of tert-butyl 3-(N-methyl-N-(7-tosyl-7H-pyrrolo[2,3-d]pyrimidin-4-yl)amino)azepane-1-carboxylate To a solution of tert-butyl 3-(7-tosyl-7H-pyrrolo[2,3-d]pyrimidin-4-ylamino)azepane-1-carboxylate (400 mg, 0.82 mmol) in DMF was added NaH (29 mg, 1.23 mmol) in portions at 0° C. The reaction mixture was stirred at rt for 30 min followed by the addition of MeI (0.08 mL, 1.23 mmol). The reaction mixture was stirred at rt for 1 h, and then quenched upon addition of ice-cooled water (50 mL). The reaction mixture was then extracted with EtOAc (3×50 mL), the combined organic layer was dried over $Na_2SO_4$ and evaporated in vacuo to give the crude product that was purified by column chromatography (silica gel, gradient 0-20% EtOAc hexane) to afford the titled intermediate (320 mg, 77%). LC-MS: m/z [M+1]=500.

Synthesis of N-(azepan-3-yl)-N-methyl-7-tosyl-7H-pyrrolo[2,3-d]pyrimidin-4-amine To a solution of tert-butyl-3-(N-methyl-N-(7-tosyl-7H-pyrrolo[2,3-d]pyrimidin-4-yl)amino) azepane-1-carboxylate (320 mg, 0.641 mmol) was added 4 N HCl in 1,4-dioxane (5 mL) and the reaction mixture was stirred for 1 h. The reaction mixture was concentrated in vacuo to give a residue which was dissolved in EtOAc and washed with sat. 10% $NaHCO_3$. The EtOAc layer was separated, dried over $Na_2SO_4$ and concentrated in vacuo to afford the titled intermediate (200 mg, 79%), which was used in the next step without purification. LC-MS: m/z [M+1]=400.2.

Synthesis of 2-(3,5-Dichloro-phenylamino)-1-(3-{methyl-[7-(tosyl)-7H-pyrrolo[2,3-d]pyrimidin-4-yl]-amino}-azepan-1-yl)-ethanone To a solution of N-(azepan-3-yl)-N-methyl-7-tosyl-7H-pyrrolo[2,3-d]pyrimidin-4-amine (200 mg, 0.5 mmol), in DMF (4 mL) was added EDCI (144 mg, 0.75 mmol), HOBt (101 mg, 0.75 mmol), 2-(3,5-dichlorophenylamino)acetic acid (109 mg, 0.5 mmol) and DIEA (129 mg, 1.0 mmol) at 0° C. The reaction mixture was stirred at rt overnight and diluted with EtOAc (100 mL) and washed with water (50 mL). The aqueous layer was extracted with the EtOAc (50 mL), the combined organic layer was dried over $Na_2SO_4$ and evaporated in vacuo to give a residue that was subjected to flash column chromatography using 0-4% MeOH in $CH_2Cl_2$ as an eluent to give (235 mg, 77%) of the titled compound. LC-MS: m/z [M+1]=601.

Synthesis of 2-(3,5-dichloro-phenylamino)-1-{3-[methyl-(7H-pyrrolo[2,3-d]pyrimidin-4-yl)-amino]-azepan-1-yl}-ethanone To a solution of 2-(3,5-dichloro-phenylamino)-1-(3-{methyl-[7-(tosyl)-7H-pyrrolo[2,3-d]pyrimidin-4-yl]-amino}-azepan-1-yl)-ethanone (235 mg. 0.39 mmol) in $MeOH:H_2O$ (4:1, 5 mL) was added $K_2CO_3$ (216 mg, 1.56 mmol) and heated at 90° C. for 1 h. The reaction mixture was cooled to rt and concentrated in vacuo to give a residue which was subjected to column chromatography (silica gel, gradient MeOH in $CH_2Cl_2$) to afford the titled compound (80.6 mg, 46%). $^1H$ NMR (DMSO-$d_6$, 400 MHz): 11.60 (1s, 1H), 8.08 (s, 1H), 7.12 (d, J=4 Hz, 1H), 6.72 (s, 1H), 6.69 (s, 1H), 6.63 (s, 1H), 6.62 (s, 1H), 6.38-6.35 (m, 1H), 4.98-4.85 (m, 1H), 4.29 and 1.28 (2d, J=2.1 Hz, 1H), 4.10-3.88 (m, 3H), 3.65-2.32 (m, 2H), 3.17 (s, 3H), 1.93-1.76 (m, 6H). LC-MS: m/z [M+1]=447.

Example 81

Synthesis of 1-(6-(1H-pyrazolo[3,4-d]pyrimidin-4-ylamino)-2-aza-bicyclo[2.2.1]heptan-2-yl)-2-(3,5-dichlorophenylamino)ethanone

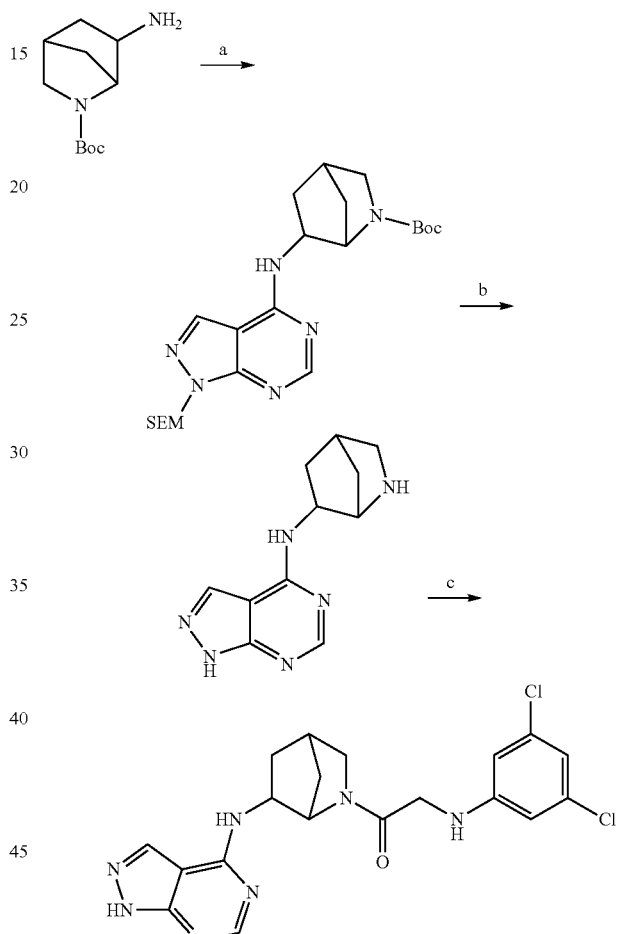

Reagents and condition: a) 4-chloro-1-((2-(trimethylsilyl)ethoxy)methyl)-1H-pyrazolo[3,4-d]pyrimidine, DIEA, DMF, 100° C., 4 h; b) EtOH•HCl, 60° C.; c) 2-(3,5-dichlorophenylamino)acetic acid, EDCI, HOBt, DIEA, DMF, rt, 15 h.

Synthesis of 1-(6-(1H-pyrazolo[3,4-d]pyrimidin-4-ylamino)-2-aza-bicyclo[2.2.1]heptan-2-yl)-2-(3,5-dichlorophenylamino)ethanone A similar procedure was used as described for the synthesis of 1-(3-(1H-pyrazolo[3,4-d]pyrimidin-4-ylamino) azepan-1-yl)-2-(3,5-dichlorophenylamino) ethanone to give the crude material that purified by column chromatography (silica gel, gradient MeOH in $CH_2Cl_2$) to afford (30 mg, 16%) the titled compound. $^1H$ NMR (DMSO-$d_6$, 400 MHz): 13.38 and 13.30 (2s, 1H), 8.32 and 8.20 (2s, 1H), 8.08 and 8.00 (2s, 1H), 6.72 (s, 1H), 6.60 (s, 1H), 6.48 (s, 1H), 6.14-6.12 (m, 2H), 4.78-4.48 (m, 1H), 3.82-3.68 (m, 1H), 3.60-3.42 (m, 1H), 3.12-

2.80 (m, 1H), 2.72-2.58 (m, 1H), 2.32-2.10 (m, 2H), 2.08-1.92 (m, 2H), 1.80-1.52 (m, 2H). LC-MS: m/z [M+1]=433.

Example 82

2-(3,5-dichlorophenylamino)-1-(6-(methyl(1H-pyrazolo[3,4-d]pyrimidin-4-yl)amino)-2-azabicyclo[2.2.1]heptan-2-yl) ethanone

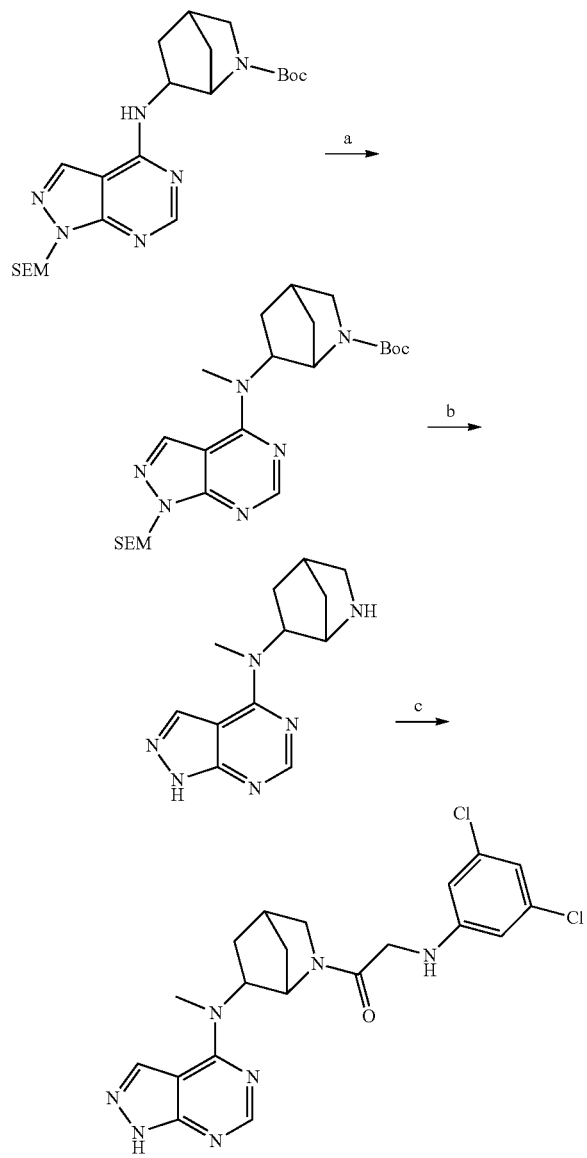

Reagents and condition: a) NaH, DMF, MeI, rt, 1 h; b) EtOH·HCl, 60° C., 4 h, then MeOH, resin, 2 h; c) 2-(3,5-dichlorophenylamino)acetic acid, EDCI, HOBt, DIEA, DMF, rt, 15 h.

2-(3,5-dichlorophenylamino)-1-(6-(methyl(1H-pyrazolo[3,4-d]pyrimidin-4-yl)amino)-2-azabicyclo[2.2.1]heptan-2-yl) ethanone A similar procedure was used as described for the synthesis of 1-(3-(1H-pyrazolo[3,4-d]pyrimidin-4-yl-N-methylamino)azepan-1-yl)-2-(3,5-dichlorophenylamino)ethanone to give the crude compound that purified by column chromatography (silica gel, gradient MeOH in CH$_2$Cl$_2$) to afford (25 mg, 32%) of the titled compound. $^1$H NMR (CD$_3$OD, 400 MHz): 8.17 (1s, 1H), 8.15 and 7.97 (2s, 1H), 6.63 and 6.61 (2s, 1H), 6.57 and 6.50 (2s, 2H), 4.22-4.16 (m, 1H), 3.88-3.71 (m, 2H), 3.68-3.54 (m, 1H), 2.94-2.89 (m, 2H), 2.67 and 2.61 (2s, 3H), 2.15-2.03 (m, 2H), 1.98-1.76 (m, 3H). LC-MS: m/z [M+1]=446.

Example 83

Synthesis of 2-(3,5-dichlorophenylamino)-1-(6-(7H-pyrrolo[2,3-d]pyrimidin-4-ylamino)-2-aza-bicyclo[2.2.1]heptan-2-yl)ethanone

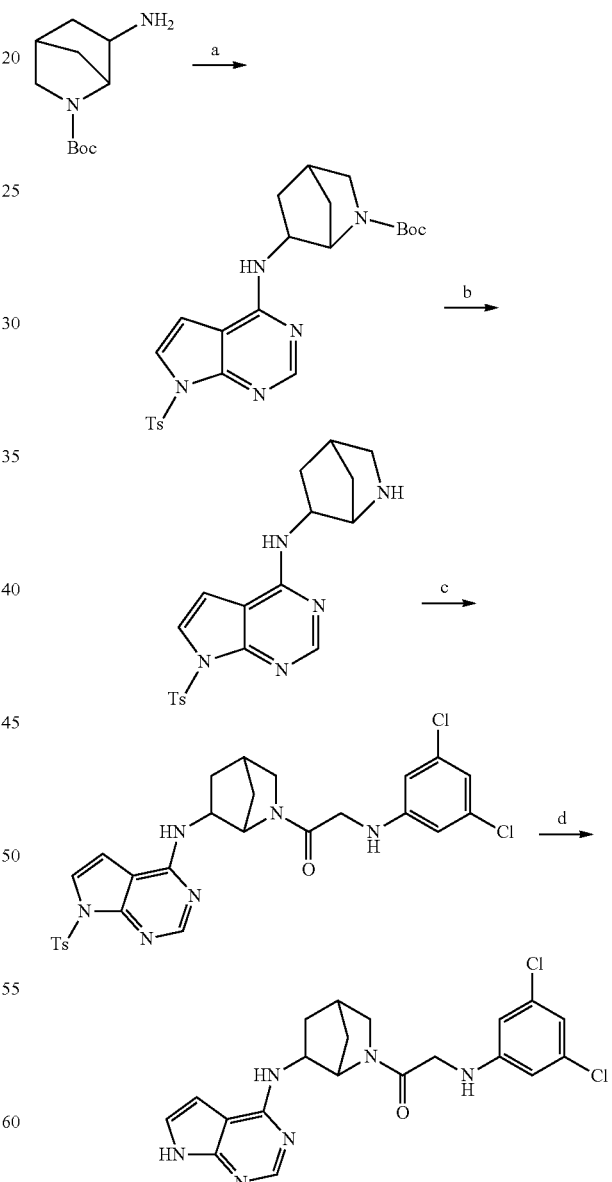

Reagents and condition: a) 4-chloro-7-tosyl-7H-pyrrolo[2,3-d]pyrimidine, DIEA, DMF, 100° C., 4 h; b) Dioxane·HCl, rt, 2 h; c) 2-(3,5-dichlorophenylamino)acetic acid, EDCI, HOBt, DIEA, DMF, rt, 15 h; d) K$_2$CO$_3$, MeOH:H$_2$O, 60° C., 1 h.

Synthesis of 2-(3,5-dichlorophenylamino)-1-(6-(7H-pyrrolo[2,3-d]pyrimidin-4-ylamino)-2-aza-bicyclo[2.2.1]heptan-2-yl)ethanone A similar procedure was used as describe for the synthesis of 2-(3,5-dichlorophenylamino)-1-(3-(7H-pyrrolo[2,3-d]pyrimidin-4-ylamino) azepan-1-yl) ethanone to afford a residue which was subjected to column chromatography (silica gel, gradient MeOH in CH$_2$Cl$_2$) to afford (45 mg, 51%) the titled compound. $^1$H NMR (DMSO-d$_6$, 400 MHz): 11.50 and 11.40 (2s, 1H), 8.18-8.10 (2s, 1H), 7.18 (bs, 1H), 7.08 (bs, 1H), 6.66 and 6.60 (2s, 2H), 6.58 and 6.50 (2s, 1H), 6.21 and 6.08 (2s, 2H), 4.62 and 4.46 (2s, 1H), 3.88-3.48 (m, 2H), 3.10-2.90 (m, 2H), 2.72-2.50 (m, 1H), 2.24-2.10 (m, 2H), 1.82-1.62 (m, 3H). LC-MS: m/z [M+1]=431.

Example 84

Synthesis of 2-(3,5-dichlorophenylamino)-1-(6-(N-methyl-N-(7H-pyrrolo[2,3-d]pyrimidin-4-yl)amino)-2-aza-bicyclo[2.2.1]heptan-2-yl)ethanone

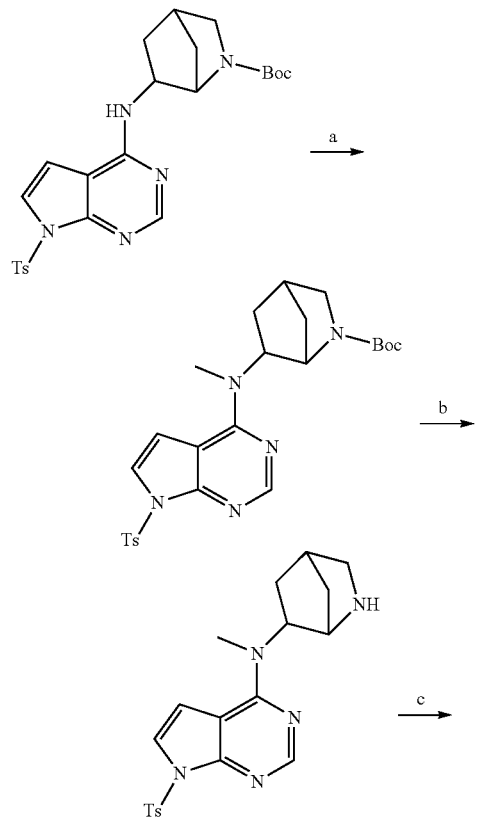

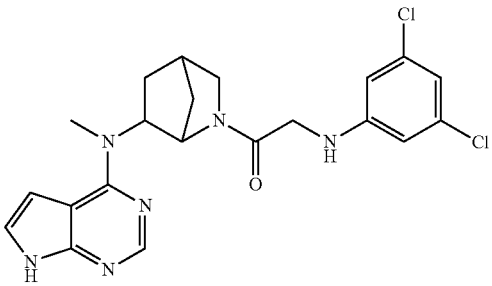

Reagents and condition: a) NaH, MeI, DMF, rt, 1 h; b) Dioxane·HCl, rt, 2 h; c) 2-(3,5-dichlorophenylamino)acetic acid, EDCI, HOBt, DIEA, DMF, rt, 15 h; d) K$_2$CO$_3$, MeOH·H$_2$O, 60° C., 1 h.

2-(3,5-dichlorophenylamino)-1-(6-(N-methyl-N-(7H-pyrrolo[2,3-d]pyrimidin-4-yl)amino)-2-aza-bicyclo[2.2.1]heptan-2-yl)ethanone A similar procedure was used as describe for the synthesis of 2-(3,5-dichloro-phenylamino)-1-{3-[methyl-(7H-pyrrolo[2,3-d]pyrimidin-4-yl)-amino]-azepan-1-yl}-ethanone to afford a residue which was subjected to column chromatography (silica gel, gradient MeOH in CH$_2$Cl$_2$) to afford (60 mg 45%) of the titled compound. $^1$H NMR (DMSO-d$_6$, 400 MHz): 11.70 and 11.62 (2s, 1H), 8.20 and 8.12 (2s, 1H), 7.18-7.06 (m, 1H), 6.64 and 6.58 (2s, 2H), 6.62 and 6.54 (2s, 1H), 6.36-6.24 (m, 2H), 4.68 and 4.62 (2s, 1H), 3.96-3.72 (m, 1H), 3.60-3.52 (m, 2H), 3.18 and 3.16 (2s, 3H), 3.14-3.12 (m, 1H), 2.70-2.64 (m, 1H), 2.14-1.98 (m, 2H), 1.92-1.52 (m, 3H), LC-MS: m/z [M+1]=445.

Example 85

Synthesis of 1-((S)-3-(1H-pyrazolo[3,4-d]pyrimidin-4-ylamino)pyrrolidin-1-yl)-2-(3,5-dichlorophenylamino)ethanone

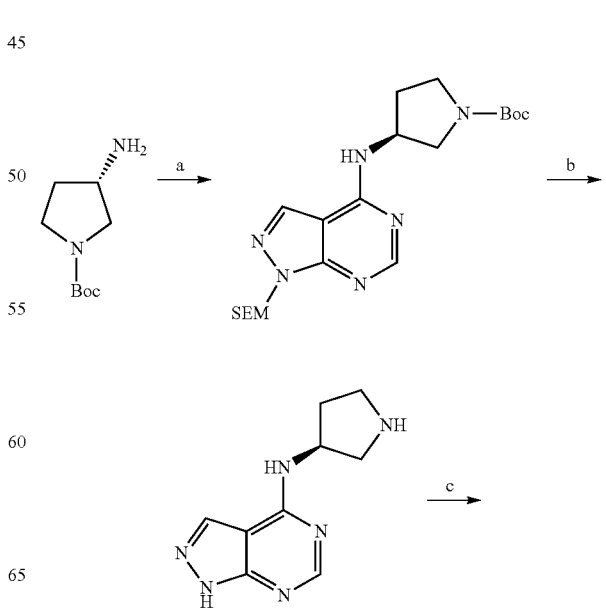

151

-continued

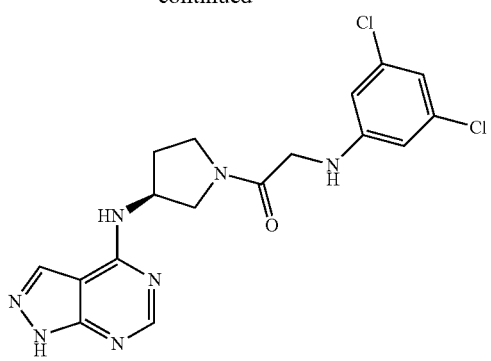

Reagents and condition: a) 4-chloro-1-((2-(trimethylsilyl)ethoxy)methyl)-1H-pyrazolo[3d]pyrimidine, DIEA, DMF, 100° C., 4 h; b) EtOH•HCl, 60° C., 4 h, then MeOH, resin, 2 h; c) 2-(3,5-dichlorophenylamino)acetic acid, EDCI, HOBt, DIEA, DMF, rt, 15 h.

Synthesis of 1-((S)-3-(1H-pyrazolo[3,4-d]pyrimidin-4-ylamino)pyrrolidin-1-yl)-2-(3,5-dichlorophenylamino)ethanone A similar procedure was used as described for the synthesis of 1-(3-(1H-pyrazolo[3,4-d]pyrimidin-4-ylamino) azepan-1-yl)-2-(3,5-dichlorophenylamino) ethanone to give the crude material residue that was purified by column chromatography (silica gel, gradient MeOH in CH$_2$Cl$_2$) to afford (45 mg, 15%) the titled compound. $^1$H NMR (DMSO-d$_6$, 400 MHz): 13.45 (s, 1H), 8.40 (2d, J=6.4 Hz, 1H), 8.22-8.07 (m, 2H), 6.61 (s, 1H), 6.57 (bs, 1H), 6.52 (s, 2H), 4.55-4.39 (m, 1H), 3.94-3.84 (m, 1H), 3.82-3.60 (m, 3H), 2.36-2.22 (m, 1H), 2.20-2.08 (m, 1H), 2.06-1.96 (m, 1H), 1.94-1.84 (m, 1H). LC-MS: m/z [M+1]=406.

Example 86

Synthesis of 2-(3,5-Dichloro-phenylamino)-1-{(S)-3-[methyl-(1H-pyrazolo[3,4-d]pyrimidin-4-yl)-amino]-pyrrolidin-1-yl}-ethanone

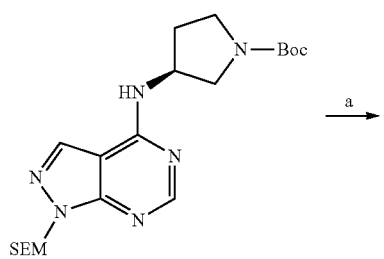

152

-continued

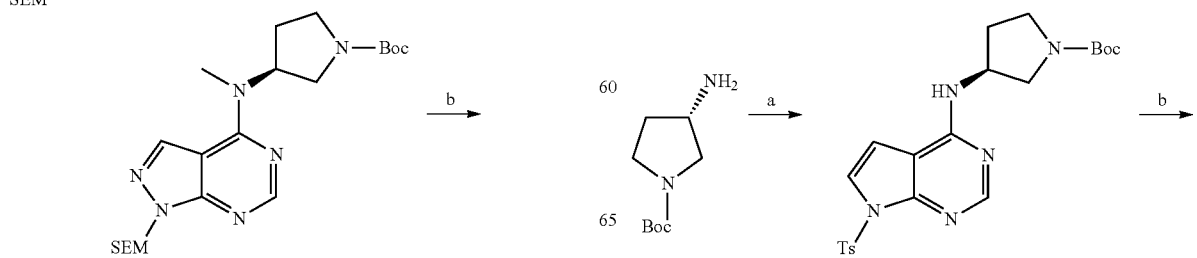

Reagents and condition: a) NaH, DMF, MeI, rt, 1 h; b) EtOH•HCl, 60° C., 4 h, then MeOH, resin, 2 h; c) 2-(3,5-dichlorophenylamino)acetic acid, EDCI, HOBt, DIEA, DMF, rt, 15 h.

2-(3,5-Dichloro-phenylamino)-1-{(S)-3-[methyl-(1H-pyrazolo[3,4-d]pyrimidin-4-yl)-amino]-pyrrolidin-1-yl}-ethanone A similar procedure was used as described for the synthesis of 1-(3-(1H-pyrazolo[3,4-d]pyrimidin-4-yl-N-methylamino) azepan-1-yl)-2-(3,5-dichlorophenylamino)ethanone to give the crude compound that purified by column chromatography (silica gel, gradient MeOH in CH$_2$Cl$_2$) to afford (190 mg, 66%) the titled compound. $^1$H NMR (DMSO-d$_6$, 400 MHz): 13.45 (s, 1H), 8.31 (s, 1H), 8.15 (s, 1H), 6.78 (s, 1H), 6.75 (s, 1H), 6.62 (s, 1H), 6.30 (bs, 1H), 4.26-3.52 (m, 3H), 3.32 (s, 3H), 3.12-2.90 (m, 2H), 2.86-2.80 (m, 2H), 2.34-2.10 (m, 1H), 2.45-2.31 (m, 1H). LC-MS: m/z [M+1]=420.

Example 87

Synthesis of 2-(3,5-dichlorophenylamino)-1-((S)-3-(7H-pyrrolo[2,3-d]pyrimidin-4-ylamino)pyrrolidin-1-yl)ethanone

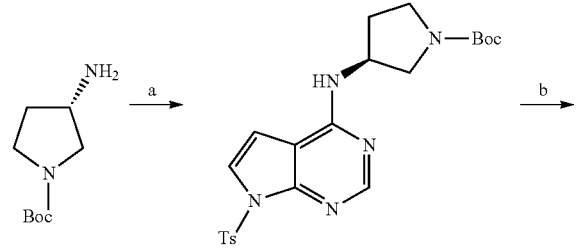

-continued

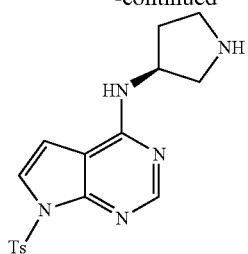

Hz, 1H), 3.38-3.36 (m, 2H), 2.24-2.12 (m, 1H), 1.98-1.90 (m, 1H). LC-MS: m/z [M+1]=405.

Example 88

Synthesis of 2-(3,5-Dichloro-phenylamino)-1-{(S)-3-[methyl-(7H-pyrrolo[2,3-d]pyrimidin-4-yl)-amino]-pyrrolidin-1-yl}-ethanone

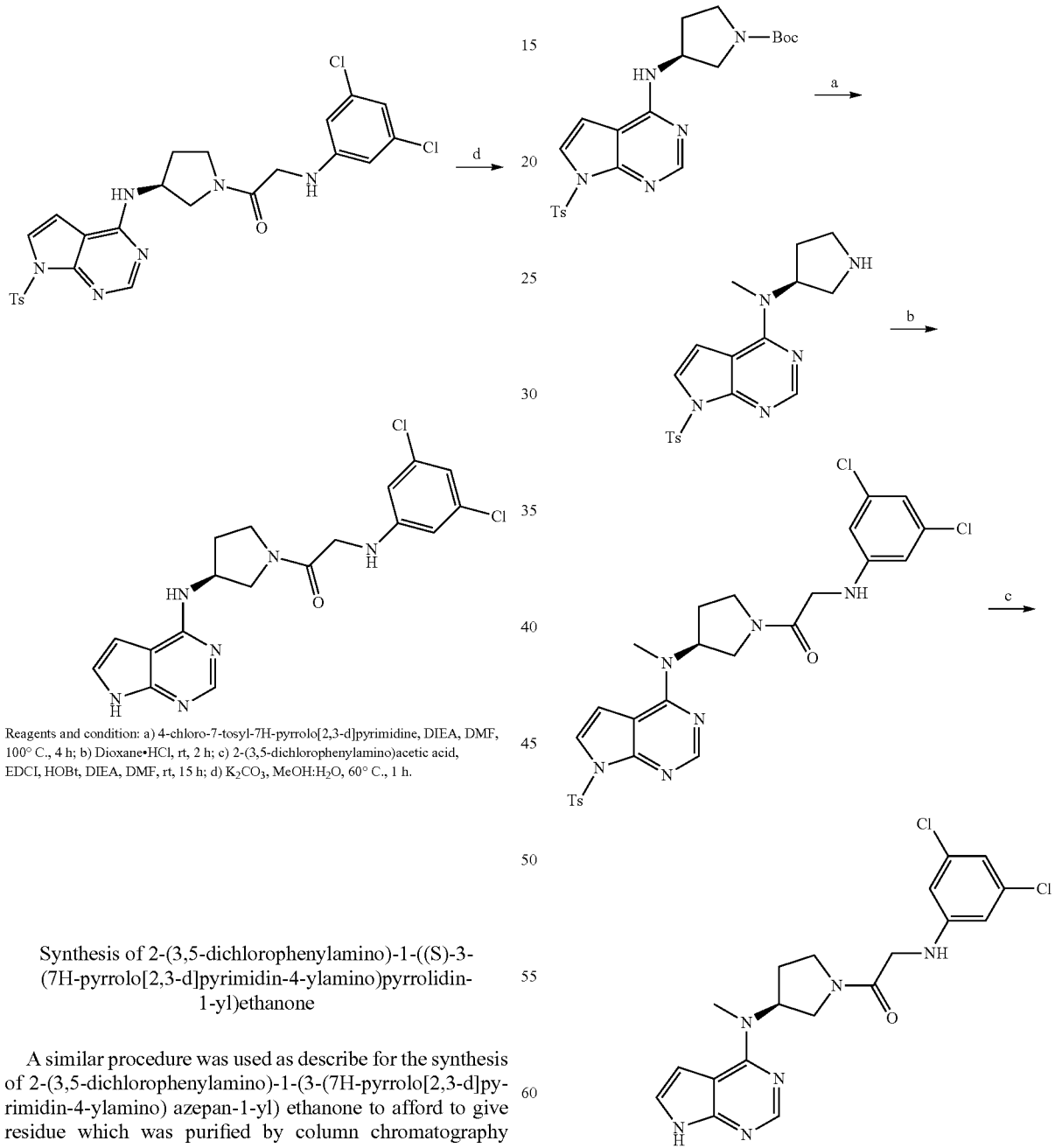

Reagents and condition: a) 4-chloro-7-tosyl-7H-pyrrolo[2,3-d]pyrimidine, DIEA, DMF, 100° C., 4 h; b) Dioxane•HCl, rt, 2 h; c) 2-(3,5-dichlorophenylamino)acetic acid, EDCI, HOBt, DIEA, DMF, rt, 15 h; d) K$_2$CO$_3$, MeOH:H$_2$O, 60° C., 1 h.

Synthesis of 2-(3,5-dichlorophenylamino)-1-((S)-3-(7H-pyrrolo[2,3-d]pyrimidin-4-ylamino)pyrrolidin-1-yl)ethanone A similar procedure was used as describe for the synthesis of 2-(3,5-dichlorophenylamino)-1-(3-(7H-pyrrolo[2,3-d]pyrimidin-4-ylamino) azepan-1-yl) ethanone to afford to give residue which was purified by column chromatography (silica gel, gradient MeOH in CH$_2$Cl$_2$) to afford (85 mg, 39%) the titled compound. $^1$H NMR (DMSO-d$_6$, 400 MHz): 11.58 (s, 1H), 8.36 (d, J=6.4 Hz, 1H), 8.08 (s, 1H), 7.11 (bs, 1H), 6.58 (s, 1H), 6.57 (t, J=6.4 Hz, 1H), 6.55-6.53 (s, 2H), 4.42 (m, 1H), 3.81 (m, 2H), 3.67 (d, J=6.4 Hz, 2H), 3.63 (d, J=9.2

Reagents and conditions: a) NaH, MeI, DMF, rt, 1 h; b) Dioxane•HCl, rt, 2 h; c) 2-(3,5-dichlorophenylamino)acetic acid, EDCI, HOBT, DIEA, DMF, rt, 15 h; d) K$_2$CO$_3$, MeOH:H$_2$O, 60° C., 1 h.

Synthesis of 2-(3,5-Dichloro-phenylamino)-1-{(S)-3-[methyl-(7H-pyrrolo[2,3-d]pyrimidin-4-yl)-amino]-pyrrolidin-1-yl}-ethanone A similar procedure was used as describe for the synthesis of 2-(3,5-dichloro-phenylamino)-1-{3-[methyl-(7H-pyrrolo[2,3-d]pyrimidin-4-34)-amino]-azepan-1-yl}-ethanone to afford a residue was purified by column chromatography (silica gel, gradient MeOH in CH$_2$Cl$_2$) to afford (35 mg, 68%) of the titled compound. $^1$H NMR (DMSO-d$_6$, 400 MHz): 11.60 (s, 1H), 8.09 (d, J=1.6 Hz, 1H), 7.12 (s, 1H), 6.77 (s, 1H), 6.74 (s, 1H), 6.66 (s, 1H), 6.62 (s, 1H), 6.31 (s, 1H), 5.24-5.08 (m, 1H), 4.84-4.60 (m, 1H), 4.18-4.02 (m, 2H), 4.00-3.86 (m, 2H), 3.76-3.60 (m, 1H), 2.85 (s, 3H), 2.28-2.10 (m, 2H). LC-MS: m/z [M+1]=419.

Example 89

Synthesis of 1-((R)-3-(1H-pyrazolo[3,4-d]pyrimidin-4-ylamino) pyrrolidin-1-yl)-2-(3,5-dichlorophenylamino) ethanone

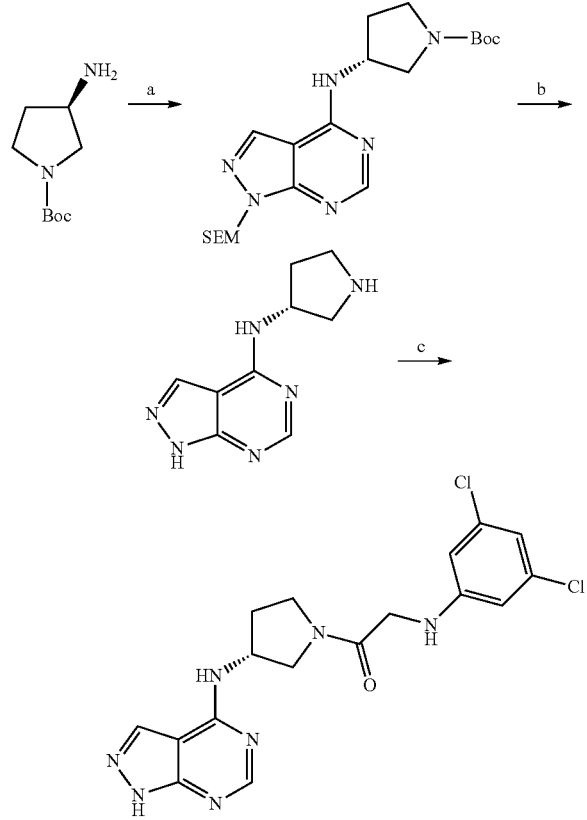

Reagents and condition: a) 4-chloro-1-((2-(trimethylsilyl)ethoxy)methyl)-1H-pyrazolo[3d]pyrimidine, DIEA, DMF, 100° C., 4 h; b) EtOH•HCl, 60° C., 4 h, then MeOH, resin, 2 h; c) 2-(3,5-dichlorophenylamino)acetic acid, EDCI, HOBt, DIEA, DMF, rt, 15 h.

Synthesis of 1-((R)-3-(1H-pyrazolo[3,4-d]pyrimidin-4-ylamino) pyrrolidin-1-yl)-2-(3,5-dichlorophenylamino) ethanone A similar procedure was used as described for the synthesis of 1-(3-(1H-pyrazolo[3,4-d]pyrimidin-4-ylamino) azepan-1-yl)-2-(3,5-dichlorophenylamino) ethanone to give the crude compound that was purified by column chromatography (silica gel, gradient MeOH in CH$_2$Cl$_2$) to afford (45 mg, 15%) of the titled compound. $^1$H NMR (DMSO-d$_6$, 400 MHz): 13.42 (s, 1H), 8.42 and 8.36 (2d, J=6.4 Hz, 1H), 8.35-8.06 (m, 2H), 6.60 (s, 1H), 6.57 (s, 1H), 6.52 (s, 2H), 4.55-4.39 (m, 1H), 3.94-3.84 (m, 1H), 3.82-3.60 (m, 3H), 2.36-2.22 (m, 1H), 2.20-2.08 (m, 1H), 2.06-1.96 (m, 1H), 1.94-1.84 (m, 1H). LC-MS: m/z [M+1]=406.

Example 90

Synthesis of 2-(3,5-Dichloro-phenylamino)-1-{(R)-3-[methyl-(1H-pyrazolo[3,4-d]pyrimidin-4-yl)-amino]-pyrrolidin-1-yl}-ethanone

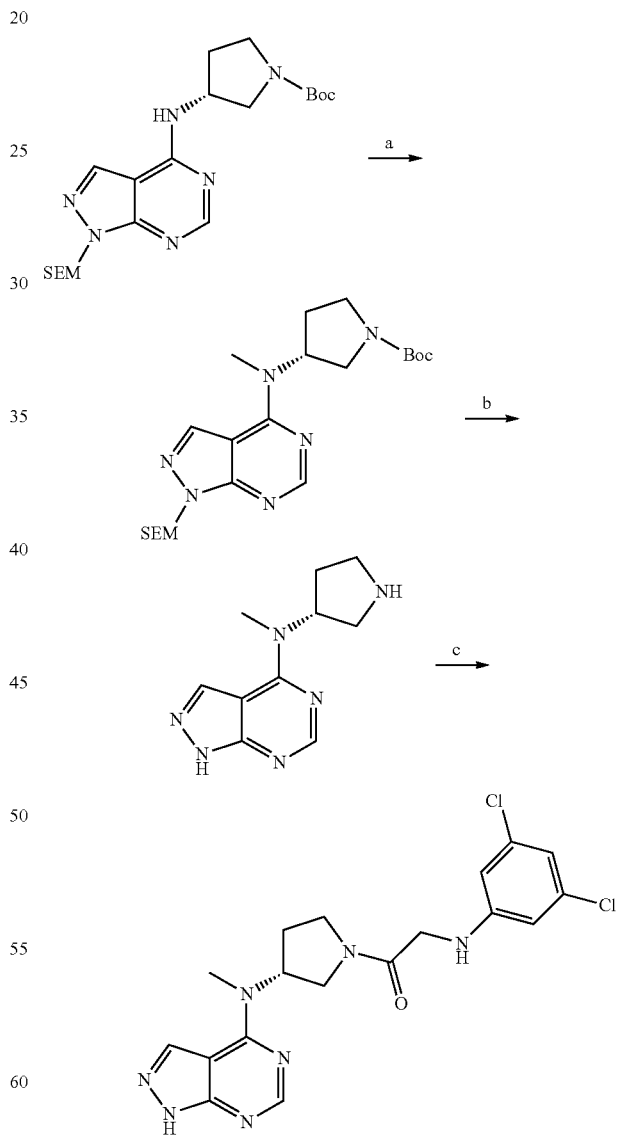

Reagents and condition: a) NaH, DMF, MeI, rt, 1 h; b) EtOH•HCl, 60° C., 4 h, then MeOH, resin, 2 h; c) 2-(3,5-dichlorophenylamino)acetic acid, EDCI, HOBt, DIEA, DMF, rt, 15 h.

2-(3,5-Dichloro-phenylamino)-1-{(R)-3-[methyl-(1H-pyrazolo[3,4-d]pyrimidin-4-yl)-amino]-pyrrolidin-1-yl}-ethanone A similar procedure was used as described for the synthesis of 1-(3-(1H-pyrazolo[3,4-d]pyrimidin-4-yl-N-methylamino)azepan-1-yl)-2-(3,5-dichlorophenylamino)ethanone to give the crude compound that purified by column chromatography (silica gel, gradient MeOH in CH$_2$Cl$_2$) to afford (200 mg, 88%) the titled compound. $^1$H NMR (DMSO-d$_6$, 400 MHz): 13.52 (s, 1H), 8.24 (s, 1H), 8.14 (s, 1H), 6.78 (s, 1H), 6.74 (s, 1H), 6.61 (s, 1H), 6.25 (s, 1H), 4.10 (m, 1H), 4.04-3.92 (m, 2H), 3.92-3.84 (m, 1H), 3.66-3.52 (m, 2H), 3.06-2.96 (m, 1H), 2.92-2.80 (s, 3H), 2.31-2.14 (m, 2H). LC-MS: m/z [M+1]=420.

Example 91

Synthesis of 2-(3,5-dichlorophenylamino)-1-((R)-3-(7H-pyrrolo[2,3-d]pyrimidin-4-ylamino)pyrrolidin-1-yl)ethanone

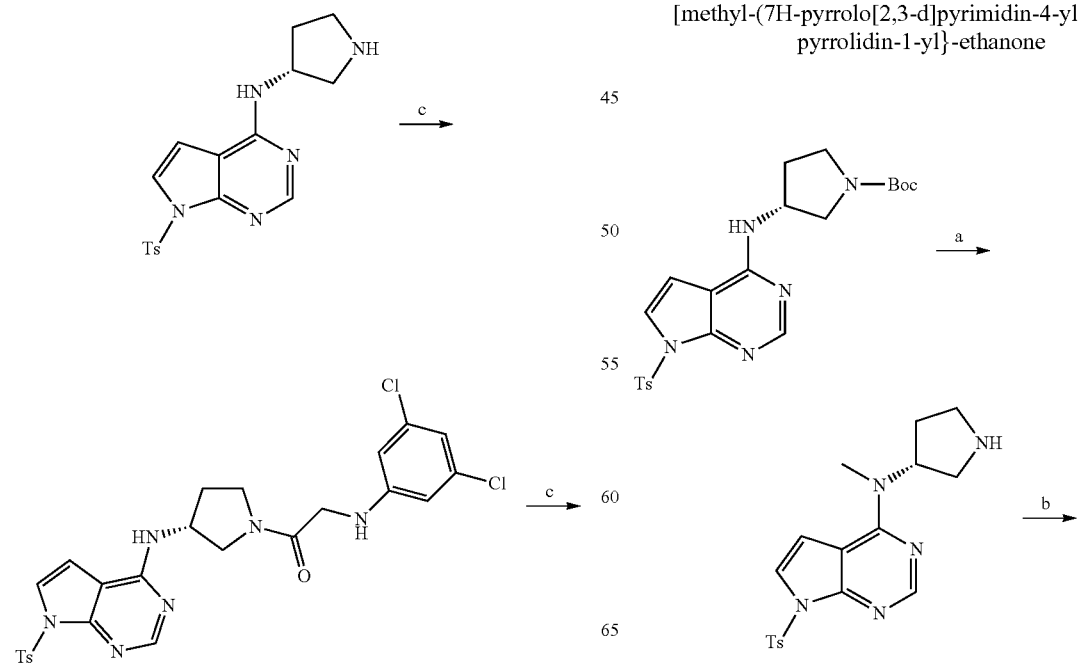

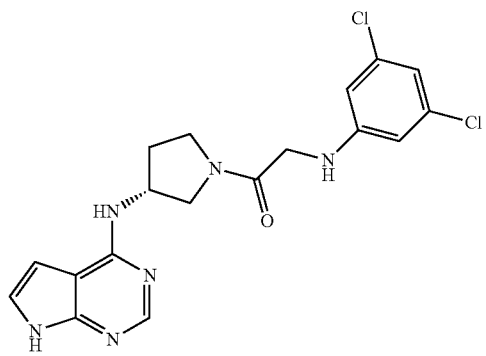

Reagents and condition: a) 4-chloro-7-tosyl-7H-pyrrolo[2,3-d]pyrimidine, DIEA, DMF, 100° C., 4 h; b) Dioxane•HCl, rt, 2 h; c) 2-(3,5-dichlorophenylamino)acetic acid, EDCI, HOBt, DIEA, DMF, rt, 15 h; d) K$_2$CO$_3$, MeOH:H$_2$O, 60° C., 1 h.

Synthesis of 2-(3,5-dichlorophenylamino)-1-((R)-3-(7H-pyrrolo[2,3-d]pyrimidin-4-ylamino)pyrrolidin-1-yl)ethanone A similar procedure was used as describe for the synthesis of 2-(3,5-dichlorophenylamino)-1-(3-(7H-pyrrolo[2,3-d]pyrimidin-4-ylamino) azepan-1-yl) ethanone to afford a residue which was purified by column chromatography (silica gel, gradient MeOH in CHCl$_3$) to afford (87 mg, 60%) the titled compound. $^1$H NMR (DMSO-d$_6$, 400 MHz): 11.56 (s, 1H), 8.34 (bs, 1H), 8.08 (s, 1H), 7.10 (bs, 1H), 6.61 (s, 1H), 6.53 (s, 3H), 4.48 (m, 1H), 3.96-3.78 (m, 3H), 3.65 (d, J=6 Hz, 2H), 3.62 (d, J=8.8 Hz, 1H), 2.22-2.10 (m, 2H), 1.98-1.86 (m, 1H). LC-MS: m/z [M+1]=405.

Example 92

Synthesis of 2-(3,5-dichloro-phenylamino)-1-{(R)-3-[methyl-(7H-pyrrolo[2,3-d]pyrimidin-4-yl)-amino]-pyrrolidin-1-yl}-ethanone -continued

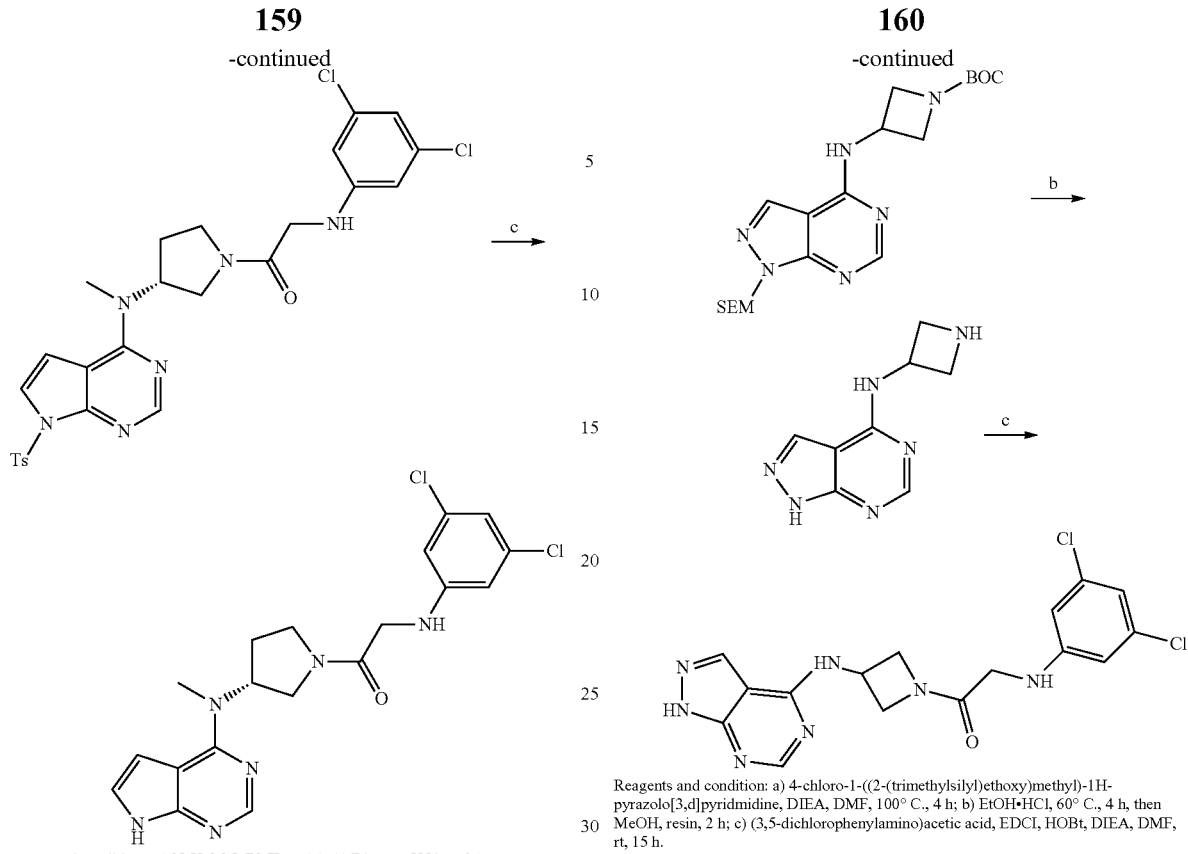

Reagents and conditions: a) NaH, MeI, DMF, rt, 1 h; b) Dioxane•HCl, rt, 2 h; c) 2-(3,5-dichlorophenylamino)acetic acid, EDCI, HOBT, DIEA, DMF, rt, 15 h; d) K₂CO₃, MeOH:H₂O, 60° C., 1 h.

Synthesis of 2-(3,5-Dichloro-phenylamino)-1-{(R)-3-[methyl-(7H-pyrrolo[2,3-d]pyrimidin-4-yl)-amino]-pyrrolidin-1-yl}-ethanone A similar procedure was used as describe for the synthesis of 2-(3,5-dichloro-phenylamino)-1-{3-[methyl-(7H-pyrrolo[2,3-d]pyrimidin-4-yl)-amino]-azepan-1-yl}-ethanone to afford a residue which was purified by column chromatography (silica gel, gradient MeOH in CHCl₃) to give (70 mg, 35%) the titled compound. ¹H NMR (DMSO-d₆, 400 MHz): 11.60 (s, 1H), 8.10 (d, J=3.2 Hz, 1H), 7.12 (bs, 1H), 6.77 (s, 1H), 6.74 (s, 1H), 6.68-6.54 (m, 2H), 6.32 (bs, 1H), 4.20-3.92 (m, 4H), 2.78-2.60 (m, 3H), 2.49 (s, 3H), 2.12-2.07 (m, 2H). LC-MS: m/z [M+1]=419.

Example 93

Synthesis of 1-(3-(1H-pyrazolo[3,4-d]pyrimidin-4-ylamino) azetidin-1-yl)-2-(3, 5-dichlorophenylamino)ethanone

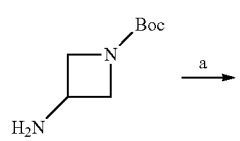

Reagents and condition: a) 4-chloro-1-((2-(trimethylsilyl)ethoxy)methyl)-1H-pyrazolo[3,d]pyridmidine, DIEA, DMF, 100° C., 4 h; b) EtOH•HCl, 60° C., 4 h, then MeOH, resin, 2 h; c) (3,5-dichlorophenylamino)acetic acid, EDCI, HOBt, DIEA, DMF, rt, 15 h.

Synthesis of 1-(3-(1H-pyrazolo[3,4-d]pyrimidin-4-ylamino)azetidin-1-yl)-2-(3,5-dichlorophenylamino)ethanone A similar procedure was used as described for the synthesis of 1-(3-(1H-pyrazolo[3,4-d]pyrimidin-4-ylamino) azepan-1-yl)-2-(3,5-dichlorophenylamino) ethanone to give the crude compound that was purified by column chromatography (silica gel, gradient MeOH in CH₂Cl₂) to afford (100 mg, 26%) the titled compound. ¹H NMR (DMSO-d₆, 400 MHz): 13.5 (s, 1H), 8.74 (bs, 1H), 8.25 (s, 1H), 8.11 (s, 1H), 6.63 (s, 3H), 6.41 (s, 1H), 4.94-4.82 (m, 1H), 4.78-4.54 (m, 1H), 4.36-4.24 (m, 1H), 4.18-4.08 (m, 1H), 4.00-3.92 (m, 1H), 3.84-3.72 (m, 2H). LC-MS: m/z [M+1]=392.

Example 94

Synthesis of 1-(3-(7H-pyrrolo[2,3-d]pyrimidin-4-ylamino)azetidin-1-yl)-2-(3,5-dichlorophenylamino) ethanone

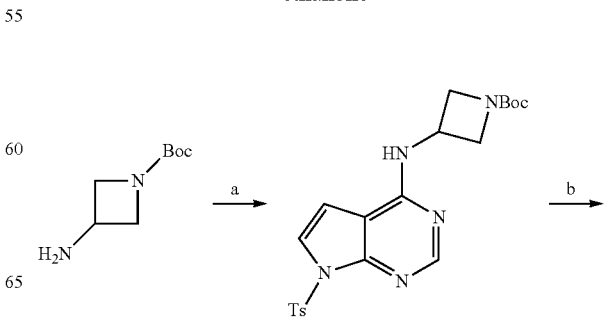

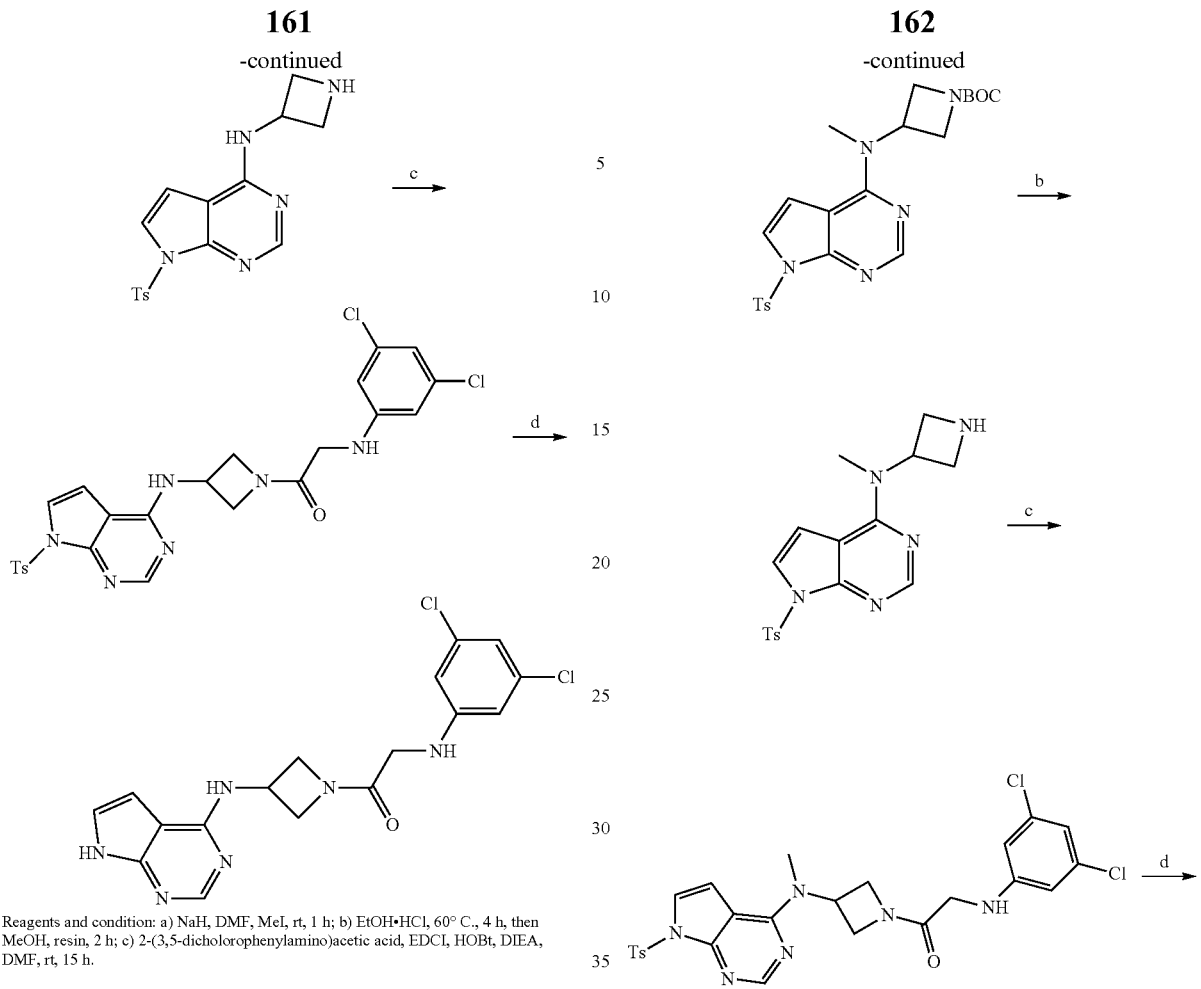

Synthesis of 1-(3-(7H-pyrrolo[2,3-d]pyrimidin-4-ylamino)azetidin-1-yl)-2-(3,5-dichlorophenylamino)ethanone A similar procedure was used as describe for the synthesis of 2-(3,5-dichlorophenylamino)-1-(3-(7H-pyrrolo[2,3-d]pyrimidin-4-ylamino) azepan-1-yl) ethanone to give a residue, that was subjected to column chromatography (silica gel, gradient MeOH in $CH_2Cl_2$) to afford (107 mg, 51%) the titled compound. $^1$H NMR (DMSO-$d_6$, 400 MHz): 11.70 (s, 1H), 8.14 (s, 1H), 7.96 (d, J=2.0 Hz, 1H), 7.16 (s, 1H), 6.64 (s, 3H), 6.56 (s, 1H), 6.40 (bs, 1H), 4.94-4.80 (m, 1H), 4.58 (t, J=8.0 Hz, 1H), 4.30 (t, J=8.0 Hz, 1H), 4.16-4.04 (m, 1H), 3.98-3.86 (m, 1H), 3.78 (d, J=1.6 Hz, 2H). LC-MS: m/z [M+1]=391.

Example 95

Synthesis of 2-(3,5-dichlorophenylamino)-1-(3-(methyl(7-tosyl-7H-pyrrolo[2,3-d]pyrimidin-4-yl)amino)azetidin-1-yl)ethanone

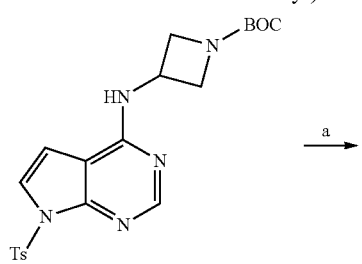

Synthesis of 2-(3,5-dichlorophenylamino)-1-(3-(methyl(7H-pyrrolo[2,3-d]pyrimidin-4-yl)amino)azetidin-1-yl)ethanone A similar procedure was used as describe for the synthesis of 2-(3,5-dichloro-phenylamino)-1-{3-[methyl-(7H-pyrrolo[2,3-d]pyrimidin-4-yl)-amino]-azepan-1-yl}-ethanone to give a residue that was subjected to column chromatography (silica gel, gradient MeOH in $CH_2Cl_2$) to afford (10 mg, 23%) the titled compound. $^1$H NMR (DMSO-$d_6$, 400 MHz): 11.88 (bs, 1H), 8.18 (s, 1H), 7.22 (d, J=4.0 Hz, 1H), 6.66 (s, 2H), 6.60 (s, 1H), 6.50-6.22 (m, 1H), 5.58-5.42 (m, 1H), 4.54 (t, J=8.0 Hz, 2H), 4.40-4.28 (m, 1H), 4.24 (t, J=8.0 Hz, 1H), 4.16-4.08 (m, 1H), 3.36 (s, 3H) 3.80 (d, J=2.0 Hz, 1H). LC-MS: m/z [M+1]=405.

Example 96

Synthesis of 1-(3-(7H-pyrrolo[2,3-d]pyrimidin-4-ylamino)-4-methylpiperidin-1-yl)-2-(3,5-dichlorophenylamino)ethanone

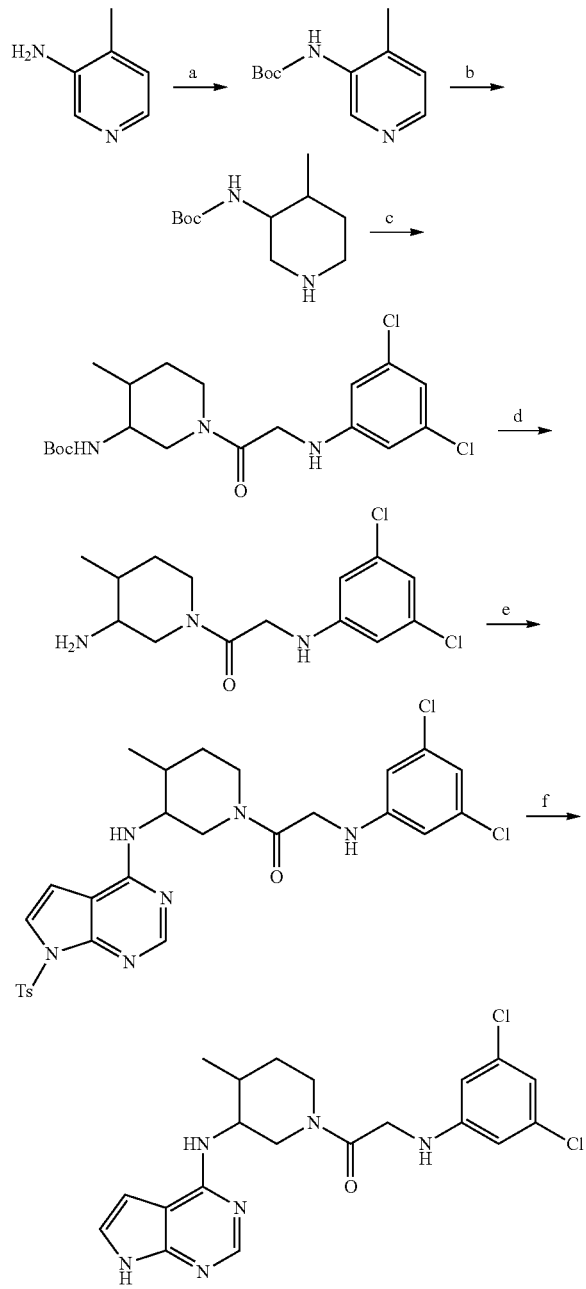

Reagents and conditions: a) Boc₂O, THF, rt, 15 h; b) H₂, PtO₂, AcOH, rt, 15 h; c) 2-(3,5-dichlorophenylamino)acetic acid, EDCI, HOBt, DIEA, DMF, rt, 5 h; d) Dioxane•HCl, rt, 2 h; e) 4-chloro-7-tosyl-7H-pyrrolo[2,3-d]pyrimidine, DIEA, DMF, 100° C., 5 h; f) K₂CO₃, MeOH:H₂O, 60° C., 30 min.

Synthesis of tert-butyl 4-methylpyridin-3-ylcarbamate

To a solution of 4-Methylpyridin-3-amine (1 g, 0.92 mmol) in THF (20 mL) was added Boc anhydride (2.12 mL, 0.92 mmol) and the reaction mixture was stirred at rt for overnight. The reaction mixture was concentrated in vacuo and the crude material was purified by column chromatography (silica gel, EtOAc: hexane as eluent) to obtain the titled compound (210 mg, 10%). ¹H NMR (400 MHz, CDCl₃): δ 8.87 (s, 1H), 8.24 (d, J=4.8 Hz, 1H), 7.08 (d, J=4.8 Hz, 1H), 6.19 (s, 1H), 2.27 (s, 3H), 1.52 (s, 9H). LC-MS: m/z [M+1]=209.

Synthesis of tert-butyl 4-methylpiperidin-3-ylcarbamate

Tert-butyl 4-methylpyridin-3-ylcarbamate (200 mg, 0.96 mmol) was dissolved in glacial acetic acid (5 mL) and treated with PtO₂ (200 mg, 1:1 w/w) under an atmosphere of hydrogen. The reaction mixture was stirred at rt for 15 h. The reaction mixture was then filtered through a pad of Celite. The filtrate was neutralized with solid NaHCO₃, and extracted with EtOAc (5×50 mL). The organic layer was dried over Na₂SO₄, concentrated in vacuo to yield the titled compound (160 mg, 77%), which was used for next step without further purification. ¹H NMR (400 MHz, CDCl₃): δ 4.38-4.21 (m, 1H), 3.32-2.81 (m, 3H), 2.63-2.49 (m, 2H), 2.41-2.32 (m, 1H), 1.78-1.56 (m, 3H), 1.59 (s, 9H), 1.05 and 0.98 (2d, J=6.8 Hz, 3H). ES-MS: m/z [M+1]=215.

Synthesis of tert-butyl 1-(2-(3,5-dichlorophenylamino)acetyl)-4-methylpiperidin-3-ylcarbamate To a solution of 2-(3,5-dichlorophenylamino)acetic acid (153 mg, 0.69 mmol) in DMF (5 mL) was added HOBt (141 mg, 1.0 mmol), EDCI (201 mg, 1.0 mmol), tert-butyl 4-methylpiperidin-3-ylcarbamate (150 mg, 0.69 mmol), and DIEA (0.18 mL, 1.3 mmol) at 0° C. Then the reaction mixture was stirred at rt for 5 h, partitioned between EtOAc and water. The organic phase was separated and washed with brine, and concentrated in vacuo to yield the crude product, which was purified by column chromatography using 0-2% MeOH:DCM solvent mixture to yield the titled intermediate (160 mg, 54%) as a thick liquid. ¹H NMR (400 MHz, CDCl₃): δ 6.92 (s, 1H), 6.49 (s, 1H), 6.38 (s, 1H), 6.29 (s, 1H), 5.22-5.15 (m, 1H), 4.65-4.56 (m, 1H), 4.35-4.16 (m, 2H), 3.25-2.89 (m, 2H), 2.85-2.69 (m, 2H), 1.82-1.75 (m, 2H), 1.69-1.45 (m, 1H), 1.22 and 1.14 (2s, 9H), 1.05 and 0.95 (2d, J=6.8 Hz, 3H). LC-MS: m/z [M+1]=416.

Synthesis of 1-(3-amino-4-methylpiperidin-1-yl)-2-(3,5-dichlorophenylamino)ethanone Tert-butyl 1-(2-(3,5-dichlorophenylamino)acetyl)-4-methylpiperidin-3-ylcarbamate (150 mg, 0.36 mmol) was treated with dioxane.HCl (5 mL) at rt for 2 h. The solvent was concentrated in vacuo, the resulting residue was dissolved in water (10 mL) and treated with solid NaHCO₃. The aqueous solution was extracted with EtOAc (3×25 mL) and the combined organic layers were dried over Na₂SO₄, concentrated in vacuo to yield the titled intermediate (100 mg, 87%), which was used next without further purification. LC-MS: m/z [M+1]=316.

Synthesis of 2-(3,5-dichlorophenylamino)-1-(4-methyl-3-(7-tosyl-7H-pyrrolo[2,3-d]pyrimidin-4-ylamino)piperidin-1-yl)ethanone To a solution of 1-(3-amino-4-methylpiperidin-1-yl)-2-(3, 5-dichlorophenylamino)ethanone (180 mg, 0.56 mmol) and 4-chloro-7-tosyl-7H-pyrrolo[2,3-d]pyrimidine (192 mg, 0.62 mmol) in DMF (5 mL), was added DIEA (0.15 mL, 0.85 mmol) and the reaction mixture was stirred at 60° C. overnight. The reaction mixture was cooled to rt and diluted with EtOAc/water (1:2, 120 mL). The EtOAc layer was separated, dried over Na$_2$SO$_4$ and evaporated in vacuo to give a residue that was purified by column chromatography (silica gel, gradient EtOAc in hexanes) to afford the titled intermediate (120 mg, 35%). LC-MS: m/z [M+1]=587.

Synthesis of 1-(3-(7H-pyrrolo[2,3-d]pyrimidin-4-ylamino)-4-methylpiperidin-1-yl)-2-(3,5-dichlorophenylamino)ethanone To a solution of 2-(3,5-dichlorophenylamino)-1-(4-methyl-3-(7-tosyl-7H-pyrrolo[2,3-d]pyrimidin-4-ylamino)piperidin-1-yl)ethanone (100 mg, 0.17 mmol) in MeOH:H$_2$O (4:1 mL) was added K$_2$CO$_3$ (94 mg, 0.68 mmol) and the reaction mixture was heated to 60° C. for 1 h. The reaction mixture was concentrated in vacuo and the residue obtained was diluted in EtOAc (50 mL). The EtOAc suspension was filtered through celite, the filtrate was dried over Na$_2$SO$_4$, and concentrated in vacuo to give a residue that was subjected to purification by column chromatography (silica gel, gradient MeOH in DCM) to afford the titled intermediate (20 mg, 27%). $^1$H NMR (400 MHz, DMSO-d$_6$): δ 11.61-11.45 (m, 1H), 8.19-8.06 (m, 1H), 7.08-6.43 (m, 5H), 6.22-6.15 (m, 1H), 4.59-4.21 (m, 2H), 4.15-3.75 (m, 3H), 3.25-2.98 (m, 2H), 2.78-2.45 (m, 1H), 2.15-1.99 (m, 1H), 1.86-1.7-62 (m, 2H), 0.98-0.77 (m, 3H). LC-MS: m/z [M+1]=433.

Example 98

Synthesis of 1-(5-(7H-pyrrolo[2,3-d]pyrimidin-4-ylamino)-2-methylpiperidin-1-yl)-2-(3,5-dichlorophenylamino)ethanone

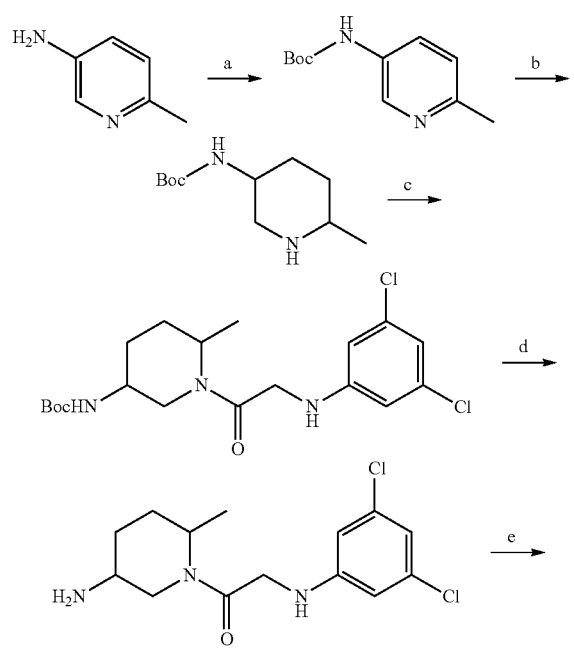

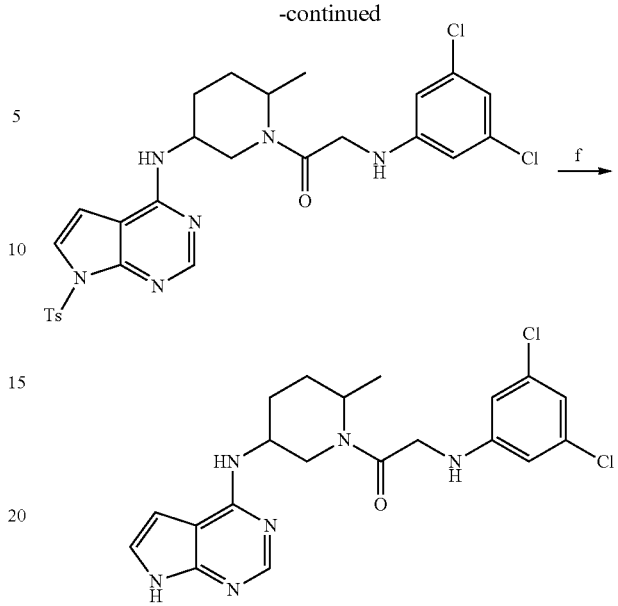

Reagents and conditions: a) Boc$_2$O, THF, rt, 15 h; b) H$_2$, PtO$_2$, AcOH, rt, 15 h; c) 2-(3,5-dichlorophenylamino)acetic acid, EDCI, HOBt, DIEA, DMF, rt, 5 h; d) Dioxane•HCl, rt, 2 h; e) 4-chloro-7-tosyl-7H-pyrrolo[2,3-d]pyrimidine, DIEA, DMF, 100° C., 5 h; f) K$_2$CO$_3$, MeOH:H$_2$O, 60° C., 30 min.

Synthesis of tert-butyl 6-methylpyridin-3-ylcarbamate

Following a similar procedure as for tert-butyl 4-methylpyridin-3-ylcarbamate, the titled compound (1.7 g, 88%) was synthesized. $^1$H NMR (400 MHz, CDCl$_3$): δ 8.31 (s, 1H), 7.83 (s, 1H), 7.08 (d, J=4.8 Hz, 1H), 6.81 (s, 1H), 2.65 (s, 3H), 1.51 (s, 9H). LC-MS: m/z [M+1]=209.

Synthesis of tert-butyl 6-methylpiperidin-3-ylcarbamate

Following a similar procedure as for tert-butyl 4-methylpiperidin-3-ylcarbamate, the titled compound (550 mg, 76%) was synthesized. $^1$H NMR (400 MHz, DMSO-d$_6$): δ 6.85 and 6.75 (2d, J=4.2 Hz, 1H), 3.42-3.01 (m, 1H), 2.96-2.80 (m, 2H), 2.78-2.45 (m, 1H), 2.41-2.19 (m, 1H), 1.82-1.62 (m, 1H), 1.58-1.59 (m, 2H), 1.53 (s, 9H), 1.25-1.17 (m, 1H), 1.98 (d, =6.8 Hz, 3H). ES-MS: m/z [M+1]=215.

Synthesis of tert-butyl 1-(2-(3,5-dichlorophenylamino)acetyl)-6-methylpiperidin-3-ylcarbamate Following a similar procedure as for tert-butyl 1-(2-(3,5-dichlorophenylamino)acetyl)-4-methylpiperidin-3-ylcarbamate, the titled compound (760 mg, 78%) was synthesized. LC-MS: m/z [M+1]=416.

Synthesis of 1-(5-amino-2-methylpiperidin-1-yl)-2-(3,5-dichlorophenylamino)ethanone Following a similar procedure as for 1-(3-amino-4-methylpiperidin-1-yl)-2-(3,5-dichlorophenylamino)ethanone, the titled intermediate (450 mg, 79%) was synthesized. $^1$H NMR (400 MHz, DMSO-d$_6$): δ 6.78 (s, 1H), 6.75 (s, 1H), 6.64 (s, 1H), 6.25 (s, 1H), 4.69-4.62 (m, 1H), 4.36-3.85 (m, 3H), 3.62-3.09 (m, 2H), 2.79-2.35 (m, 2H), 1.82-1.45 (m, 4H), 1.25 and 1.09 (2d, J=6.8 Hz, 3H) LC-MS: m/z [M+1]=316.

Synthesis of 2-(3,5-dichlorophenylamino)-1-(2-methyl-5-(7-tosyl-7H-pyrrolo[2,3-d]pyrimidin-4-ylamino)piperidin-1-yl)ethanone Following a similar procedure as for 2-(3,5-dichlorophenylamino)-1-(4-methyl-3-(7-tosyl-7H-pyrrolo[2,3-d]pyrimidin-4-ylamino)piperidin-1-yl)ethanone, the titled compound (310 mg, 66%) was synthesized. LC-MS: m/z [M+1]=587.

Synthesis of 1-(5-(7H-pyrrolo[2,3-d]pyrimidin-4-ylamino)-2-methylpiperidin-1-yl)-2-(3,5-dichlorophenylamino)ethanone Following a similar procedure as for 1-(3-(7H-pyrrolo[2,3-d]pyrimidin-4-ylamino)-4-methylpiperidin-1-yl)-2-(3,5-dichlorophenylamino)ethanone, the titled compound (110 mg, 20%) was synthesized. $^1$H NMR (400 MHz, DMSO-d$_6$): δ 11.54-11.48 (m, 1H), 8.15 and 8.08 (2s, 1H), 7.37-7.04 (m, 2H), 6.77 (s, 1H), 6.72 (s, 1H), 6.62 (s, 1H), 6.57-6.41 (m, 1H), 6.29-6.18 (m, 1H), 4.77-4.53 (m, 1H), 4.27-3.90 (m, 4H), 2.95 and 2.60 (2t, J=11.6 Hz, 1H), 2.06-1.64 (m, 4H), 1.26 and 1.16 (2d, J=6.8 Hz, 3H). LC-MS: m/z [M+1]=433.

Example 99

Synthesis of 1-(3-(7H-pyrrolo[2,3-d]pyrimidin-4-ylamino)-2-methylpiperidin-1-yl)-2-(3,5-dichlorophenylamino)ethanone

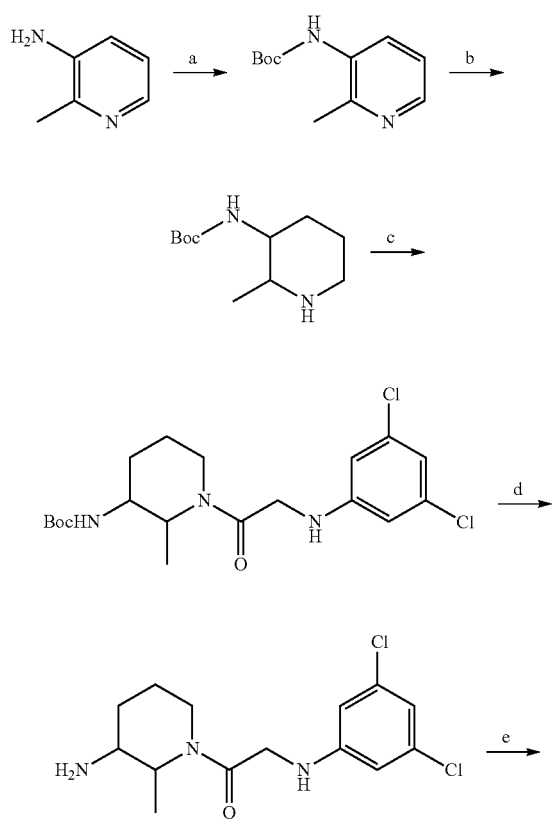

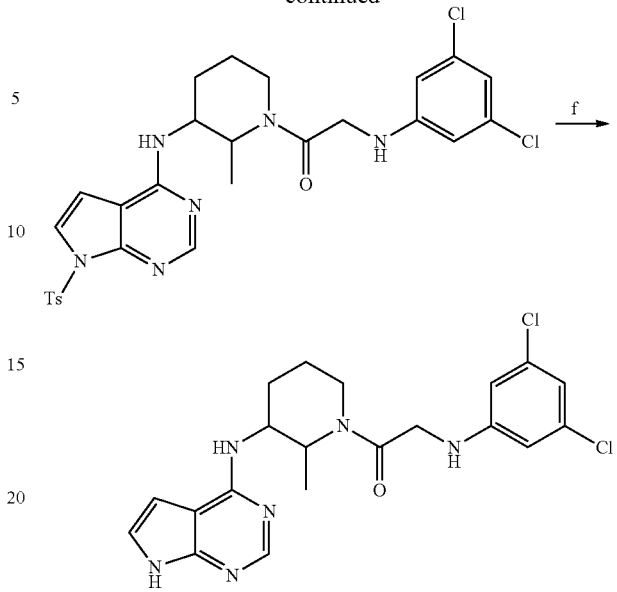

Reagents and conditions: a) Boc$_2$O, THF, rt, 15 h; b) H$_2$, PtO$_2$, AcOH, rt, 15 h; c) 2-(3,5-dichlorophenylamino)acetic acid, EDCI, HOBt, DIEA, DMF, rt, 5 h; d) Dioxane•HCl, rt, 2 h; e) 4-chloro-7-tosyl-7H-pyrrolo[2,3-d]pyrimidine, DIEA, DMF, 100° C., 5 h; f) K$_2$CO$_3$, MeOH:H$_2$O, 60° C., 30 min.

Synthesis of tert-butyl 2-methylpyridin-3-ylcarbamate

Following a similar procedure as for tert-butyl 4-methylpyridin-3-ylcarbamate, the titled compound (1.4 g, 72%) was synthesized. $^1$H NMR (400 MHz, DMSO-d$_6$): δ 8.26 (d, J=4.8 Hz, 1H), 8.18 (s, 1H), 7.15 (dd, J=4.8, 7.8 Hz, 1H), 6.39 (s, 1H), 2.55 (s, 3H), 1.57 (s, 9H). LC-MS: m/z [M+1]=209.

Synthesis of tert-butyl 2-methylpiperidin-3-ylcarbamate

Following a similar procedure as for tert-butyl 4-methylpiperidin-3-ylcarbamate, the titled compound (600 mg, 83%) was synthesized. $^1$H NMR (400 MHz, CDCl$_3$): δ 6.81 and 6.28 (2d, J=4.2 Hz, 1H), 3.42-3.35 (m, 1H), 2.82-2.65 (m, 2H), 2.51-2.26 (m, 2H), 1.77-1.62 (m, 3H), 1.41 (s, 9H), 1.38-1.22 (m, 1H), 0.95 and 0.85 (2d, J=6.4 Hz, 3H). ES-MS: m/z=215.

Synthesis of tert-butyl 1-(2-(3,5-dichlorophenylamino)acetyl)-2-methylpiperidin-3-ylcarbamate Following a similar procedure as for tert-butyl 1-(2-(3,5-dichlorophenylamino)acetyl)-4-methylpiperidin-3-ylcarbamate, the titled compound (820 mg, 52%) was synthesized. $^1$H NMR (400 MHz, DMSO-d$_6$): δ 7.58 (s, 1H), 6.75 (s, 1H), 6.68 (s, 1H), 6.59 (s, 1H), 6.38-6.25 (m, 1H), 4.82-4.75 (m, 1H), 4.25-3.61 (m, 4H), 3.01-2.61 (m, 1H), 1.88-1.65 (m, 4H), 1.43 (s, 9H), 1.16 and 0.95 (2d, J=6.4 Hz, 3H). LC-MS: m/z [M+1]=416.

Synthesis of 1-(3-amino-2-methylpiperidin-1-yl)-2-(3,5-dichlorophenylamino)ethanone Following a similar procedure as for 1-(3-amino-4-methylpiperidin-1-yl)-2-(3,5-dichlorophenylamino)ethanone, the titled compound (400 mg, 42%) was synthesized. $^1$H NMR (400 MHz, DMSO-d$_6$): δ 7.58 (s, 1H), 6.75 (s, 2H), 6.62 (s, 1H), 6.24 (s, 1H), 4.63-4.21 (m, 1H), 4.02-3.91 (m, 2H), 3.89-3.80 (m, 2H), 3.05-2.65 (m, 2H), 1.79-1.38 (m, 4H), 1.14 and 0.98 (2d, J=6.4 Hz, 3H). LC-MS: m/z [M+1]=316.

Synthesis of 2-(3,5-dichlorophenylamino)-1-(2-methyl-3-(7-tosyl-7H-pyrrolo[2,3-d]pyrimidin-4-ylamino)piperidin-1-yl)ethanone Following a similar procedure as for 2-(3,5-dichlorophenylamino)-1-(4-methyl-3-(7-tosyl-7H-pyrrolo[2,3-d]pyrimidin-4-ylamino)piperidin-1-yl)ethanone, the titled compound (350 mg, 94%) was synthesized. $^1$H NMR (400 MHz, DMSO-d$_6$): δ 8.24 and 8.20 (2s, 1H), 7.95 (2d, J=8.4 Hz, 2H), 7.81-7.46 (m, 2H), 7.42 (d, J=8.4 Hz, 2H), 7.01 (d, J=4.2 Hz, 1H), 6.78 (s, 1H), 6.75 (s, 1H), 6.69 (s, 1H), 6.41-6.22 (m, 1H), 5.09-5.00 (m, 1H), 4.44-4.12 (m, 2H), 4.05-3.72 (m, 2H), 3.09 and 2.75 (2t, J=11.6 Hz, 1H), 2.36 (s, 3H), 1.89-1.45 (m, 4H), 1.16 and 0.99 (2d, J=6.4 Hz, 3H). LC-MS: m/z [M+1]=587.

Synthesis of 1-(3-(7H-pyrrolo[2,3-d]pyrimidin-4-ylamino)-2-methylpiperidin-1-yl)-2-(3,5-dichlorophenylamino)ethanone Following a similar procedure as for 1-(3-(7H-pyrrolo[2,3-d]pyrimidin-4-ylamino)-4-methylpiperidin-1-yl)-2-(3,5-dichlorophenylamino)ethanone, the titled compound was synthesized. $^1$H NMR (400 MHz, DMSO-d$_6$): δ 11.52 and 11.49 (2s, 1H), 8.14 and 8.07 (2s, 1H), 7.41 and 7.22 (2d, J=7.2 Hz, 1H), 7.09-7.04 (m, 1H), 6.76 (s, 1H), 6.72 (s, 1H), 6.65 (s, 1H), 6.62-6.46 (m, 1H), 6.30-6.20 (m, 1H), 5.10-4.57 (m, 1H), 4.28-4.05 (m, 3H), 3.88-3.72 (m, 1H), 3.07 and 2.78 (2t, J=11.6 Hz, 1H), 2.01-1.74 (m, 3H), 1.60-4.41 (m, 1H), 1.16 and 1.01 (2d, J=6.4 Hz, 3H). LC-MS: m/z [M+1]=433.

Example 100

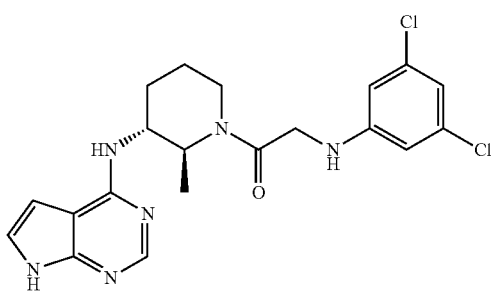 [SMILES: C[C@H]1[C@H](Nc2ncnc3[nH]ccc23)CCCN1C(=O)CNc1cc(Cl)cc(Cl)c1]

Synthesis of 1-((2R,3S)-3-(7H-pyrrolo[2,3-d]pyrimidin-4-ylamino)-2-methylpiperidin-1-yl)-2-(3,5-dichlorophenylamino)ethanone The title compound was obtained from chiral separation of 1-(3-(7H-pyrrolo[2,3-d]pyrimidin-4-ylamino)-2-methylpiperidin-1-yl)-2-(3,5-dichlorophenylamino)ethanone using SFC separation on a Chiralpak AS-H (2×15 cm) column. $^1$H NMR (400 MHz, CDCl$_3$-d) δ 7.05 (d, J=3.01 Hz, 1H), 6.70 (s, 1H), 6.57 (s, 1H), 6.49 (s, 1H), 6.33 (br. s., 1H), 6.18 (s, 1H), 5.23 (br. s., 1H), 4.95-5.09 (m, 1H), 4.61 (d, J=13.30 Hz, 1H), 4.37 (br. s., 2H), 3.78-4.02 (m, 1H), 3.49-3.66 (m, 1H), 2.85-3.38 (m, 1H), 2.11-2.25 (m, 1H), 1.60-1.94 (m, 4H), 1.34-1.53 (m, 3H). LC-MS: m/z [M+1]=433.

Example 101

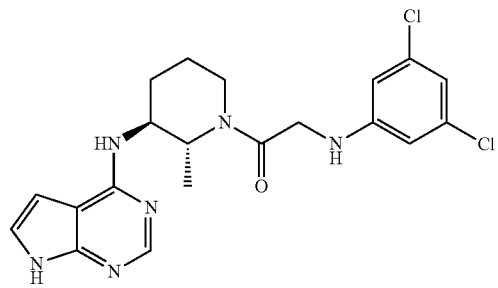 [SMILES: C[C@@H]1[C@@H](Nc2ncnc3[nH]ccc23)CCCN1C(=O)CNc1cc(Cl)cc(Cl)c1]

Synthesis of 1-((2R,3S)-3-(7H-pyrrolo[2,3-d]pyrimidin-4-ylamino)-2-methylpiperidin-1-yl)-2-(3,5-dichlorophenylamino)ethanone The title compound was obtained using the same procedure as described in Example 100. 1H NMR (400 MHz, CDCl3-d) d 7.06 (d, J=3.01 Hz, 1H), 6.70 (s, 1H), 6.57 (s, 1H), 6.49 (s, 1H), 6.33 (br. s., 1H), 6.18 (s, 1H), 5.24 (br. s., 1H), 4.99-5.09 (m, 1H), 4.59 (d, J=13.30 Hz, 1H), 4.37 (br. s., 2H), 3.84-3.97 (m, 1H), 3.49-3.58 (m, 1H), 2.92 (m, 1H), 2.11-2.25 (m, 1H), 1.60-1.94 (m, 4H), 1.34-1.49 (m, 3H). LC-MS: m/z [M+1]=433.

Example 102

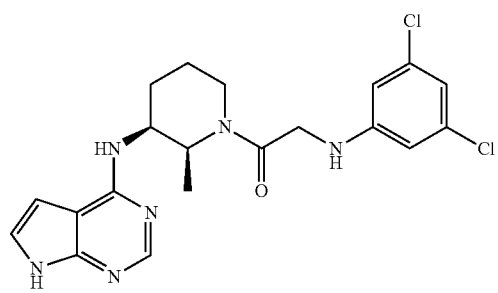 [SMILES: C[C@H]1[C@@H](Nc2ncnc3[nH]ccc23)CCCN1C(=O)CNc1cc(Cl)cc(Cl)c1]

Synthesis of 1-((2S,3S)-3-(7H-pyrrolo[2,3-d]pyrimidin-4-ylamino)-2-methylpiperidin-1-yl)-2-(3,5-dichlorophenylamino)ethanone The title compound was obtained using the same procedure as described in Example 100. $^1$H NMR (400 MHz, CDCl$_3$-d): δ 11.00 (br. s., 1H), 8.48 (br. s., 1H), 7.15 (br. s., 1H), 6.69 (s, 1H), 6.61 (s, 1H), 6.34-6.52 (m, 1H), 5.43 (br. s., 1H), 4.91 (br. s., 1H), 4.78 (br. s., 1H), 4.54 (d, J=10.29 Hz, 1H), 4.20-4.44 (m, 2H), 3.84 (d, J=11.80 Hz, 1H), 2.83 (t, J=12.55 Hz, 1H), 1.94 (br. s., 1H), 1.77-1.90 (m, 4H), 1.15-1.28 (m, 3H). LC-MS: m/z [M+1]=433.

Example 103

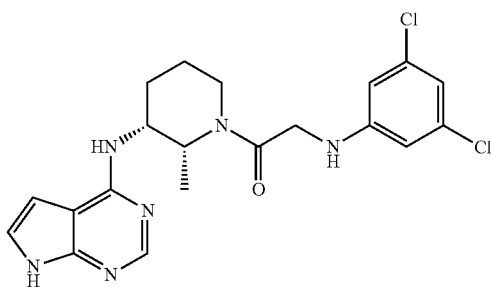 [SMILES: C[C@@H]1[C@H](Nc2ncnc3[nH]ccc23)CCCN1C(=O)CNc1cc(Cl)cc(Cl)c1]

Synthesis of 1-((2R,3R)-3-(7H-pyrrolo[2,3-d]pyrimidin-4-ylamino)-2-methylpiperidin-1-yl)-2-(3,5-dichlorophenylamino)ethanone The title compound was obtained using the same procedure as described in Example 100. $^1$H NMR (400 MHz, CDCl$_3$-d) δ 8.47 (br. s., 1H), 7.13 (br. s., 1H), 6.69 (s, 1H), 6.57 (s, 2H), 6.35-6.51 (m, 2H), 5.42 (br. s., 1H), 4.72-4.92 (m, 2H), 4.30-4.58 (m, 2H), 4.21-4.30 (m, 1H), 3.83 (d, J=11.55 Hz, 1H), 2.83 (t, J=12.67 Hz, 1H), 1.67 (br. m, 4H), 1.24 (d, J=6.78 Hz, 3H). LC-MS: m/z [M+1]=433.

Example 104

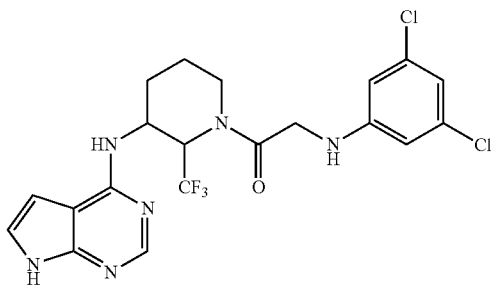 [SMILES: O=C(CNc1cc(Cl)cc(Cl)c1)N1CCCC(Nc2ncnc3[nH]ccc23)C1C(F)(F)F]

Synthesis of 1-(3-(7H-pyrrolo[2,3-d]pyrimidin-4-ylamino)-2-(trifluoromethyl)piperidin-1-yl)-2-(3,5-dichlorophenylamino)ethanone A similar procedure was used as described for the 1-(3-(7H-pyrrolo[2,3-d]pyrimidin-4-ylamino)-2-methylpiperidin-1-yl)-2-(3,5-dichlorophenylamino)ethanone to afford the title compound.

Example 105

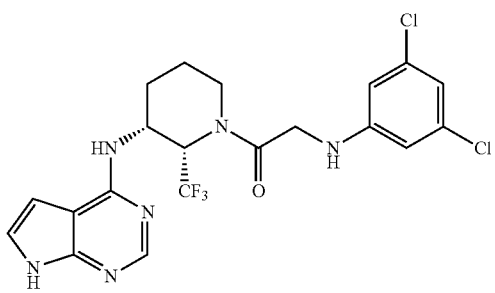 [SMILES: O=C(CNc1cc(Cl)cc(Cl)c1)N1CCC[C@@H](Nc2ncnc3[nH]ccc23)[C@H]1C(F)(F)F]

Synthesis of 1-((2S,3R)-3-(7H-pyrrolo[2,3-d]pyrimidin-4-ylamino)-2-(trifluoromethyl)piperidin-1-yl)-2-(3,5-dichlorophenylamino)ethanone The title compound was obtained from chiral separation of 1-(3-(7H-pyrrolo[2,3-d]pyrimidin-4-ylamino)-2-(trifluoromethyl)piperidin-1-yl)-2-(3,5-dichlorophenylamino)ethanone using SFC separation on a Chiralpak IC (3×15 cm) column. $^1$H NMR (400 MHz, CHLOROFORM-d) δ 7.09-7.19 (m, 2H), 6.72 (ddd, J=1.88, 2.01, 6.90 Hz, 2H), 6.52-6.60 (m, 2H), 6.46-6.52 (m, 2H), 6.36-6.46 (m, 2H), 5.95-6.09 (m, 1H), 5.31-5.42 (m, 1H), 4.92-5.04 (m, 2H), 4.63-4.75 (m, 2H), 4.43-4.59 (m, 1H), 4.21-4.31 (m, 1H), 3.94 (t, J=3.89 Hz, 2H), 3.90 (d, J=4.27 Hz, 1H), 3.22-3.38 (m, 1H), 2.81-2.94 (m, 1H), 1.93-2.23 (m, 6H), 1.53-1.88 (m, 6H).

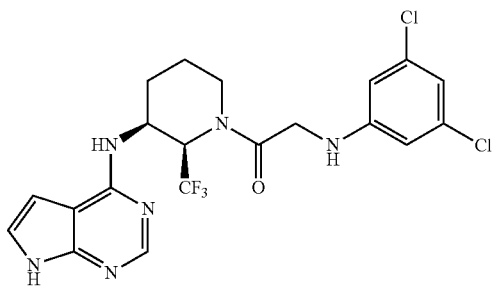 [SMILES: O=C(CNc1cc(Cl)cc(Cl)c1)N1CCC[C@H](Nc2ncnc3[nH]ccc23)[C@@H]1C(F)(F)F]

Synthesis of 1-((2R,3S)-3-(7H-pyrrolo[2,3-d]pyrimidin-4-ylamino)-2-(trifluoromethyl)piperidin-1-yl)-2-(3,5-dichlorophenylamino)ethanone The title compound was obtained from chiral separation of 1-(3-(7H-pyrrolo[2,3-d]pyrimidin-4-ylamino)-2-(trifluoromethyl)piperidin-1-yl)-2-(3,5-dichlorophenylamino)ethanone using SFC separation on a Chiralpak IC (3×15 cm) column. $^1$H NMR (400 MHz, CHLOROFORM-d) δ 7.09-7.19 (m, 2H), 6.72 (ddd, J=1.88, 2.01, 6.90 Hz, 2H), 6.52-6.60 (m, 2H), 6.46-6.52 (m, 2H), 6.36-6.46 (m, 2H), 5.95-6.09 (m, 1H), 5.31-5.42 (m, 1H), 4.92-5.04 (m, 2H), 4.63-4.75 (m, 2H), 4.43-4.59 (m, 1H), 4.21-4.31 (m, 1H), 3.94 (t, J=3.89 Hz, 2H), 3.90 (d, J=4.27 Hz, 1H), 3.22-3.38 (m, 1H), 2.81-2.94 (m, 1H), 1.93-2.23 (m, 6H), 1.53-1.88 (m, 6H).

Example 106

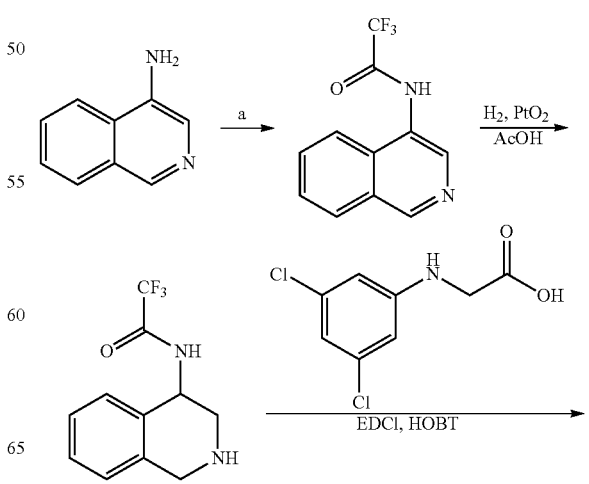

173

-continued

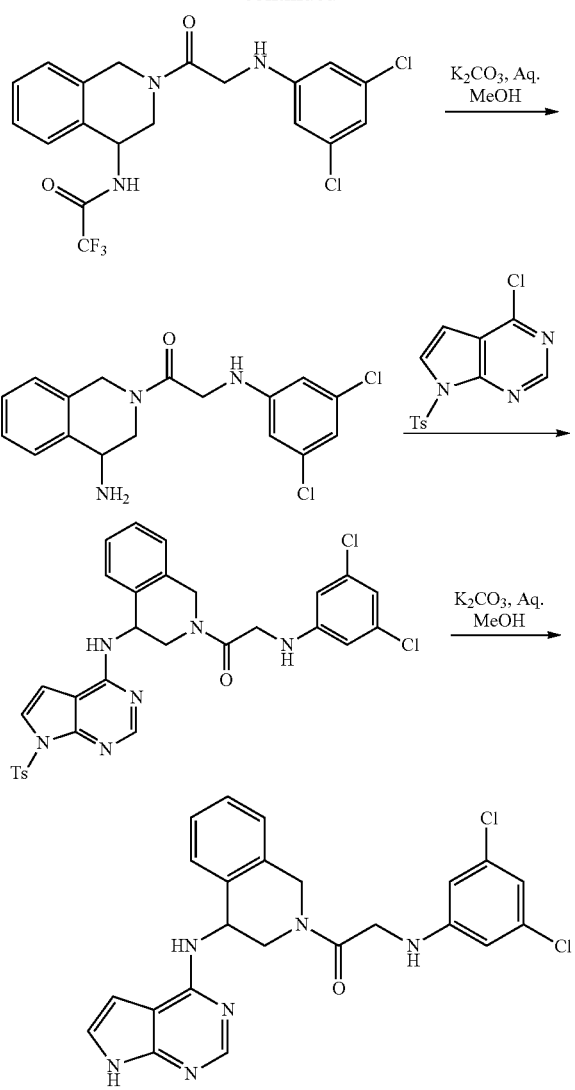

Reagents and conditions: (a) Trifluoroacetic anhydride, 100° C., 1 h. (b) PtO₂, H₂, acetic acid, rt, 10 h. (c) C₈H₇NO₂Cl₂, EDCI, HOBt, DIEA, rt. (d) K₂CO₃, aqu. MeOH 80° C. (e) C₁₃H₁₀ClN₃O₂S, DIEA, DMF, 90° C. (f) K₂CO₃, MeOH/water 80° C.

Synthesis of 2-(3,5-dichlorophenylamino)-1-(4-(7H-pyrrolo[2,3-d]pyrimidin-4-ylamino)-3,4-dihydroisoquinolin-2(1H)-yl)ethanone

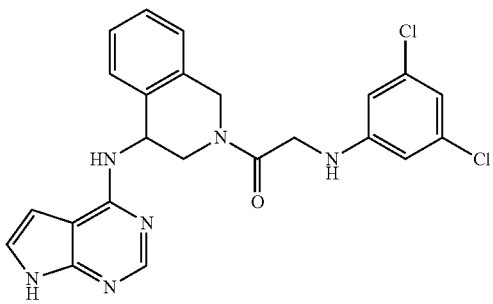 [SMILES: O=C(CNc1cc(Cl)cc(Cl)c1)N1Cc2ccccc2C(Nc2ncnc3[nH]ccc23)C1]

174

Synthesis of 2,2,2-trifluoro-N-(isoquinolin-4-yl)acetamide

To a solution of isoquinolin-4-amine (0.5 g, 3.4 mmol) in pyridine (25 mL) was added trifluoroacetic anhydride (0.73 g, 3.4 mmol) at 0° C. The reaction was heated at 100° C. for 1 h, and the solvent was concentrated in vacuo to afford a mixture which was diluted with CHCl₃ and washed several times with water. The CHCl₃ layer was concentrated in vacuo to give a crude mixture which was purified by column chromatography (silica gel, gradient EtOAc in Hexanes) to give (0.710 g, 97%) of the titled intermediate. ¹H NMR (DMSO-d6, 400 MHz): δ 11.62 (s, 1H), 9.34 (s, 1H), 8.56 (s, 1H), 8.24 (d, J=8 Hz, 1H), 7.77 (m, 1H). LCMS: M/z: (M+1):241

Synthesis of 2,2,2-trifluoro-N-(1,2,3,4-tetrahydroisoquinolin-4-yl)acetamide

To a solution of 2,2,2-trifluoro-N-(isoquinolin-4-yl)acetamide (1.0 g, 1.49 mmol) in AcOH (20 mL) was adde PtO₂ (0.2 g) was added under nitrogen atmosphere. The reaction mixture placed under an atmosphere of hydrogen at rt for 10 h. The reaction mixture was filtered through a pad of celite, washed several times with MeOH. The filtrate was concentrated in vacuo to give a residue that was diluted with water, neutralized with NaHCO₃, extracted with EtOAc (100 mL×3), the combined EtOAc layer was washed with water, dried over Na₂SO₄ and concentrated in vacuo to give a crude reaction mixture which was purified by column chromatography (silica gel, gradient MeOH in EtOAc) to give (0.380 g, 33%) of the titled intermediate. ¹H NMR (DMSO-d6, 400 MHz): δ 9.72 (s, 1H), 7.24-7.07 (m, 4H), 4.98 (s, 1H), 3.89 (d, J=16.4 Hz, 1H), 3.82 (d, J=16.4 Hz, 1H), 3.10 (dd, J=4.8, 12.8 Hz, 1H), 2.88 (dd, J=6.8 Hz, 12.8 Hz, 1H), 2.50 (m, 1H). LCMS: M/z: (M+1):245

Synthesis of N-(2-(2-(3,5-dichlorophenylamino)acetyl)-1,2,3,4-tetrahydroisoquinolin-4-yl)-2,2,2-trifluoroacetamide To a solution of 2-(3,5-dichlorophenylamino)acetic acid (0.332 g, 1.5 mmol) in DMF (10 mL) was added HOBt (0.30 g, 2.2 mmol) EDCI: HCl (0.434 g, 2.2 mmol), DIEA (0.39 g, 3.0 mmol) and 2,2,2-trifluoro-N-(1,2,3,4-tetrahydroisoquinolin-4-yl)acetamide (370 mg, 1.5 mmol) at 0° C. The reaction mixture was warmed to rt and stirred overnight. After the reaction was shown to be complete as indicated by TLC the reaction mixture was diluted with EtOAc (50 mL), and washed with water (20 mL×3). The EtOAc layer was concentrated in vacuo to give crude reaction mixture which was purified by column chromatography (silica gel, gradient MeOH in CH₂Cl₂) to give (0.45 g, 74%) of the titled intermediate. ¹H NMR (DMSO-d6, 400 MHz): δ 7.56 (s, 1H), 7.37-7.21 (m, 4H), 6.74 (d, J=11.6 Hz, 2H), 6.61 (s, 1H), 6.4-6.2 (m, 1H), 5.20-5.06 (m, 1H), 4.85 (t, J=16.4 Hz, 1H), 4.60 (d, J=16.8 Hz, 1H), 4.58 (d, J=17.6, 1 H), 4.12-4.03 (m, 1H), 3.9-3.8 (m, 1H), 3.58-3.39 (m, 1H). LCMS: M/z: (M+1): 446

Synthesis of 2-(3,5-dichlorophenylamino)-1-(4-amino-3,4-dihydroisoquinolin-2(1H)-yl)ethanone To a mixture of N-(2-(2-(3,5-dichlorophenylamino)acetyl)-1,2,3,4-tetrahydroisoquinolin-4-yl)-2,2,2-trifluoroacetamide (0.45 g, 1.0 mmol), in aq. MeOH (15 mL) was added K₂CO₃ (1.0 g, 6.0 mmol) and the reaction mixture was heated to reflux for 2.5 h. The reaction mixture was concentrated in vacuo to give a residue which was purified by column chromatography (silica gel, gradient MeOH in DCM) to give (0.120 g, 35%) of the titled intermediate. ¹H NMR (DMSO-d6, 400 MHz): δ 7.30-7.19 (m, 3H), 7.05-6.95 (m, 1H), 9.71 (s, 1H), 6.45 (d, 2H, J=11.2 Hz), 5.19 (d, J=8.0 Hz, 1H), 4.65 (s, 1H), 4.89-3.99 (m, 2H), 3.85-3.69 (m, 3H), 3.3-3.2 (m, 2H). LCMS: M/z: (M+1):350

Synthesis of 2-(3,5-dichlorophenylamino)-1-(4-(7-tosyl-7H-pyrrolo[2,3-d]pyrimidin-4-ylamino)-3,4-dihydroisoquinolin-2(1H)-yl)ethanone To a solution of 2-(3,5-dichlorophenylamino)-1-(4-amino-3,4-dihydroisoquinolin-2(1H)-yl)ethanone (0.2 g, 0.6 mmol) in DMF was added 4-chloro-7-tosyl-7H-pyrrolo[2,3-d]pyrimidine (0.17 g, 0.57 mmol) and DIEA (0.11 g, 0.85 mmol). The reaction mixture was stirred at 90° C. overnight, the mixture was diluted with EtOAc (100 mL) and washed with water (20 mL×3). The EtOAc layer was concentrated in vacuo to give a mixture which was purified by column chromatography (silica gel, gradient EtOAc in Hexanes) to give (0.160 g, 57%) of the titled intermediate. ¹H NMR (CDCl₃, 400 MHz): δ 8.41 (s, 1H), 8.08 (s, 1H), 8.06 (s, 1H), 8.01 (s, 1H), 7.54 (d, 1H, J=3.6 Hz), 7.33-7.19 (m, 6H), 6.83-6.67 (m, 3H), 6.35 (s, 2H), 5.35-5.25 (m, 1H), 5.18 (d, J=16.4 Hz, 1H), 4.76 (d, J=16.4 Hz, 1H), 4.51 (dd, J=1.8, 16 Hz, 1H), 4.33 (t, J=1.8 Hz, 1H), 3.82 (dd, J=1.8, 10 Hz, 1H), 3.72 (d, J=5.2 Hz, 1H), 2.38 (s, 3H). LCMS: M/z: (M+1):621

Synthesis of 2-(3,5-dichlorophenylamino)-1-(4-(7H-pyrrolo[2,3-d]pyrimidin-4-ylamino)-3,4-dihydroisoquinolin-2(1H)-yl)ethanone To a solution of 2-(3,5-dichlorophenylamino)-1-(4-(7-tosyl-7H-pyrrolo[2,3-d]pyrimidin-4-ylamino)-3,4-dihydroisoquinolin-2(1H)-yl)ethanone (0.15 g, 0.24 mmol) in MeOH (4 mL) and water (1 mL) was added K₂CO₃ (0.133 g, 0.96 mmol) and heated to 60° C. for 2 h. The reaction mixture was concentrated in vacuo to give a residue that was purified by column chromatography (silica gel, gradient MeOH in DCM) to give (25 mg, 23%) of the titled compound. ¹H NMR (DMSO-d6, 400 MHz): δ 11.75 (s, 1H), 8.52 (s, 1H), 8.18 (s, 1H), 7.68-7.62 (m, 1H), 7.42-7.18 (4H, m), 6.71-6.56 (m, 3H), 5.19 (s, 1H), 5.06 (s, 1H), 4.23 (d, J=12 Hz, 1H) 4.12-3.94 (bs, 1H), 3.82-3.65 (m, 1H), 2.75 (m, 2H)
LCMS: M/z: (M+1):467 (M+23):489.

Example 107

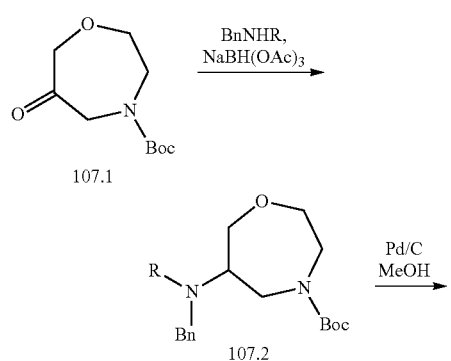

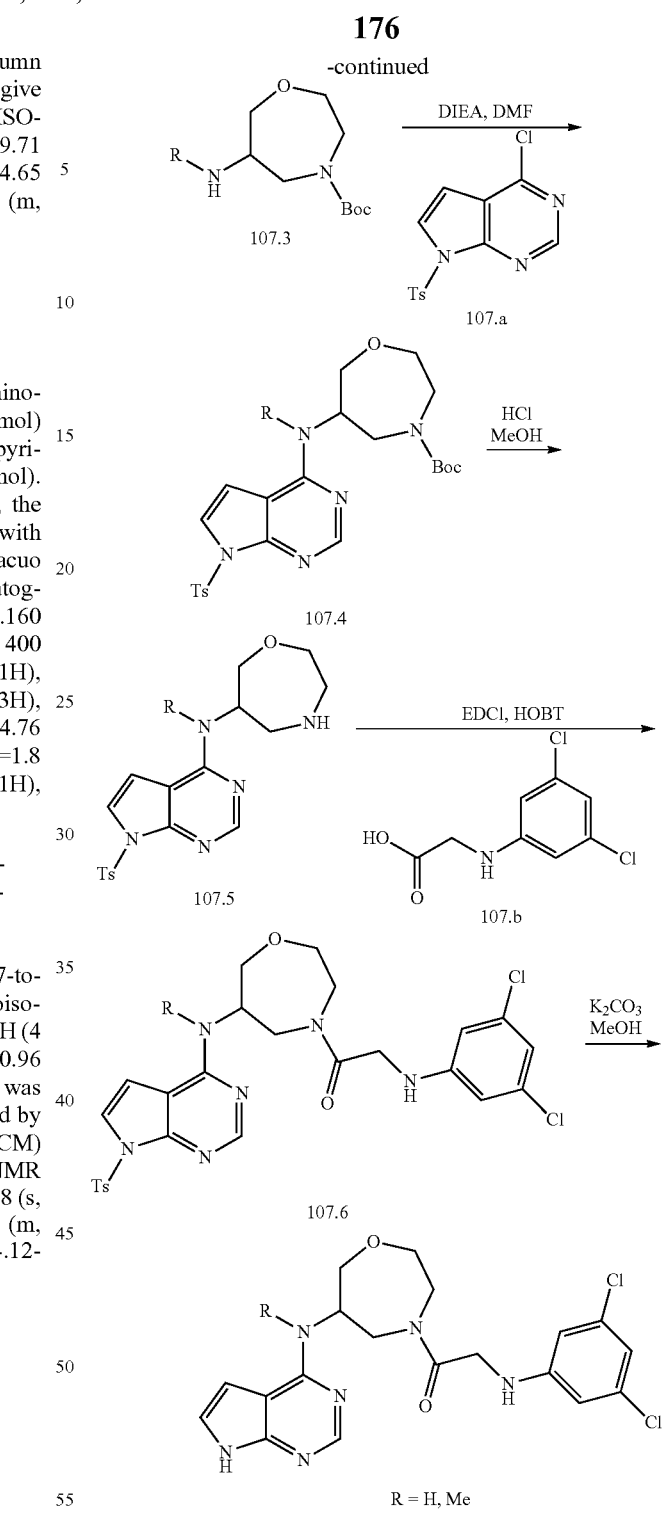

R = H, Me
107.7

Cmpd 107.2 (tert-butyl 6-(benzyl(methyl)amino)-1,4-oxazepane-4-carboxylate)

A solution of tert-butyl 6-oxo-1,4-oxazepane-4-carboxylate (1.30 g (6.04 mmol) 107.1 (prepared as described in WO2004074291) in DCM (20 mL) was treated with N-methyl-benzylamine (0.857 mL, 6.64 mmol) and stirred at rt for 30 min. Sodium triacetoxyborohydride (1.54 g, 7.25 mmol) was then added, and the reaction mixture was stirred at room temperature for 24 hr. Excess hydride was quenched by the addition of H₂O and the mixture was extracted with EtOAc (2×). The combined organic layers were dried with MgSO₄, filtered, and concentrated in vacuo, absorbing onto 8 g SiO₂. Purification by flash column chromatography (ISCO 40 g SiO₂, 20% EtOAc/Hexanes then gradient to 80% EtOAc/hexanes) afforded tert-butyl 6-(benzyl(methyl)amino)-1,4-oxazepane-4-carboxylate (0.759 g) 107.2 as a clear oil. ¹H NMR (400 MHz, CHLOROFORM-d) δ 7.35-7.28 (m, 4H), 7.27-7.19 (m, 1H), 4.19-4.10 (m, 1H), 4.06-4.03 (m, 1H), 3.99-3.95 (m, 1H), 3.87 (m, 1H), 3.77-3.75 (m, 2H), 3.64-3.56 (m, 1H), 3.50 (ddd, J=3.0, 9.9, 12.5 Hz, 1H), 3.26-3.12 (m, 2H), 3.11-2.98 (m, 1H), 2.33-2.22 (m, 3H), 1.53-1.33 (m, 9H); LCMS (ESI) m/z: 321.20 [M+H]⁺.

Cmpd 107.3 (tert-butyl 6-(methylamino)-1,4-oxazepane-4-carboxylate)

A solution of tert-butyl 6-(benzyl(methyl)amino)-1,4-oxazepane-4-carboxylate (0.795 g (2.48 mmol) 107.2 in MeOH (20 mL) was treated with 5% Pd/C (0.26 g) and HCO₂H (1 mL). The black suspension was stirred under a 60 PSI H₂ atmosphere for 22 hr. The catalyst was removed by filtration through celite and the filtrate was concentrated in vacuo to remove volatiles. The residue was diluted with EtOAc and washed with sat'd NaHCO3, dried over MgSO4, filtered, and concentrated to yield 0.tert-butyl 6-(methylamino)-1,4-oxazepane-4-carboxylate (0.17 g) 107.3 as a clear viscous oil that was used without further purification. ¹H NMR (400 MHz, CHLOROFORM-d) δ 3.82-3.60 (m, 5H), 3.59-3.48 (m, 1H), 3.47-3.33 (m, 3H), 3.26 (dd, J=6.5, 14.6 Hz, 1H), 2.93-2.82 (m, 2H), 2.46 (s, 3H), 1.48 (s, 9H); LCMS (ESI) m/z: 231.10 [M+H]⁻.

Cmpd 107.4 (tert-butyl 6-(methyl-(7-tosyl-7H-pyrrolo[2,3-d]pyrimidin-4-yl)amino)-1,4-oxazepane-4-carboxylate)

A solution of 4-chloro-7-(toluene-4-sulfonyl)-7H-pyrrolo[2,3-d]pyrimidine (110 mg (0.36 mmol) 107.a, of tert-butyl 6-(methylamino)-1,4-oxazepane-4-carboxylate (84 mg (0.36 mmol) X.3, and DIEA (0.127 mL (0.730 mmol) in DMF (2.8 mL) was heated at 90° C. in a sealed tube for 18 hr. The mixture was diluted with H₂O and extracted with EtOAc (2×). The combined organics were washed with H₂O and brine, dried over MgSO₄, filtered, and concentrated in vacuo, absorbing onto 4 g SiO₂. Purification by flash column chromatography (ISCO 24 g SiO₂, 10% EtOAc/hexanes then gradient to 80% EtOAc/hexanes) afforded tert-butyl 6-(methyl-(7-tosyl-7H-pyrrolo[2,3-d]pyrimidin-4-yl)amino)-1,4-oxazepane-4-carboxylate (0.142 g) 107.4 as a yellow glassy solid. LCMS (ESI) m/z: 502.20 [M+H]⁺.

Cmpd 107.5 (N-methyl-N-(7-tosyl-7H-pyrrolo[2,3-d]pyrimidin-4-yl)-1,4-oxazepan-6-amine)

A solution of tert-butyl 6-(methyl-(7-tosyl-7H-pyrrolo[2,3-d]pyrimidin-4-yl)amino)-1,4-oxazepane-4-carboxylate (0.142 g, 0.283 mmole) 107.4 in MeOH (5 mL) was treated with 4 M HCl in 1,4-Dioxane (0.28 mL (1.13 mmol) and stirred at rt for 24 hr. An additional of 4 M HCl in 1,4-dioxane (0.4 mL) was added and the mixture stirred for an additional 24 hr and then heated at 50° C. for 2 hours. The mixture was cooled to rt and concentrated in vacuo to give a residue was dissolved in DCM (10 mL) and 5 mL MeOH and neutralized by addition of 0.43 g of polymer-supported carbonate resin (3.5 mmol/g) and stirring at room temperature for 2 hours. The resin was removed by filtered through celite, and the filtrate was concentrated to dryness to yield 125.6 mg of N-methyl-N-(7-tosyl-7H-pyrrolo[2,3-d]pyrimidin-4-yl)-1,4-oxazepan-6-amine 107.5 as a yellowish solid glass that was used without further purification. LCMS (ESI) m/z: 402.20 [M+H]⁺.

Cmpd 107.6 (2-(3,5-dichlorophenylamino)-1-(6-(methyl(7-tosyl-7H-pyrrolo[2,3-d]pyrimidin-4-yl)amino)-1,4-oxazepan-4-yl)ethanone)

A mixture of N-methyl-N-(7-tosyl-7H-pyrrolo[2,3-d]pyrimidin-4-yl)-1,4-oxazepan-6-amine ((0.114 g (0.283 mmol) 107.5, (3,5-dichloro-phenylamino)-acetic acid (0.0685 g (0.311 mmol) 107.b, and 1-hydroxybenzotriazole hydrate (9 mg (0.057 mmol) were dissolved in DMF (4 mL). The resulting solution was treated with N-(3-dimethylaminopropyl)-N'-ethylcarbodiimide hydrochloride (60 mg, 0.311 mmol) and DIEA (100 uL (0.566 mmol) and stirred at rt for 24 hr. The mixture was diluted with H₂O and extracted with EtOAc (2×) and 1:1 EtOAc/THF (2×). The combined organics were washed with 10% citric acid and brine, dried over MgSO₄, filtered, and concentrated, absorbing onto 3 g SiO₂. Purification by flash column chromatography (ISCO 12 g SiO₂, 40% EtOAc/hex then gradient to 100% EtOAc) afforded (2-(3,5-dichlorophenylamino)-1-(6-(methyl(7-tosyl-7H-pyrrolo[2,3-d]pyrimidin-4-yl)amino)-1,4-oxazepan-4-yl)ethanone (0.179 g) 107.6 as a white solid. LCMS (ESI) m/z: 603.20 [M+H]⁺.

Cmpd 107.7 (2-(3,5-dichlorophenylamino)-1-(6-(methyl(7H-pyrrolo[2,3-d]pyrimidin-4-yl)amino)-1,4-oxazepan-4-yl)ethanone)

A solution of (2-(3,5-dichlorophenylamino)-1-(6-(methyl(7-tosyl-7H-pyrrolo[2,3-d]pyrimidin-4-yl)amino)-1,4-oxazepan-4-yl)ethanone (179 mg, 0.30 mmol) 107.6 in MeOH (3 mL) & H₂O (7 mL) was treated with of K₂CO₃ (0.205 g (1.48 mmol) and heated at 70° C. for 72 hours. The white suspension was cooled and diluted with H₂O. The precipitate was collected on a Whatman 0.45 urn nylon membrane filter and dried under vacuum. Purification by preparatory reverse-phase HPLC (CH₃N/H₂O/0.1% TFA as eluent) afforded 31 mg of the TFA salt of a 2-(3,5-dichlorophenylamino)-1-(6-(methyl(7H-pyrrolo[2,3-d]pyrimidin-4-yl)amino)-1,4-oxazepan-4-yl)ethanone 107.7 as a white solid that exists as a mixture of amide rotamers. ¹H NMR (400 MHz, DMSO-d₆) δ 12.69 (br. s., 1H), 8.37 (s, 1H), 7.47 (br. s., 1H), 6.79 (d, J=1.8 Hz, 1H), 6.69 (d, J=1.8 Hz, 1H), 6.64 (t, J=1.8 Hz, 1H), 5.09 (br. s., 1H), 4.25-4.11 (m, 2H), 4.10-3.98 (m, 2H), 3.98-3.88 (m, 1H), 3.84 (dd, J=5.5, 14.3 Hz, 2H), 3.38 (br. s., 3H); LCMS (ESI) m/z: 449.10 [M+H]⁺.

Diagnostic peaks for minor rotamer: 12.38 (br. s., 1H), 8.34 (s, 1H), 7.34 (br. s, 1H), 6.87 (m, 1H), 5.26 (br. s., 1H).

Example 108

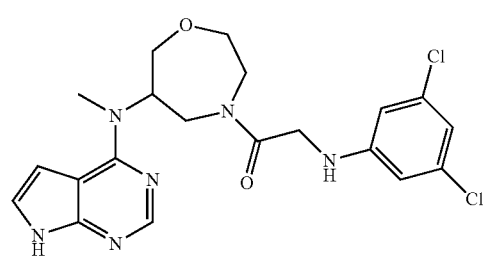 [SMILES: CN(c1ncnc2[nH]ccc12)C1COCCN(C(=O)CNc2cc(Cl)cc(Cl)c2)C1]

(2-(3,5-dichlorophenylamino)-1-(6-(methyl(7H-pyrrolo[2,3-d]pyrimidin-4-yl)amino)-1,4-oxazepan-4-yl)ethanone)

The title compound was prepared as previously described and exists as a mixture of rotational isomers. $^1$H NMR (400 MHz, DMSO-d$_6$) δ 12.69 (br. s., 1H), 8.37 (s, 1H), 7.47 (br. s., 1H), 6.78 (d, J=1.8 Hz, 2H), 6.66-6.61 (m, 2H), 5.09 (br. s., 1H), 4.30 (m, 1H), 4.25-4.10 (m, 2H), 4.03 (m, 2H), 3.84 (dd, J=5.5, 14.3 Hz, 1H), 3.37 (br. s., 3H); LCMS (ESI) m/z: 449.1 [M+H]$^+$.

Diagnostic peaks for rotational isomer: $^1$H NMR (400 MHz, DMSO-d$_6$) δ 12.37 (br. s., 1H), 8.33 (s, 1H), 7.37-7.27 (m, 1H), 6.89-6.83 (m, 1H), 6.69 (d, J=1.8 Hz, 1H), 5.25 (br. s., 1H).

Example 109

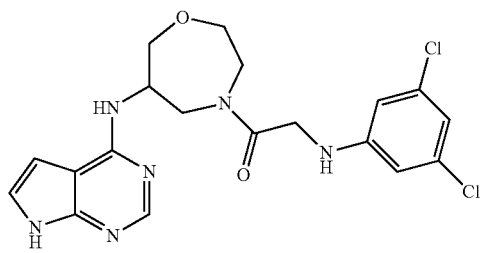 [SMILES: O=C(CNc1cc(Cl)cc(Cl)c1)N1CCOCC(Nc2ncnc3[nH]ccc23)C1]

(1-(6-(7H-pyrrolo[2,3-d]pyrimidin-4-ylamino)-1,4-oxazepan-4-yl)-2-(3,5-dichlorophenylamino)ethanone)

The title compound was prepared as previously described and isolated as the TFA salt. $^1$H NMR (400 MHz, DMSO-d$_6$) δ 12.55 (br. s., 1H), 9.09-8.90 (m, 1H), 8.33 (d, 0.1=14.8 Hz, 1H), 7.32 (br. s., 1H), 6.95-6.86 (m, 1H), 6.68 (d, J=1.8 Hz, 2H), 6.58 (br. s, 1H), 6.55 (td, J=1.8, 5.5 Hz, 1H), 4.59-4.42 (m, 1H), 4.12-3.84 (m, 5H), 3.79 (dd, J=5.1, 14.2 Hz, 3H), 3.69-3.50 (m, 2H), 3.37 (br. s., 1H); LCMS (ESI) m/z: 435.1 [M+H]$^+$.

Example 110

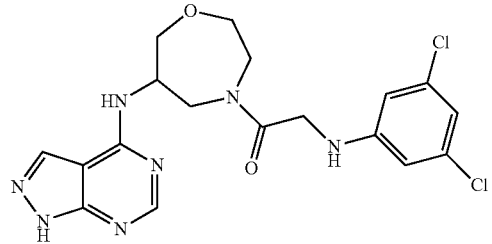 [SMILES: O=C(CNc1cc(Cl)cc(Cl)c1)N1CCOCC(Nc2ncnc3[nH]ncc23)C1]

(1-(6-(1H-pyrazolo[3,4-d]pyrimidin-4-ylamino)-1,4-oxazepan-4-yl)-2-(3,5-dichlorophenylamino)ethanone)

The title compound was prepared as previously described and isolated as the TFA salt. $^1$H NMR (400 MHz, DMSO-d$_6$) δ 8.35 (br. s., 1H), 6.72-6.62 (m, 2H), 6.61-6.51 (m, 3H), 4.65 (br. s., 2H), 4.03-3.85 (m, 4H), 3.83-3.72 (m, 3H), 3.69-3.46 (m, 2H), 3.42-3.30 (m, 1H); LCMS (ESI) m/z: 436.1 [M+H]$^+$.

Example 111

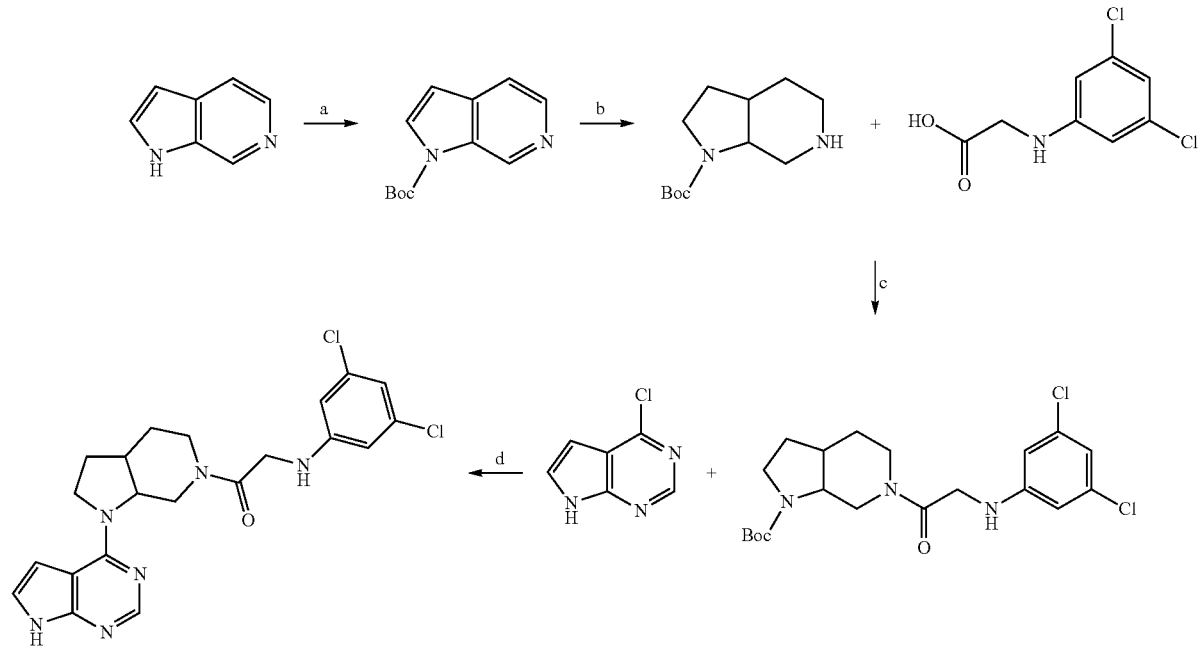

Reagents and conditions: a) Boc$_2$O, THF, rt, 15 h; b) H$_2$, PtO$_2$, AcOH, rt, 15 h; c) 2-(3,5-dichlorophenylamino)acetic acid, EDCI, HOBt, DIEA, DMF, rt, 5 h; d) Dioxane•HCl, rt, 2 h; e) 4-chloro-7-tosyl-7H-pyrrolo[2,3-d]pyrimidine, DIEA, DMF, 100° C., 5 h.

tert-Butyl 1H-pyrrolo[2,3-c]pyridine-1-carboxylate

To a solution of 1H-pyrrolo[2,3-c]pyridine (4 g, 34 mmol) in THF (40 mL) was added di-tert-butyldicarbonate (8.9 g, 41 mmol) at 0° C. The solution was stirred for 16 h at rt, concentrated in vacuo, diluted with water (100 mL) and extracted with EtOAc (2×50 mL). The combined organic phase was washed subsequently with water (50 mL), aqueous 5% citric acid (50 mL) and sat. NaHCO$_3$ (50 mL). The organic phase was separated, dried (Na$_2$SO$_4$), filtered and concentrated in vacuo to afford crude material which was purified by column chromatography (gradient hexane-EtOAc) to afford the named compound (7.2 g, 97% yield). $^1$H NMR (400 MHz, CDCl$_3$) δ=9.56-9.27 (m, 1H), 8.40 (d, J=5.3 Hz, 1H), 7.83-7.64 (m, 1H), 7.57-7.42 (m, 1H), 6.59 (d, J=3.5 Hz, 1H), 1.70 (s, 9H). LC/MS (m/z): calc'd. for C$_{12}$H$_{14}$N$_2$O$_2$ (M+1H) 219. found 219.

tert-butyl octahydro-1H-pyrrolo[2,3-c]pyridine-1-carboxylate

To a solution of tert-butyl 1H-pyrrolo[2,3-c]pyridine-1-carboxylate (0.5 g, 2.3 mmol) in AcOH (15 mL) was added PtO$_2$ (0.25 g, 1.1 mmol). The mixture was treated with an atmosphere of hydrogen atmosphere (60 psi) and stirred for 12 h at rt. The suspension was filtered through a pad celite and concentrated in vacuo to afford a residue. The crude material was diluted with ethyl acetate (50 mL) and washed with sat. NaHCO$_3$ (100 mL), the organic phase was separated, dried (Na$_2$SO$_4$) filtered and concentrated in vacuo to afford the title compound (0.53 g, 99% yield). $^1$H NMR (400 MHz, CDCl$_3$) δ=6.07-5.58 (m, 1H), 4.03-3.68 (m, 1H), 3.57-3.22 (m, 3H), 3.05-2.66 (m, 2H), 2.49-2.19 (m, 1H), 1.96 (s, 4H), 1.77-1.64 (m, 1H), 1.45 (s, 9H). LC/MS (m/z): calc; d. For C$_{12}$H$_{22}$N$_2$O$_2$ (M+1H) 227. found 227.2.

tert-Butyl 6-(2-(3,5-dichlorophenylamino)acetyl) octahydro-1H-pyrrolo[2,3-c]pyridine-1-carboxylate To a solution of tert-butyl octahydro-1H-pyrrolo[2,3-c]pyridine-1-carboxylate (0.43 g, 1.9 mmol) in DMF (6 mL) was added HOBt (0.25 g, 1.9 mmol) and N-(3-Dimethylaminopropyl)-N'-ethylcarbodiimide hydrochloride (0.54 g, 2.8 mmol) was added 0° C. and stirred for 10 min. A solution of the piperidine (0.43 g, 1.9 mmol), Et$_3$N (0.8 mL) in DMF (2 mL) was added dropwise and the solution was stirred at rt for 6 hr. The reaction mixture was diluted with water (50 mL) and EtOAc (50 mL), the organic phase was separated washed with sat. NaHCO$_3$ (50 mL), 5% aqueous citric acid (50 mL), dried (Na$_2$SO$_4$) and concentrated in vacuo to the crude material which was purified by column chromatography (gradient hexane-EtOAc) to afford the named compound (0.66 g, 80% yield). LC/MS (m/z): calcd. for C$_{20}$H$_{27}$Cl$_2$N$_3$O$_3$ (M+Na) 450. found 450.

2-(3,5-Dichloro-phenylamino)-1-[1-(7H-pyrrolo[2,3-d]pyrimidin-4-yl)-octahydro-pyrrolo[2,3-c]pyridin-6-yl]-ethanone A mixture of tert-butyl 6-(2-(3,5-dichlorophenylamino) acetyl)octahydro-1H-pyrrolo[2,3-c]pyridine-1-carboxylate (0.66 g, 1.55 mmol) and 4 N HCl (1.5 mL) in 1,4-dioxane (6 mL) was stirred for 2 h at rt. The mixture concentrated in vacuo and the residue was triturated with sat. NaHCO$_3$, extracted with EtOAc, dried (Na$_2$SO$_4$) and concentrated in vacuo to afford the amine which was used without further purification. A solution of the crude amine (0.23 g, 1.55 mmol), 4-chloro-7-tosyl-7H-pyrrolo[2,3-d]pyrimidine (0.58 g, 3.8 mmol) and Et$_3$N (0.65 mL, 4.5 mmol) in DMF (5 mL) was heated at 80° C. for 12 h, cooled to rt and diluted with water and EtOAc. The organic phase washed with sat. NaHCO$_3$, dried (Na$_2$SO$_4$), filtered and concentrated in vacuo to afford a residue which was purified by column chromatography (gradient CH$_2$Cl$_2$-MeOH) to afford the named compound (0.44 g, 65% yield). $^1$H NMR (400 MHz, DMSO-d$_6$) δ=12.88-12.25 (m, 1H), 8.29 (s, 1H), 7.56-7.24 (m, 1H), 7.17-6.95 (m, 1H), 6.71 (br. s., 2H), 6.56 (s, 2H), 4.69-4.47 (m, 1H), 4.37 (d, J=5.5 Hz, 1H), 4.14-3.52 (m, 5H), 3.22 (br. s., 1H), 2.95-2.70 (m, 1H), 2.64-2.50 (m, 1H), 2.35-2.14 (m, 1H), 2.12-1.85 (m, 2H), 1.85-1.56 (m, 1H). LC/MS (m/z): calcd. For C$_{21}$H$_{22}$Cl$_2$N$_6$O (M+1H) 445. found 445.

Example 112

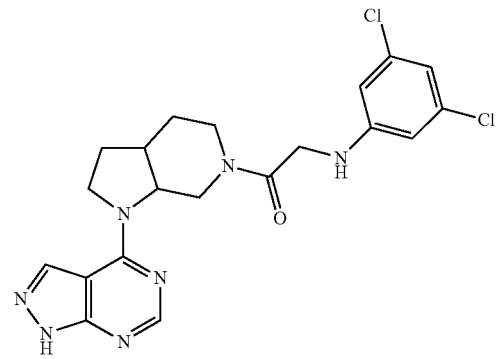 [SMILES: O=C(CNc1cc(Cl)cc(Cl)c1)N1CCC2CCN(c3ncnc4[nH]ncc34)C2C1]

1-(1-(1H-Pyrazolo[3,4-d]pyrimidin-4-yl)tetrahydro-1H-pyrrolo[2,3-c]pyridine-6(2H,7H,7aH)-yl)-2-(3,4-dichlorophenylamino)ethanone A solution of 2-(3,5-dichloro-phenylamino)-1-(octahydro-pyrrolo[2,3-c]pyridin-6-yl)-ethanone (0.14 g, 0.41 mmol), 4-chloro-1-(2-trimethylsilanyl-ethoxymethyl)-1H-pyrazolo[3,4-d]pyrimidine (0.12 g, 0.41 mmol) and Et$_3$N (0.12 mL, 0.8 mmol) in DMF (4 mL) was heated for 5 h at 70° C. The mixture diluted with EtOAc and washed with water, sat. NaHCO$_3$ and 5% aq citric acid, the organic phase dried (Na$_2$SO$_4$) and concentrated in vacuo to afford the SEM protected material which was used without further purification. The crude SEM deprotected cmpd was treated with a 25% ethanolic HCl solution (4 mL) for 2 h at rt, concentration in vacuo and the crude product purified by reversed phase chromatography (CH$_3$CN-water gradient) to afford the named compound (65 mg, 36% yield). $^1$H NMR (400 MHz, DMSO-d$_6$) δ=8.50-8.11 (m, 1H), 6.72 (br. s., 1H), 6.66 (s, 2H), 6.61-6.49 (m, 2H), 4.73-3.57 (m, 6H), 3.47-3.14 (m, 2H), 2.82-2.67 (m, 1H), 2.36-2.13 (m, 1H), 2.13-1.85 (m, 2H), 1.68 (m, 1H). LC/MS (m/z): calcd. For $C_{20}H_{21}Cl_2N_7O$ (M+1H) 447. found 447.2.

Example 113

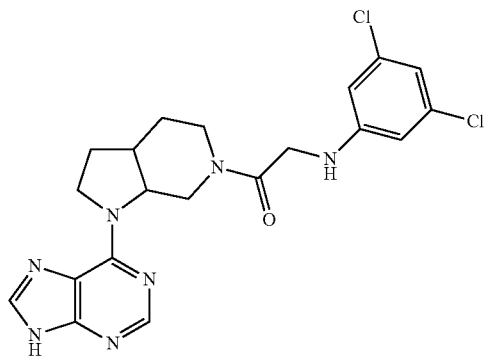 [SMILES: O=C(CNc1cc(Cl)cc(Cl)c1)N1CCC2CCN(c3ncnc4[nH]cnc34)C2C1]

1-(1-(9H-Purin-6-yl)tetrahydro-1H-pyrrolo[2,3-c]pyridine-6(2H,7H,7aH)-yl)-2-(3,4-dichlorophenylamino)ethanone A similar procedure was used as described for the synthesis 2-(3,5-Dichloro-phenylamino)-1-[1-(7H-pyrrolo[2,3-d]pyrimidin-4-yl)-octahydro-pyrrolo[2,3-c]pyridin-6-yl]-ethanone to afford the title compound (16 mg, 22% yield). $^1$H NMR (400 MHz, DMSO-$d_6$) δ=7.92 (s, 1H), 7.63-7.53 (m, 1H), 6.65 (d, J=1.5 Hz, 2H), 6.55 (s, 1H), 6.50 (s, 1H), 6.48-6.36 (m, 1H), 5.44-5.43 (m, 1H), 4.35-4.22 (m, 1H), 4.20-4.03 (m, 1H), 3.89 (br. s., 2H), 3.77 (d, J=6.5 Hz, 3H), 3.29-3.13 (m, 2H), 2.94-2.72 (m, 1H), 2.04 (none, 2H), 1.93-1.76 (m, 2H), 1.76-1.60 (m, 1H). LC/MS (m/z): calcd. for $C_{20}H_{21}Cl_2N_7O$ (M+1H) 447. found 447.1.

Example 114

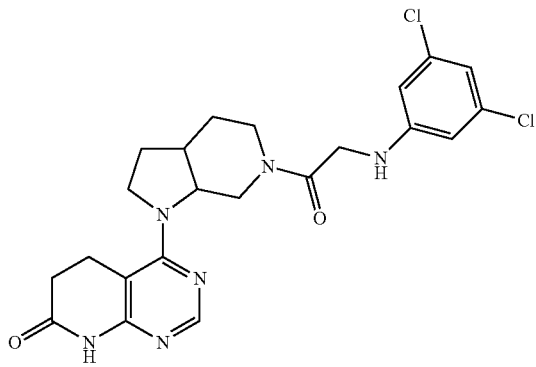 [SMILES: O=C1CCc2c(ncnc2N2CCC3CCN(C(=O)CNc4cc(Cl)cc(Cl)c4)CC32)N1]

4-(6-(2-(3,5-Dichlorophenylamine)acetyl)octahydro-1H-pyrrolo[2,3-c]pyridine-1-yl)5,6-dihydropyrido[2,3-d]pyrimidin-7(8H)-one A similar procedure was used as described for the synthesis 2-(3,5-Dichloro-phenylamino)-1-[1-(7H-pyrrolo[2,3-d]pyrimidin-4-yl)-octahydro-pyrrolo[2,3-c]pyridin-6-yl]-ethanone to afford the title compound (35 mg, 27% yield). $^1$H NMR (400 MHz, DMSO-$d_6$) δ=10.36 (d, J=3.3 Hz, 1H), 8.21 (s, 1H), 6.64 (d, J=1.5 Hz, 1H), 6.59-6.43 (m, 1H), 6.30 (d, J=1.3 Hz, 1H), 4.29-3.11 (m, 6H), 2.91 (d, J=11.0 Hz, 2H), 2.76-2.60 (m, 1H), 2.41-2.21 (m, 3H), 2.00 (s, 1H), 1.87-1.70 (m, 2H), 1.70-1.48 (m, 2H), 1.48-1.29 (m, 1H).). LC/MS (m/z): calcd. For $C_{22}H_{24}Cl_2N_6O_2$ (M+1H) 476. found 476.2.

Example 115

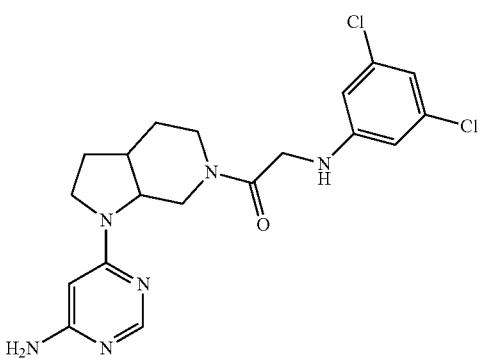 [SMILES: Nc1cc(N2CCC3CCN(C(=O)CNc4cc(Cl)cc(Cl)c4)CC32)ncn1]

1-(1-(6-Aminopyrimidin-4-yl)tetrahydro-1H-pyrrolo[2,3-c]pyridin-6(2H,7H,7aH)-yl-2-(3,5-dichlorophenylamino)ethanone A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone to afford the title compound (15 mg, 15% yield). $^1$H NMR (400 MHz, DMSO-$d_6$) δ=8.25 (s, 1H), 7.78-7.56 (m, 2H), 6.65 (d, J=1.3 Hz, 2H), 6.56 (br. s., 2H), 6.54-6.44 (m, 1H), 5.53-5.32 (m, 1H), 4.55-3.02 (m, 9H), 3.03-2.86 (m, 1H), 2.70-2.55 (m, 1H), 2.24-2.01 (m, 1H), 2.03-1.81 (m, 2H), 1.73-1.49 (m, 2H). LC/MS (m/z): calcd. For $C_{29}H_{22}Cl_2N_6O$ (M+1H) 421. found 421.1.

Example 116

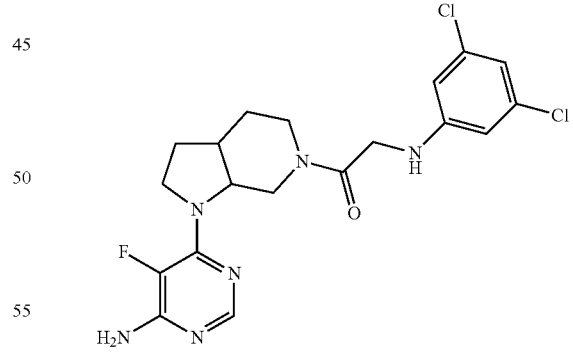

1-(1-(6-Amino-5-fluoropyrimidin-4-yl)tetrahydro-1H-pyrrolo[2,3-c]pyridin-6(2H,7H,7aH)-yl)-2-(3,5-dichlorophenylamino)ethanone A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone to afford the title compound (0.22 g, 30% yield). $^1$H NMR (400 MHz, DMSO-$d_6$) δ=8.25 (s, 1H), 7.74-7.51 (m, 2H), 6.65 (d, J=1.3 Hz, 2H), 6.56 (br. s., 1H), 6.51-6.41 (m, 1H), 5.51-5.30 (m, 1H), 4.53-3.08 (m, 9H), 3.03-2.86 (m, 1H), 2.70-2.55 (m, 1H), 2.24-2.01 (m, 1H), 2.03-1.81 (m, 2H), 1.73-1.49 (m, 2H). LC/MS (m/z): calcd. For $C_{19}H_{21}Cl_2FN_6O$ (M+1H) 439. found 439.1.

Example 117

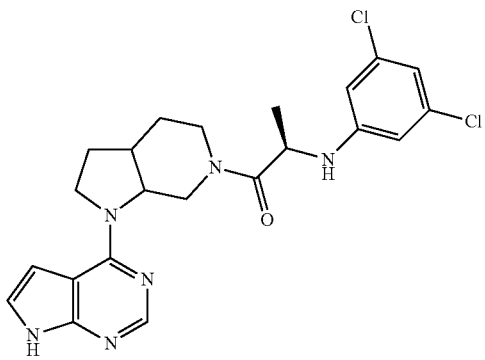 [SMILES: C[C@@H](Nc1cc(Cl)cc(Cl)c1)C(=O)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H,7aH)-yl)-2-(3,5-dichlorophenylamino)propan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-(3,5-dichlorophenylamino)-1-[1-(7H-pyrrolo[2,3-d]pyrimidin-4-yl)-octahydro-pyrrolo[2,3-c]pyridin-6-yl]propan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone to afford the title compound. $^1$H NMR (400 MHz, DMSO-$d_6$) δ=12.74 (br. s., 1H), 8.33 (s, 2H), 7.50 (br. s., 1H), 7.11 (br. s., 1H), 6.89-6.70 (m, 1H), 6.70-6.55 (m, 3H), 6.55-6.27 (m, 1H), 4.72-4.27 (m, 1H), 4.27-3.49 (m, 2H), 3.31 (br. s., 1H), 3.08-2.90 (m, 1H), 2.79 (br. s., 3H), 2.69-2.56 (m, 1H), 2.32 (dd, J=1.9, 3.6 Hz, 1H), 2.18-2.02 (m, 1H), 2.02-1.64 (m, 3H), 1.40-1.01 (m, 4H). LC/MS (m/z): calcd. For $C_{22}H_{24}Cl_2N_6O$ (M+1H) 459. found 459.2.

Example 118

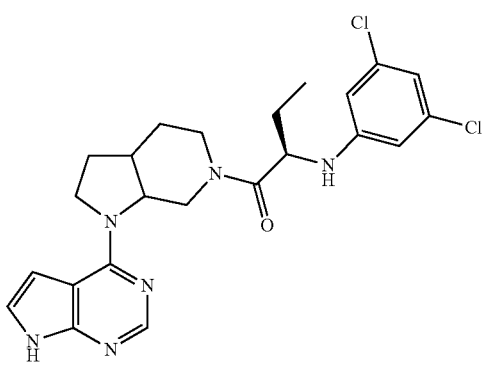 [SMILES: CC[C@@H](Nc1cc(Cl)cc(Cl)c1)C(=O)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H,7aH)-yl)-2-(3,5-dichlorophenylamino)butan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-(3,5-dichlorophenylamino)-1-[1-(7H-pyrrolo[2,3-d]pyrimidin-4-yl)-octahydro-pyrrolo[2,3-c]pyridin-6-yl]butan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone. $^1$H NMR (400 MHz, CDCl$_3$) δ=10.58 (br. s., 1H), 8.51-8.26 (m, 1H), 7.26 (s, 1H), 7.15-6.95 (m, 1H), 6.74-6.39 (m, 4H), 6.25 (d, J=1.5 Hz, 1H), 4.89 (d, J=8.3 Hz, 1H), 4.58-4.27 (m, 3H), 4.27-3.53 (m, 6H), 3.53-2.99 (m, 2H), 2.72-2.41 (m, 1H), 2.26-2.07 (m, 3H), 2.07-1.88 (m, 3H), 1.88-1.40 (m, 6H), 1.26 (t, J=7.2 Hz, 1H), 1.02 (t, J=7.3 Hz, 2H), 0.80 (t, 2H). LC/MS (m/z): calcd. For $C_{23}H_{26}Cl_2N_6O$ (M+1H) 473. found 473.2.

Example 119

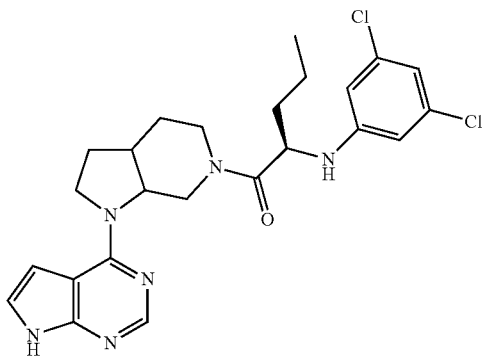 [SMILES: CCC[C@@H](Nc1cc(Cl)cc(Cl)c1)C(=O)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H,7aH)-yl)-2-(3,5-dichlorophenylamino)pentan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-(3,5-dichlorophenylamino)-1-[1-(7H-pyrrolo[2,3-d]pyrimidin-4-yl)-octahydro-pyrrolo[2,3-c]pyridin-6-yl]pentan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone. $^1$H NMR (400 MHz, CDCl$_3$) δ=10.42-9.95 (m, 1H), 8.47-8.26 (m, 1H), 7.17-6.90 (m, 1H), 6.61-6.46 (m, 1H), 6.46-6.12 (m, 1H), 5.91 (d, J=11.0 Hz, 1H), 4.86 (d, J=8.3 Hz, 1H), 4.61-4.24 (m, 2H), 4.24-3.83 (m, 3H), 3.83-3.62 (m, 1H), 3.58-3.11 (m, 2H), 2.69-2.48 (m, 1H), 2.28-2.06 (m, 2H), 2.06-1.08 (m, 4H), 1.07-0.84 (m, 2H), 0.74 (t, 2H). LC/MS (m/z): calcd. For $C_{24}H_{28}Cl_2N_6O$ (M+1H) 487. found 487.2.

Example 120

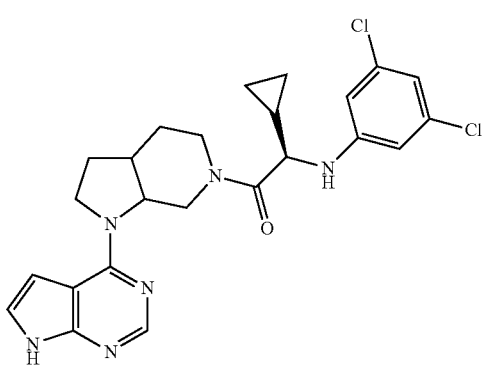 [SMILES: O=C([C@H](Nc1cc(Cl)cc(Cl)c1)C1CC1)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H,7aH)-yl)-2-cyclopropyl-(3,5-dichlorophenylamino)ethanone A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-cyclopropyl-(3,5-dichlorophenylamino)-1-[1-(7H-pyrrolo[2,3-d]pyrimidin-4-yl)-octahydro-pyrrolo[2,3-c]pyridin-6-yl]pentan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone. $^1$H NMR (400 MHz, DMSO-$d_6$) δ=11.37 (br. s., 1H), 7.98-7.75 (m, 1H), 6.89 (br. s., 1H), 6.59-6.14 (m, 3H), 5.52 (s, 1H), 4.56-4.27 (m, 1H), 4.03 (br. s., 2H), 3.83-3.37 (m, 3H), 2.13-1.91 (m, 2H), 1.91-1.38 (m, 3H), 1.04-0.80 (m, 2H), 0.35--0.25 (m, 4H). LC/MS (m/z): calcd. For $C_{24}H_{26}Cl_2N_6O$ (M+1H) 485. found 485.

Example 121

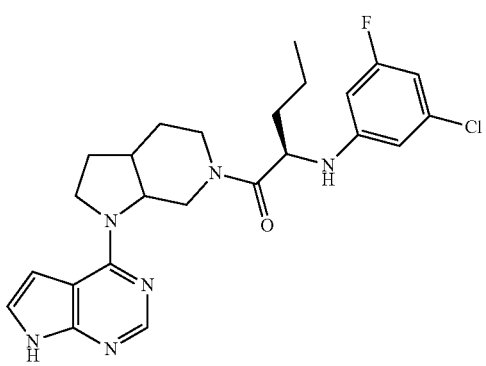 [SMILES: CCC[C@@H](Nc1cc(F)cc(Cl)c1)C(=O)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H, 7aH)-yl)-2-(3-chloro-5-fluorophenylamino)pentan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-(3-chloro-5-fluorophenylamino)-1-[1-(7H-pyrrolo[2,3-d]pyrimidin-4-yl)-octahydro-pyrrolo[2,3-c]pyridin-6-yl]pentan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone. $^1$H NMR (400 MHz, CDCL$_3$) δ=10.46-9.98 (m, 1H), 8.49-8.24 (m, 1H), 7.17-6.98 (m, 1H), 6.62-6.46 (m, 1H), 6.46-6.12 (m, 2H), 5.91 (d, J=11.0 Hz, 2H), 4.86 (d, J=8.3 Hz, 2H), 4.59-4.26 (m, 3H), 4.26-3.65 (m, 2H), 3.59-3.05 (m, 1H), 2.69-2.48 (m, 2H), 2.31-1.08 (m, 4H), 1.08-0.86 (m, 2H), 0.74 (t, 2H). LC/MS (m/z): calcd. For $C_{24}H_{28}ClFN_6O$ (M+1H) 470. found 470.2.

Example 122

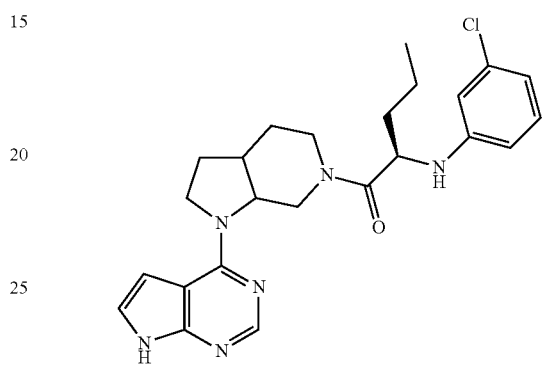

(2R)-1-(1-(7H-pyrrolo[2,3-d]pyrimidin-4-yl)tetrahydro-1H-pyrrolo[2,3-c]pyridine-6(2H,7H,7aH)-yl)-2-(3-chlorophenylamino)pentan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-2-(3-chlorophenylamino)-1-[1-(7H-pyrrolo[2,3-d]pyrimidin-4-yl)-octahydro-pyrrolo[2,3-c]pyridin-6-yl]pentan-1-one in place of 2-(3,5-dichloro-phenylamino)-1-[1-(7H-pyrrolo[2,3-d]pyrimidin-4-yl)-octahydro-pyrrolo[2,3-c]pyridin-6-yl]-ethanone. $^1$H NMR (400 MHz, CDCl$_3$) δ=10.40-10.08 (m, 1H), 8.47-8.28 (m, 1H), 7.17-6.95 (m, 2H), 6.82 (t, J=8.0 Hz, 1H), 6.73 (br. s., 1H), 6.65 (dd, J=8.2, 13.4 Hz, 1H), 6.60-6.49 (m, 1H), 6.44 (s, 1H), 6.16 (d, J=7.0 Hz, 1H), 4.72-4.29 (m, 2H), 4.29-3.65 (m, 3H), 3.54-3.13 (m, 1H), 2.57 (d, J=6.3 Hz, 1H), 2.31-1.11 (m, 8H), 1.11-0.84 (m, 2H), 0.74 (t, 1H). LC/MS (m/z): calcd. For $C_{24}H_{29}ClN_6O$ (M+1H) 454. found 454.2.

Example 123

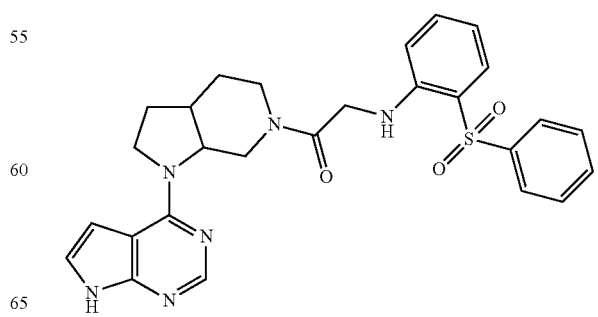

(2R)-1-(1-(7H-pyrrolo[2,3-d]pyrimidin-4-yl)tetrahydro-1H-pyrrolo[2,3-c]pyridine-6(2H,7H,7aH)-yl)-(2-(2-phenylsulfonyl)phenylamino)pentan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-(2-(2-phenylsulfonyl)phenylamino)-1-[1-(7H-pyrrolo[2,3-d]pyrimidin-4-yl)-octahydro-pyrrolo[2,3-d]pyridin-6-yl]ethanone in place of 2-(3,5-dichloro-phenylamino)-1-[1-(7H-pyrrolo[2,3-d]pyrimidin-4-yl)-octahydropyrrolo[2,3-c]pyridin-6-yl]-ethanone. $^1$H NMR (400 MHz, DMSO-$d_6$) δ=11.73-11.50 (m, 2H), 8.13 (s, 1H), 7.95 (s, 3H), 7.86-7.73 (m, 1H), 7.72-7.61 (m, 1H), 7.57 (d, J=7.5 Hz, 2H), 7.51-7.31 (m, 1H), 7.26-7.01 (m, 1H), 6.86-6.70 (m, 1H), 4.82-4.64 (m, 1H), 4.49-4.26 (m, 1H), 4.13-4.00 (m, 1H), 4.00-3.83 (m, 1H), 3.83-3.59 (m, 1H), 2.97-2.76 (m, 3H), 2.27-2.13 (m, 3H), 2.12-1.79 (m, 2H), 1.66 (m, 1H). LC/MS (m/z): calcd. For $C_2H_{28}N_6O_3S$ (M+1H) 517. found 517.2.

Example 124

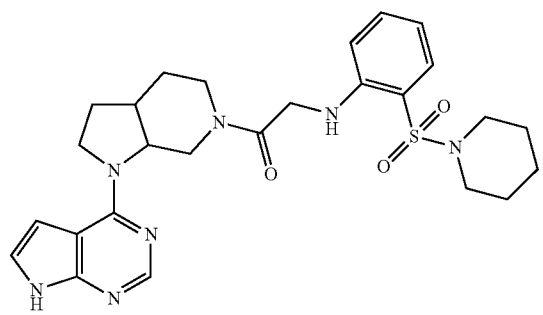 [SMILES: O=C(CNc1ccccc1S(=O)(=O)N1CCCCC1)N1CCC2CCN(c3ncnc4[nH]ccc34)C2C1]

(2R)-1-(1-(7H-pyrrolo[2,3-d]pyrimidin-4-yl)tetrahydro-1H-pyrrolo[2,3-c]pyridine-6(2H,7H,7aH)-yl)-(2-(2-piperidin-1-ylsulfonyl)phenylamino)pentan-1-one A similar procedure was used as described for the synthesis 2-(3,5-dichloro-phenylamino)-1-[1-(7H-pyrrolo[2,3-d]pyrimidin-4-yl)-octahydro-pyrrolo[2,3-c]pyridin-6-yl]-ethanone using (2R)-(2-(2-piperidin-1-ylsulfonyl)phenylamino)-1-[1-(7H-pyrrolo[2,3-d]pyrimidin-4-yl)-octahydro-pyrrolo[2,3-c]pyridin-6-yl]ethanone in place of 2-(3,5-dichloro-phenylamino)-1-[1-(7H-pyrrolo[2,3-d]pyrimidin-4-yl)-octahydropyrrolo[2,3-c]pyridin-6-yl]-ethanone. $^1$H NMR (400 MHz, DMSO-$d_6$) δ=11.67 (br. s., 1H), 8.33-8.11 (m, 1H), 7.63-7.47 (m, 2H), 7.15 (br. s., 2H), 6.95 (s, 1H), 6.77 (d, J=7.3 Hz, 2H), 4.87-4.66 (m, 1H), 4.57-4.35 (m, 1H), 4.06-3.90 (m, 2H), 3.90-3.71 (m, 2H), 3.13-2.94 (m, 4H), 2.92-2.78 (m, 2H), 2.36-2.19 (m, 4H), 2.17-2.01 (m, 4H), 1.61-1.36 (m, 4H). LC/MS (m/z): calcd. For $C_{26}H_{33}N_7O_3S$ (M+1H) 524. found 524.3.

Example 125

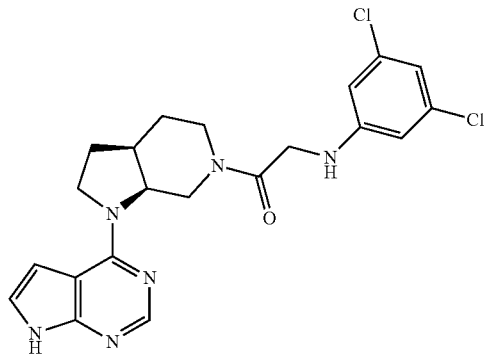 [SMILES: O=C(CNc1cc(Cl)cc(Cl)c1)N1CC[C@@H]2CCN(c3ncnc4[nH]ccc34)[C@@H]2C1]

1-((3aS,7aS)-1-(7H-Pyrrolo[2,3-d]pyrimidin-4-yl)tetrahydro-1H-pyrrolo[2,3-c]pyridine-6(2H,7H,7aH)-yl)-2-(3,5-dichlorophenylamino)ethanone The title compound was obtained from chiral separation of 2-(3,5-dichloro-phenylamino)-1-[1-(7H-pyrrolo[2,3-d]pyrimidin-4-yl)-octahydro-pyrrolo[2,3-c]pyridin-6-yl]-ethanone using SFC separation on a Chiralpak IC (3×15 cm) column. $^1$H NMR (400 MHz, DMSO-$d_6$) δ=11.73-11.48 (m, 1H), 8.24-7.97 (m, 1H), 7.12 (br. s., 1H), 6.76 (s, 2H), 6.67-6.47 (m, 2H), 6.33 (d, J=4.5 Hz, 1H), 4.65 (dd, J=5.3, 12.8 Hz, 1H), 4.29 (br. s., 1H), 4.07-3.87 (m, 3H), 3.75 (d, J=16.3 Hz, 3H), 3.29-3.15 (m, 1H), 2.79 (br. s., 1H), 1.99 (br. s., 2H), 1.89-1.51 (m, 1H), 1.34-1.04 (m, 1H). LC/MS (m/z): calcd. For $C_{26}H_{33}N_7O_3S$ (M+1H) 445. found 445.4.

Example 126

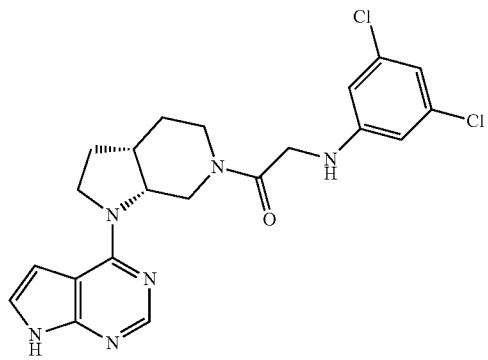 [SMILES: O=C(CNc1cc(Cl)cc(Cl)c1)N1CC[C@H]2CCN(c3ncnc4[nH]ccc34)[C@H]2C1]

1-((3aR,7aR)-1-(7H-Pyrrolo[2,3-d]pyrimidin-4-yl)tetrahydro-1H-pyrrolo[2,3-c]pyridine-6(2H,7H,7aH)-yl)-2-(3,5-dichlorophenylamino)ethanone The title compound was obtained from chiral separation of 2-(3,5-dichloro-phenylamino)-1-[1-(7H-pyrrolo[2,3-d]pyrimidin-4-yl)-octahydro-pyrrolo[2,3-c]pyridin-6-yl]-ethanone using SFC separation on a Chiralpak IC (3×15 cm) column.

¹H NMR (400 MHz, DMSO-d₆) δ=11.75-11.50 (m, 1H), 8.27-7.98 (m, 1H), 7.15 (br. s., 1H), 6.78 (s, 2H), 6.69-6.49 (m, 2H), 6.35 (d, J=4.5 Hz, 1H), 4.67 (dd, J=5.3, 12.8 Hz, 1H), 4.30 (br. s., 1H), 4.09-3.89 (m, 3H), 3.798 (d, J=16.3 Hz, 3H), 3.30-3.17 (m, 1H), 2.81 (br. s., 1H), 1.99 (br. s., 2H), 1.89-1.51 (m, 1H), 1.36-1.04 (m, 1H). LC/MS (m/z): calcd. For C₂₆H₃₃N₇O₃S (M+1H) 445. found 445.

Example 127

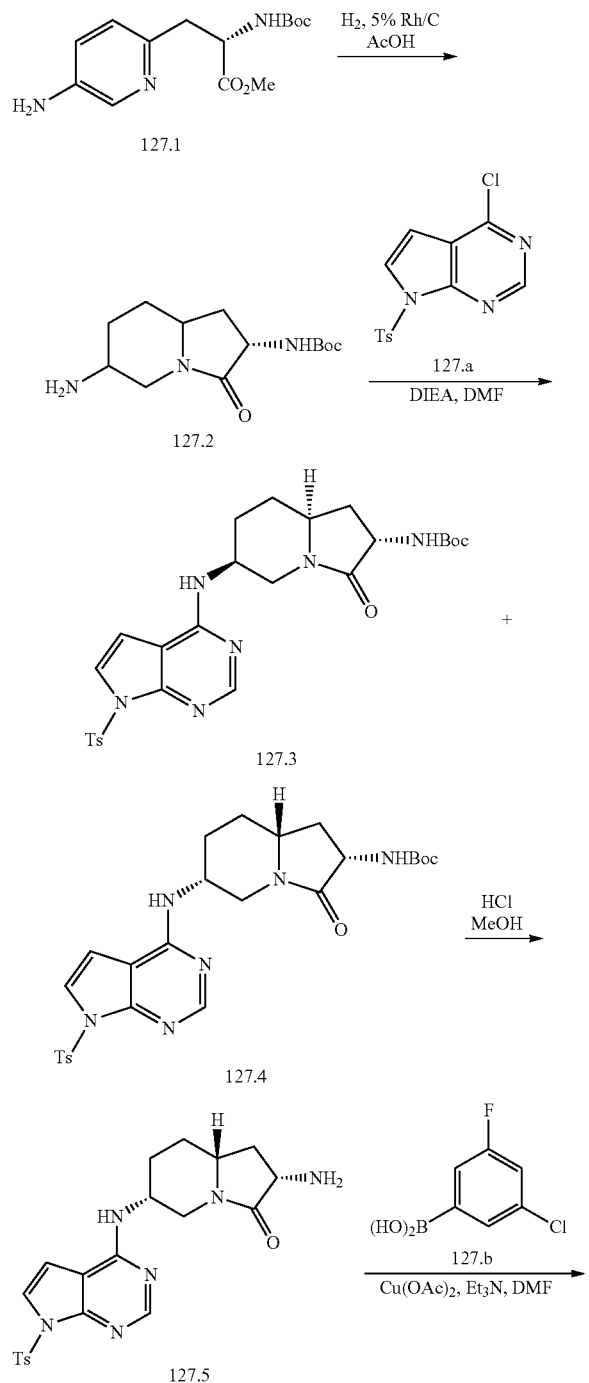

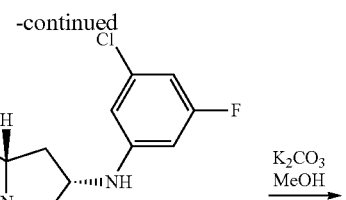

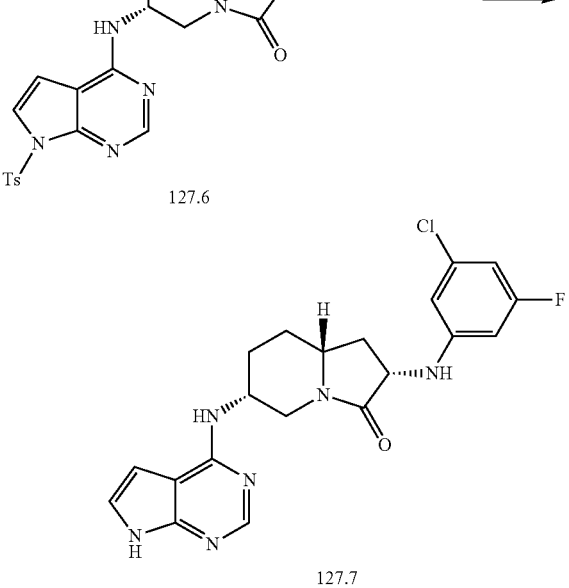

Cmpd 127.2 (tert-butyl(2S)-6-amino-3-oxooctahydroindolizin-2-ylcarbamate)

A solution of (S)-methyl 3-(5-aminopyridin-2-yl)-2-(tert-butoxycarbonylamino)propanoate (0.965 g, 3.27 mmol) 127.1 (prepared as described in WO2002068393) in glacial AcOH (40 mL) was treated with 5% Rh/C (0.67 g) and stirred at room temperature under a 60 psi H₂ atmosphere for 25 hr. The catalyst was removed by filtration through a celite pad, rinsing with MeOH. The filtrate was concentrated to dryness and azeotroped from toluene (2×). The residue was dissolved in MeOH (50 mL) and treated with polymer-supported carbonate resin (2.5 g, 3.5 mmole/g) and stirred at room temperature for 24 hr. The resin was removed by filtration and the filtrate concentrated in vacuo to afford of tert-butyl (2S)-6-amino-3-oxooctahydroindolizin-2-ylcarbamate (0.913 g) 127.2 as a clear viscous oil that was used without further purification. LCMS (ESI) m/z: 270.2 [M+H]⁺.

Cmpd 127.3 (tert-butyl(2S,6S,8aR)-3-oxo-6-(7-tosyl-7H-pyrrolo[2,3-d]pyrimidin-4-ylamino)octahydroindolizin-2-ylcarbamate) and Cmpd 127.4 (tert-butyl(2S,6R,8aS)-3-oxo-6-(7-tosyl-7H-pyrrolo[2,3-d]pyrimidin-4-ylamino)octahydroindolizin-2-ylcarbamate)

To a solution of tert-butyl(2S)-6-amino-3-oxooctahydroindolizin-2-ylcarbamate 127.2 (0.913 g, 3.39 mmol) in DMF (25 ml) and was added 4-chloro-7-tosyl-7H-pyrrolo[2,3-d]pyrimidine (100 mg (3.4 mmole) 127.a and DIEA (1.18 mL (6.78 mmole) at solution was heated 90° C. for 24 hr. After cooling to room temperature, the mixture was diluted with H₂O and washed with EtOAc (2×). The combined organics were washed with H₂O and brine, dried over MgSO₄, filtered, and concentrated in vacuo, absorbing onto 6 g silica gel.

Purification by flash column chromatography (ISCO 40 g SiO$_2$, 50% EtOAc/hexanes then gradient to 100% EtOAc/hexanes) yielded 0.52 g of tert-butyl (2S,6S,8aS)-3-oxo-6-(7-tosyl-7H-pyrrolo[2,3-d]pyrimidin-4-ylamino)octahydroindolizin-2-ylcarbamate 127.3 and 0.55 g of tert-butyl (2S,6R,8aR)-3-oxo-6-(7-tosyl-7H-pyrrolo[2,3-d]pyrimidin-4-ylamino)octahydroindolizin-2-ylcarbamate 127.4.

Compound 127.3 (tert-butyl (2S,6S,8aR)-3-oxo-6-(7-tosyl-7H-pyrrolo[2,3-d]pyrimidin-4-ylamino)octahydroindolizin-2-ylcarbamate)

$^1$H NMR (400 MHz, DMSO-d$_6$) δ 8.26 (s, 1H), 7.96 (d, J=8.3 Hz, 2H), 7.56 (d, J=4.0 Hz, 1H), 7.42 (d, J=8.0 Hz, 2H), 7.24 (d, J=5.0 Hz, 1H), 7.15 (d, J=8.8 Hz, 1H), 7.06 (d, J=3.8 Hz, 1H), 4.29 (br. s., 1H), 4.15-4.06 (m, 2H), 3.55-3.41 (m, 1H), 2.96-2.81 (m, 2H), 2.73 (m, 1H), 2.35 (s, 3H), 1.95 (dd, J=4.0, 9.3 Hz, 1H), 1.82 (m, 3H), 1.67-1.56 (m, 1H), 1.36 (s, 9H); LCMS (ESI) m/z: 541.3 [M+H]$^+$.

Compound 127.4 (tert-butyl (2S,6R,8aS)-3-oxo-6-(7-tosyl-7H-pyrrolo[2,3-d]pyrimidin-4-ylamino)octahydroindolizin-2-ylcarbamate)

$^1$H NMR (400 MHz, DMSO-d$_6$) δ 8.28 (s, 1H), 7.95 (d, J=8.3 Hz, 2H), 7.57 (d, J=3.8 Hz, 1H), 7.42 (d, J=8.0 Hz, 2H), 7.09-6.95 (m, 3H), 4.30 (br. s., 1H), 4.13 (d, J=12.8 Hz, 1H), 3.44-3.33 (m, 1H), 2.89 (m, 1H), 2.35 (s, 3H), 1.92 (d, J=13.3 Hz, 2H), 1.82 (dt, J=3.5, 13.3 Hz, 1H), 1.75 (d, J=15.8 Hz, 2H), 1.70-1.60 (m, 1H), 1.37 (s, 9H); LCMS (ESI) m/z: 541.3 [M+H]$^+$.

Compound 127.5 ((2S,6R,8aR)-2-amino-6-(7-tosyl-7H-pyrrolo[2,3-d]pyrimidin-4-ylamino)hexahydroindolizin-3(5H)-one)

A solution of tert-butyl (2S,6R,8aR)-3-oxo-6-(7-tosyl-7H-pyrrolo[2,3-d]pyrimidin-4-ylamino)-octahydroindolizin-2-ylcarbamate 127.4 (550 mg (1.02 mmole) in MeOH (21 mL) was treated with of 4 M HCl in 1,4-dioxane (4.0 mL (20.3 mmol) and stirred at room temperature for 23 hr. The mixture was concentrated to dryness, and the residue was dissolved in MeOH (20 ml) and treated with polymer-supported carbonate resin (1.2 g, 3.5 mmol/g). The suspension was stirred at room temperature for 1 hour. The resin was removed by filtration through a celite plug, and the filtrate was concentrated in vacuo to yield 414 mg of (2S,6R,8aR)-2-amino-6-(7-tosyl-7H-pyrrolo[2,3-d]pyrimidin-4-ylamino)hexahydroindolizin-3(5H)-one 127.5 as pale yellow solid that was used without further purification. $^1$H NMR (400 MHz, CHLOROFORM-d) δ 8.42 (s, 1H), 8.04 (d, J=8.3 Hz, 2H), 7.43 (d, J=4.0 Hz, 1H), 7.28 (d, J=8.8 Hz, 2H), 6.49 (d, J=3.8 Hz, 1H), 5.64-5.46 (m, 1H), 4.41 (br. s., 1H), 4.22 (d, J=14.1 Hz, 1H), 3.72-3.54 (m, 2H), 3.08 (dd, J=3.1, 13.9 Hz, 1H), 2.38 (s, 3H), 2.10 (ddd, 0.1=4.3, 8.7, 13.3 Hz, 1H), 2.04-1.91 (m, 1H), 1.90-1.61 (m, 4H), 1.47 (dd, J=2.9, 11.9 Hz, 1H); LCMS (ESI) m/z: 441.2 [M+H]$^+$.

Compound 127.6 ((2S,6R,8aR)-2-(3-chloro-5-fluorophenylamino)-6-(7-tosyl-7H-pyrrolo[2,3-d]pyrimidin-4-ylamino)hexahydroindolizin-3 (5H)-one)

A mixture of 3-chloro-5-fluorophenylboronic acid (44 mg, 0.25 mmole) 127.b, powdered 4 Å molecular sieves (0.3 g), cupric acetate (83 mg, 0.45 mmole), triethylamine (69 μL (0.68 mmole), and anhydrous THF (3 mL) was stirred under a N$_2$ atmosphere for 5 min. A solution of (2S,6R,8aR)-2-amino-6-(7-tosyl-7H-pyrrolo[2,3-d]pyrimidin-4-ylamino)hexahydroindolizin-3(5H)-one (0.1 g) 127.5 in anhydrous THF (1.5 mL) was added and the reaction mixture was stirred at room temperature for 24 hr and then heated at 60° C. for 48 hr. The mixture was diluted with EtOAc and filtered through a celite plug. The filtrate was concentrated in vacuo, absorbing onto 3 g silica gel. Purification by flash column chromatography (ISCO 24 g SiO$_2$, 40% EtOAc/hex then gradient to 100% EtOAc) afforded 19.4 mg of (2S,6R,8aR)-2-(3-chloro-5-fluorophenylamino)-6-(7-tosyl-7H-pyrrolo[2,3-d]pyrimidin-4-ylamino)hexahydroindolizin-3(5H)-one 127.6 as a white solid. LCMS (ESI) m/z: 569.2 [M+H]$^+$.

Compound 127.7 ((2S,6R,8aR)-6-(7H-pyrrolo[2,3-d]pyrimidin-4-ylamino)-2-(3-chloro-5-fluorophenylamino)hexahydroindolizin-3(5H)-one)

A solution of (2S,6R,8aR)-2-(3-chloro-5-fluorophenylamino)-6-(7-tosyl-7H-pyrrolo[2,3-d]pyrimidin-4-ylamino)hexahydroindolizin-3(5H)-one (19 mg) 127.6 in MeOH (0.5 mL) & H$_2$O (2 mL) was treated with of K$_2$CO$_3$ (5 mg, 0.033 mmol) and heated at 70° C. for 24 hours. The white suspension was cooled and diluted with H$_2$O. The precipitate was collected on a Whatman 0.45 um nylon membrane filter and concentrated in vacuo to afford of (2S,6R,8aR)-6-(7H-pyrrolo[2,3-d]pyrimidin-4-ylamino)-2-(3-chloro-5-fluorophenylamino)hexahydroindolizin-3(5H)-one 127.7 (7 mg) as a white solid that exists as 3:1 mixture of diasteromers. LCMS (ESI) m/z: 415.2 [M+H]$^+$.

Example 128

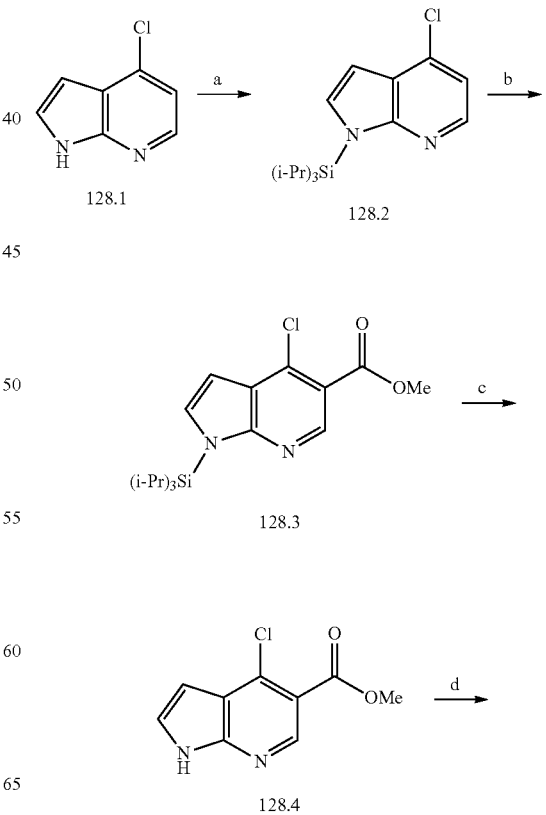

-continued

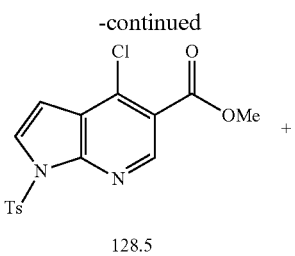
128.5

+

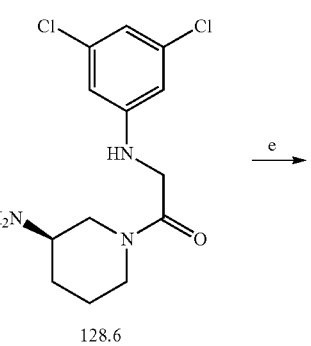
128.6

→ e

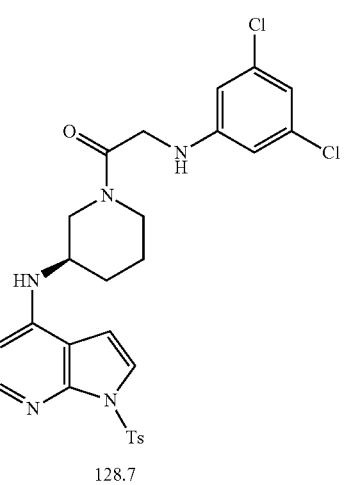
128.7

→ f

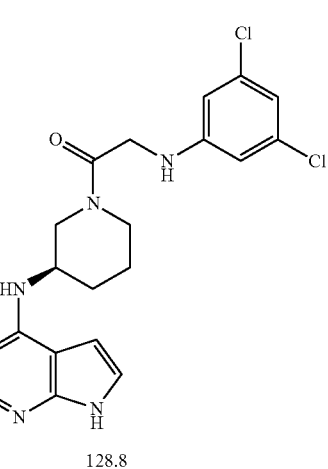
128.8

→ g

-continued

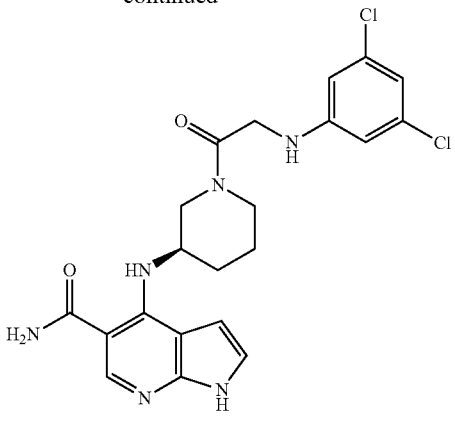
128.9

Reagents and conditions: (a) i. NaH, THF, rt, 30 min. ii. TIPSCl, 80° C., 3 h. (b) i. sec-BuLi, THF, -78° C., 30 min. ii. ClCOOCH$_3$, -78° C., 1 h. (c) TBAF, THF, rt, 16 h. (d) i. NaH, THF, 0° C., 30 min. ii. TsCl, 16 h, rt. (e) Pd(OAc)$_2$, X-Phos, Cs$_2$CO$_3$, PhCH$_3$, 100° C., 3 h. (f) i. Cs$_2$CO$_3$, THF/CH$_3$OH, rt, 16 h. ii. NaOH, CH$_3$OH/H$_2$O, 80° C., 10 h. (h) NH$_3$, HBTU, DIPEA, DMF, rt, 16 h.

Synthesis of methyl 4-chloro-1-(triisopropylsilyl)-1H-pyrrolo[2,3-b]pyridine-5-carboxylate To a solution of 4-chloro-1-(triisopropylsilyl)-1H-pyrrolo[2,3-b]pyridine in THF (50 mL) at -78° C. was added dropwise sec-BuLi (25 mL, 32.4 mmol, 1.3M in THF, 2.0 eq) under N$_2$. The reaction mixture was stirred for 30 min followed by the addition of ClCOOCH$_3$ (2.28 g, 24.3 mmol, 1.5 eq) was then allowed to warm to rt for 1 h. The mixture was quenched with MeOH (20 mL), the solvent was removed in vacuo and the residue was purified by silica gel column chromatography (PE/EA=50:1) to afford 128.2 colorless oil (5.46 g, yield: 92%). $^1$H NMR (400 MHz, DMSO-d$_6$) δ: 8.80 (s, 1H), 7.36 (d, 1H), 6.77 (d, 1H), 3.96 (s, 3H), 1.88-1.80 (m, 3H), 1.05-0.91 (m, 18H). ESI-MS: 367.1 (M+H)+.

Synthesis of methyl 4-chloro-1H-pyrrolo[2,3-b]pyridine-5-carboxylate

To a solution of methyl 4-chloro-1-(triisopropylsilyl)-1H-pyrrolo[2,3-b]pyridine-5-carboxylate (7 g, 19 mmol, 1.0 eq) in THF (40 mL) was added TBAF (4.98 g, 19 mmol, 1.0 eq). The mixture was stirred at rt for 16 h and concentrated in vacuo to afford a residue which was purified by silica gel column chromatography (PE/EA=10:1) to give 128.4 a white solid (1.758 g, yield: 43%). $^1$H NMR (400 MHz, CDCl$_3$) δ: 10.21 (s, 1H), 8.89 (s, 1H), 7.43 (d, 1H), 6.76 (d, 1H), 3.99 (s, 3H). ESI-MS: 211.1 (M+H)$^+$.

Synthesis of methyl 4-chloro-1-tosyl-1H-pyrrolo[2,3-b]pyridine-5-carboxylate

Sodium hydride (341 mg, 8.53 mol, 1.2 eq) was added in portions to a solution of methyl 4-chloro-1H-pyrrolo[2,3-b]pyridine-5-carboxylate (1.5 g, 7.1 mmol, 1.0 eq) in THF (20 mL). The suspension was stirred at 0° C. for 30 min, then a solution of 4-methylbenzene-1-sulfonyl chloride (2.7 g, 14.2 mmol, 2.0 eq) in THF (10 mL) was added at 0° C. The resulting suspension was stirred at this temperature for 15 min and 1 h at room temperature. The suspension was filtered through Celite. The filtrate was diluted with EtOAc (200 mL), washed with brine (100 mL×3). The combined organic layer was dried (MgSO₄) and concentrated in vacuo to afford a residue which was purified by silica gel column chromatography (PE/EA=10:1) to give 128.5 a white solid (1.6 g, yield: 60%). ¹H NMR (400 MHz, DMSO-d₆) δ: 8.84 (s, 1H), 8.12 (d, 1H), 8.06 (d, 2H), 7.46 (d, 2H), 6.98 (d, 1H), 3.93 (s, 3H), 2.39 (s, 3H). ESI-MS: 365.0 (M+H)+.

Synthesis of (R)-methyl 4-((1-(2-((3,5-dichlorophenyl)amino)acetyl)piperidin-3-yl)amino)-1-tosyl-1H-pyrrolo[2,3-b]pyridine-5-carboxylate To a solution of methyl 4-chloro-1-tosyl-1H-pyrrolo[2,3-b]pyridine-5-carboxylate (1.35 g, 3.70 mmol, 1.0 eq), (R)-1-(3-aminopiperidin-1-yl)-2-((3,5-dichlorophenyl)amino)ethanone (1.34 g, 4.44 mmol, 1.2 eq) in PhCH₃ (10 mL) was added Pd(OAc)₂ (83 mg, 0.370 mmol, 0.1 eq), xantphos (250 mg, 0.43 mmol, 0.15 eq) and Cs₂CO₃ (2.82 g, 8.64 mmol, 3.0 eq) and the mixture was heated at 100° C. for 16 h. The reaction was cooled to rt, filtered through Celite, and concentrated in vacuo to afford a residue which was purified by silica gel column chromatography (PE/EA=10:1) to give brown solid (451 mg, yield: 21%). 1H NMR (400 MHz, CDCl3) δ: 8.90 (d, 1H), 8.74~8.73 (m, 1H), 8.01~7.94 (m, 2H), 7.54~7.48 (m, 1H), 7.21~7.19 (m, 2H), 6.75 (d, 1H), 6.69~6.68 (m, 1H), 6.42~6.32 (m, 2H), 5.11~5.10 (m, 1H), 4.42~4.38 (m, 1H), 3.92~3.75 (m, 5H), 3.56~3.52 (m, 2H), 3.23~3.20 (m, 1H), 3.09~3.03 (m, 1H), 2.30 (m, 3H), 2.14~2.10 (m, 1H), 1.86~1.72 (m, 1H), 1.69~1.57 (m, 2H). ESI-MS: 630.0 (M+H)+.

Synthesis of (R)-methyl 4-((1-(2-(3,5-dichlorophenyl)amino)acetyl)piperidin-3-yl)amino)-1H-pyrrolo[2,3-b]pyridine-5-carboxylate To a solution of (R)-methyl 4-((1-(2-((3,5-dichlorophenyl)amino)acetyl)piperidin-3-yl)amino)-1-tosyl-1H-pyrrolo[2,3-b]pyridine-5-carboxylate (430 mg, 0.60 mmol, 1 eq) in THF (20 mL) and water (20 mL) was added Cs₂CO₃ (588 mg, 1.80 mmol, 3.0 eq). The mixture was stirred at room temperature for 16 h. The solvent was concentrated in vacuo to afford a residue which was purified by silica gel column (PE/ethyl acetate=2:1) to give yellow solid (305 mg, yield: 94%). ¹H NMR (400 MHz, DMSO-d₆) b: 11.80~11.74 (m, 1H), 8.86 (d, 1H), 8.54 (s, 1H), 7.23~7.18 (m, 1H), 6.78~6.52 (m, 4H), 6.3~66.30 (m, 1H), 4.36~4.27 (m, 1H), 3.99~3.70 (m, 8H), 3.50~3.47 (m, 2H), 2.10~2.05 (m, 1H), 1.71~1.68 (m, 3H). ESI-MS: 476.0 (M+H)

Synthesis of (R)-4-((1-(2-((3,5-dichlorophenyl)amino)acetyl)piperidin-3-yl)amino)-1H-pyrrolo[2,3-b]pyridine-5-carboxylic acid To a solution of (R)-methyl 4-((1-(2-((3,5-dichlorophenyl)amino)acetyl)piperidin-3-yl)amino)-1H-pyrrolo[2,3-b]pyridine-5-carboxylate (173 mg, 0.36 mmol, 1.0 eq) in CH₃OH (20 mL) and water (10 mL) was added NaOH (73 mg, 1.82 mmol, 5.0 eq). The mixture was stirred at 80° C. for 10 h, cooled to rt, adjusted pH to 6 with HCl (1N) the aqueous layer was extracted with EtOAc (50 mL×3). The organic layer was separated and concentrated in vacuo to afford the title compound as a yellow solid which was used to next step without further purification (120 mg, yield: 71%) to use next step. ¹H NMR (400 MHz, CD₃OD) δ: 8.6~88.63 (m, 1H), 7.37~7.32 (m, 1H), 7.02~6.95 (m, 1H), 6.6~06.57 (m, 2H), 6.34 (s, 1H), 4.57~4.41 (m, 1H), 4.10~3.75 (m, 5H), 3.65~0.362 (m, 1H), 2.22~2.21 (m, 1H), 2.04~1.79 (m, 3H). ESI-MS: 462.1 (M+H)

Synthesis of (R)-4-((1-(2-((3,5-dichlorophenyl)amino)acetyl)piperidin-3-yl)amino)-1H-pyrrolo[2,3-b]pyridine-5-carboxamide To a solution of (R)-4-((1-(2-(3,5-dichlorophenyl)amino)acetyl)piperidin-3-yl)amino)-1H-pyrrolo[2,3-b]pyridine-5-carboxylic acid (60 mg, 0.13 mmol, 1.0 eq) and ammonia in 1,4-dioxane (90 mL, 0.8 mmol, 6.0 eq) in DMF (6 mL) were added HBTU (98 mg, 0.26 mmol, 2.0 eq) and DIPEA (50 mg, 0.39 mmol, 3.0 eq) respectively. The resulting mixture was stirred at rt for 16 h. Then the solvent was removed under reduced pressure. The crude product was purified by prep-HPLC (MeOH/H₂O with 0.05% TFA as mobile phase) to give 128.9 as a brown yellow solid (22 mg, yield: 22%). ¹H NMR (400 MHz, CD₃OD) δ: 8.44 (s, 1H), 7.36-7.29 (m, 1H), 6.99-6.92 (m, 1H), 6.60-6.56 (m, 2H), 6.38 (m, 1H), 4.53-4.39 (m, 1H), 4.09-3.80 (m, 4H), 3.64-3.62 (m, 1H), 2.20-2.17 (m, 1H), 2.02-1.77 (m, 3H). ESI-MS (M+H)+: 461.0.

Example 129

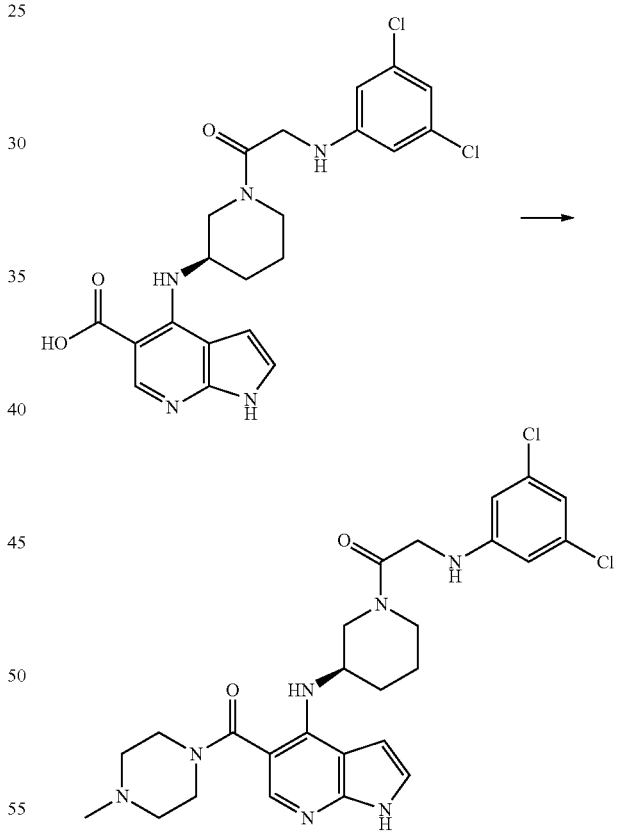

Synthesis of (S)-2-((3,5-dichlorophenyl)amino)-1-(3-((5-(4-methylpiperazine-1-carbonyl)-1H-pyrrolo[2,3-b]pyridin-4-yl)amino)piperidin-1-yl)ethanone A similar procedure was used as described for the synthesis of 128.9 to afford the title compound (21 mg, 30%). ¹H NMR (400 MHz, CD₁OD) δ: 8.10 (s, 1H), 7.36 (d, 1H), 6.98 (d, 1H), 6.63 (s, 2H), 6.44 (s, 1H), 4.40~4.39 (m, 2H), 4.14~3.93

(m, 5H), 3.64~3.36 (m, 6H), 3.32~3.10 (m, 1H), 2.90 (s, 3H), 2.1~92.17 (m, 4H), 2.01~1.85 (m, 4H). ESI-MS (M+H): 544.0.

Example 130

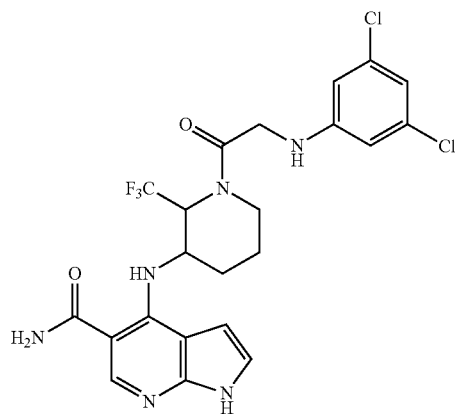 [SMILES: NC(=O)c1cnc2[nH]ccc2c1NC1CCCN(C(=O)CNc2cc(Cl)cc(Cl)c2)C1C(F)(F)F]

Synthesis of 4-((1-(2-((3,5-dichlorophenyl)amino)acetyl)-2-(trifluoromethyl)piperidin-3-yl)amino)-1H-pyrrolo[2,3-b]pyridine-5-carboxamide The title compound was obtained using the same procedure as described in Example 128 except (R)-1-(3-aminopiperidin-1-yl)-2-((3,5-dichlorophenyl)amino)ethanone was substituted with 1-(3-amino-2-(trifluoromethyl)piperidin-1-yl)-2-((3,5-dichlorophenyl)amino)ethanone. $^1$H NMR (400 MHz, DMSO-$d_6$) δ: 11.63 (s, 1H), 10.00 (d, 1H), 8.41 (s, 1H), 7.84 (br s, 1H), 7.16 (s, 1H), 7.06 (br s, 1H), 6.76 (s, 2H), 6.63 (s, 1H), 6.52-6.46 (m, 2H), 5.77-5.68 (m, 1H), 4.47-4.36 (m, 1H), 4.22-3.99 (m, 3H), 3.09-2.98 (m, 1H), 2.15-2.05 (m, 4H), 1.92-1.78 (m, 3H). ESI-MS: 528.9 (M+H)+.

Example 131

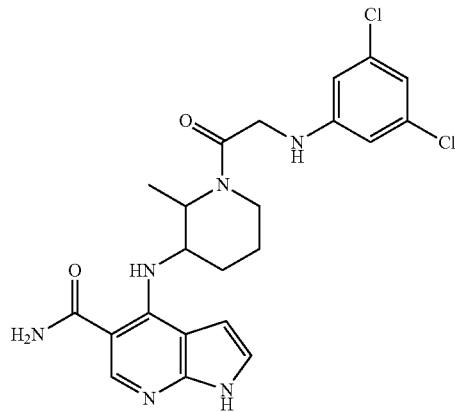 [SMILES: CC1C(Nc2c(C(N)=O)cnc3[nH]ccc23)CCCN1C(=O)CNc1cc(Cl)cc(Cl)c1]

Synthesis of 4-((1-(2-((3,5-dichlorophenyl)amino)acetyl)-2-(tmethyl)piperidin-3-yl)amino)-1H-pyrrolo[2,3-b]pyridine-5-carboxamide The title compound was obtained using the same procedure as described in Example 128 except (R)-1-(3-aminopiperidin-1-yl)-2-((3,5-dichlorophenyl)amino)ethanone was substituted with 1-(3-amino-2-methylpiperidin-1-yl)-2-((3,5-dichlorophenyl)amino)ethanone to yield title compound (54 mg, yield: 25%). $^1$H NMR (400 MHz, DMSO-$d_6$) δ: 11.60-11.58 (m, 1H), 9.76-9.74 (m, 1H), 8.43 (d, 1H), 7.88 (s, 1H), 7.15 (d, 1H), 6.80 (s, 1H), 6.73-6.58 (m, 2H), 6.42 (s, 1H), 5.13 (t, 1H), 4.37-3.77 (m, 4H), 3.19 (s, 1H), 2.91 (s, 1H), 1.98-1.89 (m, 4H), 1.78-1.59 (m, 2H), 1.25-1.06 (m, 3H). ESI-MS: 475.1 (M+H)$^+$.

Example 132

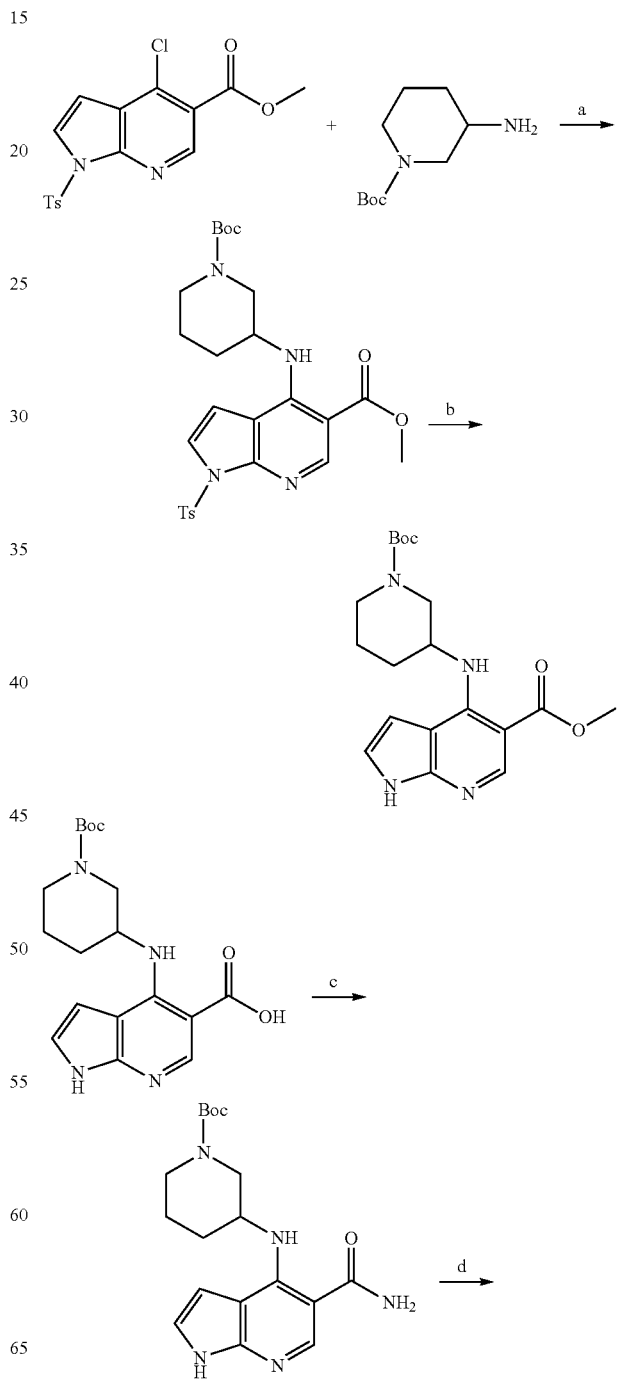

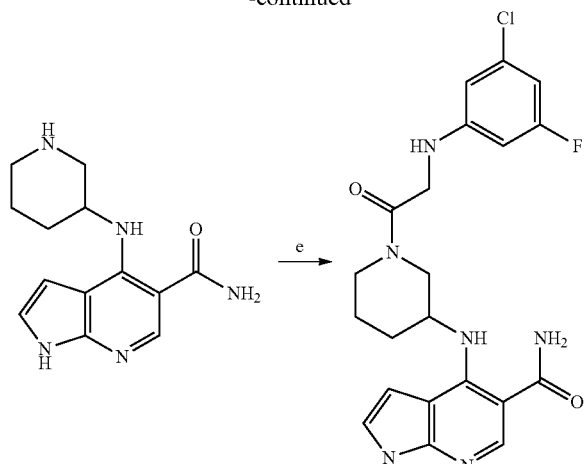

Reagents and conditions: (a) Pd(OAc)$_2$, Xantphos, Cs$_2$CO$_3$, PhCH$_3$, 100 C., 16 h. (b) i. Cs$_2$CO$_3$, THF/MeOH. ii. NaOH, MeOH/water, 80° C. (c) HBTU, DIEA, NH$_4$Cl, DMF, 80° C. 18 h. (d) TFA/DCM. (e) HBTU, Et$_3$N, 80° C.

Synthesis of methyl 4-((1-(tert-butoxycarbonyl)piperidin-3-yl)amino)-1-tosyl-1H-pyrrolo[2,3-b]pyridine-5-carboxylate To a solution of methyl 4-chloro-1-tosyl-1H-pyrrolo[2,3-b]pyridine-5-carboxylate (1 g, 2.7 mmol, 1.0 eq) and tert-butyl 3-aminopiperidine-1-carboxylate (659 mg, 3.3 mmol, 1.2 eq) in PhCH$_3$ (20 mL) was added Pd(OAc)$_2$ (65 mg, 0.27 mmol, 0.1 eq), xantphos (250 mg, 0.41 mmol, 0.15 eq) and Cs$_2$CO$_3$ (2.64 g, 8.1 mmol, 3.0 eq) and the mixture was heated at 100° C. for 16 h. After cooling to rt, the mixture was filtered and the filtrate was concentrated in vacuo to afford an oil which was purified by silica gel column chromatography (PE/EA=8:1) to give the title compound as white solid (667 mg, yield: 46%). $^1$H NMR (400 MHz, CDCl$_3$) δ: 8.91 (d, 1H), 8.72 (s, 1H), 7.96 (d, 2H), 7.45 (d, 1H), 7.18 (d, 2H), 3.77 (s, 3H), 3.67-3.57 (m, 1H), 3.13-2.97 (m, 2H), 2.29 (s, 3H), 1.98-1.96 (m, 2H), 1.83-1.67 (m, 2H), 1.64-1.46 (m, 3H), 1.40-1.25 (m, 9H). ESI-MS (M+H)+: 529.20.

Synthesis of methyl 4-((1-(tert-butoxycarbonyl)piperidin-3-yl)amino)-1H-pyrrolo[2,3-b]pyridine-5-carboxylate A mixture of methyl 4-((1-(tert-butoxycarbonyl)piperidin-3-yl)amino)-1-tosyl-1H-pyrrolo[2,3-b]pyridine-5-carboxylate (667 mg, 1.26 mmol, 1.0 eq) and Cs$_2$CO$_3$ (824 mg, 2.52 mmol) in THF/MeOH (1:1, 5 mL) was stirred at rt for 16 h. The solvent was removed in vacuo and the residue suspended in H$_2$O/MeOH (1:1, 5 mL) and treated with NaOH (77 mg, 1.92 mmol, 2 eq) and then heated to 80° C. for 16. The solvent was reduced in vacuo and adjusted to pH 4-5. The precipitate was filtered to give the title compound (263 mg, yield: 76%) as a brown solid which was used without further purification. ESI-MS (M+H) 361.18.

Synthesis of methyl 4-((1-(tert-butoxycarbonyl)piperidin-3-yl)amino)-1-tosyl-1H-pyrrolo[2,3-b]pyridine-5-carboxylate To a solution of methyl 4-((1-(tert-butoxycarbonyl)piperidin-3-yl)amino)-1H-pyrrolo[2,3-b]pyridine-5-carboxylate (263 mg, 0.73 mmol, 1.0 eq) and NH$_4$Cl (77 mg, 1.46 mmol, 2.0 eq) in DMF (6 mL) was added HBTU (553 mg, 1.46 mmol, 2.0 eq) and DIPEA (188 mg, 1.46 mmol, 2 eq). The reaction mixture was stirred at 80° C. for 16 h and the solvent was removed under in vacuo to afford a residue which was purified by prep-HPLC (MeOH/H$_2$O with 0.05% TFA as mobile phase) to give the title compound as a brown yellow solid (183 mg, yield: 70%). $^1$H NMR (400 MHz, CDCl$_3$) δ: 8.47-8.41 (m, 1H), 7.21-7.10 (m, 1H), 6.82-6.70 (m, 1H), 6.57-6.17 (br, 1H), 4.22-3.83 (m, 3H), 3.78-3.43 (m, 1H), 3.42-3.15 (m, 1H), 2.22-2.09 (m, 1H), 1.88-1.73 (m, 2H), 1.66-1.57 (m, 1H), 1.38 (s, 9H). ESI-MS (M+H)+: 360.20.

Synthesis of 4-(piperidin-3-ylamino)-1H-pyrrolo[2,3-b]pyridine-5-carboxamide A solution of methyl 4-((1-(tert-butoxycarbonyl)piperidin-3-yl)amino)-1-tosyl-1H-pyrrolo[2,3-b]pyridine-5-carboxylate (183 mg, 0.51 mmol, 1.0 eq) in TFA/DCM (1:2,3 mL) was stirred at rt for 3 h. After the reaction was completed the solvent was removed in vacuo and the residue was used in the next step without further purification (132 mg, brown solid, yield: 100%). ESI-MS (M+H)+: 260.14.

Synthesis of 4-((1-(2-((3-chloro-5-fluorophenyl)amino)acetyl)piperidin-3-yl)amino)-1H-pyrrolo[2,3-b]pyridine-5-carboxamide To a solution of 4-(piperidin-3-ylamino)-1H-pyrrolo[2,3-b]pyridine-5-carboxamide (132 mg, 0.51 mmol, 1.0 eq) and 2-((3-chloro-5-fluorophenyl)amino)acetic acid (124 mg, 0.61 mmol, 1.2 eq) in DMF (3 mL) was added HBTU (387 mg, 1.02 mmol, 2.0 eq) and DIPEA (1 mL). The resulting mixture was stirred at 80° C. for 16 h and the solvent was concentrated in vacuo to afford a residue which was purified by prep-HPLC (MeOH/H$_2$O with 0.05% TFA as mobile phase) to give afford the title compound as a light brown solid (110 mg, yield: 50%). $^1$H NMR (400 MHz, CD$_3$OD) δ: 8.23 (s, 1H), 7.09-7.02 (m, 1H), 6.66-6.61 (m, 1H), 6.42-5.94 (m, 3H), 4.35-4.10 (m, 1H), 4.08-3.91 (m, 2H), 3.79-3.74 (m, 1H), 3.65-3.53 (m, 2H), 3.43-3.40 (m, 2H), 2.06-2.04 (m, 1H), 1.82-1.73 (m, 2H), 1.62-1.59 (m, 1H). ESI-MS (M+H)+: 445.15.

Example 133

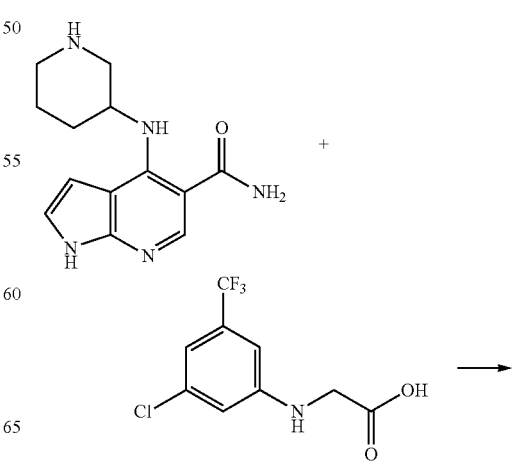

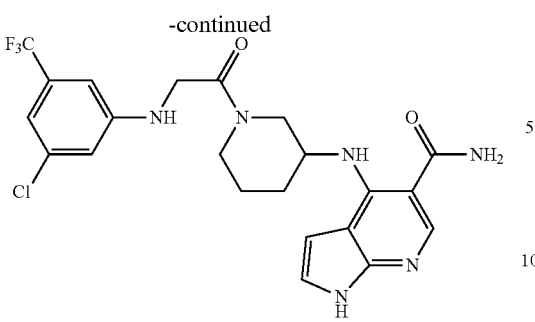

Synthesis of 4-((1-(2-((3-chloro-5-trifluoromethylphenyl)amino)acetyl)piperidin-3-yl)amino)-1H-pyrrolo[2,3-b]pyridine-5-carboxamide The title compound was obtained using the same procedure as described in Example 132 except 2-((3-chloro-5-(trifluoromethyl)phenyl)amino)acetic acid was substituted for 2-((3-chloro-5-fluorophenyl)amino)acetic acid. ¹H NMR (400 MHz, CD₃OD) δ: 8.23 (s, 1H), 7.07-6.99 (m, 1H), 6.77-6.68 (m, 2H), 6.62-6.49 (m, 2H), 4.33-4.03 (m, 2H), 3.98 (s, 1H), 3.87-3.62 (m, 2H), 3.61-3.49 (m, 1H), 3.43-3.30 (m, 1H), 3.25 (s, 1H), 2.10-1.98 (m, 1H), 1.86-1.67 (m, 2H), 1.65-1.52 (m, 1H). ESI-MS (M+H)⁺: 495.1.

Example 134

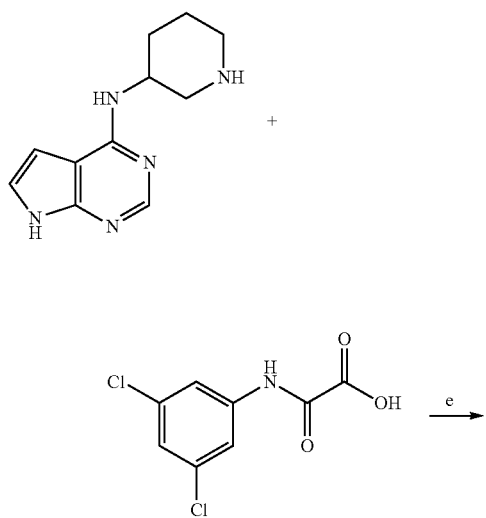

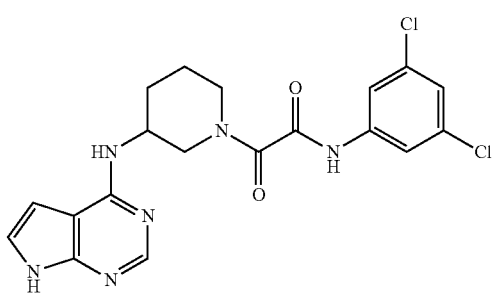

Synthesis of 2-(3-((7H-pyrrolo[2,3-d]pyrimidin-4-yl)amino)piperidin-1-yl)-N-(3,5-dichlorophenyl)-2-oxoacetamide The title compound was obtained using the same procedure as described in Example 133 except 2-((3,5-dichlorophenyl)amino)-2-oxoacetic acid (Klaubert, D. J. Med. Chem. 1981, 24, 742) was substituted for 2-((3-chloro-5-(trifluoromethyl)phenyl)amino)acetic acid. ¹H NMR (400 MHz, CD₃OD) δ: 11.56 (s, 0.5H), 11.45 (s, 0.5H), 11.24 (s, 0.5H), 11.11 (s, 0.5H), 8.13 (s, 0.5H), 7.74 (s, 1H), 7.62 (s, 0.5H), 7.60 (d, J=1.6 Hz, 1H), 7.39-7.35 (m, 1H), 7.11-7.09 (m, 1H), 6.59-6.56 (m, 1H), 4.56-4.52 (m, 0.5H), 4.22-4.12 (m, 1H), 4.01-4.97 (m, 1H), 3.77-3.74 (m, 0.5H), 3.24-3.06 (m, 2H), 2.07-1.96 (m, 2H), 1.89-1.57 (m, 3H). ESI-MS (M+H)⁺ 433.09.

Example 135

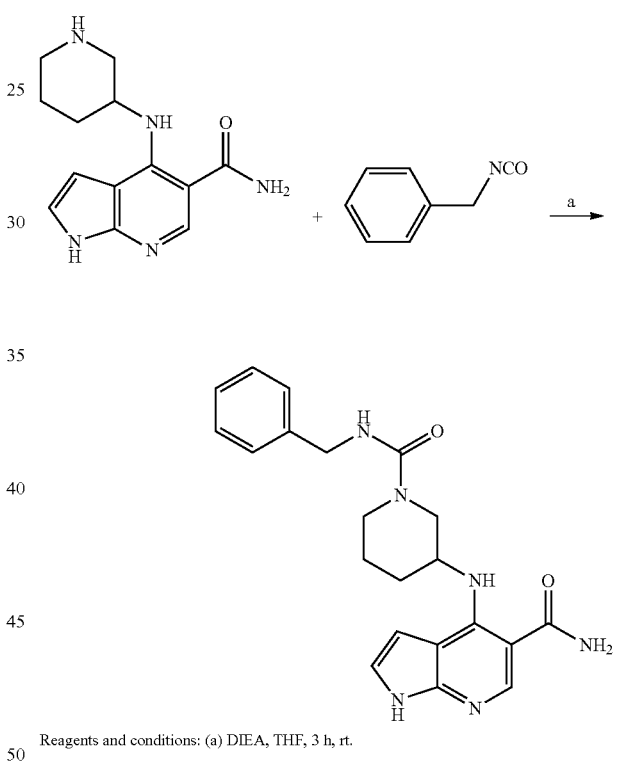

Reagents and conditions: (a) DIEA, THF, 3 h, rt.

Synthesis of 4-((1-(benzylcarbamoyl)piperidin-3-yl)amino)-1H-pyrrolo[2,3-b]pyridine-5-carboxamide To a solution of 4-(piperidin-3-ylamino)-1H-pyrrolo[2,3-b]pyridine-5-carboxamide (62 mg, 0.24 mmol, 1.0 eq) and (isocyanatomethyl)benzene (35 mg, 0.26 mmol, 1.1 eq) in THF (2 mL) were added DIPEA (93 mg, 0.72 mmol, 3.0 eq). The mixture was stirred at rt for 3 h and the solvent was removed in vacuo to afford a residue which was purified by prep-HPLC (MeOH/H₂O with 0.05% NH₃.H₂O) to give the title compound as a light brown solid (23 mg, yield: 11%). ¹H NMR (400 MHz, CD₃OD) δ: 8.32 (s, 1H), 7.15-7.09 (m, 6H), 6.91 (d, J=3.6 Hz, 1H), 4.23-4.20 (m, 3H), 3.87-3.83 (m, 1H), 3.46-3.34 (m, 3H), 2.09-2.05 (m, 1H), 1.81-1.80 (m, 2H), 1.62-1.59 (m, 1H). ESI-MS (M+H)+: 393.20.

Example 136

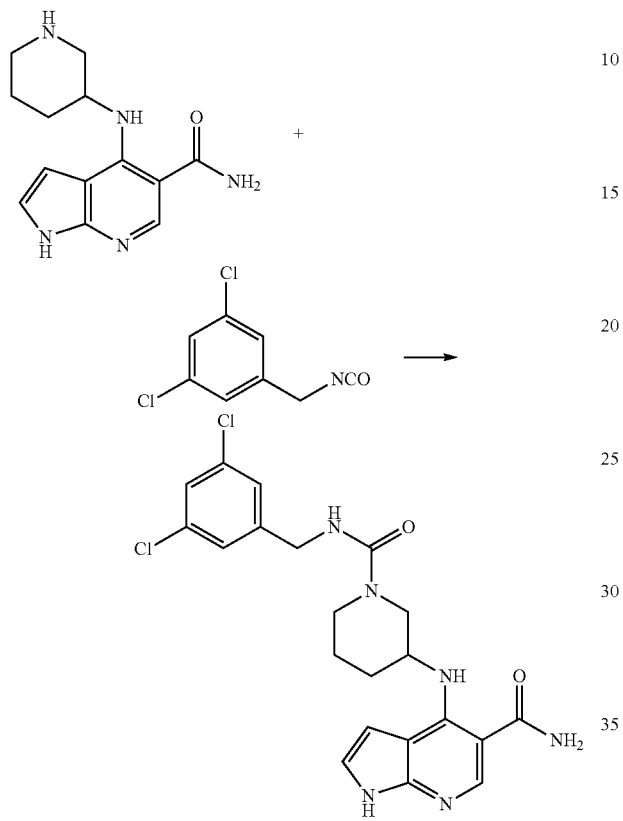

Synthesis of 4-((1-((3,5-dichlorobenzyl)carbamoyl)piperidin-3-yl)amino)-1H-pyrrolo[2,3-b]pyridine-5-carboxamide The title compound was obtained using the same procedure as described in Example 135 except 1,3-dichloro-5-(isocyanatomethyl)benzene was substituted for (isocyanatomethyl)benzene. $^1$H NMR (400 MHz, CD$_3$OD) δ: 8.43 (s, 1H), 7.31-7.26 (m, 4H), 7.03 (d, J=3.6 Hz, 1H), 4.35-4.32 (m, 3H), 3.98-3.94 (m, 1H), 3.56-3.51 (m, 3H), 2.22-2.17 (m, 1H), 1.92-1.87 (m, 2H), 1.75-1.73 (m, 1H). ESI-MS (M+H)$^+$: 461.12.

Example 137

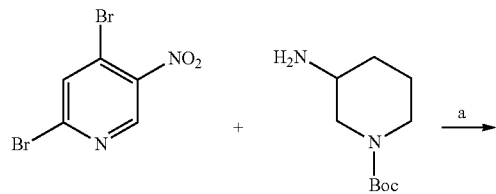

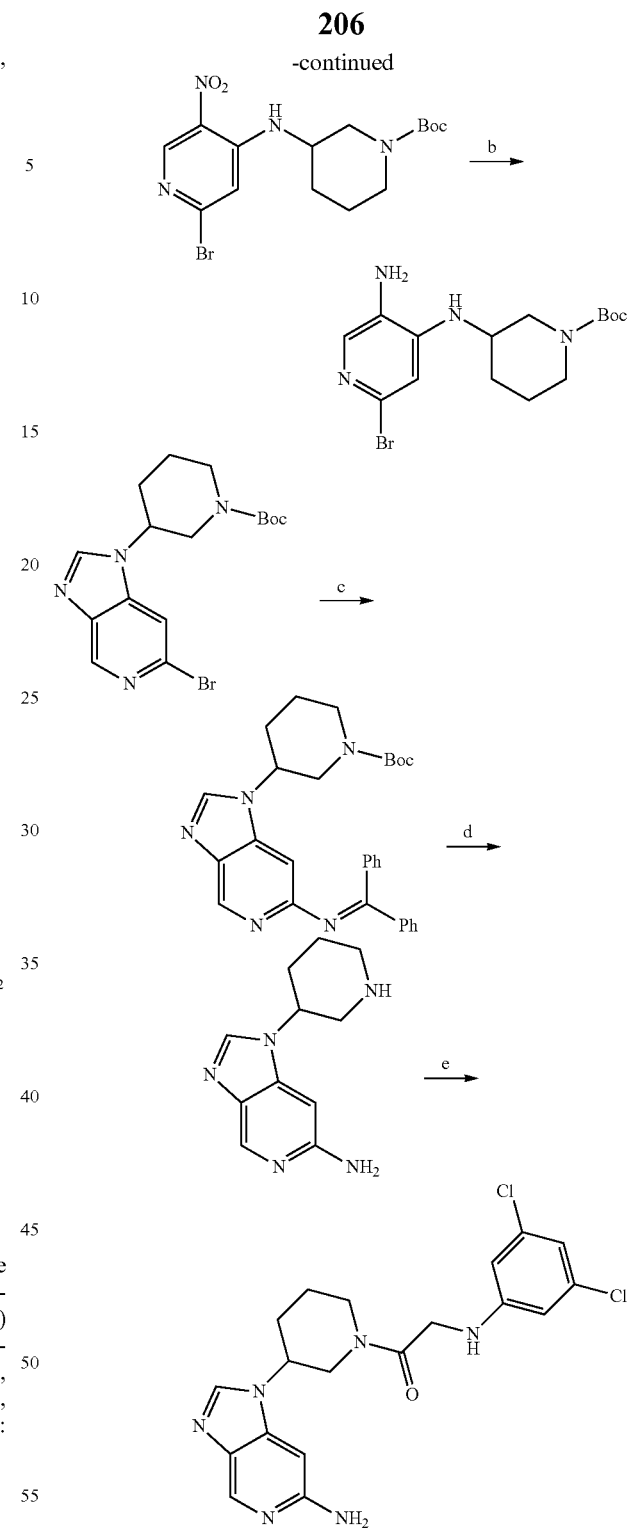

Reagents and conditions: (a) Et$_3$N, EtOH, 85 C. 16 h. (b) Fe(powder), NH$_4$Cl, EtOH/water, reflux. (c) CH(OEt)$_3$, reflux, 40 h. (d) Ph$_2$NH, Pd(dba), Xantphos, Cs$_2$CO$_3$, DMA, 115 C. (e) HCl in 1,4 dioxane, THF, rt, 3 h. (f) HBTU, Et$_3$N, rt.

Synthesis of tert-butyl 3-((2-bromo-5-nitropyridin-4-yl)amino)piperidine-1-carboxylate The tert-butyl 3-aminopiperidine-1-carboxylate (1.43 g, 7.14 mmol, 1.0 eq) was added dropwise to a solution of 2,4-dibromo-5-nitropyridine (2 g, 7.14 mmol, 1.0 eq) and Et₃N (0.73 g, 7.14 mmol, 1.0 eq) in EtOH (20 mL) at reflux temperature. The reaction mixture was heated at refluxing for 16 h and then the solvent was concentrated in vacuo to afford a residue. The residue was treated with 1 N NaOH solution and extraction with EtOAc. The organic phase was separated, dried (Na₂SO₄) and concentration in vacuo to afford an residue which was purified by silica gel column chromatography with EtOAc in PE (⅕ v/v) to give the title compound (1.24 g, 42%) as yellow solid. ¹H NMR (400 MHz, CDCl₃) δ: 8.99 (s, 1H), 8.25 (s, 1H), 6.98 (s, 1H), 3.81-3.79 (m, 1H), 3.61-3.60 (m, 2H), 3.37-3.35 (m, 2H), 2.02 (m, 1H), 1.86-1.77 (m, 3H), 1.47 (s, 9H). ESI-MS (M+H⁺): 401.0.

Synthesis of tert-butyl 3-((5-amino-2-bromopyridin-4-yl)amino)piperidine-1-carboxylate To a mixture of tert-butyl 3-((2-bromo-5-nitropyridin-4-yl)amino)piperidine-1-carboxylate. (1.24 g, 3.01 mmol, 1.0 eq) and NH₄Cl (2.43 g, 45 mmol, 15 eq) was added a 2:1 mixture EtOH/water (30 mL). The reaction mixture was heated to reflux, then iron powder (0.67 g, 12 mmol, 3.5 eq) was added in portions over 15 min and the suspension was continued to be heated at refluxed for 16 h. The reaction mixture was cooled to rt, diluted with CH₂Cl₂ (300 mL) and filtered through celite. The organic layer was washed with water (50 mL×2) and brine (50 mL), dried (Na₂SO₄), filtered and concentrated in vacuo to give the title compound (1.2 g, 100%) which was used to next step without further purification. ¹H NMR (400 MHz, CDCl₃) δ: 7.66 (s, 1H), 6.63 (s, 1H), 4.51-4.39 (m, 1H), 3.89-3.86 (m, 1H), 3.67-3.63 (m, 1H), 3.41-3.10 (m, 4H), 2.09-1.95 (m, 1H), 1.74-1.60 (m, 3H), 1.47 (s, 9H). ESI-MS (M+H⁺): 371.0.

Synthesis of tert-butyl 3-(6-bromo-1H-imidazo[4,5-c]pyridin-1-yl)piperidine-1-carboxylate A mixture of tert-butyl 3-((5-amino-2-bromopyridin-4-yl)amino)piperidine-1-carboxylate (1.1 g, 3.0 mmol, 1.0 eq) in CH(OCH₂CH₃)₃ (214 mg, 30 mmol, 10 eq) was refluxed for 40 h. Then the residual CH(OCH₂CH₃)₃ was removed in vacuum and the crude product was purified by silica gel column chromatography with EtOAc in PE (½ v/v) to give the title compound (0.8 g, 70%) as yellow oil. ¹H NMR (400 MHz, CDCl₃) δ: 8.87 (s, 1H), 8.06 (s, 1H), 7.62 (s, 1H), 4.30-4.28 (m, 2H), 4.02-4.00 (m, 1H), 3.27-3.22 (m, 1H), 3.09-3.03 (m, 1H), 2.31-2.30 (m, 1H), 2.13-2.10 (m, 1H), 1.88-1.85 (m, 1H), 1.74-1.71 (m, 1H), 1.50 (s, 9H). ESI-MS (M+H⁺): 381.0.

Synthesis of tert-butyl 3-(6-((diphenylmethylene)amino)-1H-imidazo[4,5-c]pyridin-1-yl)piperidine-1-carboxylate To a solution of tert-butyl 3-(6-bromo-1H-imidazo[4,5-c]pyridin-1-yl)piperidine-1-carboxylate (0.6 g, 1.58 mmol, 1.0 eq) in DMA (5 mL) were added Ph₂NH (430 mg, 2.37 mmol, 1.5 eq), Pd₃(dba)₂ (87 mg, 0.095 mmol, 0.06 eq), Xantphos (91 mg, 0.16 mmol, 0.1 eq) and Cs₂CO₃ (0.8 g, 2.5 mmol, 1.6 eq) at rt under N₂. The mixture was stirred at 115° C. for 16 h, cooled to rt and the solid was filtered off and washed with EtOAc (30 mL). The organic layer was washed with H₂O (20 mL×2) and brine (10 mL), separated, dried (Na₂SO₄) and concentration in vacuo to afford a residue which was purified by silica gel column chromatography with EtOAc in PE (1/1 v/v) to give the title compound (0.4 g, 50%) as brown solid. ¹H NMR (400 MHz, CDCl₃) δ: 8.80 (s, 1H), 7.89 (s, 1H), 7.82 (d, 2H), 7.52-7.48 (m, 1H), 7.44-7.40 (m, 2H), 7.27-7.24 (m, 3H), 7.24-7.17 (m, 2H), 6.68 (s, 1H), 4.13-4.09 (m, 2H), 3.95-3.92 (m, 1H), 3.18-3.14 (m, 1H), 3.01-2.94 (m, 1H), 1.95-1.90 (m, 2H), 1.79-1.76 (m, 1H), 1.63-1.60 (m, 1H), 1.53 (s, 9H). ESI-MS (M+H⁺): 382.0.

Synthesis of 1-(piperidin-3-yl)-1H-imidazo[4,5-c]pyridin-6-amine hydrochloride

To a solution of tert-butyl 3-(6-((diphenylmethylene)amino)-1H-imidazo[4,5-c]pyridin-1-yl)piperidine-1-carboxylate (400 mg, 0.83 mmol, 1.0 eq) in THF (4 mL) was added HCl (4 N solution in 1,4 dioxane, 4 mL). The mixture was stirred at rt for 3 h and concentrated in vacuo to afford a residue which was washed with EtOAc (10 mL×3) to give crude title compound (180 mg, 95%) as brown solid. ¹H NMR (400 MHz, DMSO-d₆) δ: 9.82 (s, 1H), 8.73-8.65 (m, 1H), 7.74-7.70 (m, 1H), 7.58-7.56 (m, 1H), 4.04-4.02 (m, 1H), 3.67-3.66 (m, 0.5H), 3.48-3.32 (m, 2H), 2.95-2.79 (m, 1.5H), 2.18 (s, 1H), 1.99-1.96 (m, 3H), 1.75-1.73 (m, 1H). ESI-MS (M+H⁺): 218.0.

Synthesis of 1-(3-(6-amino-1H-imidazo[4,5-c]pyridin-1-yl)piperidin-1-yl)-2-((3,5-dichlorophenyl)amino)ethanone To a solution of 1-(piperidin-3-yl)-1H-imidazo[4,5-c]pyridin-6-amine hydrochloride (180 mg, 0.71 mmol, 1.0 eq) in THF (4 mL), was added XXX (171 mg, 0.78 mmol, 1.1 eq), HBTU (540 mg, 1.4 mmol, 2.0 eq) and DIPEA (275 mg, 2.1 mmol, 3.0 eq). The mixture was stirred at rt for 2 h, the solvent was removed to afford a residue which dissolved in CH₂Cl₂ (20 mL) and washed with brine (10 mL×3), dried (Na₂SO₄) and concentration in vacuo to afford the crude product which was purified by reverse phase chromatography (MeOH/H₂O with 0.05% TFA as mobile phase) to give the title compound (45 mg, 13%) as light yellow solid. ¹H NMR (400 MHz, DMSO-d₆) δ: 8.71 (d, 1H), 8.66-8.60 (m, 1H), 7.30 (s, 2H), 7.07 (s, 0.5H), 6.93 (s, 0.5H), 6.76-6.74 (m, 2H), 6.63-6.61 (m, 1H), 6.52-6.02 (s, 1H), 4.56-4.53 (m, 0.5H), 4.48-4.45 (m, 1H), 4.36-4.34 (m, 0.5H), 4.24-4.20 (m, 0.5H), 4.05 (s, 1H), 4.00 (s, 0.5H), 3.95-3.91 (m, 1H), 3.56-3.50 (t, 0.5H), 3.23-3.17 (m, 1H), 2.73-2.67 (t, 0.5H), 2.17-2.14 (m, 1.5H), 2.13-2.06 (m, 0.5H), 2.06-1.99 (m, 1H), 1.71-1.68 (m, 0.5H), 1.57-1.53 (m, 0.5H) ESI-MS (M+H⁺): 419.0.

Example 138

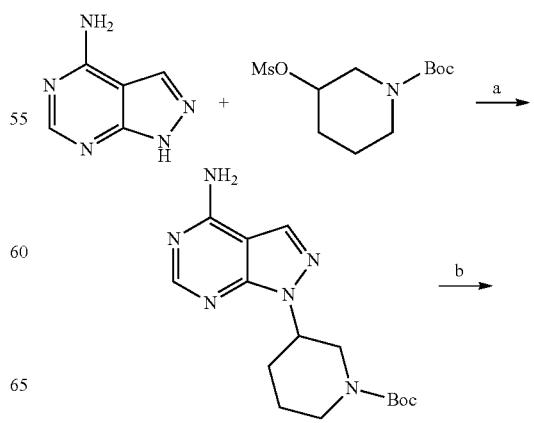

209

-continued

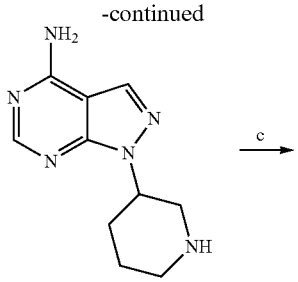

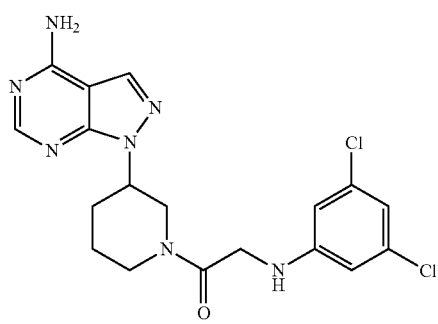

Reagents and conditions: (a) NaH, DMF, 100 C., 16 h. (b) TFA, DCM, rt 1 h. (c) C₈H₇O₂NCl₂, HBTU, DIEA, THF, 50 C. 16 h.

Synthesis of tert-butyl 3-((methylsulfonyl)oxy)piperidine-1-carboxylate

To the solution of tert-butyl 3-hydroxypiperidine-1-carboxylate (2.01 g, 10 mmol, 1.0 eq) in THF (30 mL) was added DMAP (122 mg, 1.0 mmol, 0.1 eq), TEA (2.8 mL, 20 mmol, 2.0 eq) and methanesulfonic anhydride (1.91 g, 11 mmol, 1.1 eq). The mixture was stirred at rt for 16 h, filtered off and concentrated in vacuo to afford a residue which purified by column chromatography (silica gel, PE/EtOAc=3:1) to give the title product (2.5 g, yield: 90%) as a colorless oil. $^1$H NMR (400 MHz, CDCl₃) δ: 4.72 (s, 1H), 3.74-3.61 (m, 3H), 3.45-3.42 (m, 1H), 3.34-3.32 (m, 1H), 2.05-1.08 (m, 4H), 1.45-1.40 (m, 11H). ESI-MS (M+H$^+$-56): 224.0.

Synthesis of tert-butyl 3-(4-amino-1H-pyrazolo[3,4-d]pyrimidin-1-yl)piperidine-1-carboxylate To a solution of 1H-pyrazolo[3,4-d]pyrimidin-4-amine (675 mg, 5 mmol) in DMF (12 mL) was added NaH (60% wt in mineral oil, 240 mg, 6.0 mmol, 1.2 eq) and the mixture was stirred at rt for 0.5 h. The tert-butyl 3-((methylsulfonyl)oxy) piperidine-1-carboxylate (1.67 g, 6 mmol, 1.2 eq) was added and the mixture was heated to 100° C. for 16 h. The solution was cooled to rt and the reaction was quenched with brine (50 mL) and extracted with EtOAc (80 mL×4). The organic layers were dried over Na₂SO₄, concentrated in vacuo to afford a residue which was purified by column chromatography (silica gel, pure EtOAc) to give the title product (700 mg, yield: 50%) as a light yellow solid. $^1$H NMR (400 MHz, DMSO-d₆) δ: 9.24 (br s, 1H), 8.72 (br s, 1H), 8.41 (s, 1H), 8.33 (s, 1H), 4.67-4.62 (m, 1H), 4.05-3.58 (m, 3H), 3.40-3.33 (m, 1H), 2.98-2.95 (m 1H), 2.16-2.04 (m, 1H), 1.61-1.24 (m, 11H). ESI-MS (M+H$^+$): 319.0.

210

Synthesis of 1-(piperidin-3-yl)-1H-pyrazolo[3,4-d]pyrimidin-4-amine

To the solution of tert-butyl 3-(4-amino-1H-pyrazolo[3,4-d]pyrimidin-1-yl)piperidine-1-carboxylate (700 mg, 2.2 mmol) in CH₂Cl₂ (10 mL) was added TFA (2 mL). The resulting mixture was stirred at rt for 1 h, and concentrated in vacuo to afford the title compound (620 mg, 100%) which was used without further purification. ESI-MS (M+H'): 219.0.

Synthesis of 1-(3-(4-amino-1H-pyrazolo[3,4-d]pyrimidin-1-yl)piperidin-1-yl)-2-((3,5-dichlorophenyl)amino)ethanone A mixture of 1-(piperidin-3-yl)-1H-pyrazolo[3,4-d]pyrimidin-4-amine (620 mg, 2.2 mmol), 2-((3,5-dichlorophenyl)amino)acetic acid (475 mg, 2.2 mmol, 1 eq), HBTU (822 mg, 2.2 mmol, 1 eq) and DIPEA (560 mg, 4.4 mmol, 2.0 eq) in THF (10 mL) was heated to 50° C. for 16 h. The mixture was concentrated in vacuo and purified by silica gel column with EA in PE (20% to 100%, v/v) to give the title product (63 mg, yield: 7%). $^1$H NMR (400 MHz, DMSO-d₆) δ: 8.21 (d, 1H), 8.11 (d, 1H), 7.85-7.65 (m, 2H), 6.76 (s, 1H), 6.73 (s, 1H), 6.60 (d, 1H), 6.32 (t, 1H), 4.76-4.71 (m 0.5H), 4.61-4.54 (m, 1H), 4.48 (d, 0.5H), 4.19 (d, 0.5H), 4.11-4.08 (m, 1H), 4.02-3.94 (m, 1.5H), 3.86-3.81 (m, 0.5H), 3.17-3.09 (m, 1H), 2.95-2.90 (m, 0.5H), 2.20-2.12 (m, 1H), 2.08-2.05 (m, 1H), 1.89-1.82 (m, 1H), 1.72-1.51 (m, 1H). ESI-MS: 420.1 (M+H)$^+$.

Example 139

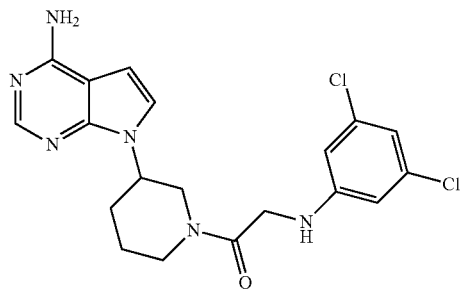 [SMILES: Nc1ncnc2c1ccn2C1CCCN(C(=O)CNc2cc(Cl)cc(Cl)c2)C1]

Synthesis of 1-(3-(4-amino-7H-pyrrolo[2,3-d]pyrimidin-7-yl)piperidin-1-yl)-2-((3,5-dichlorophenyl)amino)ethanone A similar procedure was used as described for the synthesis of Example 138 except N-(4-methoxybenzyl)-7H-pyrrolo[2,3-d]pyrimidin-4-amine was substituted for 1H-pyrazolo[3,4-d]pyrimidin-4-amine to afford the title compound which was purified by reverse phase chromatography (0.05% TFA:H₂O: MeOH=0~80% as mobile phase) to give white solid 60 mg, yield: 25%). $^1$H NMR (400 MHz, DMSO-d₆) δ: 8.88 (br s, 2H), 8.39-8.37 (m, 1H), 7.63 (d, 1H), 6.95-6.94 (m, 1H), 6.76-6.62 (m, 3H), 6.34 (br s, 1H), 4.72-4.34 (m, 2H), 4.13-

3.88 (m, 3H), 3.55-3.50 (m, 0.5H), 3.21-3.12 (m, 1H), 2.78-2.71 (m, 0.5H), 2.18-2.09 (m, 2H), 1.88-1.53 (m, 2H). ESI-MS: 419.1 (M+H⁺).

Example 140

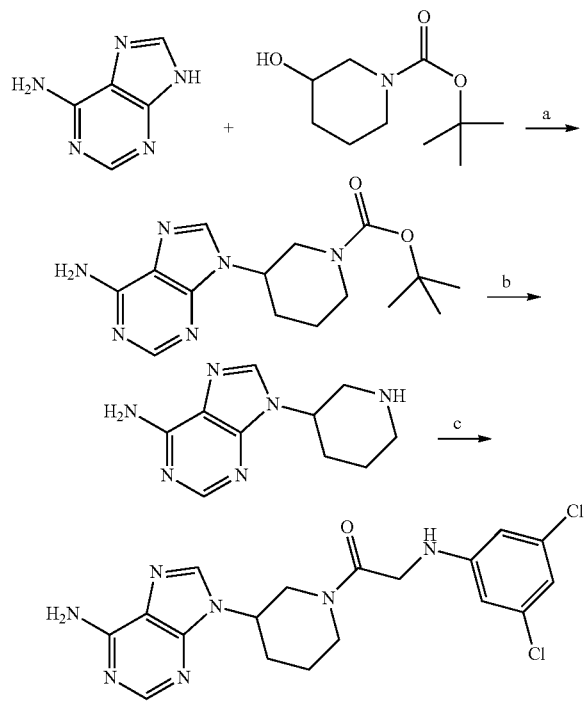

Reagents and conditions: (a) PPh₃, DIAD, THF, rt, 1 h. (b) TFA, CH₂Cl₂, rt, 1 h. (c) C₈H₇O₂NCl₂——, HBTU, DIEA, THF, 50 C., 1 h.

Synthesis of tert-butyl 3-(6-amino-9H-purin-9-yl)piperidine-1-carboxylate

To a solution of 9H-purin-6-amine (945 mg, 7 mmol, 1.0 eq) in THF (1 mL) was added tert-butyl 3-hydroxypiperidine-1-carboxylate (2.996 g, 14 mmol, 2.0 eq) and PPh₃ (3.67 g, 14 mmol, 2.0 eq). After stirring for the solution for 15 min, DIAD (2.83 g, 14 mmol, 2.0 eq) was added the reaction was continued to be stirred rt for 1 h. The solvent was removed in vacuo and the residue was purified on a silica gel column (PE/EA=5:1) to afford the title compound as a yellow solid (245 mg, yield 11%). $^1$H NMR (400 MHz, CD₃OD) δ: 8.44 (s, 1H), 8.42 (s, 1H), 5.04-4.98 (m, 1H), 3.77-3.73 (m, 1H), 3.68-3.62 (m, 1H), 3.52-3.48 (m, 1H), 3.18-3.11 (m, 1H), 2.45-2.32 (m, 2H), 2.22-2.17 (m, 1H), 2.05-1.97 (m, 1H), 1.49 (s, 9H). ESI-MS: 319.1 (M+H⁺).

Synthesis of 1-(3-(6-amino-9H-purin-9-yl)piperidin-1-yl)-2-((3,5-dichlorophenyl)amino)ethanone A similar procedure was used as described for the synthesis of Example 138 except tert-butyl 3-(6-amino-9H-purin-9-yl)piperidine-1-carboxylate was substituted for tert-butyl 3-(4-amino-1H-pyrazolo[3,4-d]pyrimidin-1-yl)piperidine-1-carboxylate to afford the title compound as a yellow solid (79 mg, yield 19%). $^1$H NMR (400 MHz, DMSO-d₆) δ: 8.22 (d, 1H), 8.16 (d, 1H), 7.72 (d, 2H), 6.74, (d, 2H), 6.62 (s, 1H), 6.34 (s, 1H), 4.52-4.39 (m, 2H), 4.22-4.01 (m, 2H), 3.95-3.91 (m, 1H), 3.66-3.60 (m, 0.5; H), 3.27-3.16 (0.5; H), 3.19-3.16 (m, 0.5H), 2.75-2.69 (m, 0.5H), 2.29-2.26 (m, 1H), 2.14 (s, 1H), 1.87-1.74 (m, 1H), 1.73-1.49 (m, 1H). ESI-MS: 420.0 (M+H)⁺.

Example 141

In vitro BTK Kinase Assay

BTK-POLYGAT-LS ASSAY

The purpose of the BTK in vitro assay is to determine compound potency against BTK through the measurement of IC₅₀. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 μL aliquot of a ATP/peptide master mix (final concentration; ATP 10 μM, polyGAT 100 nM) in kinase buffer (10 mM Tris-HCl pH 7.5, 10 mM MgCl₂, 200 μM Na₃PO₄, 5 mM DTT, 0.01% Triton X-100, and 0.2 mg/ml casein) is added to each well. Next, 1 μL of a 4-fold, 40×compound titration in 100% DMSO solvent is added, followed by adding 15 uL of BTK enzyme mix in 1× kinase buffer (with a final concentration of 0.25 nM). The assay is incubated for 30 minutes before being stopped with 28 μL of a 50 mM EDTA solution. Aliquots (5 μL) of the kinase reaction are transferred to a low volume white 384 well plate (Corning 3674), and 5 μL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC₅₀ values are calculated using a four parameter fit with 100% enzyme activity determined from the DMSO control and 0% activity from the EDTA control.

Example 142

In Vitro Tec Kinase Selectivity Assay

Tec-POLYGT-LS ASSAY.

The purpose of the Tec in vitro assay is to determine compound potency against Tec through the measurement of IC₅₀. Compound inhibition is measured after monitoring the amount of phosphorylation of a fluorescein-labeled polyGT peptide (Invitrogen PV3610) in the presence of active Tec enzyme (Carna Biosciences 08-182), ATP, and inhibitor. The Tec kinase reaction was done in a black 96 well plate (costar 3694). For a typical assay, a 29 μL aliquot of a ATP/peptide master mix (final concentration; ATP 25 μM, polyGT 100 nM) in kinase buffer (10 mM Tris-HCl pH 7.5, 10 mM MgCl₂, 200 μM Na₃PO₄, 5 mM DTT, 0.01% Triton X-100, and 0.2 mg/ml casein) is added to each well. Next, 1 μL of a 3-fold, 50× compound titration in 100% DMSO solvent is added, followed by adding 20 uL of Tec enzyme mix in 1× kinase buffer (with a final concentration of 0.125 nM). The assay is incubated for 15 minutes before being stopped with 5 μl, of a 220 mM EDTA solution. Aliquots (5 μL) of the kinase reaction are transferred to a low volume white 384 well plate (Corning 3674), and 5 μL of a 2× detection buffer (Invitrogen PV3574, with 2 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC₅₀ values are calculated using a four parameter fit with 100% enzyme activity determined from the DMSO control and 0% activity from the EDTA control.

Example 143

Using the procedure described in Example 142, with the modifications shown in Table 3, selectivity for Itk, Txk, and Lck was measured.

TABLE 3

| Kinase | Carna Bioscience No. | Final concentration, ATP (μM) | Final concentration of kinase (nM) | Assay incubation time (min) |
|---|---|---|---|---|
| Itk | 08-181 | 10 | 0.150 | 15 |
| Txk | 08-183 | 100 | 2.0 | 15 |
| Lck | 08-170 | 5 | 0.750 | 30 |

Example 144

Protocol for Human B Cell Stimulation

Human B cells were purified from 150 ml of blood. Briefly, the blood was diluted ½ with PBS and centrifuged through a Ficoll density gradient. The B cells were isolated from the mononuclear cells by negative selection using the B cell isolation kit II from Milenyi (Auburn, Calif.). 50,000 B cells per well were then stimulated with 10 μg/ml of goat F(ab')2 anti-human IgM antibodies (Jackson ImmunoResearch Laboratories, West Grove, Pa.) in a 96-well plate. Compounds were diluted in DMSO and added to the cells. Final concentration of DMSO was 0.5%. Proliferation was measured after 3 days using Promega CellTiter-Glo (Madison, Wis.). Certain compounds of formula I were tested and found to be active.

Tables 4 and 5 shows the activity of selected compounds of this invention in in vitro kinase assays. Compounds have an activity designated as "A" provided an $IC_{50}$<100 nM; compounds having an activity designated as "B" provided an $IC_{50}$ of 100-999 nM; compounds having an activity designated as "C" provided an $IC_{50}$ of 1000-10,000 nM; and compounds having an activity designated as "D" provided an $IC_{50}$ of >10,000 nM.

TABLE 4

Exemplary compounds of formula I.

| Cmpd | Structure | $IC_{50}$ (10 uM ATP)[a] |
|---|---|---|
| 1 | 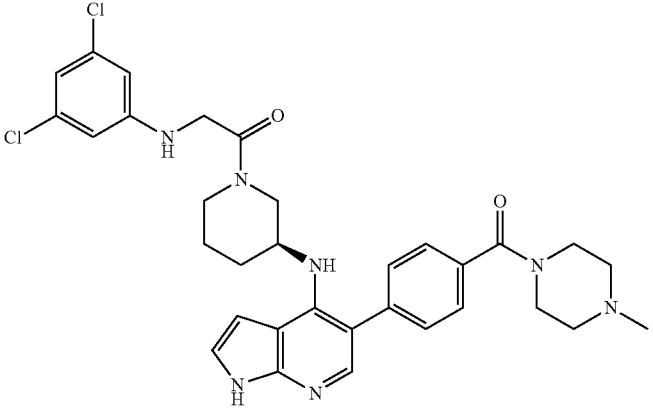 [SMILES: CN1CCN(C(=O)c2ccc(-c3cnc4[nH]ccc4c3N[C@H]3CCCN(C(=O)CNc4cc(Cl)cc(Cl)c4)C3)cc2)CC1] | A |
| 2 | 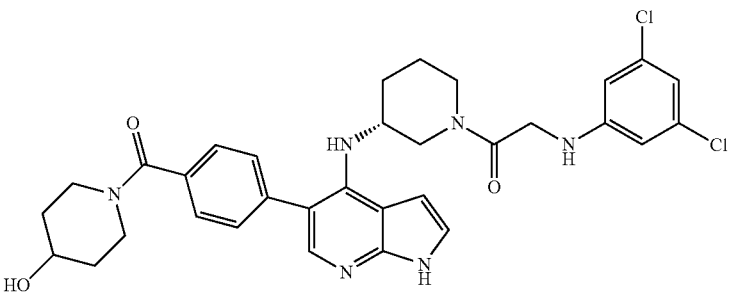 [SMILES: O=C(CNc1cc(Cl)cc(Cl)c1)N1CCC[C@@H](Nc2c(-c3ccc(C(=O)N4CCC(O)CC4)cc3)cnc3[nH]ccc23)C1] | A |

TABLE 4-continued

Exemplary compounds of formula I.

| Cmpd | Structure | IC$_{50}$ (10 uM ATP)$^a$ |
|---|---|---|
| 3 | 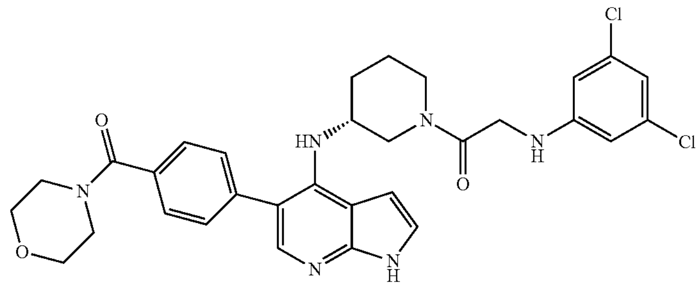 [SMILES: O=C(CNc1cc(Cl)cc(Cl)c1)N1CCC[C@@H](Nc2c(-c3ccc(C(=O)N4CCOCC4)cc3)cnc3[nH]ccc23)C1] | A |
| 4 | 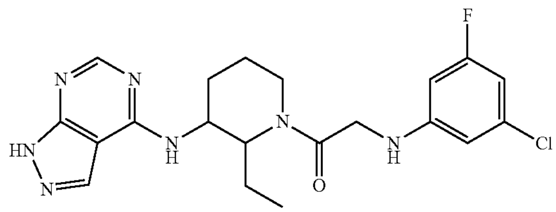 [SMILES: CCC1C(Nc2ncnc3[nH]ncc23)CCCN1C(=O)CNc1cc(F)cc(Cl)c1] | A |
| 5 | 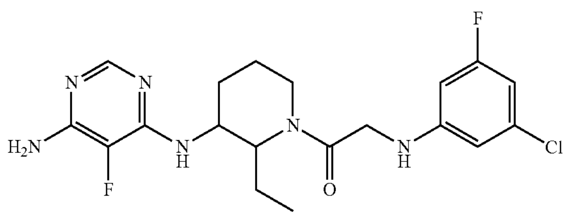 [SMILES: CCC1C(Nc2ncnc(N)c2F)CCCN1C(=O)CNc1cc(F)cc(Cl)c1] | C |
| 6 | 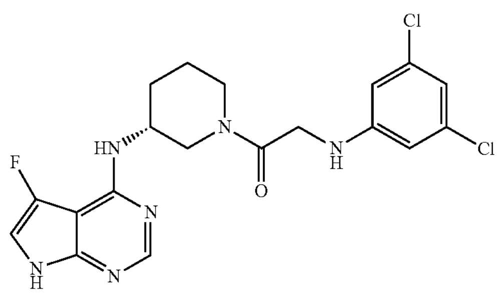 [SMILES: O=C(CNc1cc(Cl)cc(Cl)c1)N1CCC[C@@H](Nc2ncnc3[nH]cc(F)c23)C1] | B |
| 7 | 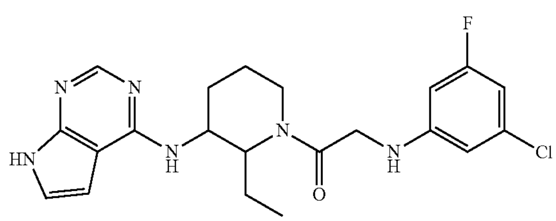 [SMILES: CCC1C(Nc2ncnc3[nH]ccc23)CCCN1C(=O)CNc1cc(F)cc(Cl)c1] | B |
| 8 | 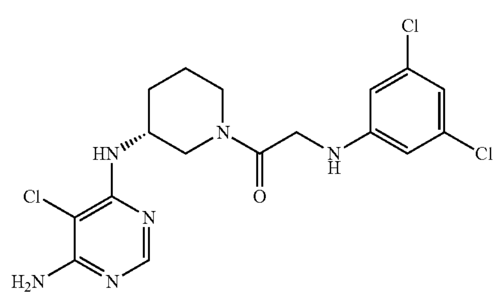 [SMILES: Nc1ncnc(N[C@@H]2CCCN(C(=O)CNc3cc(Cl)cc(Cl)c3)C2)c1Cl] | C |

TABLE 4-continued

Exemplary compounds of formula I.

| Cmpd | Structure | IC$_{50}$ (10 uM ATP)$^a$ |
|---|---|---|
| 9 | | A |
| 10 | | C |
| 11 | | B |
| 12 | | A |
| 13 | | A |
| 14 | | A |

TABLE 4-continued

Exemplary compounds of formula I.

| Cmpd | Structure | IC$_{50}$ (10 uM ATP)$^a$ |
|---|---|---|
| 15 | 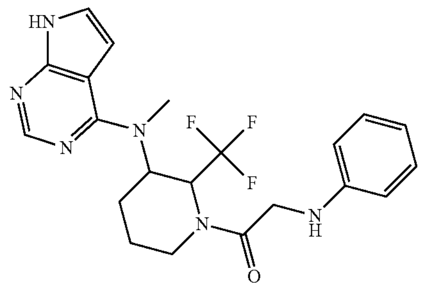 [SMILES: CN(c1ncnc2[nH]ccc12)C1CCCN(C(=O)CNc2ccccc2)C1C(F)(F)F] | A |
| 16 | 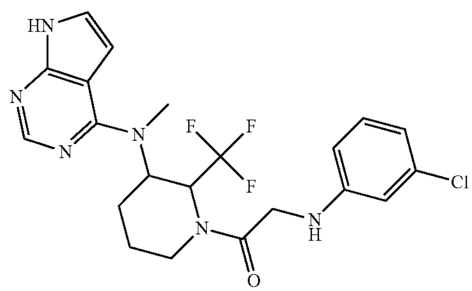 [SMILES: CN(c1ncnc2[nH]ccc12)C1CCCN(C(=O)CNc2cccc(Cl)c2)C1C(F)(F)F] | A |
| 17 | 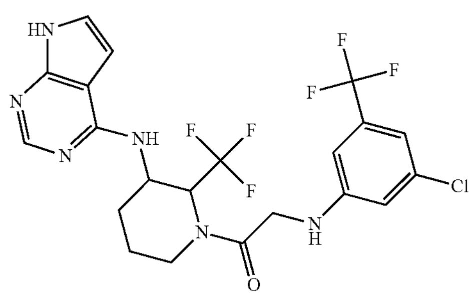 [SMILES: O=C(CNc1cc(Cl)cc(C(F)(F)F)c1)N1CCCC(Nc2ncnc3[nH]ccc23)C1C(F)(F)F] | A |
| 18 | 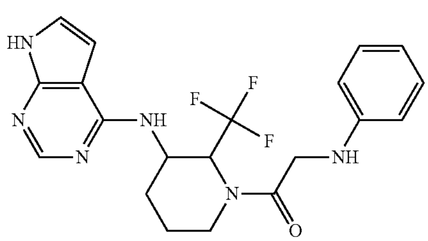 [SMILES: O=C(CNc1ccccc1)N1CCCC(Nc2ncnc3[nH]ccc23)C1C(F)(F)F] | B |
| 19 | 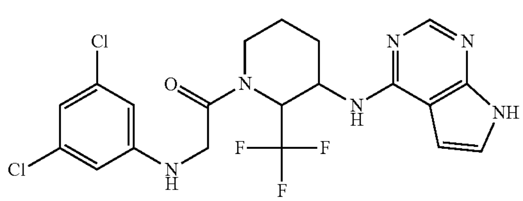 [SMILES: O=C(CNc1cc(Cl)cc(Cl)c1)N1CCCC(Nc2ncnc3[nH]ccc23)C1C(F)(F)F] | A |
| 20 | 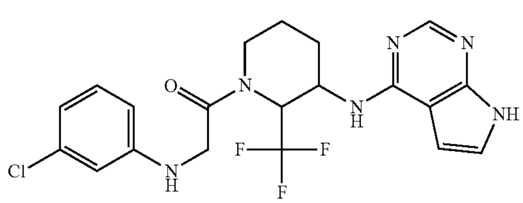 [SMILES: O=C(CNc1cccc(Cl)c1)N1CCCC(Nc2ncnc3[nH]ccc23)C1C(F)(F)F] | A |

TABLE 4-continued

Exemplary compounds of formula I.

| Cmpd | Structure | IC$_{50}$ (10 uM ATP)$^a$ |
|---|---|---|
| 21 | 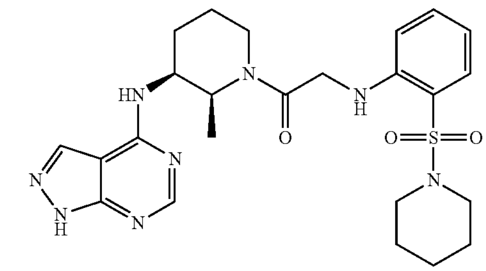 [SMILES: C[C@H]1[C@@H](Nc2ncnc3[nH]ncc23)CCCN1C(=O)CNc1ccccc1S(=O)(=O)N1CCCCC1] | C |
| 22 | 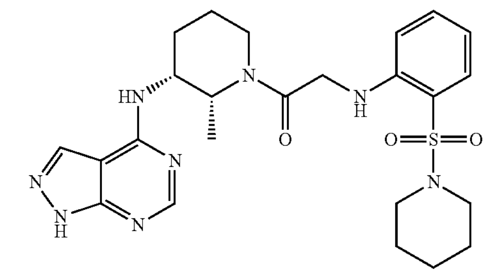 [SMILES: C[C@@H]1[C@H](Nc2ncnc3[nH]ncc23)CCCN1C(=O)CNc1ccccc1S(=O)(=O)N1CCCCC1] | A |
| 23 | 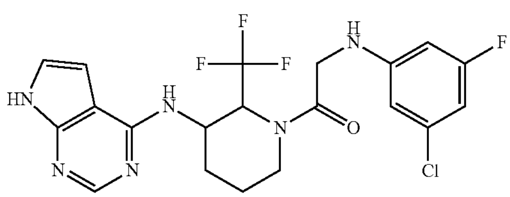 [SMILES: O=C(CNc1cc(F)cc(Cl)c1)N1CCCC(Nc2ncnc3[nH]ccc23)C1C(F)(F)F] | A |
| 24 | 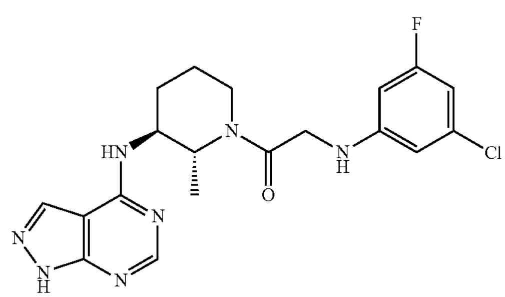 | C |
| 25 | 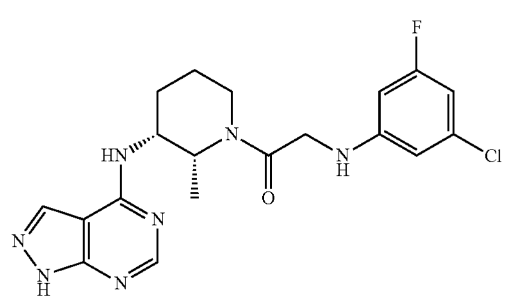 [SMILES: C[C@@H]1[C@H](Nc2ncnc3[nH]ncc23)CCCN1C(=O)CNc1cc(F)cc(Cl)c1] | A |

TABLE 4-continued
Exemplary compounds of formula I.
| Cmpd | Structure | IC$_{50}$ (10 uM ATP)$^a$ |
|---|---|---|
| 26 | 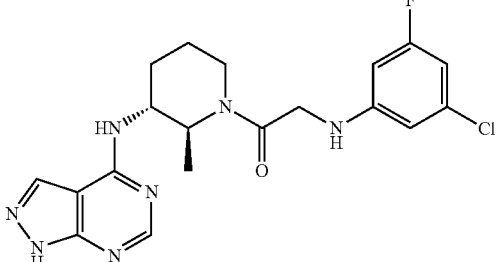 | B |
| 27 | 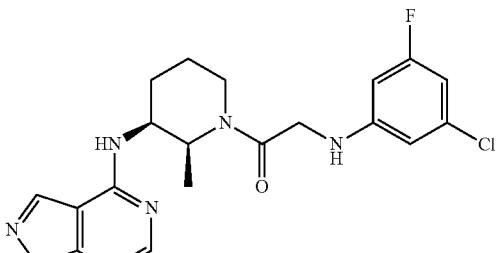 | B |
| 28 | 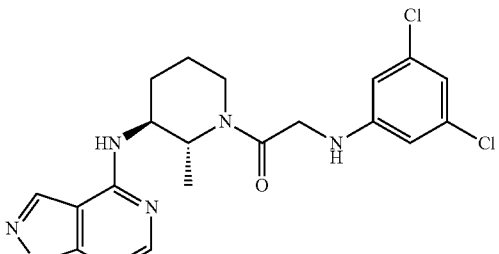 | B |
| 29 | 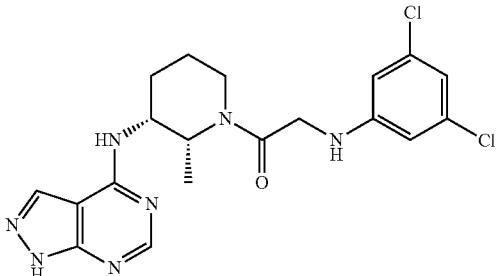 | A |
| 30 | 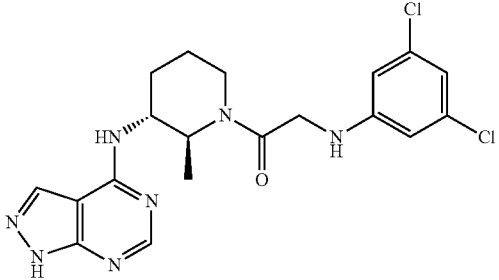 | B |

TABLE 4-continued

Exemplary compounds of formula I.

| Cmpd | Structure | IC$_{50}$ (10 uM ATP)$^a$ |
|---|---|---|
| 31 | 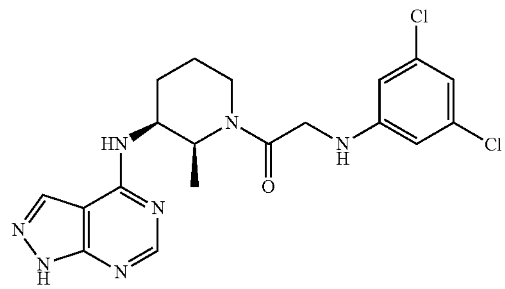 [SMILES: C[C@H]1[C@@H](Nc2ncnc3[nH]ncc23)CCCN1C(=O)CNc1cc(F)cc(Cl)c1] | A |
| 32 | 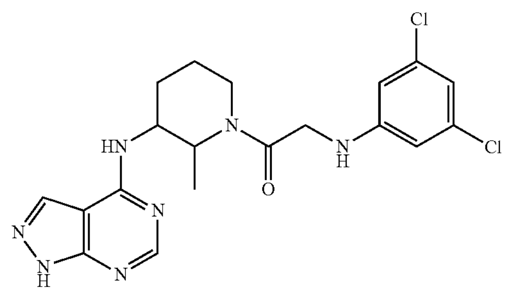 [SMILES: CC1C(Nc2ncnc3[nH]ncc23)CCCN1C(=O)CNc1cc(Cl)cc(Cl)c1] | |
| 33 | 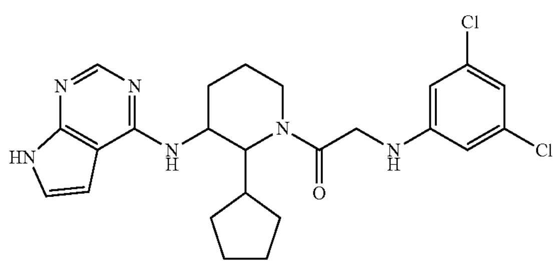 [SMILES: O=C(CNc1cc(Cl)cc(Cl)c1)N1CCCC(Nc2ncnc3[nH]ccc23)C1C1CCCC1] | A |
| 34 | 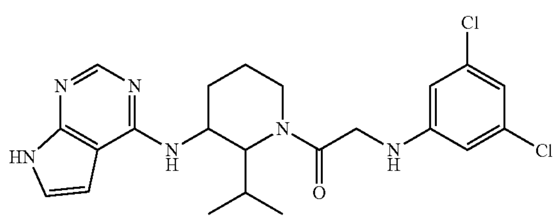 [SMILES: CC(C)C1C(Nc2ncnc3[nH]ccc23)CCCN1C(=O)CNc1cc(Cl)cc(Cl)c1] | A |
| 35 | 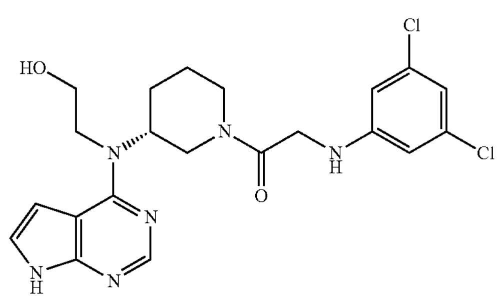 [SMILES: O=C(CNc1cc(Cl)cc(Cl)c1)N1CCC[C@@H](N(CCO)c2ncnc3[nH]ccc23)C1] | A |

TABLE 4-continued

Exemplary compounds of formula I.

| Cmpd | Structure | IC$_{50}$ (10 uM ATP)$^a$ |
|---|---|---|
| 36 | | C |
| 37 | | C |
| 38 | | |
| 39 | | |
| 40 | | B |

TABLE 4-continued

Exemplary compounds of formula I.

| Cmpd | Structure | IC$_{50}$ (10 uM ATP)$^a$ |
|---|---|---|
| 41 | 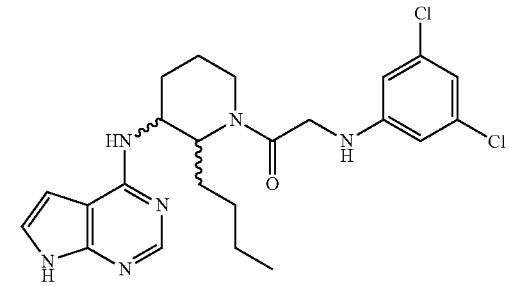 [SMILES: CCCCC1C(Nc2ncnc3[nH]ccc23)CCCN1C(=O)CNc1cc(Cl)cc(Cl)c1] | B |
| 42 | 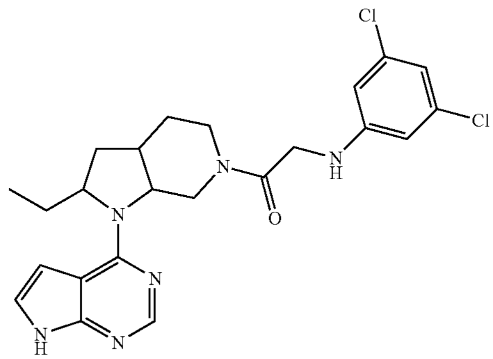 [SMILES: CCC1CC2CCN(C(=O)CNc3cc(Cl)cc(Cl)c3)CC2N1c1ncnc2[nH]ccc12] | A |
| 43 | 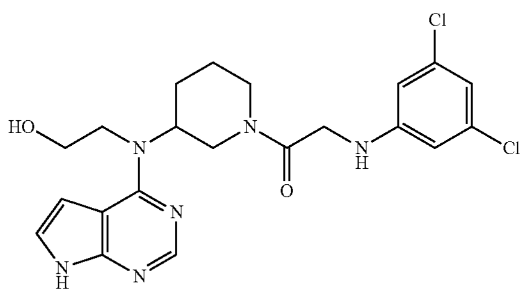 [SMILES: O=C(CNc1cc(Cl)cc(Cl)c1)N1CCCC(N(CCO)c2ncnc3[nH]ccc23)C1] | A |
| 44 | 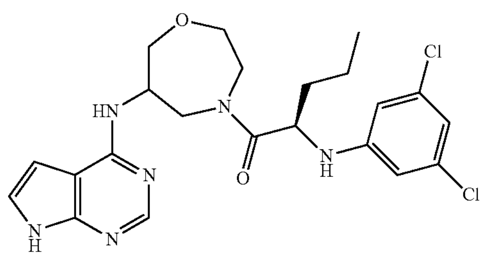 [SMILES: CCC[C@@H](Nc1cc(Cl)cc(Cl)c1)C(=O)N1CCOCC(Nc2ncnc3[nH]ccc23)C1] | B |
| 45 | 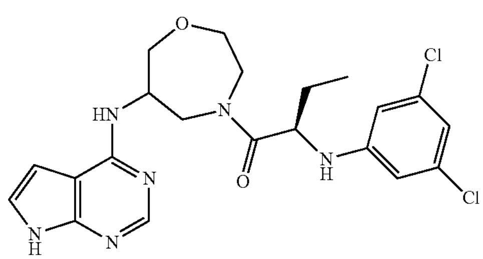 [SMILES: CC[C@@H](Nc1cc(Cl)cc(Cl)c1)C(=O)N1CCOCC(Nc2ncnc3[nH]ccc23)C1] | B |

TABLE 4-continued

Exemplary compounds of formula I.

| Cmpd | Structure | IC$_{50}$ (10 uM ATP)$^a$ |
|---|---|---|
| 46 | 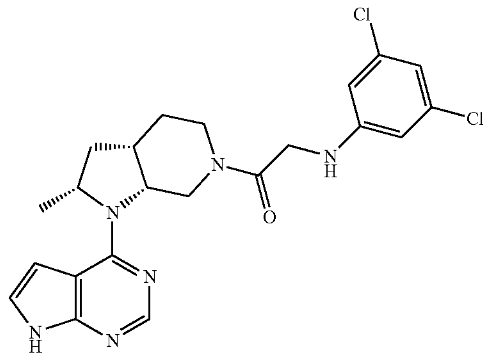 [SMILES: C[C@@H]1C[C@@H]2CCN(C(=O)CNc3cc(Cl)cc(Cl)c3)C[C@@H]2N1c1ncnc2[nH]ccc12] | A |
| 47 | 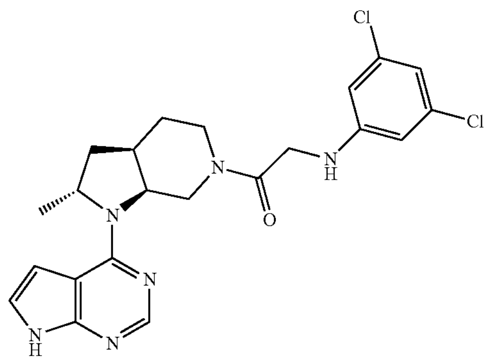 [SMILES: C[C@@H]1C[C@H]2CCN(C(=O)CNc3cc(Cl)cc(Cl)c3)C[C@H]2N1c1ncnc2[nH]ccc12] | A |
| 48 | 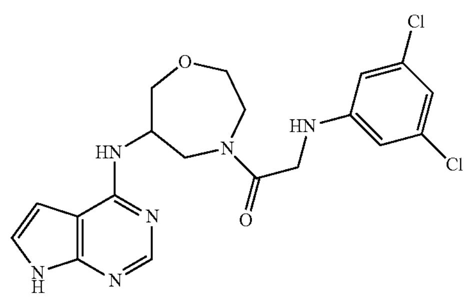 [SMILES: O=C(CNc1cc(Cl)cc(Cl)c1)N1CCOCC(Nc2ncnc3[nH]ccc23)C1] | B |
| 49 | 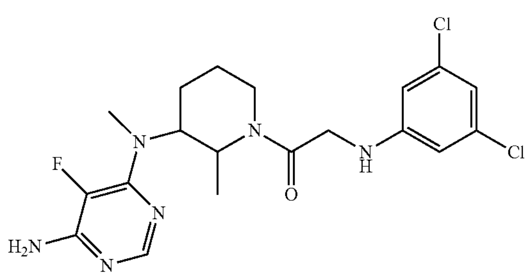 [SMILES: CC1C(N(C)c2ncnc(N)c2F)CCCN1C(=O)CNc1cc(Cl)cc(Cl)c1] | A |
| 50 | 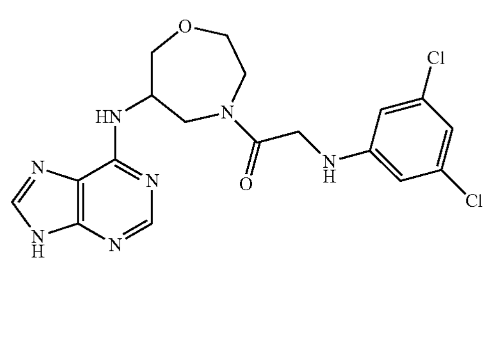 [SMILES: O=C(CNc1cc(Cl)cc(Cl)c1)N1CCOCC(Nc2ncnc3[nH]cnc23)C1] | B |

TABLE 4-continued
Exemplary compounds of formula I.
| Cmpd | Structure | IC$_{50}$ (10 uM ATP)$^a$ |
|---|---|---|
| 51 | 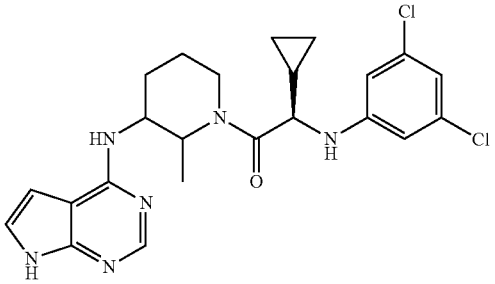 [SMILES: CC1C(Nc2ncnc3[nH]ccc23)CCCN1C(=O)[C@H](Nc1cc(Cl)cc(Cl)c1)C1CC1] | B |
| 52 | 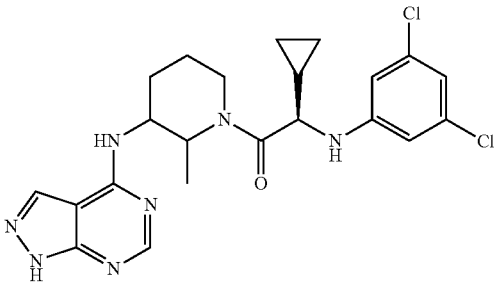 [SMILES: CC1C(Nc2ncnc3[nH]ncc23)CCCN1C(=O)[C@H](Nc1cc(Cl)cc(Cl)c1)C1CC1] | A |
| 53 | 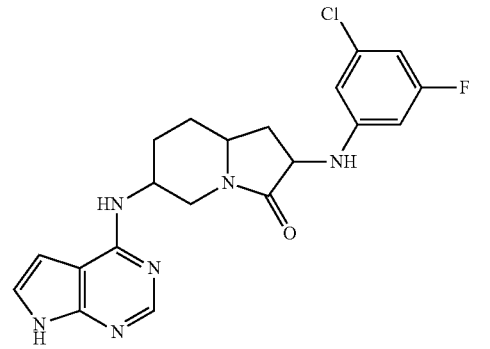 [SMILES: O=C1C(Nc2cc(F)cc(Cl)c2)CC2CCC(Nc3ncnc4[nH]ccc34)CN12] | C |
| 54 | 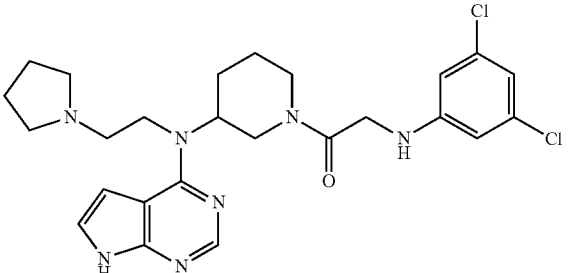 | C |
| 55 | 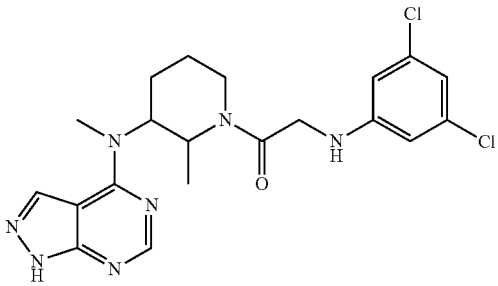 [SMILES: CC1C(N(C)c2ncnc3[nH]ncc23)CCCN1C(=O)CNc1cc(Cl)cc(Cl)c1] | A |

TABLE 4-continued

Exemplary compounds of formula I.

| Cmpd | Structure | IC$_{50}$ (10 uM ATP)$^a$ |
|---|---|---|
| 56 | 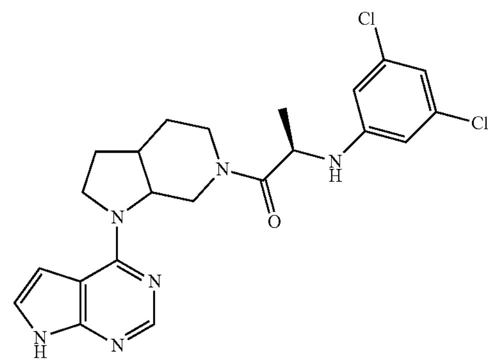 [SMILES: C[C@@H](Nc1cc(Cl)cc(Cl)c1)C(=O)N1CCC2CCN(c3ncnc4[nH]ccc34)C2C1] | A |
| 57 | 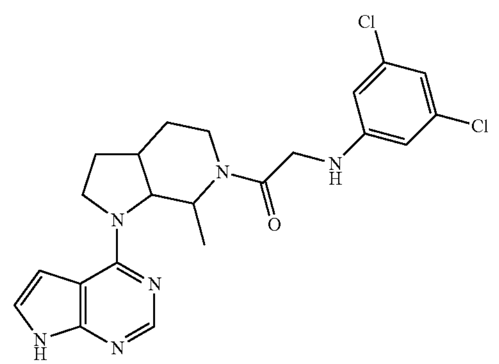 [SMILES: CC1C2C(CCN1C(=O)CNc1cc(Cl)cc(Cl)c1)CCN2c1ncnc2[nH]ccc12] | A |
| 58 | 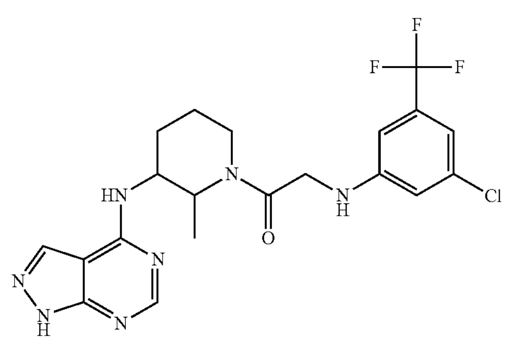 [SMILES: CC1C(Nc2ncnc3[nH]ncc23)CCCN1C(=O)CNc1cc(Cl)cc(C(F)(F)F)c1] | A |
| 59 | 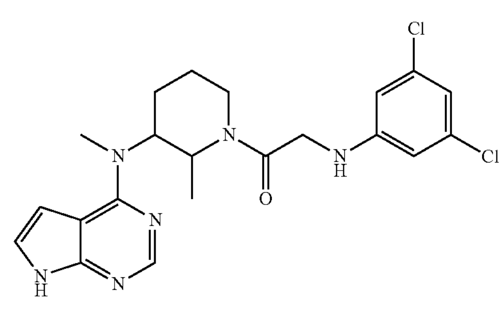 [SMILES: CC1C(N(C)c2ncnc3[nH]ccc23)CCCN1C(=O)CNc1cc(Cl)cc(Cl)c1] | A |

TABLE 4-continued

Exemplary compounds of formula I.

| Cmpd | Structure | IC$_{50}$ (10 uM ATP)$^a$ |
|---|---|---|
| 60 | 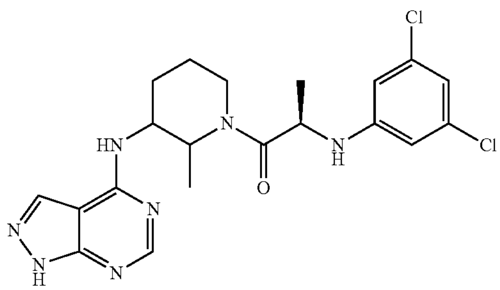 [SMILES: CC1C(Nc2ncnc3[nH]ncc23)CCCN1C(=O)[C@@H](C)Nc1cc(Cl)cc(Cl)c1] | A |
| 61 | 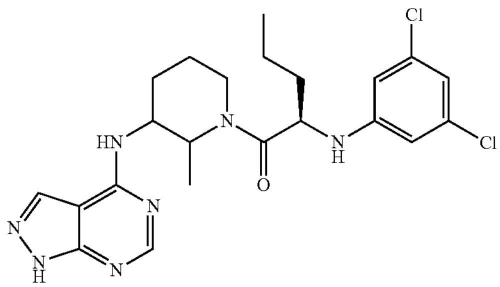 [SMILES: CCC[C@@H](Nc1cc(Cl)cc(Cl)c1)C(=O)N1CCCC(Nc2ncnc3[nH]ncc23)C1C] | A |
| 62 | 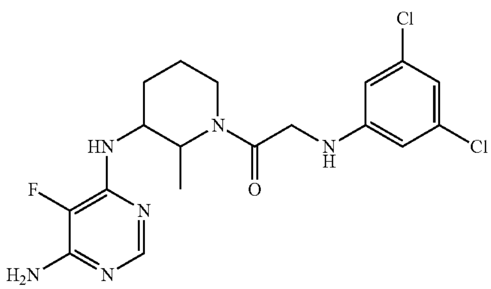 [SMILES: CC1C(Nc2ncnc(N)c2F)CCCN1C(=O)CNc1cc(Cl)cc(Cl)c1] | A |
| 63 | 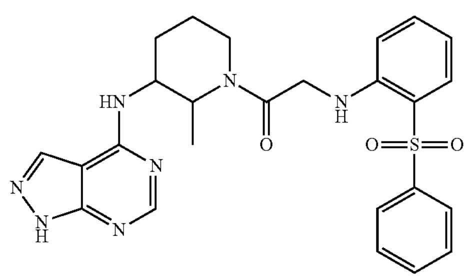 [SMILES: CC1C(Nc2ncnc3[nH]ncc23)CCCN1C(=O)CNc1ccccc1S(=O)(=O)c1ccccc1] | A |
| 64 | 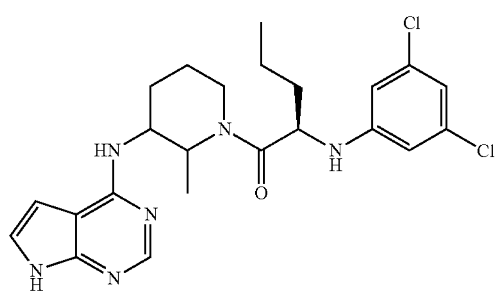 [SMILES: CCC[C@@H](Nc1cc(Cl)cc(Cl)c1)C(=O)N1CCCC(Nc2ncnc3[nH]ccc23)C1C] | A |

TABLE 4-continued

Exemplary compounds of formula I.

| Cmpd | Structure | IC$_{50}$ (10 uM ATP)$^a$ |
|------|-----------|---------------------------|
| 65 | 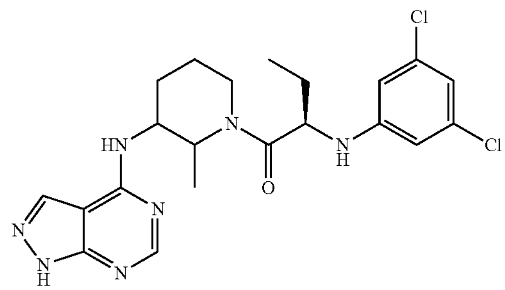 [SMILES: CC[C@@H](Nc1cc(Cl)cc(Cl)c1)C(=O)N1CCCC(Nc2ncnc3[nH]ncc23)C1C] | A |
| 66 | 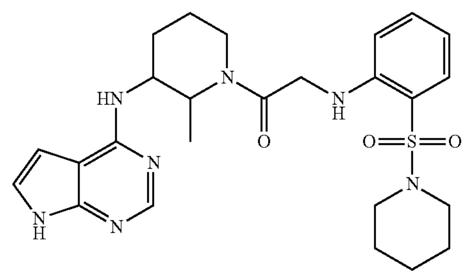 [SMILES: CC1C(Nc2ncnc3[nH]ccc23)CCCN1C(=O)CNc1ccccc1S(=O)(=O)N1CCCCC1] | A |
| 67 | 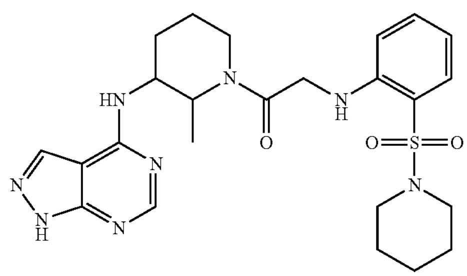 [SMILES: CC1C(Nc2ncnc3[nH]ncc23)CCCN1C(=O)CNc1ccccc1S(=O)(=O)N1CCCCC1] | A |
| 68 | 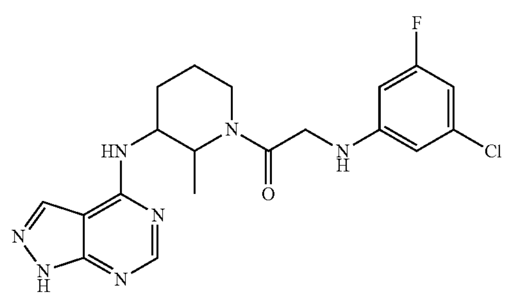 [SMILES: CC1C(Nc2ncnc3[nH]ncc23)CCCN1C(=O)CNc1cc(F)cc(Cl)c1] | A |
| 69 | 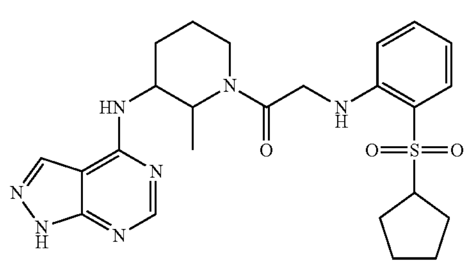 [SMILES: CC1C(Nc2ncnc3[nH]ncc23)CCCN1C(=O)CNc1ccccc1S(=O)(=O)C1CCCC1] | A |

TABLE 4-continued
Exemplary compounds of formula I.
| Cmpd | Structure | IC$_{50}$ (10 uM ATP)$^a$ |
|---|---|---|
| 70 | 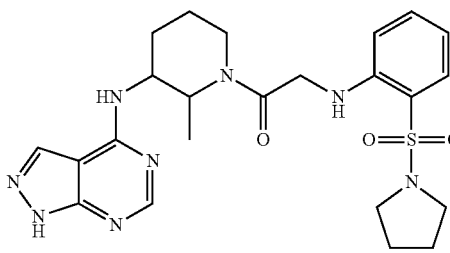 | A |
| 71 | 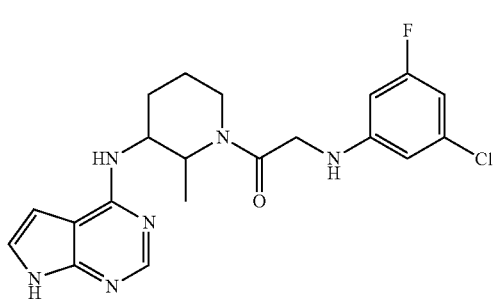 | A |
| 72 | 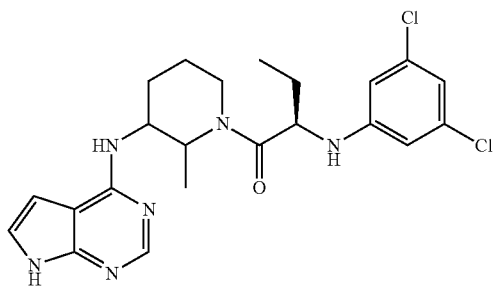 [SMILES: CC[C@@H](Nc1cc(Cl)cc(Cl)c1)C(=O)N1CCCC(Nc2ncnc3[nH]ccc23)C1C] | A |
| 73 | 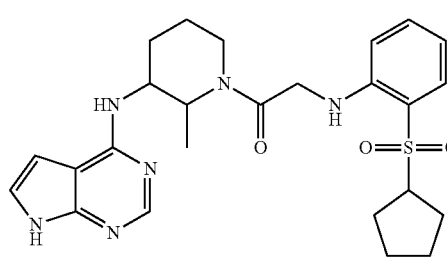 | A |
| 74 | 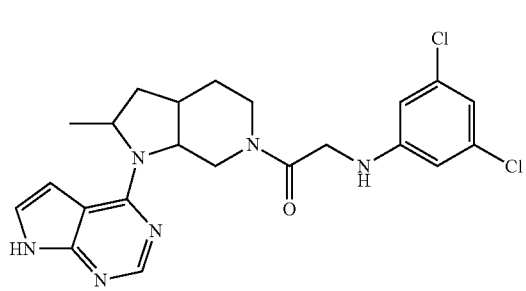 [SMILES: CC1CC2CCN(C(=O)CNc3cc(Cl)cc(Cl)c3)CC2N1c1ncnc2[nH]ccc12] | A |

TABLE 4-continued

Exemplary compounds of formula I.

| Cmpd | Structure | IC$_{50}$ (10 uM ATP)$^a$ |
|---|---|---|
| 75 | 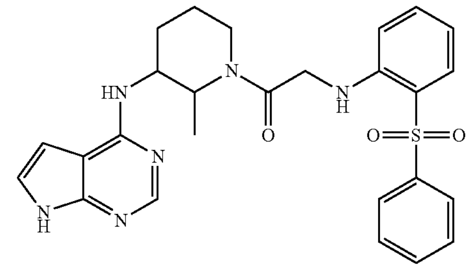 [SMILES: CC1C(Nc2ncnc3[nH]ccc23)CCCN1C(=O)CNc1ccccc1S(=O)(=O)c1ccccc1] | A |
| 76 | 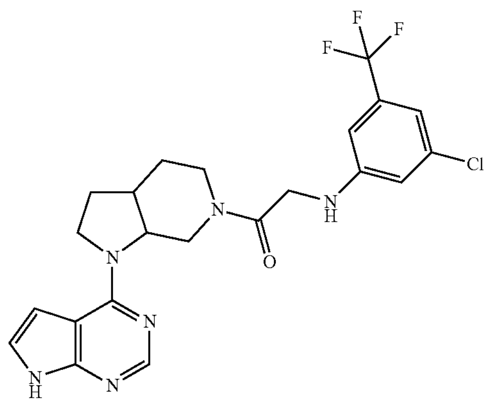 [SMILES: O=C(CNc1cc(Cl)cc(C(F)(F)F)c1)N1CCC2CCN(c3ncnc4[nH]ccc34)C2C1] | A |
| 77 | 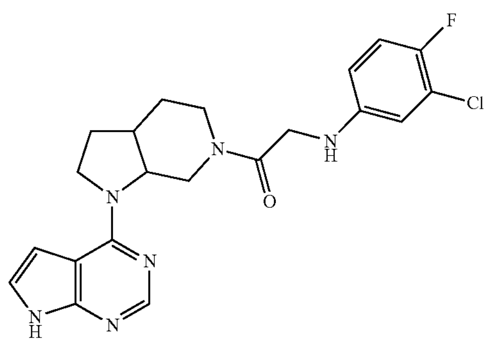 [SMILES: O=C(CNc1ccc(F)c(Cl)c1)N1CCC2CCN(c3ncnc4[nH]ccc34)C2C1] | A |
| 78 | 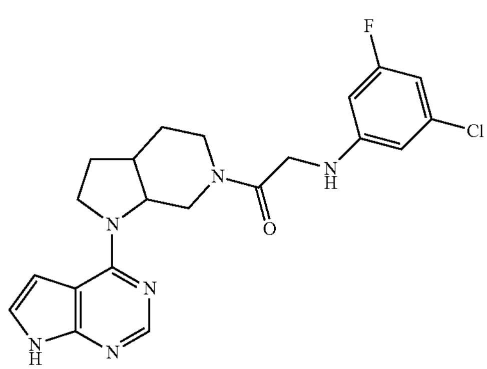 [SMILES: O=C(CNc1cc(F)cc(Cl)c1)N1CCC2CCN(c3ncnc4[nH]ccc34)C2C1] | A |

TABLE 4-continued

Exemplary compounds of formula I.

| Cmpd | Structure | IC$_{50}$ (10 uM ATP)$^a$ |
|---|---|---|
| 79 | 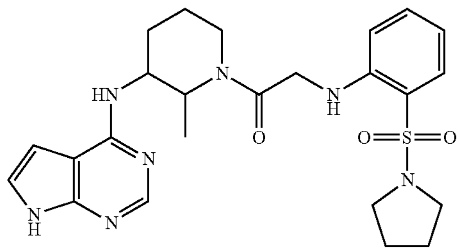 [SMILES: CC1C(Nc2ncnc3[nH]ccc23)CCCN1C(=O)CNc1ccccc1S(=O)(=O)N1CCCC1] | A |
| 80 | 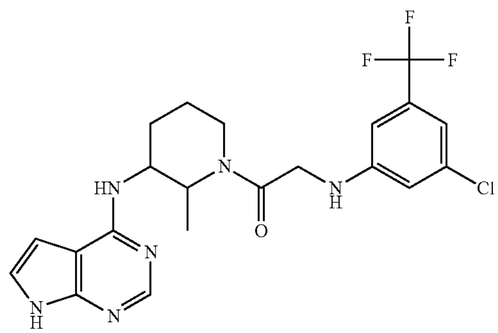 [SMILES: CC1C(Nc2ncnc3[nH]ccc23)CCCN1C(=O)CNc1cc(Cl)cc(C(F)(F)F)c1] | A |
| 81 | 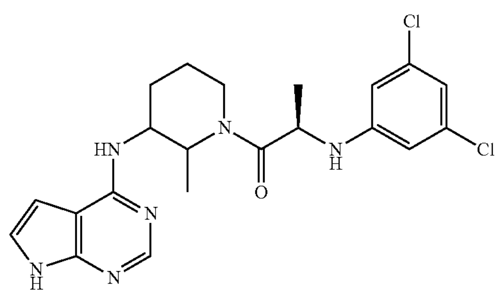 [SMILES: CC1C(Nc2ncnc3[nH]ccc23)CCCN1C(=O)[C@@H](C)Nc1cc(Cl)cc(Cl)c1] | A |
| 82 | 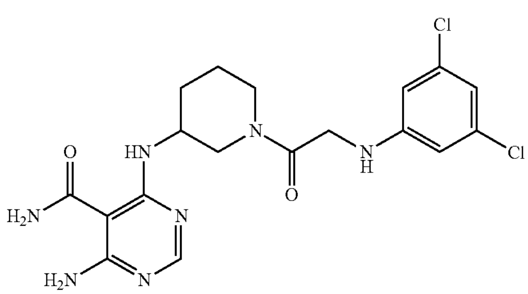 [SMILES: NC(=O)c1c(N)ncnc1NC1CCCN(C(=O)CNc2cc(Cl)cc(Cl)c2)C1] | D |
| 83 | 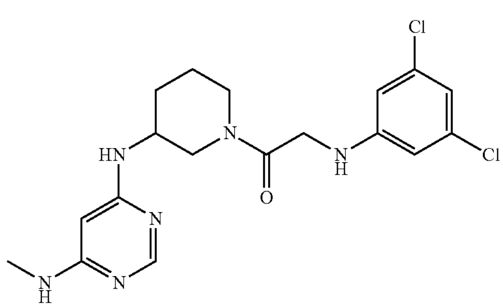 [SMILES: CNc1cc(NC2CCCN(C(=O)CNc3cc(Cl)cc(Cl)c3)C2)ncn1] | B |

TABLE 4-continued

Exemplary compounds of formula I.

| Cmpd | Structure | IC$_{50}$ (10 uM ATP)$^a$ |
|---|---|---|
| 84 | 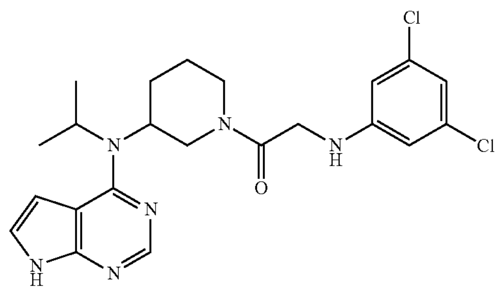 [SMILES: CC(C)N(c1ncnc2[nH]ccc12)C1CCCN(C(=O)CNc2cc(Cl)cc(Cl)c2)C1] | B |
| 85 | 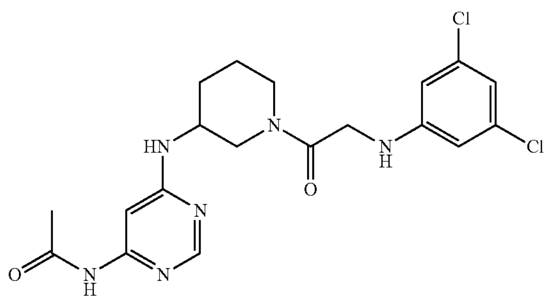 [SMILES: CC(=O)Nc1cc(NC2CCCN(C(=O)CNc3cc(Cl)cc(Cl)c3)C2)ncn1] | C |
| 86 | 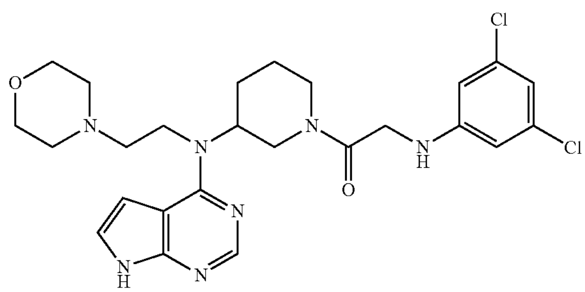 [SMILES: O=C(CNc1cc(Cl)cc(Cl)c1)N1CCCC(N(CCN2CCOCC2)c2ncnc3[nH]ccc23)C1] | B |
| 87 | 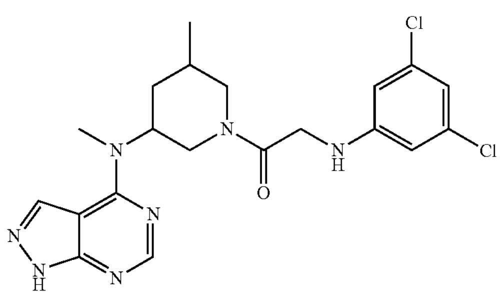 [SMILES: CC1CC(N(C)c2ncnc3[nH]ncc23)CN(C(=O)CNc2cc(Cl)cc(Cl)c2)C1] | A |
| 91 | 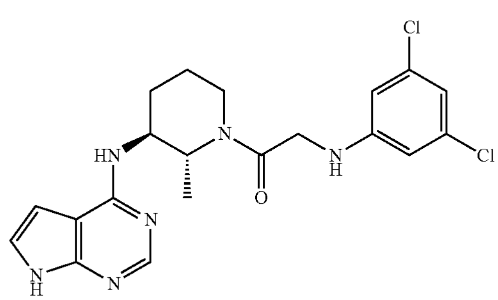 [SMILES: C[C@@H]1[C@@H](Nc2ncnc3[nH]ccc23)CCCN1C(=O)CNc1cc(Cl)cc(Cl)c1] | B |

TABLE 4-continued

Exemplary compounds of formula I.

| Cmpd | Structure | IC$_{50}$ (10 uM ATP)$^a$ |
|---|---|---|
| 88 | 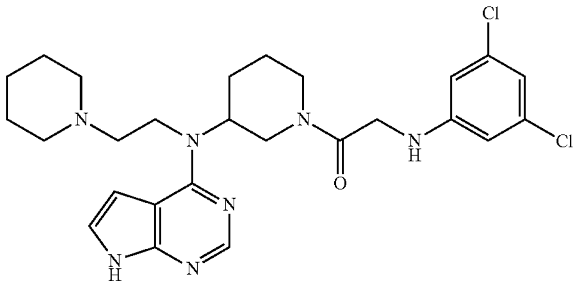 [SMILES: O=C(CNc1cc(Cl)cc(Cl)c1)N1CCCC(N(CCN2CCCCC2)c2ncnc3[nH]ccc23)C1] | C |
| 89 | 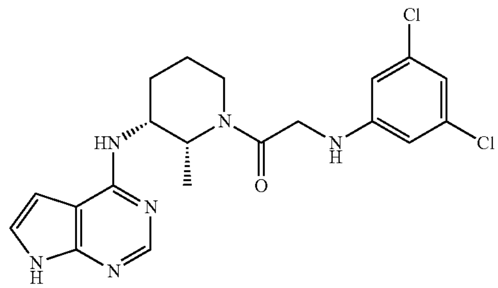 [SMILES: C[C@@H]1[C@H](Nc2ncnc3[nH]ccc23)CCCN1C(=O)CNc1cc(Cl)cc(Cl)c1] | A |
| 90 | 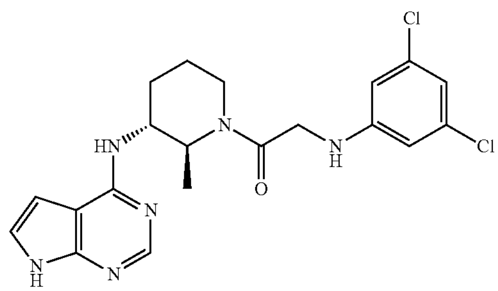 [SMILES: C[C@H]1[C@H](Nc2ncnc3[nH]ccc23)CCCN1C(=O)CNc1cc(Cl)cc(Cl)c1] | A |
| 95 | 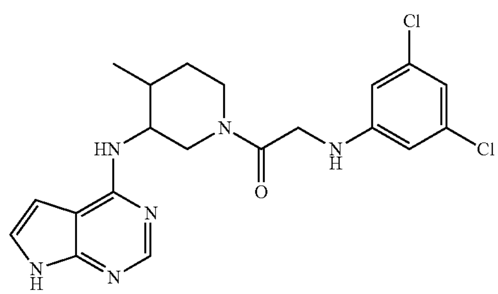 [SMILES: CC1CCN(C(=O)CNc2cc(Cl)cc(Cl)c2)CC1Nc1ncnc2[nH]ccc12] | B |
| 92 | 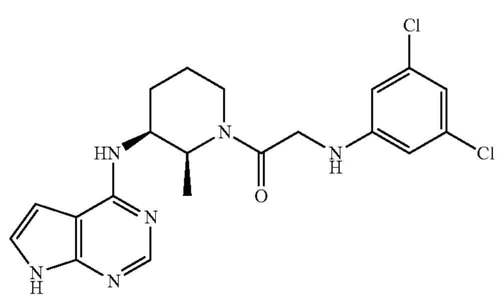 [SMILES: C[C@H]1[C@@H](Nc2ncnc3[nH]ccc23)CCCN1C(=O)CNc1cc(Cl)cc(Cl)c1] | B |

TABLE 4-continued

Exemplary compounds of formula I.

| Cmpd | Structure | IC$_{50}$ (10 uM ATP)$^a$ |
|---|---|---|
| 93 | 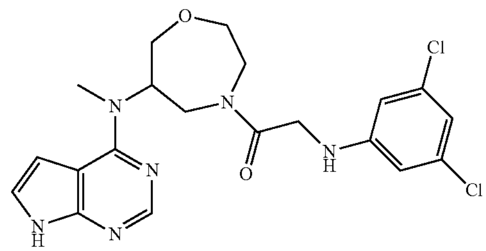 [SMILES: CN(c1ncnc2[nH]ccc12)C1COCCN(C(=O)CNc2cc(Cl)cc(Cl)c2)C1] | A |
| 94 | 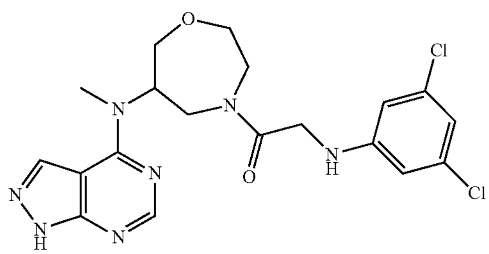 [SMILES: CN(c1ncnc2[nH]ncc12)C1COCCN(C(=O)CNc2cc(Cl)cc(Cl)c2)C1] | A |
| 96 | 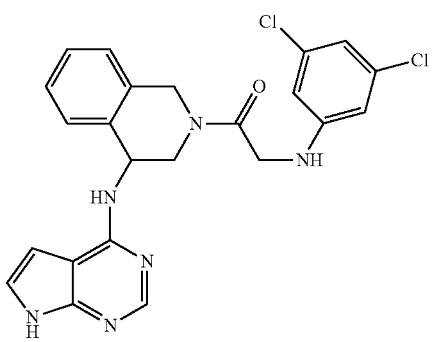 [SMILES: O=C(CNc1cc(Cl)cc(Cl)c1)N1Cc2ccccc2C(Nc2ncnc3[nH]ccc23)C1] | A |
| 97 | 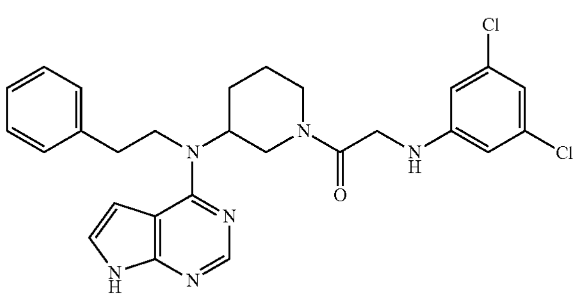 [SMILES: O=C(CNc1cc(Cl)cc(Cl)c1)N1CCCC(N(CCc2ccccc2)c2ncnc3[nH]ccc23)C1] | D |
| 98 | 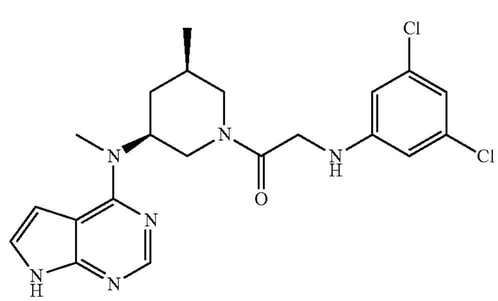 [SMILES: C[C@@H]1C[C@H](N(C)c2ncnc3[nH]ccc23)CN(C(=O)CNc2cc(Cl)cc(Cl)c2)C1] | A |

TABLE 4-continued

Exemplary compounds of formula I.

| Cmpd | Structure | IC$_{50}$ (10 uM ATP)$^a$ |
|---|---|---|
| 99 | 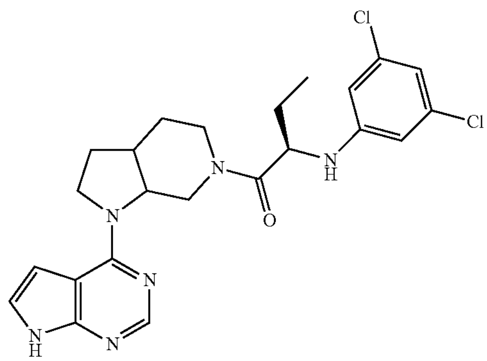 [SMILES: CC[C@@H](Nc1cc(Cl)cc(Cl)c1)C(=O)N1CCC2CCN(c3ncnc4[nH]ccc34)C2C1] | A |
| 100 | 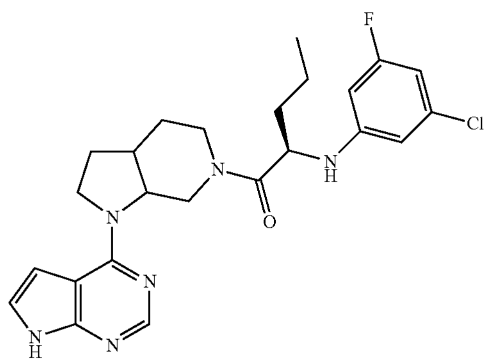 [SMILES: CCC[C@@H](Nc1cc(F)cc(Cl)c1)C(=O)N1CCC2CCN(c3ncnc4[nH]ccc34)C2C1] | A |
| 101 | 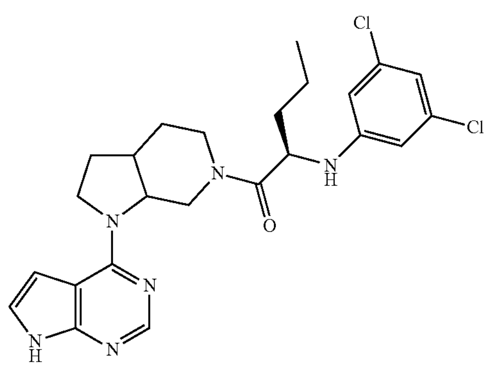 [SMILES: CCC[C@@H](Nc1cc(Cl)cc(Cl)c1)C(=O)N1CCC2CCN(c3ncnc4[nH]ccc34)C2C1] | A |
| 102 | 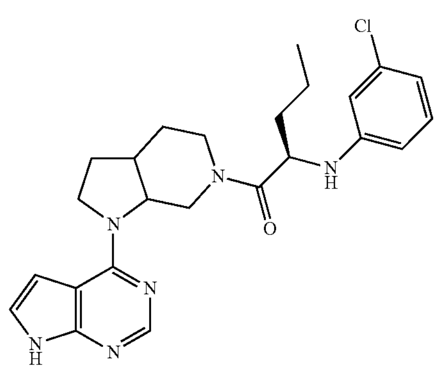 [SMILES: CCC[C@@H](Nc1cccc(Cl)c1)C(=O)N1CCC2CCN(c3ncnc4[nH]ccc34)C2C1] | A |

TABLE 4-continued

Exemplary compounds of formula I.

| Cmpd | Structure | IC$_{50}$ (10 uM ATP)$^a$ |
|---|---|---|
| 103 | 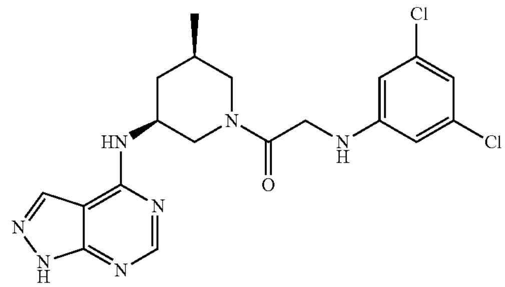 [SMILES: C[C@@H]1C[C@H](Nc2ncnc3[nH]ncc23)CN(C(=O)CNc2cc(Cl)cc(Cl)c2)C1] | A |
| 104 | 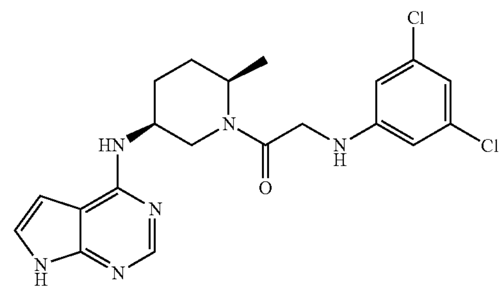 [SMILES: C[C@@H]1CC[C@H](Nc2ncnc3[nH]ccc23)CN1C(=O)CNc1cc(Cl)cc(Cl)c1] | A |
| 105 | 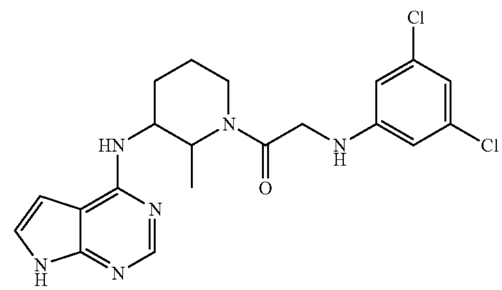 [SMILES: CC1C(Nc2ncnc3[nH]ccc23)CCCN1C(=O)CNc1cc(Cl)cc(Cl)c1] | A |
| 106 | 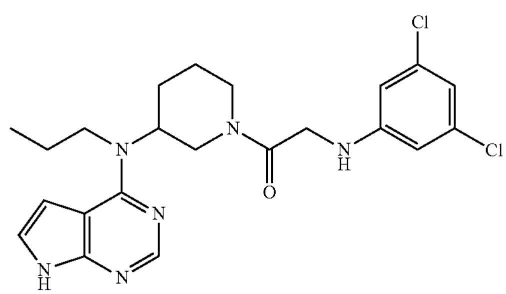 [SMILES: CCCN(c1ncnc2[nH]ccc12)C1CCCN(C(=O)CNc2cc(Cl)cc(Cl)c2)C1] | A |
| 107 | 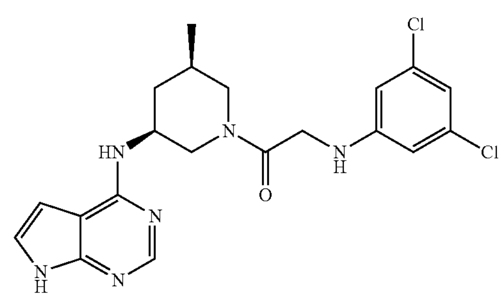 [SMILES: C[C@@H]1C[C@H](Nc2ncnc3[nH]ccc23)CN(C(=O)CNc2cc(Cl)cc(Cl)c2)C1] | A |

TABLE 4-continued

Exemplary compounds of formula I.

| Cmpd | Structure | IC$_{50}$ (10 uM ATP)$^a$ |
|---|---|---|
| 108 | 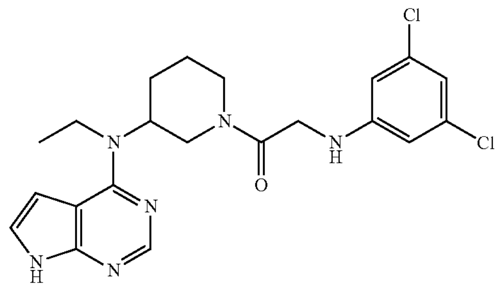 [SMILES: CCN(c1ncnc2[nH]ccc12)C1CCCN(C(=O)CNc2cc(Cl)cc(Cl)c2)C1] | B |
| 109 | 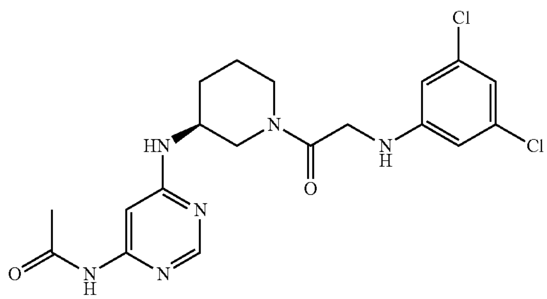 [SMILES: CC(=O)Nc1cc(N[C@H]2CCCN(C(=O)CNc3cc(Cl)cc(Cl)c3)C2)ncn1] | D |
| 110 | 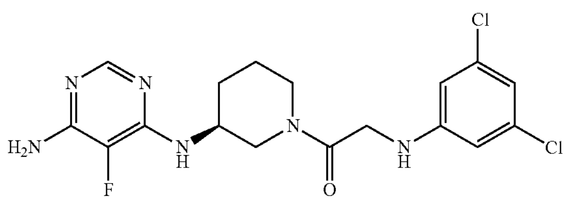 | B |
| 111 | 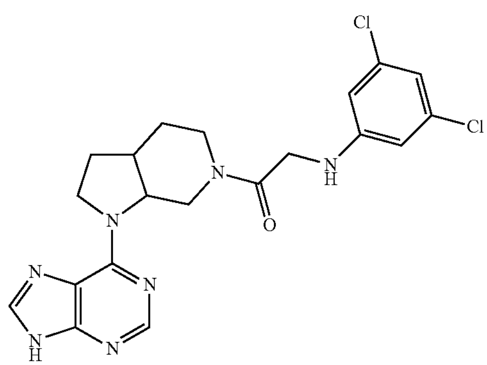 [SMILES: O=C(CNc1cc(Cl)cc(Cl)c1)N1CCC2CCN(c3ncnc4[nH]cnc34)C2C1] | A |
| 112 | 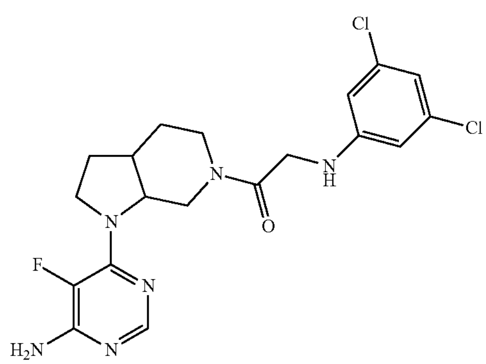 [SMILES: Nc1ncnc(N2CCC3CCN(C(=O)CNc4cc(Cl)cc(Cl)c4)CC32)c1F] | A |

TABLE 4-continued

Exemplary compounds of formula I.

| Cmpd | Structure | IC$_{50}$ (10 uM ATP)$^a$ |
|---|---|---|
| 113 | 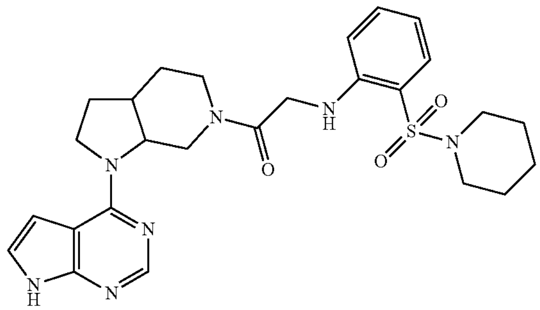 [SMILES: O=C(CNc1ccccc1S(=O)(=O)N1CCCCC1)N1CCC2CCN(c3ncnc4[nH]ccc34)C2C1] | A |
| 114 | 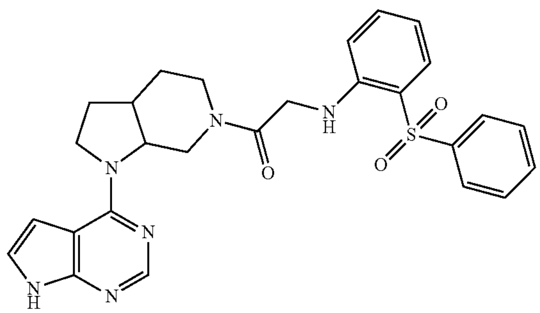 [SMILES: O=C(CNc1ccccc1S(=O)(=O)c1ccccc1)N1CCC2CCN(c3ncnc4[nH]ccc34)C2C1] | A |
| 115 | 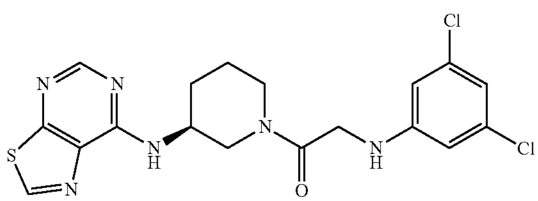 [SMILES: O=C(CNc1cc(Cl)cc(Cl)c1)N1CCC[C@H](Nc2ncnc3scnc23)C1] | D |
| 116 | 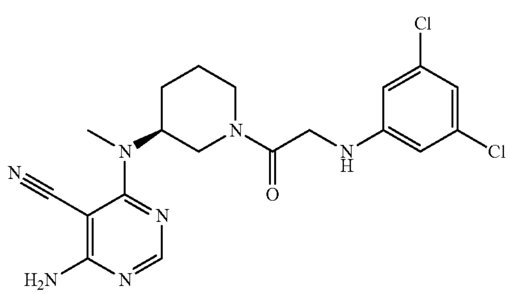 [SMILES: CN(c1ncnc(N)c1C#N)[C@H]1CCCN(C(=O)CNc2cc(Cl)cc(Cl)c2)C1] | D |
| 117 | 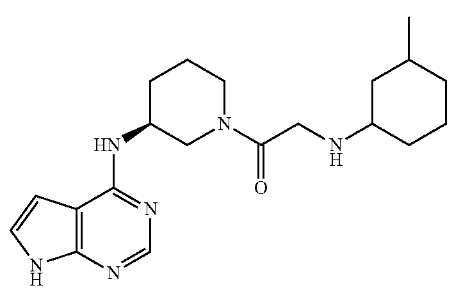 [SMILES: CC1CCCC(NCC(=O)N2CCC[C@H](Nc3ncnc4[nH]ccc34)C2)C1] | D |

TABLE 4-continued

Exemplary compounds of formula I.

| Cmpd | Structure | IC$_{50}$ (10 uM ATP)$^a$ |
|---|---|---|
| 118 | 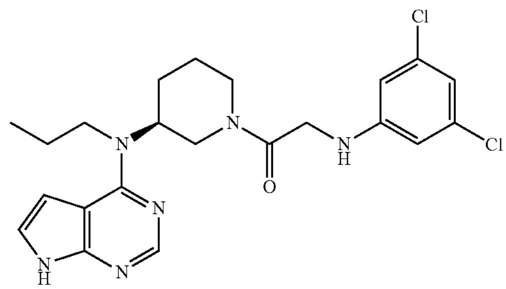 [SMILES: CCCN(c1ncnc2[nH]ccc12)[C@H]1CCCN(C(=O)CNc2cc(Cl)cc(Cl)c2)C1] | D |
| 119 | 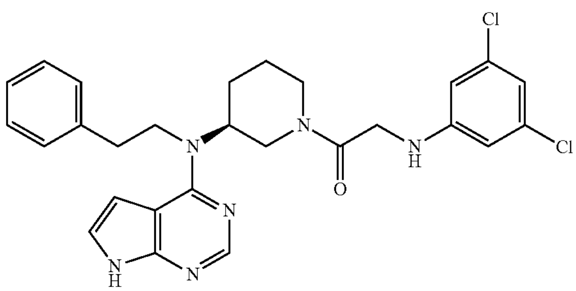 [SMILES: O=C(CNc1cc(Cl)cc(Cl)c1)N1CCC[C@H](N(CCc2ccccc2)c2ncnc3[nH]ccc23)C1] | D |
| 120 | 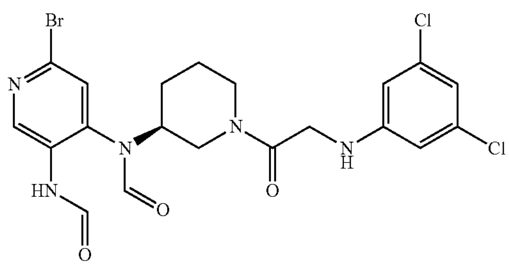 [SMILES: O=CNc1cnc(Br)cc1N(C=O)[C@H]1CCCN(C(=O)CNc2cc(Cl)cc(Cl)c2)C1] | D |
| 121 | 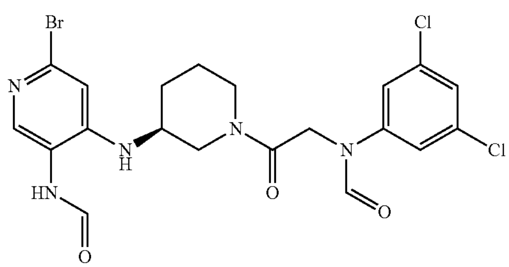 [SMILES: O=CNc1cnc(Br)cc1N[C@H]1CCCN(C(=O)CN(C=O)c2cc(Cl)cc(Cl)c2)C1] | D |
| 122 | 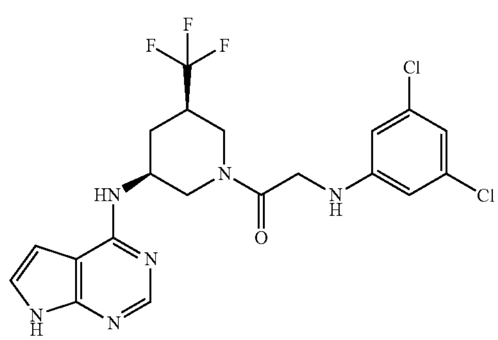 [SMILES: O=C(CNc1cc(Cl)cc(Cl)c1)N1C[C@@H](Nc2ncnc3[nH]ccc23)C[C@@H](C(F)(F)F)C1] | B |

TABLE 4-continued

Exemplary compounds of formula I.

| Cmpd | Structure | IC$_{50}$ (10 uM ATP)$^a$ |
|---|---|---|
| 123 | 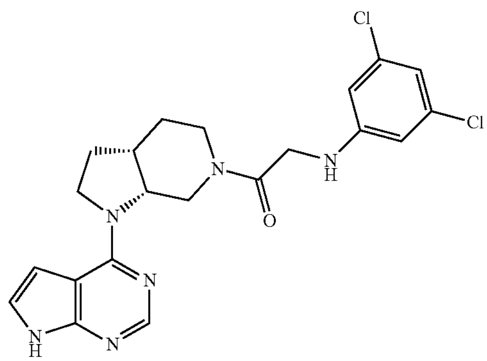 [SMILES: O=C(CNc1cc(Cl)cc(Cl)c1)N1CC[C@H]2CCN(c3ncnc4[nH]ccc34)[C@H]2C1] | A |
| 124 | 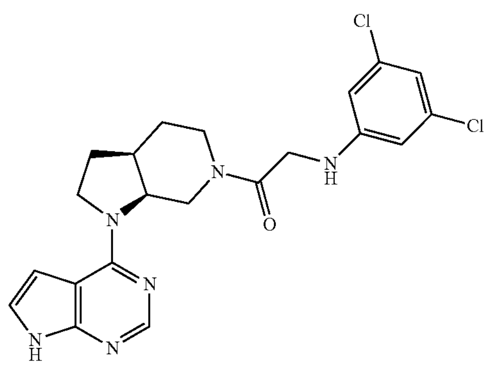 [SMILES: O=C(CNc1cc(Cl)cc(Cl)c1)N1CC[C@@H]2CCN(c3ncnc4[nH]ccc34)[C@@H]2C1] | A |
| 125 | 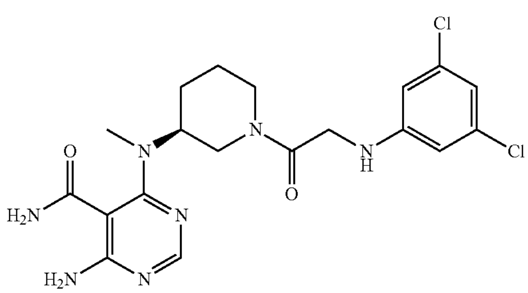 [SMILES: CN(c1ncnc(N)c1C(N)=O)[C@H]1CCCN(C(=O)CNc2cc(Cl)cc(Cl)c2)C1] | D |
| 126 | 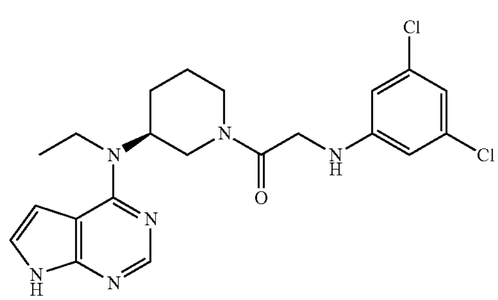 [SMILES: CCN(c1ncnc2[nH]ccc12)[C@H]1CCCN(C(=O)CNc2cc(Cl)cc(Cl)c2)C1] | D |

TABLE 4-continued

Exemplary compounds of formula I.

| Cmpd | Structure | IC$_{50}$ (10 uM ATP)$^a$ |
|---|---|---|
| 127 | 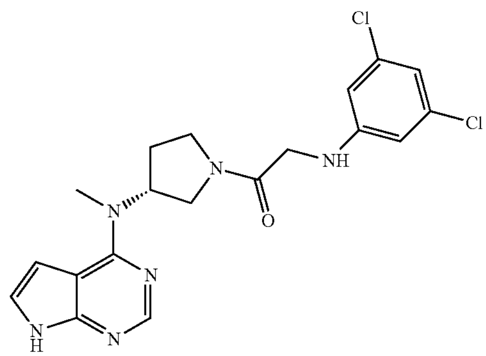 [SMILES: CN(c1ncnc2[nH]ccc12)[C@@H]1CCN(C(=O)CNc2cc(Cl)cc(Cl)c2)C1] | C |
| 128 | 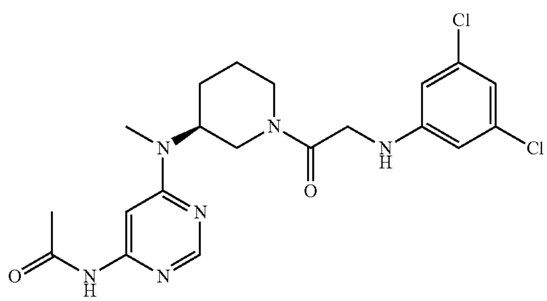 [SMILES: CC(=O)Nc1cc(N(C)[C@H]2CCCN(C(=O)CNc3cc(Cl)cc(Cl)c3)C2)ncn1] | D |
| 129 | 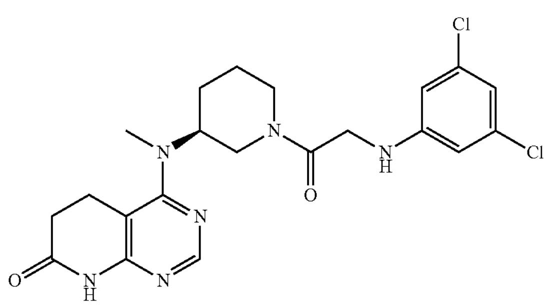 [SMILES: CN(c1ncnc2c1CCC(=O)N2)[C@H]1CCCN(C(=O)CNc2cc(Cl)cc(Cl)c2)C1] | D |
| 130 | 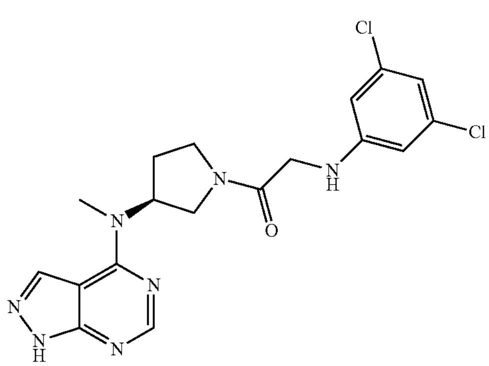 [SMILES: CN(c1ncnc2[nH]ncc12)[C@H]1CCN(C(=O)CNc2cc(Cl)cc(Cl)c2)C1] | D |

TABLE 4-continued

Exemplary compounds of formula I.

| Cmpd | Structure | IC$_{50}$ (10 uM ATP)$^a$ |
|---|---|---|
| 131 | 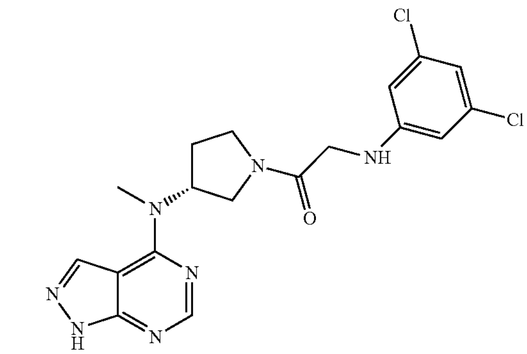 [SMILES: CN(c1ncnc2[nH]ncc12)[C@@H]1CCN(C(=O)CNc2cc(Cl)cc(Cl)c2)C1] | C |
| 132 | 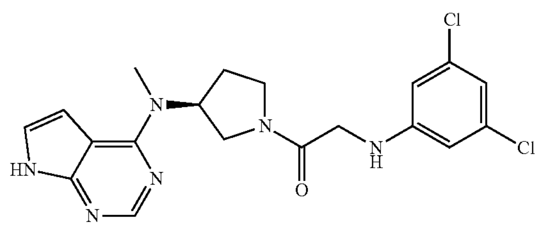 [SMILES: CN(c1ncnc2[nH]ccc12)[C@H]1CCN(C(=O)CNc2cc(Cl)cc(Cl)c2)C1] | D |
| 133 | 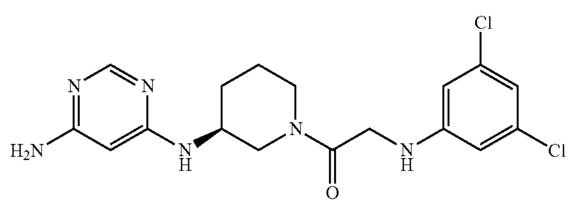 [SMILES: Nc1cc(N[C@H]2CCCN(C(=O)CNc3cc(Cl)cc(Cl)c3)C2)ncn1] | C |
| 134 | 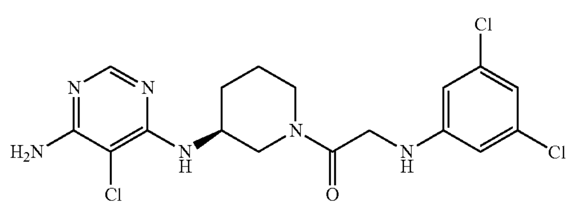 [SMILES: Nc1ncnc(N[C@H]2CCCN(C(=O)CNc3cc(Cl)cc(Cl)c3)C2)c1Cl] | D |
| 135 | 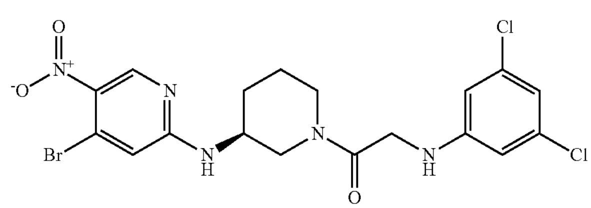 | D |
| 136 | 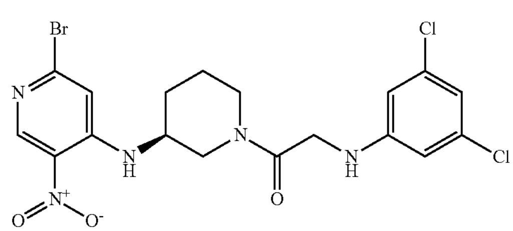 [SMILES: O=C(CNc1cc(Cl)cc(Cl)c1)N1CCC[C@H](Nc2cc(Br)ncc2[N+](=O)[O-])C1] | D |

TABLE 4-continued

Exemplary compounds of formula I.

| Cmpd | Structure | IC$_{50}$ (10 uM ATP)$^a$ |
|---|---|---|
| 137 | 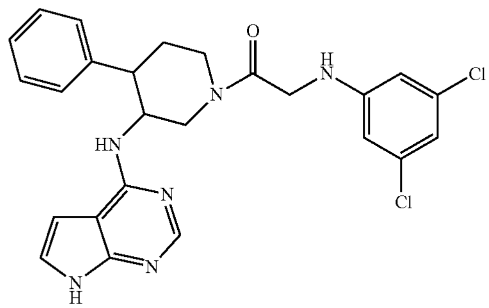 [SMILES: O=C(CNc1cc(Cl)cc(Cl)c1)N1CCC(c2ccccc2)C(Nc2ncnc3[nH]ccc23)C1] | D |
| 138 | 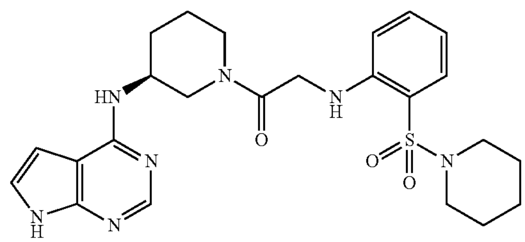 [SMILES: O=C(CNc1ccccc1S(=O)(=O)N1CCCCC1)N1CCC[C@H](Nc2ncnc3[nH]ccc23)C1] | D |
| 139 | 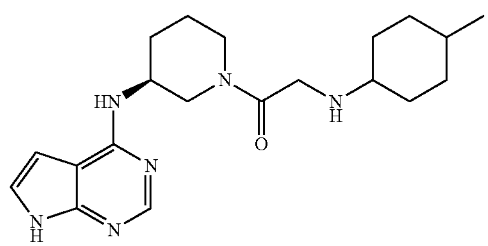 [SMILES: CC1CCC(NCC(=O)N2CCC[C@H](Nc3ncnc4[nH]ccc34)C2)CC1] | D |
| 140 | 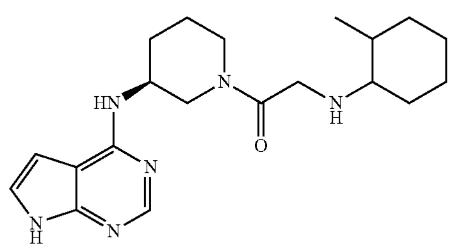 [SMILES: CC1CCCCC1NCC(=O)N1CCC[C@H](Nc2ncnc3[nH]ccc23)C1] | D |
| 141 | 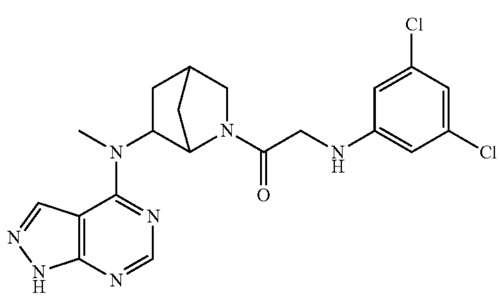 [SMILES: CN(c1ncnc2[nH]ncc12)C1CC2CC1N(C(=O)CNc1cc(Cl)cc(Cl)c1)C2] | B |

TABLE 4-continued
Exemplary compounds of formula I.
| Cmpd | Structure | IC$_{50}$ (10 uM ATP)$^a$ |
|---|---|---|
| 142 | 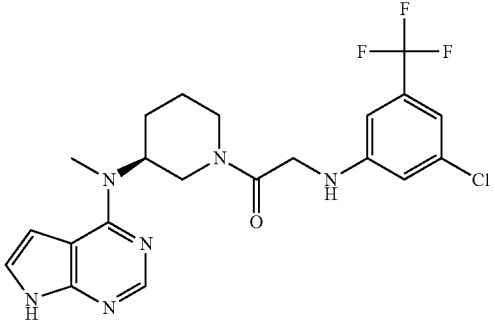 [SMILES: CN(c1ncnc2[nH]ccc12)[C@H]1CCCN(C(=O)CNc2cc(Cl)cc(C(F)(F)F)c2)C1] | B |
| 143 | 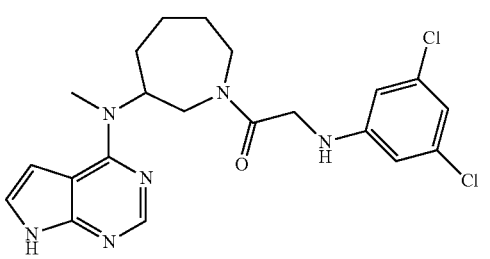 [SMILES: CN(c1ncnc2[nH]ccc12)C1CCCCN(C(=O)CNc2cc(Cl)cc(Cl)c2)C1] | A |
| 144 | 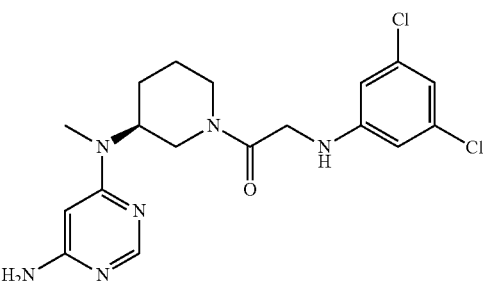 | D |
| 145 | 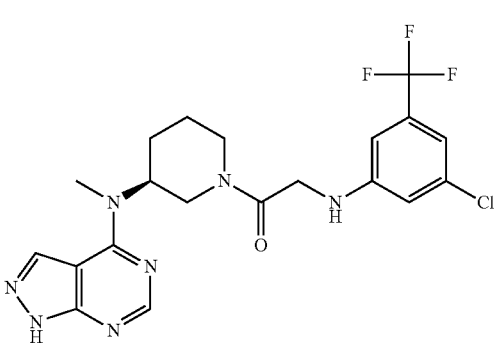 [SMILES: CN(c1ncnc2[nH]ncc12)[C@H]1CCCN(C(=O)CNc2cc(Cl)cc(C(F)(F)F)c2)C1] | C |
| 146 | 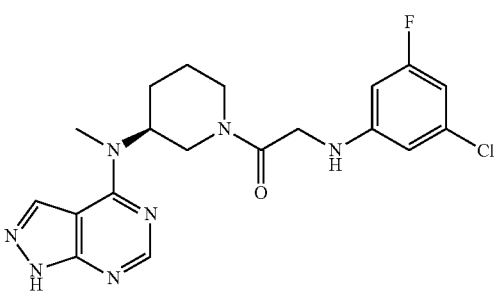 [SMILES: CN(c1ncnc2[nH]ncc12)[C@H]1CCCN(C(=O)CNc2cc(F)cc(Cl)c2)C1] | C |

TABLE 4-continued

Exemplary compounds of formula I.

| Cmpd | Structure | IC$_{50}$ (10 uM ATP)$^a$ |
|---|---|---|
| 147 | 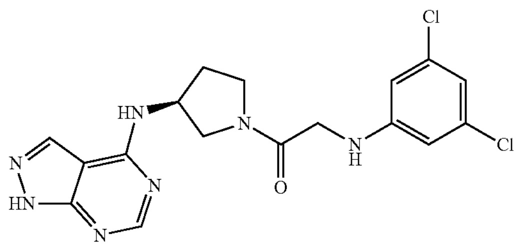 [SMILES: O=C(CNc1cc(Cl)cc(Cl)c1)N1CC[C@H](Nc2ncnc3[nH]ncc23)C1] | D |
| 148 | 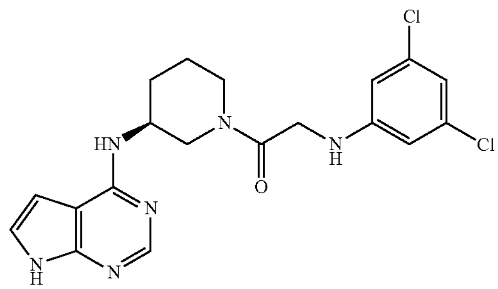 [SMILES: O=C(CNc1cc(Cl)cc(Cl)c1)N1CCC[C@H](Nc2ncnc3[nH]ccc23)C1] | B |
| 149 | 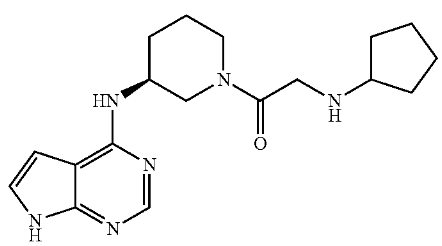 [SMILES: O=C(CNC1CCCC1)N1CCC[C@H](Nc2ncnc3[nH]ccc23)C1] | D |
| 150 | 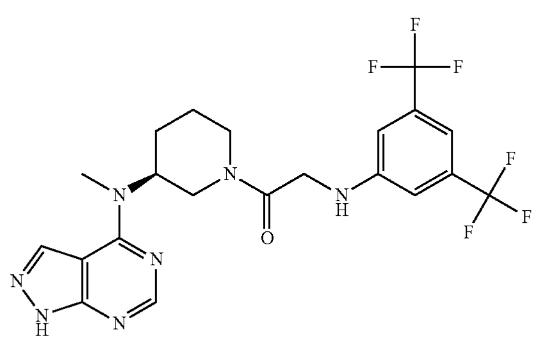 [SMILES: CN(c1ncnc2[nH]ncc12)[C@H]1CCCN(C(=O)CNc2cc(C(F)(F)F)cc(C(F)(F)F)c2)C1] | D |
| 151 | 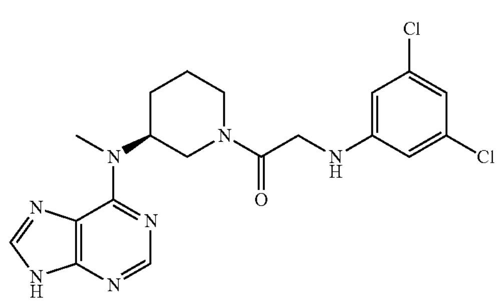 [SMILES: CN(c1ncnc2[nH]cnc12)[C@H]1CCCN(C(=O)CNc2cc(Cl)cc(Cl)c2)C1] | B |

TABLE 4-continued

Exemplary compounds of formula I.

| Cmpd | Structure | IC$_{50}$ (10 uM ATP)$^a$ |
|---|---|---|
| 152 | 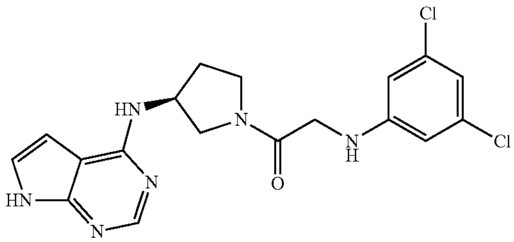 [SMILES: O=C(CNc1cc(Cl)cc(Cl)c1)N1CC[C@H](Nc2ncnc3[nH]ccc23)C1] | D |
| 153 | 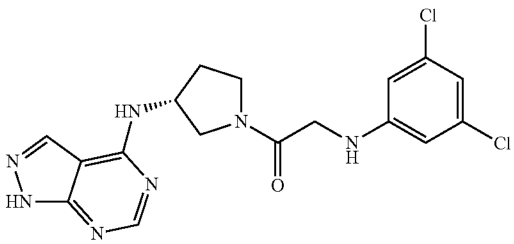 [SMILES: O=C(CNc1cc(Cl)cc(Cl)c1)N1CC[C@@H](Nc2ncnc3[nH]ncc23)C1] | D |
| 154 | 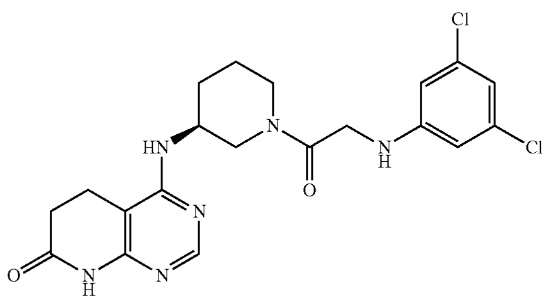 [SMILES: O=C1CCc2c(ncnc2N[C@H]2CCCN(C(=O)CNc3cc(Cl)cc(Cl)c3)C2)N1] | D |
| 155 | 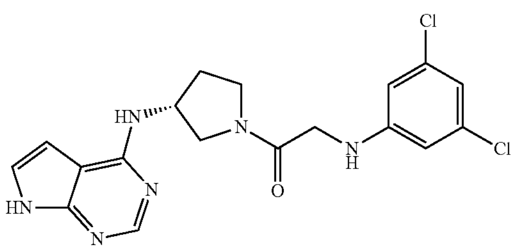 [SMILES: O=C(CNc1cc(Cl)cc(Cl)c1)N1CC[C@@H](Nc2ncnc3[nH]ccc23)C1] | D |
| 156 | 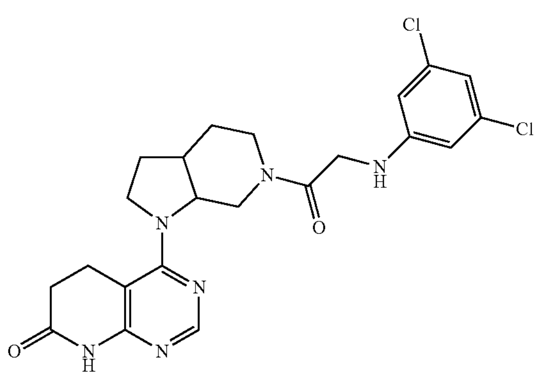 [SMILES: O=C1CCc2c(ncnc2N2CCC3CCN(C(=O)CNc4cc(Cl)cc(Cl)c4)CC32)N1] | C |

TABLE 4-continued

Exemplary compounds of formula I.

| Cmpd | Structure | IC$_{50}$ (10 uM ATP)$^a$ |
|---|---|---|
| 157 | 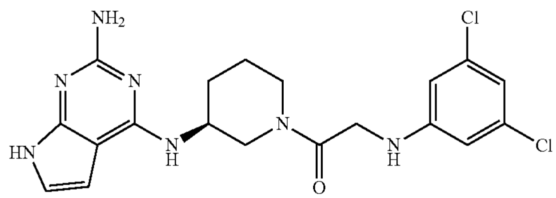 [SMILES: Nc1nc(N[C@H]2CCCN(C(=O)CNc3cc(Cl)cc(Cl)c3)C2)c2cc[nH]c2n1] | D |
| 158 | 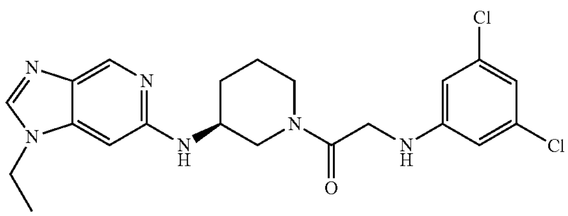 [SMILES: CCn1cnc2cnc(N[C@H]3CCCN(C(=O)CNc4cc(Cl)cc(Cl)c4)C3)cc21] | D |
| 159 | 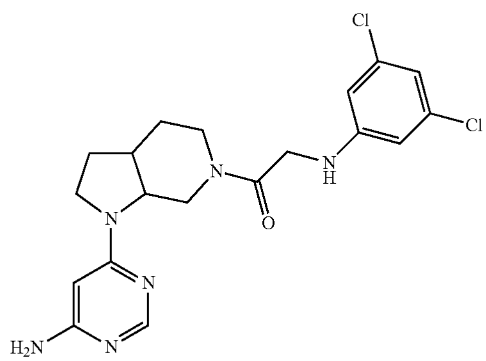 [SMILES: Nc1cc(N2CCC3CCN(C(=O)CNc4cc(Cl)cc(Cl)c4)CC32)ncn1] | A |
| 160 | 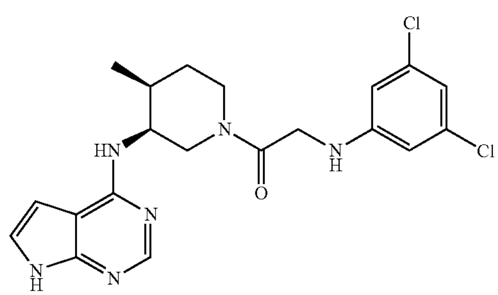 [SMILES: C[C@H]1CCN(C(=O)CNc2cc(Cl)cc(Cl)c2)C[C@H]1Nc1ncnc2[nH]ccc12] | C |
| 161 | 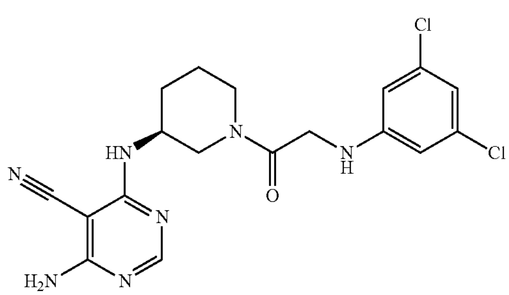 [SMILES: N#Cc1c(N)ncnc1N[C@H]1CCCN(C(=O)CNc2cc(Cl)cc(Cl)c2)C1] | D |

TABLE 4-continued

Exemplary compounds of formula I.

| Cmpd | Structure | IC$_{50}$ (10 uM ATP)$^a$ |
|---|---|---|
| 162 | 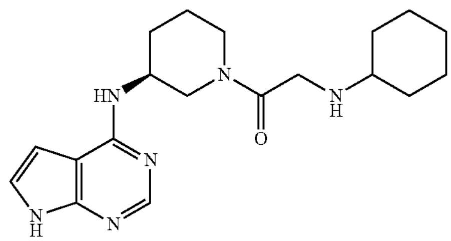 [SMILES: O=C(CNC1CCCCC1)N1CCC[C@H](Nc2ncnc3[nH]ccc23)C1] | D |
| 163 | 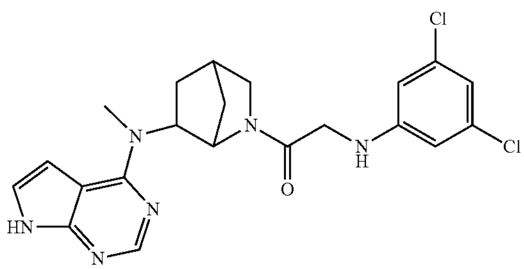 [SMILES: CN(c1ncnc2[nH]ccc12)C1CC2CC1N(C(=O)CNc1cc(Cl)cc(Cl)c1)C2] | C |
| 164 | 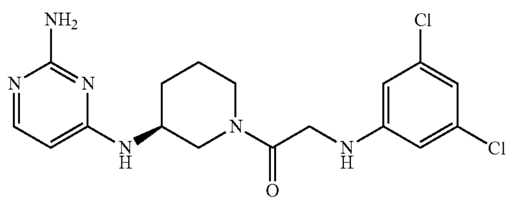 [SMILES: Nc1nccc(N[C@H]2CCCN(C(=O)CNc3cc(Cl)cc(Cl)c3)C2)n1] | D |
| 165 | 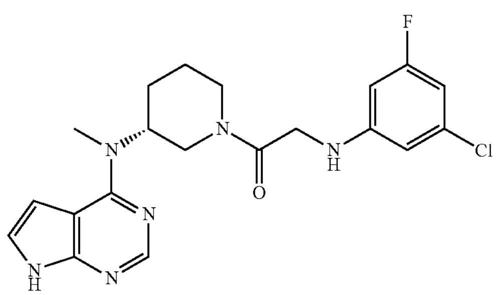 [SMILES: CN(c1ncnc2[nH]ccc12)[C@@H]1CCCN(C(=O)CNc2cc(F)cc(Cl)c2)C1] | B |
| 166 | 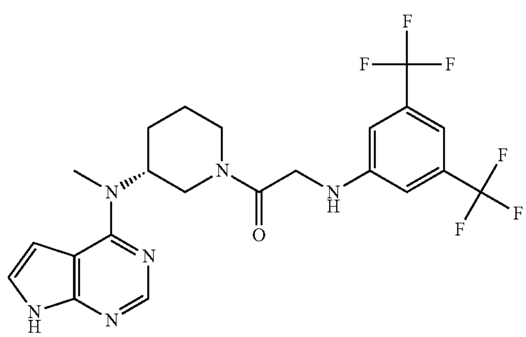 [SMILES: CN(c1ncnc2[nH]ccc12)[C@@H]1CCCN(C(=O)CNc2cc(C(F)(F)F)cc(C(F)(F)F)c2)C1] | D |

TABLE 4-continued

Exemplary compounds of formula I.

| Cmpd | Structure | IC$_{50}$ (10 uM ATP)$^a$ |
|---|---|---|
| 167 | 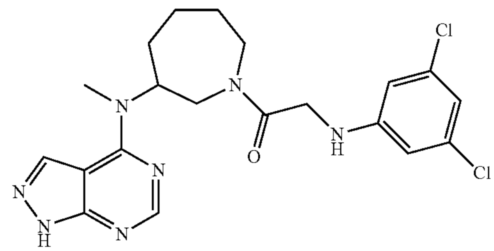 [SMILES: CN(c1ncnc2[nH]ncc12)C1CCCCN(C(=O)CNc2cc(Cl)cc(Cl)c2)C1] | A |
| 168 | 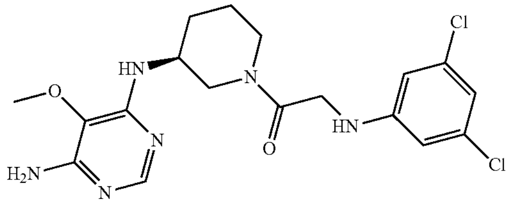 [SMILES: COc1c(N)ncnc1N[C@H]1CCCN(C(=O)CNc2cc(Cl)cc(Cl)c2)C1] | D |
| 169 | 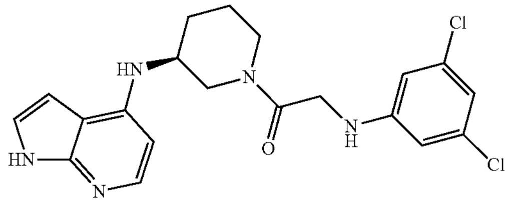 [SMILES: O=C(CNc1cc(Cl)cc(Cl)c1)N1CCC[C@H](Nc2ccnc3[nH]ccc23)C1] | A |
| 170 | 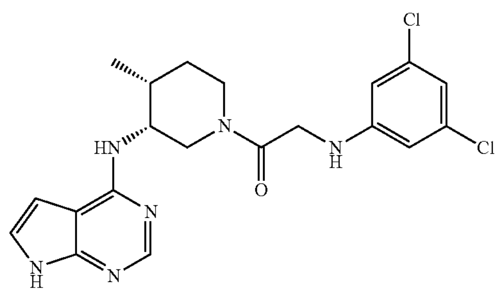 [SMILES: C[C@@H]1CCN(C(=O)CNc2cc(Cl)cc(Cl)c2)C[C@@H]1Nc1ncnc2[nH]ccc12] | C |
| 171 | 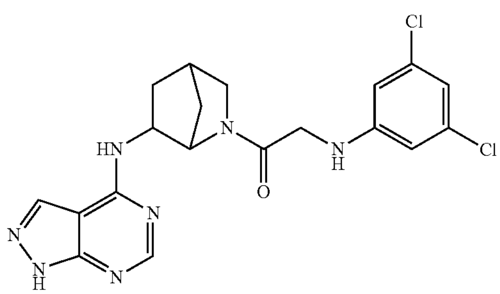 [SMILES: O=C(CNc1cc(Cl)cc(Cl)c1)N1CC2CC(Nc3ncnc4[nH]ncc34)C1C2] | A |
| 172 | 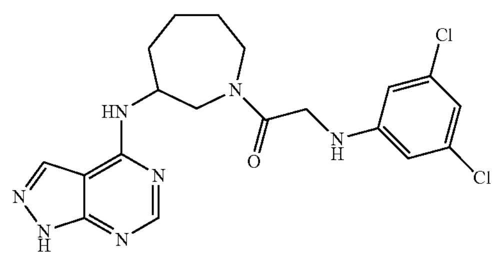 [SMILES: O=C(CNc1cc(Cl)cc(Cl)c1)N1CCCCC(Nc2ncnc3[nH]ncc23)C1] | A |

TABLE 4-continued

Exemplary compounds of formula I.

| Cmpd | Structure | IC$_{50}$ (10 uM ATP)$^a$ |
|---|---|---|
| 173 | 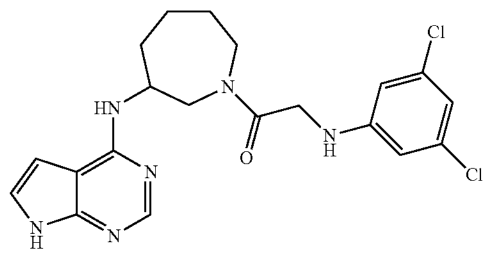 [SMILES: O=C(CNc1cc(Cl)cc(Cl)c1)N1CCCCC(Nc2ncnc3[nH]ccc23)C1] | A |
| 174 | 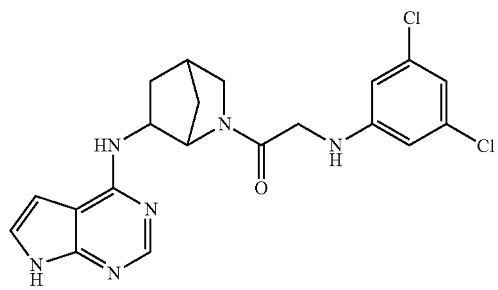 [SMILES: O=C(CNc1cc(Cl)cc(Cl)c1)N1CC2CC(Nc3ncnc4[nH]ccc34)C1C2] | A |
| 175 | 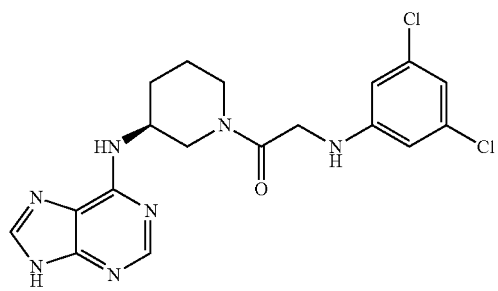 [SMILES: O=C(CNc1cc(Cl)cc(Cl)c1)N1CCC[C@H](Nc2ncnc3[nH]cnc23)C1] | B |
| 176 | 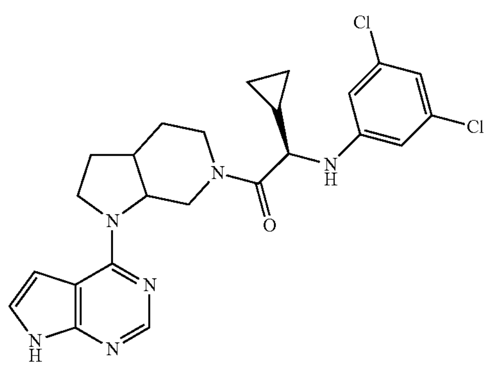 [SMILES: O=C([C@H](Nc1cc(Cl)cc(Cl)c1)C1CC1)N1CCC2CCN(c3ncnc4[nH]ccc34)C2C1] | A |
| 177 | 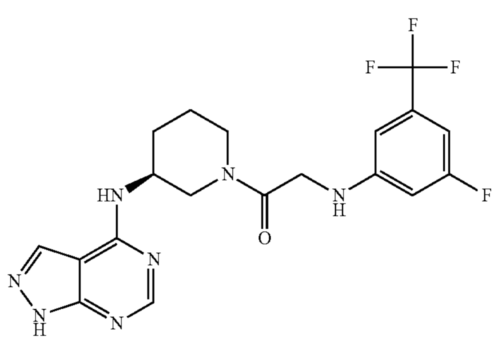 [SMILES: O=C(CNc1cc(F)cc(C(F)(F)F)c1)N1CCC[C@H](Nc2ncnc3[nH]ncc23)C1] | C |

TABLE 4-continued

Exemplary compounds of formula I.

| Cmpd | Structure | IC$_{50}$ (10 uM ATP)$^a$ |
|------|-----------|---------------------------|
| 178 | 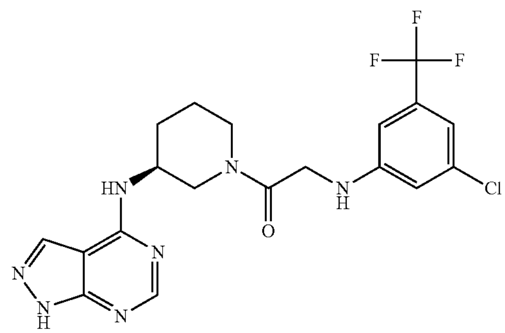 [SMILES: O=C(CNc1cc(Cl)cc(C(F)(F)F)c1)N1CCC[C@H](Nc2ncnc3[nH]ncc23)C1] | C |
| 179 | 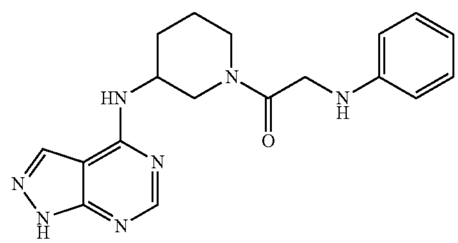 [SMILES: O=C(CNc1ccccc1)N1CCCC(Nc2ncnc3[nH]ncc23)C1] | C |
| 180 | 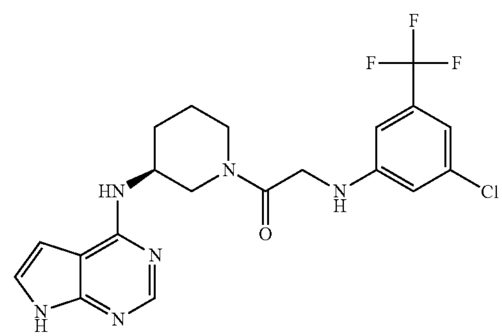 [SMILES: O=C(CNc1cc(Cl)cc(C(F)(F)F)c1)N1CCC[C@H](Nc2ncnc3[nH]ccc23)C1] | B |
| 181 | 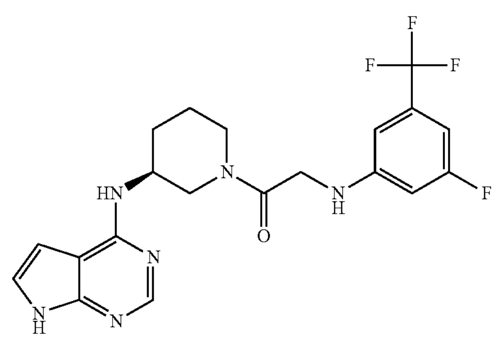 [SMILES: O=C(CNc1cc(F)cc(C(F)(F)F)c1)N1CCC[C@H](Nc2ncnc3[nH]ccc23)C1] | C |
| 182 | 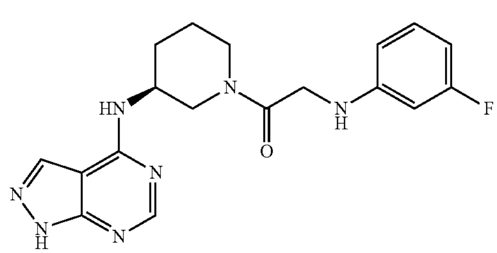 [SMILES: O=C(CNc1cccc(F)c1)N1CCC[C@H](Nc2ncnc3[nH]ncc23)C1] | D |

TABLE 4-continued

Exemplary compounds of formula I.

| Cmpd | Structure | IC$_{50}$ (10 uM ATP)$^a$ |
|---|---|---|
| 183 | 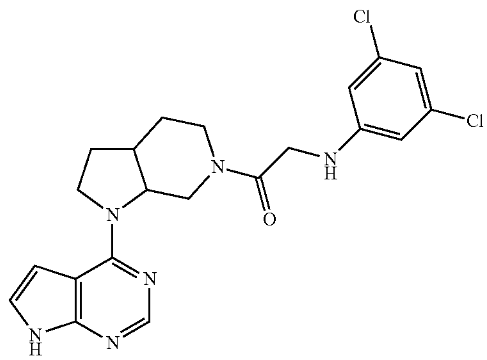 | A |
| 184 | 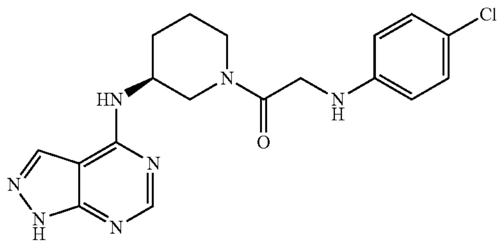 [SMILES: O=C(CNc1ccc(Cl)cc1)N1CCC[C@H](Nc2ncnc3[nH]ncc23)C1] | D |
| 185 | 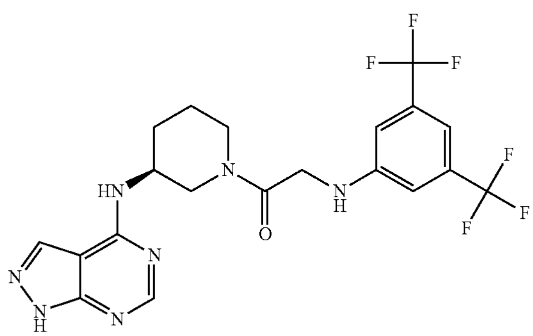 [SMILES: O=C(CNc1cc(C(F)(F)F)cc(C(F)(F)F)c1)N1CCC[C@H](Nc2ncnc3[nH]ncc23)C1] | C |
| 186 | 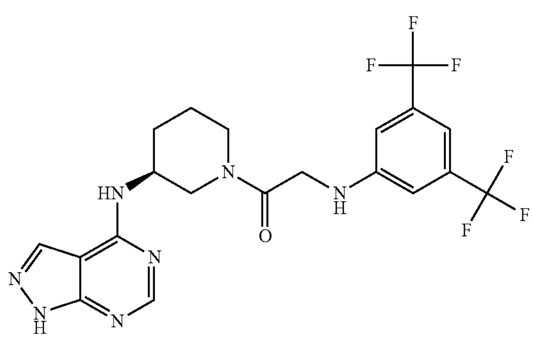 [SMILES: O=C(CNc1cc(C(F)(F)F)cc(C(F)(F)F)c1)N1CCC[C@H](Nc2ncnc3[nH]ncc23)C1] | D |

TABLE 4-continued

Exemplary compounds of formula I.

| Cmpd | Structure | IC$_{50}$ (10 uM ATP)$^a$ |
|---|---|---|
| 187 | 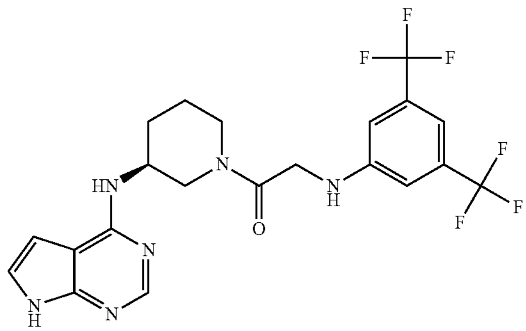 [SMILES: O=C(CNc1cc(C(F)(F)F)cc(C(F)(F)F)c1)N1CCC[C@H](Nc2ncnc3[nH]ccc23)C1] | C |
| 188 | 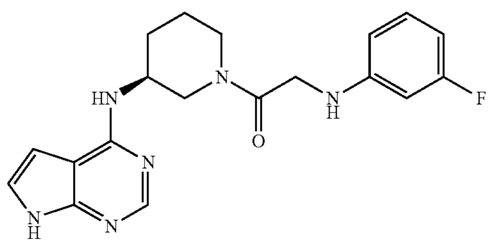 [SMILES: O=C(CNc1cccc(F)c1)N1CCC[C@H](Nc2ncnc3[nH]ccc23)C1] | C |
| 189 | 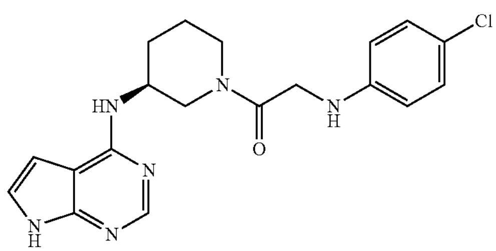 [SMILES: O=C(CNc1ccc(Cl)cc1)N1CCC[C@H](Nc2ncnc3[nH]ccc23)C1] | D |
| 190 | 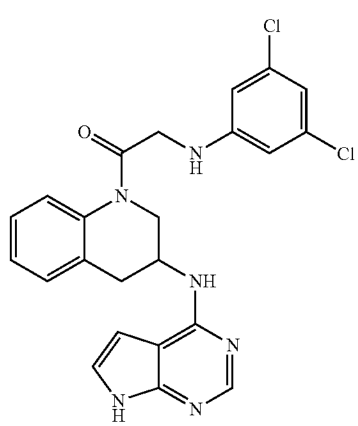 [SMILES: O=C(CNc1cc(Cl)cc(Cl)c1)N1CC(Nc2ncnc3[nH]ccc23)Cc2ccccc21] | B |

TABLE 4-continued

Exemplary compounds of formula I.

| Cmpd | Structure | IC$_{50}$ (10 uM ATP)$^a$ |
|---|---|---|
| 191 | 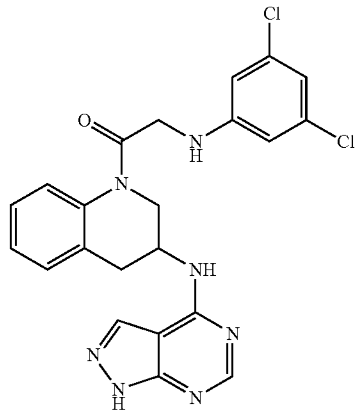 [SMILES: O=C(CNc1cc(Cl)cc(Cl)c1)N1CC(Nc2ncnc3[nH]ncc23)Cc2ccccc21] | B |
| 192 | 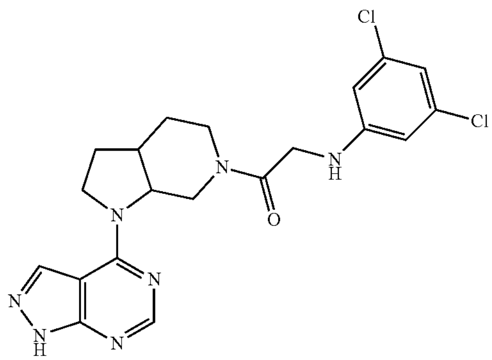 [SMILES: O=C(CNc1cc(Cl)cc(Cl)c1)N1CCC2CCN(c3ncnc4[nH]ncc34)C2C1] | A |
| 193 | 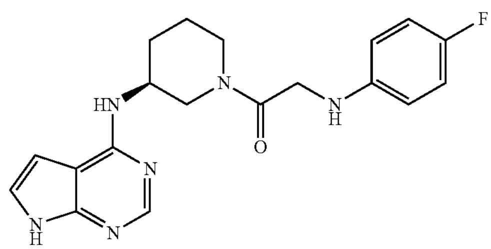 [SMILES: O=C(CNc1ccc(F)cc1)N1CCC[C@H](Nc2ncnc3[nH]ccc23)C1] | D |
| 194 | 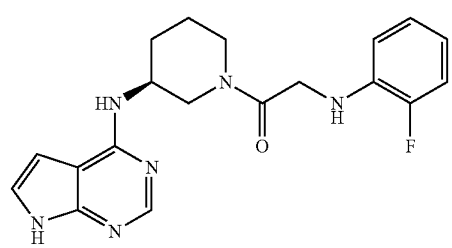 [SMILES: O=C(CNc1ccccc1F)N1CCC[C@H](Nc2ncnc3[nH]ccc23)C1] | D |
| 195 | 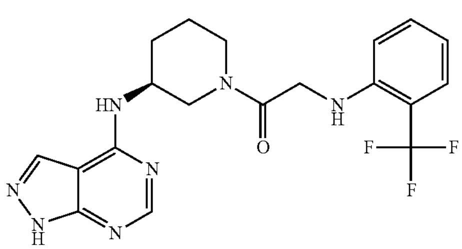 [SMILES: O=C(CNc1ccccc1C(F)(F)F)N1CCC[C@H](Nc2ncnc3[nH]ncc23)C1] | D |

TABLE 4-continued

Exemplary compounds of formula I.

| Cmpd | Structure | IC$_{50}$ (10 uM ATP)$^a$ |
|---|---|---|
| 196 | 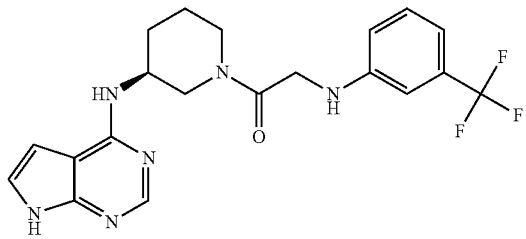 [SMILES: O=C(CNc1cccc(C(F)(F)F)c1)N1CCC[C@H](Nc2ncnc3[nH]ccc23)C1] | C |
| 197 | 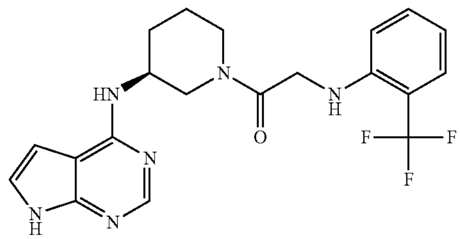 [SMILES: O=C(CNc1ccccc1C(F)(F)F)N1CCC[C@H](Nc2ncnc3[nH]ccc23)C1] | D |
| 198 | 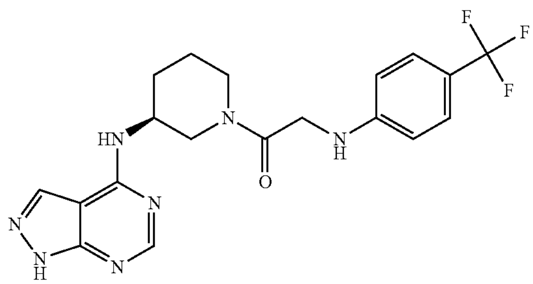 [SMILES: O=C(CNc1ccc(C(F)(F)F)cc1)N1CCC[C@H](Nc2ncnc3[nH]ncc23)C1] | D |
| 199 | 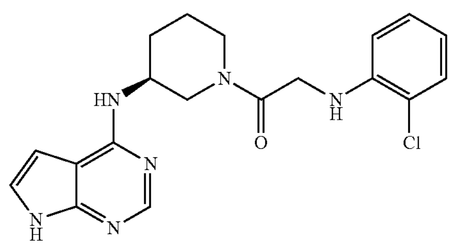 [SMILES: O=C(CNc1ccccc1Cl)N1CCC[C@H](Nc2ncnc3[nH]ccc23)C1] | D |
| 200 | 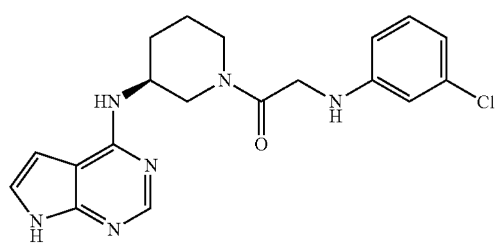 [SMILES: O=C(CNc1cccc(Cl)c1)N1CCC[C@H](Nc2ncnc3[nH]ccc23)C1] | C |
| 201 | 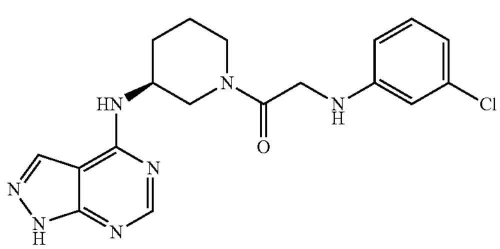 [SMILES: O=C(CNc1cccc(Cl)c1)N1CCC[C@H](Nc2ncnc3[nH]ncc23)C1] | C |

TABLE 4-continued

Exemplary compounds of formula I.

| Cmpd | Structure | IC$_{50}$ (10 uM ATP)$^a$ |
|---|---|---|
| 202 | 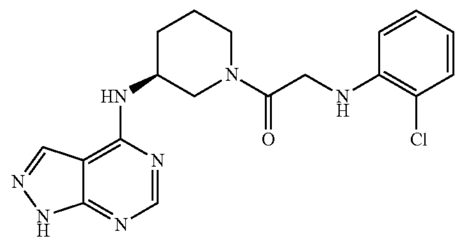 | D |
| 203 | 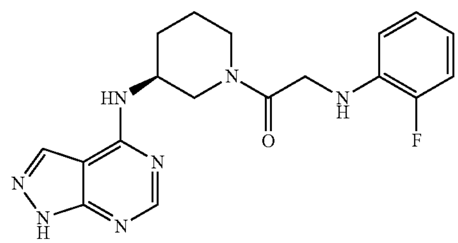 [SMILES: O=C(CNc1ccccc1F)N1CCC[C@H](Nc2ncnc3[nH]ncc23)C1] | D |
| 204 | 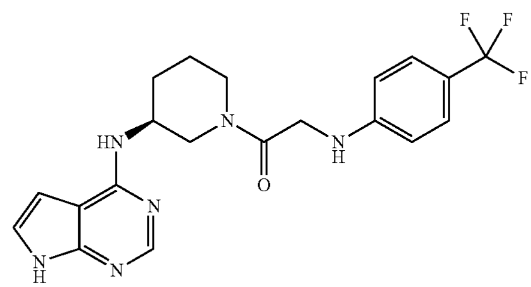 [SMILES: O=C(CNc1ccc(C(F)(F)F)cc1)N1CCC[C@H](Nc2ncnc3[nH]ccc23)C1] | D |
| 205 | 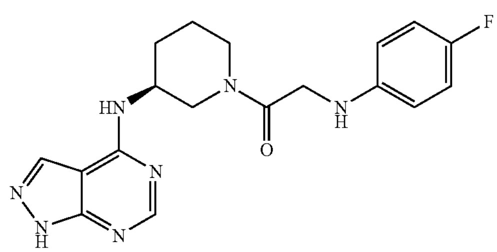 [SMILES: O=C(CNc1ccc(F)cc1)N1CCC[C@H](Nc2ncnc3[nH]ncc23)C1] | D |
| 206 | 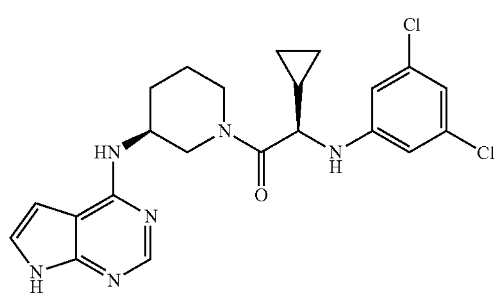 [SMILES: O=C([C@H](Nc1cc(Cl)cc(Cl)c1)C1CC1)N1CCC[C@H](Nc2ncnc3[nH]ccc23)C1] | C |

TABLE 4-continued

Exemplary compounds of formula I.

| Cmpd | Structure | IC$_{50}$ (10 uM ATP)$^a$ |
|---|---|---|
| 207 | 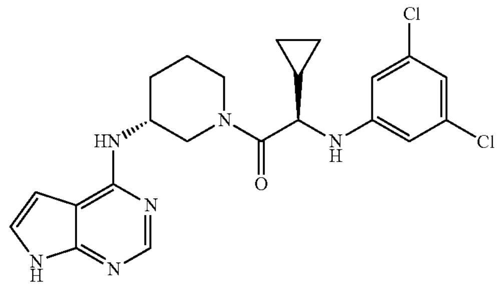 [SMILES: O=C([C@H](Nc1cc(Cl)cc(Cl)c1)C1CC1)N1CCC[C@@H](Nc2ncnc3[nH]ccc23)C1] | B |
| 208 | 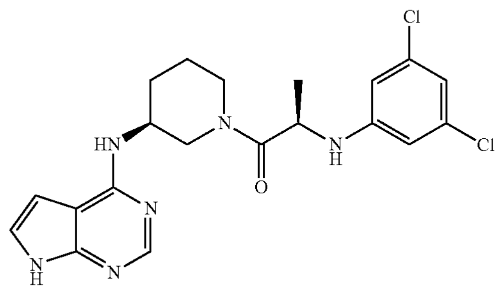 [SMILES: C[C@@H](Nc1cc(Cl)cc(Cl)c1)C(=O)N1CCC[C@H](Nc2ncnc3[nH]ccc23)C1] | B |
| 209 | 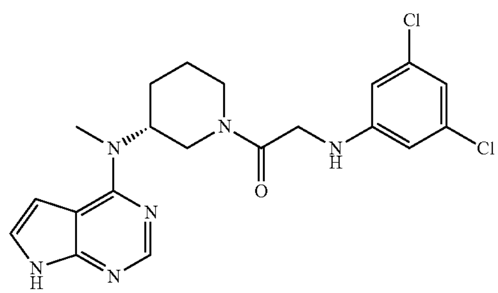 [SMILES: CN(c1ncnc2[nH]ccc12)[C@@H]1CCCN(C(=O)CNc2cc(Cl)cc(Cl)c2)C1] | A |
| 210 | 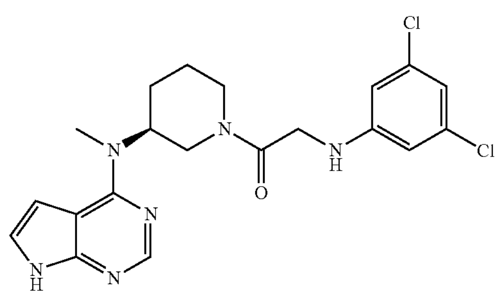 [SMILES: CN(c1ncnc2[nH]ccc12)[C@H]1CCCN(C(=O)CNc2cc(Cl)cc(Cl)c2)C1] | B |
| 211 | 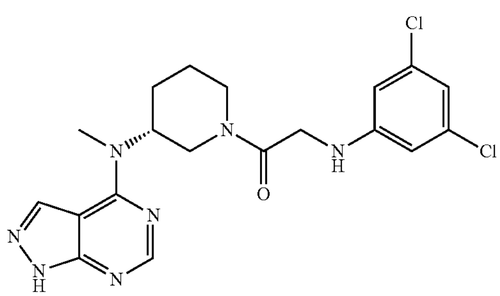 [SMILES: CN(c1ncnc2[nH]ncc12)[C@@H]1CCCN(C(=O)CNc2cc(Cl)cc(Cl)c2)C1] | A |

TABLE 4-continued

Exemplary compounds of formula I.

| Cmpd | Structure | IC$_{50}$ (10 uM ATP)$^a$ |
|---|---|---|
| 212 | 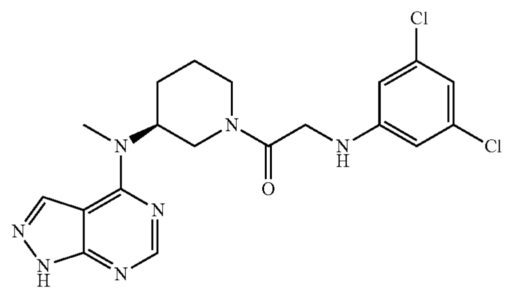 [SMILES: CN(c1ncnc2[nH]ncc12)[C@H]1CCCN(C(=O)CNc2cc(Cl)cc(Cl)c2)C1] | B |
| 213 | 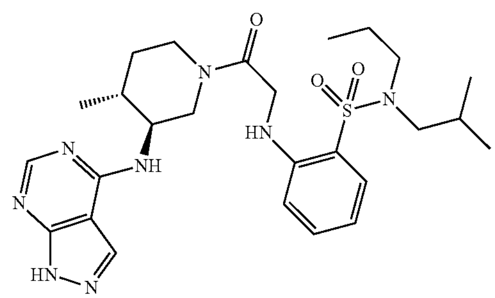 [SMILES: CCCN(CC(C)C)S(=O)(=O)c1ccccc1NCC(=O)N1CC[C@@H](C)[C@H](Nc2ncnc3[nH]ncc23)C1] | D |
| 214 | 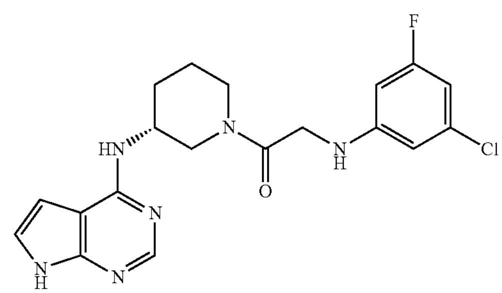 | B |
| 215 | 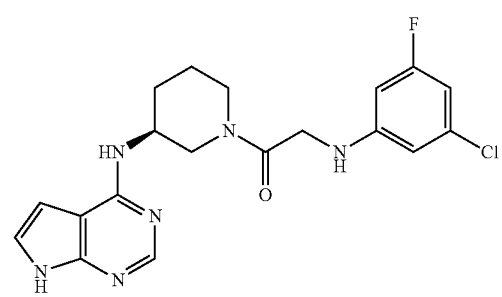 [SMILES: O=C(CNc1cc(F)cc(Cl)c1)N1CCC[C@H](Nc2ncnc3[nH]ccc23)C1] | C |
| 216 | 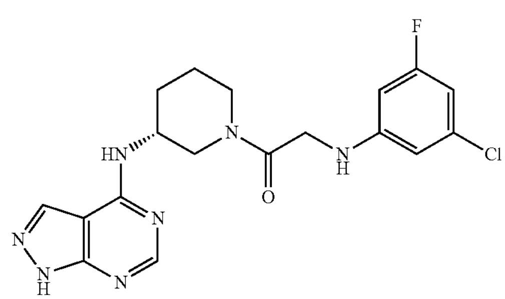 [SMILES: O=C(CNc1cc(F)cc(Cl)c1)N1CCC[C@@H](Nc2ncnc3[nH]ncc23)C1] | B |

TABLE 4-continued

Exemplary compounds of formula I.

| Cmpd | Structure | IC$_{50}$ (10 uM ATP)$^a$ |
|---|---|---|
| 217 | 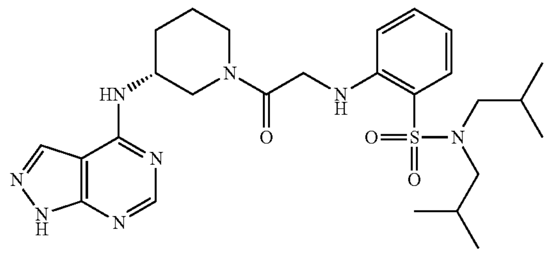 [SMILES: CC(C)CN(CC(C)C)S(=O)(=O)c1ccccc1NCC(=O)N1CCC[C@@H](Nc2ncnc3[nH]ncc23)C1] | A |
| 218 | 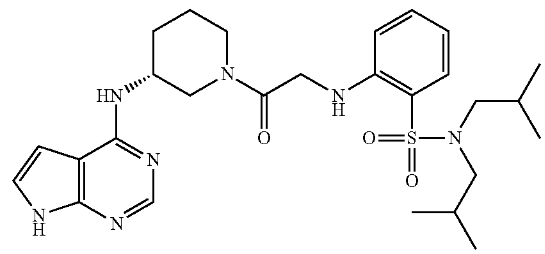 [SMILES: CC(C)CN(CC(C)C)S(=O)(=O)c1ccccc1NCC(=O)N1CCC[C@@H](Nc2ncnc3[nH]ccc23)C1] | B |
| 219 | 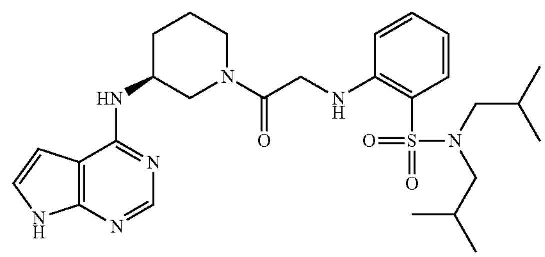 [SMILES: CC(C)CN(CC(C)C)S(=O)(=O)c1ccccc1NCC(=O)N1CCC[C@H](Nc2ncnc3[nH]ccc23)C1] | D |
| 220 | 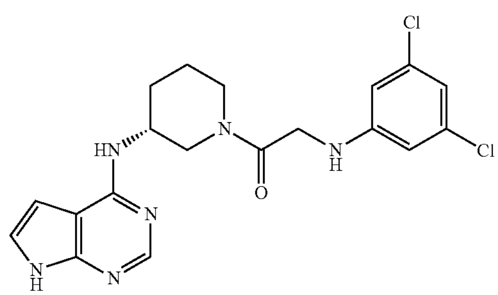 | A |
| 221 | 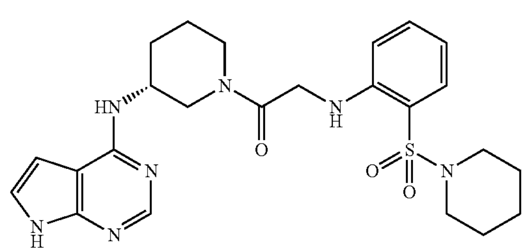 [SMILES: O=C(CNc1ccccc1S(=O)(=O)N1CCCCC1)N1CCC[C@@H](Nc2ncnc3[nH]ccc23)C1] | B |

TABLE 4-continued

Exemplary compounds of formula I.

| Cmpd | Structure | IC$_{50}$ (10 uM ATP)$^a$ |
|---|---|---|
| 222 | 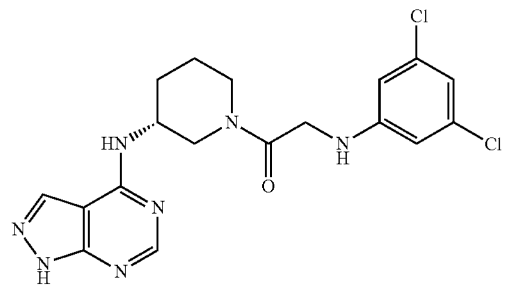 [SMILES: O=C(CNc1cc(Cl)cc(Cl)c1)N1CCC[C@@H](Nc2ncnc3[nH]ncc23)C1] | A |
| 223 | 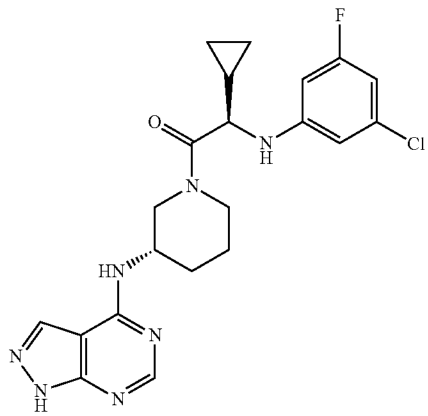 [SMILES: O=C([C@H](Nc1cc(F)cc(Cl)c1)C1CC1)N1CCC[C@H](Nc2ncnc3[nH]ncc23)C1] | C |
| 224 | 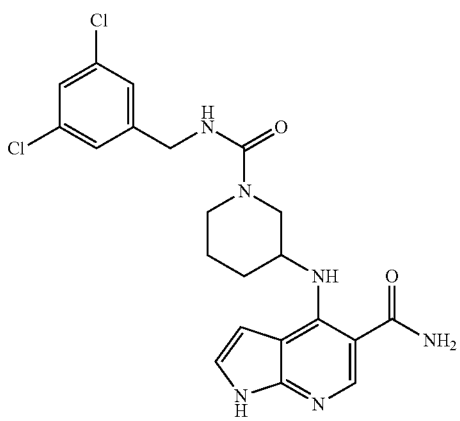 [SMILES: NC(=O)c1cnc2[nH]ccc2c1NC1CCCN(C(=O)NCc2cc(Cl)cc(Cl)c2)C1] | A |
| 225 | 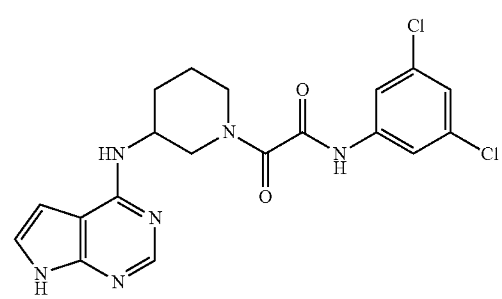 [SMILES: O=C(Nc1cc(Cl)cc(Cl)c1)C(=O)N1CCCC(Nc2ncnc3[nH]ccc23)C1] | D |

TABLE 4-continued

Exemplary compounds of formula I.

| Cmpd | Structure | IC$_{50}$ (10 uM ATP)$^a$ |
|---|---|---|
| 226 | 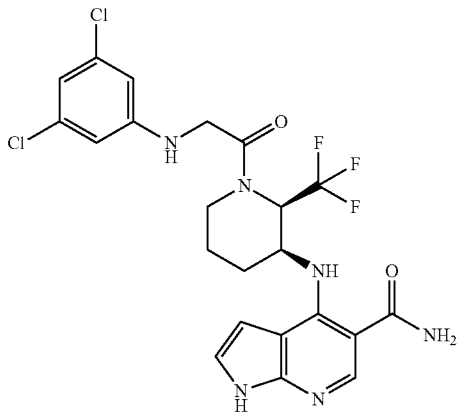 [SMILES: NC(=O)c1cnc2[nH]ccc2c1N[C@H]1CCCN(C(=O)CNc2cc(Cl)cc(Cl)c2)[C@H]1C(F)(F)F] | A |
| 227 | 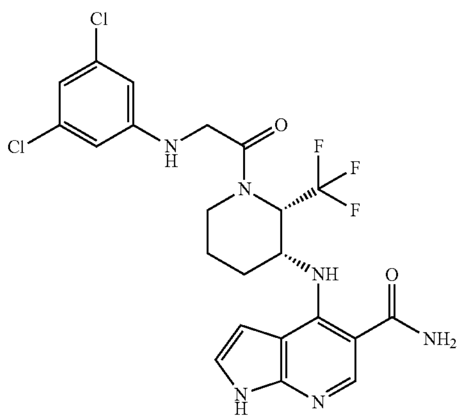 [SMILES: NC(=O)c1cnc2[nH]ccc2c1N[C@@H]1CCCN(C(=O)CNc2cc(Cl)cc(Cl)c2)[C@@H]1C(F)(F)F] | A |
| 228 | 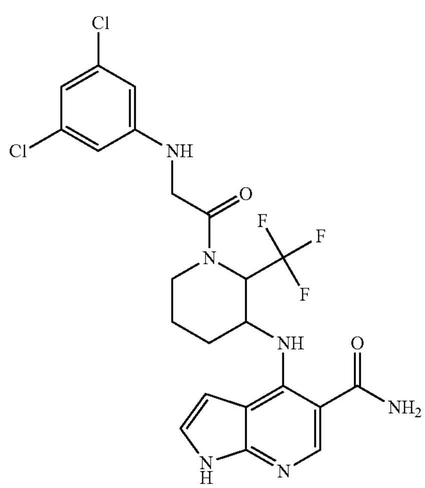 [SMILES: NC(=O)c1cnc2[nH]ccc2c1NC1CCCN(C(=O)CNc2cc(Cl)cc(Cl)c2)C1C(F)(F)F] | A |

TABLE 4-continued

Exemplary compounds of formula I.

| Cmpd | Structure | IC$_{50}$ (10 uM ATP)$^a$ |
|---|---|---|
| 229 | 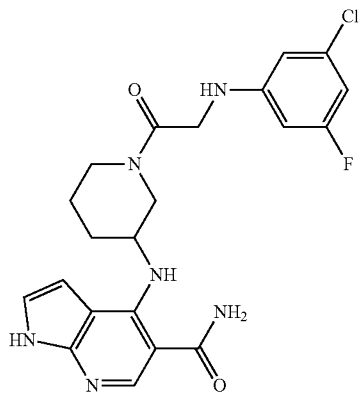 [SMILES: NC(=O)c1cnc2[nH]ccc2c1NC1CCCN(C(=O)CNc2cc(F)cc(Cl)c2)C1] | A |
| 230 | 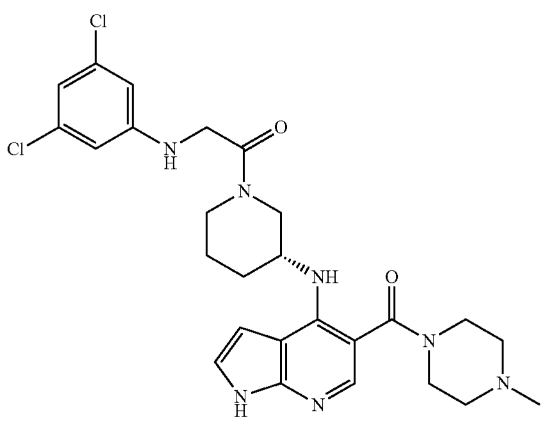 [SMILES: CN1CCN(C(=O)c2cnc3[nH]ccc3c2N[C@@H]2CCCN(C(=O)CNc3cc(Cl)cc(Cl)c3)C2)CC1] | B |
| 231 | 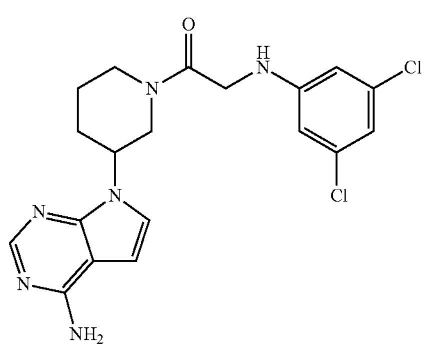 [SMILES: Nc1ncnc2c1ccn2C1CCCN(C(=O)CNc2cc(Cl)cc(Cl)c2)C1] | C |
| 232 | 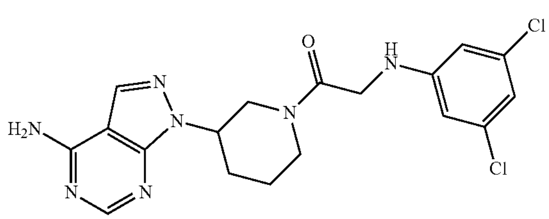 [SMILES: Nc1ncnc2c1cnn2C1CCCN(C(=O)CNc2cc(Cl)cc(Cl)c2)C1] | D |

TABLE 4-continued
Exemplary compounds of formula I.
| Cmpd | Structure | IC$_{50}$ (10 uM ATP)$^a$ |
|---|---|---|
| 233 | 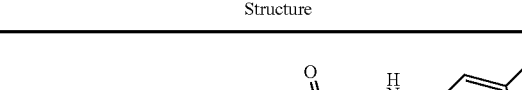 | D |
$^a$See Example 141.
TABLE 5
Exemplary compounds of formula I.
| Cmpd | Structure | TEC IC50 (uM)$^b$ | ITK IC50 (uM)$^c$ | LCK IC50 (uM)$^c$ | TXK IC50 (uM)$^c$ |
|---|---|---|---|---|---|
| 23 | 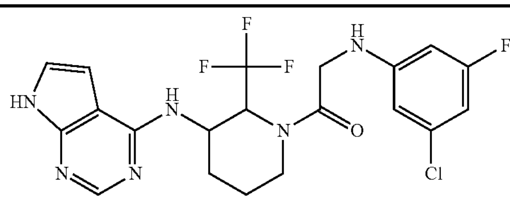 | B | C | | |
| 25 | 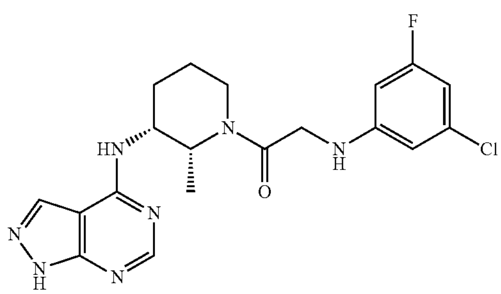 | B | B | | |
| 29 | 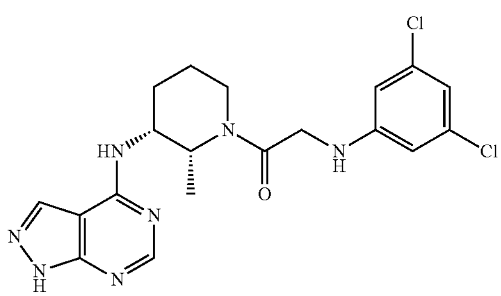 | A | B | | |
| 67 | 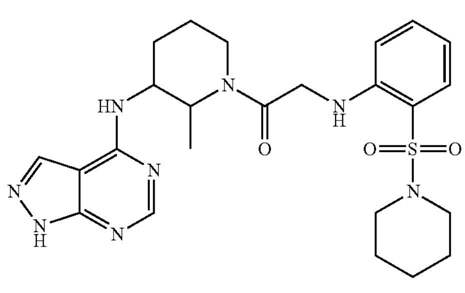 [SMILES: CC1C(Nc2ncnc3[nH]ncc23)CCCN1C(=O)CNc1ccccc1S(=O)(=O)N1CCCCC1] | B | C | | |

TABLE 5-continued
Exemplary compounds of formula I.
| Cmpd | Structure | TEC IC50 (uM)[b] | ITK IC50 (uM)[c] | LCK IC50 (uM)[c] | TXK IC50 (uM)[c] |
|---|---|---|---|---|---|
| 89 | 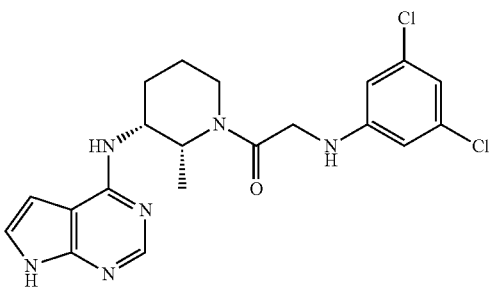 [SMILES: C[C@@H]1[C@H](Nc2ncnc3[nH]ccc23)CCCN1C(=O)CNc1cc(Cl)cc(Cl)c1] | A | B | | |
| 96 | 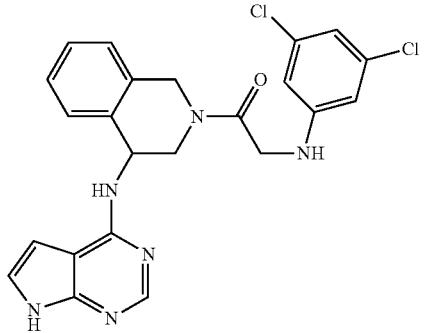 [SMILES: O=C(CNc1cc(Cl)cc(Cl)c1)N1Cc2ccccc2C(Nc2ncnc3[nH]ccc23)C1] | B | B | B | D |
| 99 | 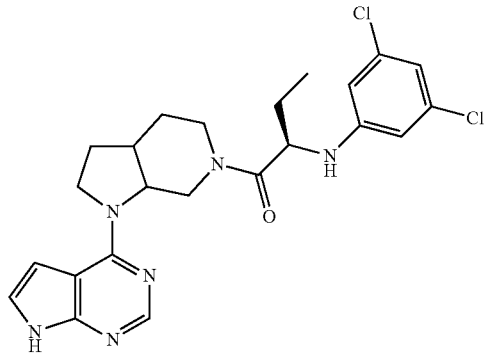 [SMILES: CC[C@@H](Nc1cc(Cl)cc(Cl)c1)C(=O)N1CCC2CCN(c3ncnc4[nH]ccc34)C2C1] | B | B | B | C |
| 100 | 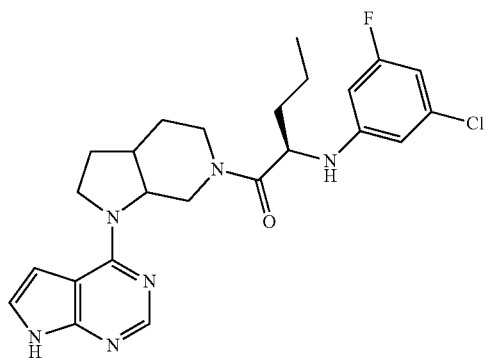 [SMILES: CCC[C@@H](Nc1cc(F)cc(Cl)c1)C(=O)N1CCC2CCN(c3ncnc4[nH]ccc34)C2C1] | B | B | B | C |

TABLE 5-continued

Exemplary compounds of formula I.

| Cmpd | Structure | TEC IC50 (uM)[b] | ITK IC50 (uM)[c] | LCK IC50 (uM)[c] | TXK IC50 (uM)[c] |
|---|---|---|---|---|---|
| 105 | 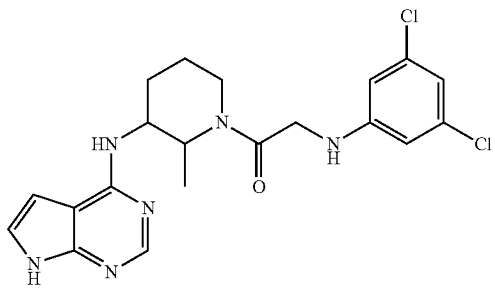 [SMILES: CC1C(Nc2ncnc3[nH]ccc23)CCCN1C(=O)CNc1cc(Cl)cc(Cl)c1] | B | B | B | C |
| 113 | 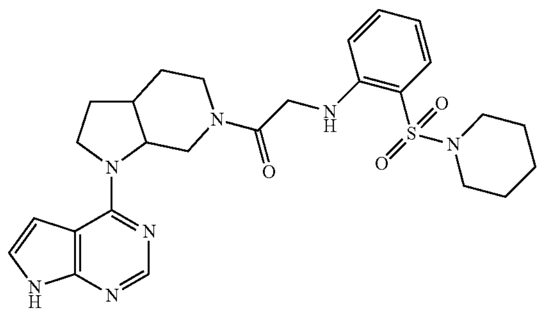 [SMILES: O=C(CNc1ccccc1S(=O)(=O)N1CCCCC1)N1CCC2CCN(c3ncnc4[nH]ccc34)C2C1] | C | C | D | C |
| 114 | 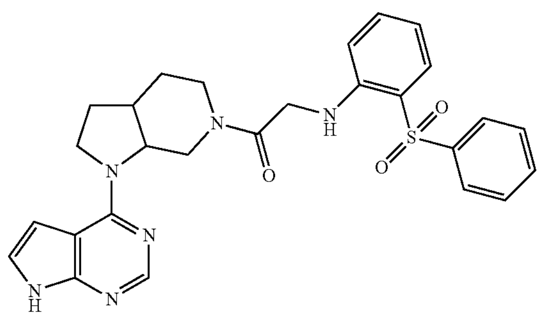 [SMILES: O=C(CNc1ccccc1S(=O)(=O)c1ccccc1)N1CCC2CCN(c3ncnc4[nH]ccc34)C2C1] | B | B | D | B |
| 123 | 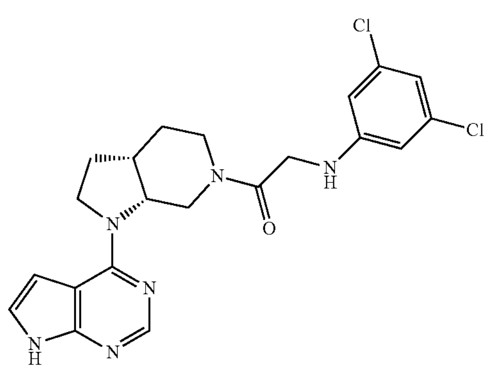 [SMILES: O=C(CNc1cc(Cl)cc(Cl)c1)N1CC[C@H]2CCN(c3ncnc4[nH]ccc34)[C@H]2C1] | A | A | B | B |

TABLE 5-continued
Exemplary compounds of formula I.
| Cmpd | Structure | TEC IC50 (uM)[b] | ITK IC50 (uM)[c] | LCK IC50 (uM)[c] | TXK IC50 (uM)[c] |
|---|---|---|---|---|---|
| 124 | 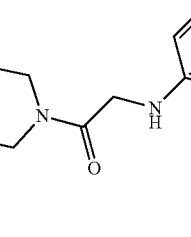 | A | B | B | B |
| 143 | 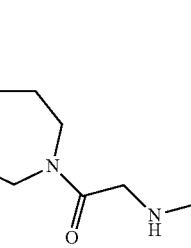 | D | D | D | D |
| 167 | 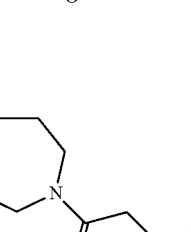 | B | C | C | D |
| 174 | 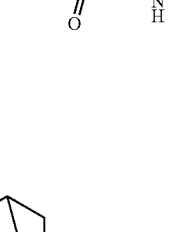 | D | D | D | D |
| 176 | 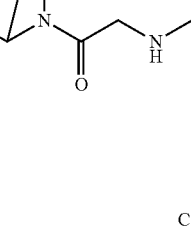 | C | C | B | C |

TABLE 5-continued

Exemplary compounds of formula I.

| Cmpd | Structure | TEC IC50 (uM)[b] | ITK IC50 (uM)[c] | LCK IC50 (uM)[c] | TXK IC50 (uM)[c] |
|---|---|---|---|---|---|
| 183 | 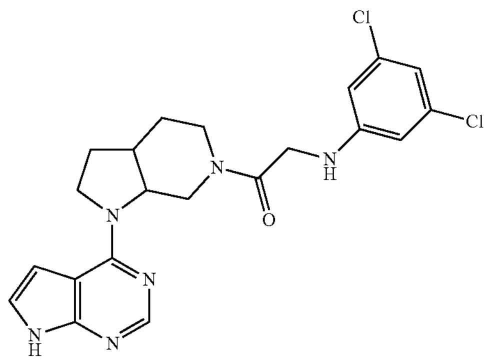 | A | A | B | B |
| 192 | 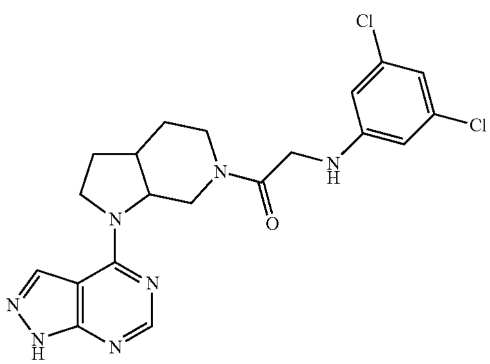 [SMILES: O=C(CNc1cc(Cl)cc(Cl)c1)N1CCC2CCN(c3ncnc4[nH]ncc34)C2C1] | B | B | B | C |
| 209 | 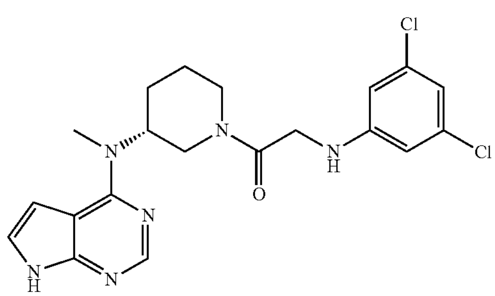 [SMILES: CN(c1ncnc2[nH]ccc12)[C@@H]1CCCN(C(=O)CNc2cc(Cl)cc(Cl)c2)C1] | B | B | B | C |
| 217 | 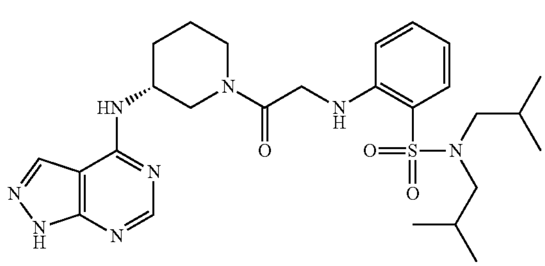 [SMILES: CC(C)CN(CC(C)C)S(=O)(=O)c1ccccc1NCC(=O)N1CCC[C@@H](Nc2ncnc3[nH]ncc23)C1] | B | B | C | C |

TABLE 5-continued

Exemplary compounds of formula I.

| Cmpd | Structure | TEC IC50 (uM)[b] | ITK IC50 (uM)[c] | LCK IC50 (uM)[c] | TXK IC50 (uM)[c] |
|---|---|---|---|---|---|
| 220 | 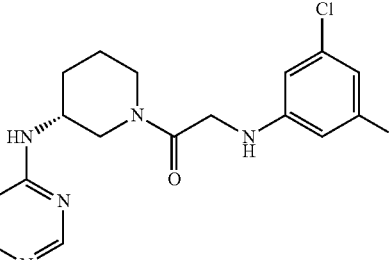 | B | C | D | D |
| 222 | 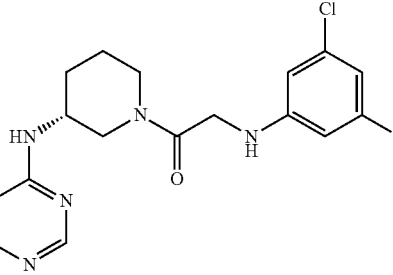 | B | C | C | D |
| 226 | 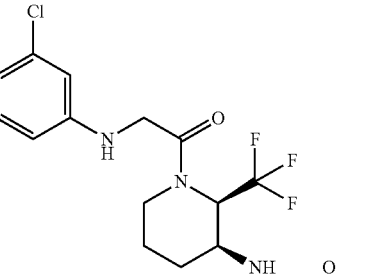 | A | A | | A |

[b]See Example 142.
[c]See Example 143.

What is claimed is:

1. A compound of formula IV:

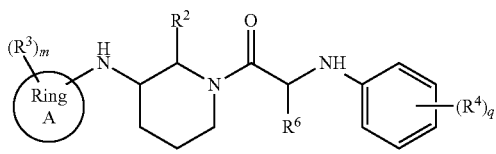

or a pharmaceutically acceptable salt thereof;
wherein:
each of m and q is independently 0-5;
Ring A is a 5-6 membered monocyclic heteroaryl ring having 1-4 heteroatoms independently selected from nitrogen, oxygen or sulfur, or an 8-10 membered bicyclic heteroaryl ring having 1-4 heteroatoms independently selected from nitrogen, oxygen, or sulfur;

$R^2$ is halogen, —$NO_2$, —CN, —OR, —SR, —$N(R)_2$, —C(O)R, —$CO_2R$, —C(O)C(O)R, —C(O)$CH_2$C(O)R, —S(O)R, —S(O)$_2$R, —C(O)$N(R)_2$, —$SO_2N(R)_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)$SO_2$N(R)$_2$, —N(R)$SO_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur, or:

two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur;

each $R^3$ and $R^4$ is independently halogen, —$NO_2$, —CN, —OR, —SR, —$N(R)_2$, —C(O)R, —$CO_2R$, —C(O)C(O)R, —C(O)$CH_2$C(O)R, —S(O)R, —S(O)$_2$R, —C(O)N(R)$_2$, —$SO_2N(R)_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from $C_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

2. The compound of claim 1, wherein Ring A is an optionally substituted 5-6 membered monocyclic heteroaryl ring having 1-4 heteroatoms independently selected from nitrogen, oxygen or sulfur.

3. The compound of claim 1, wherein Ring A is an optionally substituted 8-10 membered bicyclic heteroaryl ring having 1-4 heteroatoms independently selected from nitrogen, oxygen, or sulfur.

4. A compound listed in Table 4 selected from any one of compounds 4, 5, 7, 11, 12, 17-34, 41, 51, 52, 58, 60-73, 75, 79-81, 89-92, 105, 226-228, or a pharmaceutically acceptable salt thereof.

5. The compound of claim 3, wherein Ring A selected from:

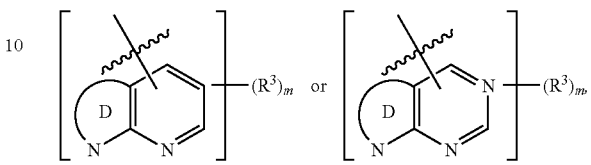

wherein each Ring D is a 5 membered saturated, partially unsaturated, or aryl fused ring having 1-2 heteroatoms in addition to the nitrogen atom independently selected from nitrogen, oxygen, or sulfur.

6. The compound of claim 1, wherein Ring A is selected from:

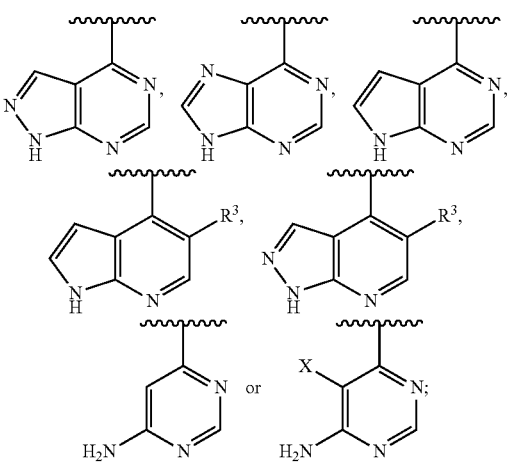

wherein X is halogen.

7. A pharmaceutical formulation comprising a compound of claim 1 and a pharmaceutically acceptable excipient.

8. A method of decreasing the enzymatic activity or a Tec kinase comprising contacting a Tec kinase with an effective amount of a compound of claim 1 or a composition thereof.

* * * * *